*US009062092B2*

United States Patent
Steadman et al.

(10) Patent No.: US 9,062,092 B2
(45) Date of Patent: Jun. 23, 2015

(54) **MACROCYCLIC INHIBITORS OF *FLAVIVIRIDAE* VIRUSES**

(71) Applicants: Gilead Sciences, Inc., Foster City, CA (US); Selcia Ltd., Ongar, Essex (GB)

(72) Inventors: Victoria Alexandra Steadman, Stansted (GB); Karine G. Poullennec, Chelmsform (GB); Linos Lazarides, London (GB); Caroline Aciro, Bottisham (GB); David Kenneth Dean, Ware (GB); Andrew John Keats, Chelmsford (GB); Dustin Scott Siegel, Foster City, CA (US); Adam James Schrier, Redwood City, CA (US); Richard Mackman, Millbrae, CA (US); Petr Jansa, San Mateo, CA (US)

(73) Assignees: Gilead Sciences, Inc., Foster City, CA (US); Selcia Ltd., Ongar (GB)

( * ) Notice: Subject to any disclaimer, the term of this patent is extended or adjusted under 35 U.S.C. 154(b) by 0 days.

(21) Appl. No.: 13/913,288

(22) Filed: Jun. 7, 2013

(65) Prior Publication Data
US 2013/0344030 A1    Dec. 26, 2013

Related U.S. Application Data

(60) Provisional application No. 61/657,562, filed on Jun. 8, 2012.

(51) Int. Cl.
| | |
|---|---|
| *A61K 38/21* | (2006.01) |
| *C07K 5/02* | (2006.01) |
| *C07D 487/08* | (2006.01) |
| *C07D 498/08* | (2006.01) |
| *C07D 498/18* | (2006.01) |
| *C07D 498/22* | (2006.01) |
| *A61K 38/12* | (2006.01) |
| *A61K 39/29* | (2006.01) |
| *A61K 45/06* | (2006.01) |
| *A61K 38/15* | (2006.01) |

(52) U.S. Cl.
CPC . *C07K 5/02* (2013.01); *A61K 38/15* (2013.01); *C07D 487/08* (2013.01); *C07D 498/08* (2013.01); *C07D 498/18* (2013.01); *C07D 498/22* (2013.01); *A61K 38/12* (2013.01); *A61K 39/29* (2013.01); *A61K 45/06* (2013.01)

(58) Field of Classification Search
CPC .............................. A61K 38/12; A61K 38/15
See application file for complete search history.

(56) References Cited

U.S. PATENT DOCUMENTS 8,513,184 B2    8/2013    Appelby et al.

FOREIGN PATENT DOCUMENTS

| WO | WO 97/02285 | 1/1997 |
|---|---|---|
| WO | WO 2006/138507 | 12/2006 |
| WO | WO 2012/078915 | 6/2012 |

OTHER PUBLICATIONS

International Search Report and Written Opinion dated Jul. 77, 2013 from PCT/US2013/044812.
Wagner, et al., "Synthesis of Macrolide Analogues of Sanglifehrin by RCM: Unique Reactivity of a Ruthenium Carbene Complex Bearing and Imidazol-2-ylidene Ligand," *J. Org. Chem.*, 2000, 65:26, 9255-9260.
U.S. Appl. No. 13/942,501, filed Jul. 15, 2013, Appleby Todd.
U.S. Appl. No. 13/913,184 Non-Final Rejection mailed Sep. 12, 2014.
U.S. Appl. No. 13/913,259 Non-Final Rejection mailed Aug. 29, 2014.

*Primary Examiner* — Marcela M Cordero Garcia
*Assistant Examiner* — Kaipeen Yang
(74) *Attorney, Agent, or Firm* — Francis O. Ginah

(57) ABSTRACT

Provided are compounds of Formula I:

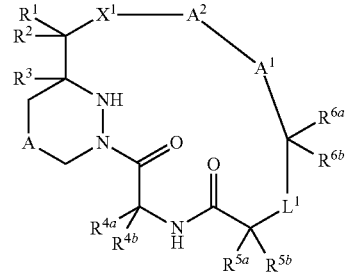

Formula I and pharmaceutically acceptable salts and esters thereof. The compounds, compositions, and methods provided are useful for the treatment of virus infections, particularly hepatitis C infections.

29 Claims, No Drawings

MACROCYCLIC INHIBITORS OF FLAVIVIRIDAE VIRUSES

CROSS-REFERENCE TO RELATED APPLICATIONS

This application claims the benefit under 35 U.S.C. §119 (e) to U.S. Provisional Application Ser. No. 61/657,562, filed on Jun. 8, 2012, the entirety of which is incorporated herein by reference.

FIELD

The present application provides novel compounds inhibiting viruses, compositions containing such compounds, and therapeutic methods comprising the administration of such compounds.

BACKGROUND

RNA viruses comprising the Flaviviridae family include at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Bescegline, A. M. and Bacon, B. R., Scientific American, October: 80-85, (1999); Gordon, C. P., et al., J. Med. Chem. 2005, 48, 1-20; Maradpour, D., et al., Nat. Rev. Micro. 2007, 5(6), 453-463). A number of HCV treatments are reviewed by Dymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., Science 1998, 282, 103-7; Fukimoto, et al., Hepatology, 1996, 24, 1351-4; Domingo, et al., Gene 1985, 40, 1-8; Martell, et al., J. Virol. 1992, 66, 3225-9.

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients given this treatment show a persistent benefit. Therefore, there is a need to develop more effective anti-HCV therapies.

The macrocycle sanglifehrin and derivatives are immunomodulatory and bind peptidyl-prolyl cis/trans isomerase (PPIase) cyclophilins in a unique manner (WO 97/02285; WO 98/07743; J. Am. Chem. Soc 2003, 125, 3849-3859; J. Org. Chem. 2000, 65, 9255-9260; Angew. Chem. Int. Ed. 1999, 38, 2443-2446). The cyclophilins are peptidyl-prolyl cis/trans isomerases (PPIase) that regulate protein folding in vivo and inhibit hepatitis C virus (Lin et al., WO2006/138507). However, none of the sanglifehrins or their derivatives has become available for human anti-viral therapy. Therefore, there is a continuing need to develop macrocyclic sanglifehrins with anti-Flaviviridae virus activity and particularly anti-HCV activity.

SUMMARY

In one embodiment, there is provided a compound represented by Formula I:

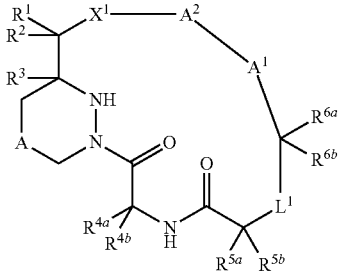

Formula I or a pharmaceutically acceptable salt, isotope, stereoisomer, mixture of stereoisomers, tautomer, ester or prodrug thereof, wherein:

A is a bond, —O—, —S(O)$_n$—, —NH—, —N((C$_1$-C$_4$) alkyl)- or (C$_1$-C$_2$)alkylene;

A$^1$ is (C$_1$-C$_8$)alkylene, (C$_2$-C$_5$)alkenylene, (C$_2$-C$_5$)alkynylene, arylene, heteroarylene, cycloalkylene, heterocycloalkylene, aryl(C$_1$-C$_2$)alkylene, heteroaryl(C$_1$-C$_2$)alkylene, cycloalkyl(C$_1$-C$_2$)alkylene or heterocycloalkyl(C$_1$-C$_2$)alkylene, wherein a sp$^3$ carbon atom of A$^1$ is optionally replaced by —O—, —S(O)$_n$—, —NH— or —N((C$_1$-C$_4$) alkyl)-, and wherein a sp$^3$ or sp$^2$ carbon atom of A$^1$ is optionally substituted with one or more substituents selected from the group consisting of halo, (C$_1$-C$_8$)alkyl, (C$_2$-C$_8$)alkenyl, (C$_2$-C$_8$)alkynyl, aryl, heterocycloalkyl, cycloalkyl, aryl(C$_1$-C$_4$)alkyl, cycloalkyl(C$_1$-C$_4$)alkyl, heterocycloalkyl(C$_1$-C$_4$) alkyl, arylheterocycloalkyl(C$_1$-C$_4$)alkyl, —OR$^9$, —SR$^9$, —S(O)R$^9$, —S(O)$_2$R$^9$ and —N(R$^9$)$_2$ where such an optional substitution is chemically feasible;

A$^2$ is —CH(R$^8$)-arylene, —CH(R$^8$)-heteroarylene, —CH (R$^8$)-heterocycloalkylene, —CH(R$^8$)— cycloalkylene, arylene, cycloalkylene, (C$_1$-C$_3$)alkylene, (C$_2$-C$_3$)alkenylene or (C$_2$-C$_3$)alkynylene, wherein the arylene, heteroarylene, heterocycloalkylene or cycloalkylene moiety of A$^2$ is optionally substituted with one or more substituents selected from the group consisting of —OR$^9$, —SR$^9$, —S(O)R$^9$, —S(O)$_2$ R$^9$, —N(R$^9$)$_2$, halo, halo(C$_1$-C$_4$)alkyl, halo(C$_1$-C$_4$)alkoxy cyano and (C$_1$-C$_8$)alkyl where such an optional substitution is chemically feasible;

L$^1$ is —O—C(O)—, —O—CH$_2$—, —NR$^{11}$—C(O)—, —NR$^{10}$—CH$_2$—, —NH—C(R$^{10}$)$_2$— or —NH—S(O)$_2$—, wherein each R$^{10}$ is independently H, (C$_1$-C$_4$)alkyl, halo(C$_1$-C$_4$)alkyl, (C$_1$-C$_4$)alkenyl or cycloalkyl; and R$^{11}$ is (C$_1$-C$_4$) alkyl, halo(C$_1$-C$_4$)alkyl, (C$_1$-C$_4$)alkenyl or cycloalkyl;

X$^1$ is a bond, —O—, —NH—, —N((C$_1$-C$_4$)alkyl)- or heterocycloalkylene;

$R^1$ and $R^2$ are independently H, $(C_1-C_4)$alkyl, $(C_2-C_4)$alkenyl, $(C_2-C_4)$alkynyl, halo, cyano or —C(O)—$(C_1-C_4)$alkyl; or $R^1$ and $R^2$, when taken together with the carbon to which they are both attached, form —C(=O)—, —C(=S)— or —C(=N($C_1-C_4$)alkyl)-;

$R^3$ is H or $(C_1-C_4)$alkyl which is optionally substituted with halo, cyano, hydroxyl or $(C_1-C_4)$alkoxy;

$R^{4a}$ and $R^{4b}$ are independently H, $(C_1-C_8)$alkyl, aryl, aryl$(C_1-C_4)$alkyl, heterocycloalkyl, heterocycloalkyl$(C_1-C_4)$alkyl, cycloalkyl or cycloalkyl$(C_1-C_4)$alkyl, wherein each $R^{4a}$ and $R^{4b}$ is optionally substituted with one or more substituents selected from the group consisting of cyano, —COOH, halo, hydroxyl, $(C_1-C_8)$alkoxy, amino, mono$(C_1-C_8)$alkylamino, di$(C_1-C_8)$alkylamino, aryl and heteroaryl where such an optional substitution is chemically feasible;

$R^{5a}$ and $R^{5b}$ are independently H, $(C_1-C_8)$alkyl, $(C_2-C_8)$alkenyl, $(C_2-C_8)$alkynyl, $(C_1-C_8)$alkoxy, aryl, heterocycloalkyl, cycloalkyl, aryl$(C_1-C_4)$alkyl, cycloalkyl$(C_1-C_4)$alkyl or heterocycloalkyl$(C_1-C_4)$alkyl, wherein each $R^{5a}$ and $R^{5b}$ is optionally substituted with one or more substituents selected from the group consisting of —$N_3$, cyano, —COOH, halo, hydroxyl, amino, mono$(C_1-C_8)$alkylamino, di$(C_1-C_8)$alkylamino, $(C_1-C_8)$alkoxy, aryl and heteroaryl, or $R^{5a}$ and $R^{5b}$ together form a spirocycle having Formula (a):

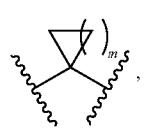

(a)

wherein one or more carbon ring atoms of Formula (a) is optionally replaced by a nitrogen, oxygen or sulfur atom, and wherein a ring atom of Formula (a) optionally has one or more substituents selected from the group consisting of oxo, =N($C_1-C_4$)alkoxy, halo, hydroxyl, —$NH_2$, $(C_1-C_4)$alkyl, halo$(C_1-C_4)$alkyl, $(C_1-C_4)$alkoxy, —OC(O)$R^9$, —C(O)$_2R^9$, and —S(O)$_2R^9$;

$R^{6a}$ and $R^{6b}$ are independently H, hydroxyl, $(C_1-C_8)$alkyl, $(C_2-C_8)$alkenyl, $(C_2-C_8)$alkynyl, $(C_1-C_8)$alkoxy, —$CH_2CH_2CR^9$(=N($C_1-C_4$)alkoxy), aryl, heterocycloalkyl, cycloalkyl, —$SR^9$, —S(O)$R^9$, —S(O)$_2R^9$ and —N($R^9$)$_2$, wherein each of $R^{6a}$ and $R^{6b}$ is optionally substituted with one or more substituents selected from the group consisting of halo, hydroxyl, cyano, $(C_1-C_4)$alkyl, $(C_1-C_4)$alkoxy, halo$(C_1-C_4)$alkoxy, aryl, cycloalkyl, heterocycloalkyl, mono$(C_1-C_8)$alkylamino, di$(C_1-C_8)$alkylamino, —NHS(O)$R^9$, —NHC(O)$R^9$ and $(C_1-C_8)$alkanoyl where such an optional substitution is chemically feasible; or $R^{6a}$ and $R^{6b}$ together form a spirocycle having Formula (a);

each $R^8$ is independently H, $(C_1-C_4)$alkyl, halo$(C_1-C_4)$alkyl, $(C_2-C_4)$alkenyl, $(C_2-C_4)$alkynyl, aryl, heteroaryl, heterocycloalkyl or cycloalkyl, wherein $R^8$ is optionally substituted with —OR, —N($R^9$)$_2$, —CON($R^9$)$_2$ or cyano;

each $R^9$ is independently H, $(C_1-C_4)$alkyl, halo$(C_1-C_4)$alkyl, $(C_2-C_4)$alkenyl or $(C_2-C_4)$alkynyl;

each n is independently 0, 1 or 2; and m is 1, 2, 3, 4 or 5.

In another embodiment, there is provided a pharmaceutical composition comprising a compound of Formula I or a pharmaceutically acceptable salt, isotope, stereoisomer, mixture of stereoisomers, tautomer, ester or prodrug thereof and one or more pharmaceutically acceptable carriers or excipients. In one aspect of the embodiment, the pharmaceutical composition further comprises one or more additional therapeutic agents.

In yet another embodiment, a method for treating Flaviviridae viral infection is provided comprising administering a therapeutically effective amount of a compound of Formula I or a pharmaceutically acceptable salt, isotope, stereoisomer, mixture of stereoisomers, tautomer, ester or prodrug thereof to a mammal in need thereof. In one aspect of the embodiment, the treatment results in the reduction of the in viral load or clearance of viral RNA in a patient.

In yet another embodiment, a method for treating Coronaviridae viral infection is provided comprising administering a therapeutically effective amount of a compound of Formula I or a pharmaceutically acceptable salt, isotope, stereoisomer, mixture of stereoisomers, tautomer, ester or prodrug thereof to a mammal in need thereof. In one aspect of the embodiment, the treatment results in the reduction of the in viral load or clearance of viral RNA in a patient.

DETAILED DESCRIPTION

Definitions

Unless stated otherwise, the following terms and phrases as used herein are intended to have the following meanings:

"Alkanoyl" is RC(O)—; "alkanoyloxy" is RC(O)O—; and "alkanoylamino" is RC(O)NR'—; where R is an alkyl group as defined herein, and $R^1$ is hydrogen or alkyl.

"Alkenyl" refers to a straight or branched hydrocarbyl group with at least one site of unsaturation, i.e., a carbon-carbon, $sp^2$ double bond. In some embodiments, alkenyl is a $C_2-C_{20}$ alkenyl group, a $C_2-C_{10}$ alkenyl group or a $C_2-C_6$ alkenyl group. Examples of alkenyl group include, but are not limited to, vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 2 to 20 carbon atoms, 2 to 10 carbon atoms, or 2 to 6 carbon atoms. Typical alkenylene radicals include, but are not limited to, 1,2-ethenylene (—CH=CH—).

"Alkoxy" is RO— where R is alkyl, as defined herein. Non-limiting examples of alkoxy groups include methoxy, ethoxy and propoxy.

"Alkyl" refers to a straight or branched chain hydrocarbyl group. In an embodiment, alkyl has from 1 to 20 carbon atoms (i.e., $C_1-C_{20}$ alkyl). In some embodiments, alkyl is a $C_1-C_{10}$ alkyl group or a $C_1-C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylene" refers to a saturated, branched or straight chain radical or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Examples of alkylene radicals include, but are not limited to, methylene (—$CH_2$—), ethylene (—$CH_2CH_2$—), propylene (—$CH_2CH_2CH_2$—) and butylene (—$CH_2CH_2CH_2CH_2$—).

"Alkynyl" refers to a hydrocarbon containing normal, secondary or tertiary carbon atoms with at least one site of unsaturation, i.e., a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,) or 2 to 6 carbon atoms (i.e., $C_2$-$C_6$ alkynyl). Examples of alkynyl groups include, but are not limited to, acetylenic (—C≡CH) and propargyl (—$CH_2$C≡CH).

"Amino" refers to —$NH_2$.

"Alkylamino" refers to an amino group substituted with one or more alkyl groups. "Mono(alkyl)amino" or "(alkyl)amino" is RNH—, and "di(alkyl)amino" or "(alkyl)$_2$-amino" is $R_2$N—, where each of the R groups is alkyl as defined herein and are the same or different. Examples of alkylamino groups include, but are not limited to, methylamino, ethylamino, propylamino, butylamino, dimethylamino, diethylamino and methylethylamno.

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 2 to 20 carbon atoms, 2 to 10 carbon atoms, or 2 to 6 carbon atoms. Typical alkynylene radicals include, but are not limited to, acetylene (—C≡C—), propargylene (—$CH_2$C≡C—), and 4-pentynylene (—$CH_2CH_2CH_2$C≡C—).

"Aryl" refers to any monocyclic or bicyclic carbon ring of up to 7 atoms in each ring, wherein at least one ring is aromatic, or an aromatic ring system of 5 to 14 carbons atoms which includes a carbocyclic aromatic group fused with a 5- or 6-membered cycloalkyl group. Examples of aryl groups include, but are not limited to, phenyl, naphthyl, tetrahydronaphthyl and indanyl.

"Arylalkyl" refers to an alkyl as defined herein substituted with an aryl radical.

"Arylene" refers to an aryl as defined above having two monovalent radical centers derived by the removal of two hydrogen atoms from two different carbon atoms of a parent aryl. Typical arylene radicals include, but are not limited to, phenylene, e.g.,

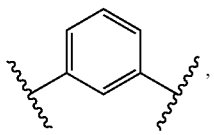 [SMILES: *c1cccc(*)c1]

and naphthylene, e.g.,

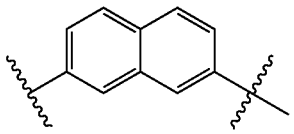

"Arylalkylene" refers to an arylalkyl as defined above having two monovalent radical centers derived by the removal of one hydrogen atom from the aryl radical and the other hydrogen removed from the alkyl radical of the group.

"Cycloalkyl" refers to a hydrocarbyl group containing at least one saturated or partially unsaturated ring structure, and attached via a ring carbon. Cycloalkyl groups include hydrocarbon mono-, bi-, and poly-cyclic rings, whether fused, bridged, or spiro. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Cycloalkylalkyl" refers to an alkyl moiety substituted with a cycloalkyl group. Examples of cycloalkylalkyl groups include cyclopropylmethyl, cyclobutylmethyl, cyclopentylethyl and cyclohexylmethyl.

"Cycloalkylalkylene" refers to an alkylene moiety substituted with a cycloalkyl group. Examples of cycloalkylalkylene groups include cyclopropylmethylene, cyclobutylmethylene, cyclopentylethylene and cyclohexylmethylene.

"Cycloalkylene" refers to a cycloalkyl, as defined herein, having two monovalent radical centers derived by the removal of two hydrogen atoms from the same or two different carbon atoms of a parent cycloalkyl. Examples of cycloalkylene include, but are not limited to, cyclopropylene, cyclobutylene, cyclopentylene and cyclohexylene.

"Dialkylaminoalkyl" refers to an alkyl moiety substituted with a dialkylamino group, wherein dialkylamino is as defined herein.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

"Halo" refers to chloro (—Cl), bromo (—Br), fluoro (—F) or iodo (—I).

"Haloalkoxy" refers to alkoxy, as defined herein, substituted with one or more halo radicals.

"Haloalkoxyalkyl" refers to an alkyl moiety substituted with a haloalkoxy group, as defined herein.

"Haloalkyl" refers to an alkyl group, in which one or more hydrogen atoms of the alkyl group is replaced with a halogen atom. Examples of haloalkyl groups include, but are not limited to, —$CF_3$, —$CHF_2$, —$CFH_2$ and —$CH_2CF_3$.

"Heterocycloalkyl" refers to a saturated or partially unsaturated monocyclic, bicyclic or tricyclic group of 2 to 14 ring-carbon atoms and, in addition to ring-carbon atoms, 1 to 4 heteroatoms selected from the group consisting of P, N, O and S. The heterocyclic group can be attached through a carbon atom or through a heteroatom, and when substituted, the substituent can be bonded to a carbon atom or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl and N-oxides thereof.

"Arylheterocycloalkyl" refers to a heterocycloalkyl group, as defined herein, in which a hydrogen atom has been replaced with an aryl group.

"Arylheterocycloalkylalkyl" refers to an alkyl group, as defined herein, in which a hydrogen atom has been replaced with a heterocycloalkyl group, and a hydrogen atom of the heterocycloalkyl group has been replaced with an aryl group.

"Heterocycloalkylalkyl" refers to an alkyl group, as defined herein, in which a hydrogen atom has been replaced with a heterocycloalkyl group.

"Heterocycloalkylalkylene" refers to an alkylene group, as defined herein, in which a hydrogen atom has been replaced with a heterocycloalkyl group.

"Heterocycloalkylene" refers to a heterocycloalkyl, as defined above, having two monovalent radical centers derived by the removal of two hydrogen atoms from the same or two different carbon atoms of a parent heterocycloalkyl group.

"Heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroarylalkyl" refers to an alkyl group, as defined herein, in which a hydrogen atom has been replaced with a heteroaryl group.

"Heteroarylalkylene" refers to an alkylene group, as defined herein, in which a hydrogen atom has been replaced with a heteroaryl group.

"Heteroarylene" refers to a heteroaryl, as defined above, having two monovalent radical centers derived by the removal of two hydrogen atoms from the same or two different carbon atoms of a parent heteroaryl group. Non-limiting examples of heteroarylene groups are:

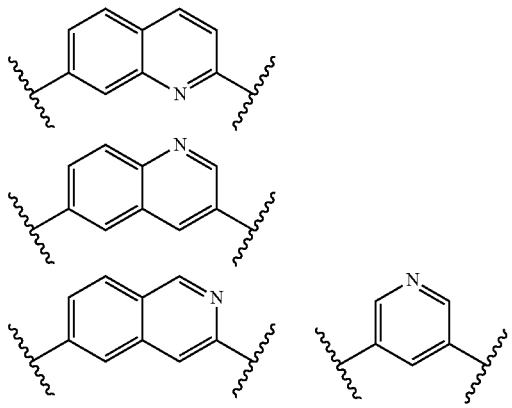

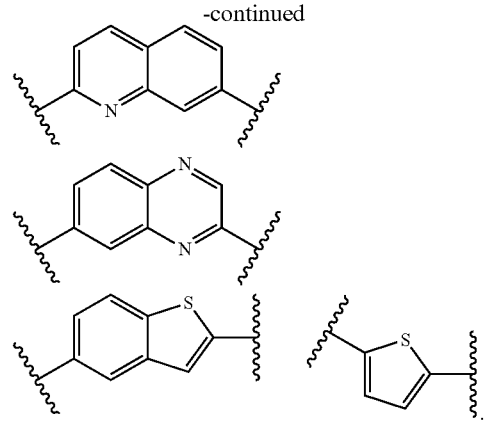

"Hydroxyalkoxy" refers to an alkoxy, as defined herein, substituted with a hydroxyl group (—OH). An example of hydroxyalkoxy is hydroxyethoxy.

"Hydroxyalkyl" refers to an alkyl group substituted with at least one hydroxyl group. Examples of hydroxyalkyl groups include, but are not limited to, hydroxymethyl, hydroxyethyl, hydroxypropyl and hydroxybutyl.

"Prodrug" refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

The term "optionally substituted" refers to a moiety wherein all substituents are hydrogen or wherein one or more of the hydrogens of the moiety are replaced by non-hydrogen substituents. Multiple substitutions on the same atom are also permitted where chemically feasible (e.g., a dioxo substitution to provide —S(O)$_2$—, geminal substituents, spiro cycloalkyl or heterocycloalkyl rings, etc.). In some embodiments, "one or more" substituents is from one to three substituents.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

"Pharmaceutically acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically acceptable carrier" refers to a diluent, adjuvant, excipient, or carrier, or other ingredient which is pharmaceutically acceptable and with which a compound of the invention is administered.

"Pharmaceutically acceptable salt" refers to a salt which may enhance desired pharmacological activity. Examples of pharmaceutically acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-enel-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

A compound of a given formula (e.g. the compound of Formula I, which also includes Formula I, II, II-a, II-b, II-c and/or III) is intended to encompass the compounds of the disclosure, and the pharmaceutically acceptable salts, stereoisomers, mixture of stereoisomers or tautomers of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space. Stereoisomers include enantiomers and diastereomers.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers or "tautomers". Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

"Therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

Any formula or structure given herein, including Formula I, II, II-a, II-b, II-c or III, is also intended to represent unlabeled forms as well as isotopically labeled forms of the compounds. An "isotope" may have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, II, II-a, II-b, II-c or III in which from 1 to n hydrogens attached to a carbon atom is/are replaced by deuterium, in which n is the number of hydrogens in the molecule. Such compounds exhibit increased resistance to metabolism and are thus useful for increasing the half life of any compound of Formula I, II, II-a, II-b, II-c or III when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, II, II-a, II-b, II-c or Ill.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Compounds

The present application provides a compound represented by Formula I:

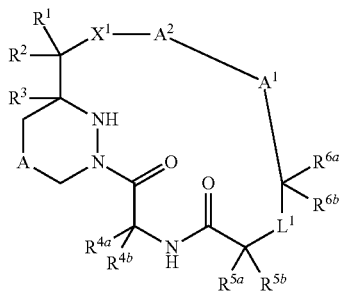

Formula I or a pharmaceutically acceptable salt, isotope, stereoisomer, mixture of stereoisomers, tautomer, ester or prodrug thereof, wherein $L^1$, $A^1$, $A^2$, $X^1$, $R^1$, $R^2$, $R^3$, $R^{4a}$, $R^{4b}$, $R^5$ and $R^{6a}$, $R^{6b}$ are as defined above.

In one embodiment, provided is a compound of Formula I:

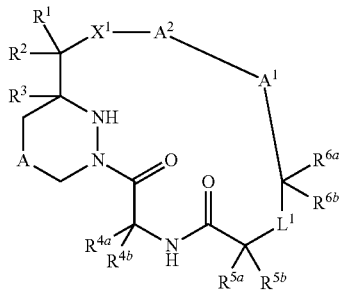

Formula I or a pharmaceutically acceptable salt thereof, wherein:

A is a bond, —O—, —S(O)$_n$—, —NH—, —N(($C_1$-$C_4$)alkyl)- or ($C_1$-$C_2$)alkylene;

$A^1$ is ($C_1$-$C_5$)alkylene, ($C_2$-$C_5$)alkenylene, ($C_2$-$C_5$)alkynylene, arylene, heteroarylene, cycloalkylene, heterocycloalkylene, aryl($C_1$-$C_2$)alkylene, heteroaryl($C_1$-$C_2$)alkylene, cycloalkyl($C_1$-$C_2$)alkylene or heterocycloalkyl($C_1$-$C_2$)alkylene, wherein a sp$^3$ carbon atom of $A^1$ is optionally replaced by —O—, —S(O)$_n$—, —NH— or —N(($C_1$-$C_4$)alkyl)-, and wherein a sp$^3$ or sp$^2$ carbon atom of $A^1$ is optionally substituted with one or more groups selected from halo, ($C_1$-$C_8$)alkyl, ($C_2$-$C_8$)alkenyl, ($C_2$-$C_8$)alkynyl, aryl, heterocycloalkyl, cycloalkyl, aryl($C_1$-$C_4$)alkyl, cycloalkyl($C_1$-$C_4$)alkyl, heterocycloalkyl($C_1$-$C_4$)alkyl, arylheterocycloalkyl($C_1$-$C_4$)alkyl, —OR$^9$, —SR$^9$, —S(O)R$^9$, —S(O)$_2$R$^9$ and —N(R$^9$)$_2$;

$A^2$ is —CH(R$^8$)-arylene, —CH(R$^8$)-heteroarylene, —CH(R$^8$)-heterocycloalkylene, —CH(R$^8$)— cycloalkylene, arylene, cycloalkylene, ($C_1$-$C_3$)alkylene, ($C_2$-$C_3$)alkenylene or ($C_2$-$C_3$)alkynylene, wherein $A^2$ is optionally substituted with one or more substituents selected from OR$^9$, —SR$^9$, —S(O)R$^9$, —S(O)$_2$R$^9$, —N(R$^9$)$_2$, halo, halo($C_1$-$C_4$)alkyl, halo($C_1$-$C_4$)alkoxy, cyano and ($C_1$-$C_8$)alkyl;

$L^1$ is —O—C(O)—, —O—CH$_2$—, —NR$^{10}$—C(O)—, —NR$^{10}$—CH$_2$—, —NH—C(R$^{10}$)$_2$— or —NH—S(O)$_2$—, wherein each R$^{10}$ is independently H, ($C_1$-$C_4$)alkyl, halo($C_1$-$C_4$)alkyl, ($C_1$-$C_4$)alkenyl or cycloalkyl;

$X^1$ is bond, —O—, —NH—, —N(($C_1$-$C_4$)alkyl)- or heterocycloalkylene;

$R^1$ and $R^2$ are independently H, ($C_1$-$C_4$)alkyl, ($C_2$-$C_4$)alkenyl, ($C_2$-$C_4$)alkynyl, halo, cyano or —C(O)—($C_1$-$C_4$)alkyl; or $R^1$ and $R^2$, when taken together with the carbon to which they are both attached, form —C(=O)—, —C(=S)— or —C(=N($C_1$-$C_4$)alkyl)-;

$R^3$ is H or ($C_1$-$C_4$)alkyl which is optionally substituted with halo, cyano, hydroxyl or ($C_1$-$C_4$)alkoxy;

$R^{4a}$ and $R^{4b}$ are independently H, ($C_1$-$C_8$)alkyl, aryl, aryl($C_1$-$C_4$)alkyl, heterocycloalkyl, heterocycloalkyl($C_1$-$C_4$)alkyl, cycloalkyl or cycloalkyl($C_1$-$C_4$)alkyl, wherein each of $R^{4a}$ and $R^{4b}$ is optionally substituted with one or more substituent selected from cyano, —COOH, halo, hydroxyl, amino, mono($C_1$-$C_8$)alkylamino, di($C_1$-$C_8$)alkylamino, aryl and heteroaryl;

$R^{5a}$ and $R^{5b}$ are independently H, ($C_1$-$C_8$)alkyl, ($C_2$-$C_8$)alkenyl, ($C_2$-$C_8$)alkynyl, ($C_1$-$C_8$)alkoxy, aryl, heterocycloalkyl, cycloalkyl, aryl($C_1$-$C_4$)alkyl, cycloalkyl($C_1$-$C_4$)alkyl or heterocycloalkyl($C_1$-$C_4$)alkyl, wherein $R^5$ is optionally substituted with one or more substituent selected from —N$_3$, cyano, —COOH, halo, hydroxyl, amino, mono($C_1$-$C_8$)alkylamino, di($C_1$-$C_8$)alkylamino, aryl and heteroaryl, or $R^{5a}$ and $R^{5b}$ together form a spirocycle having Formula (a):

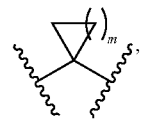

(a)

wherein a carbon ring atom of Formula (a) is optionally substituted with one or more heteroatom selected from SO, SO$_2$, O and N, and wherein a carbon ring atom of Formula (a) optionally has one or more substituents selected from halo, hydroxyl, —NH$_2$, ($C_1$-$C_4$)alkyl and ($C_1$-$C_4$)alkoxy;

$R^{6a}$ and $R^{6b}$ are independently H, hydroxyl, ($C_1$-$C_8$)alkyl, ($C_2$-$C_8$)alkenyl, ($C_2$-$C_8$)alkynyl, ($C_1$-$C_8$)alkoxy, —CH$_2$CH$_2$CR$^9$(=N($C_1$-$C_4$)alkoxy), aryl, heterocycloalkyl, cycloalkyl, —SR$^9$, —S(O)R$^9$, —S(O)$_2$R$^9$ and —N(R$^9$)$_2$, wherein each of R$^{6a}$ and R$^{6b}$ is optionally substituted with one or more substituent selected from halo, hydroxyl, cyano, ($C_1$-$C_4$)alkyl, ($C_1$-$C_4$)alkoxy, aryl, cycloalkyl, heterocycloalkyl, mono($C_1$-$C_8$)alkylamino, di($C_1$-$C_8$)alkylamino, —NHS(O)R$^9$, —NHC(O)R$^9$ and ($C_1$-$C_8$)alkanoyl; or R$^{6a}$ and R$^{6b}$ together form a spirocycle having Formula (a);

each $R^8$ is independently H, ($C_1$-$C_4$)alkyl, halo($C_1$-$C_4$)alkyl, ($C_2$-$C_4$)alkenyl, ($C_2$-$C_4$)alkynyl, aryl, heteroaryl, heterocycloalkyl or cycloalkyl, wherein R$^8$ is optionally substituted with —OR, —N(R$^9$)$_2$, —CON(R$^9$)$_2$, or cyano;

each $R^9$ is independently H, ($C_1$-$C_4$)alkyl, ($C_2$-$C_4$)alkenyl or ($C_2$-$C_4$)alkynyl;

each n is independently 0, 1 or 2; and m is 1, 2, 3, 4 or 5.

In one aspect of the embodiment, $A^1$ is ethenylene, propenylene, butenylene, ethylene, propylene, butylene, oxypropylene, oxypropenylene, pyrazolylene, phenylene or pyrimidinylene.

In another aspect of the embodiment, $A^2$ is —CH($R^8$)-quinolinylene, —CH($R^8$)— isoquinolinylene, —CH($R^8$)-naphthyridinylene, —CH($R^8$)-cinnolinylene, —CH($R^8$)-quinoxalinylene, —CH($R^8$)-phenylene, —CH($R^8$)-naphthylene or —CH($R^8$)-halophenylene. In various aspects of the embodiment, $A^2$ is selected from the group consisting of

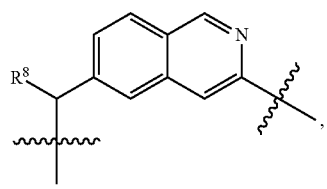

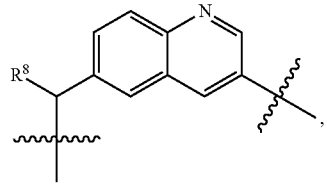

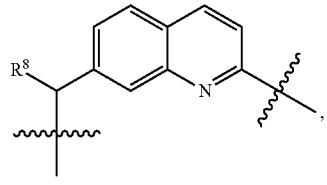

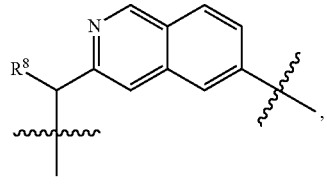

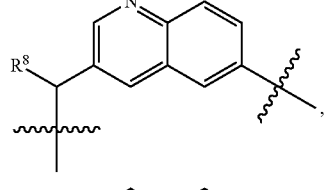

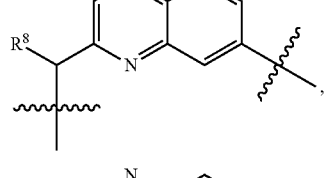

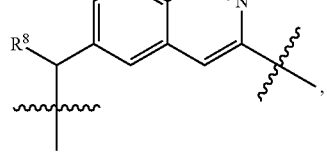

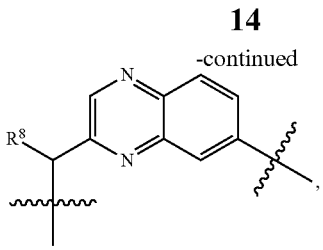

wherein the left bond of $A^5$ linker is attached to $X^1$. In certain embodiments, $R^8$ is methyl.

In some embodiments, $X^1$ is —O—, —NH— or —N(CH$_3$)—; $R^1$ and $R^2$, when taken together with the carbon to which they are both attached, form —C(=O)—; and $R^3$ is H. In another embodiments, $X^1$ is —O—, —NH— or —N(CH$_3$)—; $R^1$ and $R^2$, when taken together with the carbon to which they are both attached, form —C(=O)—; $R^3$ is H; one of $R^{4a}$ and $R^{4b}$ is H and the other is methyl; and one of $R^{5a}$ and $R^{5b}$ is H and the other is iso-propyl.

In one embodiment, $X^1$ is —O—, —NH— or —N(CH$_3$)—; $R^1$ and $R^2$, when taken together with the carbon to which they are both attached, form —C(=O)—; $R^3$ is H; one of $R^{4a}$ and $R^{4b}$ is H and the other is methyl; one of $R^{5a}$ and $R^{5b}$ is H and the other is iso-propyl; $A^2$ is —CH($R^8$)—heteroarylene, and $R^8$ is methyl.

In another embodiment, $X^1$ is —O— or —NH—; $R^1$ and $R^2$, when taken together with the carbon to which they are both attached, form —C(=O)—; $R^3$ is H; $R^{4a}$ is H; $R^{4b}$ is methyl; $R^5$ is isopropyl; and $R^8$ is methyl.

In one embodiment, one of $R^{6a}$ and $R^{6b}$ is H; and the other H, hydroxyl, —CH$_2$CH$_2$CR$^9$(=N(C$_1$-C$_4$)alkoxy), (C$_1$-C$_8$)alkyl or (C$_1$-C$_8$)alkoxy, wherein $R^{6a}$ or $R^{6b}$ is optionally substituted with one or more substituents selected from the group consisting of halo, hydroxyl, (C$_1$-C$_4$)alkoxy, halo(C$_1$-C$_4$)alkoxy, heterocycloalkyl, (C$_1$-C$_4$)alkanoyl or di(C$_1$-C$_4$)alkylamino. In another embodiment, $R^{6a}$ is H; and $R^{6b}$ is H, (C$_1$-C$_8$)alkyl or (C$_1$-C$_8$)alkyl substituted with heterocycloalkyl, (C$_1$-C$_4$)alkanoyl or di(C$_1$-C$_4$)alkylamino.

In one embodiment, $L^1$ is —O—C(O)—. In another embodiment, $L^1$ is —O—CH$_2$—. In yet another embodiment, $L^1$ is —N(CH$_3$)—C(O)—. In still another embodiment, $L^1$ is —NH—CH$_2$—. In certain embodiments, $L^1$ is —NH—S(O)$_2$—.

In another aspect of the embodiment, $X^1$ is 4- to 7-membered heterocycloalkylene. In a particular embodiment, the heterocycloalkylene has a N ring atom which is bonded to —C(R$^1$)(R$^2$)—, and non-limiting examples include:

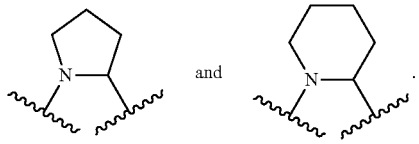 [SMILES: *C1CCCN1* ; *C1CCCCN1*]

In another embodiment, there is provided a compound of Formula II:

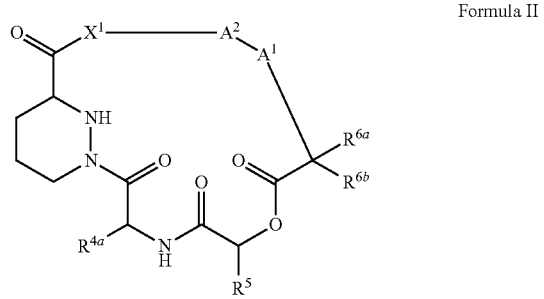

Formula II or a pharmaceutically acceptable salt, isotope, stereoisomer, mixture of stereoisomers, tautomer, ester or prodrug thereof, wherein:

$A^1$ is

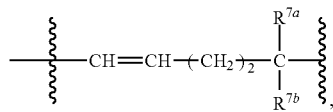

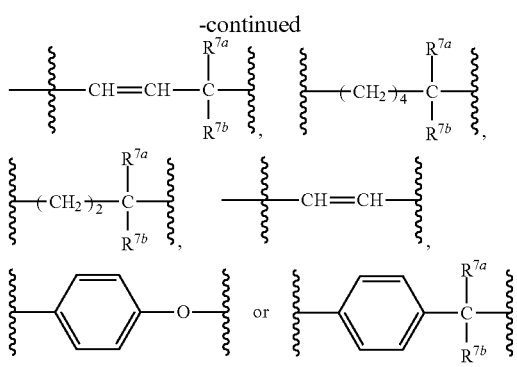

$A^2$ is —CH($R^8$)-arylene, —CH($R^8$)-heteroarylene, —CH($R^8$)-heterocycloalkylene, —CH($R^8$)— cycloalkylene, arylene or cycloalkylene;

$X^1$ is a bond, —CH$_2$—, —O—, —NH—, —N(CH$_3$)—,

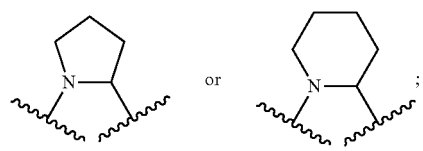

$R^{4a}$ is H, (C$_1$-C$_4$)alkoxy, halo(C$_1$-C$_4$)alkoxy, hydroxyl(C$_1$-C$_8$)alkyl, (C$_1$-C$_4$)alkoxy(C$_1$-C$_8$)alkyl or (C$_1$-C$_8$)alkyl;

$R^5$ is H, (C$_1$-C$_4$)alkyl, halo(C$_1$-C$_8$)alkyl, hydroxy(C$_1$-C$_4$)alkyl, (C$_1$-C$_4$)alkoxy(C$_1$-C$_8$)alkyl, cycloalkyl or heterocycloalkyl;

$R^{6a}$ and $R^{6b}$ are independently H, hydroxyl, (C$_1$-C$_8$)alkyl, (C$_2$-C$_8$)alkenyl, (C$_2$-C$_8$)alkynyl, (C$_1$-C$_8$)alkoxy, —CH$_2$CH$_2$CR$^9$(=N(C$_1$-C$_4$)alkoxy), aryl, heterocycloalkyl, cycloalkyl, —SR$^9$, —S(O)R$^9$, —S(O)$_2$R$^9$ and —N(R$^9$)$_2$, wherein each of $R^{6a}$ and $R^{6b}$ is optionally substituted with one or more substituents selected from the group consisting of halo, hydroxyl, cyano, (C$_1$-C$_4$)alkyl, (C$_1$-C$_4$)alkoxy, halo(C$_1$-C$_4$)alkoxy, aryl, cycloalkyl, heterocycloalkyl, mono(C$_1$-C$_8$)alkylamino, di(C$_1$-C$_8$)alkylamino, —NHS(O)R$^9$, —NHC(O)R$^9$ and (C$_1$-C$_8$)alkanoyl where such an optional substitution is chemically feasible; or $R^{6a}$ and $R^{6b}$ together form a spirocycle having Formula (a); or $R^{6a}$ and $R^{6b}$ together form a spirocycle having Formula (a):

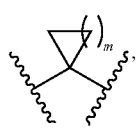

(a)

wherein one or more carbon ring atoms of Formula (a) is optionally replaced by a nitrogen, oxygen or sulfur atom, and wherein a ring atom of Formula (a) optionally has one or more substituents selected from the group consisting of oxo, =N(C$_1$-C$_4$)alkoxy, halo, hydroxyl, —NH$_2$, (C$_1$-C$_4$)alkyl, halo(C$_1$-C$_4$)alkyl, (C$_1$-C$_4$)alkoxy, —OC(O)R$^9$, —C(O)$_2$R$^9$, and —S(O)$_2$R$^9$;

$R^{7a}$ and $R^{7b}$ are independently H, —OH, (C$_1$-C$_4$)alkoxy, halo(C$_1$-C$_4$)alkoxy or (C$_1$-C$_8$)alkyl;

$R^8$ is H or (C$_1$-C$_4$)alkyl; and each $R^9$ is independently H, (C$_1$-C$_4$)alkyl, halo(C$_1$-C$_4$)alkyl, (C$_2$-C$_4$)alkenyl or (C$_2$-C$_4$)alkynyl.

In certain embodiments of Formula II, A$^1$ is

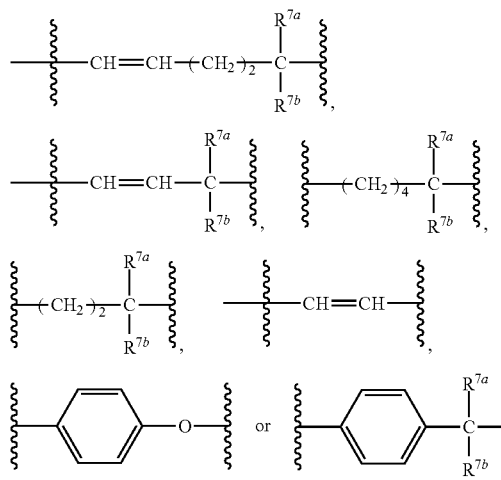

wherein the left bond of A$^1$ linker is attached to A$^2$;

A$^2$ is —CH(R$^8$)-arylene, —CH(R$^8$)-heteroarylene, —CH(R$^8$)-heterocycloalkylene, —CH(R$^8$)— cycloalkylene, arylene or cycloalkylene, wherein the left bond of A$^2$ linker is attached to X$^1$;

X$^1$ is bond, —CH$_2$—, —O—, —NH—, —N(CH$_3$)—,

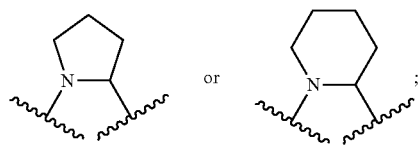 [SMILES: *C1CCCN1* ; *C1CCCCN1*]

R$^{4a}$ is H, (C$_1$-C$_4$)alkoxy, halo(C$_1$-C$_4$)alkoxy or (C$_1$-C$_8$)alkyl;

R$^5$ is H or (C$_1$-C$_4$)alkyl;

R$^{6a}$ and R$^{6b}$ are independently H, —OH, (C$_1$-C$_4$)alkoxy, halo(C$_1$-C$_4$)alkoxy or (C$_1$-C$_8$)alkyl,

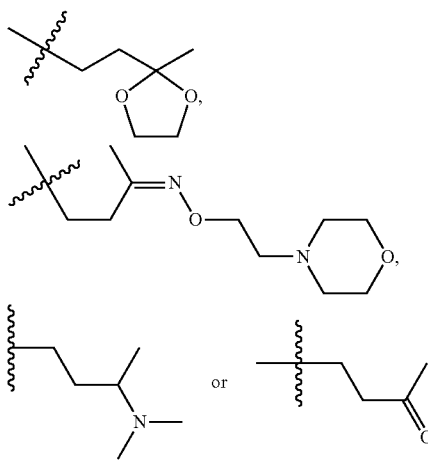

or

R$^{6a}$ and R$^{6b}$ together form

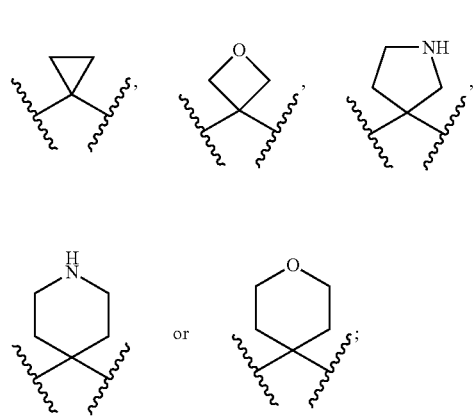

R$^{7a}$ and R$^{7b}$ are independently H, —OH, (C$_1$-C$_4$)alkoxy, halo(C$_1$-C$_4$)alkoxy or (C$_1$-C$_8$)alkyl; and R$^8$ is H or (C$_1$-C$_4$)alkyl.

In certain embodiments of Formula II, R$^{4a}$ is methyl; R$^5$ is iso-propyl; R$^8$ is methyl; and is

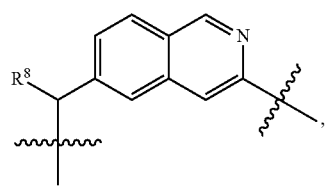

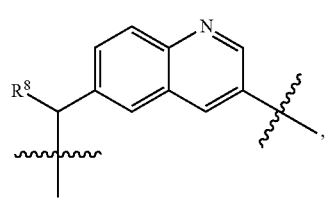

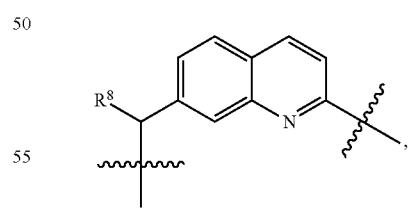

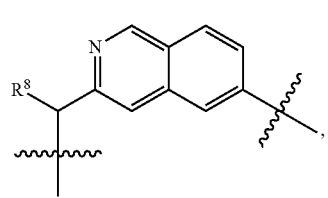

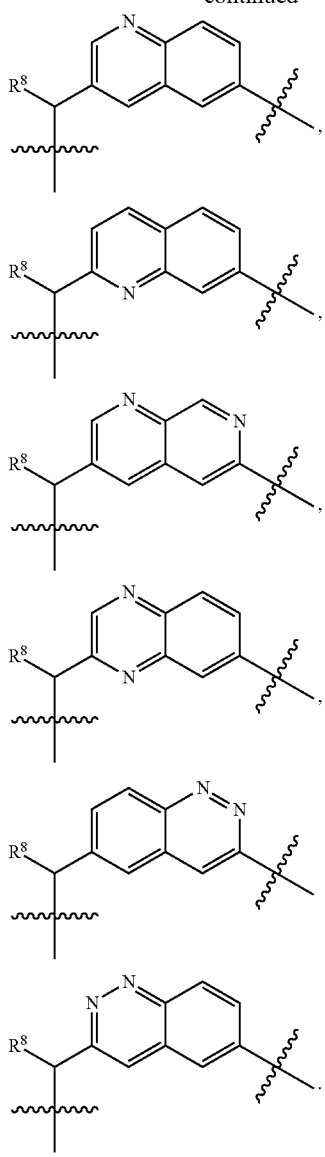
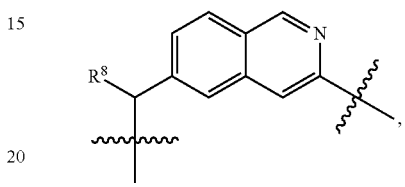
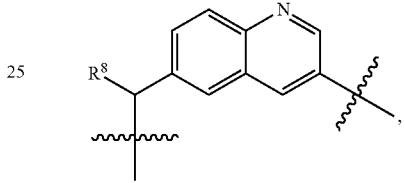
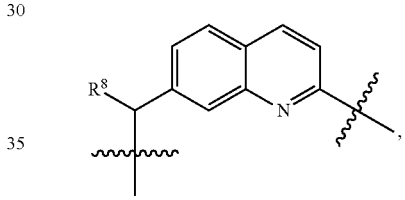

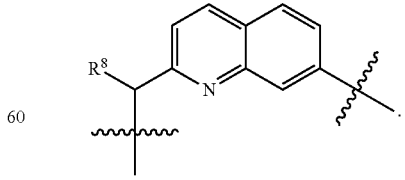
In certain embodiments of Formula II, $R^{4a}$ is methyl; $R^5$ is iso-propyl; $R^8$ is methyl; and $A^2$ is
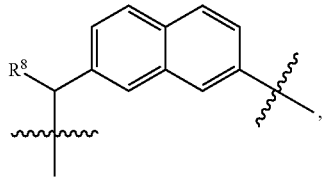
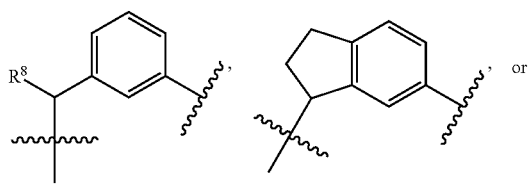
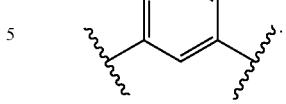
In one embodiment, $R^{4a}$ is methyl; $R^5$ is isopropyl; $R^8$ is methyl; and $A^2$ is
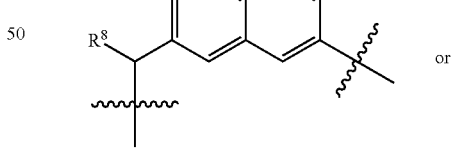
Non-limiting examples of such compounds include the following compounds and pharmaceutically acceptable salts thereof:

Formula (II-a)

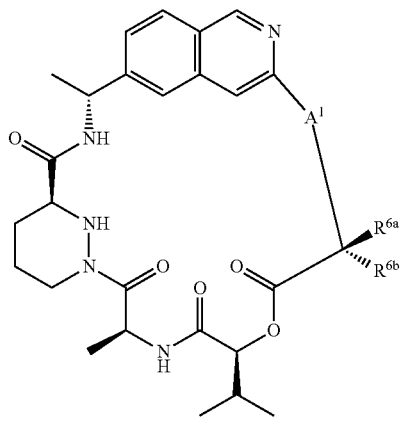

| Compound No. | A¹ | R$^{6a}$ | R$^{6b}$ |
|---|---|---|---|
| a-1 (Example 3) | —CH=CH— | H | H |
| a-2 (Example 5) | —CH=CH— | Methyl | H |
| a-3 (Example 5) | —CH=CH— | H | Methyl |
| a-4 | —CH=CH— | Methyl | Methyl |
| a-5 (Example 4) | —CH=CH$_2$— | Propyl | H |
| a-6 (Example 12) | —CH=CHCH$_2$— | Methyl | Methyl |
| a-7 (Example 13) | —CH=CHCH$_2$— | ![dioxolane group] | H |
| a-8 (Example 15) | —CH=CHCH$_2$— | ![oxime-morpholine group] | H |
| a-9 (Example 16) | —CH=CHCH$_2$— | ![dimethylamino group] | H |
| a-10 (Example 14) | —CH=CHCH$_2$— | ![ketone group] | H |
| a-11 | —CH=CH—CH(OCH$_3$)— | Methyl | H |
| a-12 (Example 11) | —CH=CHCH(CH$_3$)— | —CH$_3$ | H |
| a-13 (Example 11) | —CH=CHCH(CH$_3$)— | H | —CH$_3$ |
| a-14 (Example 9) | —CH$_2$CH$_2$CH$_2$— | Propyl | H | wherein the left bond of A¹ linker is attached to A².

A² linker of the compounds above can be replaced by various position isomers. Non-limiting examples thereof include compounds having the following formulae:

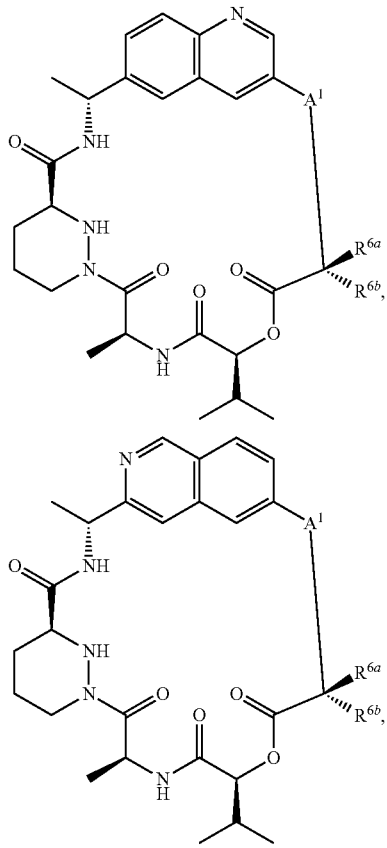

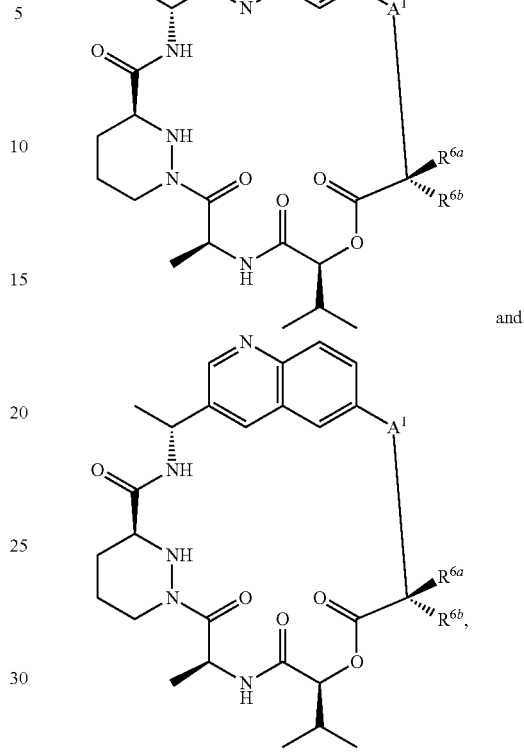

wherein the compounds of the formulae above have the same combination or pattern of substituents given in the table for Compounds a-1 to a-14.

Also included are compounds having the following formulae:

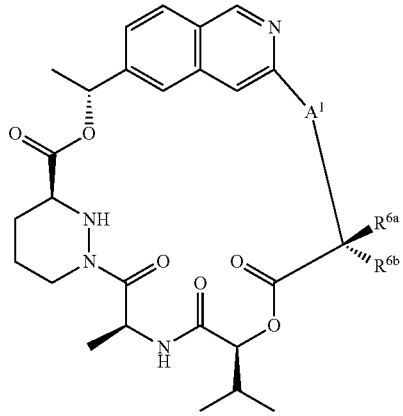

Formula (II-a2)

| Compound No. | A¹ | $R^{6a}$ | $R^{6b}$ |
| --- | --- | --- | --- |
| a2-1 | —CH=CH— | H | H |
| a2-2 | —CH=CH— | Methyl | H |
| a2-3 | —CH=CH— | H | Methyl |
| a2-4 | —CH=CH— | Methyl | Methyl |
| a2-5 | —CH=CHCH₂— | Propyl | H |
| a2-6 | —CH=CHCH₂— | Methyl | Methyl |

-continued
Formula (II-a2)
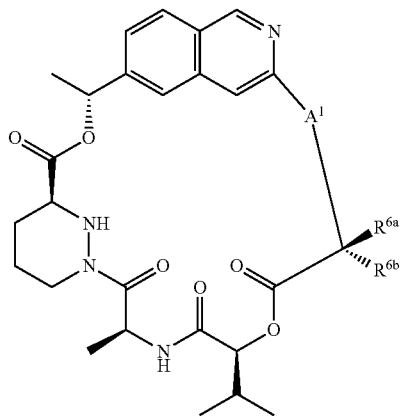
| Compound No. | A¹ | R⁶ᵃ | R⁶ᵇ |
|---|---|---|---|
| a2-7 | —CH=CHCH₂— | (2-methyl-1,3-dioxolan-2-yl)ethyl group | H |
| a2-8 | —CH=CHCH₂— | (morpholinoethoxyimino)methyl group | H |
| a2-9 | —CH=CHCH₂— | (dimethylamino)methylpropyl group | H |
| a2-10 | —CH=CHCH₂— | oxobutyl group | H |
| a2-11 (Example 2) | —CH=CH—CH(OCH₃)— | Methyl | H |
| a2-12 | —CH=CHCH(CH₃)— | —CH₃ | H |
| a2-13 | —CH=CHCH(CH₃)— | H | —CH₃ |
| a2-14 | —CH₂CH₂CH₂— | Propyl | H |
wherein the left bond of A¹ linker is attached to A².

A² linker of the compounds above can be replaced by various position isomers. Non-limiting examples thereof include compounds having the following formulae:

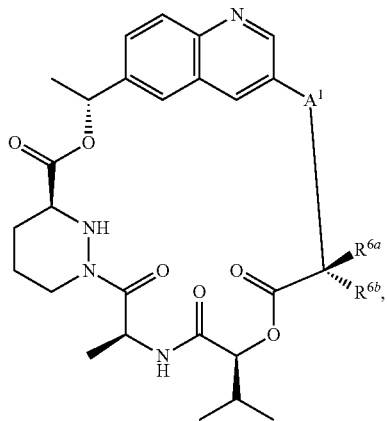

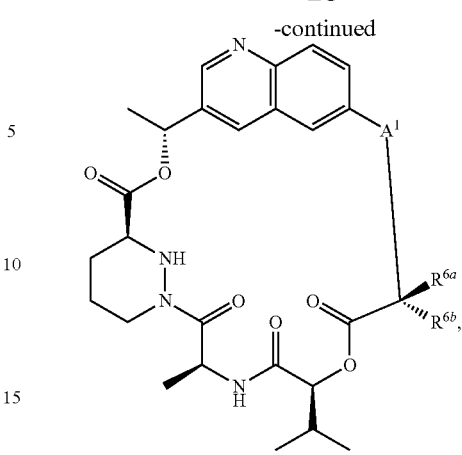

wherein the compounds of the formulae above have the same combination or pattern of substituents given in the table for Compounds a2-1 to a2-14.

In another aspect of the embodiment, $R^{4a}$ is methyl; $R^5$ is isopropyl; $R^8$ is methyl; and $A^2$ is

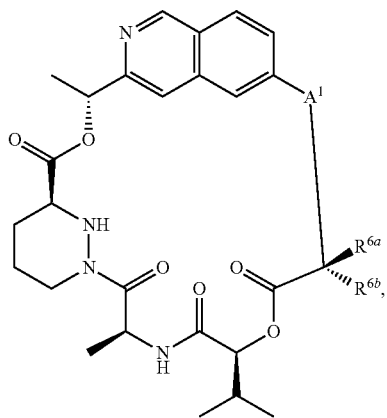

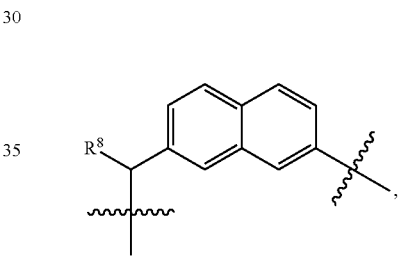


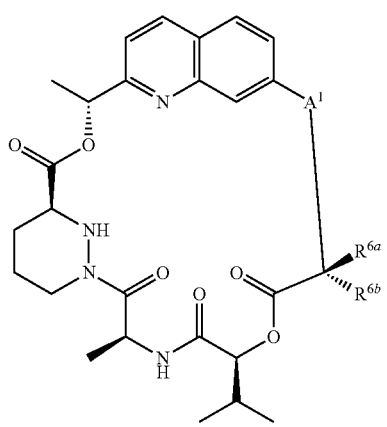

and

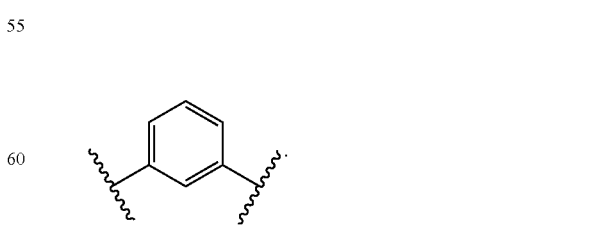

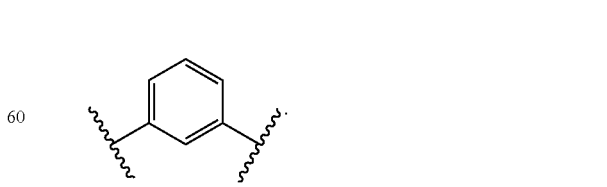

Non-limiting examples of such compounds include the following compounds and pharmaceutically acceptable salts thereof:

Formula (II-b)

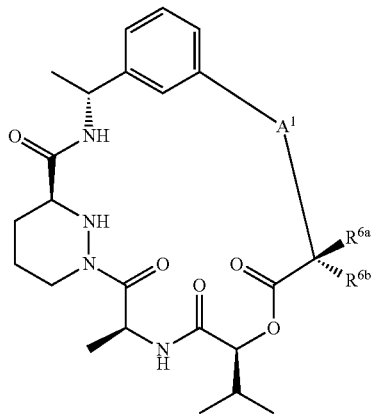

| Compound No. | A¹ | $R^{6a}$ | $R^{6b}$ |
|---|---|---|---|
| b-1 (Example 6) |  | H | H |
| b-2 | 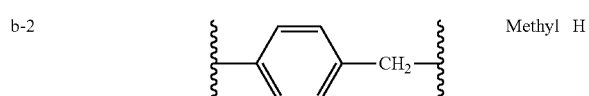 | Methyl | H |
| b-3 |  | H | H |
| b-4 (Example 1) | 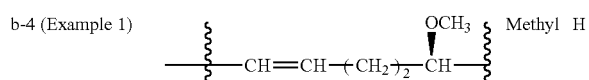 | Methyl | H |
| b-5 (Example 8) | —CH=CH—(CH₂)₃— | H | H |
| b-6 | —CH=CH—(CH₂)₃— | Methyl | H |
| b-7 | 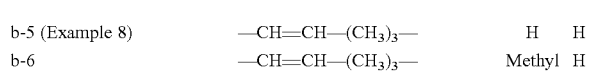 | H | H |
| b-8 (Example 7) | 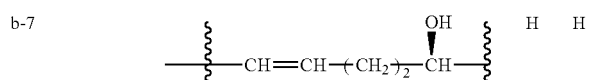 | Methyl | H |
| b-9 | 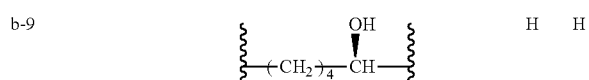 | H | H |
| b-10 (Example 10) |  | Methyl | H |

In another embodiment, is provided a compound of Formula II-c:

Formula II-c

or a pharmaceutically acceptable salt, isotope, stereoisomer, mixture of stereoisomers, tautomer, ester or prodrug thereof, wherein:

$R^{6a}$ and $R^{6b}$ are independently H, hydroxyl, $(C_1-C_8)$alkyl, $(C_2-C_8)$alkenyl, $(C_2-C_8)$alkynyl, $(C_1-C_8)$alkoxy, —CH$_2$CH$_2$CR$^9$(=N(C$_1$-C$_4$)alkoxy), aryl, heterocycloalkyl, cycloalkyl, —SR$^9$, —S(O)R$^9$, —S(O)$_2$R$^9$ and —N(R$^9$)$_2$, wherein each of $R^{6a}$ and $R^{6b}$ is optionally substituted with one or more substituents selected from the group consisting of halo, hydroxyl, cyano, $(C_1-C_4)$alkyl, $(C_1-C_4)$alkoxy, halo($C_1$-$C_4$)alkoxy, aryl, cycloalkyl, heterocycloalkyl, mono($C_1$-$C_8$)alkylamino, di($C_1$-$C_8$)alkylamino, —NHS(O)R$^9$, —NHC(O)R$^9$ and $(C_1-C_8)$alkanoyl where such an optional substitution is chemically feasible; or $R^{6a}$ and $R^{6b}$ together form a spirocycle having Formula (a); or $R^{6a}$ and $R^{6b}$ together form a spirocycle having Formula (a):

(a)

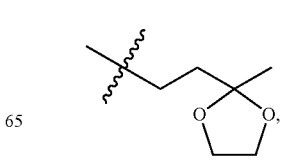

wherein one or more carbon ring atoms of Formula (a) is optionally replaced by a nitrogen, oxygen or sulfur atom, and wherein a ring atom of Formula (a) optionally has one or more substituents selected from the group consisting of oxo, =N(C$_1$-C$_4$)alkoxy, halo, hydroxyl, —NH$_2$, (C$_1$-C$_4$)alkyl, halo(C$_1$-C$_4$)alkyl, (C$_1$-C$_4$)alkoxy, —OC(O)R$^9$, —C(O)$_2$R$^9$, and —S(O)$_2$R$^9$;

each $R^9$ is independently H, $(C_1-C_4)$alkyl, halo($C_1-C_4$)alkyl, $(C_2-C_4)$alkenyl or $(C_2-C_4)$alkynyl.

In one embodiment of the compounds described herein, $R^{6a}$ and $R^{6b}$ are independently H, —OH, $(C_1-C_4)$alkoxy, halo$(C_1-C_4)$alkoxy, $(C_1-C_8)$alkyl, halo$(C_1-C_8)$alkyl, hydroxy$(C_1-C_8)$alkyl, $(C_1-C_4)$alkoxy$(C_1-C_8)$alkyl, halo$(C_1-C_4)$alkoxy$(C_1-C_8)$alkyl, -continued
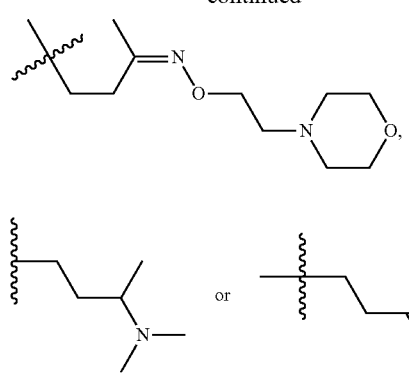
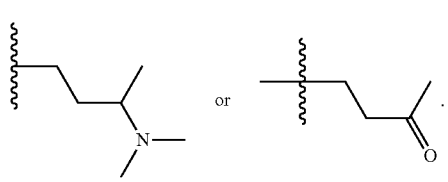
In one embodiment of the compounds described herein, R$^{6a}$ and R$^{6b}$ together from
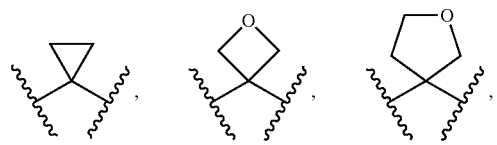
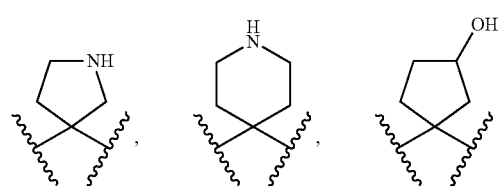
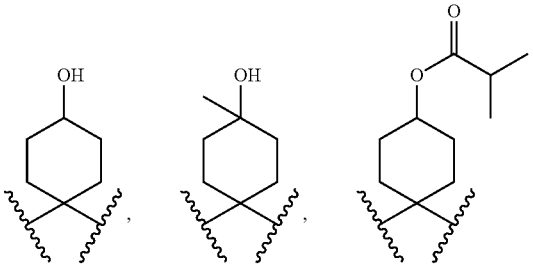
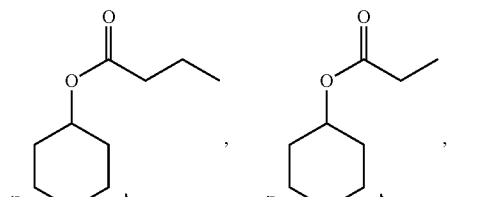
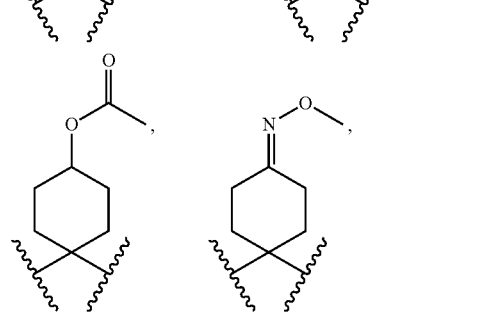
-continued
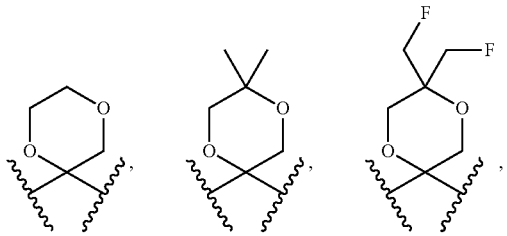
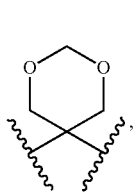
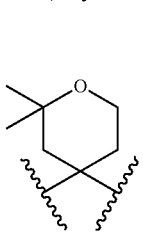
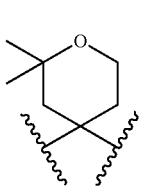
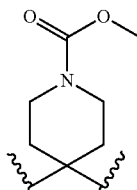
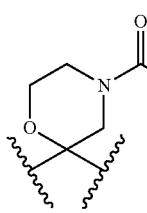
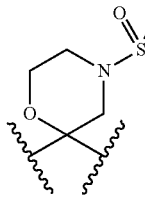
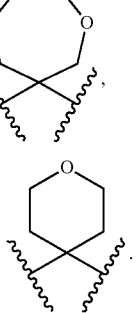 or
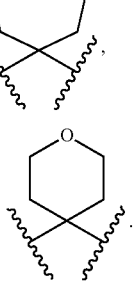

In some embodiments, $R^{6a}$ and $R^{6b}$ together form

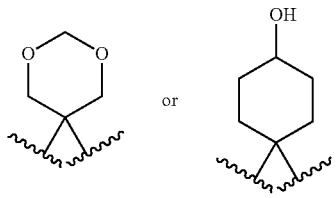

In one embodiment, the compound is

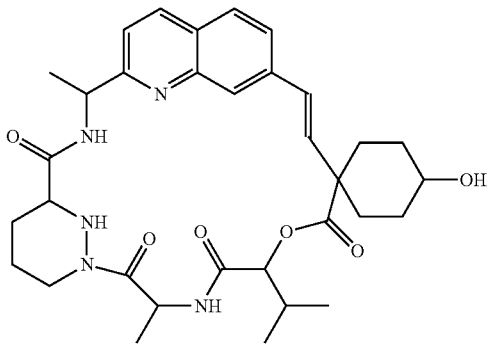 [SMILES: CC1NC(=O)C(C(C)C)OC(=O)C2(/C=C/c3ccc4ccc(nc4c3)C(C)NC(=O)C3CCCN(N3)C1=O)CCC(O)CC2]

or a pharmaceutically acceptable salt, isotope, stereoisomer, mixture of stereoisomers, tautomer, ester or prodrug thereof.

In another embodiment, the compound is

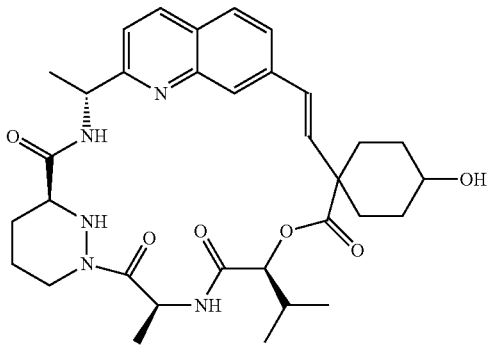 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)CCC(O)CC2]

or a pharmaceutically acceptable salt, isotope, stereoisomer, mixture of stereoisomers, tautomer, ester or prodrug thereof.

In yet another embodiment, the compound is

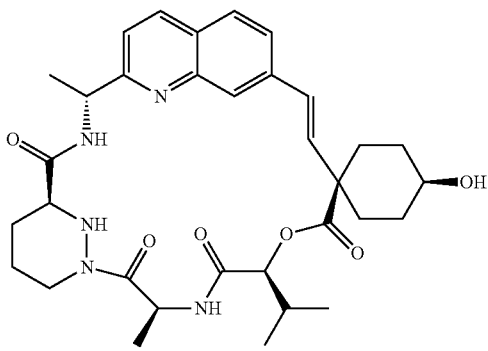 [SMILES: CC(C)[C@@H]1OC(=O)[C@]2(/C=C/c3ccc4ccc(nc4c3)[C@@H](C)NC(=O)[C@@H]3CCCN(N3)C(=O)[C@H](C)NC1=O)CC[C@H](O)CC2]

or a pharmaceutically acceptable salt, isotope, stereoisomer, mixture of stereoisomers, tautomer, ester or prodrug thereof.

In one embodiment, the compound is

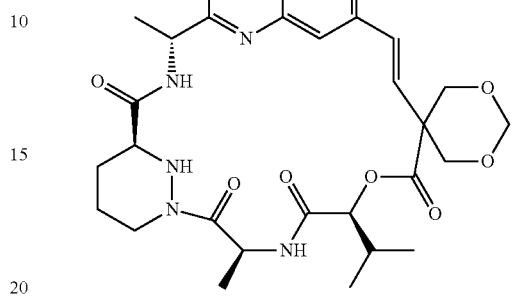

or a pharmaceutically acceptable salt, isotope, stereoisomer, mixture of stereoisomers, tautomer, ester or prodrug thereof.

In certain embodiments, there is provided a compound of Formula III:

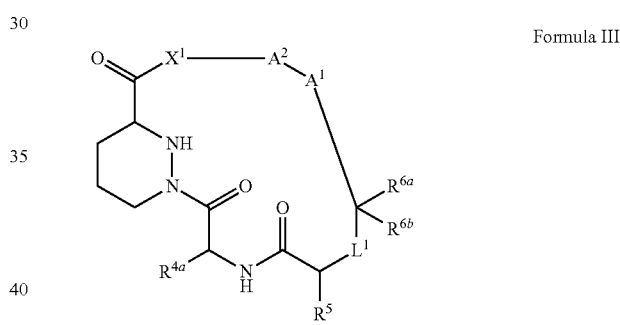

Formula III or a pharmaceutically acceptable salt, isotope, stereoisomer, mixture of stereoisomers, tautomer, ester or prodrug thereof, wherein $L^1$ is —O—$CH_2$—, —N($CH_3$)—C(O)—, —NH—$CH_2$—, —N($CH_3$)—$CH_2$—, —NH—CH($CF_3$)— or —NH—$S(O)_2$—;

$A^1$ is

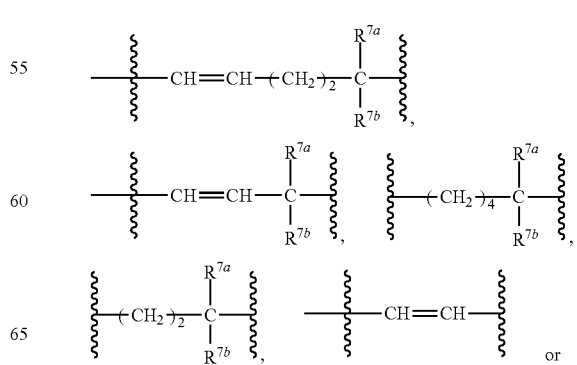

or

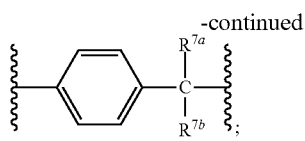

A² is —CH(R⁸)-arylene, —CH(R⁸)-heteroarylene, —CH(R⁸)-heterocycloalkylene, —CH(R⁸)— cycloalkylene, arylene or cycloalkylene;
X¹ is —O—, —N(CH₃)— or —NH—;
R$^{4a}$ is H, (C₁-C₄)alkoxy, halo(C₁-C₄)alkoxy or (C₁-C₈)alkyl;
R⁵ is H or (C₁-C₄)alkyl;
R$^{6a}$ and R$^{6b}$ are independently H, hydroxyl, —CH₂CH₂CR⁹(=N(C₁-C₄)alkoxy), (C₁-C₈)alkyl or (C₁-C₈)alkoxy, optionally substituted with one or more substituents selected from the group consisting of halo, hydroxyl, (C₁-C₄)alkoxy, halo(C₁-C₄)alkoxy, heterocycloalkyl, (C₁-C₄)alkanoyl or di(C₁-C₄)alkylamino; or
R$^{6a}$ and R$^{6b}$ together form a spirocycle having Formula (a):

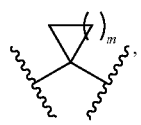

(a)

wherein one or more carbon ring atoms of Formula (a) is optionally replaced by a nitrogen, oxygen or sulfur atom, and wherein a ring atom of Formula (a) optionally has one or more substituents selected from the group consisting of oxo, halo, hydroxyl, —NH₂, (C₁-C₄)alkyl, (C₁-C₄)alkoxy, —OC(O)R⁹, —C(O)₂R⁹, and —S(O)₂R⁹;
R$^{7a}$ and R$^{7b}$ are independently H, —OH, (C₁-C₄)alkoxy, halo(C₁-C₄)alkoxy or (C₁-C₈)alkyl; and
R⁸ is H or (C₁-C₄)alkyl.
In some embodiments of Formula III, L¹ is —O—CH₂—, —N(CH₃)—C(O)—, —NH—CH₂— or —NH—S(O)₂—;
A¹ is

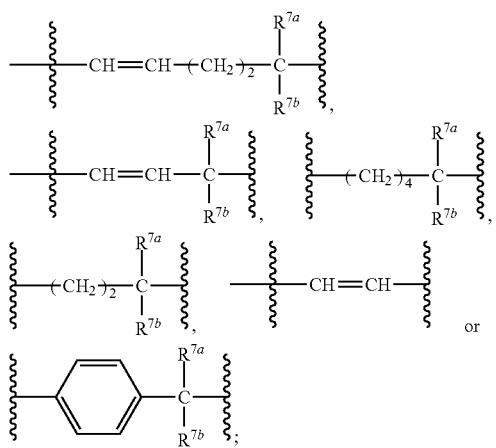

A² is —CH(R⁸)-arylene, —CH(R⁸)-heteroarylene, —CH(R⁸)-heterocycloalkylene, —CH(R⁸)— cycloalkylene, arylene or cycloalkylene;
X¹ is —O—, —N(CH₃)— or —NH—;
R$^{4a}$ is H, (C₁-C₄)alkoxy, halo(C₁-C₄)alkoxy or (C₁-C₈)alkyl;
R⁵ is H or (C₁-C₄)alkyl;
R$^{6a}$ and R$^{6b}$ are independently H, —OH, (C₁-C₄)alkoxy, halo(C₁-C₄)alkoxy or (C₁-C₈)alkyl,

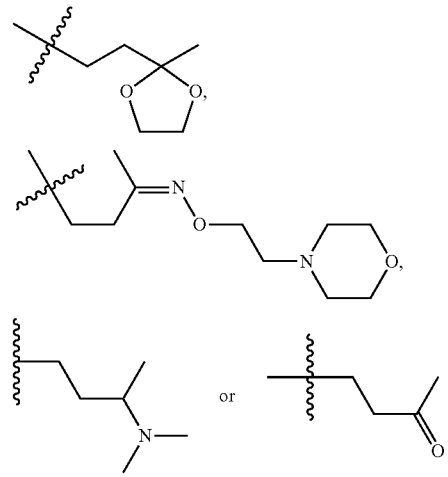

R$^{6a}$ and R$^{6b}$ together form

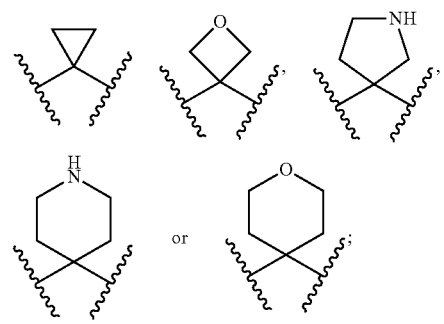

R$^{7a}$ and R$^{7b}$ are independently H, —OH, (C₁-C₄)alkoxy, halo(C₁-C₄)alkoxy or (C₁-C₈)alkyl; and
R⁸ is H or (C₁-C₄)alkyl.
In one embodiment, L¹ is —NH—CH₂—; R$^{4a}$ is methyl; R⁵ is iso-propyl; R⁸ is methyl; and A² is

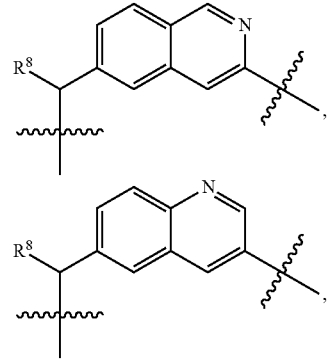

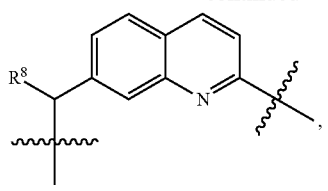,
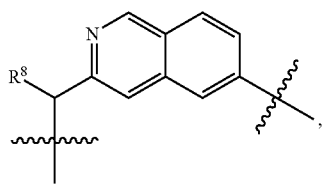,
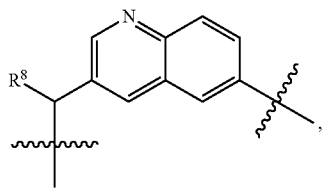,
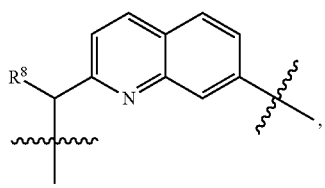,
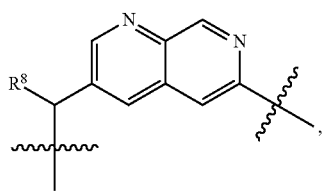,
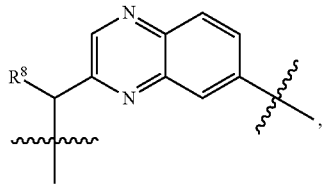,
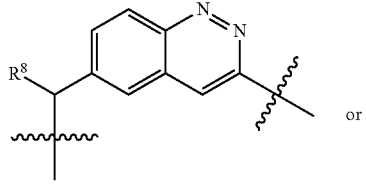 or
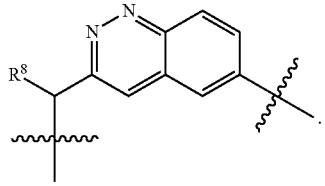.
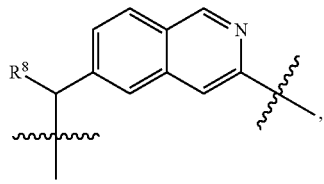,
,
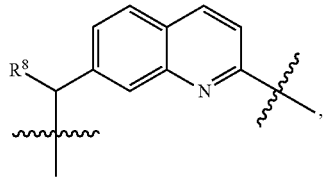,
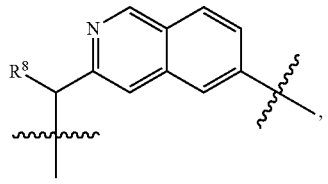,
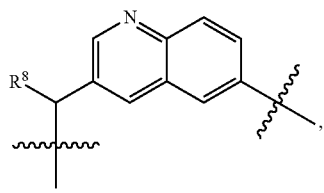,
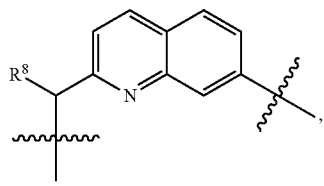,
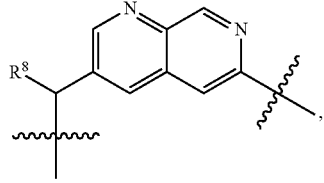,
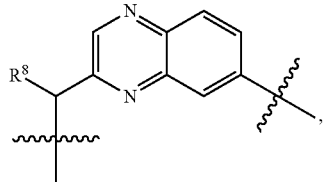,
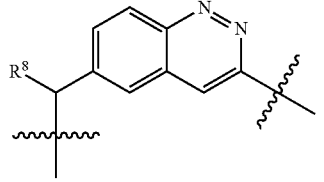 or
In one embodiment, $L^1$ is —NH—S(O)$_2$—; $R^{4a}$ is methyl; $R^5$ is iso-propyl; $R^8$ is methyl; and $A^2$ is

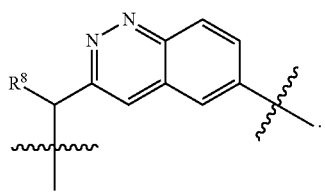
In various aspects of this embodiment, A² is selected from
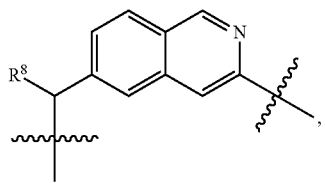,
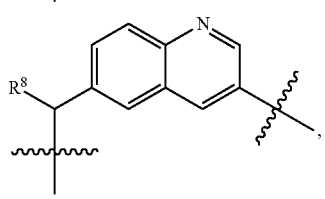,
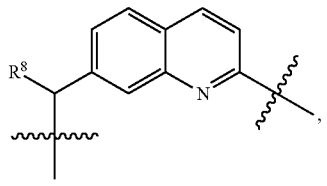,
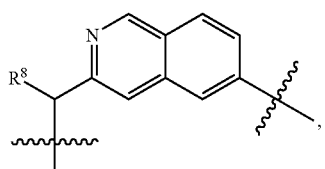,
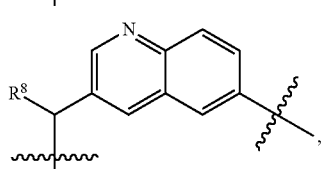,
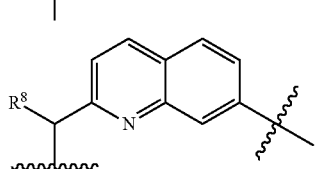,
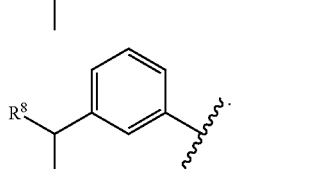
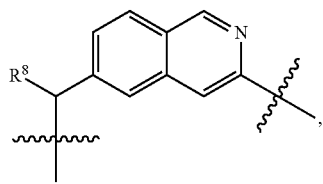,
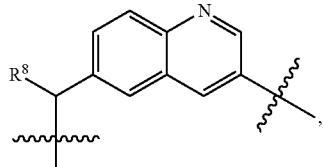,
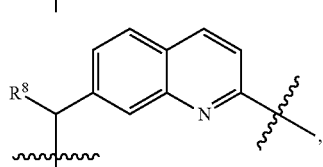,
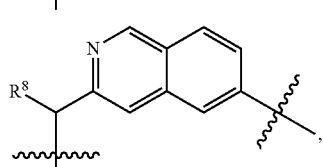,
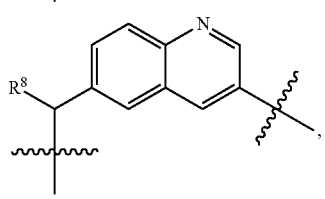,
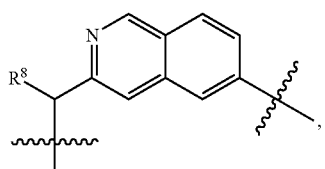,
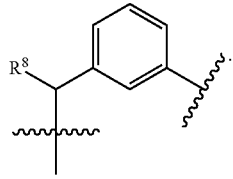 or
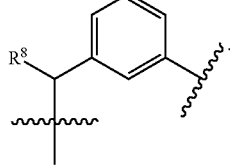.
In one embodiment, L¹ is —O—CH₂—; R^{4a} is methyl; R⁵ is iso-propyl; R⁸ is methyl; and A² is
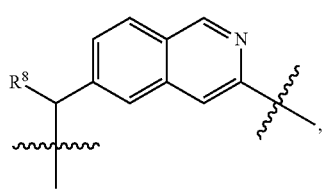,
In one embodiment, L¹ is —N(CH₃)—C(O)—; R^{4a} is methyl; R⁵ is iso-propyl; R⁸ is methyl; and A² is -continued
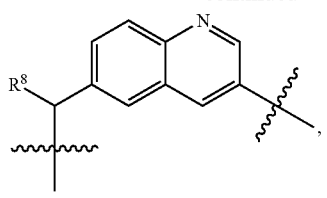
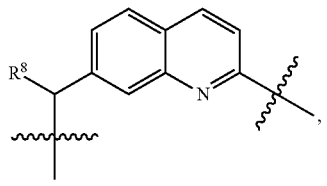
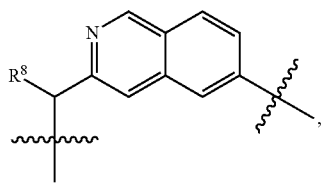
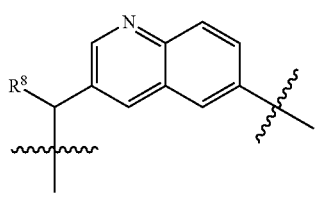
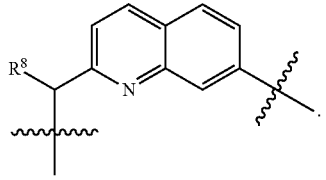
In one aspect of the embodiment, $L^1$ is —NH—CH$_2$—; $R^{4a}$ is methyl; $R^5$ is isopropyl; and $R^8$ is methyl. Non-limiting examples of such compounds include the following compounds and pharmaceutically acceptable salts thereof:
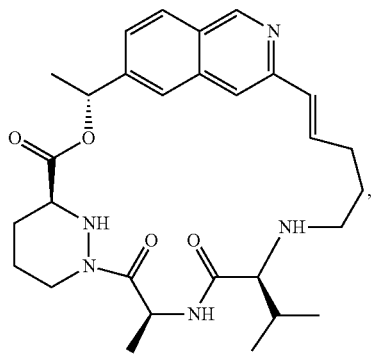
-continued
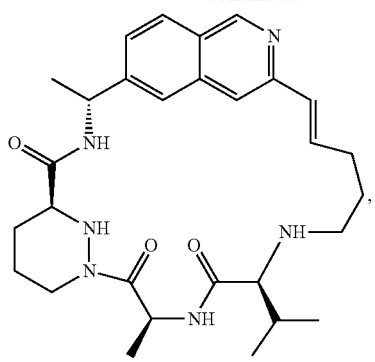
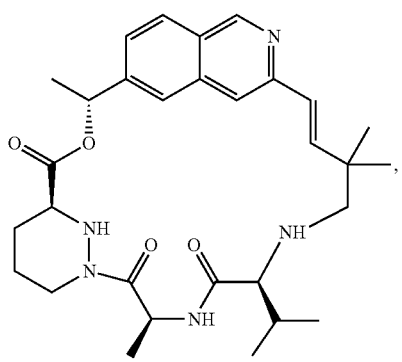
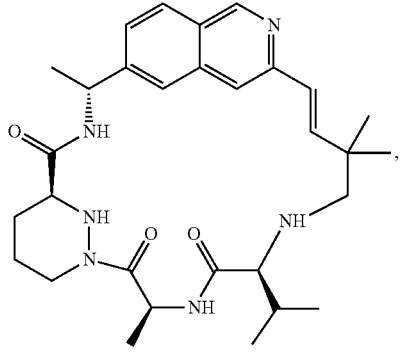 [SMILES: CC(C)[C@@H]1NCC(C)(C)/C=C/c2ccc3ccc(nc3c2)[C@@H](C)NC(=O)[C@@H]2CCCN(N2)C(=O)[C@H](C)NC1=O]
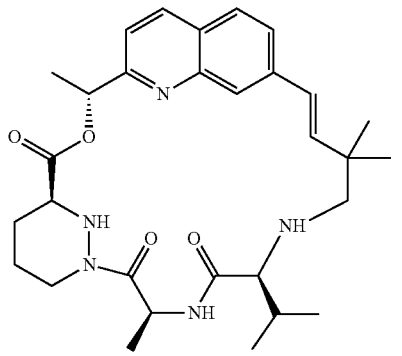
and

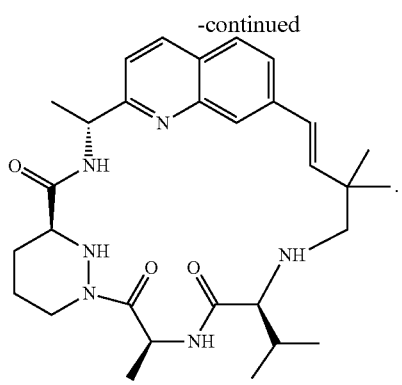

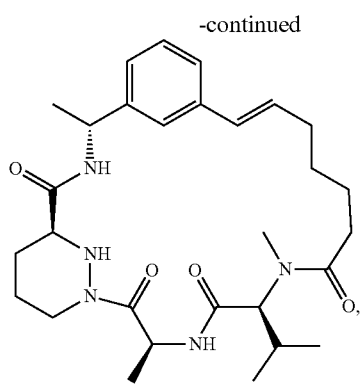

In one aspect of the embodiment, $L^1$ is —NH—S(O)$_2$—; $R^{4a}$ is methyl; $R^5$ is isopropyl; and $R^8$ is methyl. Non-limiting examples of such compounds include the following compounds and pharmaceutically acceptable salts thereof:

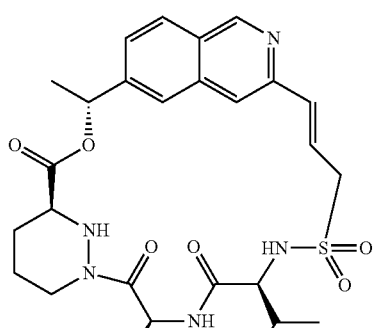

and

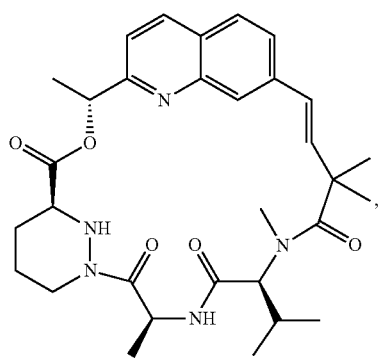

,

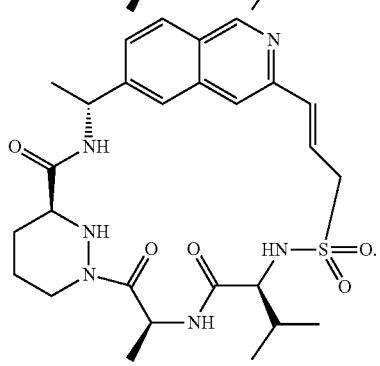

.

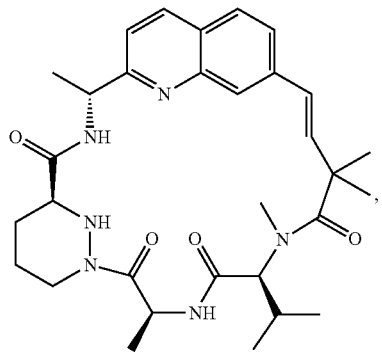 [SMILES: CC(C)[C@H]1C(=O)N[C@@H](C)C(=O)N2CCC[C@H](N2)C(=O)N[C@H](C)c2ccc3cnc(cc3c2)/C=C/C(C)(C)C(=O)N1C]

,

In one aspect of the embodiment, $L^1$ is —N(CH$_3$)—C(O)—; $R^{4a}$ is methyl; $R^5$ is isopropyl; and $R^8$ is methyl. Non-limiting examples of such compounds include the following compounds and pharmaceutically acceptable salts thereof:

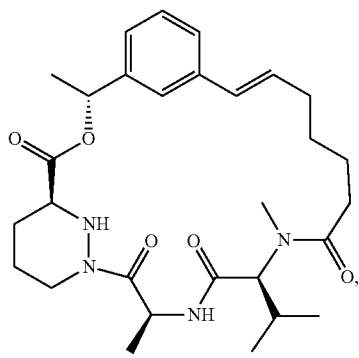

,

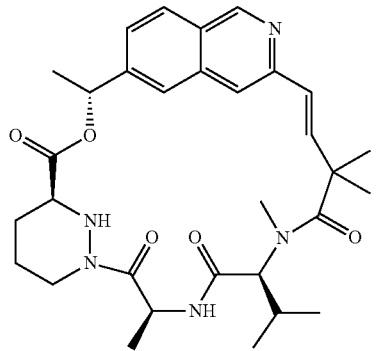

and

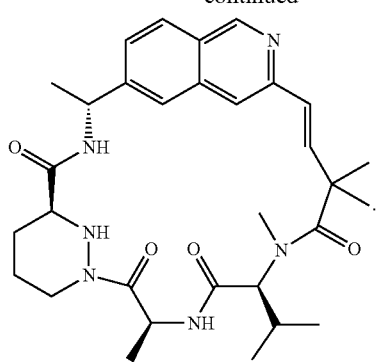

In one aspect of the embodiment, $L^1$ is —O—CH$_2$—; $R^{4a}$ is methyl; $R^5$ is isopropyl; and $R^8$ is methyl. Non-limiting examples of such compounds include the following compounds and pharmaceutically acceptable salts thereof:

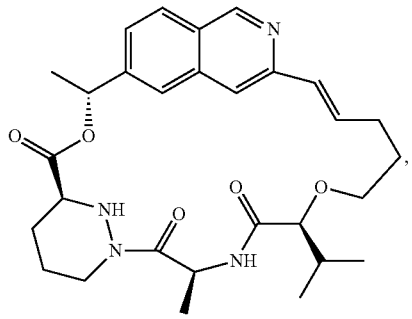

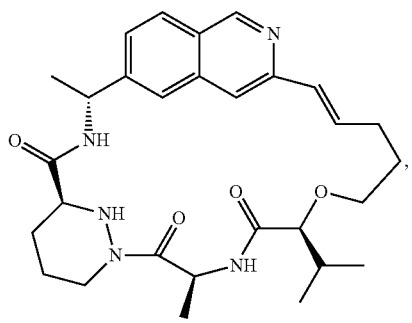

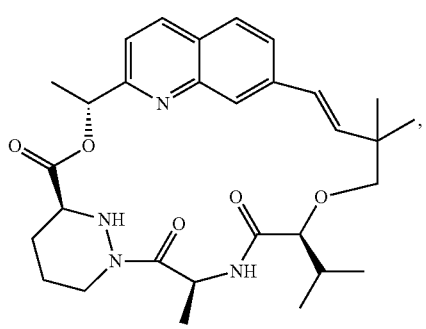

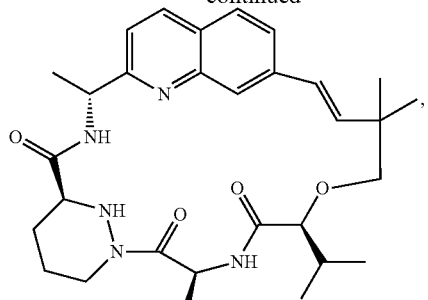

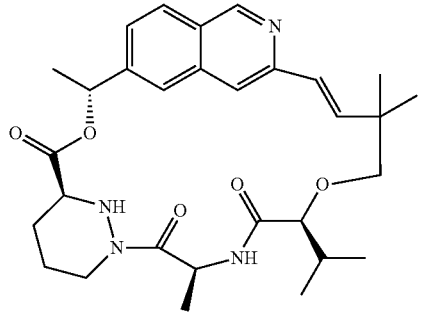

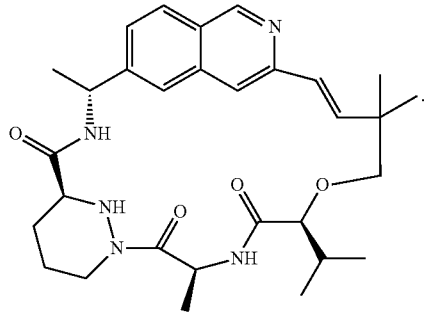

and

One skilled in the art will recognize that substituents and other moieties of the compounds of the generic formulae herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

Preparation of Macrocyclic Compounds

A compound of the present invention such as those of Formula I, II, II-a, II-b, II-c or III can be prepared according to the schemes described below, but it shall be appreciated that modifications of the illustrated process or other process can also be used. As illustrated in Scheme 1, the macrocyclic compounds M are synthesized from the five key components A-E by combining them together in sequence with the appropriate use of protecting groups (PG$_1$-PG$_8$) by one skilled in the art. The hashed lines numbered 1-5, hereby referred to as Connection 1, Connection 2, etc, respectively, are the 5 connections for combining Components A-E. The order in which the specific connections occur, can vary, and are dependent on the choice of protecting groups and chemistry required. Typically Connections 3, 4 or 5 are used as the final macrocyclization step.

Scheme 1

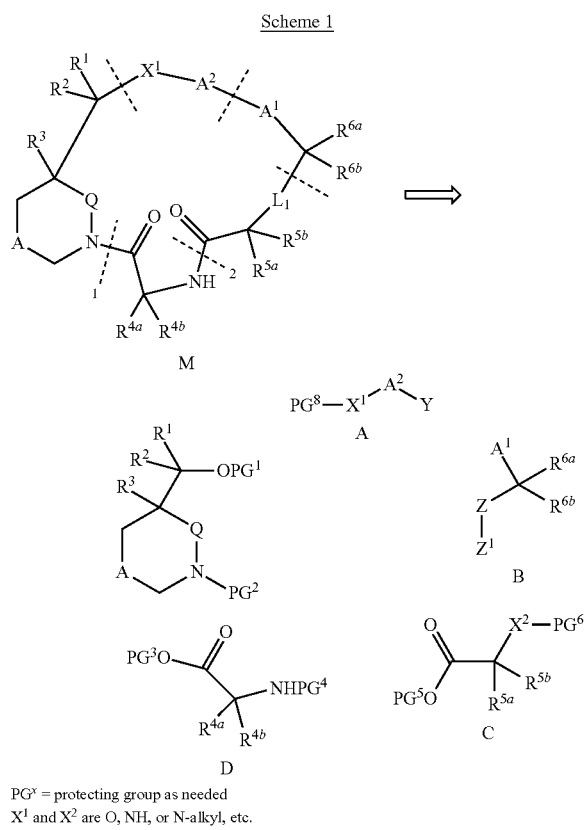

PG$^x$ = protecting group as needed
X$^1$ and X$^2$ are O, NH, or N-alkyl, etc.
Z and Z$^1$ taken together = CO$_2$H, COCl, SO$_3$H, SO$_2$Cl, CH$_2$—OH,
CH$_2$-halo, C(O)-alkyl, or C(O)—H, etc.
Y= alkene, halide, O-alkenyl, or OTf.
Q = NH or N—PG$^x$ as needed.

Illustratively, Connections 1 through 5 can be performed as described below:

Connections 1 and 2 are amide bonds. The connections are made between the respective acid and amine using standard peptide coupling agents (EDC/HOBT, DCC, PyBOP, PyBROP, HATU, HBTU, COMU, etc) known to one skilled in the art. The acid and amine coupling partners are combined with the coupling agent in an organic solvent, e.g., DMF, dichloromethane, acetonitrile, etc, in the presence of a base, e.g., DIPEA, triethylamine, etc, at room temperature or slightly elevated temperature. When either of these steps is chosen as the final macrocyclization step, then macrolactamization conditions are preferred. Suitable macrolactamization procedures include, but are not limited to, those found in the following reference: Davies, J. S. J. Peptide Sci. 2003, 9, 471-501.

Connection 4 is typically a carbon-carbon bond or a heteroatom-carbon bond where the heteroatom is O, S or N. When Connection 4 is a carbon-carbon bond, then standard carbon-carbon bond forming procedures typically involving metal mediated cross coupling reactions are preferred. Preferably the carbon-carbon bond is formed using a Heck type coupling between an sp2 halide group and an terminal alkene, a Suzuki coupling between an sp2 halide group and a vinyl or aryl boronate, or a ring closing metathesis (RCM) between two alkenes. Stille reactions can also be performed between a vinyl stannane and an aryl or vinyl halide as described in Journal of American Chemical Society 2000, 122, 3830 Nicolaou et al. In each of the examples above the aryl or vinyl halide group can also be an aryl or vinyl triflate.

For example, when Y in A is an alkene, preferably —CH=CH$_2$, and A$_1$ in B contains a terminal alkene or Me-CH=CH—, then a cross metathesis reaction is performed. The two components are mixed in solvent, e.g., acetonitrile, toluene and a metathesis catalyst, e.g., Grubbs I, Grubbs II or Hoyveda-Grubbs I, Hoyveda-Grubbs II is added followed by heating. If this connection is the final procedure to close the macrocyclic ring, RCM conditions are preferred (e.g., more dilute conditions to avoid dimerization). For relevant RCM conditions and examples see Journal of American Chemical Society 2003, 125, 3849 Sedrani et al and Journal of American Chemical Society 2000, 122, 3830 Nicolaou et al. A typical RCM procedure includes heating (either conventionally or by microwave) of the acyclic precursor in a solvent such as toluene, or 1,2-dichloroethane, in the presence of a RCM catalyst, e.g., Grubbs I, Grubbs II or Hoyveda-Grubbs I, Hoyveda-Grubbs II.

Alternatively, when connection 4 is made via a Heck coupling reaction, the vinyl or aryl halide, or the triflate A and the alkene component B are mixed in a polar solvent, e.g., acetonitrile or toluene, in the presence of a Palladium(II) catalyst, e.g., Palladium(OAc)$_2$, a phosphine ligand, e.g., P(o-toluene)$_3$, P(t-butyl)$_3$, etc, and a base, e.g., triethylamine. The reaction mixture is heated either conventionally or in a microwave reactor.

Alternatively, when Connection 4 is made via a Suzuki coupling reaction, the vinyl or aryl halide, or the triflate A and the vinyl or aryl boronate B are mixed in a suitable solvent, e.g., cyclopentyl methyl ether, toluene, DMF, DME, etc., in the presence of a Palladium catalyst (e.g., Palladium(II)Cl$_2$ (p-NMe$_2$Ph)$_2$ and K$_3$PO$_4$ or tetrakis(triphenylphosphine)palladium(0) and a base, such as potassium carbonate). The reaction mixture is heated either conventionally or in a microwave reactor. It is also possible in such a coupling reaction to reverse the reactive functionalities on the two starting materials, such that A is an aryl or vinyl boronate and B contains a vinyl or aryl halide or triflate.

Alternatively, Connection 4 can be a carbon-oxygen bond and in this case, typical alkylation or nucleophilic aromatic substitution conditions can be used between a hydroxyl group and an alkyl halide, or aryl (or heteroaryl) halide. The hydroxyl reagent is mixed with the alkyl or heteroaryl halide (preferably an iodide or bromide), in an inert solvent, e.g., CPME, DMF, THF, etc, in the presence base, e.g., cesium carbonate, cesium hydroxide, sodium hydride, NaHMDS, etc, and heated.

Alternatively, Connection 4 can be a carbon-nitrogen bond and in this case, typical alkylation, nucleophilic aromatic substitution or Buchwald conditions can be used between an amine group and an alkyl halide or heteroaryl halide. For example, the amine and the alkyl or heteroaryl halide are mixed and heated in an inert solvent, e.g., CPME, in the presence base, e.g., cesium carbonate, sodium hydride etc. An alternative procedure for the carbon-nitrogen connection is to perform a reductive amination between an amine and a carbonyl compound. Typically the amine and aldehyde or ketone are mixed in an inert solvent, e.g., THF, dioxane and treated after a period of time with sodium acetoxy borohydride or alternative reducing agent.

Connection 5 is typically an amide (X$_1$ is NH or substituted N), or ester (X$_1$ is O) bond. When forming the amide bond, standard coupling procedures described for Connection 1-3 can be used. Often, this is the final step in closing the macrocycle. As such, macrolactamization types of coupling procedures are more effective. Suitable macrolactamization procedures include, but are not limited to, those found in the following reference: Davies, J. S. J. Peptide Sci. 2003, 9, 471-501.

When forming the ester bond coupling reagents (e.g., EDC, DCC, PyBOP, HATU, COMU) can be used, or when this is the final step in formation of the macrocycle, macrolactonization procedures are preferred (e.g., Shiina, Yamaguchi). An example method for the macrolactonization step can be found in *Journal of American Chemical Society* 2002, 124, 4257 Paquette et al or *Chemical Reviews* 2006, 106(3), 911-939. Typically, the acid and alcohol are mixed in a polar solvent, e.g., DMF, acetonitrile, etc. in the presence of the coupling agent and a base, e.g., DIPEA, DMAP.

Connection 5 can also be an ether bond where $R^1$ and $R^2$ are both hydrogen or alkyl groups. In this example, the carbon-oxygen bond forming procedures described above for Connection 4 are used to connect the 2 components. Connection 5 can also be an amine bond where $R^1$ and $R^2$ are both hydrogen or alkyl groups and the procedures for connecting the amine and carbonyl components are also described above with respect to Connection 4.

Connection 3 is a C—N, C—O, or S(O)$_2$—N. Suitable bond forming reactions for Component C and Component B include the following methods.

When the bond formed in Connection 3 is $L^1$ is —OC(O)— (i.e., $X^1$ is O in C and Z/Z$^1$ is —CO$_2$H or —CO-halogen in B), this is performed using standard ester formation procedures utilizing coupling reagents described above. When this is the final step in formation of the macrocycle, macrolactonization procedures are preferred, as described above.

Alternatively, when Connection 3 is $L^1$ is —N(alkyl)C(O)— (i.e., $X^1$ is N(alkyl) in C and Z/Z$^1$ is CO$_2$H or CO-halogen in B) this step is performed using standard ester formation procedures utilizing coupling reagents described above. When this is the final step in formation of the macrocycle, macrolactamization procedures are preferred as described above.

Alternatively, when connection 3 is $L^1$ is —NHS(O)$_2$— (i.e., $X^1$ is —NH— in C and Z/Z$^1$ is —S(O)$_2$OH or —S(O)$_2$-halogen in B), this is performed using standard amide formation procedures utilizing coupling reagents described above, or when this is the final step in formation of the macrocycle, macrolactamization procedures are preferred as described above.

Alternatively, when Connection 3 is $L^1$ is —NH—CH$_2$— (i.e., $X^1$ is —NH— in C and Z/Z$^1$ is ketone or aldehyde in B), this is performed using standard reductive amination procedures as described above.

Alternatively, when Connection 3 is $L^1$ is —O—CH$_2$— (i.e., $X^1$ is O in C and Z/Z$^1$ contains a leaving group such as a halide or triflate in B), this is performed using standard nucleophilic alkylation procedures described above.

The following general schemes provide general examples and sequences for constructing the macrocyclic compounds M from the common precursors A-E.

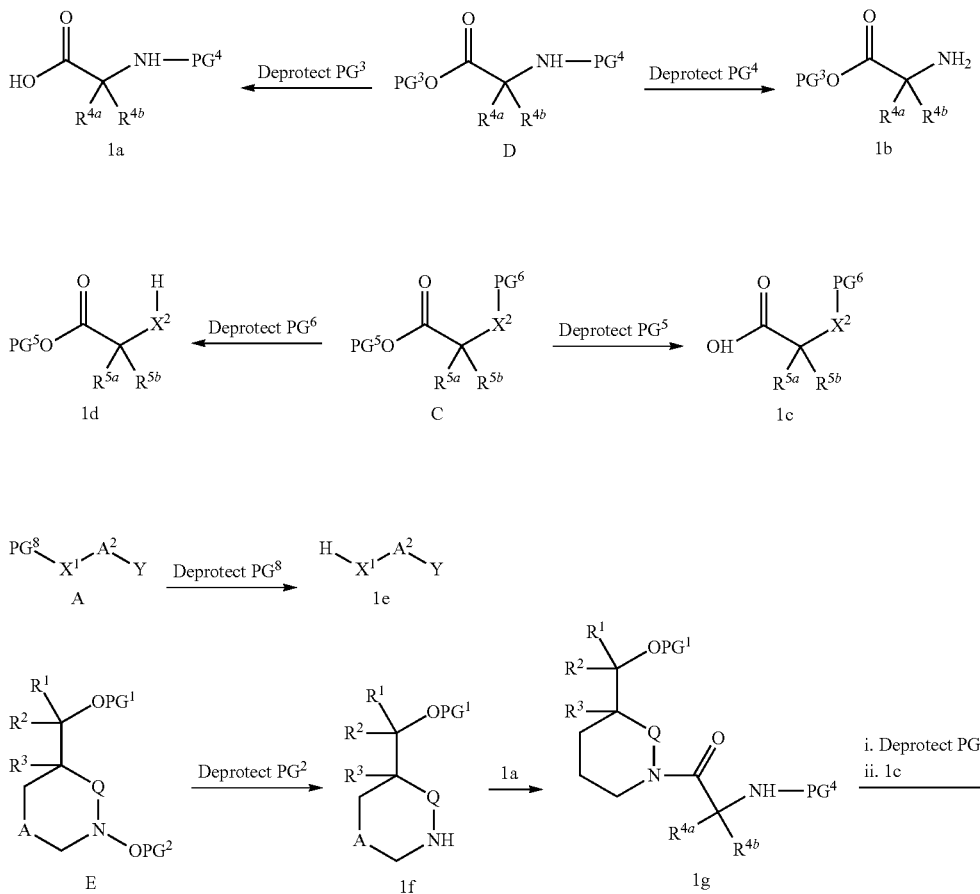

Scheme 2: RCM method

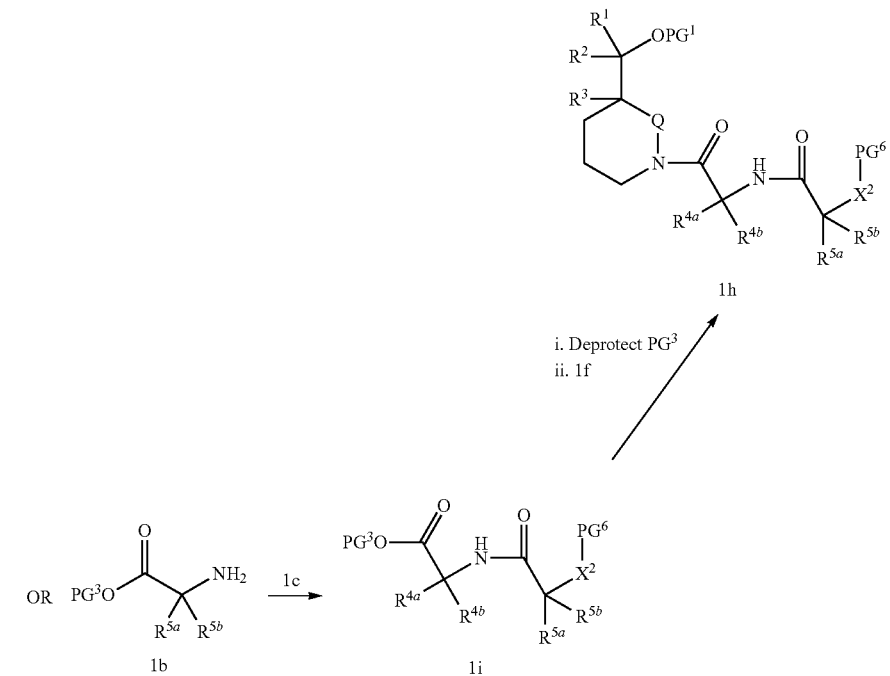

Compounds A-E are first deprotected (PG$^2$-PG$^8$) using conditions described in Greene and Wuts, Protective Groups in Organic Synthesis, John Wiley and Sons, Inc. to provide Compounds 1a-1f.

In many cases the optimal protecting groups and their deprotection methods are as follows. For Compound E the typical protecting group PG$^1$ for the acid (when R$^1$ and R$^2$ are C=O) is a methyl or trichloroethyl ester. The methyl and trichloroethyl esters can be removed by base, e.g., LiOH in a polar solvent, e.g., aqueous THF, etc. The trichloroethyl ester can also be removed by treatment with zinc and ammonium acetate in a polar solvent, e.g., THF. Typically, PG$^2$ and PG$^4$ are acid labile groups, e.g., BOC and are deprotected using HCl in dioxane or TMSOTf in dioxane, dichloromethane. Typically, PG$^3$ and PG$^5$ are ester groups, removed by treatment with alkali metal hydroxide in aqueous THF or dioxane. Typically PG$^6$ is an acid labile group, e.g., BOC for amine and removed as described for PG$^2$; or silyl ether for a hydroxyl group and removed by treatment with HF.pyridine or TBAF in an organic solvent, e.g., dichloromethane. Typically PG$^8$ is an amine protecting group, e.g., BOC and removed as described for PG$^2$ or a silyl ether of a hydroxyl group removed as described for PG$^6$, or an acetate protecting group removed by treatment with alkali metal hydroxide in aqueous THF or dioxane.

Compound 1f is coupled to acid 1a using the conditions described above for connection 1 to produce Compound 1g. Compound 1g is then PG$^4$ deprotected using conditions described in Greene and Wuts and coupled to acid 1c to provide 1 h using the conditions described above for Connection 2. An alternative sequence for generating 1 h, is first coupling amine 1b to acid 1c using conditions as described for connection 2 above, to form 1i; deprotection of the protecting group PG$^3$ in 1i using conditions described in Greene and Wuts, and finally coupling with amine 1f using conditions described for Connection 1 above to form 1h.

Scheme 3: RCM method

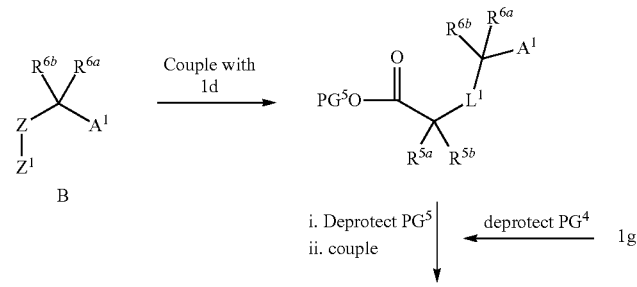

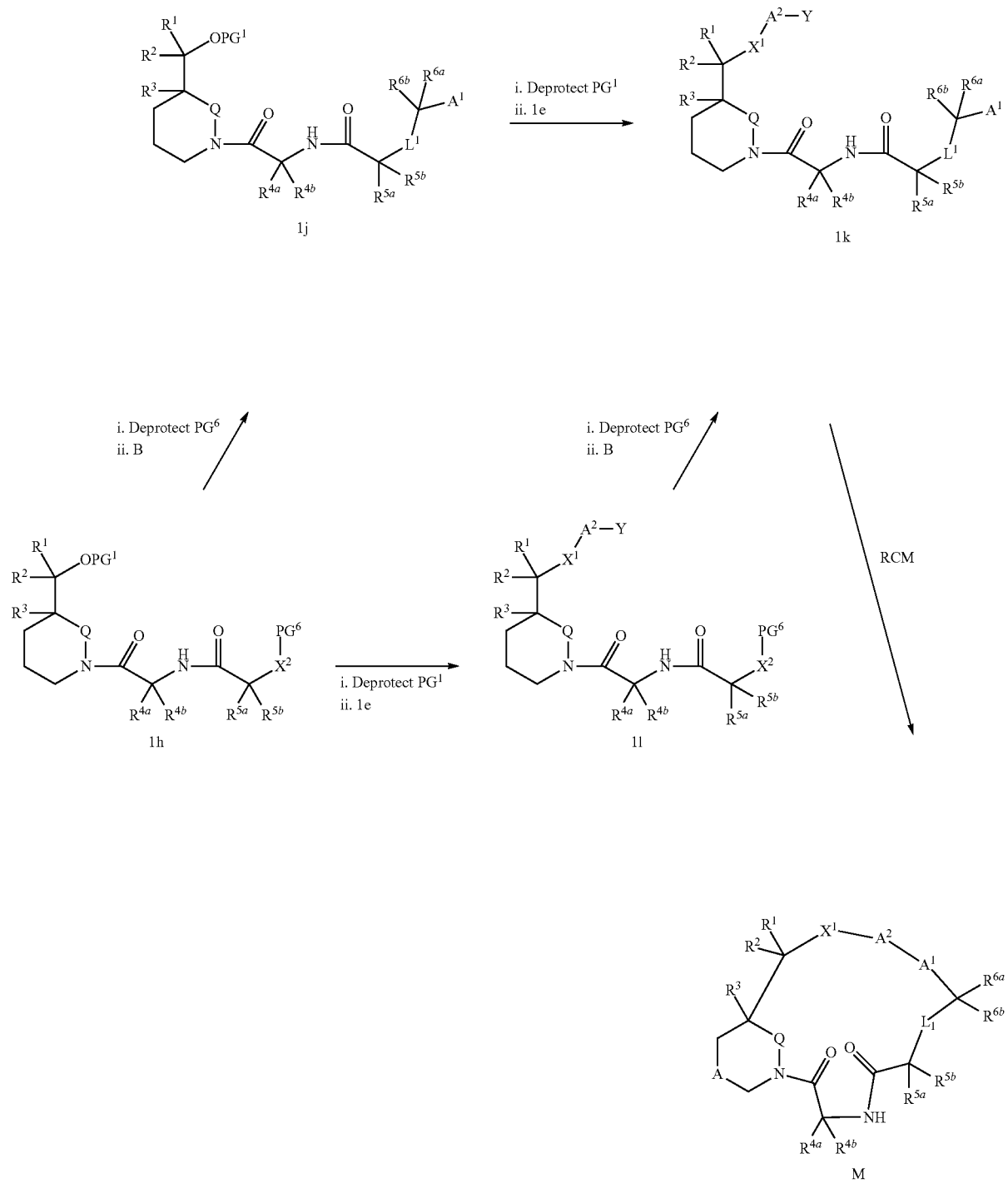

Compound 1h is deprotected at PG⁶ using conditions described in Greene and Wuts and is then coupled to B using the conditions described above for connection 3 to form 1j. An alternative route to 1j is also illustrated. Component B is coupled to 1d using the methods described above for Connection 3. The protecting group PG⁵ is then removed using conditions described in Greene and Wuts and the product coupled with the dipeptide produced from PG⁴ deprotected 1g, to provide 1j. Protecting group PG¹ in Compound 1j is then removed using conditions described in Greene and Wuts, and the acid is then coupled to 1e using conditions described for Connection 5 to form the intermediate 1k. An alternative sequence to 1k from the intermediate 1 h is first, deprotection of PG¹ and then coupling to 1e as described for Connection 5; and then deprotection of PG⁶ as described in Greene and Wuts, followed by coupling to B using the conditions described for Connection 3 to form 1k. Product 1k is then subjected to the RCM as described above for Connection 4 to form Compound M.

Scheme 4: Macrolactamization/Macrolactonization Connection 5

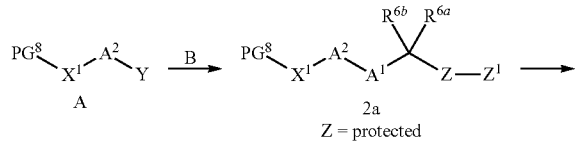

A

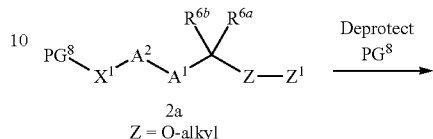

2a
Z = protected

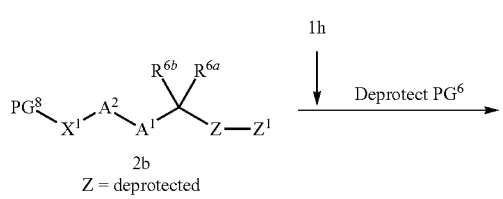

2b
Z = deprotected

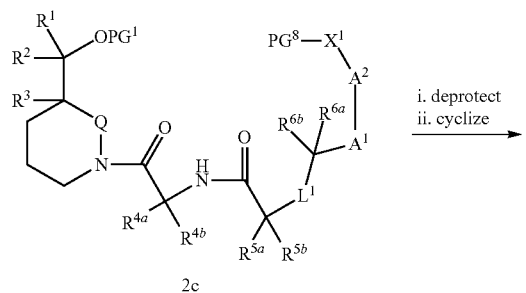

2c

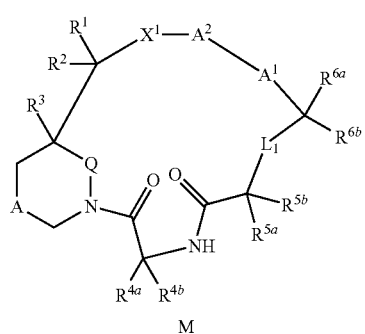

M of 2c at both PG$^8$ and PG$^1$ is carried out using conditions described in Greene and Wuts, and then the product is cyclized using the conditions described above for macrolactamization or macrolactonization in Connection 5, to provide Compound M.

Scheme 5: Macrolactamization/Macrolactonization Connection 5

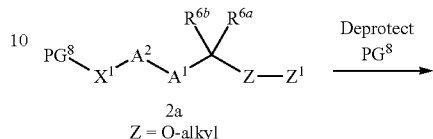

2a
Z = O-alkyl

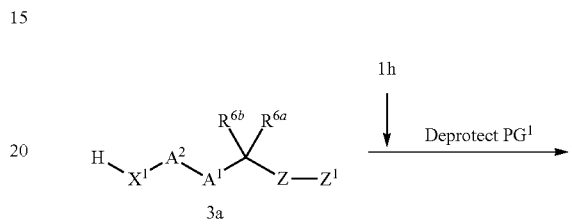

3a

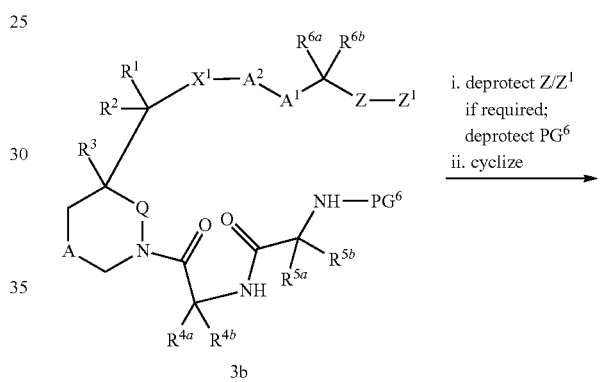

3b

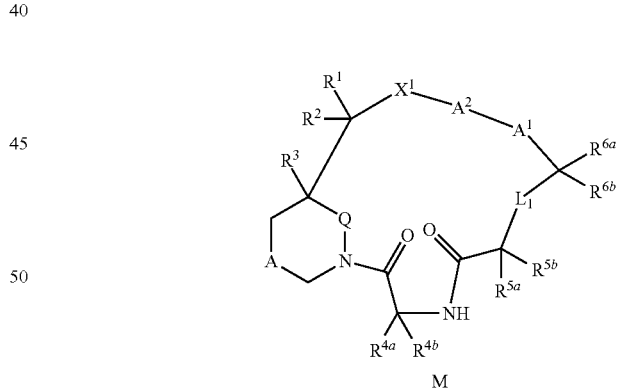

M

Compound A is coupled to Compound B using the conditions described above for Connection 4 to generate 2a. Typically in this sequence Compound B would be protected, e.g., an acid would be an ester, a sulfonic acid, a sulfonate ester, a ketone or aldehyde an acetal for example. Compound 2a is then deprotected as described in Greene and Wuts to generate acid 2b. Acid 2b is then coupled to the deprotected product of 1 h (prepared from 1h by deprotection of PG$^6$ described in Greene and Wuts) to generate the precursor 2c. Deprotection Compound 2a is deprotected at PG$_8$ as described in Greene and Wuts to generate 3a which is then coupled, using conditions described above for connection 5, to the PG$^1$ deprotected product of 1h, (prepared from 1h by deprotection of PG$^1$ described in Greene and Wuts), to generate the precursor 3b. Deprotection of 3b at both PG$^6$ and Z/Z$^1$ if required is carried out using conditions described in Greene and Wuts, and then the product is cyclized using the conditions described above for macrolactamization or macrolactonization in Connection 3, to provide Compound M.

Scheme 6: Further transformation of macrocyclic compounds M to M1-M5

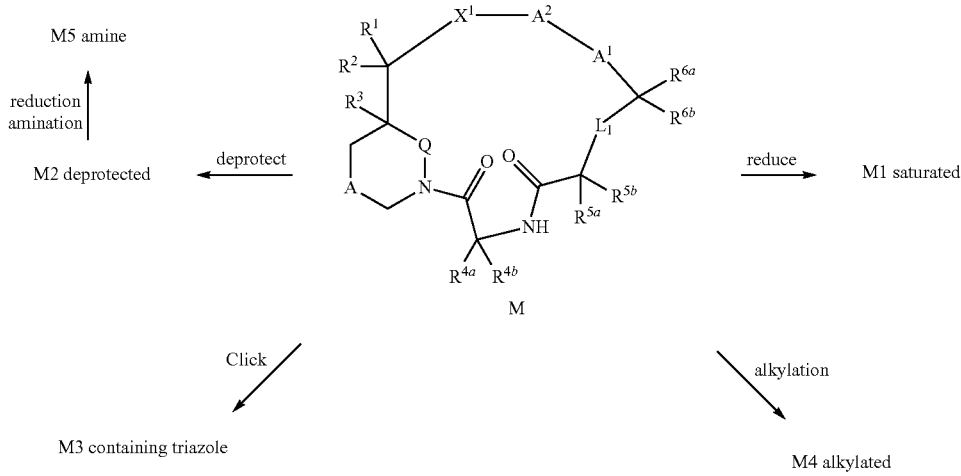

The final macrocycle M from Schemes 4-6 often contains functionalities of protecting groups on sidechains that require further removal to generate the final compound M. For example, when M contains a C═C as a result of RCM Compound M is mixed in a solvent such as ethanol, methanol, etc, in the presence of palladium on carbon catalyst under an atmosphere of hydrogen gas to provide reduced Compound M1. Protecting groups on the $R^{4a}$, $R^{4b}$, $R^5$, $A^1$, $A^2$ and/or $X^1$ are removed using conditions described in Greene and Wuts to generate Compound M2. Another transformation is click chemistry, to produce triazole M3. This transformation is performed by treating the alkyne or azide in M, in solvent (e.g., DMF) with an alkyne or azide as appropriate in the presence of CuI to form M3.

Deprotected compound M2 can be further transformed after deprotection to additional macrocycle M, for example: Treatment of M2 containing OH with an alkyl halide in the presence of base, e.g., cesium carbonate, in solvent, e.g., DMF, acetonitrile forms alkylated product M4. M2 containing a ketone group is treated in solvent (e.g., DMF, methanol, etc) with an amine followed by the addition of sodium acetoxyborohydride to form amine product M5.

Many acids, esters, ketones, aldehyde, sulfonic acid or halide component B with a terminal alkene, Me-CH═C—, or vinyl/aryl boronate, or halide in A1 are commercially available or described in the literature and these can be used in the above schemes directly. In addition, the following schemes below are examples of methods that can be used by one skilled in the art to generate additional B.

Scheme 8: Preparation of acids, etsters, ketones and aldehydes B

1.

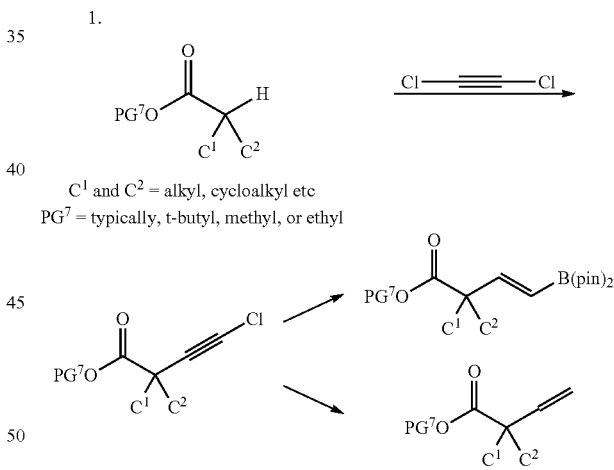

$C^1$ and $C^2$ = alkyl, cycloalkyl etc
$PG^7$ = typically, t-butyl, methyl, or ethyl Scheme 7: Preparation of acids, esters, ketones and aldehydes B

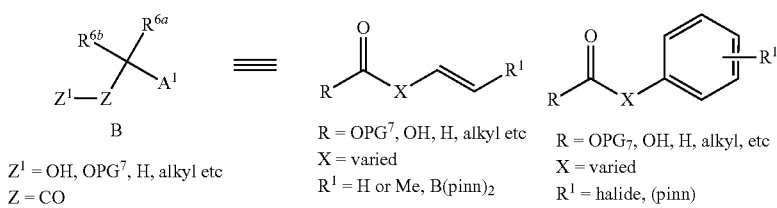

B
$Z^1$ = OH, $OPG^7$, H, alkyl etc
Z = CO

R = $OPG^7$, OH, H, alkyl etc
X = varied
$R^1$ = H or Me, B(pinn)$_2$

R = OPG$_7$, OH, H, alkyl, etc
X = varied
$R^1$ = halide, (pinn)

2.

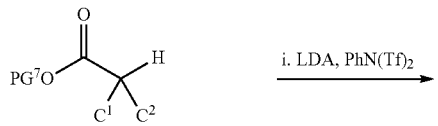

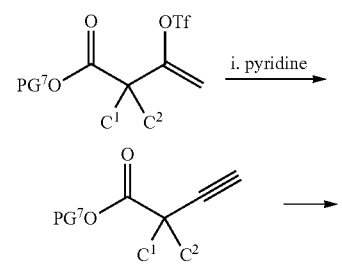

3.

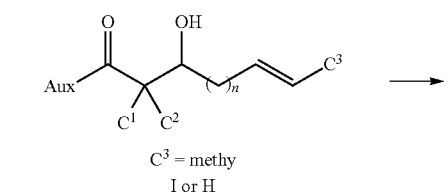

4.

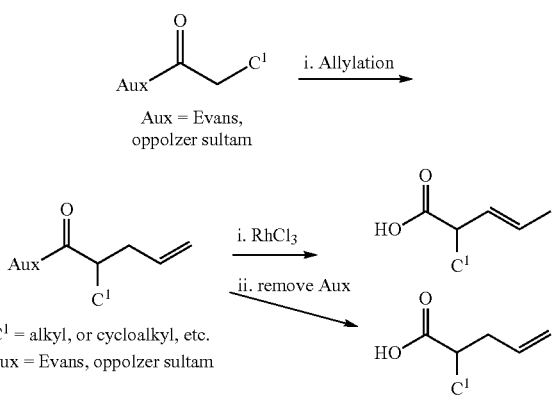

5.

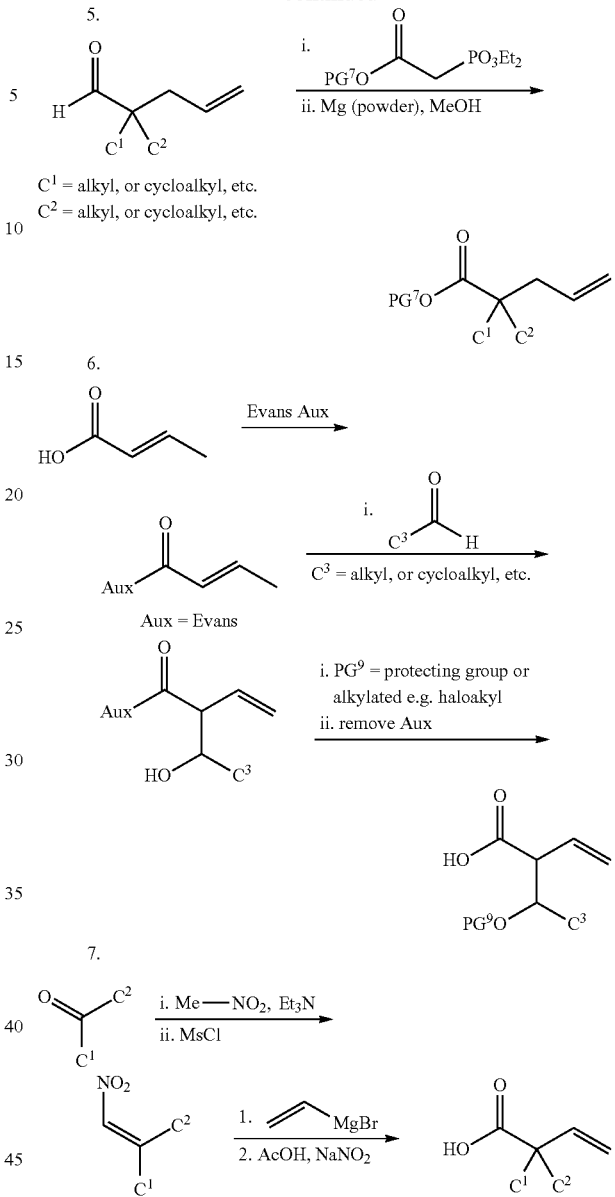

In Scheme 8, part 1, a protected acid is treated with a strong deprotonating base, e.g., LDA in an inert solvent, e.g., THF at −78° C. and HMPA. A pre-cooled solution of dichloroacteylene (prepared by treatment of trichlorethene with potassium hydride and MeOH (catalytic) in THF) is then added to generate the chloro acetylene product. This product is then reduced, for example, by treatment with Cu in acetic acid and THF to generate the alkyne which is then further reduced to the alkene, for example, by treatment of an alcoholic solution of the alkyne with a poisoned palladium reducing agent (e.g. Lindlar) in the presence of hydrogen gas. Alternatively the alkyne is treated with $Cp_2ZrHCl$ in dichloromethane, in the presence of pinnacolborane to form the vinyl boronate.

In Scheme 8, part 2 a beta-keto ester with alpha substitution is converted to the vinyl triflate, for example by treating a THF solution of the beta-keto ester with a base, e.g., LDA in THF at −78° C., followed by addition of $PhN(Tf)_2$. The triflate product is then treated with pyridine at elevated temperature to form the alkyne. The alkyne is then treated as described above in Example 1 to generate the alkene or vinyl boronate products.

In Scheme 8, part 3, a chiral aldol reaction is used. An acyl group is first attached to a chiral auxiliary, e.g., Evans, Oppolzer sultam (see *JACS* 1990, 112, p 2767) using standard amide bond formation conditions described for connection 1-3. The Oppolzer auxiliary product is treated with the aldehyde of choice, TBDMSOTf and base, e.g., triethylamine in anhydrous solvent, e.g., dichloromethane. The Evans auxiliary is treated with base, e.g., LDA, KHMDS, DIPEA in organic solvent, e.g., THF at −78° C. and the aldehyde of choice in the presence of a Lewis acid, e.g., TiCl$_4$, SnCl$_4$ or BF$_3$OEt$_2$. Protection of the resulting alcohol from the aldol reaction is performed as described in Greene and Wuts, or alternatively alkylation with an alkyl halide or Meerwein's reagent, i.e. treatment with trimethyloxonium tetrafluoroborate in an inert solvent, e.g., dichloromethane is performed. The auxiliary is then removed using standard alkali metal hydroxide removal conditions, e.g., LiOH in THF, or LiOH and hydrogen peroxide in THF to provide the free acids product.

In Scheme 8, part 4, an Evans auxiliary is allylated with an allyl halide as described in *Synlett* 2002, 12, 2039-2040. The product is then isomerized by treatment with RhCl$_3$ in ethanol and then the auxiliary removed by base and peroxide, e.g., LiOH and H$_2$O$_2$ in THF/Water. Alternatively the auxiliary is directly removed by LiOH and H$_2$O$_2$ in THF/Water to provide the terminal alkene.

In Scheme 8, part 5, a Horner Wadsworth Emmons reaction is used on an aldehyde (containing a terminal alkene) to generate the alpha-beta unsaturated ester which is then selectively reduced to the ester. For example the phosphonate is treated with base, e.g., sodium hydride in THF at low temperature, followed by addition of the aldehyde and warming to generate the unsaturated ester. The product is reduced by treatment with magnesium powder in methanol.

In Scheme 8, part 6, an alpha-beta unsaturated acid or is converted to the unsaturated Evans auxiliary (see *Organic Letters* 2007, 9, p 1635) and is treated with an aldehyde to generate the corresponding alkene product. The hydroxyl group is then protected using methods described in Greene and Wuts and then the auxiliary is removed by treatment with base and peroxide, e.g., LiOH and H$_2$O$_2$ in THF/Water. The hydroxyl can also be alkylated by as described above for aldol Scheme 8, part 3.

In Scheme 8, part 7 a ketone is transformed via the nitro olefin as described in *Angew. Chem. Int. Ed.* 2006, 45 (46), 7736. The nitro olefin is then treated with vinyl magnesium bromide in an inert solvent, e.g., THF, in the presence of a copper(I) salt, e.g., CuI and trimethylsilyl chloride. The nitro alkyl product after addition of the vinyl group is then converted to the acid by treating with sodium nitrite and acetic acid in an inert polar solvent, e.g., DMSO.

To generate the ketones, aldehydes, hydroxy, or halide compounds the acid/ester products described in Scheme 8 can be transformed using standard methods known to one skilled in the art. For example, conversion of the acid to the Weinreb amide with a coupling agent in a solvent, e.g., THF, dichloromethane, followed by treatment with a nucleophile, e.g., MeMgBr, CF$_3$SiMe and the like, generates ketones; hydroxyl groups are produced by treatment of the esters with lithium aluminum hydride in a solvent, e.g., THF, dichloromethane etc. Hydroxyls are activated to triflates with treatment with triflic anhydride, and a base, e.g., diisopropylethylamine in solvent, e.g., THF. Conversion of the hydroxyl to a halide, e.g., bromide is performed by treatment with PPh$_3$ and carbon tetrabromide.

Several types of A (or A1 as shown) are available commercially or described in the literature where X$^1$ is O or NH and Y is a halide or alkene. The schemes below describe additional general methods for generating A1.

Scheme 9: Preparation of A

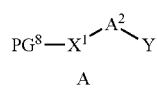 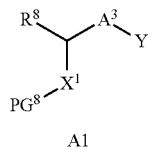

A

X$^1$ = O, NH, N(alkyl), or substituted N, etc.
Y = halogen, alkene, or O-alkylene

A1

A$^3$ = aryl, heteroayl, or biaryl, etc.
X$^1$ = O, NH, or NR
Y = halogen, alkene, or O-alkylene
R$^8$ = H, lower alkyl, or haloalkyl 1. When Y = Halogen in A1

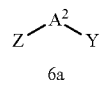 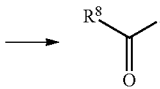 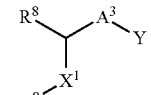

6a

A$^2$ = aryl, biaryl, heteroaryl, or alkene
Z = acid, aldehyde, halogen, or OH
Y = I, Br, or Cl 6b

X$^1$ = O

6c

X$^1$ = O

A1

X$^1$ = O

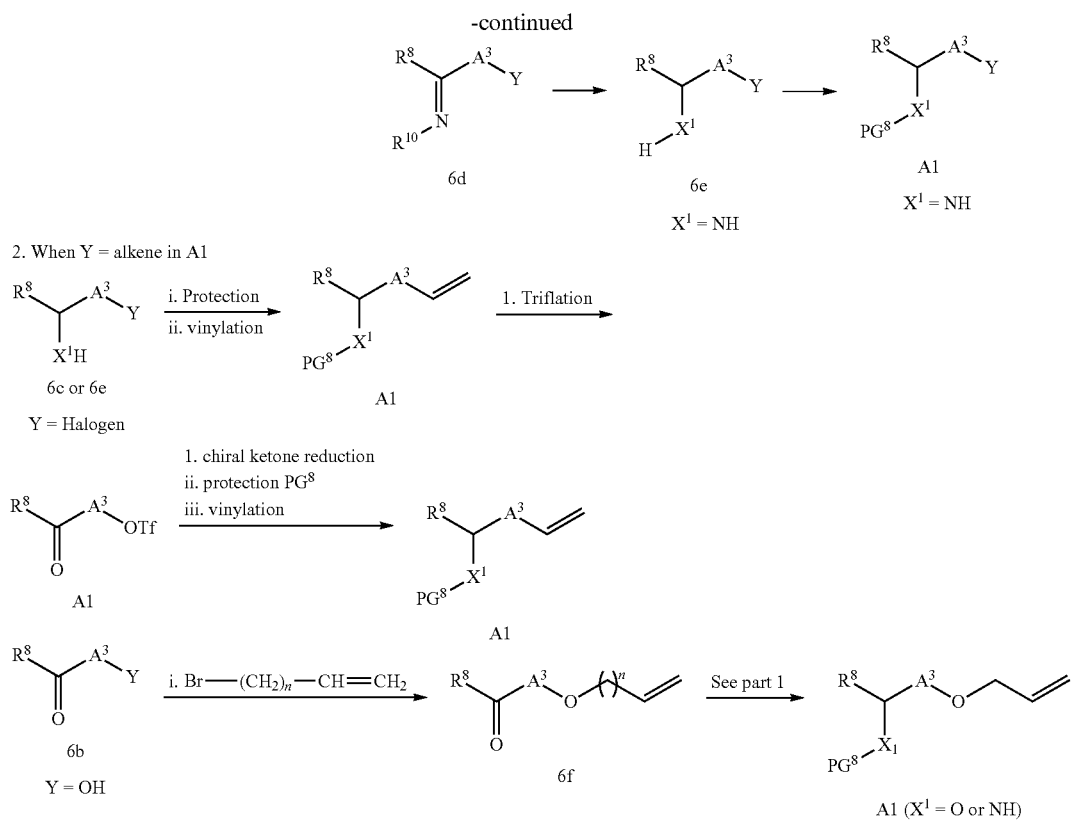

In Scheme 9, part 1 (Y is a halogen in A1); the starting compound 6a is typically a commercially available aromatic compound, that contains halogen Y and a group Z that can be transformed to the ketone 6b. Typical Z groups are halide, acid, aldehyde, for example.

When Z is an acid, 6a is treated with a coupling agent, e.g., HATU, EDC in the presence of a base, e.g., DIPEA and the Weinreb amine (Me-NH—OMe) to form the Weinreb amide. The amide is then treated with a nucleophile, e.g., TMS-CF$_3$ to form the CF$_3$ substituted ketone 6b or with a Grignard agent, e.g., MeMgBr in a solvent, e.g., THF at –78° C. to form the methyl ketone 6b.

When Z is halogen, then the initial conversion, if required, to a more reactive halogen is performed by treatment with NaI and acetyl chloride in an inert solvent, e.g., acetonitrile. The halogen is then transformed to the ketone by a Stille reaction with an ethoxyvinyl stannane. The halide is treated in an inert solvent, e.g., toluene, with the stannane and a palladium (II) catalyst, e.g., PdCl$_2$(PPh$_3$)$_2$, followed by treatment of the product with 2M HCl to afford ketone 6b. In some cases, the formation of an alkyl lithium reagent from the halide group can be performed by treatment with nBuLi at –78° C. in THF and then addition of a N-methoxy-N-methyl amide to afford the ketone 6b (e.g., N-methoxy-N-methylacetamide affords the R$^8$=methyl ketone 6b). A final method to generate the ketone 6b is through a vinyl group. 6a is treated with a vinyl-trifluoroborate in the presence of a palladium catalyst, e.g., PdCl$_2$(dppf) and then the vinyl product is subsequently ozonolysed in a polar solvent, e.g., methanol at low temperature to give an aldehyde. The aldehyde is then reacted with a nucleophile, e.g., TSM-CF$_3$ or a Grignard reagent, e.g., MeMgBr to afford a secondary alcohol product. The secondary alcohol is then oxidized with Dess Martin Periodinane to give the desired ketone 6b or can be used as A1 itself.

Chiral alcohol (X$^1$ is O) and amine (X$^1$ is NH) A1 are generated using Chiral reduction methods on the ketone 6b. Chiral alcohol 6c is formed from 6b using one of the numerous chiral reduction methods available in the literature. Typically, dichloro(p-cumene)ruthenium(II) dimer and (1R,2R)-(–)—N-p-tosyl-1,2-diphenylethylenediamine are combined in water, and sodium formate and 6b is added in a water miscible solvent such as tetrahydrofuran. The reaction is then stirred at a temperature between ambient and reflux to produce 6c where X$^1$ is O. Alternatively, a chiral CBS reduction can be performed in an inert solvent, e.g., THF at low temperature to also afford the chiral alcohol 6c. Protection of the OH in 6c is performed using methods described in Greene and Wuts, typically a TBS ether or acetyl group are used to provide A1 (X$^1$ is O).

Alternatively to make chiral A1 (X$^1$ is NH), ketone 6b is first converted to a chiral imine (R$^{10}$ is chiral group) and then reduced using a variety of methods described in the literature. For example, a chiral sulfinamide is reacted with the ketone 6b to afford a chiral sulfinimine 6d, which is then reduced with a suitable reducing agent, typically NaBH$_4$, or selectride, or a Noyori type reduction as described for the chiral alcohol above, with dichloro(p-cumene)ruthenium(II) dimer and (1R,2R)-(–)—N-p-tosyl-1,2-diphenylethylenediamine. The sulfinamide auxiliary is then removed by treatment with mineral acid, preferably HCl in a suitable organic solvent such as methanol, to afford 6e where X$_1$=NH. Protection of the NH group can then be performed as described in Greene and Wuts to generate A1 (X$^1$ is NH).

In part 2 of Scheme 9, the synthesis of compound A1 where Y is —CH═CH$_2$, a precursor for metathesis and cross coupling reactions is illustrated. Exemplary methods are as follows.

Compound 6c or 6e generated in Scheme 9, part 1 is first optionally protected on $X^1$ using a suitable protecting group as described in Greene and Wuts, and then a vinyl group is introduced by a suitable cross coupling method onto the aryl or sp2 halide. For example, a transition metal mediated coupling with an vinyl stannane or vinyl tetrafluoroborate using a suitable palladium catalyst, e.g., $PdCl_2(dppf)_2$ or $PdCl_2(PPh_3)_2$ in a suitable organic solvent, e.g., acetonitrile, dichloromethane, etc., with either thermal or microwave heating affords alkene A1.

Another typical method that can be used to introduce a vinyl group is starting from the ketone 6b where Y is OH. Initially, triflation of the alcohol is performed by treatment with $Tf_2O$ in the presence of a base, e.g., pyridine. The ketone group is then reduced with a Noyori reduction, or as described above through the sulfonamide, to provide the chiral alcohol or amine. The chiral alcohol or amine is then protected as described in Greene and Wuts, and then the triflate is reacted with a vinyl cross coupling reagent, e.g., vinyl stannane in a Stille coupling, or a vinyltrifluoroborate as described above to introduce the alkene. A further example of alkene generation using 6b ketone is via introduction of an allyl group. Thus, 6b where Y is OH is treated in an inert solvent in the presence of a suitable base, e.g., alkali metal carbonate, preferably potassium carbonate with allyl bromide to form 6f. Compound 6f is then similar to ketone 6b and is therefore able to be transformed as described above in part 1 to compound A1 where $X^1$ is O or NH with protecting group $PG^8$.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

The effective dose of an active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. The effective dose can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Combination Therapy

The compounds of the present invention may be combined with one or more active agents. Non-limiting examples of suitable active agents to be combined include one or more interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

More specifically, one or more compounds to be combined are selected from the group consisting of:

1) interferons, e.g., pegylated rIFN-alpha 2b (PEG-Intron), pegylated rIFN-alpha 2a (Pegasys), rIFN-alpha 2b (IntronA), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon;

2) ribavirin and its analogs, e.g., ribavirin (Rebetol, Copegus), and taribavirin (Viramidine);

3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227);

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) nucleoside or nucleotide inhibitors of HCV NS5B polymerase, e.g., R1626, R7128 (R4048), IDX184, IDX-102, PSI-7851, BCX-4678, valopicitabine (NM-283), GS-6620 and MK-0608;

7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190;

8) HCV NS5A inhibitors, e.g., AZD-2836 (A-831), AZD-7295 (A-689), and BMS-790052;

9) TLR-7 agonists, e.g., imiquimod, 852A, GS-9524, ANA-773, ANA-975, AZD-8848 (DSP-3025), PF-04878691, and SM-360320;

10) cyclophillin inhibitors, e.g., DEBIO-025, SCY-635, and NIM811;

11) HCV IRES inhibitors, e.g., MCI-067;

12) pharmacokinetic enhancers, e.g., BAS-100, SPI-452, PF-4194477, TMC-41629, GS-9350, GS-9585, and roxythromycin;

13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOc-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib);

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride; and 18) endothelin antagonists, e.g. bosentan and ambrisentan.

In yet another embodiment, the present application provides a combination therapy comprising a composition of the present invention and a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, non-nucleoside inhibitors of HCV, and other drugs for treating HCV, and combinations thereof.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, Mb-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, Mb-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831, A-689 and BMS-790052, 14) NS5b polymerase inhibitors, e.g., NM-283, valopicitabine, R1626, PSI-6130 (R1656), IDX184, PSI-7851, HCc-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOc-205, tarvacin, EHC-18, and NIM811, 19) pharmacokinetic enhancers, e.g., BAS-100, SPI-452, PF-4194477, TMC-41629, GS-9350, GS-9585, and roxythromycin, 20) RNAse H inhibitors, e.g., ODN-93 and ODN-112, 21) other anti-HIV agents, e.g., VGc-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

In a specific aspect of this embodiment, the additional therapeutic agent is selected from ribavirin, telaprevir, boceprevir and sofosbuvir (GS-7977 (formerly PSI-7977)).

A combination therapy described herein may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

One or more compounds of the disclosure are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this disclosure is that they are orally bioavailable and can be dosed orally.

Method for Treating Viral Infection

The present application provides a method for treating a Flaviviridae viral infection comprising administering a therapeutically effective amount of a compound described herein or a pharmaceutically acceptable salt, isotope, stereoisomer, mixture of stereoisomers, tautomer, ester or prodrug thereof, to a human subject in need thereof.

Also provided is a method for treating a Coronaviridae viral infection comprising administering a therapeutically effective amount of a compound described herein or a pharmaceutically acceptable salt, isotope, stereoisomer, mixture of stereoisomers, tautomer, ester or prodrug thereof, to a human subject in need thereof.

In one embodiment, the method of inhibiting or treating a disease comprises administering to an animal a composition comprising an effective amount of one or more compounds of the invention and a pharmaceutically acceptable carrier. The composition to be administered may further contain a secondary therapeutic agent as described above.

A method of the present application is particularly suitable for use with humans, but may be used with other animals, particularly mammals, such as, for example, non-human primates, companion animals, farm animals, laboratory animals, and wild and zoo animals.

A method of the present application is particularly useful to treat diseases caused directly or indirectly by Flaviviridae virus since the compounds of the present invention have inhibitory activity against those viruses. In some embodiments, therefore, a method of the present invention is used in inhibiting or treating diseases caused by a Hepatitis C virus. In some embodiments, therefore, a method of the present invention is used in inhibiting or treating diseases caused by a Hepatitis B virus. In an aspect, such a method is applied to a patient with a disease caused by the viral infection such as dengue fever, yellow fever, hepatitis C, Japanese encephalitis, Kyasanur forest disease, Murray valley encephalitis, St. Louis encephalitis, tick-borne encephalitis or West Nile encephalitis.

In some embodiments, a sustained virologic response is achieved at about 12 weeks, at about 10 weeks, at about 8 weeks, at about 6 weeks, or at about 4 weeks, or at about 4 months, or at about 5 months, or at about 6 months, or at about 1 year, or at about 2 years.

A method of the present application is also particularly useful to treat diseases caused directly or indirectly by Coronaviridae virus since the compounds of the present invention have inhibitory activity against those viruses. In some embodiments, therefore, a method of the present invention is used in inhibiting or treating diseases caused by a SARS coronarirus. In an aspect, such a method is applied to a patient with a disease caused by the viral infection such as severe acute respiratory syndrome (SARS), cancer, inflammation, obesity, acquired immune deficiency syndrome (AIDS), or cirrhosis.

In another aspect, the compounds disclosed herein can be used for treating cancer. In yet another aspect, the compounds disclosed herein can be used for immunomodulation. In some embodiments, therefore, a method of the present invention comprises adjusting an immune response to a desired level, as in immunopotentiation, immunosuppression, or induction of immunologic tolerance.

In some embodiments, the compound is administered for about 12 weeks. In further embodiments, the compound is administered for about 12 weeks or less, for about 10 weeks or less, for about 8 weeks or less, for about 6 weeks or less, or for about 4 weeks or less. The compound may be administered once daily, twice daily, once every other day, two times a week, three times a week, four times a week, or five times a week.

EXAMPLES

The following examples are merely illustrative, and do not limit this disclosure in any way.

| List of Abbreviations and Acronyms | |
|---|---|
| Abbreviation | Meaning |
| ° C. | Degree Celsius |
| di-tBuXPhos | 2-Di-tert-butylphosphino-3,4,5,6-tetramethyl-2',4',6'-triisopropyl-1,1'-biphenyl |
| 2,6-lut. | 2,6-lutidine |
| MNBA | 2-Methyl-6-nitrobenzoic Anhydride |
| 4AMS | 4 Angstrom molecular sieves |
| Ac | Acetyl |
| app | Apparent |
| aq | Aqueous |
| atm | atmosphere |
| BINAP | (2,2'-bis(diphenylphosphino)-1,1'-binaphthyl) |
| Bn | Benzyl |
| Boc | tert-Butoxycarbonyl |
| BOP | Benzotriazole-1-yl-oxy-tris-(dimethylamino)-phosphonium hexafluorophosphate |
| br | Broad |
| Bu | Butyl |
| cat | Catalytic |
| cm | Centimeter |
| cod | cyclooctadiene |
| COMU | (1-Cyano-2-ethoxy-2-oxoethylidenaminooxy)-dimethylamino-morpholino-carbenium hexafluorophosphate |
| CP/Cp | Cyclopentyl |
| CPME | Cyclopentyl methyl ether |
| CSA | Camphorsulfonic acid |
| Cy/cHex | Cyclohexyl |
| d | Doublet |
| DAST | Diethylaminosulfur trifluoride |
| dba | dibenzylideneacetone |
| DBU | 1,8-Diazabicyclo[5.4.0]undec-7-ene |
| DCC | N,N'-dicyclohexylcarbodiimide |
| DCE | Dichloroethane |
| DCM | Dichloromethane |
| dd | Doublet of doublets |
| DIPEA | N,N-Diisopropylethylamine |
| DMAP | 4-Dimethylaminopyridine |
| DMF | Dimethylformamide |
| DMSO | Dimethylsulfoxide |
| dq | Double quartet |
| EDC | 1-Ethyl-3-(3-dimethylaminopropyl)carbodiimide |
| equiv | Equivalents |
| ESI | Electron Spray Ionization |
| Et | Ethyl |
| g | Grams |
| HATU | (Dimethylamino)-N,N-dimethyl(3H-[1,2,3]triazolo[4,5-b]pyridin-3-yloxy)methaniminium hexafluorophosphate |
| HDMS | Hexamethyldisilazane |
| HOBT | Hydroxybenzotriazole |
| HPLC | High-performance liquid chromatography |
| hrs/h | Hours |
| Hz | Hertz |
| IC$_{50}$ | The half maximal inhibitory concentration |
| i-Pr/iPr | Isopropyl |
| J | Coupling constant |
| Kg | Kilogram |
| LCMS | Liquid chromatography-mass spectrometry |
| LDA | Lithium diisopropylamide |
| M | Molar |
| m | Multiplet |
| m/z | mass-to-charge ratio |
| M+ | Mass peak |
| m-CPBA | meta-Chloroperoxybenzoic acid |
| Me | Methyl |
| mg | Milligram |
| MHz | Megahertz |
| min | Minute |
| mL | Milliliter |
| mM | Millimolar |
| mm | Millimeter |
| mmol | Millimole |
| mol | Mole |
| Ms | Methanesulfonyl |
| MW | Microwave |
| nM | Nanomolar |
| NMR | Nuclear magnetic resonance |
| o-Tol | o-Tolyl |

List of Abbreviations and Acronyms

| Abbreviation | Meaning |
|---|---|
| Ph | Phenyl |
| Pin | Pinacolato |
| Piv | Pivaloyl |
| ppm | parts per million |
| pTSA | p-Toluenesulfonic acid |
| py | Pyridine |
| q | Quartet |
| quant | Quantitative |
| rac | Racemic |
| Rf | Retention factor |
| RT/rt/r.t. | Room temperature |
| s | Singlet or seconds |
| sat. | Saturated |
| SEMCl | 2-Trimethylsilylethyoxymethyl chloride |
| t | Triplet |
| TBAF | Tetra-n-butylammonium fluoride |
| TBDMS/TBS | tert-Butyldimethylsilyl |
| td | Triplet of doublets |
| TEA | Triethylamine |
| Tf | Trifluoromethanesulfonyl |
| TFA | Trifluoroacetic acid |
| THF | Tetrahydrofuran |
| TLC | Thin layer chromatography |
| TMS | Trimethylsilyl |
| Tr/tr | Retention time |
| Ts | Tosyl |
| UV | Ultraviolet |
| δ | Chemical shift |
| μL | Microliter |
| μM | Micromolar |
| μmol | Micromole |

For Examples 1 to 58, and Examples 93 to 107, unless otherwise stated, preparative HPLC was performed on a Gilson HPLC system, using an Agilent Eclipse XDB/C18 7 micron, 250×21.2 mm semi-preparative column and an acetonitrile/water mobile phase at a flow rate of 20 mL/min.

For Examples 59 to 92, and Examples 108 to 112, unless otherwise stated, preparative HPLC was performed on a Shimadzu HPLC system, using a 21.2×250 mm 10 micron C18 Phenomenex Gemini semi-preparative column and acetonitrile/water mobile phase at a flow rate of 20 mL/min.

Example 1

(E)-(2R,3R)-7-(3-{(R)-1-[((S)-Hexahydro-pyridazine-3-carbonyl)-amino]-ethyl}-phenyl)-3-methoxy-2-methyl-hept-6-enoic acid (S)-2-methyl-1-((S)-1-methyl-2-oxo-ethylcarbamoyl)-propyl ester— Compound 1

Compound 1a

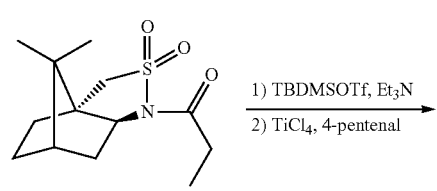

Compound 1b

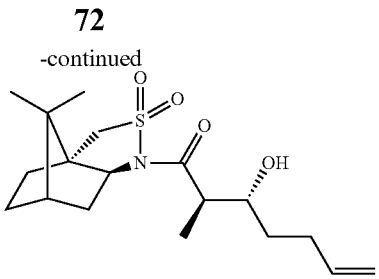

Synthesis of Compound 1a:

A solution of 1-((1R,5S)-10,10-dimethyl-3,3-dioxo-3lambda*6*-thia-4-aza-tricyclo[5.2.1.0*1,5*]dec-4-yl)-propan-1-one (3.95 g, 14.55 mmol) in toluene (50 mL) was prepared, then evaporated to dryness. This process was repeated and the resulting white solid was dissolved in anhydrous dichloromethane (16 mL). A small quantity of calcium hydride was added before adding tert-butyldimethylsilyl trifluoromethanesulfonate (3.83 mL, 14.5 mmol) and anhydrous triethylamine (2.33 mL, 16.7 mmol). The reaction mixture was stirred at room temperature (RT) under a nitrogen atmosphere for 15 hours ("h"). The resulting solution was evaporated to yield a thick paste, which was re-dissolved in anhydrous dichloromethane (15 mL) and added drop-wise to a stirred solution of 4-pentenal (2.69 g, 32.0 mmol) and titanium tetrachloride (1 M in dichloromethane, 32 mL, 32 mmol) in anhydrous dichloromethane (20 mL) at −78° C., under a nitrogen atmosphere. The reaction was stirred at −78° C. for 30 min before diluting with saturated aqueous ammonium chloride solution (100 mL). The layers were separated and the aqueous layer was extracted with further dichloromethane (2×50 mL). The combined extract was dried over sodium sulfate, filtered and evaporated to give a brown gum. This was purified by silica gel chromatography using isohexane/ethyl acetate 4:1 to yield the title compound (3.09 g, 60%) as a colorless gum.

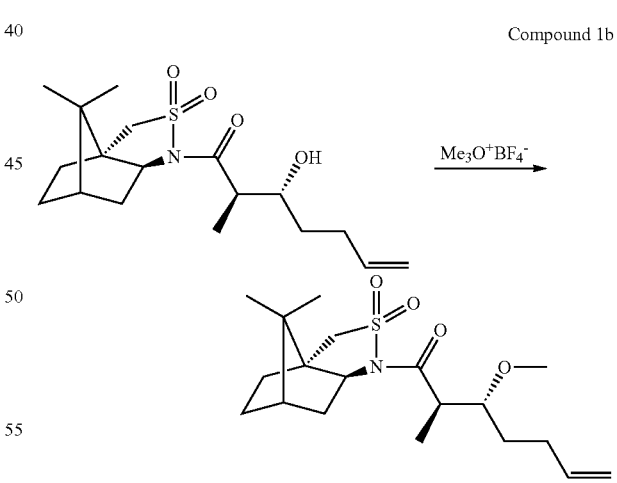

Synthesis of Compound 1b:

A solution of 1a (250 mg, 0.703 mmol) in anhydrous dichloromethane (7 mL) was prepared and trimethyloxonium tetrafluoroborate (208 mg, 1.406 mmol) was added. The reaction mixture was stirred at room temperature for 15 h. The reaction mixture was treated with methanol (1 mL), then 2 M hydrochloric acid (20 mL) and saturated brine (20 mL). The mixture was extracted with ethyl acetate (3×15 mL) and the extract was dried over sodium sulfate, filtered and evaporated to give a yellow gum. The gum was purified by silica gel chromatography using iso-hexane/ethyl acetate 4:1 to give the title compound (223 mg, 86%) as a colorless gum.

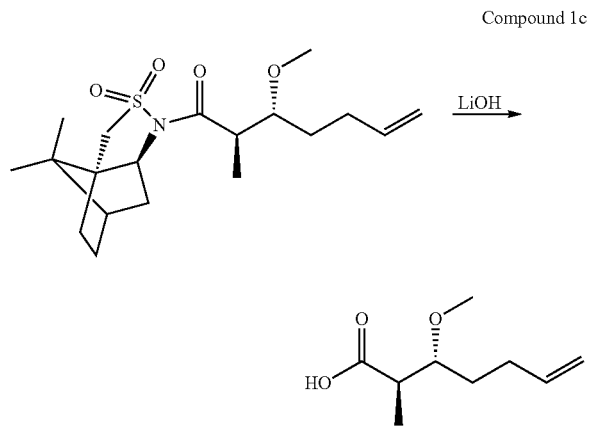

Compound 1c

Synthesis of Compound 1c:

A solution of 2 M lithium hydroxide in water (5 mL) was added to a stirred solution of 1b (223 mg, 0.60 mmol) in tetrahydrofuran (15 mL). The stirred mixture was heated to 60° C. for 15 h. The reaction mixture was partially evaporated before adding 2 M hydrochloric acid (20 mL). The solution was extracted with ethyl acetate (3×15 mL). The extract was dried over sodium sulfate, filtered and evaporated to give a yellow gum (209 mg). The gum was purified by silica gel chromatography using iso-hexane/ethyl acetate 3:1 to yield the title compound (68 mg, 66%) as a yellow gum.

Compound 1d

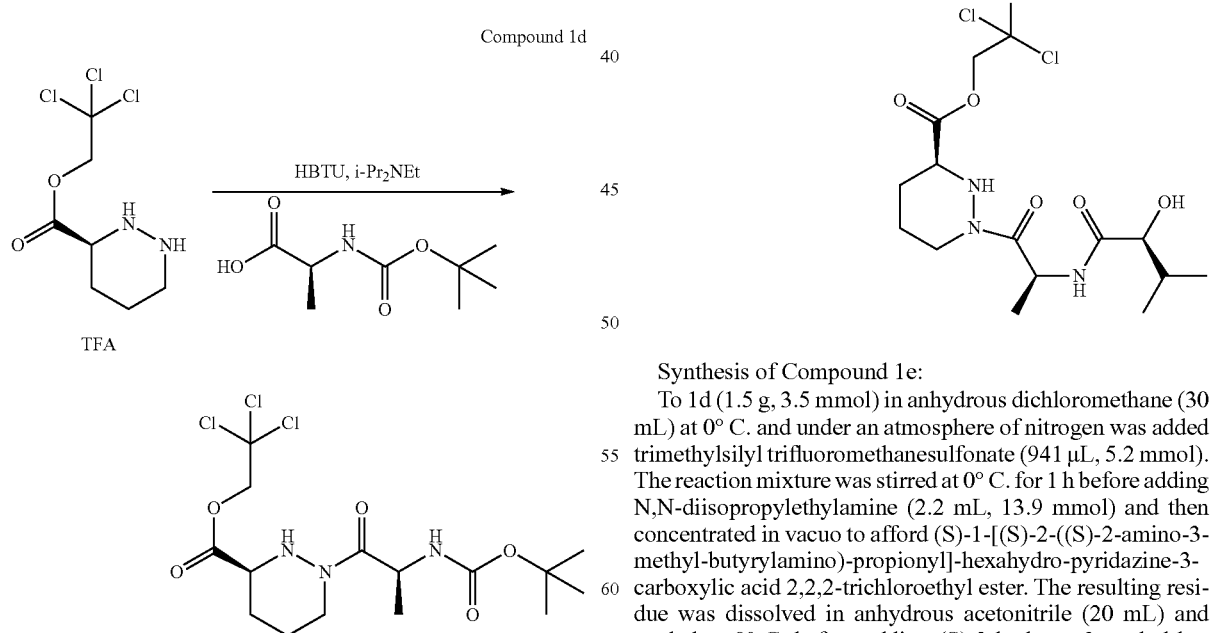

Synthesis of Compound 1d:

A solution of (S)-2-tert-butoxycarbonylamino-propionic acid (3.28 g, 17.32 mmol) in acetonitrile (160 mL) was cooled to 0° C. before addition of N,N-diisopropylethylamine (12 mL, 69.3 mmol) then 2-(1H-benzotriazole-1-yl)-1,1,3,3-tetramethyluronium hexafluorophosphate (6.57 g, 17.32 mmol). The reaction mixture was stirred at 0° C. for 20 min and a solution of (S)-hexahydropyridazine-3-carboxylic acid 2,2,2-trichloroethyl ester trifluoroacetic acid salt (preparation described in *Angew. Chem. Int. Ed. Engl.* 1999, 38, 2443, 6.49 g, 17.3 mmol) in acetonitrile (80 mL) was added. The reaction was allowed to warm to room temperature and was stirred for 15 h. The reaction mixture was evaporated then re-dissolved in ethyl acetate (150 mL). The solution was washed with brine (150 mL). The brine was back extracted with ethyl acetate (50 mL). The organic layers were combined, dried over sodium sulfate, filtered and evaporated to give a dark oil. The oil was purified by silica gel chromatography using iso-hexane/ethyl acetate 1:1 to yield the title compound (6.88 g, 92%) as a colorless gum.

Compound 1e

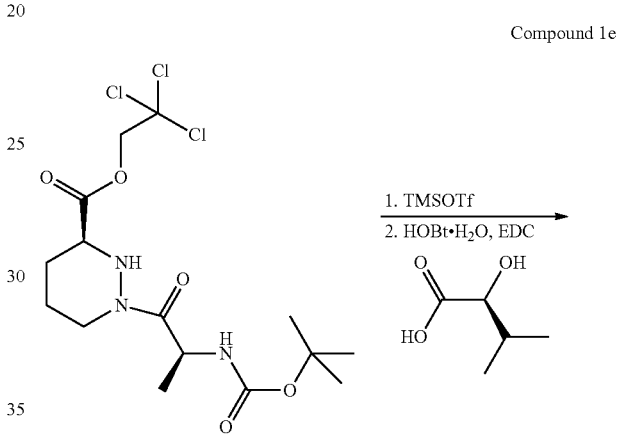

Synthesis of Compound 1e:

To 1d (1.5 g, 3.5 mmol) in anhydrous dichloromethane (30 mL) at 0° C. and under an atmosphere of nitrogen was added trimethylsilyl trifluoromethanesulfonate (941 μL, 5.2 mmol). The reaction mixture was stirred at 0° C. for 1 h before adding N,N-diisopropylethylamine (2.2 mL, 13.9 mmol) and then concentrated in vacuo to afford (S)-1-[(S)-2-((S)-2-amino-3-methyl-butyrylamino)-propionyl]-hexahydro-pyridazine-3-carboxylic acid 2,2,2-trichloroethyl ester. The resulting residue was dissolved in anhydrous acetonitrile (20 mL) and cooled to 0° C. before adding (S)-2-hydroxy-3-methyl-butyric acid (413 mg, 3.5 mmol), hydroxybenzotriazole monohydrate (796 mg, 5.2 mmol), 1-ethyl-3-(3-dimethylamino-propyl)carbodiimide (1.02 g, 5.2 mmol) and N,N-diisopropylethylamine (1.7 mL, 10.4 mmol). The reaction mixture was stirred at 0° C. for 90 min, warmed to room temperature and stirred for 72 h and concentrated in vacuo. Ethyl acetate was added to the residue, which was then washed with saturated ammonium chloride and brine. The organic layer was dried over magnesium sulfate, filtered and concentrated in vacuo. The residue was purified by silica gel chromatography using iso-hexane/acetone 2:1 to give the title compound (1.1 g, 73% over 2 steps) as a white solid.

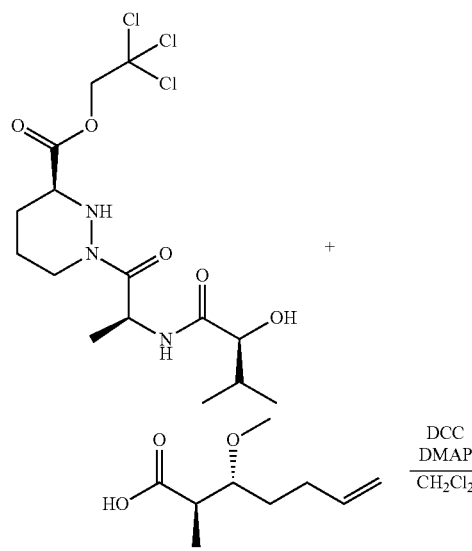

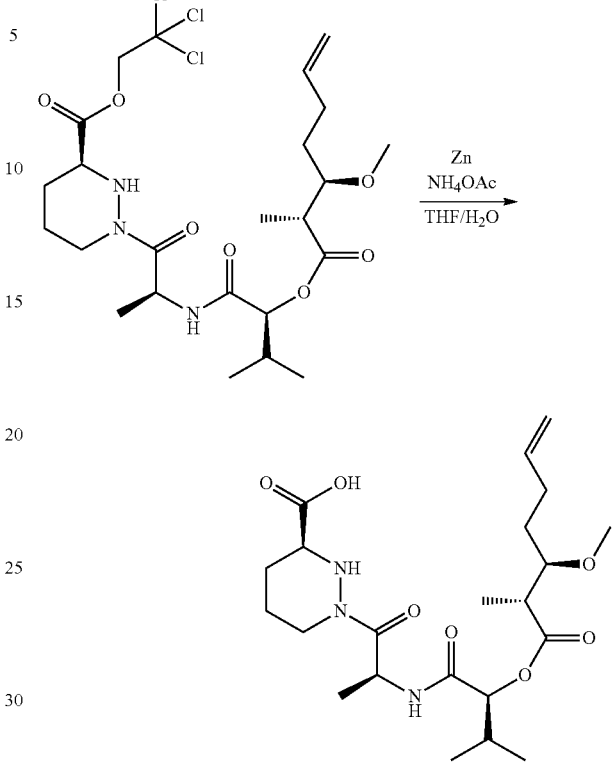

Synthesis of Compound 1f:

A stirred solution of 1e (830 mg, 1.92 mmol) in dichloromethane (20 mL) was prepared and 1c (34 mg, 2.00 mmol), N,N'-dicyclohexylcarbodiimide (594 mg, 2.88 mmol) and N,N-dimethylaminopyridine (23 mg, 0.192 mmol) were added. The reaction was stirred at room temperature for 18 h. A further quantity of 1c (34 mg, 2.00 mmol), N,N'-dicyclohexylcarbodiimide (594 mg, 2.88 mmol) and N,N-dimethylaminopyridine (23 mg, 0.192 mmol) were added and the reaction was stirred at room temperature for a further 22 h. The reaction mixture was washed with water and the aqueous layer was back extracted with dichloromethane (2×15 mL) and ethyl acetate (2×15 mL). The organic layers were combined, dried over sodium sulfate, filtered and evaporated to give a brown gum. The gum was purified by silica gel chromatography using iso-hexane/ethyl acetate 1:1 then ethyl acetate to give the title compound (656 mg, 58%) as a white solid.

Synthesis of Compound 1g:

A solution of 1f (656 mg, 1.12 mmol) in tetrahydrofuran (30 mL) was prepared and zinc powder (732 mg, 11.2 mmol) and aqueous ammonium acetate solution (1 M, 8 mL, 8 mmol) were added. The reaction was stirred at room temperature for 18 h. The mixture was filtered through hyflo-supercel then acidified with ammonium chloride then further with 2 M hydrochloric acid to pH 1. The mixture was extracted with ethyl acetate (3×25 mL). The extract was dried over sodium sulfate, filtered and evaporated to give a solid which was azeotroped with toluene (40 mL) to give the title product (343 mg, 67%) as a colorless solid.

Synthesis of Compound 1h:

A solution of (R)-bromo-α-methylbenzylamine (1.023 g, 5.112 mmol) in dichloromethane (20 mL) was subsequently treated with triethylamine (720 µL, 5.112 mmol) and di-tert-butyl dicarbonate (1.784 g, 8.179 mmol). After overnight stirring at room temperature, the volatiles were removed in vacuo and the residue was purified by silica gel chromatography using a 50 g Isolute cartridge eluted with a continuous gradient of iso-hexane/diethyl ether 1:0 to 4:1 to afford the title compound (1.552 g, 100%) as a white solid.

Compound 1i

Synthesis of Compound 1i:

A solution of 1h (10.26 g, 0.0342 mol.) and tributyl(vinyl)stannane (32.5 g, 30 mL, 0.103 mol.) in toluene (175 mL) was purged with nitrogen for 30 minutes before addition of bis(triphenylphosphine palladium(II) dichloride (2.38 g, 0.0034 mol). The stirred mixture was heated to 60° C. for 16 h before cooling to room temperature. The reaction mixture was filtered through hyflo-supercel then evaporated to give a dark colored oil. The oil was purified by silica gel chromatography using iso-hexane/ethyl acetate 19:1 to yield the title compound (6.95 g, 82%) as a yellow oil.

Compound 1j

Synthesis of Compound 1j:

A solution of 1j (6.95 g, 28.1 mmol.) in 1,4-dioxane (30 mL) was prepared and a solution of hydrogen chloride in 1,4 dioxane (4M, 60 mL) was added. The reaction mixture was stirred at room temperature for 2 h then evaporated to dryness. The resultant solid was re-dissolved in toluene and evaporated. The solid was triturated with diethyl ether, which was removed by decanting. The solid was then dried under vacuum to give the title compound (4.96 g, 96%) as an off-white solid.

Compound 1k

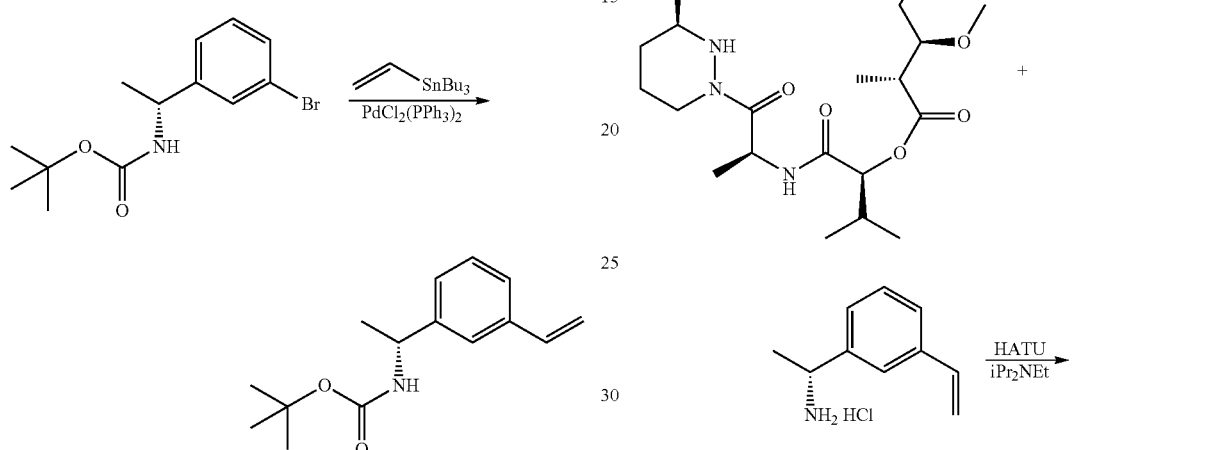

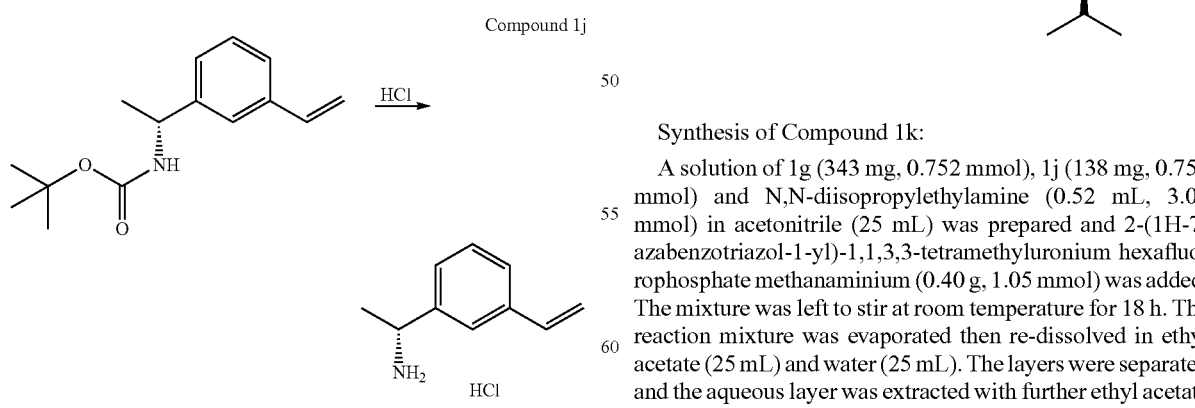

Synthesis of Compound 1k:

A solution of 1g (343 mg, 0.752 mmol), 1j (138 mg, 0.752 mmol) and N,N-diisopropylethylamine (0.52 mL, 3.00 mmol) in acetonitrile (25 mL) was prepared and 2-(1H-7-azabenzotriazol-1-yl)-1,1,3,3-tetramethyluronium hexafluorophosphate methanaminium (0.40 g, 1.05 mmol) was added. The mixture was left to stir at room temperature for 18 h. The reaction mixture was evaporated then re-dissolved in ethyl acetate (25 mL) and water (25 mL). The layers were separated and the aqueous layer was extracted with further ethyl acetate (2×20 mL). The combined organic layers were dried over sodium sulfate, filtered and evaporated to give a brown gum. The gum was purified by silica gel chromatography using iso-hexane/ethyl acetate 1:3 to give the title compound (217 mg, 49%) as a colorless solid.

Compound 1

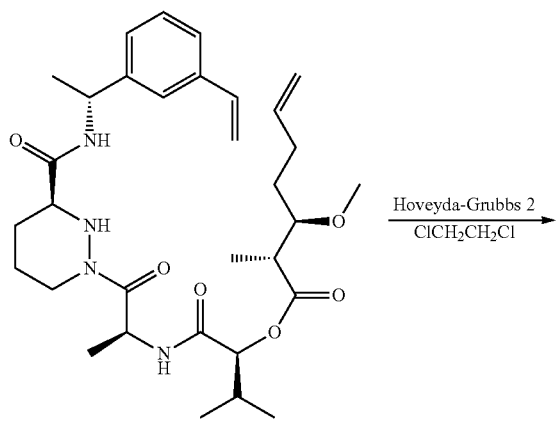

Example 2

Compound 2

Compound 2a

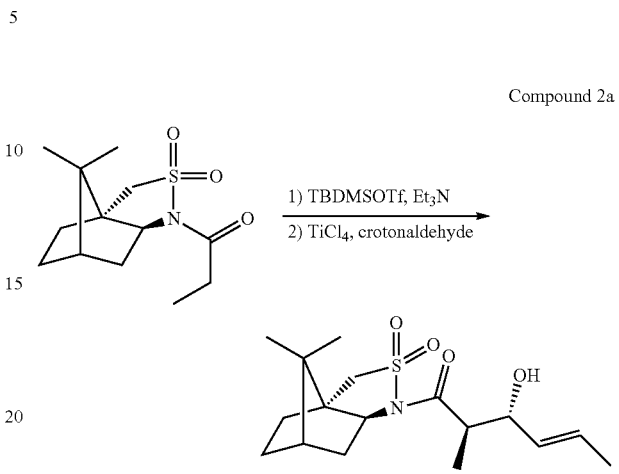

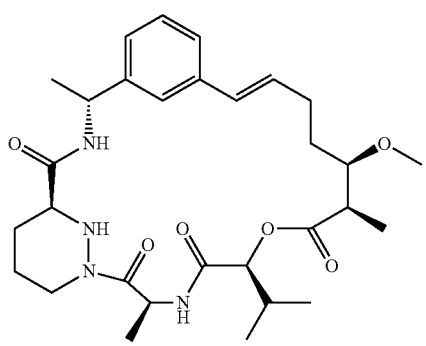

Synthesis of the Title Compound:

A stirred solution of 1k (217 mg, 0.37 mmol) in 1,2-dichloroethane (125 mL) was prepared and Hoveyda-Grubbs $2^{nd}$ generation catalyst (23 mg, 0.037 mmol) was added. The stirred solution was heated to reflux for 3 h. Further Hoveyda-Grubbs $2^{nd}$ generation catalyst (46 mg, 0.074 mmol) was added and the reaction was heated to 85° C. for a further 2 h. The cooled reaction mixture was treated with silica gel. The mixture was evaporated then purified by silica gel chromatography using ethyl acetate to give an off-white solid (177 mg). This was re-purified by silica gel chromatography using a 5 g cartridge and ethyl acetate to give the title compound (67 mg, 32%) as a white solid. $^1$H NMR (300 MHz, $d_6$-acetone) 0.93 (d, J=7.1 Hz, 3H), 0.95 (d, J=7.3 Hz, 3H), 1.15 (d, J=6.9 Hz, 3H), 1.34 (d, J=6.7 Hz, 3H), 1.43 (d, J=7.1 Hz, 3H), 1.47-1.69 (m, 3H), 1.70-1.91 (m, 3H), 1.92-2.17 (m, 3H), 2.32-2.48 (m, 1H), 3.02-3.13 (m, 1H), 3.35 (s, 3H), 3.40-3.65 (m, 3H), 4.27-4.43 (m, 2H), 4.80 (d, J=5.3 Hz, 1H), 5.00-5.15 (m, 1H), 5.32-5.44 (m, 1H), 6.20-6.33 (m, 1H), 6.42 (d, J=15.8 Hz, 1H), 7.10-7.32 (m, 3H), 7.34 (s, 1H), 7.87 (d, J=8.0 Hz, 1H). LCMS (m/z) 557.3 [M+H], Tr=2.59 min.

Synthesis of Compound 2a:

A solution of 1-((1R,5S)-10,10-dimethyl-3,3-dioxo-3lambda*6*-thia-4-aza-tricyclo[5.2.1.0*1,5*]dec-4-yl)-propan-1-one (6.0 g, 22.1 mmol) in anhydrous dichloromethane (24 mL) was prepared and tert-butyldimethylsilyl trifluoromethanesulfonate (5.0 mL, 22.1 mmol) was added, followed by anhydrous triethylamine (3.54 mL, 25.4 mmol). The reaction mixture was stirred at room temperature under a nitrogen atmosphere for 15 h. This gave a dark solution that was evaporated to give an oil. The oil was dissolved in anhydrous dichloromethane (22 mL) and the solution was added dropwise to a solution of crotonaldehyde (3.66 mL, 44.2 mmol) and titanium tetrachloride (1 M in dichloromethane, 44.2 mL, 44.2 mmol) in dichloromethane (22 mL) at −78° C. under a nitrogen atmosphere. The reaction mixture was stirred at −78° C. for 1 h, before addition of ammonium chloride solution (30 mL). The stirred mixture was allowed to warm to room temperature before separating the layers. The aqueous layer was extracted with dichloromethane (2×25 mL). The organic layers were combined, dried over sodium sulfate, filtered and evaporated to give a brown oil. The oil was purified by silica gel chromatography using iso-hexane/ethyl acetate 4:1 to yield the title compound (6.7 g, 89%) as a colorless solid.

Compound 2b

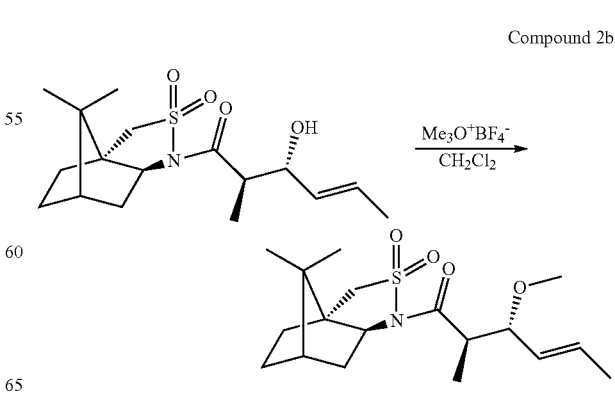

Synthesis of Compound 2b:

A solution of 2a (4.15 g, 12.1 mmol) in anhydrous dichloromethane (80 mL) was prepared and 1,8-bis(dimethylamino)naphthalene (7.78 g, 36.3 mmol) was added followed by trimethyloxonium tetrafluoroborate (3.6 g, 24.2 mmol). The reaction mixture was stirred at room temperature for 3 h. The reaction mixture was treated with methanol (3 mL) and stirred for 5 min before adding hydrochloric acid (2 M, 200 mL) and ethyl acetate (250 mL). The mixture was filtered to remove an insoluble solid and the layers were separated. The aqueous layer was extracted with ethyl acetate (2×100 mL). The organic layers were combined and washed with brine, dried over sodium sulfate, filtered and evaporated to give the title compound (4.80 g, 100%) as a pale brown solid.

Compound 2c

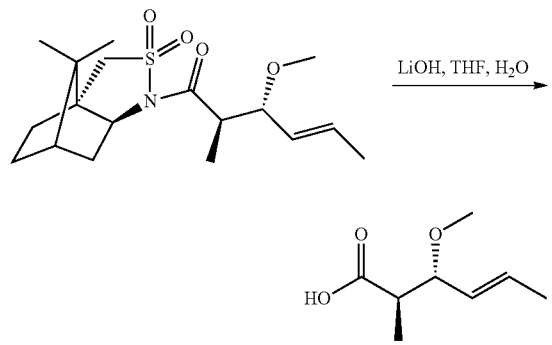

Synthesis of Compound 2c:

A solution of lithium hydroxide in water (2 M, 50 mL, 100 mmol) was added to a stirred solution of 2b (4.80 g, 12.1 mmol) in tetrahydrofuran (130 mL). The reaction mixture was heated to 60° C. for 15 h. The reaction mixture was cooled to room temperature, before partially evaporating and adding hydrochloric acid (2 M, 150 mL). The mixture was extracted with ethyl acetate (3×50 mL). The extract was dried over sodium sulfate, filtered and evaporated to give a brown oil (3.5 g). The oil was purified by silica gel chromatography using iso-hexane/diethyl ether 1:1 to give the title compound (1.132 g, 59%) as a colorless oil.

Compound 2d

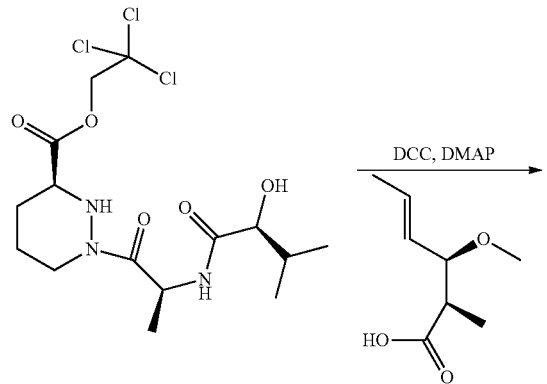

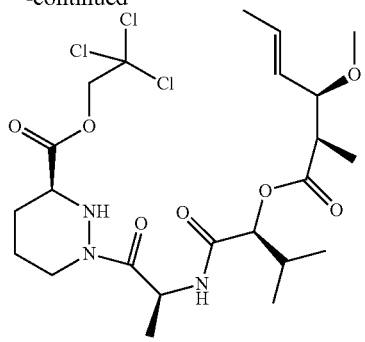

Synthesis of Compound 2d:

Compound 2d was prepared in the same manner as compound 1f replacing 1c with 2c (148 mg, 0.94 mmol) to afford the title compound (340 mg, 76%) as a white solid.

Compound 2e

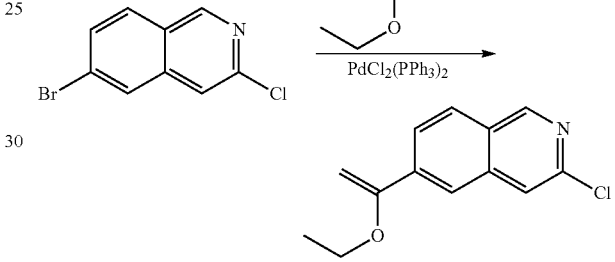

Synthesis of Compound 2e:

A solution of 6-bromo-3-chloro-isoquinoline (Frontier Scientific, Logan, Utah USA) (8.0 g, 33 mmol) and tributyl-(1-ethoxy-vinyl)-stannane (14.88 g, 14 mL, 41.2 mmol) in toluene (100 mL) was degassed with nitrogen for 30 min. Bis(triphenylphosphine)palladium(II) dichloride (1.16 g, 1.65 mmol, 5 mol %) was added and the reaction mixture was heated at 60° C. for 20 h. The reaction mixture was cooled to room temperature, the mixture was filtered and the filtrate was evaporated. The residue was purified by silica gel chromatography using a gradient of iso-hexanes/ethyl acetate 20:1 to 10:1 to afford the title compound (7.1 g, 92%) as a pale yellow solid.

Compound 2f

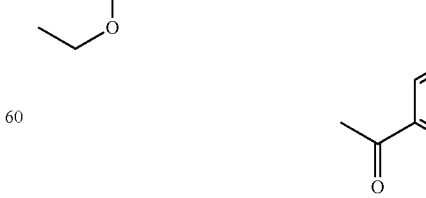

Synthesis of Compound 2f:

A solution of 2e (7.1 g, 30 mmol) in 1,4-dioxane (60 mL) and 2 M hydrochloric acid (30 mL) was stirred at room Compound 2g

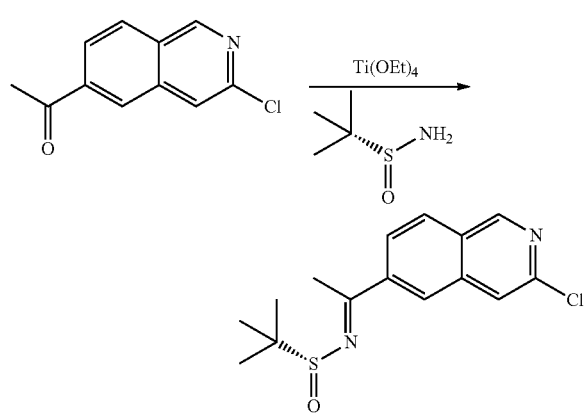

Synthesis of Compound 2g:

A solution of 2f (1.72 g, 8.3 mmol) in tetrahydrofuran (40 mL) was stirred under nitrogen. Titanium (IV) ethoxide (3.8 g, 3.45 mL, 16.6 mmol, tech. grade) was added followed by (R)-(+)-2-methyl-propanesulfinimide (1.11 g, 9.2 mmol) and the reaction mixture was stirred at 60° C. under nitrogen for 18 h. Additional (R)-(+)-2-methyl-propanesulfinimide (190 mg, 0.2 equiv) was added and the reaction mixture was stirred at 65° C. for a further 2 h. The reaction mixture was cooled to room temperature and ethyl acetate and brine were added. The suspension was filtered through celite and the filter pad was washed with ethyl acetate. The ethyl acetate layer was separated, washed with brine, dried over sodium sulfate, filtered and evaporated. The residue was purified by silica gel chromatography using a gradient of iso-hexanes/ethyl acetate 7:3 to 3:7 to afford the title compound (2.2 g, 86%).

Compound 2h

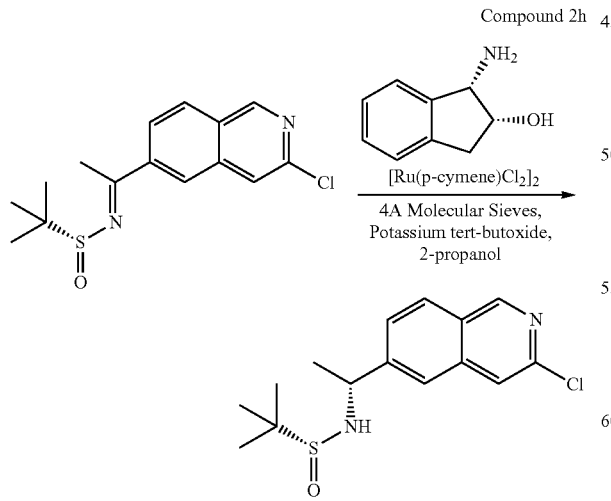

Synthesis of Compound 2h:

A mixture of (1S,2R)-(−)-cis-1-amino-2-Indanol (60 mg, 0.4 mmol), [Ru(p-cymen)Cl₂]₂ (122 mg, 0.2 mmol) and powdered 4 Å molecular sieves (2g) was suspended in anhydrous 2-propanol (9 mL) and stirred under nitrogen. The suspension was heated at 90° C. for 20 min. The reaction mixture was cooled to 40° C. and a solution of 2g (1.23 g, 4 mmol) in 2-propanol (28 mL) was added followed by a solution of potassium tert-butoxide (122 mg, 1.1 mmol) in 2-propanol (10 mL). The reaction mixture was stirred for 2 h at 40° C. and then allowed to cool. The mixture was poured directly onto a silica gel cartridge and eluted with ethyl acetate to give, after evaporation, the title compound as a brown gum (1.19 g, 96%).

Compound 2i

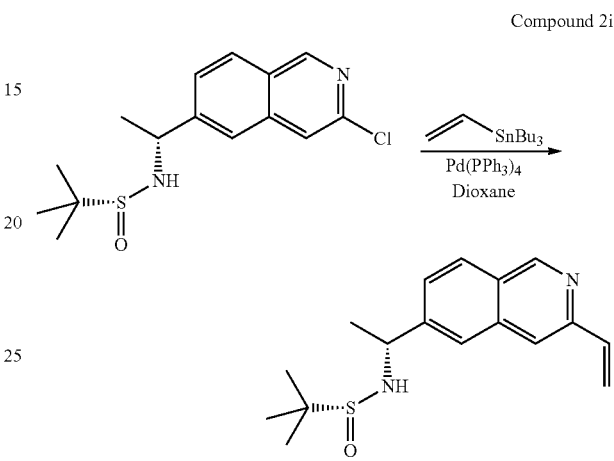

Synthesis of Compound 2i:

A mixture of 2h (1.66 g, 2.11 mmol), tributyl(vinyl)tin (1.85 mL, 6.35 mmol) and palladium tetrakis(triphenylphosphine) (488 mg, 0.42 mmol in 1,4-dioxane (10.5 mL) was capped in a microwave vial. The reaction mixture was heated and stirred at 160° C. for 40 min in a microwave reactor. A second reaction was carried under identical scale and conditions and the reactions combined and evaporated. The residue was purified by silica gel chromatography using a gradient of 25 to 100% ethyl acetate in iso-hexanes to afford the title compound as a brown gum (1g).

Compound 2j

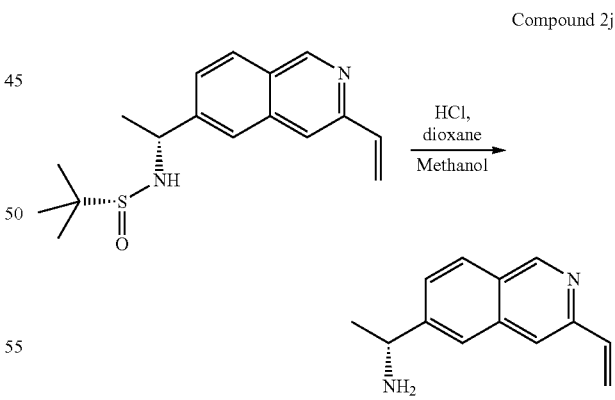

Synthesis of Compound 2j:

2i was suspended in 4 M HCl in 1,4-dioxane (17 mL, 68 mmol) and methanol was added (34 mL). The reaction mixture was stirred for 90 min and then evaporated to give the title compound as the di-HCl salt. The residue was passed through an SCX cartridge eluting with methanol and then methanolic ammonia. The basic fraction was collected and evaporated to give the title compound as a beige solid (530 mg, 63% over 2 steps).

Compound 2k

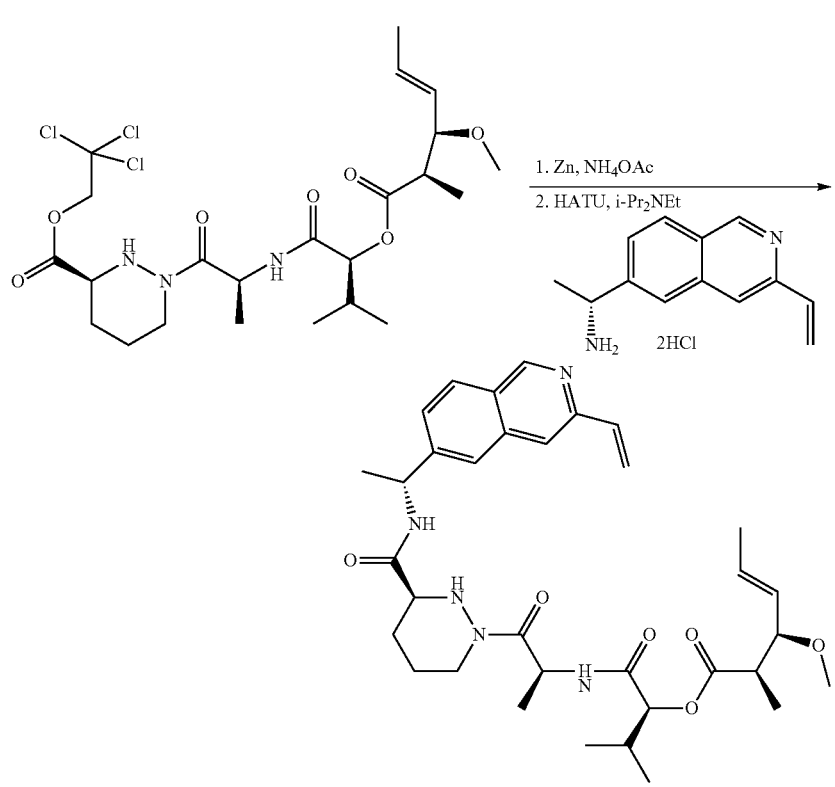

Synthesis of Compound 2k:

Compound 2k was prepared in the same manner as compound 1k, by first replacing 1g with (S)-1-{(S)-2-[(S)-2-((E)-(2R,3R)-3-methoxy-2-methyl-hex-4-enoyloxy)-3-methyl-butyrylamino]-propionyl}-hexahydro-pyridazine-3-carboxylic acid 2,2,2-trichloro-ethyl ester (340 mg, 0.59 mmol) and following the synthesis for compound 1g and then replacing (R)-1-(3-vinyl-phenyl)-ethylamine hydrochloride with 2j dihydrochloride (160 mg, 0.59 mmol) in the synthesis of compound 1k to give the title compound (240 mg, 66%, 2 steps) as a viscous light brown oil.

Compound 2

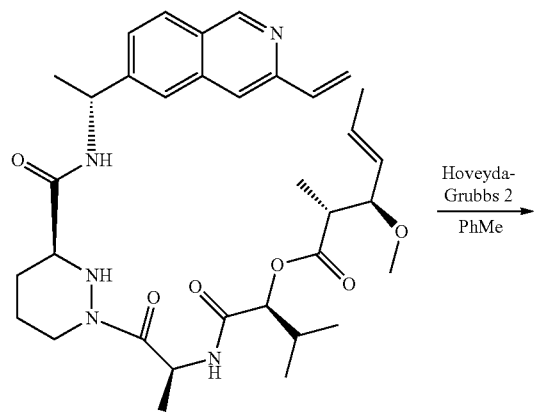

-continued

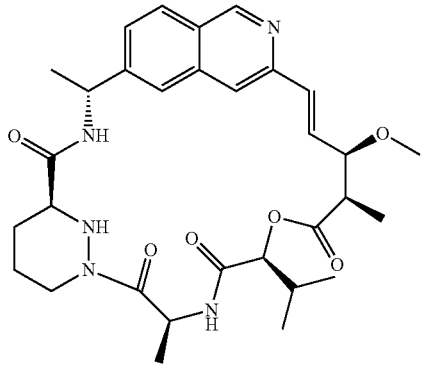

Synthesis of the Title Compound:

A solution of 2k (300 mg, 0.48 mmol) in toluene (161 mL) was degassed with nitrogen for 10 min before adding Hoveyda Grubbs $2^{nd}$ generation catalyst (61 mg, 0.1 mmol). The stirred solution was heated to 125° C. for 2 h before a further amount of Hoveyda Grubbs $2^{nd}$ generation catalyst (61 mg, 0.1 mmol) was added and heating continued for 4 h. The reaction was cooled to ambient temperature and concentrated to dryness. The residue was purified by silica gel chromatography using ethyl acetate/acetone 1/0 then 3/1 followed by preparative TLC using ethyl acetate/acetone 8/1 to yield the title compound (4 mg, 1%) as an off-white solid. $^1$H NMR (300 MHz, CDCl$_3$) 0.80-1.11 (m, 6H), 1.20-1.38 (m, 3H), 1.42-1.70 (m, 6H), 1.67-1.88 (m, 2H), 1.89-2.25 (m, 3H), 2.60-2.75 (m, 2H), 2.98-3.18 (m, 1H), 3.48 (s, 3H), 3.58-3.77 (m, 1H), 4.36-4.67 (m, 2H), 4.91 (s, 1H), 5.18-5.43 (m, 1H), 5.61-5.76 (m, 1H), 6.40-6.65 (m, 1H), 6.82-7.10 (m, 3H), 7.36-7.50 (m, 1H), 7.64 (s, 1H), 7.85-8.01 (m, 1H), 8.18 (s, 1H), 9.16 (s, 1H). LCMS (m/z)=580.3 [M+H], Tr=1.50 min.

Example 3

Compound 3

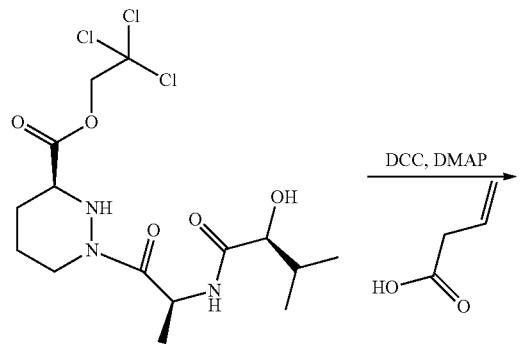

Compound 3a

Synthesis of Compound 3a:

Compound 3a was prepared in the same manner as compound 1f by replacing 1c with 3-butenoic acid to afford the title compound (397 mg, 66%) as a white solid.

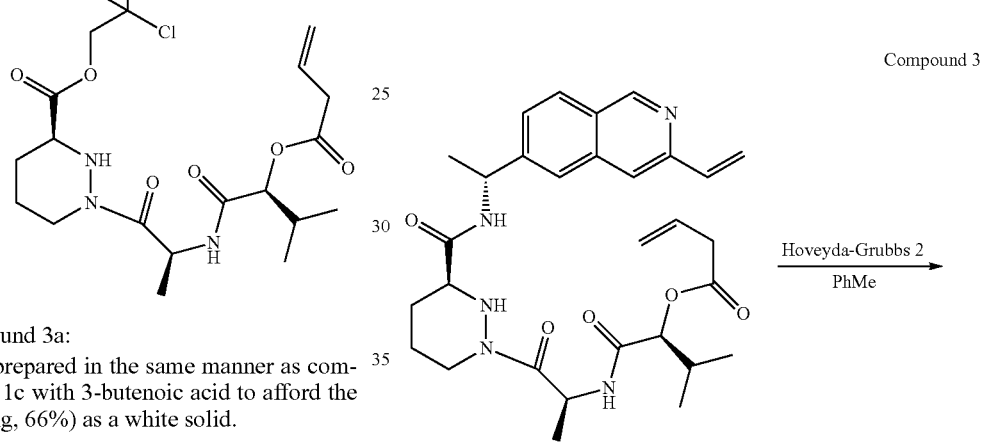

Compound 3b

Synthesis of Compound 3b:

To a solution of 3a (390 mg, 0.78 mmol) in tetrahydrofuran (17 mL) and water (9 mL) was added powdered zinc (1.11 g, 17.1 mmol) followed by ammonium acetate (899 mg, 11.7 mmol). The reaction mixture was stirred at room temperature for 15 h. The reaction was filtered through Celite, the filtrate was acidified to pH 2 with concentrated hydrochloric acid and extracted twice with ethyl acetate. The organic layers were dried through a hydrophobic frit and concentrated in vacuo, followed by co-evaporation from toluene (2×). The ensuing residue was dissolved in anhydrous acetonitrile (15 mL) and 2j (211 mg, 0.78 mmol) was added followed by hydroxybenzotriazole monohydrate (119 mg, 0.78 mmol), 1-ethyl-3-(3-dimethylaminopropyl)carbodiimide (210 mg, 1.1 mmol). The reaction mixture was stirred at room temperature for 16 h. Silica gel was added to the reaction mixture and concentrated in vacuo. The residue was purified by silica gel chromatography using iso-hexane/ethyl acetate 1/1 then ethyl acetate to give the title compound (276 mg, 57%, 2 steps) as a white solid.

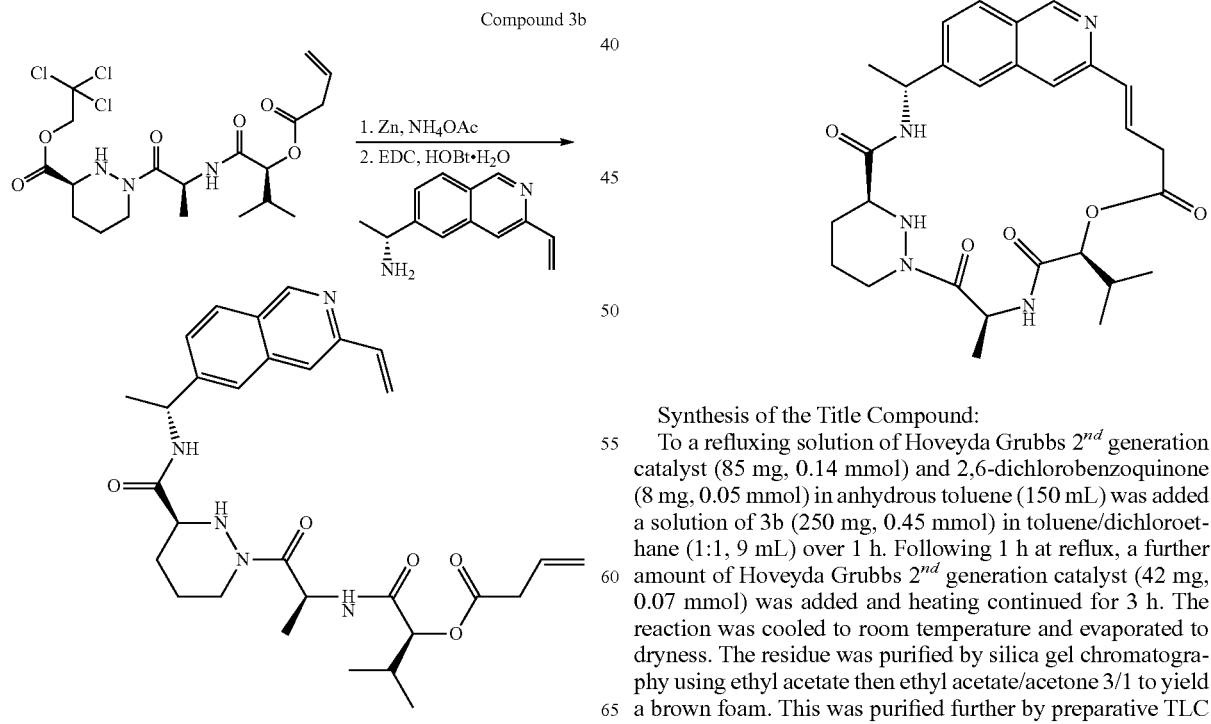

Compound 3

Synthesis of the Title Compound:

To a refluxing solution of Hoveyda Grubbs $2^{nd}$ generation catalyst (85 mg, 0.14 mmol) and 2,6-dichlorobenzoquinone (8 mg, 0.05 mmol) in anhydrous toluene (150 mL) was added a solution of 3b (250 mg, 0.45 mmol) in toluene/dichloroethane (1:1, 9 mL) over 1 h. Following 1 h at reflux, a further amount of Hoveyda Grubbs $2^{nd}$ generation catalyst (42 mg, 0.07 mmol) was added and heating continued for 3 h. The reaction was cooled to room temperature and evaporated to dryness. The residue was purified by silica gel chromatography using ethyl acetate then ethyl acetate/acetone 3/1 to yield a brown foam. This was purified further by preparative TLC using ethyl acetate/acetone 8/1 (2×) to yield the title compound (2 mg, 1%) as a white solid. $^1$H NMR (300 MHz, CDCl$_3$) 0.73-1.20 (m, 9H), 1.40-2.08 (m, 5H), 2.15-2.61 (m, 4H), 3.14-4.15 (m, 6H), 4.78-5.63 (m, 3H), 6.67-7.03 (m, 2H), 7.38-7.58 (m, 2H), 7.83-8.04 (m, 2H), 9.17 (s, 1H). LCMS (m/z)=522.2 [M+H], Tr=1.33 min.

Example 4

Compound 4

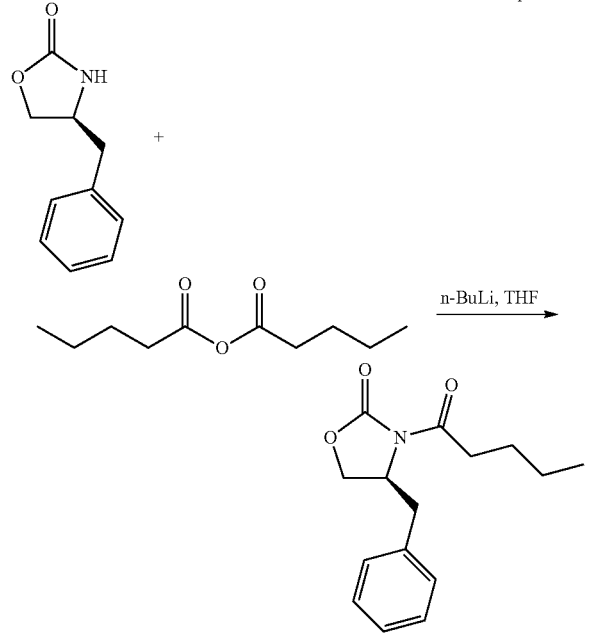

Compound 4a

Synthesis of Compound 4a:

To a solution of (S)-4-benzyl-2-oxazolidinone (3.85 g, 21.7 mmol) in tetrahydrofuran (10 mL) at −78° C., was added 2.5 M butyllithium in hexanes (10 mL, 25 mmol) and the mixture stirred for 5 min. Valeric anhydride (5.15 mL, 26.1 mmol) was then added and the solution stirred at −78° C. for 50 min before addition of brine (10 mL). The mixture was then allowed to warm to room temperature when more brine (20 mL) was added. The organics were extracted with ethyl acetate (2×50 mL) and the combined extract was dried over sodium sulfate, filtered and evaporated to give a crude oil. This was purified by silica gel chromatography using iso-hexane/ethyl acetate 9:1 to yield the title compound (5.24 g, 92%).

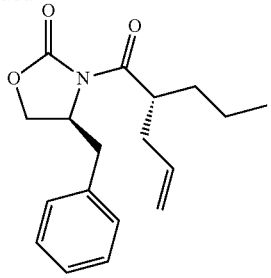

Synthesis of Compound 4b:

A solution of 4a (5.24 g, 20.0 mmol) in tetrahydrofuran (50 mL) was cooled to −78° C. 1 M sodium hexamethyldisilazane in tetrahydrofuran (32.1 mL, 32 mmol) was added dropwise and the internal temperature kept below −70° C. Upon complete addition, stirring was continued at −78° C. for 1 h. After this time allyl bromide (6.98 mL, 80.2 mmol) was added dropwise and the internal temperature kept between −55° C. to −40° C. Upon complete addition stirring was continued between −55° C. and −40° C. for 3 h, after which saturated ammonium chloride (20 mL) was added and the mixture allowed to warm to room temperature. The organics were extracted with ethyl acetate (2×100 mL), washed with brine, dried over sodium sulfate and evaporated to give a crude yellow oil. This was purified by silica gel chromatography using iso-hexane/ethyl acetate 1:0 then 95:5 then 9:1 to yield the title compound (2.95 g, 49%).

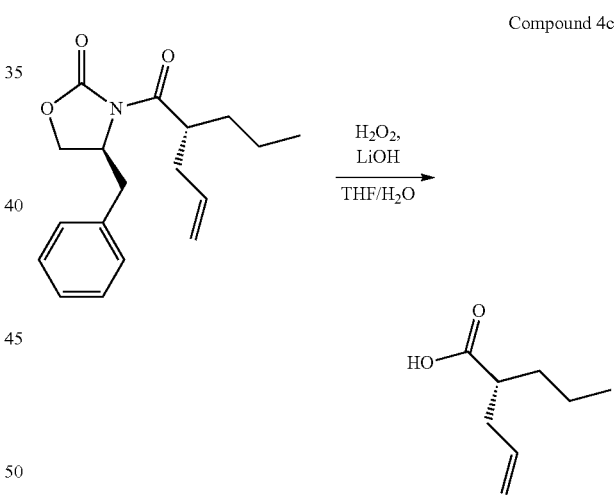

Compound 4c

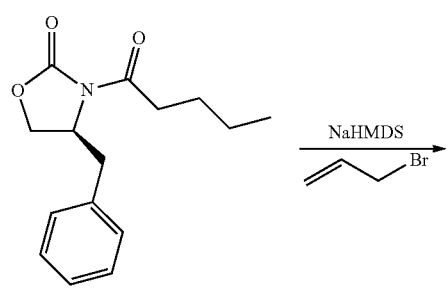

Synthesis of Compound 4c:

A solution of 4b (2.95 g, 9.79 mmol) in tetrahydrofuran (72 mL) and water (36 mL) was cooled to 0° C. 30% aqueous hydrogen peroxide (4.72 mL, 48.9 mmol) was added followed by a solution of lithium hydroxide (470 mg, 19.6 mmol) in water (7.2 mL). The mixture was stirred at 0° C. and after 3.42 h a solution of sodium sulphite (11.3 g, 90 mmol) in water (36 mL) was added and the solution stirred at 0° C. for 15 min. The solution was treated with saturated sodium hydrogen carbonate until pH=9-10, then the aqueous phase was washed with ethyl acetate (3×100 mL) then acidified to pH=1-2 with 1 M sulphuric acid and extracted with diethyl ether (3×100 mL). The diethyl ether extracts were dried over sodium sulfate, filtered and evaporated to give the title compound (649 mg, 47%) as a colorless oil.

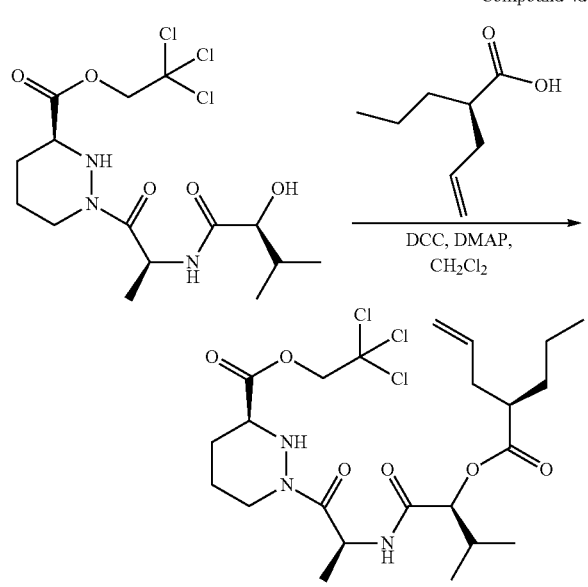

Compound 4d

Synthesis of Compound 4d:

To a solution of 1e (790 mg, 1.82 mmol) in dichloromethane (9 mL) at room temperature, was added 4c (388 mg, 2.19 mmol), N,N'-dicyclohexylcarbodiimide (564 mg, 2.74 mmol) and 4-dimethylaminopyridine (223 mg, 1.82 mmol) and the reaction mixture stirred at room temperature for 3 h. After this time the reaction mixture was diluted with dichloromethane (50 mL) and washed with a saturated ammonium chloride solution. The aqueous phase was re-extracted with dichloromethane (2×50 mL) and the combined organics washed with brine (100 mL), dried over magnesium sulfate and evaporated to give a white residue. This was purified by silica gel chromatography using iso-hexane/ethyl acetate 1:0 to 1:1 to yield the title compound (916 mg, 90%).

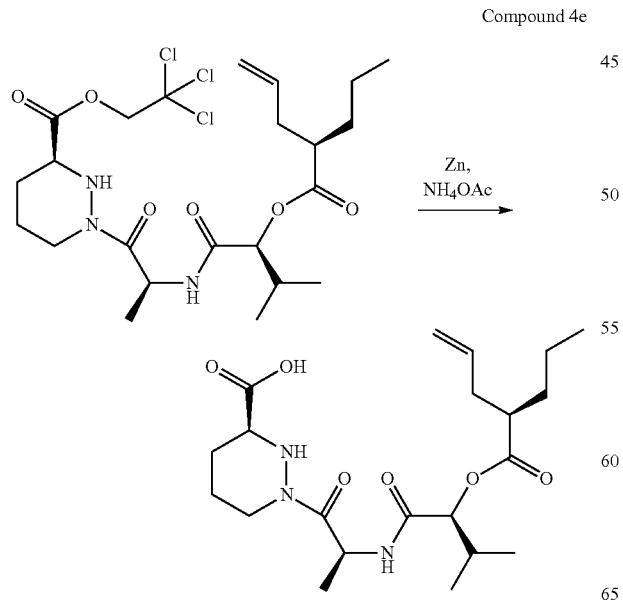

Compound 4e

Synthesis of Compound 4e:

A solution of 4d (916 mg, 1.65 mmol) in tetrahydrofuran (41 mL) was prepared and powdered zinc (2.37 g, 36.2 mmol) was added followed by a solution of ammonium acetate (1.90 g, 24.7 mmol) in water (10.2 mL). The reaction mixture was stirred at room temperature for 24 h. The reaction was filtered through hyflo-supercel washing through with ethyl acetate and saturated aqueous potassium hydrogen sulfate. The mixture was treated with hydrochloric acid (1 M, 5 mL) and the layers were separated. The aqueous layer was extracted with ethyl acetate (2×100 mL). The organic layers were combined, washed with brine, dried over sodium sulfate, filtered and evaporated to give a colorless gum. The residue was azeotroped with toluene (3×100 mL) to give the title compound (675 mg, 89%) as a white solid.

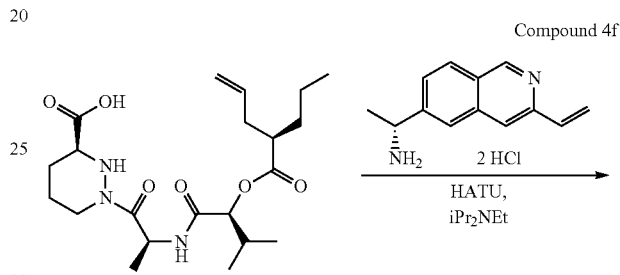

Compound 4f

Synthesis of Compound 4f:

4e (368 mg, 0.87 mmol) was dissolved in acetonitrile (5 mL) and 2j (180 mg, 0.77 mmol) was added followed by N,N-diisopropylethylamine (535 µL, 3.07 mmol) and 2-(1H-7-azabenzotriazol-1-yl)-1,1,3,3-tetramethyl uronium hexafluorophosphate methanaminium (409 mg, 1.08 mmol). The reaction mixture was stirred at room temperature for 72 h. To the reaction mixture was added 2 M hydrochloric acid (15 mL) and the mixture was concentrated in vacuo. The residue was partitioned between water (100 mL) and ethyl acetate (100 mL). The aqueous layer was separated and re-extracted with ethyl acetate (100 mL). The organic layers were combined, dried over sodium sulfate, filtered and evaporated to give a crude residue. The residue was purified by silica gel chromatography using ethyl acetate to give the title compound (440 mg, 95%) as an off-white solid.

Compound 4

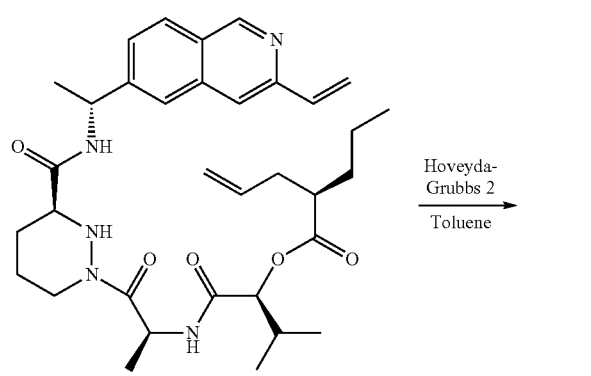

Synthesis of the Title Compound:

A solution of 4f (440 mg, 0.73 mmol) in toluene (242 mL) was degassed with nitrogen for 15 min then Hoveyda-Grubbs $2^{nd}$ generation catalyst (91 mg, 0.15 mmol) was added and the reaction mixture heated at 100-110° C. for 2.5 h. After this time more Hoveyda-Grubbs $2^{nd}$ generation catalyst (91 mg, 0.15 mmol) was added and the reaction mixture heated at 110° C. for 1 h and allowed to cool to room temperature. The residue was purified by silica gel chromatography using a gradient of iso-hexane/ethyl acetate 1:1 to neat ethyl acetate. Impure product (160 mg) was further purified by silica gel chromatography using a gradient of dichloromethane/acetone 99:1 to 4:1. Pure product (4.4 mg) was obtained along with impure fractions which were further purified by reverse phase preparative HPLC where pure product (22.6 mg) was collected. After purification the title compound was collected (27 mg total, 6%) as a white solid. $^1$H NMR (300 MHz, CD$_3$OD) 0.93-1.11 (m, 11H), 1.24-1.47 (m, 6H), 1.63-1.82 (m, 3H), 1.84-2.01 (m, 3H), 2.41-2.72 (m, 2H), 2.82 (td, J=13.1, 3.1 Hz, 1H), 3.59-3.70 (m, 1H), 4.46 (dd, J=9.8, 3.3 Hz, 1H), 4.70-4.79 (m, 2H), 5.17 (q, J=6.9 Hz, 1H), 5.83-5.96 (m, 1H), 6.70 (d, J=16.5 Hz, 1H), 6.85-6.99 (m, 1H), 7.59 (dd, J=8.5, 1.6 Hz, 1H), 7.71 (s, 1H), 7.96 (s, 1H), 8.03 (d, J=8.5 Hz, 1H), 8.54 (br d, J=8.9 Hz, 1H), 9.10 (s, 1H). LCMS (m/z) 578.3 [M+H], Tr=1.67 min.

Example 5

Compound 5

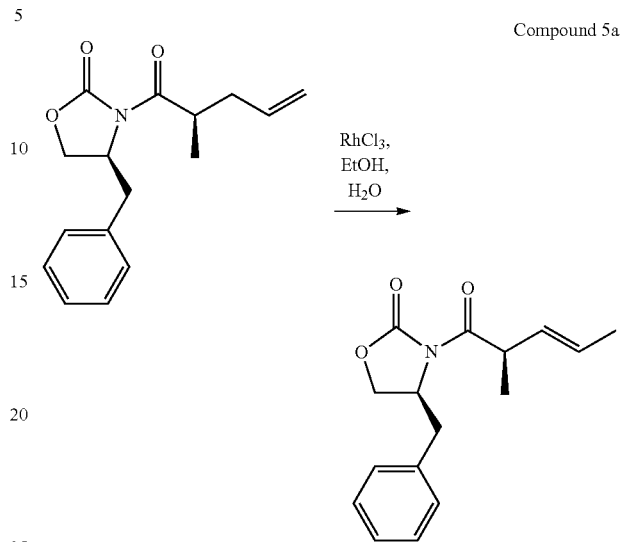

Synthesis of Compound 5a:

To (S)-4-benzyl-3-((R)-2-methyl-pent-4-enoyl)-oxazolidin-2-one (Prepared as in JACS 1990, 112 (8) 2998-3017, 2.5 g, 9.16 mmol) in ethanol (13 mL) and water (1.5 mL) at room temperature was added rhodium trichloride hydrate (48 mg, 0.23 mmol). The reaction was heated to 80° C. for 8 h, cooled and concentrated in vacuo. To the ensuing residue was added water and extracted with dichloromethane. The organic layer was dried through a hydrophobic frit and concentrated in vacuo to yield the title compound (2.2 g, 88%) as a brown oil.

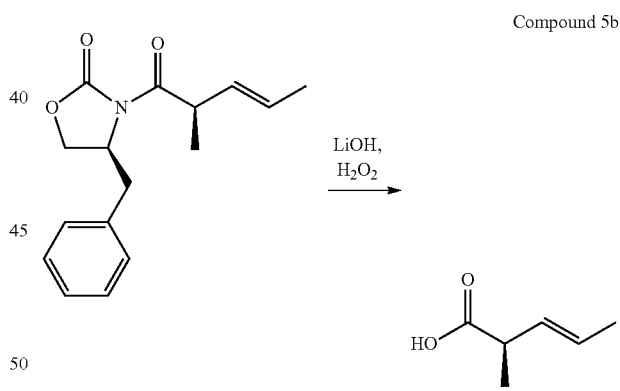

Synthesis of Compound 5b:

To 5a (2.2 g, 8.1 mmol) in tetrahydrofuran (60 mL) and water (20 mL) at 0° C. was added lithium hydroxide (16 mL, 2.0 M solution in water, 32.2 mmol) and hydrogen peroxide (6.6 mL, 30% aqueous solution, 64.5 mmol). The reaction was stirred at 0° C. for 16 h and then quenched by careful addition of aqueous sodium thiosulfate. The reaction mixture was concentrated to remove the tetrahydrofuran and then washed twice with dichloromethane. The aqueous layer was acidified to pH 1 with 2 M hydrochloric acid and extracted twice with diethyl ether. The combined organic layers were dried through a hydrophobic frit and concentrated in vacuo. The residue was purified by silica gel chromatography using iso-hexane/ethyl acetate 5/1 to afford the title compound (530 mg, 57%) as a clear oil.

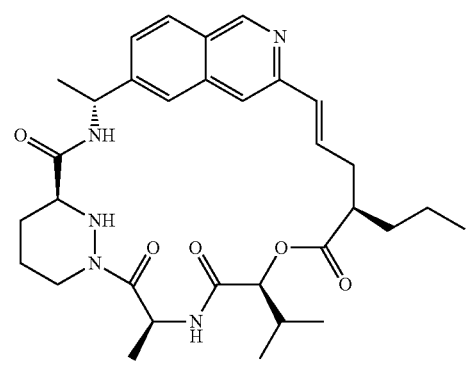

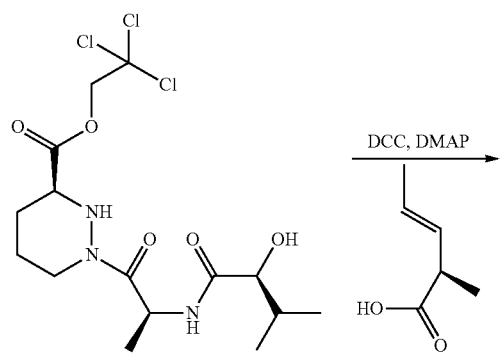

Compound 5c

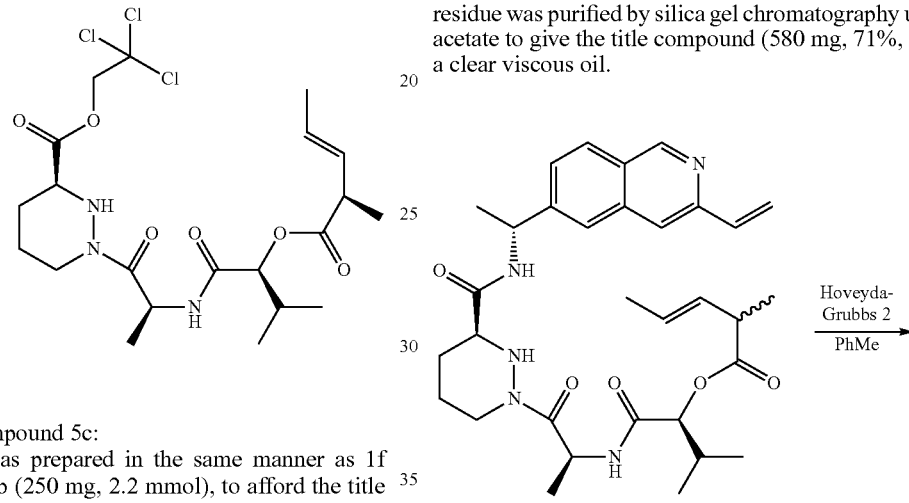

Synthesis of Compound 5c:
Compound 5c was prepared in the same manner as 1f replacing 1c with 5b (250 mg, 2.2 mmol), to afford the title compound (750 mg, 77%) as a white foam.

Synthesis of Compound 5d:
To a solution of 5c (750 mg, 1.42 mmol) in tetrahydrofuran (35 mL) and water (20 mL) was added powdered zinc (2.03 g, 31.2 mmol) followed by ammonium acetate (1.64 g, 21.3 mmol). The reaction mixture was stirred at room temperature for 15 h. The reaction was filtered through Celite, the filtrate was acidified to pH 2 with concentrated hydrochloric acid and extracted twice with ethyl acetate. The organic layers were dried through a hydrophobic frit and concentrated in vacuo, followed by co-evaporation from toluene (2×). The ensuing residue was dissolved in anhydrous acetonitrile (15 mL) and 2j (385 mg, 1.4 mmol) was added followed by N,N-diisopropylethylamine (743 μL, 4.3 mmol) and 2-(1H-7-azabenzotriazol-1-yl)-1,1,3,3-tetramethyl uronium hexafluorophosphate methanaminium (755 mg, 2.0 mmol). The reaction mixture was stirred at room temperature for 3 h. Silica gel was added to the reaction mixture and concentrated in vacuo. The residue was purified by silica gel chromatography using ethyl acetate to give the title compound (580 mg, 71%, 2 steps) as a clear viscous oil.

Compound 5

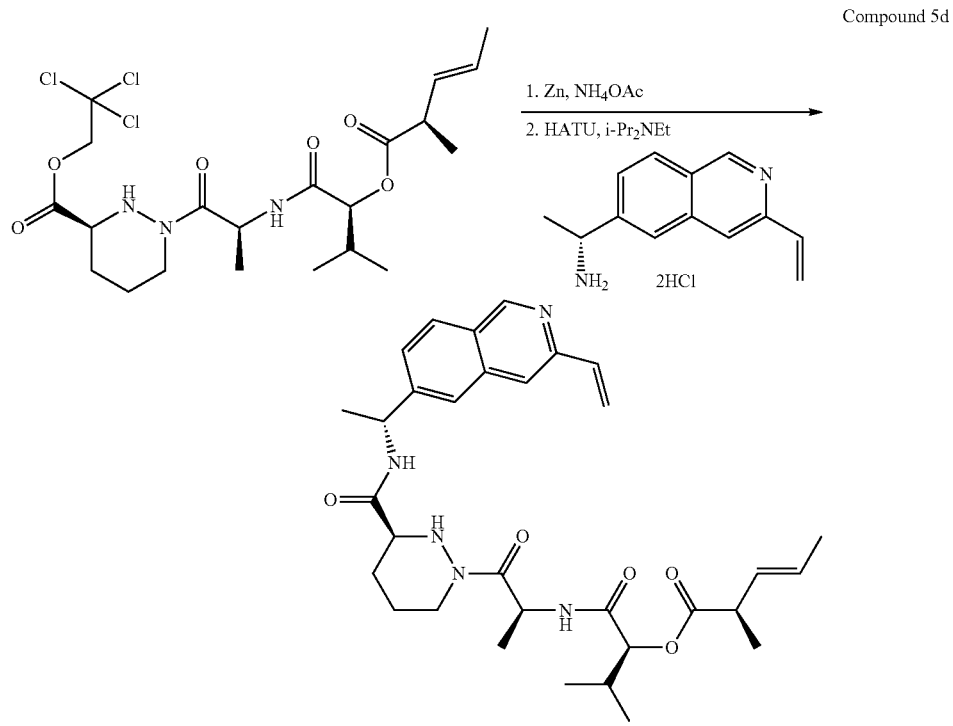

Compound 5d

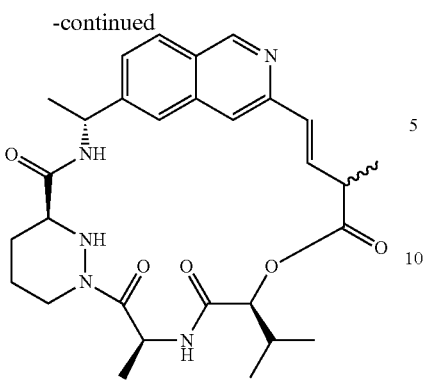

Synthesis of the Title Compound:

A solution of 5d (250 mg, 0.43 mmol) in toluene (144 mL) was degassed with nitrogen for 30 min before warming to 70° C. and adding Hoveyda Grubbs 2$^{nd}$ generation catalyst (54 mg, 0.09 mmol). The stirred solution was heated to 125° C. for 45 min. A further amount of Hoveyda Grubbs 2$^{nd}$ generation catalyst (50 mg, 0.08 mmol) was added and heating continued for 2 h. Another portion of Hoveyda Grubbs 2$^{nd}$ generation catalyst (27 mg, 0.04 mmol) was added and heating continued for 3 h. The reaction was cooled to room temperature and potassium isocyanoacetate (120 mg) in methanol (2 mL) was added. After stirring for 1 h, the reaction mixture was concentrated to approximately half its original volume, treated with silica gel and then evaporated to dryness. The residue was purified by silica gel chromatography using ethyl acetate/acetone 1/0 then 5/1 to yield a white solid. This was purified further by reverse phase preparative HPLC to yield the title compound (2 mg, 1%) as a white solid. $^1$H NMR (300 MHz, d$_4$-MeOH, 2:1 diastereomeric mix, major diastereomer peaks quoted) 0.99 (d, J=6.7 Hz, 3H), 1.01 (d, J=6.7 Hz, 3H), 1.47 (d, J=6.9 Hz, 3H), 1.56-1.64 (m, 6H), 1.65-1.79 (m, 1H), 1.83-2.00 (m, 3H), 2.09-2.25 (m, 1H), 2.73-2.87 (m, 1H), 3.41-3.52 (m, 1H), 3.63-3.71 (m, 1H), 4.38-4.48 (m, 1H), 5.12 (d, J=8.5 Hz, 1H), 5.18 (q, J=6.7 Hz, 1H), 5.82 (q, J=7.1 Hz, 1H), 6.47 (dd, J=16.0, 6.3 Hz, 1H), 6.67 (dd, J=16.0, 1.0 Hz, 1H), 7.60-7.67 (m, 2H), 7.75 (s, 1H), 8.06 (d, J=8.7 Hz, 1H), 9.14 (s, 1H). LCMS (m/z)=536.2 [M+H], Tr=1.30 min.

Example 6

Compound 6

Compound 6a

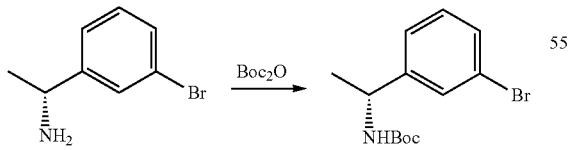

Synthesis of Compound 6a:

A solution of (R)-bromo-α-methylbenzylamine (2.0 g, 10 mmol) in dichloromethane (20 mL) was treated with a solution of di-tert-butyl dicarbonate (2.4 g, 11 mmol) in dichloromethane (20 mL) and the reaction mixture was stirred at room temperature for 1 h. The solution was washed with 2 M hydrochloric acid, water and brine, dried over sodium sulfate, filtered and evaporated. The residue was purified by silica gel chromatography using a gradient of iso-hexane/ethyl acetate 20:1 to 6:1 to afford the title compound (2.51 g, 84%) as a white solid.

Compound 6b

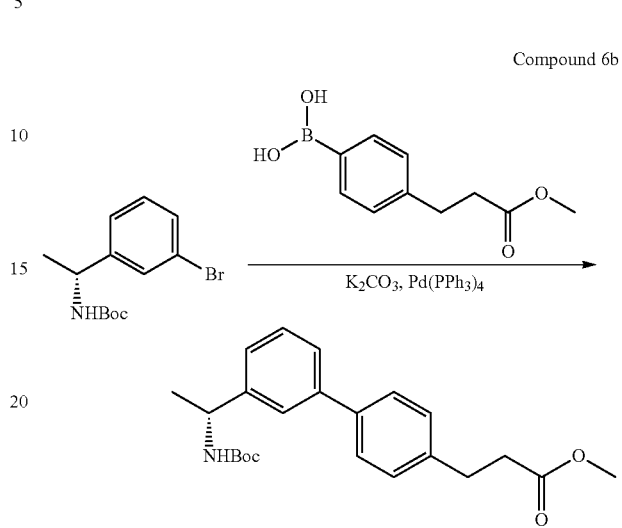

Synthesis of Compound 6b:

A mixture of 6a (900 mg, 3 mmol), 4-(2-methoxycarbonylethyl)phenylboronic acid (624 mg, 3 mmol) in 1,2-dimethoxyethane (10 mL) and potassium carbonate (828 mg, 6 mmol) in water (2 mL), was stirred at room temperature. Tetrakis(triphenylphosphine)palladium(0) (172 mg, 0.15 mmol) was added and the reaction mixture was heated at 100° C. in a microwave reactor for 1 hour. The organic layer was separated. The organic layer was filtered through a hydrophobic frit and the filtrate was evaporated. The residue was purified by silica gel chromatography using a gradient of iso-hexanes/ethyl acetate 20:1 to 5:1 to afford the title compound (958 mg, 83%) as a white solid.

Compound 6c

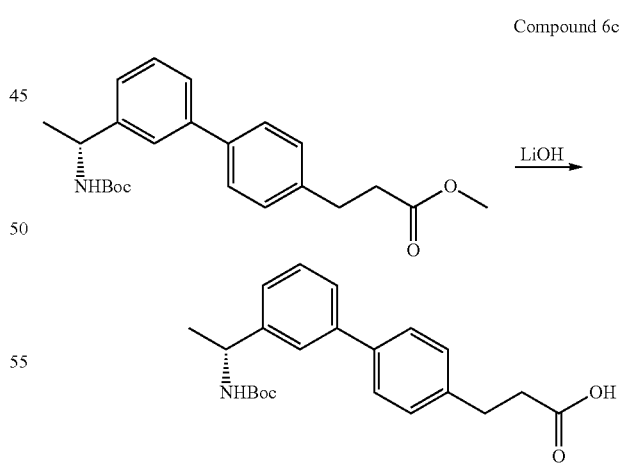

Synthesis of Compound 6c:

A solution of 6b (958 mg, 2.5 mmol) in tetrahydrofuran (15 mL) was stirred at 5° C. A solution of lithium hydroxide hydrate (300 mg, 5 mmol) in water (5 mL) was added and the reaction mixture was stirred at 5° C. for 1 hour and then at room temperature for 1 hour. The majority of the solvent was evaporated and water was added and 2 M hydrochloric acid was added to adjust the pH of the solution to pH 2. The mixture was extracted with ethyl acetate. The organic extracts were combined, washed with water and brine. The organic layer was filtered through a hydrophobic frit and the filtrate was evaporated to afford the title compound (883 mg, 96%) as a white solid.

Compound 6d

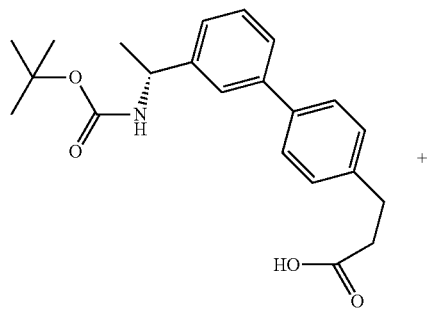

+

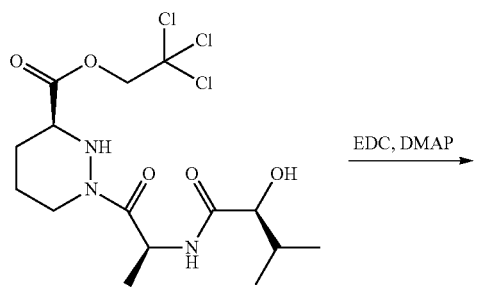

EDC, DMAP →

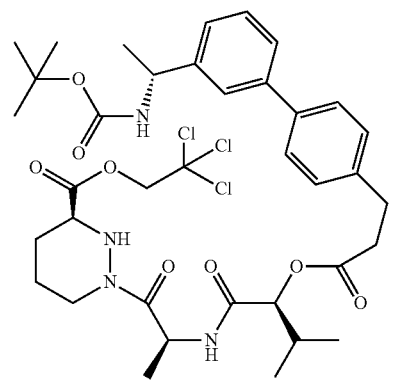

Synthesis of Compound 6d:

A solution of 6c (1.6 g, 4.3 mmol), 1e (1.86 g, 4.3 mmol) in dichloromethane (60 mL) was stirred at room temperature under nitrogen. N-(3-Dimethylaminopropyl)-N'-ethylcarbodiimide hydrochloride (1.25 g, 6.5 mmol) and 4-dimethylaminopyridine (525 mg, 4.3 mmol) was added and the reaction mixture was stirred at room temperature under nitrogen for 24 h. The reaction mixture was diluted with dichloromethane and the solution was washed with an aqueous citric acid solution (pH 2-3), water and brine. The organic layer was filtered through a hydrophobic frit and the filtrate was evaporated. The residue was purified by silica gel chromatography using iso-hexanes/ethyl acetate 6:4 followed by silica gel chromatography using iso-hexanes/ethyl acetate 6:4 to afford the title compound (2.0 g, 60%) as a white foam.

Compound 6e

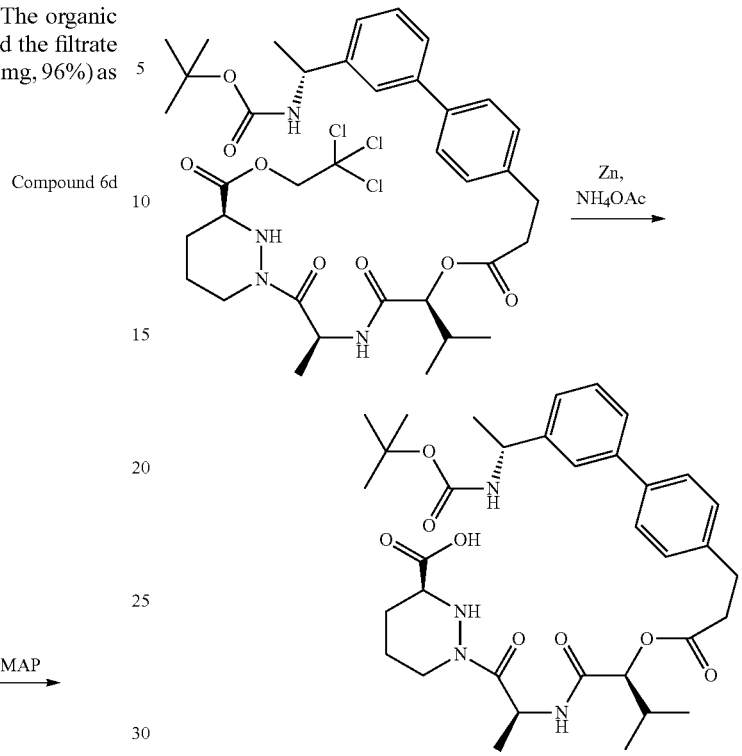

Synthesis of Compound 6e:

A solution of 6d (1.96 g, 2.5 mmol) in tetrahydrofuran (50 mL) was stirred at room temperature under nitrogen. Zinc dust (3.58 g, 55 mmol) was added followed by a solution of ammonium acetate (2.9 g, 37.5 mmol) in water (25 mL) and the reaction mixture was stirred at room temperature under nitrogen for 24 hours. The reaction mixture was filtered through Celite and the filter pad was washed with ethyl acetate and 2 M hydrochloric acid. The filtrate was acidified to pH 2 with 2 M hydrochloric acid and sodium chloride was added to saturate the aqueous layer. The mixture was extracted with ethyl acetate (3×). The organic extracts were combined, washed with water and brine, dried over anhydrous magnesium sulfate and the solvent was evaporated. The residue was co-evaporated with ethyl acetate (3×), toluene (4×) and dried to afford the title compound (1.56 g, 95%) as a white solid.

Compound 6

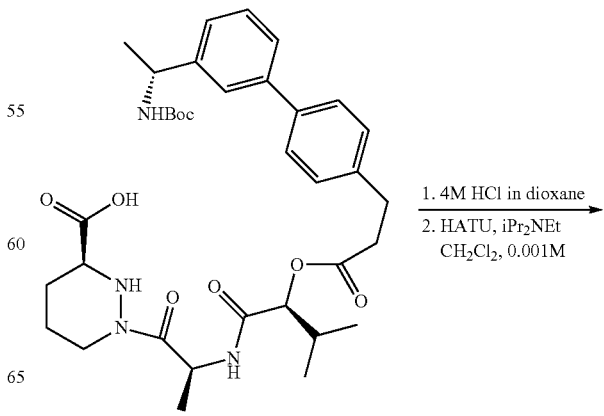

1. 4M HCl in dioxane
2. HATU, iPr₂NEt
   CH₂Cl₂, 0.001M

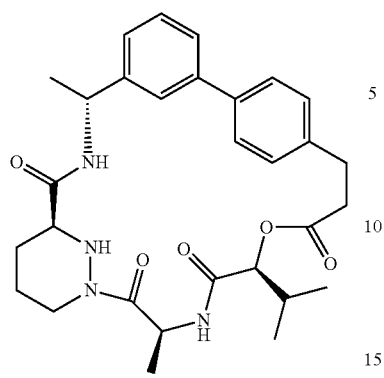

Synthesis of the Title Compound:

A mixture of 6e (850 mg, 1.3 mmol) in 4M HCl in 1,4-dioxane (12 mL) was stirred at room temperature under nitrogen for 1 h. The solvent was evaporated and the residue was triturated with diethyl ether (3×). The resulting solid was collected, washed with diethyl ether and dried to afford (S)-1-[(S)-2-((S)-2-{3-[3'-((R)-1-amino-ethyl)-biphenyl-4-yl]-propionyloxy}-3-methyl-butyrylamino)-propionyl]-hexahydro-pyridazine-3-carboxylic acid hydrochloride (1.3 mmol). A solution of (S)-1-[(S)-2-((S)-2-{3-[3'-((R)-1-amino-ethyl)-biphenyl-4-yl]-propionyloxy}-3-methyl-butyrylamino)-propionyl]-hexahydro-pyridazine-3-carboxylic acid hydrochloride (1.3 mmol) and N,N-diisopropylethylamine (671 mg, 0.9 mL, 5.2 mmol) in dichloromethane (1300 mL) was stirred at 0° C. under nitrogen. 2-(1H-7-Azabenzotriazol-1-yl)-1,1,3,3-tetramethyl uronium hexafluorophosphate methanaminium (988 mg, 2.6 mmol) was added and the reaction mixture was stirred at room temperature for 20 h. The solvent was evaporated and the residue was purified by silica gel chromatography using a gradient of iso-hexanes/acetone 7:3 to 1:1 followed by silica gel chromatography using ethyl acetate. The resulting solid was triturated with ether and the solid was collected and dried to afford the title compound (395 mg, 57%) as a white solid. $^1$H NMR (300 MHz, CD$_3$OD) δ 0.94 (d, J=6.7 Hz, 3H), 1.00 (d, J=6.7 Hz, 3H), 1.31 (d, J=7.1 Hz, 3H), 1.54 (d, J=6.9 Hz, 3H), 1.85-2.20 (m, 5H), 2.65-3.10 (m, 5H), 3.53-3.59 (m, 1H), 4.38-4.25 (m, 1H), 4.64 (d, J=12.5 Hz, 1H), 4.72 (d, J=9.6 Hz, 1H), 5.05 (q, J=6.9 Hz, 1H), 5.24 (q, J=7.1 Hz, 1H), 4.82-4.90 (m, 2H), 7.23-7.30 (m, 3H), 7.37-7.55 (m, 5H). LCMS (m/z) 535.2 [M+H], Tr=5.11 min.

Example 7

(E)-(2R,5S,11S,14S,17R,18R)-18-Hydroxy-14-isopropyl-2,11,17-trimethyl-15-oxa-3,9,12,28-tetraazatricyclo[21.3.1.1*5,9*]octacosa-1(26),21,23(27),24-tetraene 4,10,13,16-tetraone—Compound 7

Compound 7a

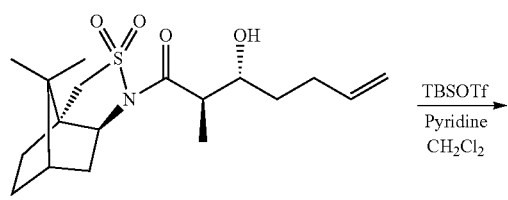

Synthesis of Compound 7a:

A solution 1a (12.0 g, 0.034 mol) in anhydrous dichloromethane (520 mL) was cooled to 0° C. before addition of pyridine (5.5 mL, 0.068 mol), then trifluoromethanesulfonic acid tert-butyldimethylsilyl ester (9 mL, 0.039 mol). The reaction was stirred at 0° C. for 15 min then allowed to warm to room temperature for 1.5 h. The reaction mixture was quenched with saturated aqueous sodium bicarbonate solution (400 mL). The aqueous layer was back extracted with dichloromethane (200 mL). The organic layers were combined and washed with brine (200 mL) and then 2 M hydrochloric acid (200 mL). The solution was dried over sodium sulfate, filtered and evaporated to give the title product (15.29 g, 96%) as a white solid.

Compound 7b

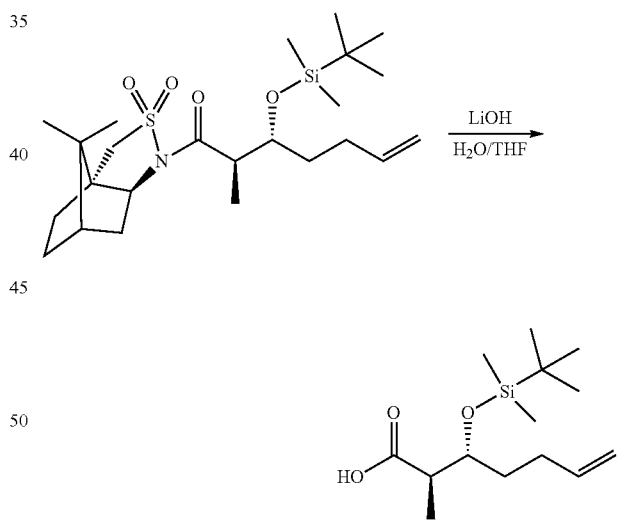

Synthesis of Compound 7b:

A solution of 7a (15.29 g, 0.0325 mol) in tetrahydrofuran (300 mL) was prepared and an aqueous solution of lithium hydroxide (2 M, 120 mL) was added. The stirred mixture was heated to 60° C. for 16 h. The reaction mixture was cooled to room temperature then treated with 2 M hydrochloric acid (250 mL). The layers were separated and the aqueous layer was extracted with ethyl acetate (2×200 mL). The organic layers were combined, dried over sodium sulfate, filtered and evaporated to give an off-white solid. The solid was purified by silica gel chromatography using diethyl ether/iso-hexane 3:7 to yield the title product (7.18 g, 81%) as a colorless gum.

Compound 7c

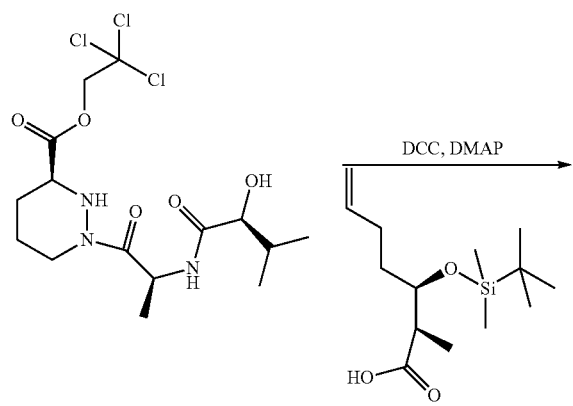

Synthesis of Compound 7c:

To 1e (510 mg, 1.2 mmol) in anhydrous dichloromethane (4 mL) at room temperature and under an atmosphere of nitrogen was added 7b (385 mg, 1.41 mmol), dicyclohexylcarbodiimide (364 mg, 1.8 mmol) and 4-N,N-dimethylaminopyridine (142 mg, 1.2 mmol). The white suspension was stirred at room temperature for 20 h before adding silica gel and concentrating in vacuo. The residue was purified by silica gel chromatography using iso-hexane/ethyl acetate 2/1 to afford the title compound (700 mg, 86%) as a viscous, clear oil.

Compound 7d

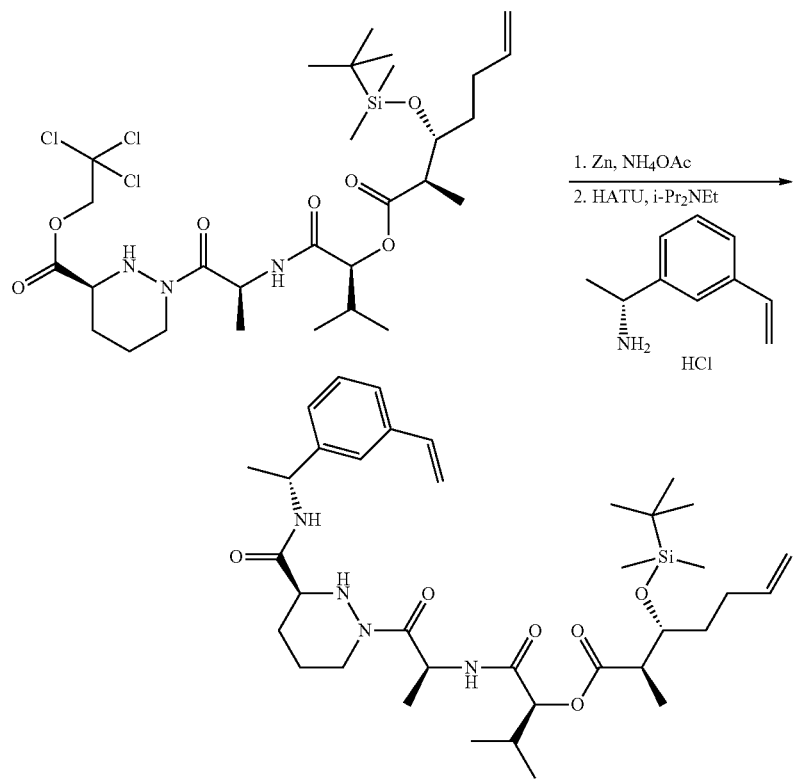

-continued

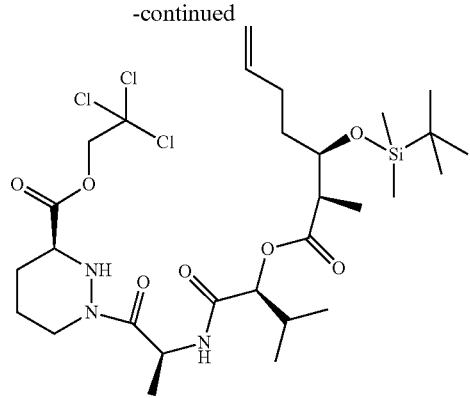

Synthesis of Compound 7d:

To a solution of 7c (700 mg, 1.02 mmol) in tetrahydrofuran (22 mL) and water (13 mL) was added powdered zinc (1.46 g, 22.4 mmol) followed by ammonium acetate (1.2 g, 15.3 mmol). The reaction mixture was stirred at room temperature for 15 h. The reaction was filtered through Celite and concentrated in vacuo to remove the tetrahydrofuran. The ensuing solution was acidified to pH 1-2 with concentrated hydrochloric acid and extracted with dichloromethane (2×). The organic layers were dried through a hydrophobic frit and concentrated in vacuo, followed by co-evaporation from toluene (2×). The ensuing colorless viscous oil was dissolved in anhydrous acetonitrile (8 mL) and 1j (187 mg, 1.0 mmol) was added followed by N,N-diisopropylethylamine (900 µL, 5.1 mmol) and 2-(1H-7-azabenzotriazol-1-yl)-1,1,3,3-tetramethyl uronium hexafluorophosphate methanaminium (542 mg, 1.4 mmol) The reaction mixture was stirred at room temperature for 15 h. Silica gel was added to the reaction mixture and concentrated in vacuo. The residue was purified by silica gel chromatography using iso-hexane/ethyl acetate 1/1 to give the title compound (450 mg, 64%) as an off-white solid.

purified by silica gel chromatography using ethyl acetate/acetone 8/1 to afford the title compound (33 mg, 16%, 2 steps) as a white solid. $^1$H NMR (500 MHz, CD$_3$CN) 0.92 (d, J=6.7 Hz, 3H), 0.97 (d, J=6.7 Hz, 3H), 1.26 (d, J=7.3 Hz, 3H), 1.31 (d, J=6.7 Hz, 3H), 1.41 (d, J=6.7 Hz, 3H), 1.43-1.63 (m, 4H), 1.78-1.89 (m, 2H), 2.03-2.09 (m, 1H), 2.40-2.49 (m, 2H), 2.50-2.56 (m, 1H), 2.65-2.72 (m, 1H), 3.32 (td, J=11.0, 2.4

Compound 7

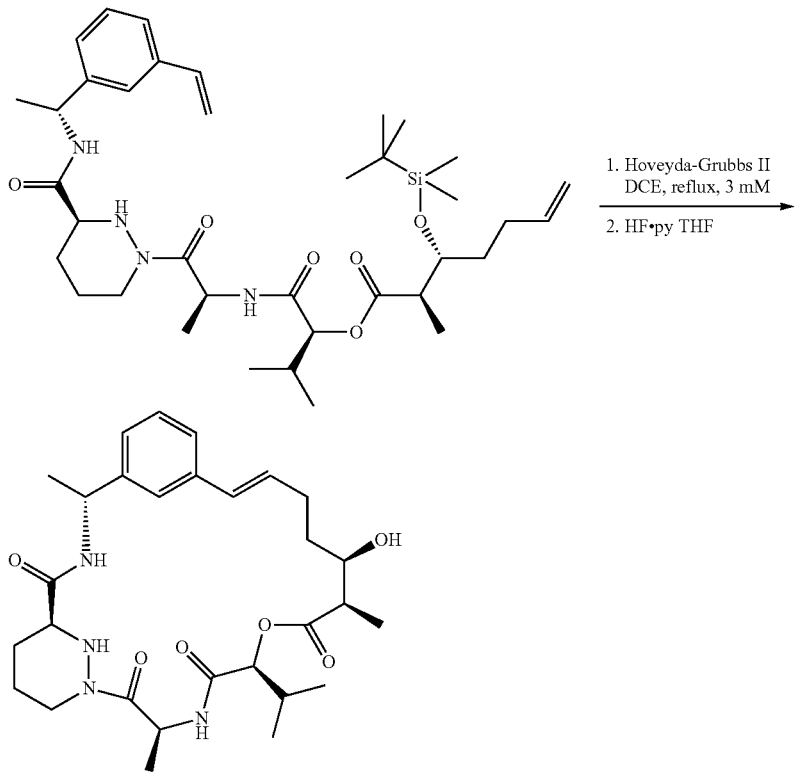

Synthesis of the Title Compound:

A solution of 7d (450 mg, 0.66 mmol) in 1,2-dichloroethane (219 mL) was degassed with nitrogen for 15 min before adding Hoveyda Grubbs 2$^{nd}$ generation catalyst (41 mg, 0.07 mmol). The stirred solution was heated to 80° C. for 2 h. The reaction was cooled, concentrated to approximately 20 mL, treated with silica gel and then evaporated to dryness. The residue was purified by silica gel chromatography using iso-hexane/ethyl acetate 1/1 then 1/3 to yield (E)-(2R,5S,11S,14S,17R,18R)-18-(tert-butyl-dimethyl-silanyloxy)-14-isopropyl-2,11,17-trimethyl-15-oxa-3,9,12,28-tetraaza-tricyclo[21.3.1.1*5,9*]octacosa-1(26),21,23(27),24-tetraene-4,10,13,16-tetraone (138 mg) as a brown foam. The foam (80 mg, 0.12 mmol) was dissolved in anhydrous tetrahydrofuran (6.5 mL) and transferred to a polypropylene vial. At ambient temperature hydrogen fluoride.pyridine (102 L, 1.2 mmol) was added to the reaction mixture followed by stirring for 1 h. An additional amount of hydrogen fluoride.pyridine (600 μL, 7.1 mmol) was added, followed by stirring for 1 h. More hydrogen fluoride.pyridine (700 μL, 8.2 mmol) was added and after 1 h the reaction was quenched by the slow addition of the reaction mixture to a stirred solution of ethyl acetate/saturated aqueous ammonium chloride. The organic layer was separated and the aqueous layer further extracted with ethyl acetate (2×). The combined organic layers were dried through a hydrophobic frit and concentrated in vacuo. The residue was Hz, 1H), 3.49-3.61 (m, 1H), 4.07 (d, J=12.2 Hz, 1H), 4.31 (d, J=12.8 Hz, 1H), 4.74 (d, J=5.5 Hz, 1H), 4.97-5.04 (m, 1H), 5.18-5.25 (m, 1H), 6.27-6.34 (m, 1H), 6.38 (d, J=15.9 Hz, 1H), 6.96-7.31 (m, 6H). LCMS (m/z)=543.2 [M+H], Tr=2.27 min.

Example 8

(E)-(2R,5S,11S,14S)-14-Isopropyl-2,11-dimethyl-15-oxa-3,9,12,28-tetraaza-tricyclo[21.3.1.1*5,9*]octacosa-1(27),21,23,25-tetraene-4,10,13,16-tetraone—Compound 8

Compound 8a

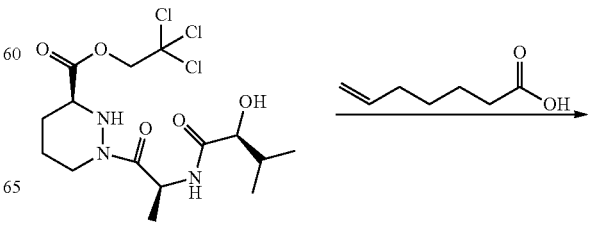

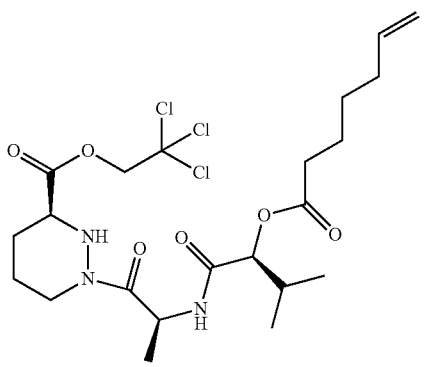

Synthesis of Compound 8a:

To a solution of 1e (791 mg, 1.83 mmol) in dichloromethane (9 mL) at room temperature, was added hept-6-enoic acid (0.296 mL, 2.19 mmol), N,N'-dicyclohexylcarbodiimide (564 mg, 2.74 mmol) and 4-N,N-dimethylaminopyridine (223 mg, 1.82 mmol) and the reaction mixture was stirred at room temperature for 2 h. After this time the reaction mixture was diluted with dichloromethane (50 mL) and washed with saturated aqueous ammonium chloride solution. The aqueous phase was re-extracted with dichloromethane (2×50 mL) and the combined organics washed with brine (100 mL) and dried over magnesium sulfate and evaporated to give a white residue. The residue was purified by silica gel chromatography using a gradient of iso-hexane:ethyl acetate 1:1 to neat ethyl acetate to yield the title compound (774 mg, 81%).

Compound 8b

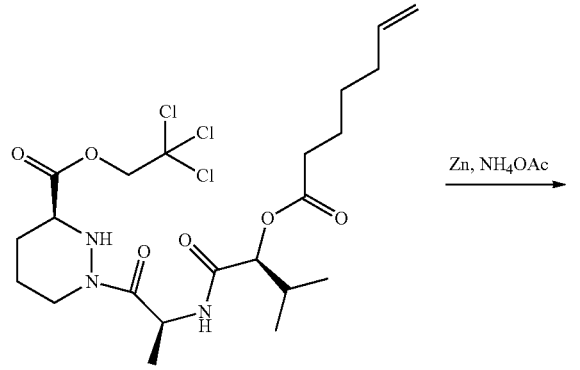

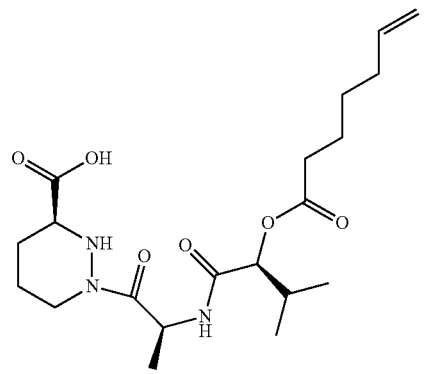

Synthesis of Compound 8b:

A solution of 8a (650 mg, 1.20 mmol) in tetrahydrofuran (29 mL) was prepared and powdered zinc (1.72 g, 26.3 mmol) was added followed by a solution of ammonium acetate (1.38 g, 18.0 mmol) in water (7.0 mL). The reaction mixture was stirred at room temperature for 72 h. The reaction was filtered through hyflo-supercel washing through with ethyl acetate and saturated aqueous potassium hydrogen sulfate. The mixture was treated with hydrochloric acid (1 M, 3 mL) and the layers were separated. The aqueous layer was extracted with ethyl acetate (2×100 mL). The organic layers were combined, washed with brine, filtered and evaporated to give a colorless gum. The residue was azeotroped with toluene (3×100 mL) to give the title compound (492 mg, quantitative yield) as a white solid.

Compound 8c

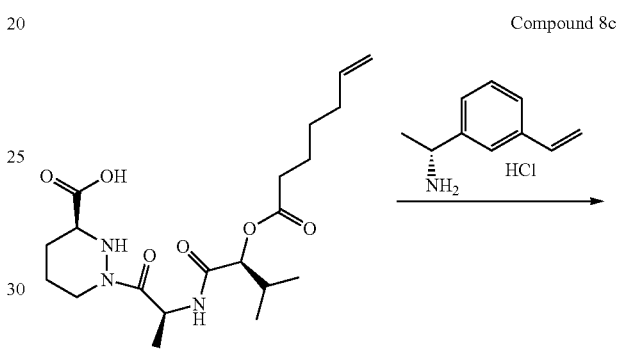

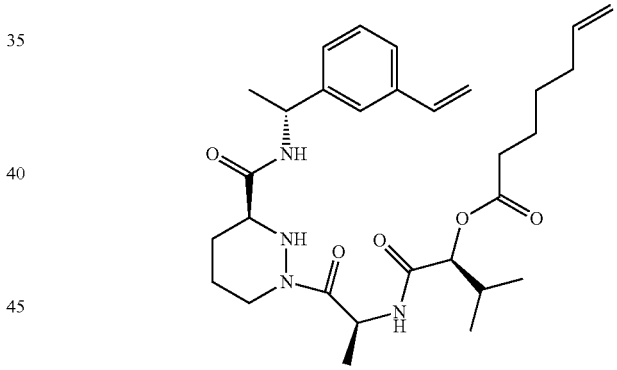

Synthesis of Compound 8c:

To 8b (257 mg, 0.63 mmol) dissolved in acetonitrile (2 mL) was added 1j (122 mg, 0.83 mmol) followed by N,N-diisopropylethylamine (435 μL, 2.5 mmol) and 2-(1H-7-azabenzotriazol-1-yl)-1,1,3,3-tetramethyl uronium hexafluorophosphate methanaminium (333 mg, 0.88 mmol). The reaction mixture was stirred at room temperature for 48 h. The mixture had evaporated to dryness over the 48 hours so this residue was partitioned between water (100 mL) and ethyl acetate (100 mL). The aqueous layer was separated and re-extracted with ethyl acetate (100 mL). The organic layers were combined, dried over magnesium sulfate, filtered and evaporated to give a crude residue. The residue was purified by silica gel chromatography using a gradient of iso-hexane:ethyl acetate 7:3 to 1:1 to neat ethyl acetate to give the title compound (194 mg, 57%).

Compound 8

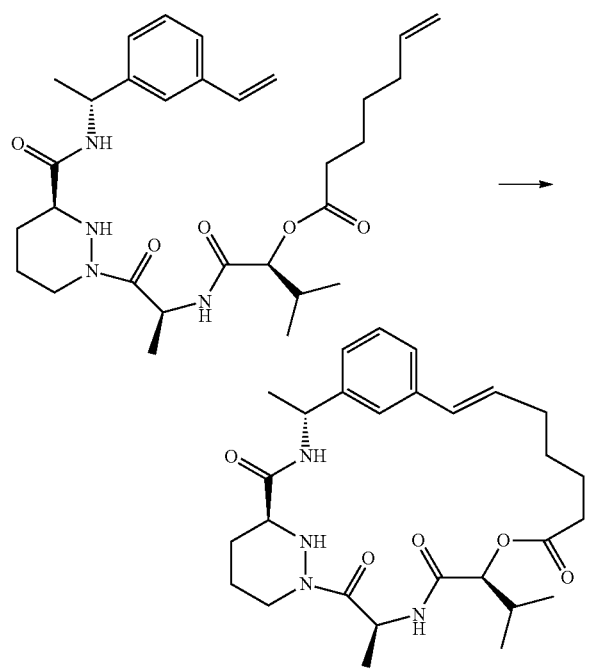

Synthesis of the Title Compound:

A solution of 8c (194 mg, 0.36 mmol) in 1,2-dichloroethane was degassed with nitrogen for 15 min then Hoveyda-Grubbs 2nd generation catalyst (23 mg, 0.04 mmol) was added and the reaction mixture heated at 80° C. for 2.3 h. After this time the reaction mixture was allowed to cool to room temperature and concentrated in vacuo. The residue was purified by silica gel chromatography using a gradient of iso-hexane/ethyl acetate 1:9 to neat ethyl acetate. Impure product (74 mg) was obtained which was further purified by preparatory reverse phase HPLC where the title compound was collected (28 mg, 15%) as a white solid. $^1$H NMR (300 MHz, CD$_3$OD). 0.96 (d, J=6.9 Hz, 3H), 0.99 (d, J=6.9 Hz, 3H), 1.41-1.51 (m, 8H), 1.59-1.82 (m, 4H), 1.85-1.96 (m, 2H), 2.02-2.26 (m, 3H), 2.32-2.57 (m, 2H), 2.80 (td, J=12.9, 2.2 Hz, 1H), 3.50 (dd, J=11.0, 2.5 Hz, 1H), 4.39 (br d, J=13.2 Hz, 1H), 4.76 (d, J=8.0 Hz, 1H), 4.99 (q, J=6.9 Hz, 1H), 5.46 (q, J=7.1 Hz, 1H), 6.19 (m, 1H), 6.40 (d, J=15.8 Hz, 1H), 7.11-7.17 (m, 1H), 7.20-7.30 (m, 3H). LCMS (m/z) 513.2 [M+H], Tr=2.58 min.

Example 9

Compound 9

Compound 9

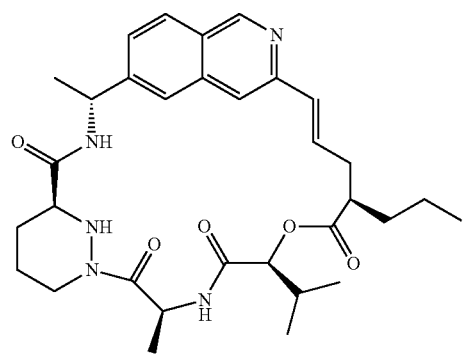

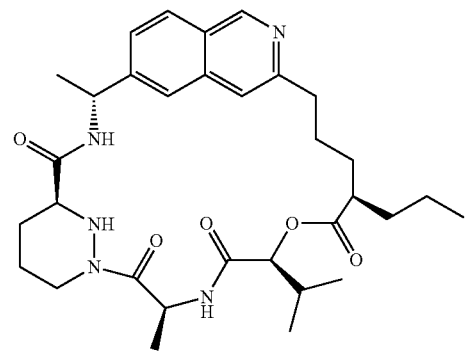

To a solution of compound 4 (16.6 mg, 0.0287 mmol) in ethyl acetate (10 mL) was added 10% palladium on carbon (5 mg) and stirred under a hydrogen atmosphere for 1.5 h. Then additional 10% palladium on carbon (5 mg) was added and stirring continued under a hydrogen atmosphere for 24 h. The reaction mixture was filtered through Celite to remove the catalyst and evaporated then purified by preparatory reverse phase preparative HPLC to yield the title compound (5.3 mg, 32%) as a white solid. $^1$H NMR (300 MHz, CD$_3$OD) 0.89-1.05 (m, 9H), 1.29-1.46 (m, 2H), 1.59 (dd, J=7.1, 1.6 Hz, 6H), 1.65-1.99 (m, 7H), 2.09-2.18 (m, 1H), 2.43-2.58 (m, 1H), 2.74-3.06 (m, 3H), 3.57-3.68 (m, 1H), 4.43 (dd, J=13.4, 2.7 Hz, 1H), 4.59 (br s, 3H), 4.66 (d, J=7.4 Hz, 1H), 5.15 (q, J=6.9 Hz, 1H), 5.66-5.78 (m, 1H), 7.58 (dd, J=8.5, 1.6 Hz, 1H), 7.69 (s, 1H), 7.70 (s, 1H), 8.03 (d, J=8.5 Hz, 1H), 8.40 (br d, J=8.7 Hz, 1H), 9.08 (s, 1H). LCMS (m/z) 580.3 [M+H], Tr=1.53 min.

Example 10

(2R,5S,11S,14S,17R,18R)-18-Hydroxy-14-isopropyl-2,11,17-trimethyl-15-oxa-3,9,12,28-tetraazatricyclo[21.3.1.1*5,9*]octacosa-1(26),23(27),24-triene-4,10,13,16-tetraone—Compound 10

Compound 10

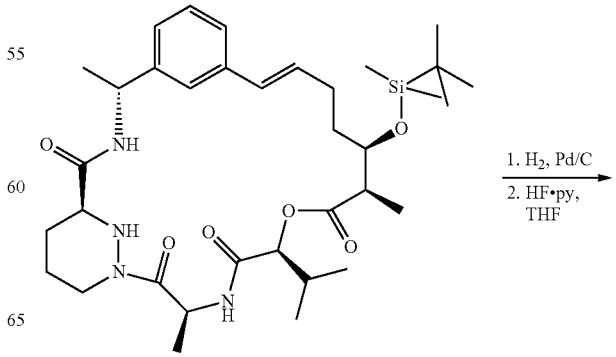

1. H$_2$, Pd/C
2. HF·py, THF

-continued

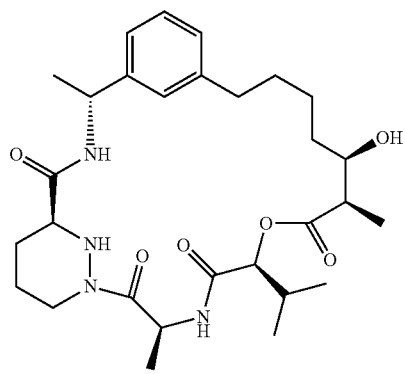

To (E)-(2R,5S,11S,14S,17R,18R)-18-(tert-butyl-dimethyl-silanyloxy)-14-isopropyl-2,11,17-trimethyl-15-oxa-3,9,12,28-tetraaza-tricyclo[21.3.1.1*5,9*]octacosa-1(26),21,23(27),24-tetraene-4,10,13,16-tetraone (50 mg, 0.08 mmol) in ethyl acetate (10 mL) at room temperature was added 10% palladium on carbon (50 mg). The system was purged with hydrogen gas and stirred vigorously for 16 h. The reaction mixture was filtered through Celite and the filter pad washed with methanol. The filtrate was concentrated in vacuo. The ensuing residue was dissolved in anhydrous tetrahydrofuran (5 mL) and transferred to a polypropylene vial. At room temperature hydrogen fluoride.pyridine (1.3 mL, 15.2 mmol) was added to the reaction mixture followed by stirring for 3 h. The reaction was diluted with ethyl acetate and quenched by cautious addition of saturated aqueous ammonium chloride. The organic layer was separated, dried through a hydrophobic frit and concentrated in vacuo. The residue was purified by silica gel chromatography using ethyl acetate/acetone 5/1 to afford the title compound as a white solid. This was further purified by triturating with diethyl ether, filtering and drying the solid in vacuo (20 mg, 48%, 2 steps). $^1$H NMR (300 MHz, CD$_3$CN) 0.90-1.00 (m, 6H), 1.24-1.30 (m, 6H), 1.43 (d, J=6.9 Hz, 3H), 1.32-2.08 (m, 11H), 2.45-2.81 (m, 4H), 3.23-3.36 (m, 1H), 3.47-3.59 (m, 1H), 3.67 (d, J=10.3 Hz, 1H), 4.02 (d, J=11.8 Hz, 1H), 4.29 (d, J=13.8 Hz, 1H), 4.75 (d, J=5.4 Hz, 1H), 4.95-5.08 (m, 1H), 5.16-5.29 (m, 1H), 7.03-7.29 (m, 6H). LCMS (m/z)=545.3 [M+H], Tr=2.15 min.

Example 11

Compound 11

Compound 11a

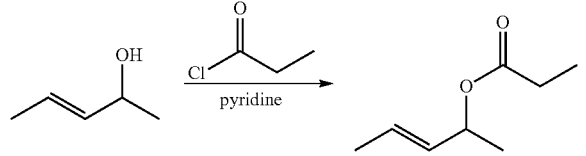

Synthesis of Compound 11a:

A cooled (0° C.) solution of (E)-pent-3-en-2-ol (1.024 g, 11.887 mmol) in dichloromethane (30 mL) was subsequently treated with pyridine (1.222 g, 1.3 mL, 15.452 mmol) and propionyl chloride (1.430 g, 1.3 mL, 15.452 mmol). After stirring for 1.5 h at 0° C. the reaction was quenched with saturated sodium bicarbonate. The aqueous layer was extracted with dichloromethane and then the organics were combined, filtered through a phase separator and the volatiles were removed in vacuo. The residue was purified by silica gel chromatography using a 50 g Isolute cartridge eluted with a continuous gradient of iso-hexane/Et$_2$O 1:0 to 9:1 to afford the title compound (787 mg, 46%) as a colorless oil.

Compound 11b

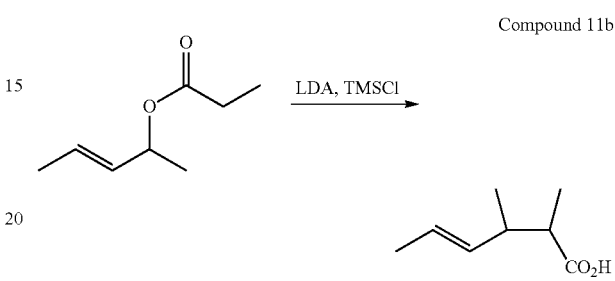

Synthesis of Compound 11b:

A cooled (0° C.) solution of N,N-diisopropylamine (672.0 mg, 930 µL, 6.641 mmol) in tetrahydrofuran (15 mL) was treated with n-butyl lithium (2.5 M in hexanes, 2.4 mL, 6.088 mmol). After stirring at 0° C. for 20 min this solution was cooled to −78° C. and subsequently treated with chlorotrimethylsilane (841.7 mg, 990 µL, 7.748 mmol) and a solution of 11a (787.0 mg, 5.534 mmol) in tetrahydrofuran (10 mL). The reaction mixture was slowly warmed to room temperature. After 16 h, the reaction was quenched with 1 M hydrochloric acid (40 mL) and the pH was adjusted to 2 with 2 M hydrochloric acid. The aqueous layer was extracted with ethyl acetate (2×40 mL), the organics were combined, dried over sodium sulfate, filtered and the volatiles were removed in vacuo. The residue was purified by silica gel chromatography using a 50 g Isolute cartridge eluted with a continuous gradient of iso-hexane/ethyl acetate 1:0 to 4:1 to afford the title compound (375 mg, 48%) as a colorless oil.

Compound 11c

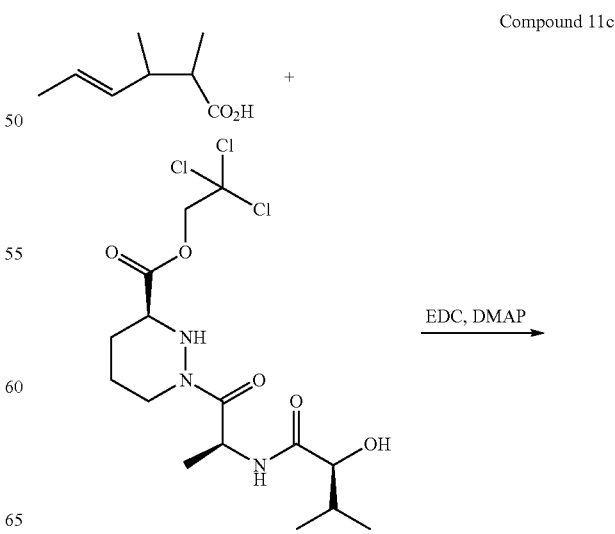

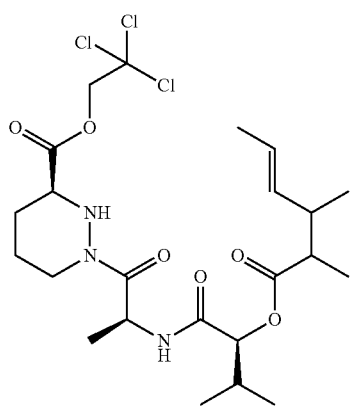

Synthesis of Compound 11c:

Compound 11c was prepared in the same manner as Compound 1f using 11b and N-(3-dimethylaminopropyl)-N'-ethylcarbodiimide hydrochloride instead of 1c and N,N'-dicyclohexyl carbodiimide in 60% yield.

Compound 11d

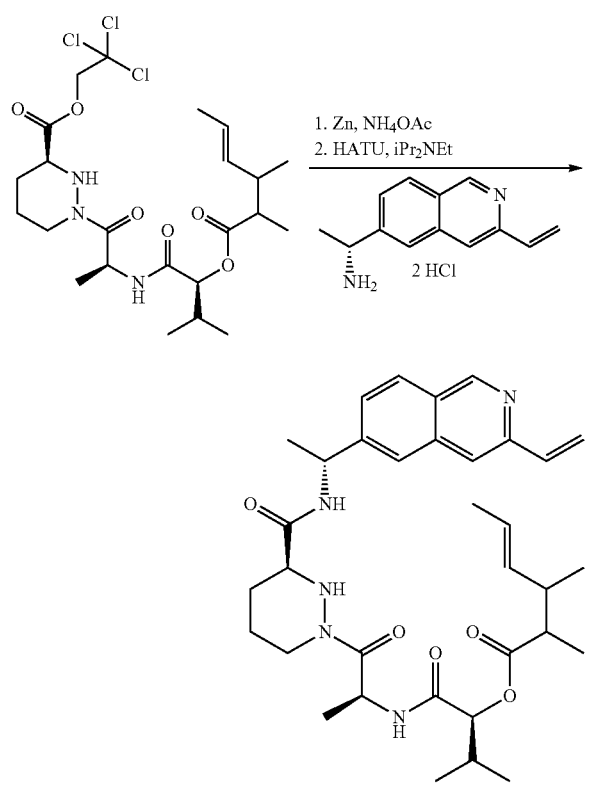

Synthesis of Compound 11d:

Compound 1d was prepared in the same manner as compound 1k, by first using 11c instead of 1f in the preparation of 1g and then, using (R)-1-(3-vinyl-isoquinolin-6-yl)-ethylamine dihydrochloride instead of (R)-1-(3-vinyl-phenyl)-ethylamine hydrochloride following the procedure described for the synthesis of 1k from 1g, in 81% yield.

Compound 11

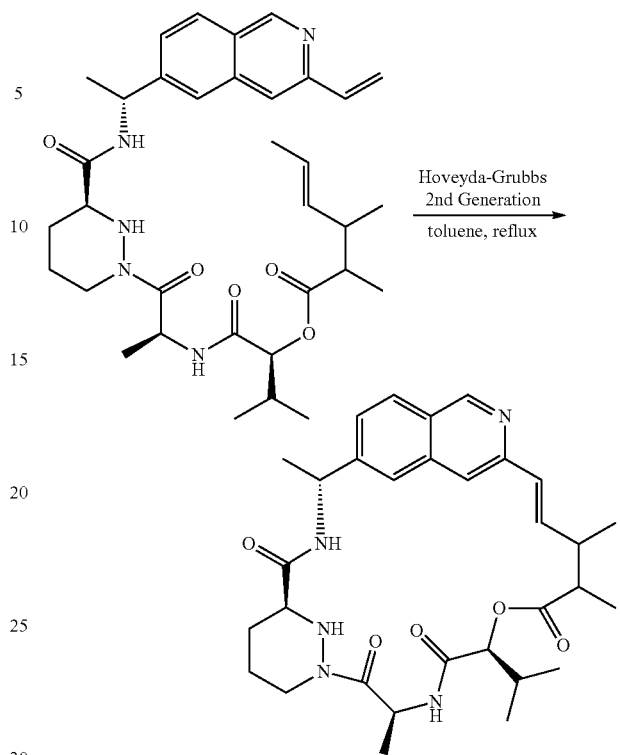

Synthesis of the Title Compound:

Compound 11 was prepared in the same manner as compound 1 using 11d instead of 1k and using toluene instead of dichloroethane in 8% yield. $^1$H NMR (300 MHz, CD$_3$OD) δ 0.97-1.07 (m, 7H), 1.25 (d, J=7.1 Hz, 3H), 1.31 (d, J=7.1 Hz, 3H), 1.55-1.63 (m, 6H), 1.65-1.78 (m, 1H), 1.83-2.00 (m, 3H), 2.14 (app sextet, J=6.7 Hz, 1H), 2.69-2.79 (m, 1H), 2.80-2.90 (m, 1H), 3.65 (app t, J=8.0 Hz, 1H), 4.45 (br d, J=13.6 Hz, 1H), 4.78 (dd, J=6.0, 19.6 Hz, 2H), 5.15 (app pentet, J=6.2 Hz, 1H), 5.83 (dq, J=7.1, 19.9 Hz, 1H), 6.65 (dd, J=6.7, 17.2 Hz, 1H), 6.79-6.93 (m, 1H), 7.53-7.61 (m, 1H), 7.71 (d, J=5.1 Hz, 1H), 7.96 (d, J=4.7 Hz, 1H), 8.03 (d, J=8.0 Hz, 1H), 9.10 (s, 1H). LCMS (m/z) 564.1 [M+H], 596.1 [M+Na], Tr=3.73 min.

Example 12

Compound 12

Compound 12a

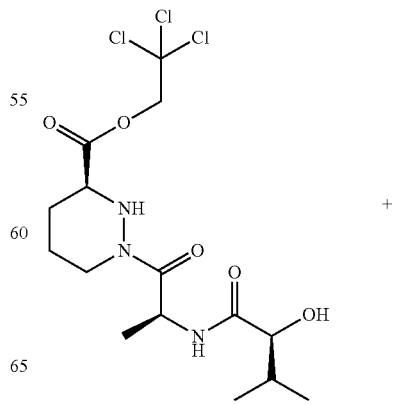

+

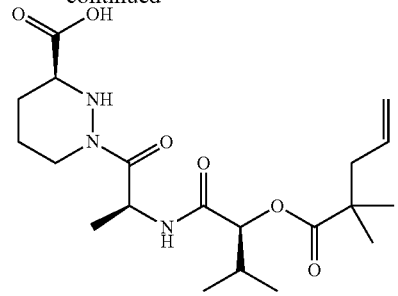

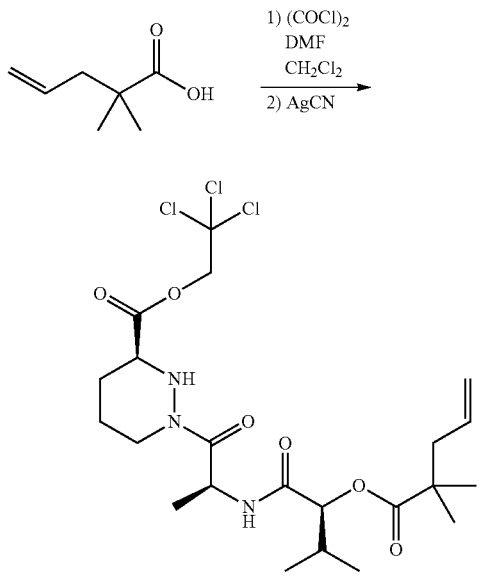

Synthesis of Compound 12a:

A solution of 2,2-dimethyl-4-pentenoic acid (202 mg, 1.58 mmol) in dichloromethane (5 mL) was prepared and oxalyl chloride (411 µL, 4.74 mmol) was added followed by dimethylformamide (5 µL). The mixture effervesced vigorously and was stirred at room temperature for 1 h before evaporating to give a solid (241 mg). The solid was dissolved in toluene (10 mL) and 1e (433 mg, 1.0 mmol) was added followed by silver cyanide (310 mg, 2.25 mmol). The flask was covered with foil to exclude light, before heating to 80° C. for 10 min. It was left at room temperature overnight. The reaction was heated to 80° C. for a further 4.5 h then allowed to cool. It was filtered and evaporated to give a pale yellow gum. The gum was purified by silica gel chromatography using ethyl acetate/iso-hexane 1:3 then ethyl acetate/iso-hexane 1:1 to yield the title compound (200 mg, 37%) as a colorless oil.

Compound 12b

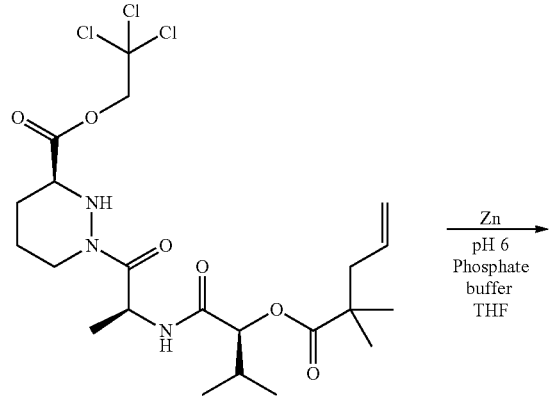

Synthesis of Compound 12b:

A solution of 12a (100 mg, 0.184 mmol) in tetrahydrofuran (10 mL) was prepared and zinc powder (360 mg, 5.52 mmol) was added, followed by pH 6 phosphate buffer (1 M, 2 mL). The reaction was stirred at room temperature for 18 h and further zinc powder (120 mg, 1.84 mmol) was added. The reaction was stirred at room temperature for a further 48 h. The reaction mixture was filtered to remove a suspended solid. The solid was washed with tetrahydrofuran (15 mL) and pH 6 buffer (5 mL) and this was added to the filtrate. The solution was evaporated and the residue purified by C18 chromatography using a gradient acetonitrile/water 0:1 to 1:3 to 1:1. This yielded the title product (69 mg, 91%) as a colorless oil.

Compound 12c

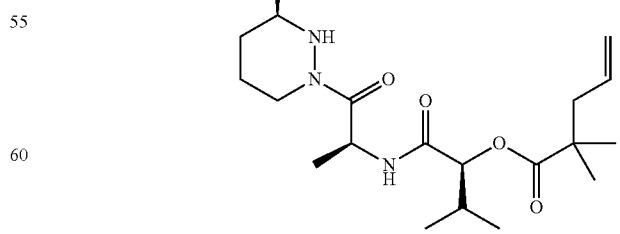

Synthesis of Compound 12c:

A solution of 12b (94 mg, 0.23 mmol) in anhydrous acetonitrile (5 mL) was prepared and cooled to 0° C. before adding 2j (54 mg, 0.23 mmol.), N,N-diisopropylethylamine (160 μL, 0.92 mmol) and 2-(1H-7-azabenzotriazol-1-yl)-1,1,3,3-tetramethyluronium hexafluorophosphate methanaminium (122 mg, 0.32 mmol). The reaction was warmed to room temperature and stirred for 16 h. The reaction mixture was evaporated onto silica gel and purified by silica gel chromatography using ethyl acetate to give the title product (119 mg, 87%) as a colorless solid.

J=8.5, 1.6 Hz, 1H), 7.70 (s, 1H), 8.00 (s, 1H), 8.03 (d, J=8.7 Hz, 1H), 9.10 (s, 1H). LCMS (m/z) 564.1 [M+H], Tr=3.57 min.

Example 13

Compound 13

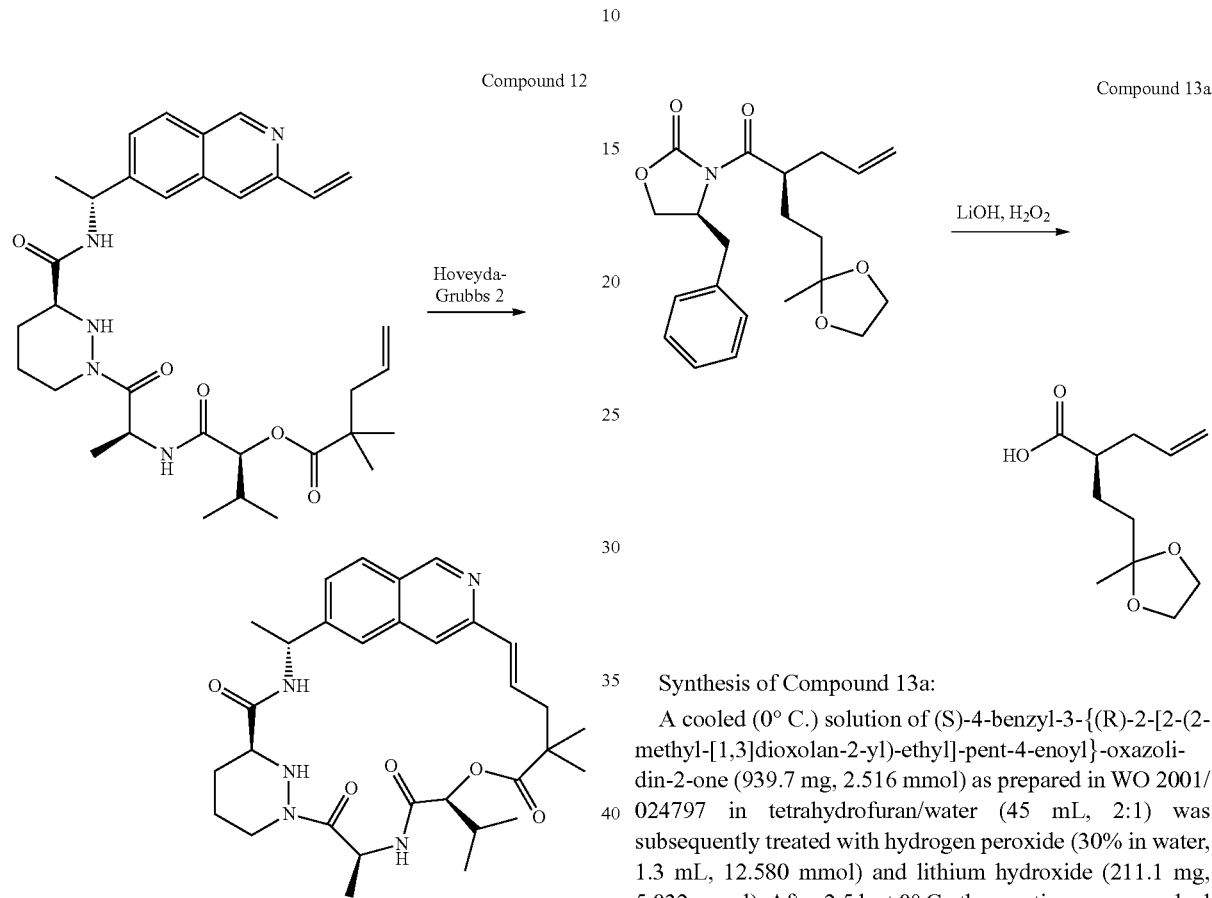

Synthesis of the Title Compound:

A solution of 12c (119 mg, 0.20 mmol) in toluene (65 mL) was prepared and Hoveyda-Grubbs 2$^{nd}$ generation catalyst (12.5 mg, 0.02 mmol) was added. The reaction mixture was heated to 110° C. under a nitrogen atmosphere for 2 h. A further quantity of Hoveyda-Grubbs 2$^{nd}$ generation catalyst (6 mg, 0.01 mmol) was added and the reaction was stirred at 110° C. for a further 1 h. The reaction mixture was cooled to room temperature then filtered, before adsorbing onto silica gel. The material was purified by silica gel chromatography using a gradient of ethyl acetate/acetone 1:0 to 9:1. The resultant gum was triturated with diethyl ether and dried under vacuum to yield a white solid (29 mg). This solid was further purified by preparatory reverse phase preparative HPLC to yield the title product (17 mg, 15%) as a white solid. $^1$H NMR (300 MHz, CD$_3$OD) 1.08 (d, J=6.9 Hz, 3H), 1.09 (d, J=6.7 Hz, 3H), 1.18 (s, 3H), 1.38 (s, 3H), 1.59 (d, J=3.3 Hz, 3H), 1.61 (d, J=3.1 Hz, 3H), 1.83-2.00 (m, 3H), 2.32-2.43 (m, 1H), 2.75-2.82 (m, 2H), 3.60-3.70 (m, 1H), 4.40-4.50 (m, 1H), 5.15 (q, J=6.9 Hz, 1H), 6.65 (d, J=16.3 Hz, 1H), 7.57 (dd, Synthesis of Compound 13a:

A cooled (0° C.) solution of (S)-4-benzyl-3-{(R)-2-[2-(2-methyl-[1,3]dioxolan-2-yl)-ethyl]-pent-4-enoyl}-oxazolidin-2-one (939.7 mg, 2.516 mmol) as prepared in WO 2001/024797 in tetrahydrofuran/water (45 mL, 2:1) was subsequently treated with hydrogen peroxide (30% in water, 1.3 mL, 12.580 mmol) and lithium hydroxide (211.1 mg, 5.032 mmol). After 2.5 h at 0° C., the reaction was quenched with sodium hydrogen sulphite (1.4 g). After 0.5 h, the volatiles were removed in vacuo and the residue diluted with water. The aqueous layer was extracted with dichloromethane (2×) then acidified to pH ~2 and extracted with dichloromethane (3×). These last organics were combined, dried over sodium sulfate, filtered and the volatiles were removed in vacuo to provide the title compound (538 mg, quant.) as a colorless oil.

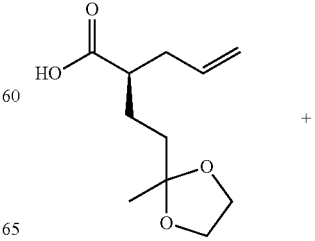

Compound 13b

119
-continued
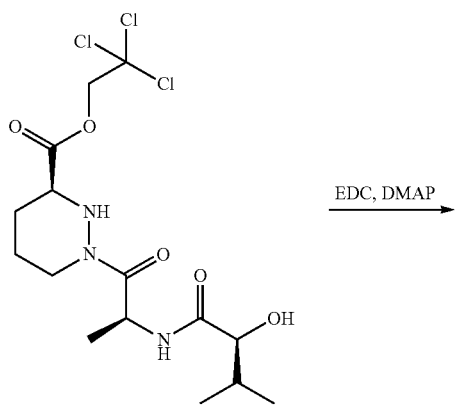
EDC, DMAP →
120
-continued
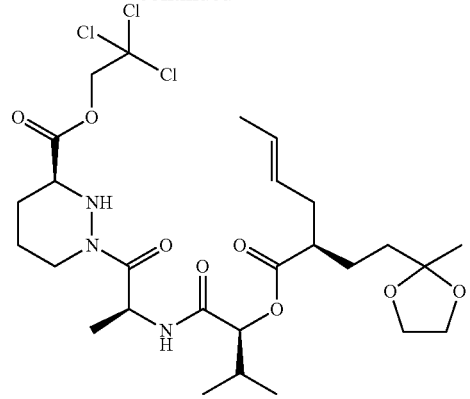
Synthesis of Compound 13b:
Compound 13b was prepared in the same manner as compound 1f using 13a and N-(3-dimethylaminopropyl)-N'-ethylcarbodiimide hydrochloride instead of 1c and N,N'-dicyclohexyl carbodiimide in 58% yield.
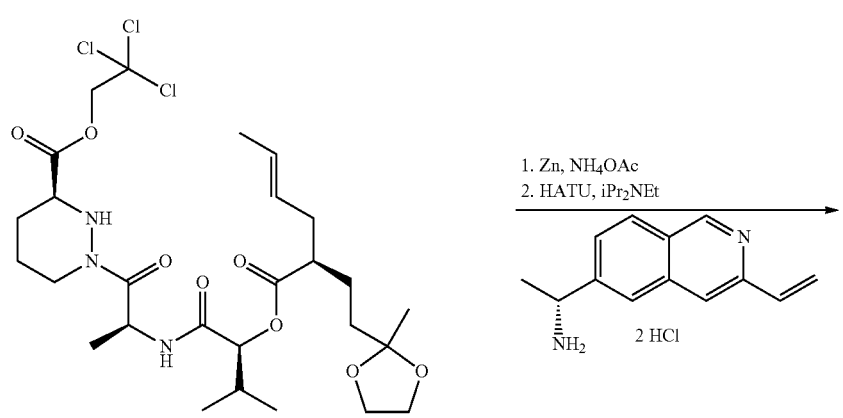
1. Zn, NH$_4$OAc
2. HATU, iPr$_2$NEt
→
Compound 13c
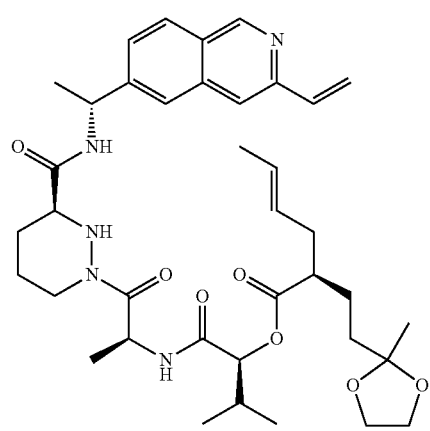

Synthesis of Compound 13c:

Compound 13c was prepared in the same manner as Compound 1k, by first using 13b instead of 1f in the synthesis of 1g, and then using (R)-1-(3-vinyl-isoquinolin-6-yl)-ethylamine dihydrochloride instead of (R)-1-(3-vinyl-phenyl)-ethylamine hydrochloride following the procedure described for the synthesis of 1k from 1g, in 73% yield.

Example 14

Compound 14

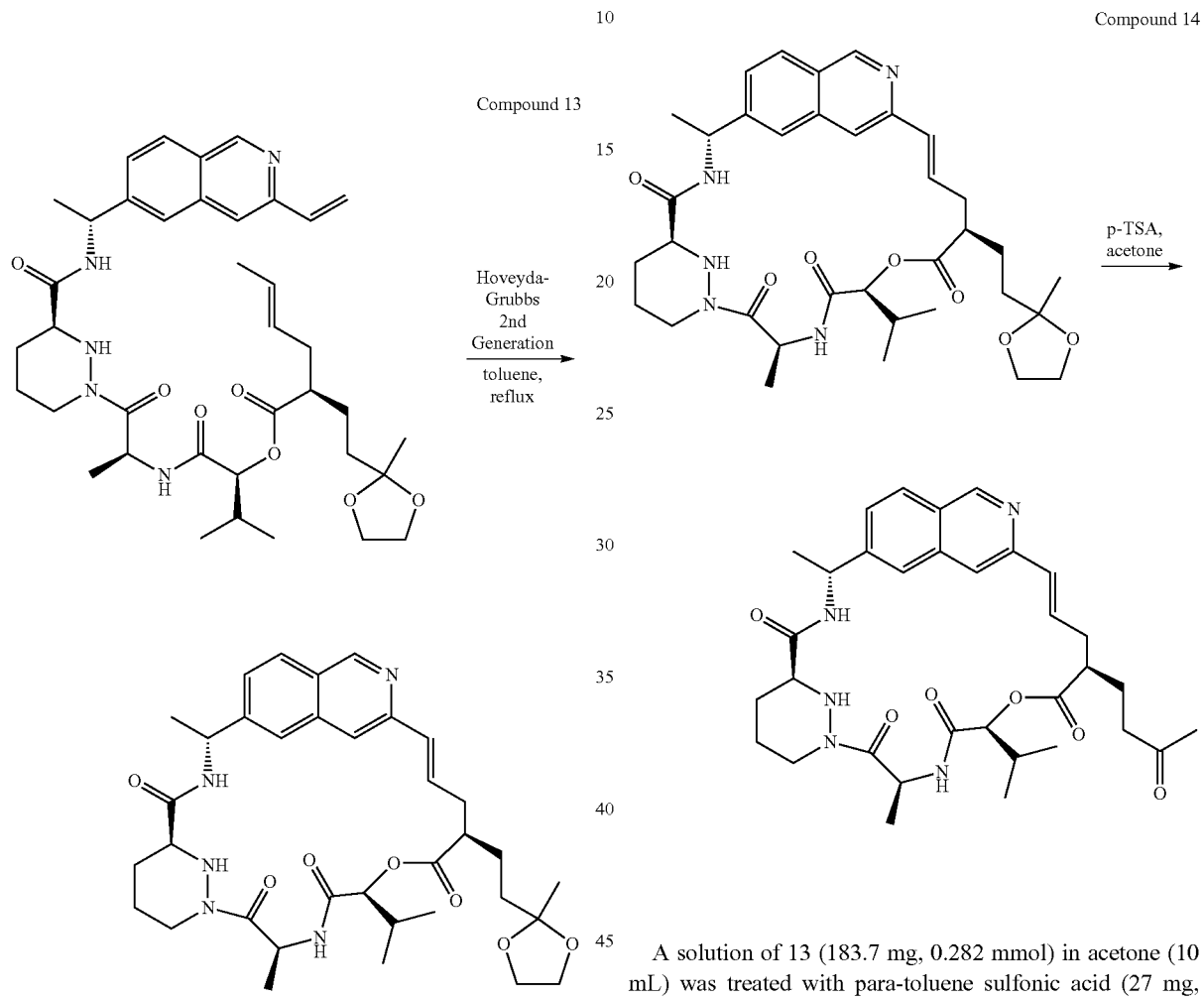

Synthesis of the Title Compound:

Compound 13 was prepared in the same manner as compound 1 using 13c instead of 1k and using toluene instead of dichloroethane in 32% yield. $^1$H NMR (300 MHz, CD$_3$OD) δ 0.88-1.00 (m, 1H), 1.06 (2d, J=6.9 Hz, 6H), 1.22-1.42 (m, 4H), 1.52-1.63 (m, 7H), 1.65-1.81 (m, 3H), 1.84-1.99 (m, 3H), 2.16 (app pentet, J=6.9 Hz, 1H), 2.38-2.50 (m, 1H), 2.51-2.61 (m, 1H), 2.62-2.74 (m, 1H), 2.83 (dt, J=2.7, 13.8 Hz, 1H), 3.59-3.72 (m, 1H), 4.46 (br dd, J=3.3, 13.6 Hz, 1H), 4.69-4.79 (m, 4H), 5.16 (q, J=7.1 Hz, 1H), 5.89 (q, J=6.9 Hz, 1H), 6.71 (d, J=16.3 Hz, 1H), 6.84-6.98 (m, 1H), 7.59 (d, J=8.5 Hz, 1H), 7.71 (s, 1H), 7.96 (s, 1H), 8.03 (d, J=8.7 Hz, 1H), 9.10 (s, 1H). LCMS (m/z) 651.2 [M+H], Tr=3.68 min.

A solution of 13 (183.7 mg, 0.282 mmol) in acetone (10 mL) was treated with para-toluene sulfonic acid (27 mg, 0.141 mmol). After stirring at room temperature for 2.5 h, the reaction was quenched with a saturated solution of sodium bicarbonate and the aqueous layer was extracted with ethyl acetate (2×20 mL). Organics were combined, dried over sodium sulfate, filtered and the volatiles were removed in vacuo. The residue was purified by silica gel chromatography using a 25 g Isolute cartridge eluted with a continuous gradient of iso-hexane/acetone 1:0 to 2:3 and then triturated with iso-hexane\acetone to provide the title compound (49.3 mg, 28%) as a white solid. $^1$H NMR (300 MHz, CD$_3$OD) 1.04 (d, J=6.9 Hz, 3H), 1.05 (d, J=6.9 Hz, 3H), 1.53-1.62 (m, 7H), 1.64-1.79 (m, 1H), 1.84-2.03 (m, 5H), 2.10-2.23 (m, 4H), 2.39-2.53 (m, 1H), 2.54-2.73 (m, 4H), 2.82 (dt, J=2.9, 13.1 Hz, 1H), 3.59-3.70 (m, 1H), 4.46 (br dd, J=4.0, 12.7 Hz, 1H), 5.17 (q, J=6.9 Hz, 1H), 5.91 (J=7.1 Hz, 1H), 6.71 (d, J=16.3 Hz, 1H), 6.86-7.00 (m, 1H), 7.59 (d, J=8.7 Hz, 1H), 7.71 (s, 1H), 7.98 (s, 1H), 8.03 (d, J=8.7 Hz, 1H), 9.10 (s, 1H). LCMS (m/z) 606.1 [M+H], Tr=3.26 min.

Example 15

Compound 15

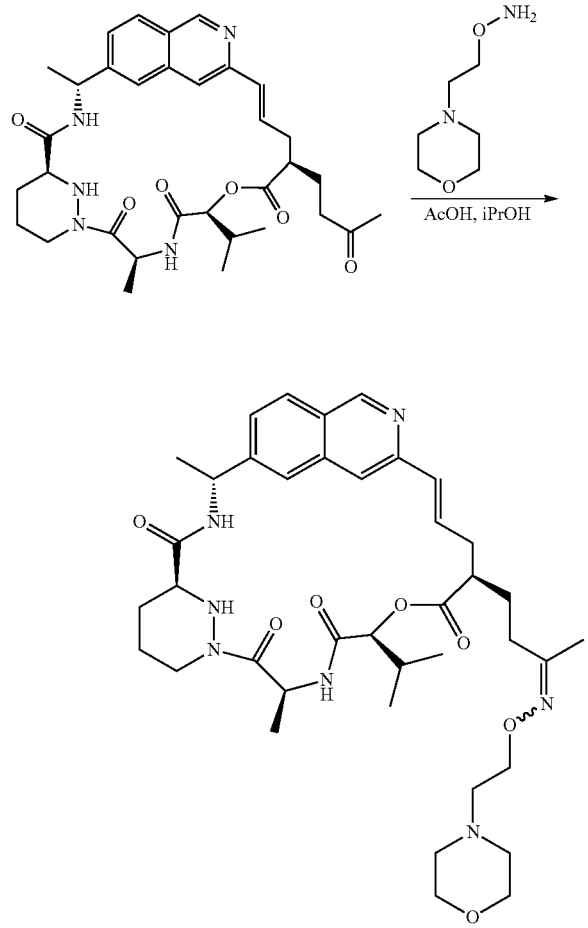

A stock solution of O-(2-morpholin-4-yl-ethyl)-hydroxylamine (18 mg, 0.125 mmol) and acetic acid (a drop) in 2 mL isopropanol was prepared. To solid Compound 14 (16.4 mg, 0.027 mmol) was added 1 mL of the stock solution and after stirring at room temperature for 18 h the compound was purified by reverse phase HPLC to provide a mixture of geometric isomers of the oxime (1:1, 13.3 mg, 67%) as a white solid. $^1$H NMR (300 MHz, CD$_3$OD) 1.00-1.10 (m, 6H), 1.54-1.64 (m, 5H), 1.65-1.78 (m, 1H), 1.81-2.04 (m, 8H), 2.09-2.22 (m, 1H), 2.23-2.33 (m, 1H), 2.34-2.90 (m, 12H), 3.53-3.76 (m, 6H), 4.18 (dt, J=5.8, 8.5 Hz, 2H), 4.41-4.51 (m, 1H), 4.68-4.82 (m, 2H), 5.16 (q, J=7.3 Hz, 1H), 5.82-5.96 (m, 1H), 6.71 (d, J=15.8 Hz, 1H), 6.84-7.00 (m, 1H), 7.59 (d, J=8.7 Hz, 1H), 7.71 (s, 1H), 7.98 (d, J=2.9 Hz, 1H), 8.04 (d, J=8.7 Hz, 1H), 8.53 (br dd, J=3.1, 9.4 Hz, 1H), 9.10 (s, 1H). LCMS (m/z) 734.7 [M+H], Tr=1.08 min.

Example 16

Compound 16

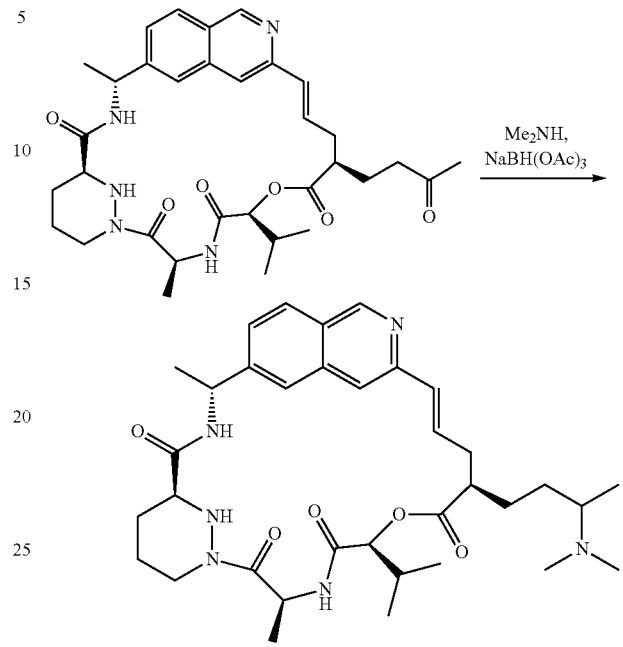

A solution of sodium triacetoxyborohydride (203.5 mg, 0.96 mmol) in methanol (1 mL) and acetic acid (100 µL) was subsequently treated with a 2 M solution of dimethylamine in methanol (480 µL, 0.96 mmol) and compound 14 (5.8 mg, 0.0096 mmol). After stirring for a month at room temperature, the reaction mixture was directly loaded onto the reverse phase preparative HPLC which was eluted with a gradient of water/CH$_3$CN 95:5 to 0:100. This provided the title compound (1.1 mg, 18%) as a white solid and as a 1:1 mixture of diastereomers. $^1$H NMR (300 MHz, CD$_3$OD) δ 0.87-0.97 (m, 1H), 1.01-1.09 (m, 6H), 1.24 (d, J=6.4 Hz, 3H), 1.55-1.63 (m, 6H), 1.64-1.80 (m, 2H), 1.84-2.02 (m, 4H), 2.10-2.24 (m, 1H), 2.41-2.72 (m, 7H), 2.73-2.90 (m, 3H), 3.60-3.69 (m, 1H), 4.41-4.51 (m, 1H), 5.17 (q, J=7.1 Hz, 1H), 5.85-5.95 (m, 1H), 6.71 (d, J=16.0 Hz, 1H), 6.85-6.99 (m, 1H), 7.56-7.63 (m, 1H), 7.71 (s, 1H), 7.98 (s, 1H), 8.04 (d, J=8.5 Hz, 1H), 9.06-9.13 (m, 1H). LCMS (m/z) 635.0 [M+H], Tr=0.94 min.

Example 17

(E)-(2R,5S,11S,14S)-14-Isopropyl-2,11,15-trimethyl-3,9,12,15,28-pentaaza-tricyclo[21.3.1.1*5,9*]octacosa-1(27),21,23,25-tetraene-4,10,13,16-tetraone—Compound 17

Compound 17a

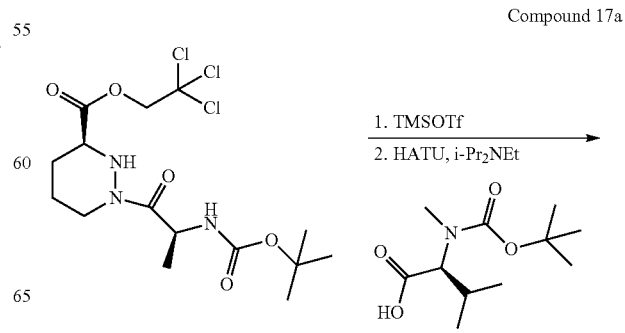

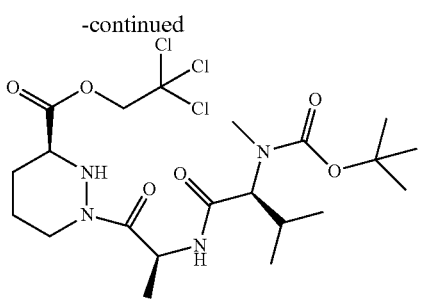

Synthesis of Compound 17a:

A solution of 1d (1.08 g, 2.5 mmol) in dichloromethane (35 mL) was stirred at 0° C. under nitrogen. Trimethylsilyl trifluoromethanesulfonate (682 mg, 0.55 mL, 3.1 mmol) was added and the reaction mixture was stirred at 0° C. for 45 minutes. N,N-diisopropylethylamine (1.29 g, 1.73 mL, 10 mmol) was added and the solvent was evaporated to afford crude (S)-1-((S)-2-amino-propionyl)-hexahydro-pyridazine-3-carboxylic acid 2,2,2-trichloro-ethyl ester (2.5 mmol), which was used in the next step. A solution of crude (S)-1-((S)-2-amino-propionyl)-hexahydro-pyridazine-3-carboxylic acid 2,2,2-trichloro-ethyl ester (2.5 mmol) in acetonitrile (30 mL) was stirred at 0° C. under nitrogen. (S)-2-(tert-Butoxycarbonyl-methyl-amino)-3-methyl-butyric acid (635 mg, 2.75 mmol) and N,N-diisopropylethylamine (1.29 g, 1.7 mL, 10 mmol) was added followed by 2-(1H-7-azabenzotriazol-1-yl)-1,1,3,3-tetramethyl uronium hexafluorophosphate methanaminium (1.33 g, 3.5 mmol) and the reaction mixture was stirred at room temperature for 18 h. The solvent was evaporated and the residue was dissolved in ethyl acetate. The solution was washed with water, 2 M hydrochloric acid, water, saturated sodium hydrogen carbonate solution, water and brine, and then dried over anhydrous sodium sulfate, filtered and evaporated. The residue was purified by silica gel chromatography using a gradient of iso-hexane/ethyl acetate 1:1 to neat ethyl acetate to afford the title compound (950 mg, 70%) as a white solid.

Compound 17b

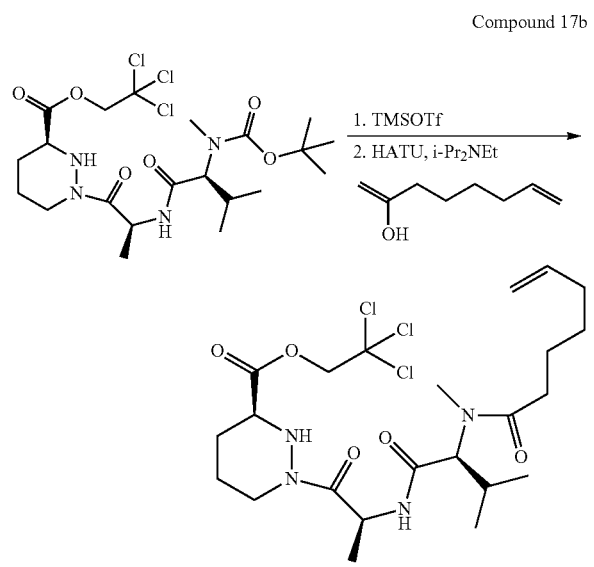

Synthesis of Compound 17b:

A solution of 17a (950 mg, 1.74 mmol) in dichloromethane (25 mL) was stirred at 0° C. under nitrogen. Trimethylsilyl trifluoromethanesulfonate (577 mg, 0.47 mL, 2.6 mmol) was added and the reaction mixture was stirred at 0° C. for 1 h. Additional trimethylsilyl trifluoromethanesulfonate (0.2 mL, 1.1 mmol) was added and the reaction mixture was stirred at 0° C. for 2 h. N,N-diisopropylethylamine (903 mg, 1.2 mL, 7 mmol) was added and the solvent was evaporated and the residue was dried to afford crude (S)-1-[(S)-2-((S)-3-methyl-2-methylamino-butyrylamino)-propionyl]-hexahydro-pyridazine-3-carboxylic acid 2,2,2-trichloro-ethyl ester (1.74 mmol), which was used in the next step. A solution of crude (S)-1-[(S)-2-((S)-3-methyl-2-methylamino-butyrylamino)-propionyl]-hexahydro-pyridazine-3-carboxylic acid 2,2,2-trichloro-ethyl ester (1.74 mmol) in acetonitrile (20 mL) was stirred at 0° C. under nitrogen. Hept-6-enoic acid (268 mg, 0.3 mL, 2.1 mmol) and N,N-diisopropylethylamine (903 mg, 1.2 mL, 7 mmol) were added. 2-(1H-7-Azabenzotriazol-1-yl)-1,1,3,3-tetramethyl uronium hexafluorophosphate methanaminium (912 mg, 2.4 mmol) was added and the reaction mixture was stirred at room temperature for 18 h. The solvent was evaporated and the residue was diluted with ethyl acetate. The solution was washed with saturated sodium hydrogen carbonate solution, water, 2 M hydrochloric acid, water and brine, dried over anhydrous sodium sulfate, filtered and evaporated. The residue was purified by silica gel chromatography using a gradient of iso-hexane/ethyl acetate 3:1 to 1:1 to afford the title compound (710 mg, 74%) as a white solid.

Compound 17c

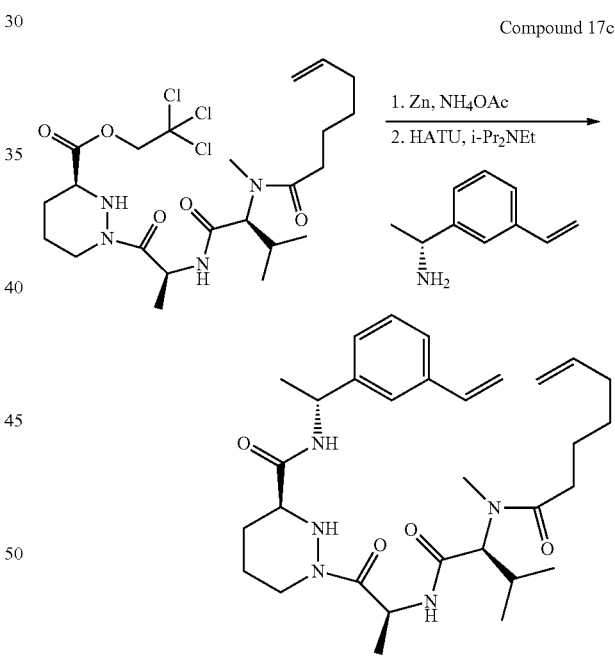

Synthesis of Compound 17c:

A solution of 17b (710 mg, 1.3 mmol) in tetrahydrofuran (30 mL) was stirred at room temperature under nitrogen. Zinc dust (1.86 g, 28.6 mmol) was added followed by a solution of ammonium acetate (1.50 g, 19.5 mmol) in water (20 mL) and the reaction mixture was stirred at room temperature for 24 hours. The reaction mixture was filtered through Celite and the filter pad was washed with ethyl acetate and potassium hydrogen sulfate solution (pH ~2). The filtrate was acidified to pH 2 with 2 M hydrochloric acid and the mixture was extracted with ethyl acetate. The organic extracts were combined, washed with water and brine, dried over anhydrous sodium sulfate, filtered and evaporated. The residue was co-evaporated with toluene and dried to afford (S)-1-{(S)-2-[(S)-2-(hept-6-enoyl-methyl-amino)-3-methyl-butyrylamino]-propionyl}-hexahydro-pyridazine-3-carboxylic acid (468 mg, 85%) as a gum. A solution of (S)-1-{(S)-2-[(S)-2-(hept-6-enoyl-methyl-amino)-3-methyl-butyrylamino]propionyl}-hexahydropyridazine-3-carboxylic acid (468 mg, 1.1 mmol) in acetonitrile (25 mL) was stirred at room temperature under nitrogen. 1j (200 mg, 1.1 mmol) and N,N-diisopropylethylamine (710 mg, 1.0 mL, 5.5 mmol) was added followed by 2-(1H-7-azabenzotriazol-1-yl)-1,1,3,3-tetramethyl uronium hexafluorophosphate methanaminium (585 mg, 1.54 mmol) and the reaction mixture was stirred at room temperature for 72 hours. The solvent was evaporated and the residue was dissolved in ethyl acetate. The solution was washed with 2 M hydrochloric acid, water, saturated sodium hydrogen carbonate solution, water and brine, dried over anhydrous sodium sulfate, filtered and evaporated. The residue was purified by silica gel chromatography using a gradient of iso-hexanel-ethyl acetate 1:1 to ethyl acetate to afford the title compound as a white solid (300 mg, 49%).

Compound 17

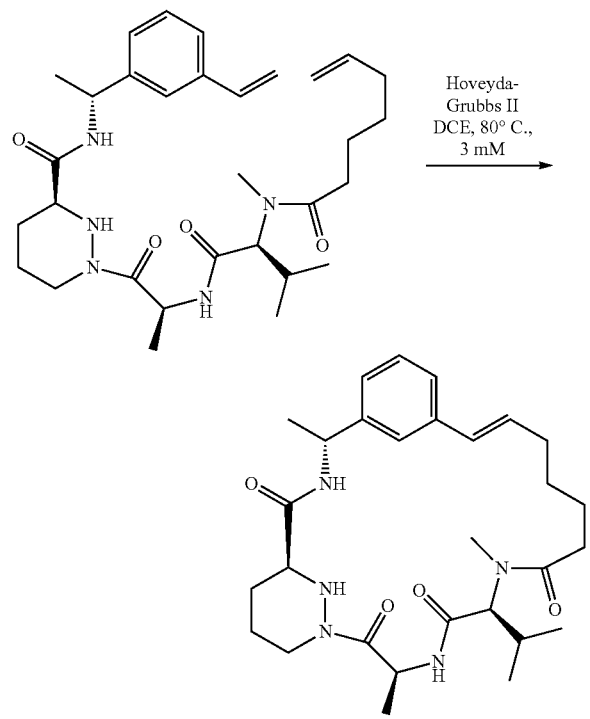

Synthesis of the Title Compound:

A solution of 17c (276 mg, 0.5 mmol) in 1,2-dichloroethane (150 mL) was stirred at room temperature under nitrogen. Hoveyda-Grubbs 2nd generation catalyst (32 mg, 0.05 mmol) was added and the reaction mixture was heated at 80° C. under nitrogen for 3 hours. The reaction mixture was cooled to room temperature, silica gel was added and the reaction mixture was evaporated. The residue was purified by silica gel chromatography using a gradient of ethyl acetate to ethyl acetate/acetone 7:3. The residue was triturated with ether and the resulting solid was collected, washed with ether and dried to afford the title compound (112 mg, 43%) as a white solid. $^1$H NMR (300 MHz, CD$_3$CN) δ0.82 (d, J=6.7 Hz, 3H), 0.90 (d, J=6.5 Hz, 3H), 1.34 (d, J=7.1 Hz, 3H), 1.39 (d, J=6.3 Hz, 3H), 1.40-1.90 (m, 10H), 2.60-2.75 (m, 2H), 2.86-2.92 (m, 4H), 3.28-3.36 (m, 1H), 3.93 (d, J=12.0 Hz, 1H), 4.33-4.38 (m, 1H), 4.58 (d, J=11.6 Hz, 1H), 4.85-4.99 (m, 2H), 6.16-6.51 (m, 3H), 7.12-7.30 (m, 6H). LCMS (m/z) 526.3 [M+H], Tr=2.16 min.

Example 18

Compound 18

Compound 18a

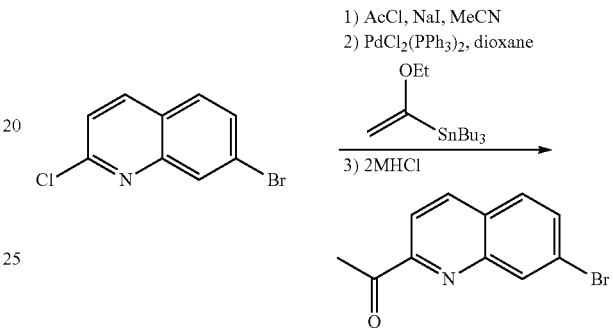

Synthesis of Compound 18a:

To a stirred slurry of 7-bromo-2-chloro-quinoline (Fluorochem, 8.10 g, 33.4 mmol) and sodium iodide (50.0 g, 334 mmol) in acetonitrile (27 mL) was added acetyl chloride (3.56 mL, 50.0 mmol) slowly. The flask was stoppered, sealed and heated at 80° C. for 3 h before being allowed to cool. The mixture was treated sequentially with 10% w/w aqueous potassium carbonate solution (80 mL), 5% w/w aqueous sodium sulfite solution (80 mL) and saturated aqueous sodium thosulfate solution (80 mL) and the mixture extracted with dichloromethane (2×). The combined organic extracts were dried over sodium sulfate, filtered and evaporated to give a crude 7-bromo-2-iodo-quinoline. To the quinoline was added tributyl(1-ethoxyvinyl)stannane (13.6 mL, 40.1 mmol), 1,4-dioxane (67 mL) and bis(triphenylphosphine)palladium(II) dichloride (2.37 g, 3.34 mmol) and the reaction mixture heated at 100° C. for 5 h before being allowed to cool. 2 M aqueous hydrochloric acid (67 mL) was added and the reaction stirred for 1 h. The mixture was filtered and the solids washed with ethyl acetate and the filtrate evaporated to remove organics. The residue was extracted with ethyl acetate (3×) and the combined organic extracts were dried over sodium sulfate, filtered and evaporated. The product was purified on silica gel doped with 10% w/w potassium carbonate, eluting with a gradient of 0 to 6% ethyl acetate in iso-hexanes to afford the title compound (5.5 g, 66%) as a white solid.

Compound 18b

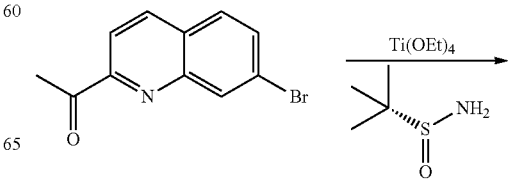

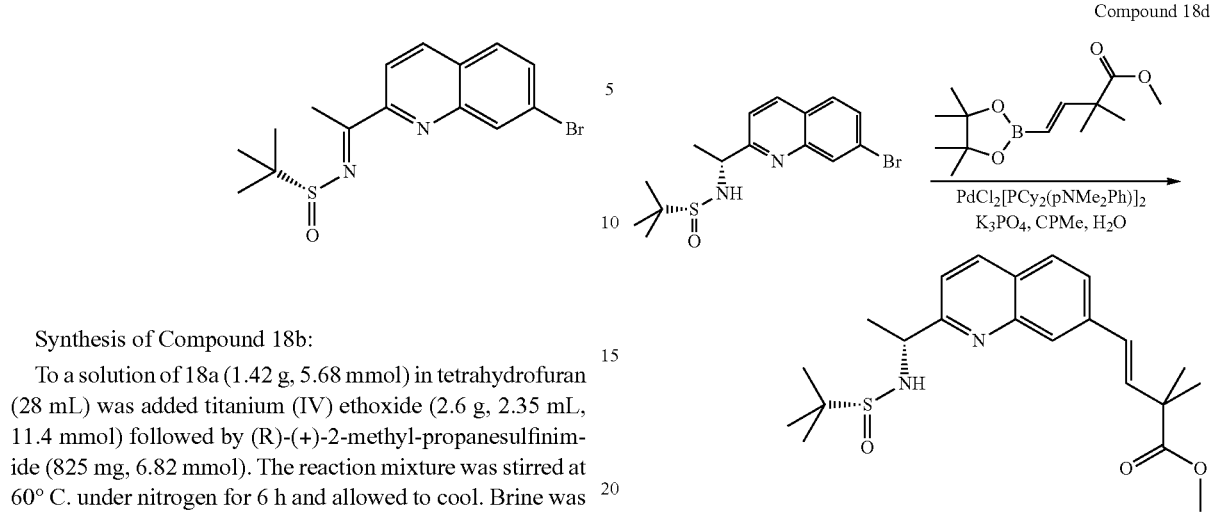

Compound 18d

Synthesis of Compound 18b:

To a solution of 18a (1.42 g, 5.68 mmol) in tetrahydrofuran (28 mL) was added titanium (IV) ethoxide (2.6 g, 2.35 mL, 11.4 mmol) followed by (R)-(+)-2-methyl-propanesulfinimide (825 mg, 6.82 mmol). The reaction mixture was stirred at 60° C. under nitrogen for 6 h and allowed to cool. Brine was added followed by ethyl acetate and the suspension filtered through celite and the filter pad was washed with ethyl acetate. The ethyl acetate layer was separated, dried over sodium sulfate, filtered and evaporated. The residue was purified by silica gel chromatography eluting with 10-25% ethyl acetate in iso-hexanes to afford the title compound (448 mg, 22%).

Compound 18d:

Synthesis of Compound 18d: A mixture of 18c (207 mg, 0.583 mmol), (E)-2,2-Dimethyl-4-(4,4,5,5-tetramethyl-[1,3,2]dioxaborolan-2-yl)-but-3-enoic acid methyl ester (170 mg, 0.670 mmol), bis[(dicyclohexyl)(4-dimethylaminophenyl)phosphine]palladium(II) chloride (24 mg, 0.029 mmol) and potassium phosphate tribasic (371 mg, 1.75 mmol) was suspended in cyclopentylmethyl ether (3 mL) and water (1.5 mL) and the mixture stirred and heated at 80° C. under nitrogen for 5 h. The reaction mixture was allowed to cool and diluted with ethyl acetate and water. The aqueous layer was separated and washed with further ethyl acetate and the combined organic extracts dried over sodium sulfate, filtered and evaporated. The residue was purified by silica gel chromatography using a gradient of ethyl acetate in iso-hexanes (1:1 to 3:1) to afford the title compound as a yellow oil (201 mg, 86%).

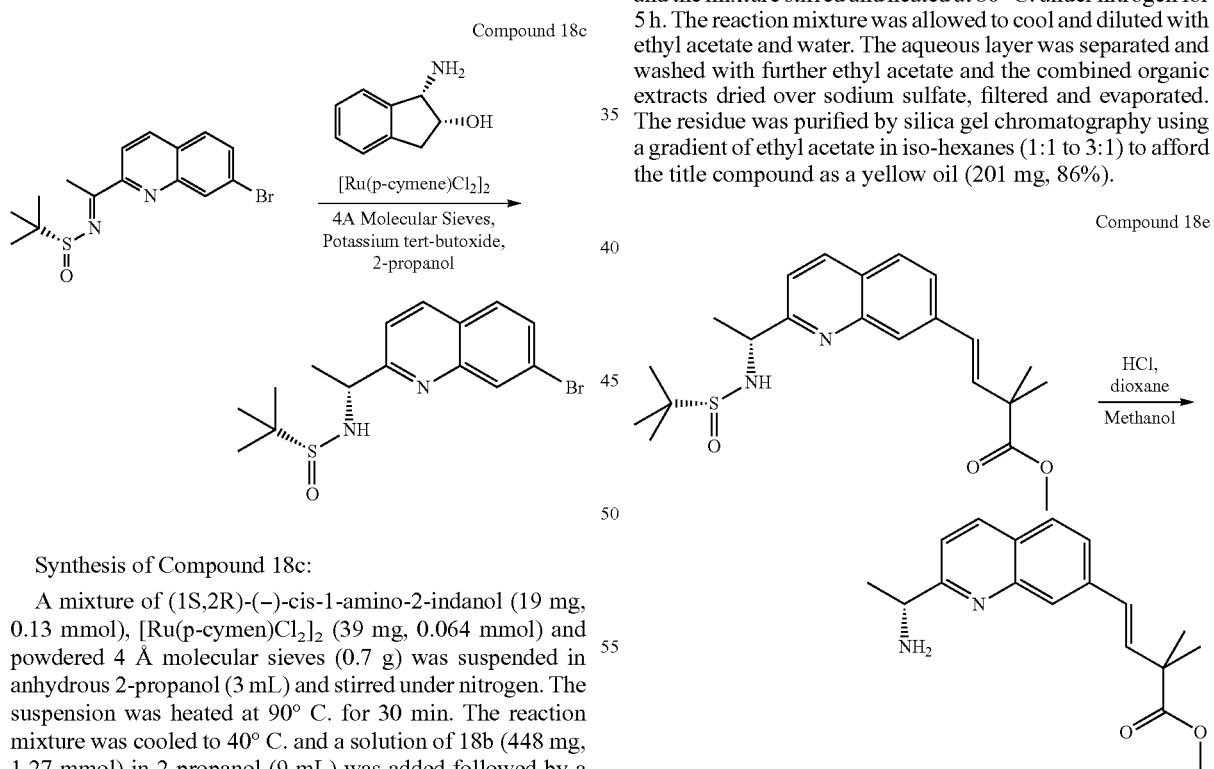

Synthesis of Compound 18c:

A mixture of (1S,2R)-(−)-cis-1-amino-2-indanol (19 mg, 0.13 mmol), [Ru(p-cymen)Cl$_2$]$_2$ (39 mg, 0.064 mmol) and powdered 4 Å molecular sieves (0.7 g) was suspended in anhydrous 2-propanol (3 mL) and stirred under nitrogen. The suspension was heated at 90° C. for 30 min. The reaction mixture was cooled to 40° C. and a solution of 18b (448 mg, 1.27 mmol) in 2-propanol (9 mL) was added followed by a solution of potassium tert-butoxide (36 mg, 0.32 mmol) in 2-propanol (3 mL). The reaction mixture was stirred for 2 h at 40° C. and then allowed to cool. The mixture was poured directly onto a silica gel cartridge and eluted with ethyl acetate. After concentration the residue was further purified on silica eluting with ethyl acetate in iso-hexanes (1:1 to 1:0) to afford the title compound (287 mg, 64%).

Synthesis of Compound 18e:

18d (193 mg, 0.48 mmol) was suspended in 4 M HCl in 1,4-dioxane (5 mL, 20 mmol) and methanol was added (10 mL). The reaction mixture was stirred for 2 h and then evaporated. The residue was triturated with ether to give the title compound as a yellow solid (166 mg).

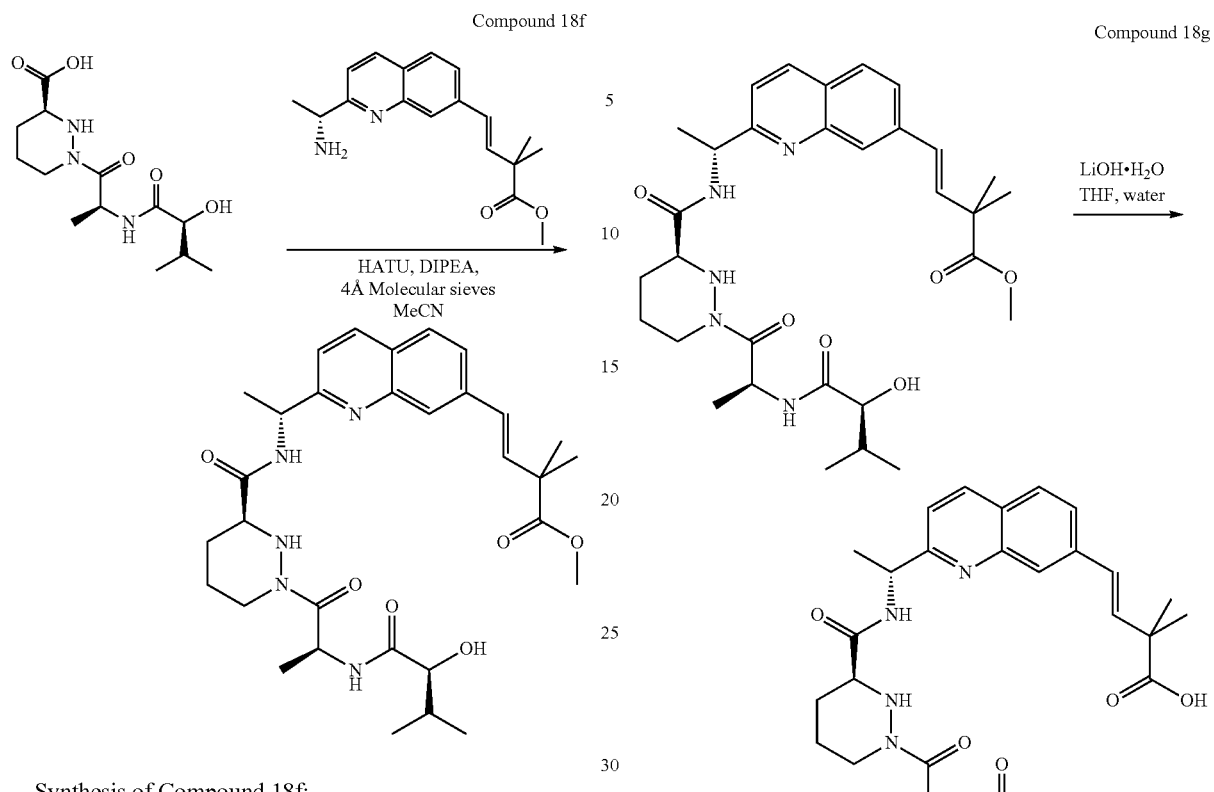

Synthesis of Compound 18f:
(S)-1-[(S)-2-((S)-2-Hydroxy-3-methyl-butyrylamino)-propionyl]-hexahydro-pyridazine-3-carboxylic acid (166 mg, 0.48 mmol), 18e (190 mg, 0.48 mmol), O-(7-azabenzotriazol-1-yl)-N,N,N',N'-tetramethyluronium hexafluorophosphate (256 mg, 0.67 mmol) and powdered 4 Å molecular sieves were suspended in acetonitrile (9.6 mL) under nitrogen. To the stirred mixture was added N,N-diisopropylethylamine (186 mg, 250 μL, 1.44 mmol) and the reaction mixture stirred for 20 h. The mixture was filtered through a phase separator and the filtrate evaporated, dissolved in dichloromethane and washed successively with saturated sodium bicarbonate solution, water and saturated ammonium chloride solution, and then dried over sodium sulfate, filtered and evaporated. The residue was purified by silica gel chromatography using a gradient of ethyl acetate in iso-hexanes (1:1 to 1:0) to afford the title compound as a yellow gum (77 mg, 28% over 2 steps).

Synthesis of Compound 18g:
To 18f (117 mg, 0.201 mmol) in tetrahydrofuran (4 mL) was added, with stirring, water (0.8 mL) and lithium hydroxide monohydrate (9.2 mg, 0.221 mmol). The reaction mixture was stirred for 1 h and then further lithium hydroxide monohydrate (36 mg, 0.857 mmol) was added and the mixture stirred for a further 19.5 hours. The reaction mixture was evaporated and the residue azeotroped with toluene. The residue was purified by preparative HPLC using a gradient of 20 to 100% acetonitrile in water to give 18g as a white solid (60 mg, 53%).

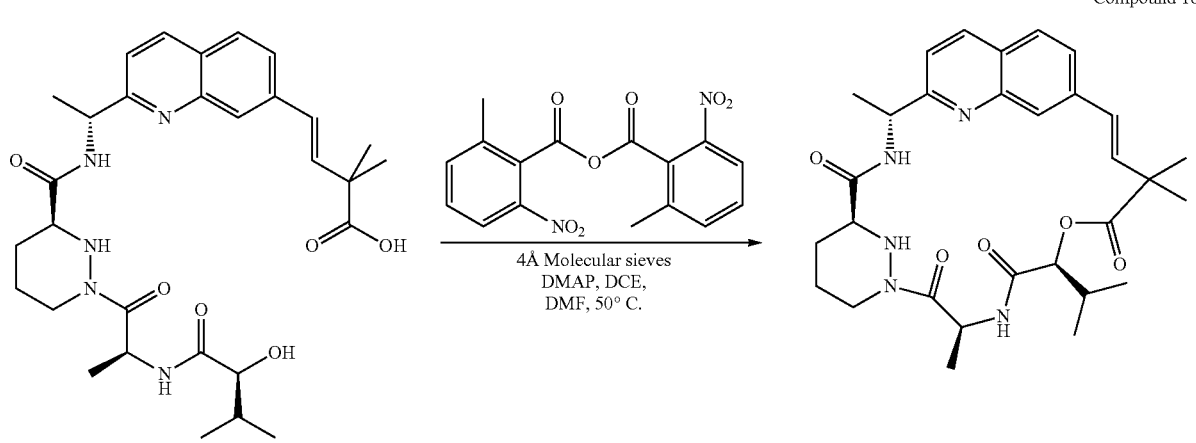

Synthesis of the Title Compound:

A slurry of 2-methyl-6-nitrobenzoic anhydride (177 mg, 0.500 mmol), DMAP (92 mg, 0.750 mmol) and powdered 4 Å molecular sieves (1 g) in 1,2-dichloroethane (33 mL) was stirred under nitrogen at 50° C. 18g (57 mg, 0.100 mmol) was dissolved in N,N-dimethylformamide (5 mL) and the solution added to the slurry over 5 h via syringe pump. After the addition was complete the original flask containing the acid was washed with further N,N-dimethylformamide (1 mL) and the washings transferred to the reaction vessel over 30 min. The reaction mixture was stirred at 50° C. for a further hour and then allowed to cool. The residue was purified by preparative HPLC using a gradient of 5 to 100% acetonitrile in water to give the title compound as a white solid (24.5 mg, 45%). $^1$H NMR (300 MHz, CD$_3$OD) δ 1.00 (d, J=6.7 Hz, 3H), 1.07 (d, J=6.7 Hz, 3H), 1.43 (s, 3H), 1.54 (s, 3H), 1.59 (d, J=7.6 Hz, 3H), 1.64 (d, J=7.4 Hz, 3H), 1.96 (m, 1H), 2.17 (m, 1H), 2.28 (m, 1H), 2.71 (m, 1H), 3.61 (m, 1H), 4.43 (m, 1H), 5.10 (m, 1H), 5.24 (d, J=8.9 Hz, 1H), 5.81 (q, J=7.1 Hz, 1H), 6.46 (ABq, Δδ$_{AB}$=0.18, J$_{AB}$=16.3 Hz, 2H), 7.45 (d, J=8.5 Hz, 1H), 7.62 (dd, J=8.5, 1.3 Hz, 1H), 7.79 (s, 1H), 7.85 (d, J=8.5 Hz, 1H), 8.26 (d, J=8.5 Hz, 1H), 9.41 (br d, J=5.6 Hz, 1H). LCMS (m/z) 550.2 [M+H], Tr 2.05 min.

Example 19

Compound 19

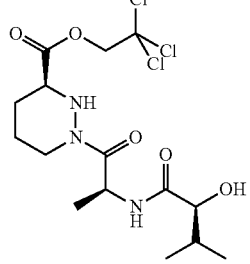

Compound 19a

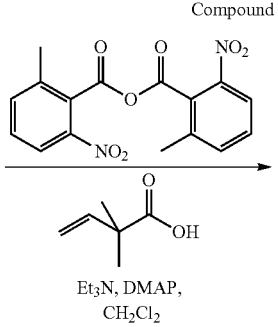

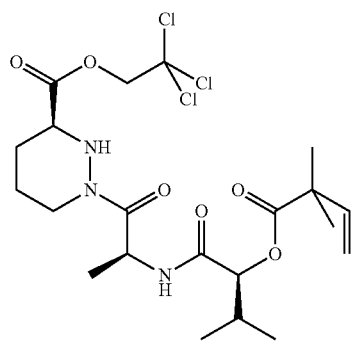

Synthesis of Compound 19a:

1e (1.08 g, 2.50 mmol), 2-methyl-6-nitrobenzoic anhydride (1.46 g, 4.25 mmol), 4-dimethylaminopyridine (122 mg, 1.00 mmol) and powdered 4 Å molecular sieves were suspended in dry dichloromethane (11 mL) and the mixture stirred under nitrogen. Triethylamine (633 mg, 871 µL, 6.25 mmol) and a solution of 2,2-dimethyl-but-3-enoic acid (390 mg, 3.43 mmol) in dry dichloromethane (1.5 mL) were added and the reaction mixture stirred for 17 h. The suspension was passed through a phase separator cartridge and the filtrate evaporated. The residue was purified by silica gel chromatography using a gradient of ethyl acetate in iso-hexanes (1:4 to 2:3) to afford the title compound as a brown gum (735 mg, 56%).

Compound 19b

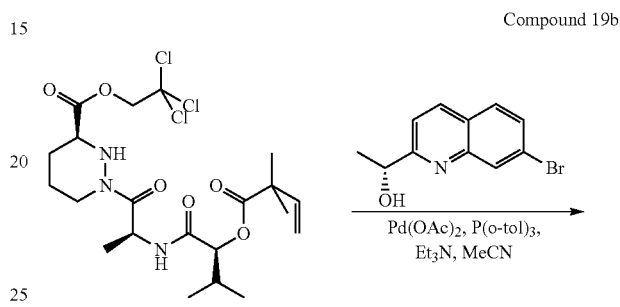

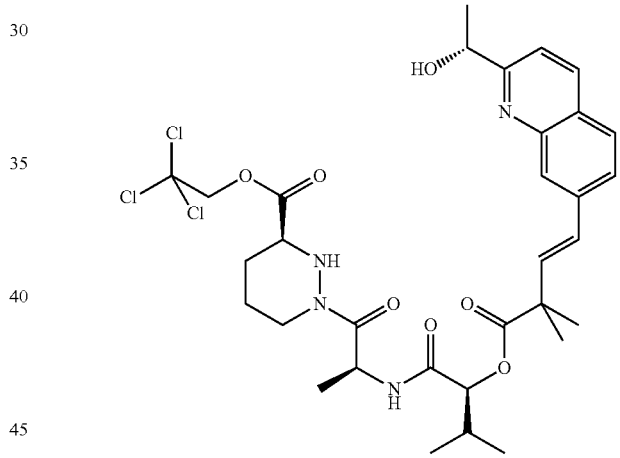

Synthesis of Compound 19b:

19a (124 mg, 0.235 mmol), (R)-1-(7-bromo-quinolin-2-yl)-ethanol (65 mg, 0.258 mmol), palladium acetate (8 mg, 0.035 mmol), tri(o-tolyl)phosphine (22 mg, 0.071 mmol) and triethylamine (48 mg, 66 µL, 0.47 mmol) were suspended in acetonitrile (2.35 mL). The reaction mixture was heated and stirred at 120° C. for 2 h in a microwave reactor. The residue was evaporated and suspended in ethyl acetate and saturated ammonium chloride solution. The organic layer was separated and washed with saturated ammonium chloride solution then water and the combined aqueous washes back-extracted with ethyl acetate. The combined organic layers were washed with brine, dried over sodium sulfate, filtered and evaporated. The residue was purified by silica gel chromatography using a gradient of ethyl acetate in iso-hexanes (1:1 to 3:1) to afford the title compound as a yellow gum (38 mg, 23%).

Compound 19c

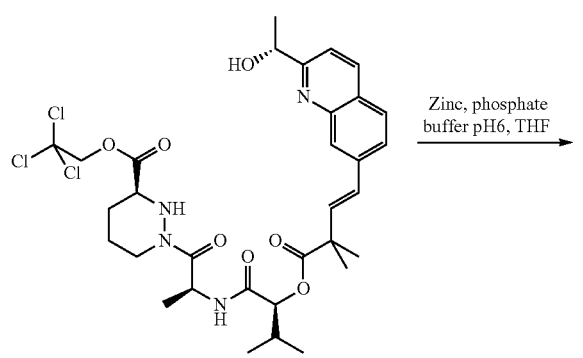

Synthesis of Compound 19c:

To a solution of 19b (58 mg, 0.083 mg) in tetrahydrofuran (5 mL) was added zinc (218 mg, 3.33 mmol) and pH 6 phosphate buffer (1 mL). The reaction mixture was rapidly stirred for 18 h. Zinc (218 mg, 3.33 mol) was added and the reaction heated to 40° C. for 1 h and allowed to cool. The mixture was filtered through a phase separator washing with tetrahydrofuran and pH 6 phosphate buffer. The filtrate was diluted with ethyl acetate and water and the aqueous phase extracted with further ethyl acetate. The combined organic extracts were dried over sodium sulfate, filtered and evaporated. The aqueous phase was evaporated to ca. half volume and extracted with ethyl acetate (5×) and the combined organic extracts dried over sodium sulfate, filtered and combined with the rest of the product and evaporated to give a yellow gum (51 mg).

Compound 19

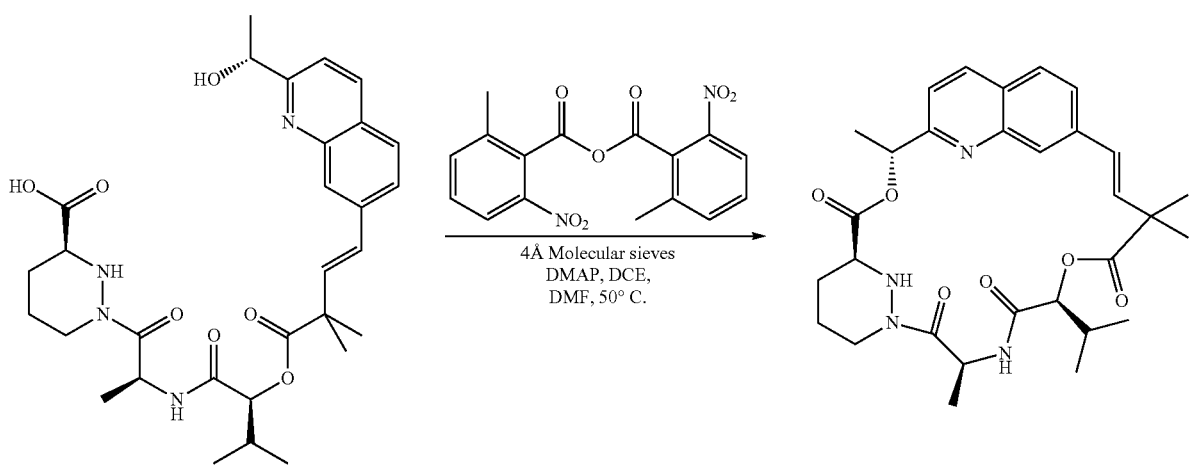

-continued

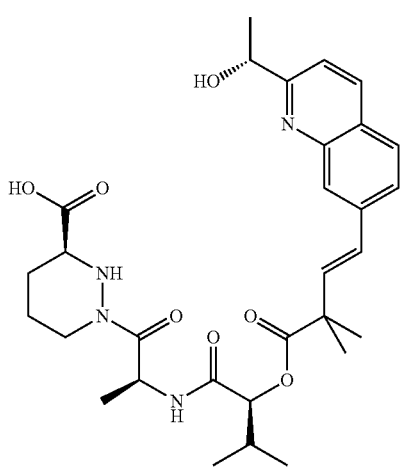

Synthesis of the Title Compound:

A slurry of 2-methyl-6-nitrobenzoic anhydride (143 mg, 0.415 mmol), 4-dimethylaminopyridine (76 mg, 0.623 mmol) and powdered 4 Å molecular sieves (1 g) in 1,2-dichloroethane (27 mL) was stirred under nitrogen at 50° C. 19c (51 mg, 0.083 mmol) was dissolved in N,N-dimethylformamide (3 mL) and the solution added to the slurry over 3.5 h via syringe pump. After the addition was complete the original flask containing the acid was washed with further N,N-dimethylformamide (1 mL) and the washings transferred to the reaction vessel over 10 min. The reaction mixture was stirred at 50° C. for a further hour and then allowed to cool. The residue was purified by preparative HPLC using a gradient of 10% to 100% acetonitrile in water. The residue was further purified by silica gel chromatography using a gradient of 50% to 60% ethyl acetate in iso-hexanes (1:1 to 3:2) to give the title compound as a colorless gum (1.7 mg, 4% over 2 steps). $^1$H NMR (300 MHz, CD$_3$OD) δ 0.94 (d, J=7.0 Hz, 3H), 0.99 (d, J=6.7 Hz, 3H), 1.41 (s, 3H), 1.52 (s, 3H), 1.65 (d, J=7.1 Hz, 3H), 1.68 (m, 2H), 1.73 (d, J=6.7 Hz, 3H), 1.89-2.03 (m, 2H), 2.15 (m, 1H), 2.76 (m, 1H), 3.82 (m, 1H), 4.39 (br d, J=13.4 Hz, 1H), 5.08 (d, J=9.8 Hz, 1H), 5.81 (q, J=7.1 Hz, 1H), 5.93 (q, J=6.9 Hz, 1H), 6.34 (ABq, Δδ$_{AB}$=0.11, J$_{AB}$=16.6 Hz, 2H), 7.41 (d, J=8.5 Hz, 1H), 7.67 (s, 1H), 7.75 (dd, J=8.7, 1.3 Hz, 1H), 7.82 (d, J=8.7 Hz, 1H), 8.22 (d, J=8.5 Hz, 1H). LCMS (m/z) 551.2 [M+H], Tr 2.22 min.

Example 20

Compound 20

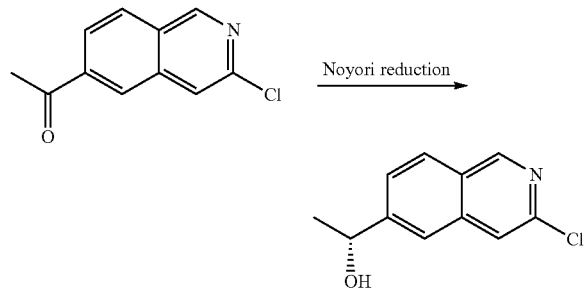

Synthesis of Compound 20a:

Dichloro(p-cumene)ruthenium(II) dimer (3 mg, 0.005 mmol) and (1R,2R)-(−)—N-p-tosyl-1,2-diphenylethylenediamine (4.4 mg, 0.012 mmol) were suspended in degassed water (2 mL) and the mixture was degassed with nitrogen for 15 min. The mixture was stirred at 70° C. under nitrogen for 90 min. The resulting yellow solution was cooled to room temperature. 2f (206 mg, 1 mmol), sodium formate (340 mg, 5 mmol) and degassed tetrahydrofuran (1 mL) were added and the reaction mixture was degassed with nitrogen for 5 min. The reaction mixture was vigorously stirred at 40° C. for 2.5 h. The reaction mixture was cooled to room temperature and was extracted with ethyl acetate. The organic layer was separated, washed with water and brine, dried over sodium sulfate, filtered and evaporated. The residue was purified by silica gel chromatography using a gradient of iso-hexanes/ethyl acetate 4:1 to 2:1 to afford the title compound (193 mg, 92%) as a white solid.

Synthesis of Compound 20b:

1,4-Dioxane (5 mL) was degassed with nitrogen, 20a (208 mg, 1 mmol), tributyl(vinyl)tin (951 mg, 0.9 mL, 3 mmol) and bis(triphenylphosphine)palladium(II) dichloride (70 mg, 0.1 mmol) were added and the reaction mixture was heated at 150° C. in a microwave reactor for 1 h. Additional tributyl(vinyl)tin (0.3 mL, 1 mmol) and bis(triphenylphosphine)palladium(II) dichloride (70 mg, 0.1 mmol) were added and the reaction mixture was heated at 150° C. in a microwave reactor for 1 h. The reaction mixture was cooled to room temperature and the mixture was filtered through filter aid and the filter pad was washed with ethyl acetate. The filtrate was evaporated and the residue was purified by silica gel chromatography using a gradient of iso-hexanes/ethyl acetate 4:1 to 2:1 followed by silica gel chromatography using iso-hexanes/ethyl acetate 3:1 to afford the title compound (100 mg, 50%) as a white solid.

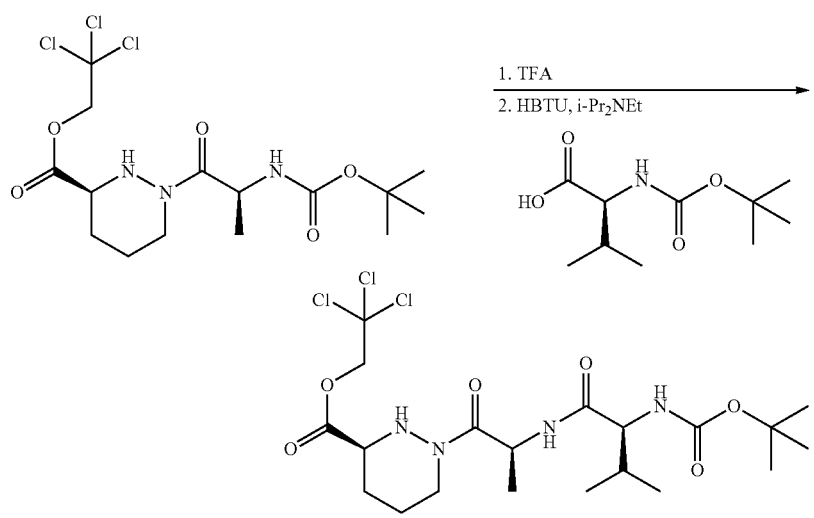

Synthesis of Compound 20c:

A solution of 1d (6.88 g, 15.9 mmol) in dichloromethane (200 mL) was prepared and trifluoroacetic acid (50 mL) was added. The reaction mixture was stirred at room temperature for 2 h. TLC showed the reaction to be complete. The solution was evaporated to give a brown oil. This was azeotroped with toluene (50 mL) and the resultant oil was dried under vacuum to give (S)-1-((S)-2-amino-propionyl)-hexahydro-pyridazine-3-carboxylic acid 2,2,2-trichloro-ethyl ester trifluoroacetic acid salt (7.8 g) as a brown gum. A solution of ((S)-1-carbamoyl-2-methylpropyl)-carbamic acid tert-butyl ester in acetonitrile (300 mL) was cooled to 0° C. before adding N,N-diisopropylethylamine (13.8 mL, 79.7 mmol) and 2-(1H-benzotriazole-1-yl)-1,1,3,3-tetramethyluronium hexafluorophosphate (6.33 g, 16.7 mmol). The reaction was stirred at 0° C. for 15 min before adding a solution of the (S)-1-((S)-2-amino-propionyl)-hexahydro-pyridazine-3-carboxylic acid 2,2,2-trichloro-ethyl ester trifluoroacetic acid salt (ca. 15.9 mmol) in acetonitrile (85 mL). The reaction was stirred at 0° C. for a further 20 min and then allowed to warm to room temperature and stirred for 15 h. The reaction mixture was evaporated then re-dissolved in ethyl acetate (250 mL). The solution was washed with water (150 mL) then dried over sodium sulfate, filtered and evaporated to give a red oil. This was purified by silica gel chromatography using iso-hexanel-ethyl acetate 7:3 then iso-hexanelethyl acetate 1:1 to yield the title compound (8.2 g, 92%) as a pale orange amorphous solid.

Synthesis of Compound 20d:

To a solution of 20c (530 mg, 1.00 mmol) in tetrahydrofuran (3 mL) and water (2 mL) was added lithium hydroxide (26 mg, 1.1 mmol) at 23° C. under an argon atmosphere. After 19 h, the reaction mixture was concentrated under reduced pressure and the crude residue was purified by silica gel flash column chromatography (12 g Combiflash HP Gold Column, 0-20% methanol/dichloromethane gradient) to afford the title compound (339 mg, 92%) as a colorless solid.

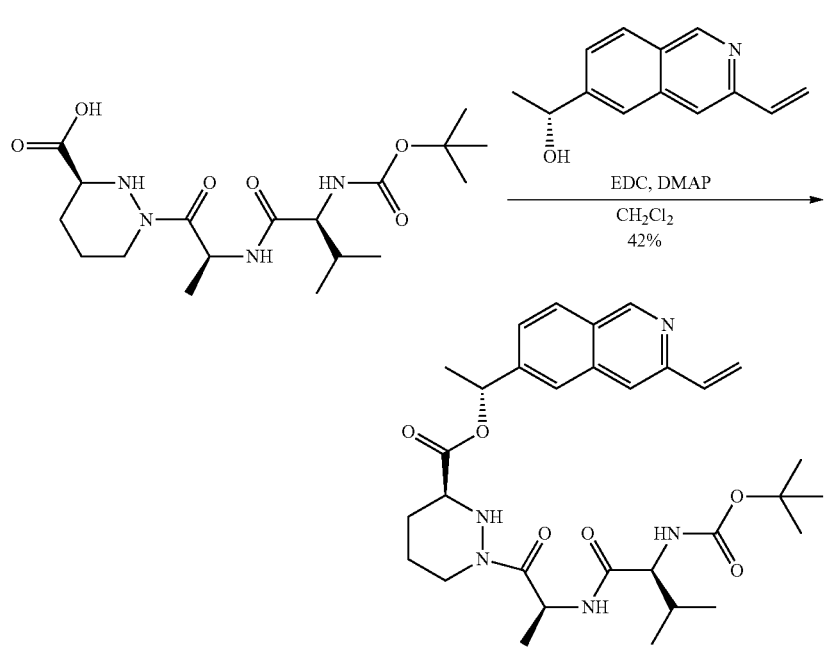

Compound 20d

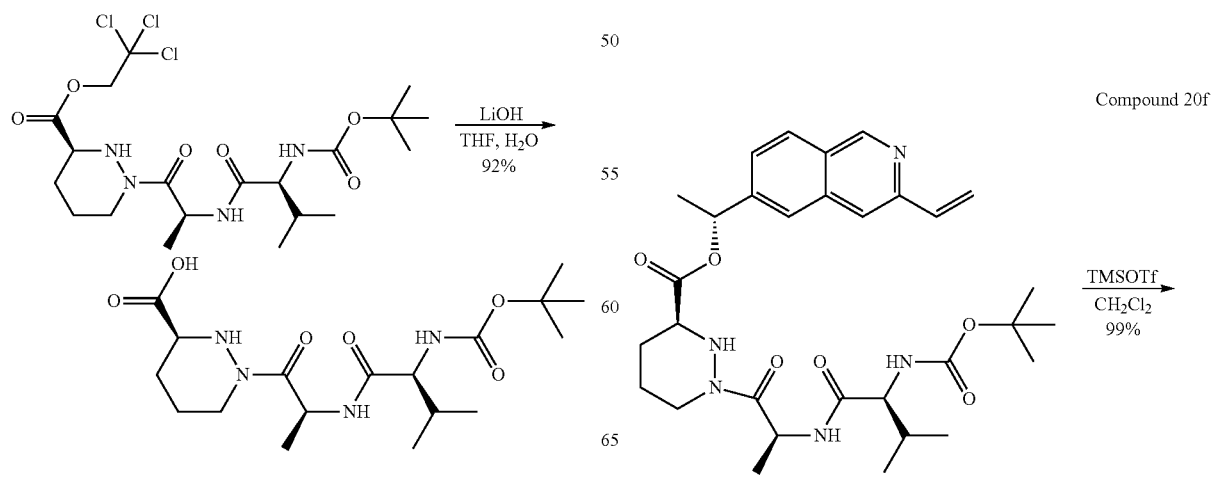

Synthesis of Compound 20e:

To a solution of 20d (339 mg, 0.920 mmol) and 20 b1 (183 mg, 0.920 mmol) in dichloromethane (4.6 mL) were added N-(3-dimethylaminopropyl)-N'-ethylcarbodiimide hydrochloride (211 mg, 1.10 mmol) and 4-dimethylaminopyridine (56.2 mg, 0.46 mmol) at 23° C. under an argon atmosphere. After 21 h, the reaction mixture was purified directly by silica gel flash column chromatography (24 g Combiflash HP Gold Column, 0-100% ethyl acetate/hexanes gradient) to afford the title compound (224 mg, 42%) as a light tan solid.

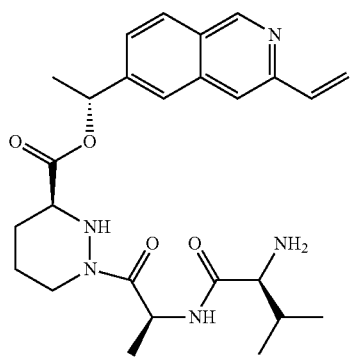

Synthesis of Compound 20f:

To a solution of 20e (224 mg, 0.390 mmol) in dichloromethane (2.0 mL) was added trimethylsilyl trifluoromethanesulfonate (128 mg, 0.58 mmol) at 0° C. under an argon atmosphere. After 2 h, the reaction mixture was concentrated under reduced pressure to afford the title compound (188 mg, 99%) as a light yellow oil, which was used without further purification.

Compound 20g

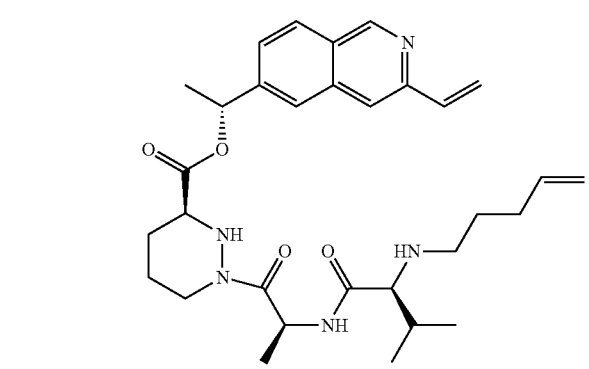

Synthesis of Compound 20g:

To a solution of 20f (94 mg, 0.195 mmol) in dimethylformamide (1.00 mL) were added cesium hydroxide monohydrate (98.5 mg, 0.585 mmol) and activated 4 Å molecular sieves (53 mg) at 23° C. under an argon atmosphere. After 10 min, 5-bromopent-1-ene (29 mg, 0.195 mmol) was added. After 4 d, the reaction mixture was diluted with brine (20 mL) and was extracted with ethyl acetate (3×20 mL). The combined organic extracts were dried over anhydrous sodium sulfate and were concentrated under reduced pressure. The crude residue was purified by silica gel flash column chromatography (12 g Combiflash HP Gold Column, 0-20% methanol/dichloromethane gradient) to afford the title compound (5.7 mg, 5%) as a light yellow solid.

Compound 20

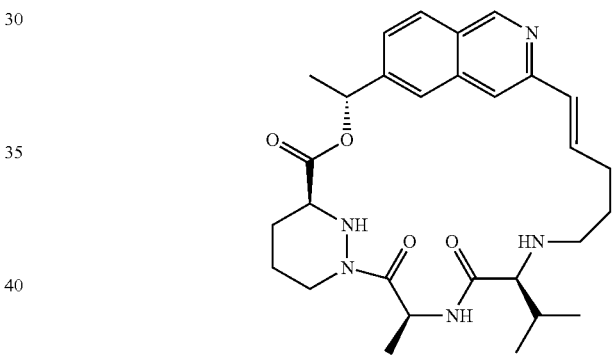

Synthesis of the Title Compound:

To a solution of 20g (5.7 mg, 11 µmol) in toluene (3.7 mL) was added the Hoveyda-Grubbs 2nd Generation Catalyst (1.0 mg, 1.7 µmol) at 23° C. under an argon atmosphere, and the resulting mixture was heated to 110° C. After 1.25 h, the reaction mixture was allowed to cool to 23° C., and was concentrated under reduced pressure. The crude residue was purified by preparatory HPLC (Gemini 5u C18 110 Å column, 5-100% MeCN/H$_2$O, 0.1% trifluoroacetic acid modifier) to afford the title compound (3.7 mg, 56%) as a white solid trifluoroacetic acid salt. $^1$H NMR (CD$_3$OD, 400 MHz): δ 9.21 (s, 1H), 8.09 (d, J=8.6 Hz, 1H), 7.84 (s, 1H), 7.79 (s, 1H), 7.60 (d, J=8.6 Hz, 1H), 6.66 (d, J=15.9 Hz, 1H), 6.57-6.45 (m, 1H), 5.99 (q, J=6.7 Hz, 1H), 5.30 (q, J=7.0 Hz, 1H), 4.31 (br-d, J=12.0 Hz, 1H), 3.69-3.61 (m, 2H), 2.91 (br-t, J=8.1 Hz, 2H), 2.68 (td, J=12.8, 3.2 Hz, 1H), 2.55-2.44 (m, 1H), 2.42-2.31 (m, 1H), 2.15-2.03 (m, 1H), 1.99-1.78 (m, 4H), 1.74-1.59 (m, 2H), 1.60 (d, J=6.7 Hz, 3H), 1.56 (d, J=7.1 Hz, 3H), 1.06 (d, J=6.9 Hz, 3H), 0.99 (d, J=6.9 Hz, 3H). HPLC t$_R$ (min), 4.169, purity %: 99%. (Phenomenex Kinetex 2.6u C18 100 Å, 100×4.60 mm 2.6 micron column, 8.5 min, 1.5 ml/min, 2-98% MeCN/H$_2$O, 0.1% trifluoroacetic acid modifier gradient). LCMS (ESI) m/z 522.2 [M+H]$^+$, t$_R$=1.68 min. (Gemini 5u C18 110 Å, 50×4.60 mm 5 micron column, 3.5 min, 2 ml/min, 5-100% MeCN/H₂O, 0.1% acetic acid modifier gradient).

Example 21

Compound 21

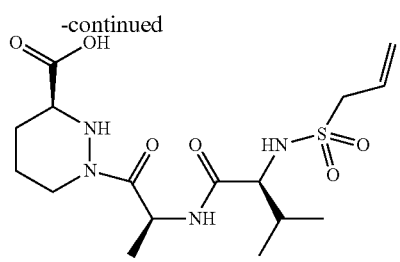
-continued

Compound 21a

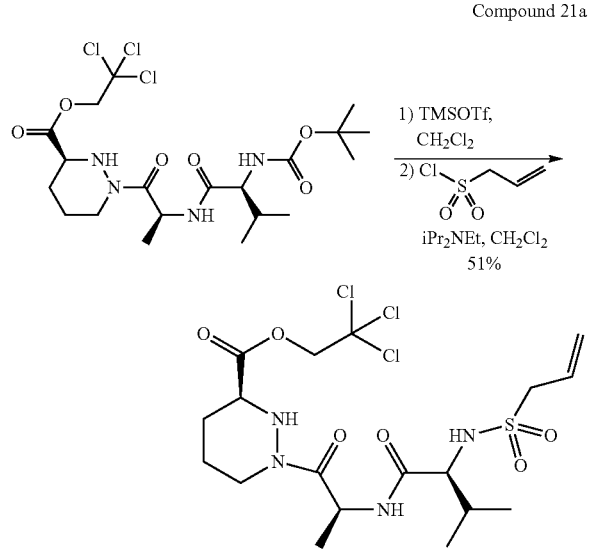

Synthesis of Compound 21a:

To a solution of 20c (500 mg, 0.945 mmol) in dichloromethane (4.7 mL) was added trimethylsilyl trifluoromethanesulfonate (314 mg, 0.141 mmol) at 0° C. under an argon atmosphere. After 1 h, the reaction mixture was concentrated under reduced pressure. The resulting residue was diluted with dichloromethane (4.7 mL) and N,N-diisopropylethylamine (657 µL, 3.78 mmol) and prop-2-ene-1-sulfonyl chloride (140 mg, 0.992 mmol) were sequentially added at 23° C. under an argon atmosphere. After 17 h, the reaction mixture was diluted with dichloromethane (50 mL) and the resulting mixture was washed with saturated aqueous sodium bicarbonate solution (50 mL). The organic layer was separated, dried over anhydrous sodium sulfate, and was concentrated under reduced pressure. The crude residue was purified by silica gel flash column chromatography (24 g Combiflash HP Gold Column, 0-100% ethyl acetate/hexanes gradient) to afford the title compound (256.4 mg, 51%) as an orange oil.

Compound 21b

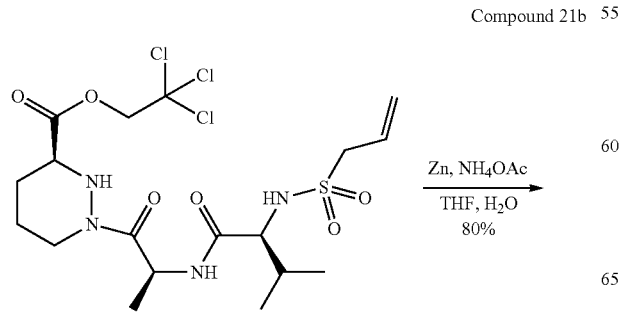

Synthesis of Compound 21b:

To a solution of 21a (256 mg, 0.478 mmol) in tetrahydrofuran (8.0 mL) were added zinc powder (625 mg, 9.57 mmol) followed by a solution of ammonium acetate (552 mg, 7.17 mmol) in water (5.31 mL) at 23° C. under an argon atmosphere. After 17 h, the reaction mixture was warmed to 45° C. After 7 h, the reaction mixture was allowed to cool to room temperature and was filtered through a pad of celite washing with water (10 mL). The filtrate was concentrated under reduced pressure to remove tetrahydrofuran and the residue was partitioned between water (25 mL) and ethyl acetate (25 mL). The layers were split and the aqueous layer was acidified to pH=2 with 12 N aqueous hydrogen chloride solution. The aqueous layer was extracted with ethyl acetate (4×50 mL), and the combined organic extracts were dried over anhydrous sodium sulfate, and were concentrated under reduced pressure. Residual acetic acid was removed azeotropically via addition of toluene (5 mL) followed by concentration under reduced pressure (3×) to afford the title compound (156 mg, 80%) as a white solid.

Compound 21c

Synthesis of Compound 21c:

To a solution of 21b (156 mg, 0.390 mmol) and 20b (92.3 mg, 0.464 mmol) in dichloromethane (1.95 mL) were added N-(3-dimethylaminopropyl)-N'-ethylcarbodiimide hydrochloride (105 mg, 0.546 mmol) and 4-dimethylaminopyridine (23.8 mg, 195 µmol) at 23° C. under an argon atmosphere. After 21 h, the reaction mixture was purified directly by silica gel flash column chromatography (24 g Combiflash HP Gold Column, 0-100% ethyl acetate/hexanes gradient) to afford the title compound (155 mg, 70%) as a colorless oil.

Compound 21

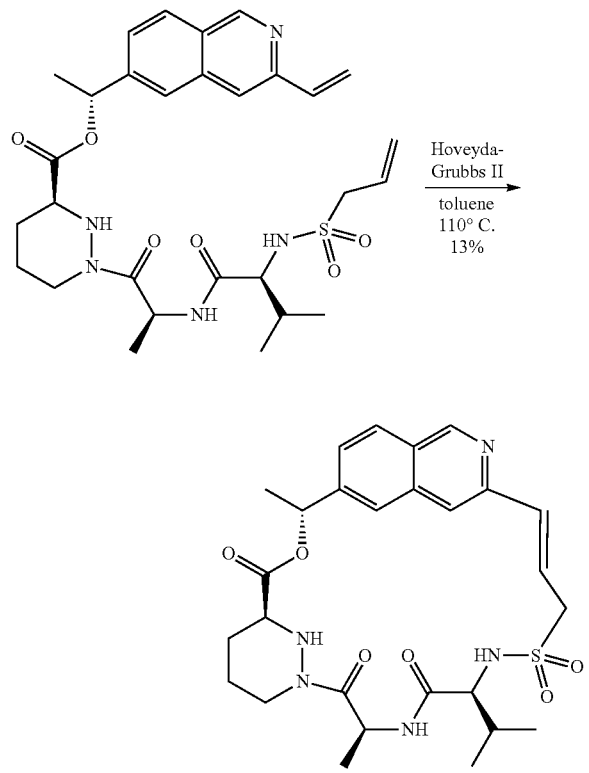

Synthesis of the Title Compound:

To a solution of 21c (150 mg, 256 μmol) in toluene (51 mL) was added the Hoveyda-Grubbs 2nd Generation Catalyst (16 mg, 25 μmol) at 23° C. under an argon atmosphere, and the resulting mixture was heated to 110° C. After 2 h, the reaction mixture was quenched with ethyl vinyl ether (500 μL) and the resulting mixture was allowed to cool to 23° C. The reaction mixture was concentrated under reduced pressure and the crude residue was purified by silica gel flash column chromatography (12 g Combiflash HP Gold Column, 0-100% ethyl acetate/hexanes gradient) to afford the title compound (18.6 mg, 13%) as a tan solid. $^1$H NMR (CD$_3$OD, 400 MHz): δ 9.37 (s, 1H), 8.23 (d, J=8.5 Hz, 1H), 8.14 (s, 1H), 7.97 (s, 1H), 7.77 (d, J=8.7 Hz, 1H), 6.85 (d, J=15.8 Hz, 1H), 6.75-6.64 (m, 1H), 6.22 (q, J=6.7 Hz, 1H), 5.62-5.52 (m, 1H), 4.40 (dd, J=13.3, 3.3 Hz, 1H), 4.21 (dd, J=14.8, 5.8 Hz, 1H), 4.10 (dd, J=13.4, 7.5 Hz, 1H), 4.06 (d, J=4.5 Hz, 1H), 3.72 (dd, J=11.5, 2.5 Hz, 1H), 2.79 (td, J=12.8, 3.2 Hz, 1H), 2.19 (app-sextet, J=7.0 Hz, 1H), 2.04-1.88 (m, 2H), 1.87-1.66 (m, 2H), 1.72 (d, J=6.7 Hz, 3H), 1.46 (d, J=7.2 Hz, 3H), 1.05 (d, J=6.7 Hz, 3H), 0.92 (d, J=6.8 Hz, 3H). HPLC $t_R$ (min), 2.882, purity %: 98%. (Synergi 4u hydro-RP, 50×4.60 mm 4 micron column, 7 min, 2 ml/min, 5-100% MeCN/H$_2$O, 0.05% trifluoroacetic acid modifier gradient). LCMS (ESI) m/z 558.44 [M+H]$^+$, $t_R$=1.88 min. (Gemini 5u C18 110 Å, 50×4.60 mm 5 micron column, 3.5 min, 2 ml/min, 5-100% MeCN/H$_2$O, 0.1% acetic acid modifier gradient). R$_f$=0.25 (ethyl acetate) UV.

Example 22

Compound 22

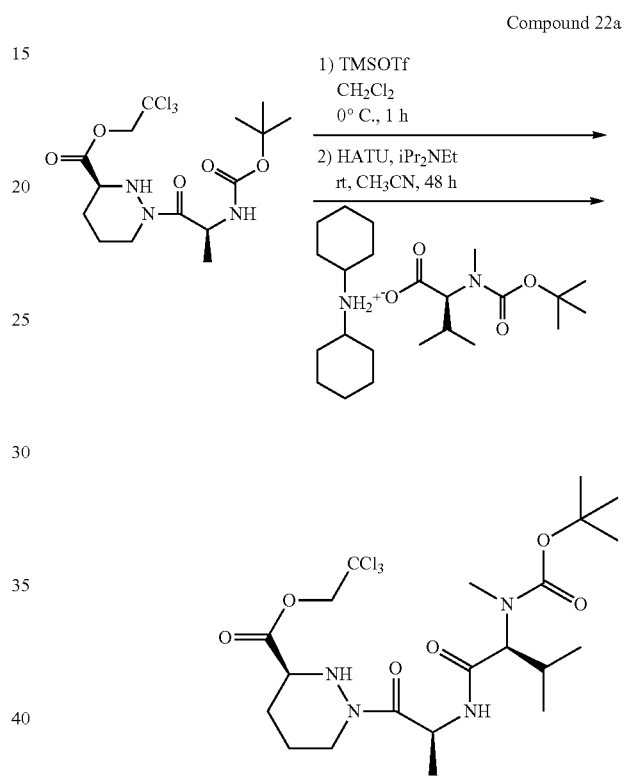

Compound 22a

Synthesis of Compound 22a:

A solution of 1d (865 mg, 2 mmol) in DCM (20 mL) was cooled in an ice water bath. Trimethylsilyl trifluoromethanesulfonate (667 mg, 3 mmol) was added dropwise at 0° C. under argon, and the resulting solution was stirred at room temperature for 30 min. The reaction mixture was evaporated to dryness and the resulting crude residue was dissolved in dry acetonitrile (25 mL) under argon. Reaction mixture was stirred at 0° C., (S)-2-(tert-butoxycarbonyl(methyl)amino)-3-methylbutanoic acid dicyclohexylamine salt (908 mg, 2.2 mmol) and N,N-diisopropylethylamine (1.034 g, 8 mmol) were added followed by 2-(1H-7-azabenzotriazol-1-yl)-1,1,3,3-tetramethyl uronium hexafluorophosphate methanaminium (1.065 g, 2.8 mmol). Reaction mixture was stirred at room temperature for 48 h. The solvent was evaporated, the residue was dissolved in ethyl acetate (100 mL) and the solution was washed twice with 20% water solution of citric acid (100 mL), water (100 mL) and brine (100 mL), dried over magnesium sulfate, filtered and evaporated. The residue was purified by silica gel chromatography (gradient from 0-40% ethyl acetate+methanol (4/1) in hexane) to afford the title compound as a white solid after evaporation (617 mg, 56%).

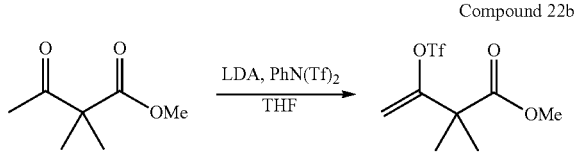

Compound 22b

Synthesis of Compound 22b:

Under argon, a solution of diisopropylamine (2.51 g, 24.8 mmol) in tetrahydrofuran (150 mL) was cooled in an ice water bath. A solution of n-butyllithium in hexanes (2.5 M, 9.7 mL, 24 mmol) was added dropwise over 2 min, and the resulting solution was stirred for 10 additional min. The solution was then cooled to −78° C. in a $CO_2$:acetone bath, and methyl 2,2-dimethyl-3-oxobutanoate (3.2 g, 22 mmol) was added dropwise over 30 sec. The solution was stirred for an additional 15 min, and N-phenyl-bis(trifluoromethanesulfonimide) (8.4 g, 23.5 mmol) was added as a solution in tetrahydrofuran (20 mL) via cannula over 5 min, washing with an additional portion of tetrahydrofuran (10 mL). The resulting solution was stirred for 10 min and was removed from the cold bath. After stirring an additional 1 h, the reaction mixture was concentrated in vacuo and diluted with diethyl ether (150 mL). The organic phase was washed with 1M aqueous sodium hydroxide (1×100 mL, 1×30 mL), dried over anhydrous magnesium sulfate, filtered, and concentrated to afford the title compound (6.2 g, 100%) as an amber liquid that was used without further purification.

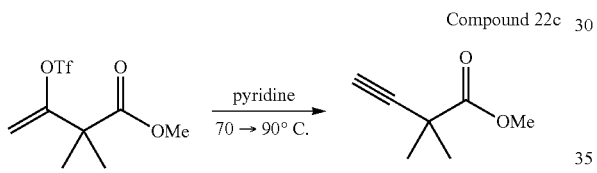

Compound 22c

Synthesis of Compound 22c:

A solution of 22b (6.2 g, 22 mmol) in anhydrous pyridine (11 mL, 140 mmol) was heated to 70° C. After 18.5 h, the temperature was increased to 90° C. After stirring for a total of 72 h, the reaction mixture was partitioned between a stirred mixture of diethyl ether (100 mL) and 3 M aqueous HCl (100 mL). The phases were separated, and the organic layer was washed with saturated aqueous sodium bicarbonate (75 mL), dried over magnesium sulfate, filtered, and concentrated to afford the title compound (2.7 g, 97%) as a slightly brown liquid that was used without further purification.

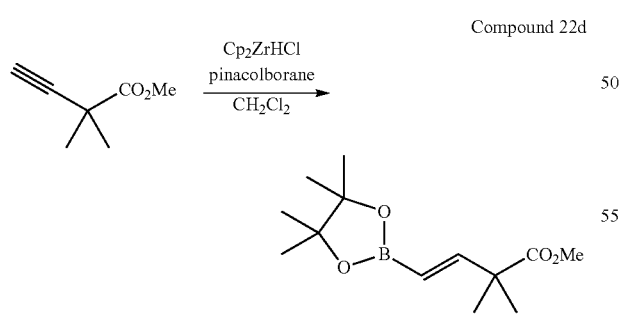

Compound 22d

Synthesis of Compound 22d:

Under argon, bis(cyclopentadienyl) zirconium chloride hydride (290 mg, 1.1 mmol) was cooled in an ice water bath. A solution of 22c (1.4 g, 11.1 mmol) and pinacolborane (2.4 mL, 16.5 mmol) in dichloromethane (3 mL) was added by cannula, washing with an additional portion of dichloromethane (2 mL). The resulting mixture was removed from the cold bath and was stirred for 72 h at room temperature.

The reaction was then diluted with ethyl acetate (50 mL), quenched with dropwise water (5 mL), and was further diluted with water (50 mL). The organic and aqueous phases were separated, and the aqueous phase was extracted with ethyl acetate (30 mL). The combined organic phase was dried over anhydrous sodium sulfate, filtered, and concentrated to afford a crude residue that was purified by silica gel chromatography (5% to 15% ethyl acetate in hexanes) to afford the title compound (1.6 g, 57%) as a colorless oil that crystallized on standing at −15° C.

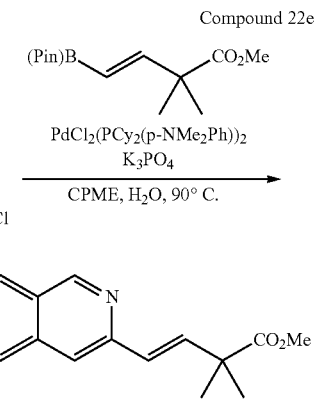

Compound 22e

Synthesis of Compound 22e:

Under argon, 20a (880 mg, 4.23 mmol), 22d (1.24 g, 4.88 mmol), $PdCl_2(PCy_2(p-NMe_2Ph))_2$ (173 mg, 0.21 mmol) and $K_3PO_4$ (2.64 g, 12.4 mmol) were dissolved in cyclopentyl methyl ether (11.9 mL) and water (5.1 mL). The resulting biphasic mixture was vigorously stirred in an oil bath at 90° C. for 3.5 h, at which time the reaction was cooled to ambient temperature and was diluted with ethyl acetate (50 mL) and water (40 mL). The phases were separated, and the aqueous phase was extracted with ethyl acetate (2×50 mL). The combined organic phase was dried over anhydrous magnesium sulfate, filtered, and concentrated to afford a crude residue that was purified by silica gel chromatography (25 to 60% ethyl acetate in hexanes) to afford the title compound as a yellow oil (1.07 g, 85%).

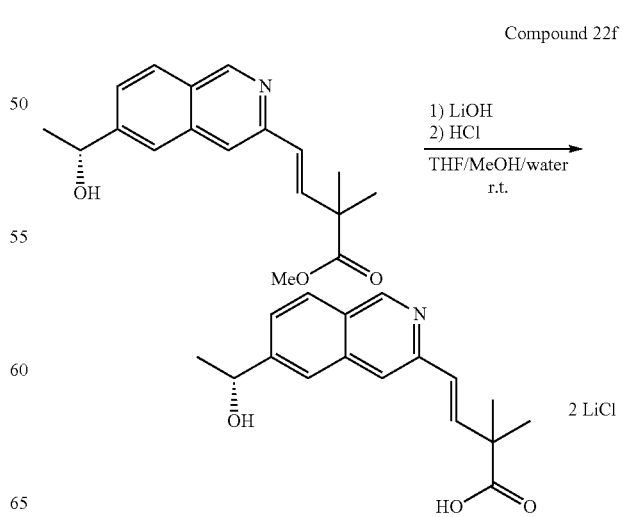

Compound 22f

Synthesis of Compound 22f:

To a solution of 22e (600 mg, 2 mmol) in tetrahydrofuran (8 mL) was added methanol (4 mL), water (4 mL) and lithium hydroxide (96 mg, 4 mmol). The resulting mixture was stirred at room temperature for 10 h and quenched with 1 M HCl (4.2 mL, 4.2 mmol). The resulting solution was concentrated to a crude residue which was co-distilled twice with tetrahydrofuran (20 mL), twice with dry acetonitrile (20 mL) and twice with dry toluene (20 mL). The resulting white solid was dried under high vacuum overnight and it was used without further purification (735 mg, quantitative yield).

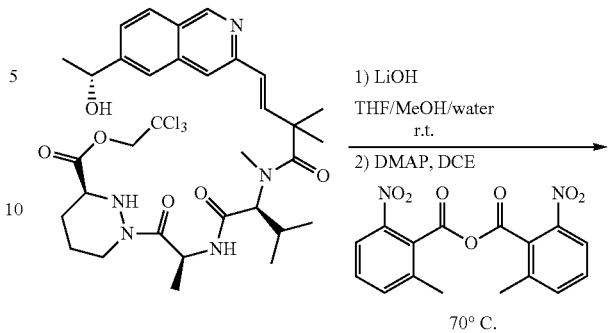

Compound 22g

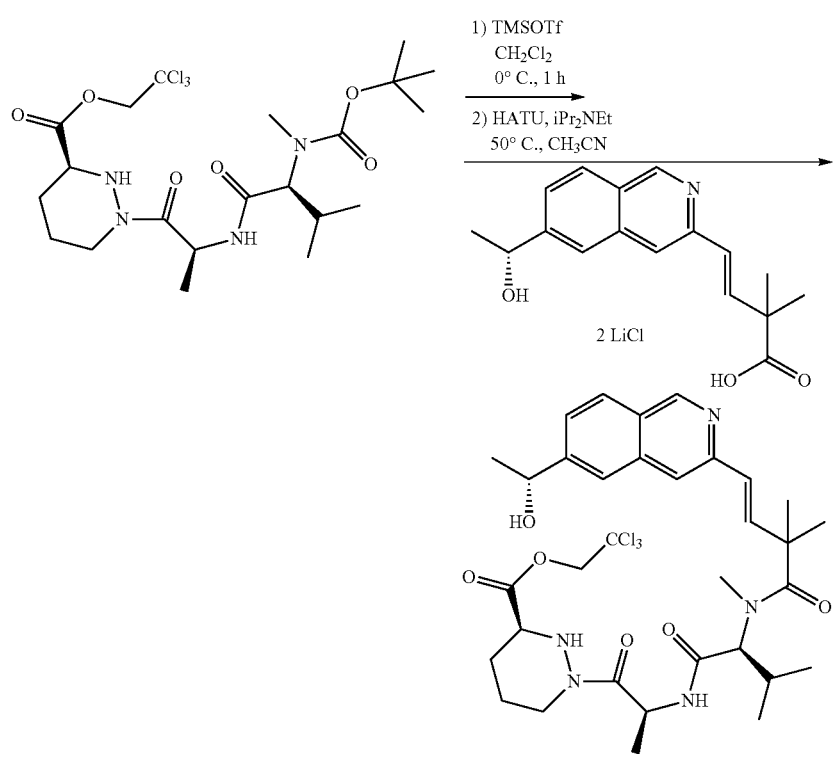

Synthesis of Compound 22g:

A solution of 17a (230 mg, 0.42 mmol) in dichloromethane (10 mL) was cooled in an ice water bath. Trimethylsilyl trifluoromethanesulfonate (128 mg, 0.575 mmol) was added dropwise at 0° C. under argon, and the resulting solution was stirred at room temperature for 30 min. The reaction mixture was evaporated to dryness and the resulting crude residue was dissolved in dry acetonitrile (20 mL) under argon. Reaction mixture was stirred at 0° C., 22f (128 mg, 0.38 mmol) and N,N-diisopropylethylamine (198 mg, 1.53 mmol) were added followed by 2-(1H-7-azabenzotriazol-1-yl)-1,1,3,3-tetramethyl uronium hexafluorophosphate methanaminium (218 mg, 0.58 mmol). Reaction mixture was stirred at 50° C. for 5 days. The solvent was evaporated, the residue was dissolved in ethyl acetate (50 mL) and the solution was washed twice with 20% water solution of citric acid (50 mL), water (50 mL) and brine (50 mL), dried over magnesium sulfate, filtered and evaporated. The residue was purified by silica gel chromatography (gradient from 0-40% ethyl acetate+methanol (4/1) in hexane) to afford after evaporation the title compound as a white solid (88 mg, 32%).

-continued

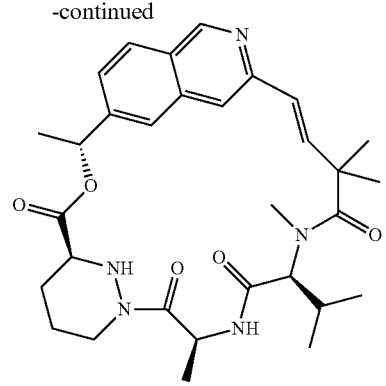

Synthesis of the Title Compound:

To a solution of 22g (45 mg, 0.06 mmol) in tetrahydrofuran (2 mL) was added methanol (1 mL), water (1 mL) and lithium hydroxide (2.9 mg, 0.12 mmol). The mixture was stirred for 2 h at ambient temperature and was quenched with aqueous 1 M HCl (0.14 mL, 0.14 mmol). The resulting solution was concentrated to a crude residue which was co-distilled twice with tetrahydrofuran (5 mL), twice with dry acetonitrile (5 mL) and twice with dry toluene (5 mL). The resulting white solid was dried under high vacuum overnight and it was used without further purification (40 mg, quantitative yield). Into oven dried, argon purged flask were placed 2-methyl-6-nitrobenzoic anhydride (83 mg, 0.24 mmol), 4-dimethylformamide (88 mg, 0.72 mmol) and dry 1,2-dichloroethane (100 mL). The resulting solution was heated at 70° C., and the crude product from the previous step was added dropwise via syringe as a solution in dry N,N-dimethylformamide (5 mL) over 12 h. An additional portion of dry N,N-dimethylformamide (2×1 ml) was used to complete the quantitative transfer. After stirring for additional 8 h at 70° C., the reaction mixture was transferred to separatory funnel and washed with water (100 mL, 5 mL of brine was added to support the separation). The aqueous phase was extracted with dichloromethane (50 mL). Combined organic extracts were washed with brine (50 mL) and dried over magnesium sulfate, filtered and concentrated under reduced pressure. The resulting residue was dissolved in ethyl acetate (100 mL) and was washed with water (100 mL, 5 mL of brine was added to support the separation). The aqueous phase was extracted with ethyl acetate (50 mL). Combined organic extracts were washed with water (100 mL, 5 mL of brine was added to support the separation). Resulting aqueous phase was extracted with ethyl acetate (50 mL). Combined organic extracts were washed with brine (50 mL) and dried over magnesium sulfate, filtered and concentrated under reduced pressure. The residue was purified by silica gel chromatography (gradient from 0-40% ethyl acetate+methanol (4/1) in hexane) to afford after evaporation the title compound (6 mg, 18%) as a colorless oil. $^1$H NMR (400 MHz, CD$_3$OD): δ 9.05 (s, 1H), 7.95 (d, J=8.5 Hz, 1H), 7.70 (s, 1H), 7.46 (d, J=8.5 Hz, 1H), 7.20 (s, 1H), 6.76 (d, J=16.2 Hz, 1H), 6.28 (d, J=16.2 Hz, 1H), 5.93 (m, 1H), 5.27-5.22 (m, 1H), 5.14 (m 1H), 4.82 (m 1H), 4.29 (m 1H), 3.70 (m, 1H), 3.38 (m, 1H), 2.77 (s, 3H), 2.63 (m, 1H), 2.09 (m, 2H), 1.93 (m, 2H), 1.86 (m, 1H), 1.79 (m, 2H), 1.59 (t, J=7.4 Hz, 6H), 1.45 (m, 2H), 0.85 (d, J=6.6 Hz, 3H), 0.76 (d, J=6.4 Hz, 3H). LC/MS (m/z) 564 (100%) [M+H]$^+$; R$_T$=3.14 min.; purity >95% (Phenomenex Gemini 5 micron C18, 30×4.6 mm, 5 to 100% acetonitrile in water over 6 min, 2 mL/min, 0.05% formic acid modifier). TLC Rf=0.43, 5% methanol in dichloromethane.

Example 23

Compound 23

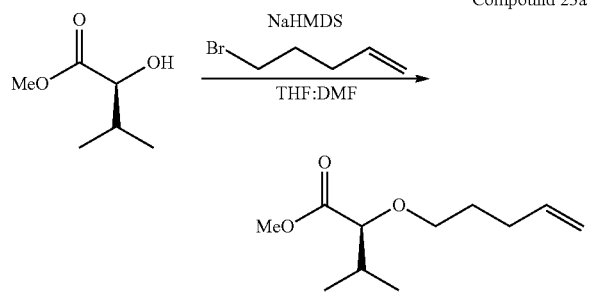

Compound 23a

Synthesis of Compound 23a:

Under argon, (S)-methyl 2-hydroxy-3-methylbutanoate (578 mg, 4.37 mmol) was dissolved in tetrahydrofuran (3.7 mL) and N,N-dimethylformamide (2.5 mL). The solution was cooled in an ice water bath. Sodium bis(trimethylsilyl) amide was added as a 1.0 M solution in tetrahydrofuran (3.7 mL, 3.7 mmol) dropwise over 1.5 min. After an additional 3.5 min, 5-bromopent-1-ene was added in one portion. The reaction was stirred for 2 min and was removed from the cold bath. After 2 h, the reaction was quenched with saturated aqueous ammonium chloride (10 mL) and was diluted with ethyl acetate (20 mL), water (10 mL), and 0.1 N HCl (5 mL). The phases were separated, and the aqueous phase was extracted with ethyl acetate (20 mL). The combined organic phase was dried over sodium sulfate, filtered, and concentrated to afford a crude residue that was purified by silica gel chromatography (0 to 10% ethyl acetate in hexanes) to afford the title compound (290 mg, 33%) as a colorless liquid

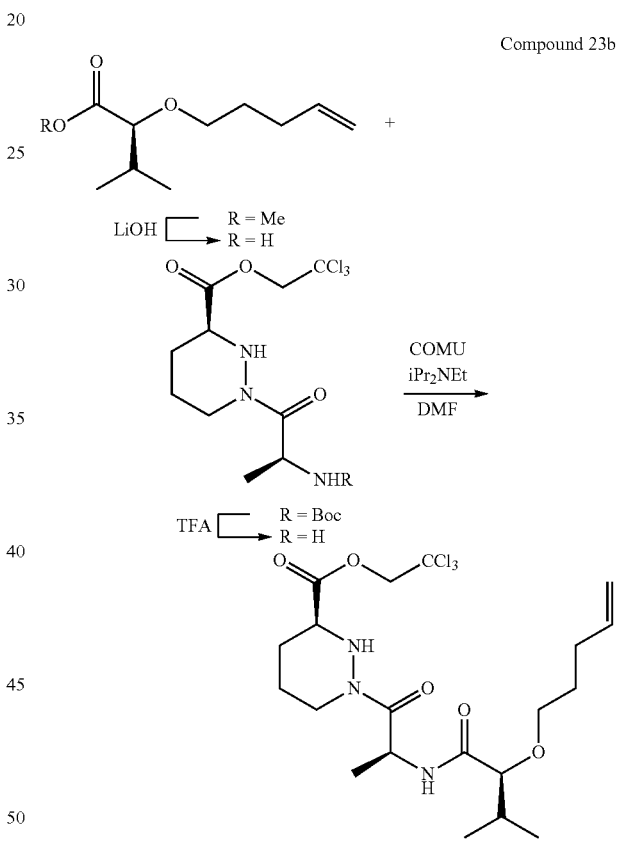

Compound 23b

Synthesis of Compound 23b:

To a solution of 23a (155 mg, 0.774 mmol) in tetrahydrofuran (3 mL) was added water (1 mL) and lithium hydroxide monohydrate (165 mg, 3.93 mmol). The reaction was stirred 18 h at which time methanol (1 mL) was added. The reaction was stirred for an additional 24 h and was then concentrated by 50% in vacuo and diluted with water (20 mL), ethyl acetate (20 mL) and 3 N aqueous HCl (15 mL). The phases were separated, and the aqueous phase was extracted with ethyl acetate (2×20 mL). The combined organic phase was dried over anhydrous sodium sulfate filtered, and concentrated to afford (S)-3-methyl-2-pent-4-enyloxy-butyric acid (115 mg, 80%) which was used without further purification. Under argon, 1d (240 mg, 0.55 mmol) was dissolved in dichloromethane (10 mL). The solution was cooled in an ice water bath and trimethylsilyl trifluoromethanesulfonate (209 mg, 0.94 mmol) was added. The reaction was stirred for 1 h and was quenched by the addition of N,N-diisopropylethylamine (296 mg, 2.3 mmol). The mixture was concentrated in vacuo and dissolved in methanol. After stirring for 10 min, the solution was concentrated in vacuo and was twice dissolved in and concentrated from toluene (10 mL portions). The resulting crude residue was used without further purification. (S)-3-methyl-2-pent-4-enyloxy-butyric acid (0.62 mmol) and (S)-1-[(S)-2-((S)-2-amino-3-methyl-butyrylamino)-propionyl]-hexahydro-pyridazine-3-carboxylic acid 2,2,2-trichloroethyl ester (ca. 0.55 mmol) were dissolved in N,N-dimethylformamide (5 mL). N,N-diisopropylethylamine (192 mg, 1.5 mmol) was added, and the solution was cooled in an ice water bath. (1-Cyano-2-ethoxy-2-oxoethylidenaminooxy)dimethylamino-morpholino-carbenium hexafluorophosphate (320 mg, 0.75 mmol) was added in one portion, and the reaction was stirred for 15 min. The reaction was then removed from the cold bath and let warm to ambient temperature. After stirring overnight, the reaction was diluted with ethyl acetate (30 mL) and saturated aqueous sodium bicarbonate (30 mL). The phases were separated, and the organic phase was washed with a mixture of 0.2 N aqueous HCl (30 mL) and brine (5 mL) followed by half-saturated brine (30 mL) and brine (30 mL). The organic phase was dried over anhydrous sodium sulfate, filtered, and concentrated to afford a crude residue that was purified by silica gel chromatography (30% to 60% ethyl acetate in hexanes) to afford the title compound (157 mg, 57%) as an amorphous residue.

was added. The reaction was stirred at 50° C. for 2 h and was then cooled to 35° C. and stirred for an additional 18.5 h. The mixture was filtered through Celite with ethyl acetate (50 mL) and was washed with a mixture of 2 N aqueous HCl (30 mL) and brine (15 mL). The layers were separated, and the aqueous phase was extracted with ethyl acetate (2×30 mL). The combined organic phase was dried over sodium sulfate, filtered, and concentrated. The resulting crude residue was twice taken up in and concentrated from toluene (10 mL), and the crude (S)-1-[(S)-2-((S)-3-methyl-2-pent-4-enyloxy-butyrylamino)-propionyl]-hexahydro-pyridazine-3-carboxylic acid was used without further purification. (S)-1-[(S)-2-((S)-3-Methyl-2-pent-4-enyloxy-butyrylamino)-propionyl]-hexahydro-pyridazine-3-carboxylic acid (74 mg, 0.37 mmol) and 4-dimethylaminopyridine (45.5 mg, 0.37 mmol) were dissolved in dichloromethane (5 mL). N-(3-Dimethylaminopropyl)-N'-ethylcarbodiimide hydrochloride (78 mg, 0.41 mmol) was added in one portion. The reaction was stirred 44 h at room temperature and was diluted with ethyl acetate (50 mL), water (25 mL), saturated aqueous sodium bicarbonate (25 mL), and brine (25 mL). The phases were separated, and the aqueous phase was extracted with ethyl acetate (50 mL). The combined organic phase was dried over anhydrous sodium sulfate, filtered, and concentrated to afford a crude residue that was purified by silica gel chromatography (50 to 80 to 100% ethyl acetate in hexanes) to afford the title compound (118 mg, 69% over 2 steps) as a white foam.

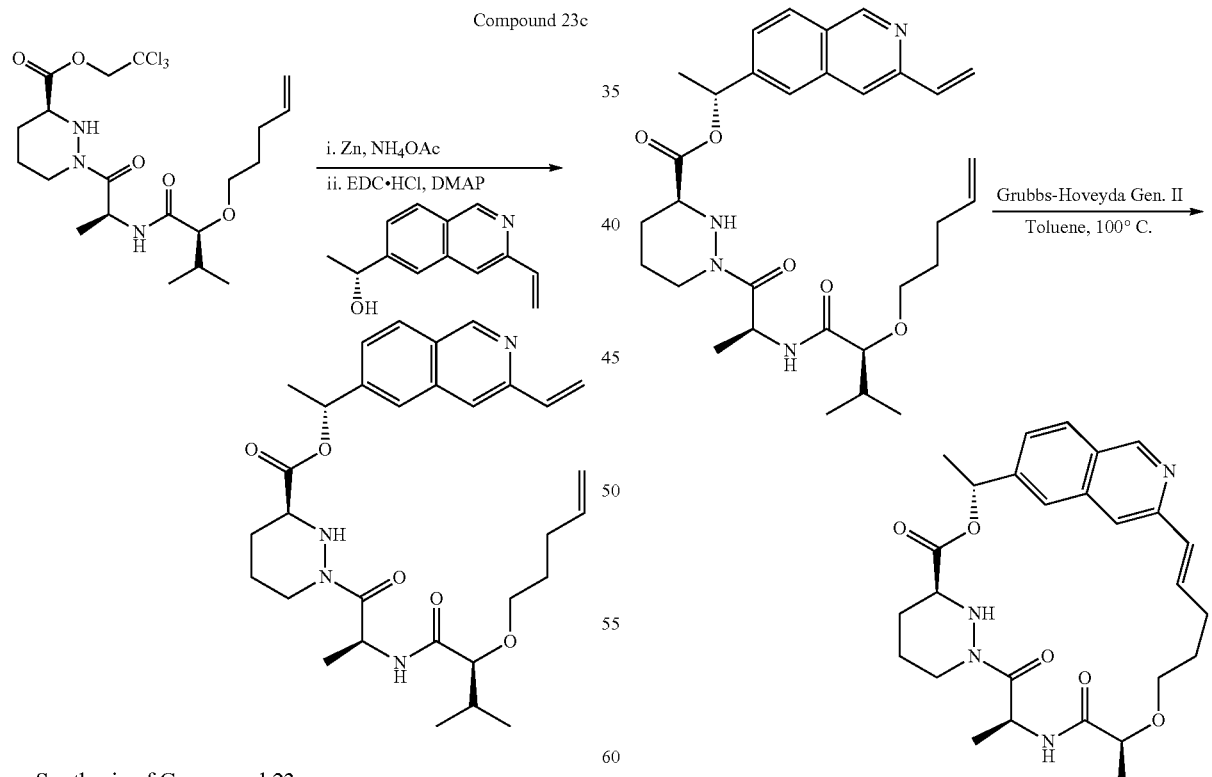

Synthesis of Compound 23c:

To a solution of 23b (157 mg, 0.31 mmol) in tetrahydrofuran (5.3 mL) was added water (2.6 mL), ammonium acetate (365 mg, 4.7 mmol) and zinc dust (460 mg, 7.0 mmol). The resulting mixture was stirred vigorously at room temperature for 24 h, and the reaction was then heated to 50° C. After an additional 3.5 h, additional zinc powder (240 mg, 3.7 mmol)

Synthesis of the Title Compound:

23c (53 mg, 0.096 mmol) was dissolved in toluene (30 mL) under argon. The solution was sparged with argon with stirring for 10 min. Grubbs-Hoveyda second generation metathesis catalyst (9.0 mg, 0.014) was then added as a solution in argon-sparged toluene (2.0 mL). The reaction was heated to 100° C. in a preheated oil bath and was stirred for 35 min. The reaction was concentrated in vacuo to ~6.5 mL final volume and was loaded directly onto a silica gel column. Elution with 60% to 85% to 100% ethyl acetate in hexanes provided 30 mg of impure material that was re-purified by reverse-phase HPLC (C18, 15% to 100% acetonitrile in water, 0.1% trifluoroacetic acid) to provide the title compound (17.8 mg, 35%) as its trifluoroacetic acid salt as an amorphous solid. $^1$H NMR (400 MHz, CD$_3$OD) δ 9.56 (s, 1H), 8.53 (s, 1H), 8.39 (d, J=8.8 Hz, 1H), 8.20 (s, 1H), 7.87 (d, J=8.6 Hz, 1H), 7.60-7.45 (m, 1H), 6.73 (d, J=16.1 Hz, 1H), 6.21 (q, J=6.7 Hz, 1H), 5.93-5.79 (m, 1H), 4.49-4.36 (m, 1H), 3.84-3.73 (m, 1H), 3.61 (d, J=6.7 Hz, 1H), 3.59-3.45 (m, 2H), 2.86-2.70 (m, 2H), 2.44-2.31 (m, 1H), 2.18-1.89 (m, 4H), 1.88-1.61 (m, 7H), 1.59 (d, J=7.1 Hz, 3H), 1.04-0.95 (m, 6H) ppm. LCMS (m/z) 523.3 [M+H], R$_T$ 2.72 min.

Example 24

Compound 24

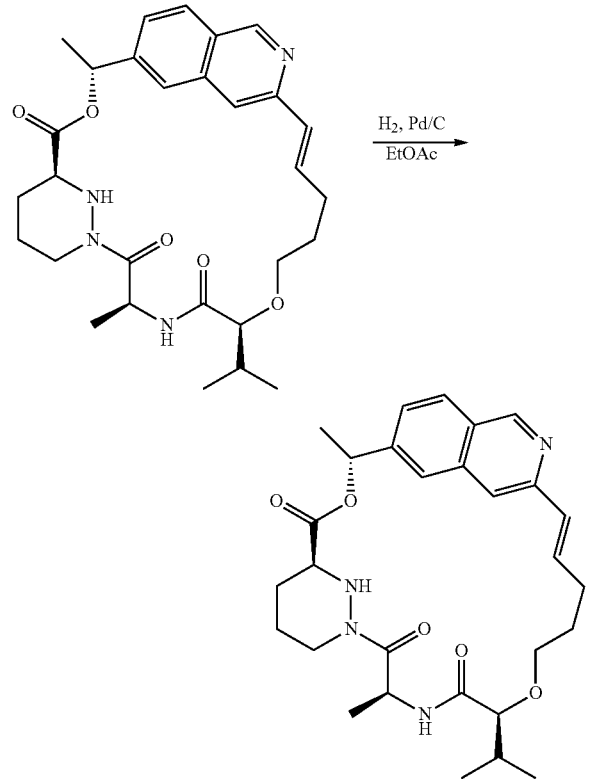

The trifluoroacetic acid salt of Compound 23 (7.9 mg, 0.012 mmol) was dissolved in ethyl acetate (0.80 mL). 10% palladium on carbon (5.6 mg) was added in one portion, and the reaction vessel was flushed with hydrogen. The reaction mixture was stirred for 2.5 h under 1 atm hydrogen gas and was then filtered through a pad of Celite with ethyl acetate. The filtrate was concentrated and the resulting crude residue was purified by reverse-phase HPLC (C18, 15% to 100% acetonitrile in water, 0.1% trifluoroacetic acid) to provide the title compound (4.2 mg, 60%) as its trifluoroacetic acid salt as an amorphous solid following lyophilization. $^1$H NMR (400 MHz, CD$_3$OD) δ 9.63 (s, 1H), 8.42 (d, J=8.8 Hz, 1H), 8.26 (s, 1H), 7.96 (s, 1H), 7.91 (d, J=8.8 Hz, 1H), 6.16 (q, J=6.5 Hz, 1H), 5.79-5.68 (m, 1H), 3.91-3.83 (m, 1H), 3.46-3.40 (m, 1H), 3.40 (d, J=5.7 Hz, 1H), 3.26-3.09 (m, 4H), 2.06-1.89 (m, 6H), 1.84 (m, 1H), 1.73-1.59 (m, 7H), 1.52 (d, J=6.9 Hz, 3H), 1.52 (m, 1H), 0.93 (s, 3H), 0.91 (s, 3H) ppm. LCMS (m/z) 525.4 [M+H], R$_T$=2.51 min.

Example 25

Compound 25

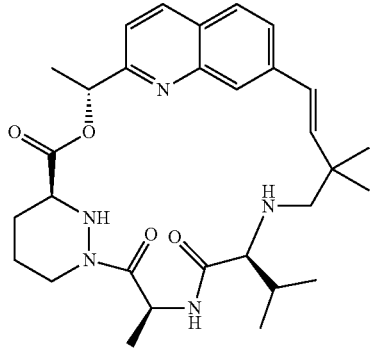 [SMILES: CC(C)[C@@H]1NCC(C)(C)/C=C/c2ccc3ccc(nc3c2)[C@@H](C)OC(=O)[C@@H]2CCCN(N2)C(=O)[C@H](C)NC1=O]

Compound 25a. 2,2-Dimethyl-but-3-en-1-ol

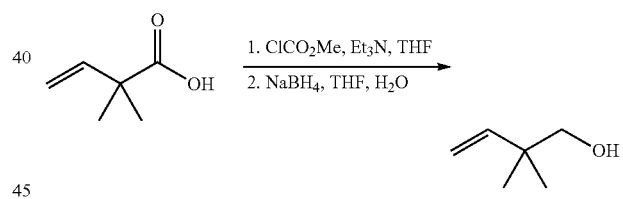

A solution of 2,2-dimethyl-but-3-enoic acid (570 mg, 5 mmol) and triethylamine (505 mg, 0.7 mL, 5 mmol) in tetrahydrofuran (15 mL) was stirred at −5° C. under nitrogen. A solution of methyl chloroformate (473 mg, 0.4 mL, 5 mmol) in tetrahydrofuran (5 mL) was added and the reaction mixture was stirred at −5° C. for 30 min. The reaction mixture was filtered, the residue was washed with tetrahydrofuran and the filtrate was evaporated. The residue was dissolved in tetrahydrofuran (5 mL), water (5 mL) was added and the reaction mixture was stirred at 0° C. Sodium borohydride (190 mg, 5 mmol) was added portion-wise and the reaction mixture was stirred at 0° C. for 15 min and then at room temperature for 30 min. Saturated ammonium chloride solution (25 mL) was added and the mixture was extracted with diethyl ether. The organic extracts were combined, washed with brine, dried over anhydrous magnesium sulfate, filtered and evaporated. The residue was purified by silica gel chromatography using a gradient of iso-hexanes/diethyl ether 10:1 to 5:1 to afford the title compound (569 mg, 95%) as an oil. $^1$H NMR (300 MHz, CDCl$_3$) δ 1.05 (s, 6H), 1.33 (t, J=6.5 Hz, 1H), 3.36 (d, J=6.5 Hz, 2H), 5.09 (dd, J=17.4, 1.3 Hz, 1H), 5.12 (dd, J=10.9, 1.3 Hz, 1H), 5.79 (dd, J=17.4, 10.9 Hz, 1H).

Compound 25b:
1-(7-Bromo-quinolin-2-yl)-ethanone

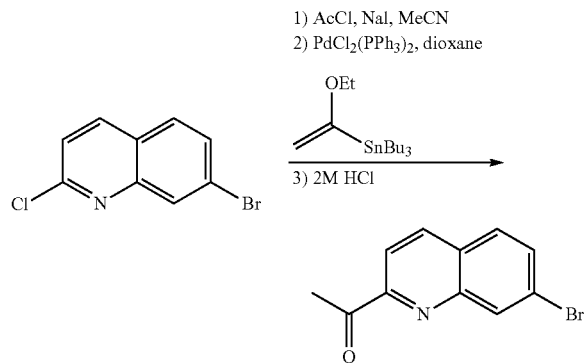

To a stirred slurry of 7-bromo-2-chloro-quinoline (obtained from AstaTech, Inc.), (8.10 g, 33.4 mmol) and sodium iodide (50.0 g, 334 mmol) in acetonitrile (27 mL) was slowly added acetyl chloride (3.56 mL, 50.0 mmol). The flask was stoppered and sealed and heated at 80° C. for 3 h before being allowed to cool. The mixture was treated sequentially with 10% w/w aqueous potassium carbonate solution (80 mL), 5% w/w aqueous sodium sulfite solution (80 mL) and saturated aqueous sodium thiosulfate solution (80 mL) and the mixture extracted with dichloromethane (2×). The combined organic extracts were dried over sodium sulfate, filtered and evaporated to give a crude 7-bromo-2-iodo-quinoline. To the quinoline was added tributyl(1-ethoxyvinyl)tin (13.6 mL, 40.1 mmol), 1,4-dioxane (67 mL) and bis(triphenylphosphine)palladium(II) dichloride (2.37 g, 3.34 mmol) and the reaction mixture heated at 100° C. for 5 h before being allowed to cool. 2 M aqueous hydrochloric acid (67 mL) was added and the reaction stirred for 1 h. The mixture was filtered and the solids washed with ethyl acetate and the filtrate evaporated to remove organics. The residue was extracted with ethyl acetate (3×) and the combined organic extracts were dried over sodium sulfate, filtered and evaporated. The product was purified on silica gel doped with 10% w/w potassium carbonate eluting with a gradient of 0% to 6% ethyl acetate in iso-hexanes to afford the title compound (5.5 g, 66%) as a white solid. $^1$H NMR (300 MHz, CDCl$_3$) δ 2.86 (s, 3H), 7.72-7.80 (m, 2H), 8.21 (ABq, Δδ$_{AB}$=0.11, J$_{AB}$=8.5 Hz, 2H), 8.42 (s, 1H). LCMS (m/z) 250.1/252.1 [M+H], Tr=2.90 min.

Compound 25c: (R)-1-(7-Bromo-quinolin-2-yl)-ethanol

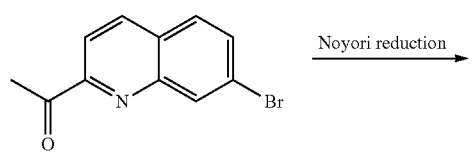

Dichloro (p-cymene) ruthenium(II) dimer (61 mg, 0.100 mmol) and (1R,2R)-(−)—N-p-tosyl-1,2-diphenylethylenediamine (88 mg, 0.012 mmol) was suspended in degassed water (40 mL) and the mixture was degassed with nitrogen for 5 min. The mixture was stirred at 70° C. under nitrogen for 90 min. The resulting turbid orange mixture was allowed to cool to room temperature. 1-(7-Bromo-quinolin-2-yl)-ethanone (5.00 g, 20 mmol) in degassed tetrahydrofuran (40 mL) was added followed by sodium formate (6.8 g, 100 mmol) and the reaction mixture was degassed with nitrogen for 5 min. The reaction mixture was vigorously stirred at 40° C. for 4 h and allowed to cool. It was then diluted with ethyl acetate and water and the organic layer was separated, washed with water and brine, dried over sodium sulfate, filtered and evaporated. The residue was purified by silica gel chromatography using a gradient of 0% to 30% ethyl acetate in iso-hexanes to afford the title compound (4.96 g, 98%) as an off-white solid. $^1$H NMR (300 MHz, CDCl$_3$) δ 1.59 (d, J=6.7 Hz, 3H), 4.85 (d, J=4.5 Hz, 1H), 5.04-5.07 (m, 1H), 7.40 (d, J=8.5 Hz, 1H), 7.64 (dd, J=8.7, 1.6 Hz, 1H), 7.71 (d, J=8.7 Hz, 1H), 8.15 (d, J=8.5 Hz, 1H), 8.28 (d, J=1.6 Hz, 1H). LCMS (m/z) 252.1/254.1 [M+H], Tr=1.74 min.

Compound 25d: Acetic acid (R)-1-(7-bromo-quinolin-2-yl)-ethyl ester

To a solution of 25c (1.00 g, 3.97 mmol) and triethylamine (1.65 mL, 11.9 mmol) in anhydrous dichloromethane at 0° C., was added acetic anhydride (0.75 mL, 7.93 mmol) and 4-(dimethylamino)pyridine (24 mg, 0.197 mmol). The reaction mixture was stirred and allowed to warm to room temperature. After 1.5 h water (100 mL) was added and the layers separated. The aqueous phase was re-extracted with dichloromethane (2×100 mL) and the combined organics were washed with brine (100 mL), dried over magnesium sulfate, filtered and concentrated in vacuo to give a crude residue. This was purified by silica gel chromatography using iso-hexanes (66 mL) then iso-hexanes/ethyl acetate 95:5 (300 mL), then iso-hexanes/ethyl acetate 9:1 (1066 mL) to yield 25d (1.16 g, 99%) as a colorless oil. $^1$H NMR (300 MHz, CD$_3$OD) δ 1.65 (d, J=6.7 Hz, 3H), 2.16 (s, 3H), 5.98 (q, J=6.7 Hz, 1H), 7.63 (d, J=8.5 Hz, 1H), 7.72 (dd, J=8.7, 1.8 Hz, 1H), 7.87 (d, J=8.7 Hz, 1H), 8.23 (d, J=1.8 Hz, 1H), 8.37 (d, J=8.5 Hz, 1H). LCMS (m/z) 293.9/296.0 [M+H], Tr=2.58 min.

Compound 25e. Acetic acid (R)-1-[7-((E)-4-hydroxy-3,3-dimethyl-but-1-enyl)-quinolin-2-yl]-ethyl ester

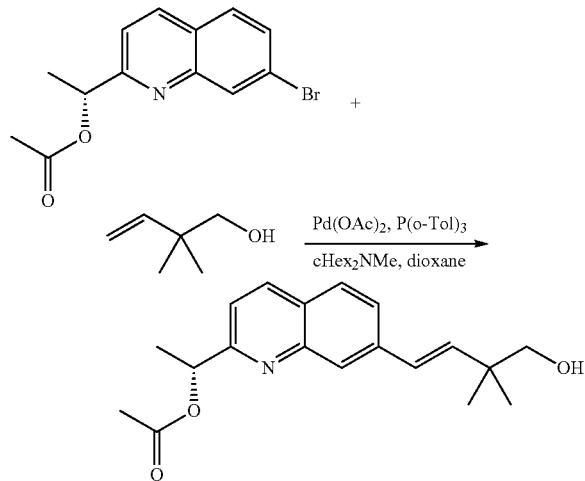

A solution of 2,2-dimethyl-but-3-en-1-ol (40 mg, 0.4 mmol) and 25d (118 mg, 0.4 mmol) in 1,4-dioxane (5 mL) was stirred at room temperature under nitrogen. Palladium(II) acetate (18 mg, 0.08 mmol) and tri(o-tolyl)phosphine (24 mg, 0.08 mmol) were added followed by a solution of N,N-dicyclohexylmethylamine (125 mg, 0.14 mL, 0.64 mmol) in 1,4-dioxane (1 mL) and the reaction mixture was heated at 100° C. for 90 min. Additional palladium(II) acetate (9 mg, 0.04 mmol), tri(o-tolyl)phosphine (12 mg, 0.04 mmol) were added and the reaction mixture was heated at 100° C. for 3 h. The reaction mixture was cooled to room temperature. Ethyl acetate was added and the mixture was washed with saturated sodium hydrogen carbonate solution and brine. The organic solution was filtered through a hydrophobic frit and the filtrate was evaporated. The residue was purified by silica gel chromatography using iso-hexanes/ethyl acetate 3:1 to 1:1 to afford 25e (85 mg, 68%) as a gum. $^1$H NMR (300 MHz, CDCl$_3$) δ 1.20 (s, 6H), 1.43 (t, J=6.3 Hz, 1H), 1.69 (d, J=6.7 Hz, 3H), 2.18 (s, 3H), 3.50 (d, J=6.3 Hz, 2H), 6.06 (q, J=6.7 Hz, 1H), 6.52 (ABq, Δδ$_{AB}$=0.18, J$_{AB}$=16.0 Hz, 2H), 7.42 (d, J=8.5 Hz, 1H), 7.62 (dd, J=8.5, 1.6 Hz, 1H), 7.75 (d, J=8.5 Hz, 1H), 8.03 (br s, 1H), 8.11 (d, J=8.5 Hz, 1H). LCMS (m/z) 314.1 [M+H], Tr=2.21 min.

Compound 25f. Acetic acid (R)-1-[7-((E)-3,3-dimethyl-4-oxo-but-1-enyl)-quinolin-2-yl]-ethyl ester

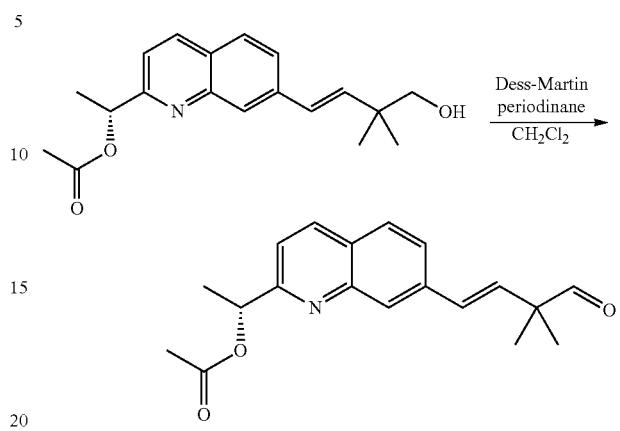

A solution of 25e (78 mg, 0.25 mmol) in dichloromethane (5 mL) was stirred 0° C. under nitrogen. Dess-Martin periodinane (106 mg, 0.25 mmol) was added and the reaction mixture was stirred at 0° C. for 60 min. Additional Dess-Martin periodinane (22 mg, 0.05 mmol) was added and the reaction mixture was stirred at 0° C. for 30 min and then at room temperature for 15 min. The reaction mixture was diluted with dichloromethane and the mixture was washed with saturated sodium hydrogen carbonate solution, water and brine. The organic solution was filtered through a hydrophobic frit and the filtrate was evaporated. The residue was purified by silica gel chromatography using iso-hexanes/ethyl acetate 4:1 to 1:1 to afford 25f (85 mg, 68%) as a gum. $^1$H NMR (300 MHz, CDCl$_3$) δ 1.37 (s, 6H), 1.69 (d, J=6.7 Hz, 3H), 2.18 (s, 3H), 6.06 (q, J=6.7 Hz, 1H), 6.40 (d, J=16.3 Hz, 1H), 6.65 (d, J=16.3 Hz, 1H), 7.44 (d, J=8.5 Hz, 1H), 7.62 (dd, J=8.5, 1.2 Hz, 1H), 7.76 (d, J=8.5 Hz, 1H), 8.04 (br s, 1H), 8.13 (d, J=8.5 Hz, 1H), 9.52 (s, 1H). LCMS (m/z) 312.1 [M+H], Tr=2.65 min.

Compound 25g. (S)-1-[(S)-2-((S)-2-{(E)-4-[2-((R)-1-Acetoxy-ethyl)-quinolin-7-yl]-2,2-dimethyl-but-3-enylamino}-3-methyl-butyrylamino)-propionyl]-hexahydro-pyridazine-3-carboxylic acid 2,2,2-trichloro-ethyl ester

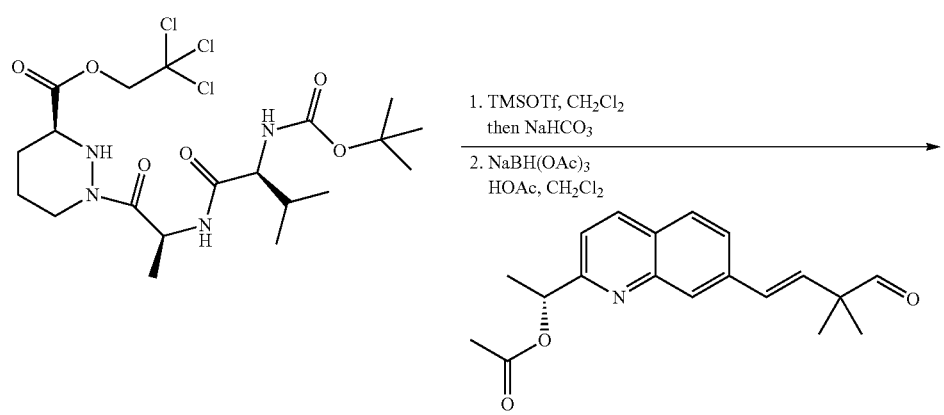

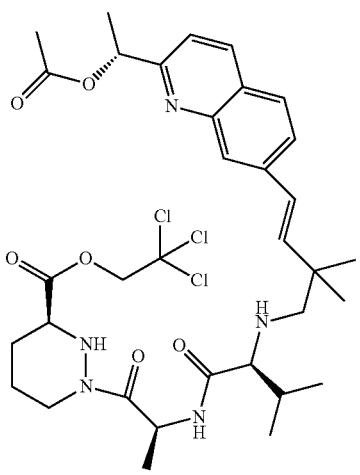

A solution of 20c (133 mg, 0.25 mmol) in dichloromethane (5 mL) was stirred at 0° C. under nitrogen. Trimethylsilyl trifluoromethanesulfonate (111 mg, 0.09 mL, 0.5 mmol) was added dropwise and the reaction mixture was stirred at 0° C. for 1 h. Cold saturated aqueous sodium hydrogen carbonate solution (10 mL) was added and the mixture was stirred at 0° C. for 15 min. Dichloromethane was added and the organic layer was separated, washed with brine, dried over anhydrous magnesium sulfate and evaporated to afford (S)-1-[(S)-2-((S)-2-amino-3-methyl-butyrylamino)-propionyl]-hexahydro-pyridazine-3-carboxylic acid 2,2,2-trichloro-ethyl ester (0.25 mmol) which was used without further purification. A solution of (S)-1-[(S)-2-((S)-2-amino-3-methyl-butyrylamino)-propionyl]-hexahydro-pyridazine-3-carboxylic acid 2,2,2-trichloro-ethyl ester (0.25 mmol) and 25f (66 mg, 0.21 mmol) in dichloromethane (5 mL) was stirred at room temperature for 10 min. Sodium triacetoxyborohydride (55 mg, 0.26 mmol) and acetic acid (1 drop) was added and the reaction mixture was stirred at room temperature for 4 h. Additional sodium triacetoxyborohydride (13 mg, 0.25 mmol) was added and the reaction mixture was stirred at room temperature for 1 h. The reaction mixture was diluted with ethyl acetate and the solution was washed with saturated sodium hydrogen carbonate solution, water and brine. The organic solution was filtered through a hydrophobic frit and the filtrate was evaporated. The residue was purified by silica gel chromatography using iso-hexanes/ethyl acetate 1:1 to 0:1 to afford 25g (84 mg, 46%) as a gum. $^1$H NMR (300 MHz, CDCl$_3$) δ 0.86 (d, J=6.9 Hz, 3H), 0.96 (d, J=6.9 Hz, 3H), 1.20 (s, 3H), 1.29 (d, J=7.0 Hz, 3H), 1.31 (s, 3H), 1.69 (d, J=6.7 Hz, 3H), 1.70-2.15 (m, 6H), 2.18 (s, 3H), 2.52-2.63 (m, 2H), 2.82-2.86 (m, 2H), 3.66-3.73 (m, 1H), 3.83 (d, J=11.4 Hz, 1H), 4.45-4.50 (m, 1H), 4.74 (d, J=12.0 Hz, 1H), 4.95 (d, J=12.0 Hz, 1H), 5.28-5.38 (m, 1H), 6.06 (q, J=6.7 Hz, 1H), 6.52 (ABq, Δδ$_{AB}$=0.14, J$_{AB}$=16.0 Hz, 2H), 7.42 (d, J=8.5 Hz, 1H), 7.66 (d, J=8.5 Hz, 1H), 7.74 (d, J=8.5 Hz, 1H), 7.93 (d, J=8.5 Hz, 1H), 8.00 (s, 1H), 8.11 (d, J=8.5 Hz, 1H). LCMS (m/z) 726.1/728.1 [M+H], Tr=2.08 min.

Compound 25

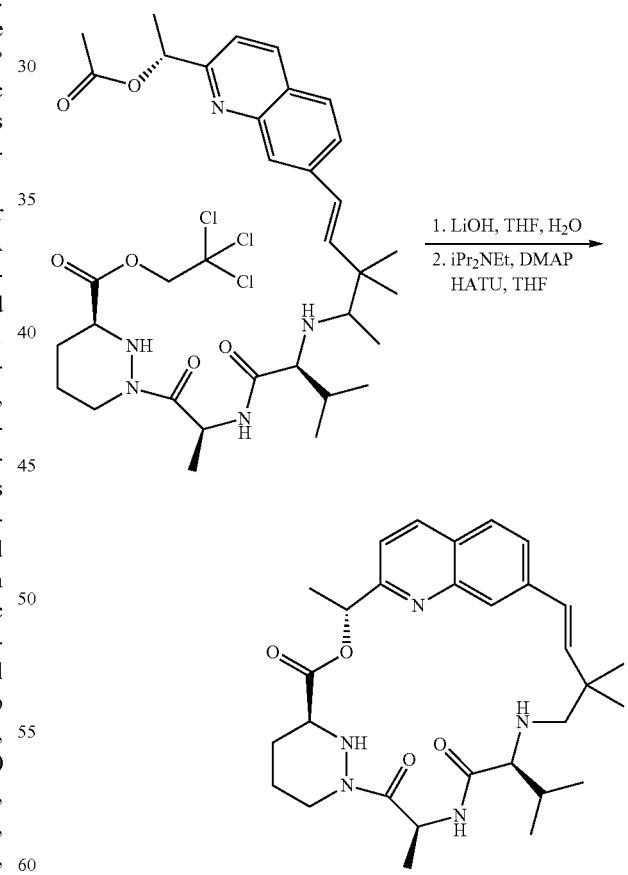

1. LiOH, THF, H$_2$O
2. iPr$_2$NEt, DMAP HATU, THF

A solution of 25g (80 mg, 0.11 mmol) in tetrahydrofuran (3 mL) was stirred at 0° C. under nitrogen. A solution of lithium hydroxide monohydrate (18.5 mg, 0.44 mmol) in water (1 mL) was added and the reaction mixture was stirred at 0° C.

for 4 h. Hydrochloric acid (1 M, 0.45 mL) was added and the solvent was evaporated. The residue was co-evaporated with tetrahydrofuran/toluene (1:1, 4×) and the residue was triturated with diethyl ether (2×) and dried to afford (S)-1-[(S)-2-((S)-2-{(E)-4-[2-((R)-1-hydroxy-ethyl)-quinolin-7-yl]-2,2-dimethyl-but-3-enylamino}-3-methyl-butyrylamino)-propionyl]-hexahydro-pyridazine-3-carboxylic acid (0.11 mmol) as a white solid which was used crude in the next reaction. LCMS (m/z) 554.2 [M+H], Tr=1.03 min.

A mixture of crude (S)-1-[(S)-2-((S)-2-{(E)-4-[2-((R)-1-hydroxy-ethyl)-quinolin-7-yl]-2,2-dimethyl-but-3-enylamino}-3-methyl-butyrylamino)-propionyl]-hexahydro-pyridazine-3-carboxylic acid (0.11 mol), N,N-diisopropylethylamine (84 mg, 0.65 mmol) and 4-dimethylaminopyridine (5 mg, 0.04 mmol) in tetrahydrofuran (130 mL) was stirred at room temperature under nitrogen. 2-(1H-7-Azabenzotriazol-1-yl)-11,1,3,3-tetramethyl uronium hexafluorophosphate methanaminium (133 mg, 0.35 mmol) was added and the reaction mixture was stirred at room temperature for 2.5 h. The solvent was evaporated and the residue was partitioned between ethyl acetate and saturated sodium hydrogen carbonate solution. The organic solution was separated and washed with brine. The organic solution was filtered through a hydrophobic frit and the filtrate was evaporated. The residue was purified by silica gel chromatography using ethyl acetate. The residue was triturated with diethyl ether and the resulting solid was dried to afford Compound 25 (21 mg, 30%) as a white solid. $^1$H NMR (300 MHz, CD$_3$OD) δ 0.80 (d, J=6.7 Hz, 3H), 0.98 (d, J=6.7 Hz, 3H), 1.11 (s, 3H), 1.25 (s, 3H), 1.62 (d, J=7.1 Hz, 3H), 1.67-1.71 (m, 3H), 1.74 (d, J=6.7 Hz, 3H), 1.88-2.05 (m, 2H), 2.64 (d, J=8.5 Hz, 1H), 2.70-2.80 (m, 3H), 3.80-3.85 (m, 1H), 4.35-4.40 (m, 1H), 5.89-5.99 (m, 2H), 6.42 (ABq, Δδ$_{AB}$=0.15, J$_{AB}$=16.5 Hz, 2H), 7.41 (d, J=8.5 Hz, 1H), 7.61 (dd, J=8.5, 1.5 Hz, 1H), 7.82 (d, J=8.5 Hz, 1H), 8.01 (br s, 1H), 8.22 (d, J=8.5 Hz, 1H). LCMS (m/z) 536.2 [M+H], Tr=1.47 min.

Example 26

Compound 26

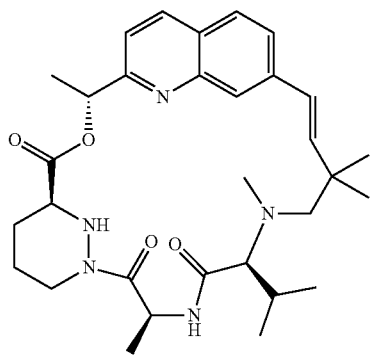 [SMILES: CC(C)[C@H]1C(=O)N[C@@H](C)C(=O)N2CCC[C@H](N2)C(=O)O[C@H](C)c2ccc3ccc(cc3n2)/C=C/C(C)(C)CN1C]

Compound 26a. (S)-1-{(S)-2-[(S)-2-(tert-Butoxycarbonyl-methyl-amino)-3-methyl-butyrylamino]-propionyl}-hexahydro-pyridazine-3-carboxylic acid 2,2,2-trichloro-ethyl ester

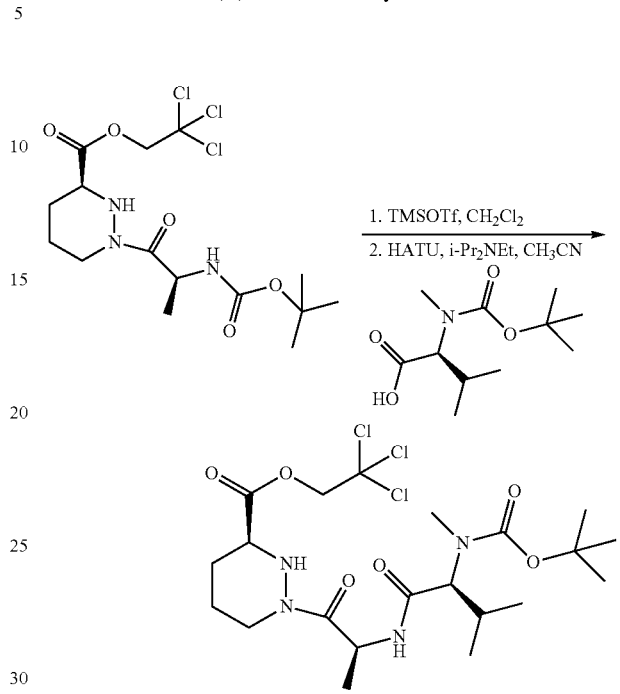

A solution of 1d (1.08 g, 2.5 mmol) in dichloromethane (35 mL) was stirred at 0° C. under nitrogen. Trimethylsilyl trifluoromethanesulfonate (682 mg, 0.55 mL, 3.1 mmol) was added and the reaction mixture was stirred at 0° C. for 45 min. N,N-diisopropylethylamine (1.29 g, 1.73 mL, 10 mmol) was added and the solvent was evaporated to afford crude (S)-1-((S)-2-amino-propionyl)-hexahydro-pyridazine-3-carboxylic acid 2,2,2-trichloro-ethyl ester (2.5 mmol), which was used in the next step. A solution of crude (S)-1-((S)-2-amino-propionyl)-hexahydro-pyridazine-3-carboxylic acid 2,2,2-trichloro-ethyl ester (2.5 mmol) in acetonitrile (30 mL) was stirred at 0° C. under nitrogen. (S)-2-(tert-Butoxycarbonyl-methyl-amino)-3-methyl-butyric acid (635 mg, 2.75 mmol, obtained from Sigma-Aldrich Inc.) and N,N-diisopropylethylamine (1.29 g, 1.7 mL, 10 mmol) was added followed by 2-(1H-7-azabenzotriazol-1-yl)-1,1,3,3-tetramethyl uronium hexafluorophosphate methanaminium (1.33 g, 3.5 mmol) and the reaction mixture was stirred at room temperature for 18 h. The solvent was evaporated and the residue was dissolved in ethyl acetate. The solution was washed with water, hydrochloric acid (2 M), water, saturated sodium hydrogen carbonate solution, water and brine, dried over anhydrous sodium sulfate, filtered and evaporated. The residue was purified by silica gel chromatography using a gradient of iso-hexanes/ethyl acetate 1:1 to 0:1 to afford the title compound (756 mg, 55%) as a white solid. $^1$H NMR (300 MHz, CDCl$_3$) δ 0.88 (d, J=6.5 Hz, 3H), 0.97 (d, J=6.7 Hz, 3H), 1.28 (d, J=6.7 Hz, 3H), 1.49-1.54 (m, 9H), 1.65-2.30 (m, 5H), 2.82 (s, 3H), 2.82-2.94 (m, 1H), 3.62-4.18 (m, 3H), 4.30-4.45 (m, 1H), 4.73 (d, J=12.0 Hz, 1H), 4.95 (d, J=12.0 Hz, 1H), 5.29-5.39 (m, 1H), 6.62-6.77 (m, 1H). LCMS (m/z) 545.2/547.1 [M+H], Tr=3.02 min.

Compound 26b. (S)-1-{(S)-2-[(S)-2-({(E)-4-[2-((R)-1-Acetoxy-ethyl)-quinolin-7-yl]-2,2-dimethyl-but-3-enyl}-methyl-amino)-3-methyl-butyrylamino]-propionyl}-hexahydro-pyridazine-3-carboxylic acid 2,2,2-trichloro-ethyl ester

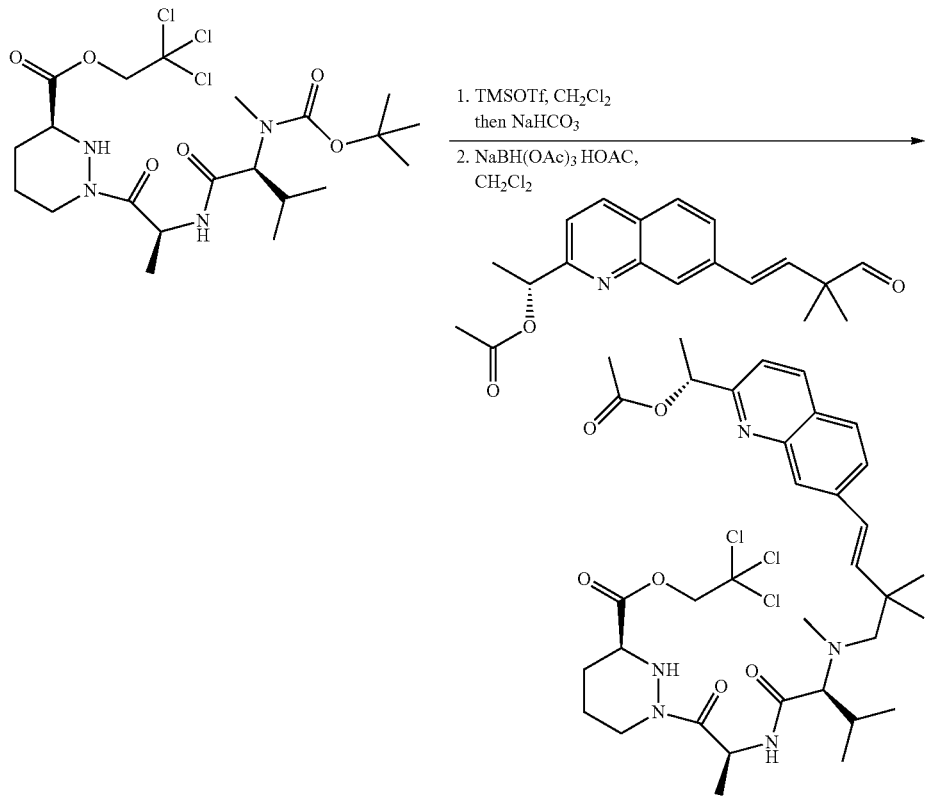

Compound 26b was prepared in the same manner as compound 25g using 26a instead of 20c in 42% yield. $^1$H NMR (300 MHz, CDCl$_3$) δ 0.90 (d, J=6.5 Hz, 3H), 1.05 (d, J=6.5 Hz, 3H), 1.16 (s, 3H), 1.19 (s, 3H), 1.33 (d, J=6.7 Hz, 3H), 1.69 (d, J=6.7 Hz, 3H), 1.70-2.15 (m, 5H), 2.17 (s, 3H), 2.40 (s, 3H), 2.57-2.62 (m, 3H), 2.82-2.89 (m, 1H), 3.66-3.73 (m, 1H), 3.83 (d, J=11.4 Hz, 1H), 4.43-4.48 (m, 1H), 4.72 (d, J=11.8 Hz, 1H), 4.94 (d, J=11.8 Hz, 1H), 5.27-5.37 (m, 1H), 6.06 (d, J=6.7 Hz, 1H), 6.50 (ABq, Δδ$_{AB}$=0.04, J$_{AB}$=16.5 Hz, 2H), 6.77 (d, J=8.0 Hz, 1H), 7.41 (d, J=8.3 Hz, 1H), 7.6 (d, J=8.5 Hz, 1H), 7.73 (d, J=8.5 Hz, 1H), 7.95 (br s, 1H), 8.11 (d, J=8.3 Hz, 1H). LCMS (m/z) 740.2/742.3 [M+H], Tr=2.44 min.

Compound 26

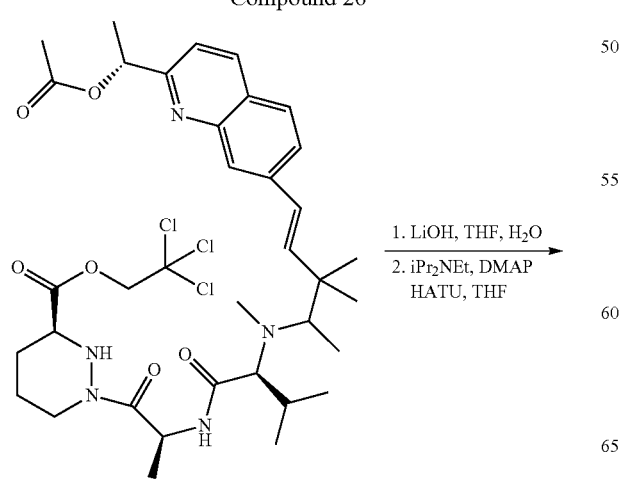

Compound 26 was prepared in the same manner as compound 25 using 26b instead of 25 g in 11% yield as a white solid. $^1$H NMR (300 MHz, CD$_3$OD) δ 0.86 (d, J=6.5 Hz, 3H), 0.96 (d, J=6.5 Hz, 3H), 1.14 (s, 3H), 1.23 (s, 3H), 1.44 (d, J=7.1 Hz, 3H), 1.67-1.72 (m, 2H), 1.75 (d, J=6.9 Hz, 3H), 1.81-2.25 (m, 3H), 2.51 (s, 3H), 2.79-2.91 (m, 4H), 3.69-3.73 (m, 1H), 4.25-4.30 (m, 1H), 5.47 (q, J=6.7 Hz, 1H), 5.97 (q, J=6.7 Hz, 1H), 6.54 (ABq, Δδ$_{AB}$=0.06, J$_{AB}$=16.0 Hz, 2H), 7.42 (d, J=8.3 Hz, 1H), 7.55 (d, J=8.3 Hz, 1H), 7.81 (d, J=8.5 Hz, 1H), 7.95 (br s, 1H), 8.21 (d, J=8.5 Hz, 1H). LCMS (m/z) 550.3 [M+H], Tr=1.50 min.

Examples 27 and 28

Compound 27 and 28

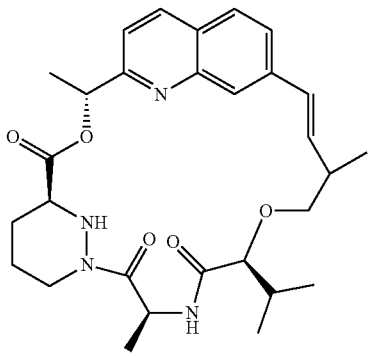 [SMILES: CC1/C=C/c2ccc3ccc(nc3c2)[C@@H](C)OC(=O)[C@@H]2CCCN(N2)C(=O)[C@H](C)NC(=O)[C@H](C(C)C)OC1]

Compound 27a. Trifluoro-methanesulfonic acid 2-methyl-but-3-enyl ester

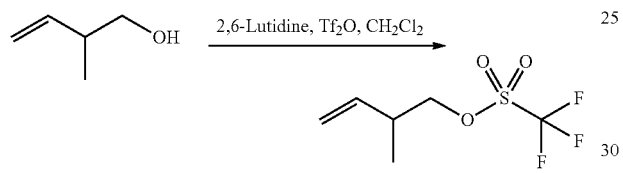

A solution of 2-methyl-but-3-en-1-ol (840 mg, 10 mmol) and 2,6-lutidine (1.5 g, 1.6 mL, 14 mmol) in dichloromethane (40 mL) was stirred at −78° C. under nitrogen. Trifluoromethanesulfonic anhydride (3.38 g, 2.0 mL, 12 mmol) was added dropwise and the reaction mixture was stirred at −78° C. for 1 h. Water was added and the reaction mixture was warmed to 0° C. Additional water was added and the organic layer was separated, washed with cold 1 M hydrochloric acid, water and brine, dried over anhydrous magnesium sulfate, filtered and evaporated to afford the crude product (14 mmol) as a pale yellow oil, which darkened on standing. The crude product was used immediately in the next step. $^1$H NMR (300 MHz, CDCl$_3$) δ 1.16 (d, J=6.9 Hz, 3H), 2.66-2.76 (m, 1H), 4.33-4.55 (m, 2H), 5.20 (dd, J=10.5, 0.9 Hz, 1H), 5.21 (dd, J=16.3, 0.9 Hz, 1H), 5.66-5.81 (m, 1H).

Compound 27b. (S)-3-Methyl-2-(2-methyl-but-3-enyloxy)-butyric acid methyl ester

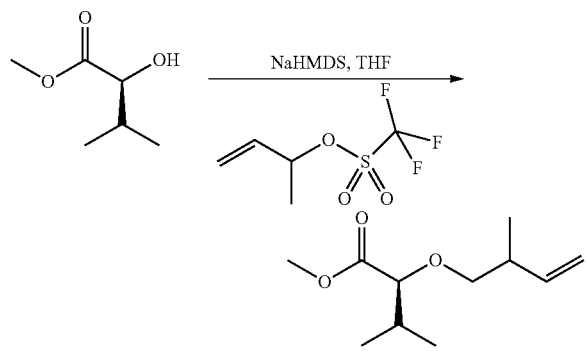

A solution of (S)-2-hydroxy-3-methyl-butyric acid methyl ester (1.32 g, 10 mmol) in tetrahydrofuran (30 mL) was stirred at −10° C. under nitrogen. Sodium bis(trimethylsilyl)amide (6 mL, 12 mmol, 2 M in tetrahydrofuran) was added dropwise and the reaction mixture was stirred at −10° C. for 10 min. Trifluoro-methanesulfonic acid 2-methyl-but-3-enyl ester (2.18 g, 10 mmol) was added in one portion and the reaction mixture was stirred at room temperature for 2 h. Saturated ammonium chloride solution was added and the mixture was extracted with ethyl acetate. The organic extracts were combined, washed with water and brine, dried over anhydrous magnesium sulfate, filtered and evaporated. The residue was purified by silica gel chromatography using a gradient of iso-hexanes/diethyl ether 20:1 to 10:1 to afford the title compound (429 mg, 21% over 2 steps) as an oil, as a 1:1 mixture of two diastereoisomers. $^1$H NMR (300 MHz, CDCl$_3$) δ 0.96-0.99 (m, 6H), 1.05 (d, J=6.9 Hz, 1.5H), 1.08 (d, J=6.6 Hz, 1.5H), 2.01-2.12 (m, 1H), 2.45-2.56 (m, 1H), 3.06-3.21 (m, 1H), 3.44-3.60 (m, 2H), 3.76 (s, 3H), 5.00-5.11 (m, 2H), 5.74-5.88 (m, 1H).

Compound 27c. (S)-3-Methyl-2-(2-methyl-but-3-enyloxy)-butyric acid

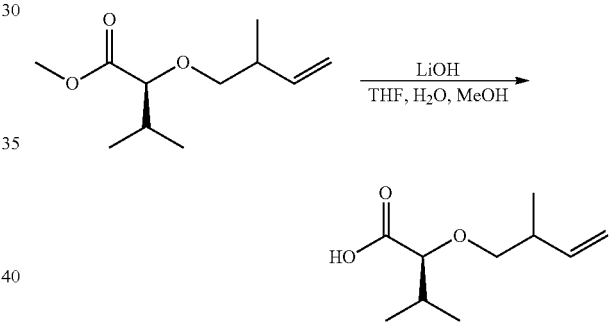

A solution of 27b (429 mg, 2.1 mmol) in tetrahydrofuran (10 mL) was stirred at 0° C. under nitrogen. A solution of lithium hydroxide monohydrate (265 mg, 6.3 mmol) in water (5 mL) was added followed by methanol (2 mL) and the reaction mixture was stirred at 0° C. for 30 minutes and then at room temperature for 4 h. Additional lithium hydroxide monohydrate (90 mg, 2.1 mmol) and methanol (3 mL) were added and the reaction mixture was stirred at room temperature for 3 days. The organic solvent was evaporated and the solution was acidified to pH 2 with 2 M hydrochloric acid and the mixture was extracted with ethyl acetate. The organic extracts were combined, washed with water and brine. The organic solution was filtered through a hydrophobic frit and the filtrate was evaporated to afford the title compound (200 mg, 54%) as a colorless oil and as a 1:1 mixture of two diastereoisomers. $^1$H NMR (300 MHz, CDCl$_3$) δ 0.97-1.11 (m, 9H), 2.14-2.23 (m, 1H), 2.48-2.59 (m, 1H), 3.37-3.50 (m, 2H), 3.70-3.72 (m, 1H), 5.11-5.19 (m, 2H), 5.70-5.88 (m, 1H), 8.50-9.50 (br s, 1H). LCMS (m/z) 185.3 [M−H], Tr=2.33 min.

169

Compound 27d. (S)-2-{(E)-4-[2-((R)-1-Acetoxy-ethyl)-quinolin-7-yl]-2-methyl-but-3-enyloxy}-3-methyl-butyric acid

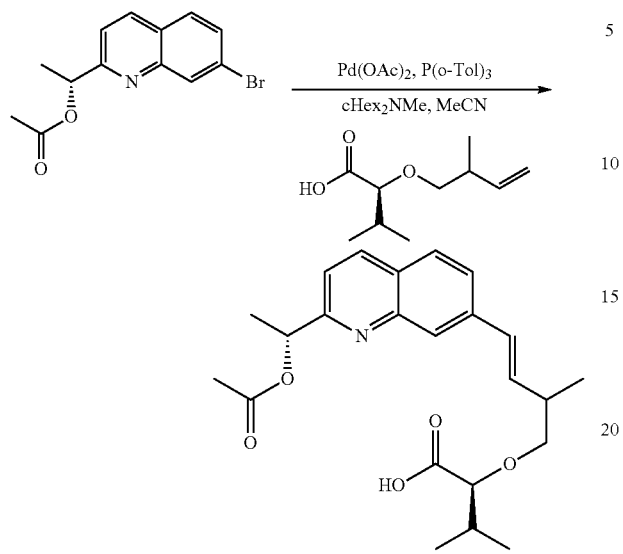

170

A solution of 27c (200 mg, 1.07 mmol) and 25d (314 mg, 1.07 mmol) in acetonitrile (10 mL) was stirred at room temperature under nitrogen. Palladium(II) acetate (48 mg, 0.2 mmol), tri(o-tolyl)phosphine (61 mg, 0.2 mmol) was added followed by N,N-dicyclohexylmethylamine (418 mg, 0.46 mL, 2.14 mmol) and the reaction mixture was heated at 120° C. in a microwave reactor for 40 minutes. Additional palladium(II) acetate (48 mg, 0.2 mmol), tri(-tolyl)phosphine (61 mg, 0.2 mmol) was added and the reaction mixture heated at 130° C. in a microwave reactor for 30 minutes. The solvent was evaporated and the residue was partitioned between ethyl acetate and 1 M hydrochloric acid. The organic extracts were combined and washed with brine. The organic solution was filtered through a hydrophobic frit and the filtrate was evaporated to afford the crude product (1.07 mmol) as a 1:1 mixture of two diastereoisomers which was used in the next step without further purification. LCMS (m/z) 400.2 [M+H], Tr=2.75 min.

Compound 27e. (S)-1-[(S)-2-((S)-2-{(E)-4-[2-((R)-1-Acetoxy-ethyl)-quinolin-7-yl]-2-methyl-but-3-enyloxy}-3-methyl-butyrylamino)-propionyl]-hexahydro-pyridazine-3-carboxylic acid 2,2,2-trichloro-ethyl ester

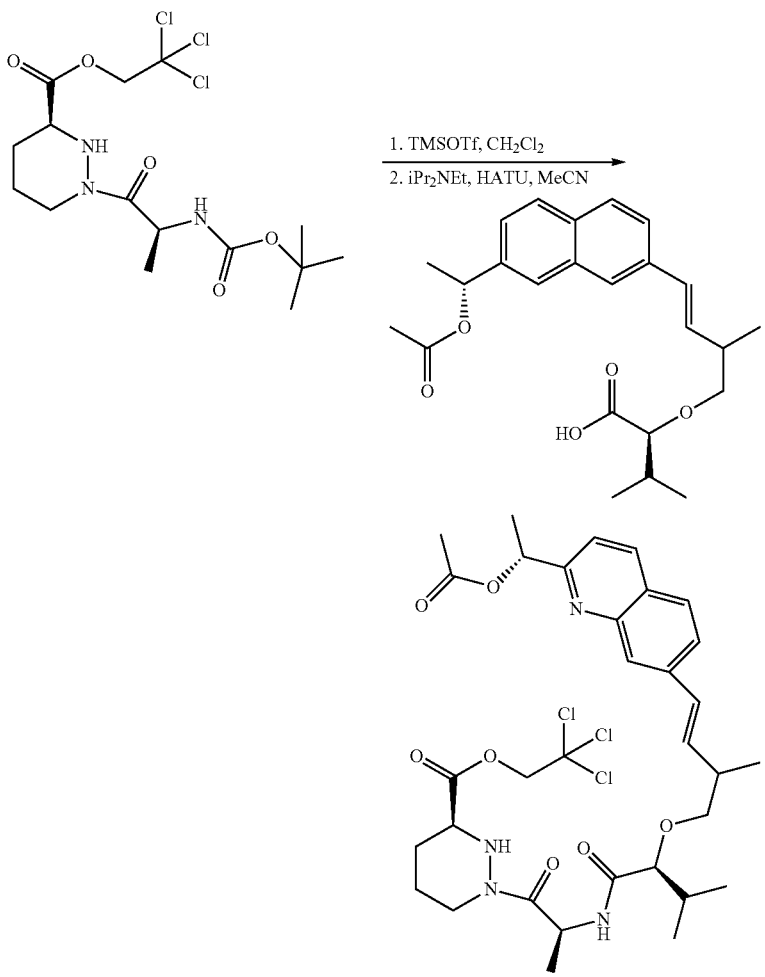

A solution of 1d (433 mg, 1.0 mmol) in dichloromethane (30 mL) was stirred at 0° C. under nitrogen. Trimethylsilyl trifluoromethanesulfonate (444 mg, 0.35 mL, 2.0 mmol) was added and the reaction mixture was stirred at 0° C. for 45 minutes. N,N-diisopropylethylamine (516 mg, 0.7 mL, 4.0 mmol) was added and the solvent was evaporated and the residue was dried to afford crude (S)-1-((S)-2-amino-propionyl)-hexahydro-pyridazine-3-carboxylic acid 2,2,2-trichloro-ethyl ester (1.0 mmol), which was used in the next step. A solution of crude (S)-1-((S)-2-amino-propionyl)-hexahydro-pyridazine-3-carboxylic acid 2,2,2-trichloro-ethyl ester (1.0 mmol) in acetonitrile (30 mL) was stirred at 0° C. under nitrogen. 27d (1.0 mmol) and N,N-diisopropylethylamine (516 mg, 0.7 mL, 4.0 mmol) was added followed by 2-(1H-7-azabenzotriazol-1-yl)-1,1,3,3-tetramethyl uronium hexafluorophosphate methanaminium (530 mg, 1.4 mmol) and the reaction mixture was stirred at 0° C. for 30 minutes and then at room temperature for 2 h. The solvent was evaporated and the residue was dissolved in ethyl acetate. The solution was washed with cold 1 M hydrochloric acid, water, saturated sodium hydrogen carbonate solution, water and brine. The organic solution was filtered through a hydrophobic frit and the filtrate was evaporated. The residue was purified by silica gel chromatography using a gradient of iso-hexanes/ethyl acetate 1:1 to 1:2 to afford the title compound (420 mg, 58% over 2 steps) as a white solid, as a 1:1 mixture of two diastereoisomers. LCMS (m/z) 713.3/715.3 [M+H], Tr=3.48 min.

Compound 27 and 28

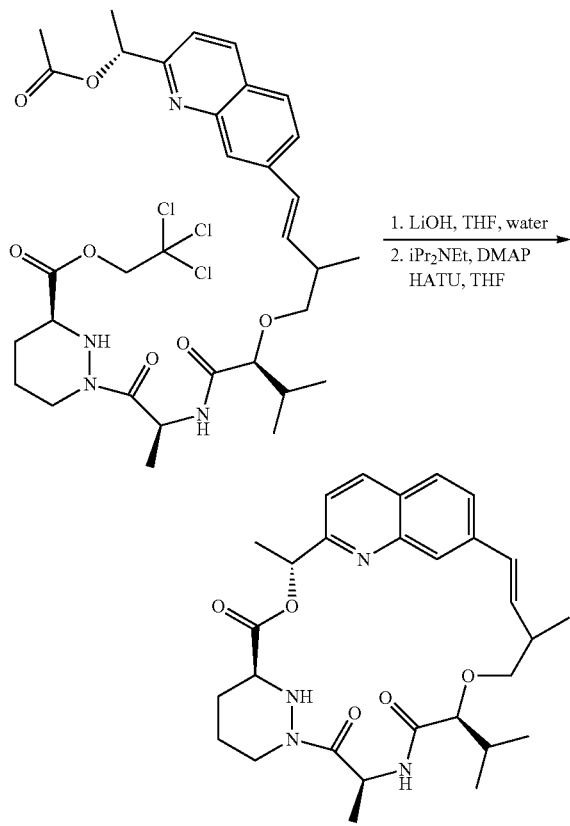

A solution of 27e (143 mg, 0.2 mmol) in tetrahydrofuran (10 mL) was stirred at 0° C. under nitrogen. A solution of lithium hydroxide monohydrate (42 mg, 1.0 mmol) in water (2 mL) was added and the reaction mixture was stirred at 0° C. for 3 h and then at 10° C. for 3 h. 1 M Hydrochloric acid (1 mL, 1.0 mmol) was added and the solvent was evaporated. The residue was co-evaporated with tetrahydrofuran/toluene (1:1, 3×) and the residue was triturated with diethyl ether (2×) and dried to afford (S)-1-[(S)-2-((S)-2-{(E)-4-[2-((R)-1-hydroxy-ethyl)-quinolin-7-yl]-2-methyl-but-3-enyloxy}-3-methyl-butyrylamino)-propionyl]-hexahydro-pyridazine-3-carboxylic acid (0.2 mmol) as a pale yellow solid, as a mixture of two diastereoisomers which was used crude in the next reaction. LCMS (m/z) 541.2 [M+H], Tr=1.77 min. A suspension of crude (S)-1-[(S)-2-((S)-2-{(E)-4-[2-((R)-1-hydroxy-ethyl)-quinolin-7-yl]-2-methyl-but-3-enyloxy}-3-methyl-butyrylamino)-propionyl]-hexahydro-pyridazine-3-carboxylic acid (0.2 mmol) in tetrahydrofuran (200 mL) was stirred at room temperature under nitrogen. N,N-Diisopropylethylamine (129 mg, 0.18 mL, 1.0 mmol) and 4-dimethylaminopyridine (8 mg, 0.06 mmol) was added and the reaction mixture was stirred at room temperature for 5 minutes. 2-(1H-7-Azabenzotriazol-1-yl)-1,1,3,3-tetramethyl uronium hexafluorophosphate methanaminium (107 mg, 0.28 mmol) was added and the reaction mixture was stirred at room temperature for 2 h. Additional 2-(1H-7-azabenzotriazol-1-yl)-1,1,3,3-tetramethyl uronium hexafluorophosphate methanaminium (30 mg, 0.08 mmol) was added and the reaction mixture was stirred at room temperature for 2 h. The solvent was evaporated and the residue was suspended in ethyl acetate. Cold 1 M hydrochloric acid was added and the organic layer was separated, washed with water, saturated sodium hydrogen carbonate solution, water and brine. The organic solution was filtered through a hydrophobic frit and the filtrate was evaporated. The residue was purified by silica gel chromatography using a gradient of iso-hexanes/ethyl acetate 1:4 to 0:1 to afford a 1:1 mixture of two diastereoisomers. The mixture was purified by reverse phase preparative HPLC eluting with acetonitrile (containing 0.1% formic acid)/water (containing 0.1% formic acid) 45:55. Fractions containing the pure diastereoisomers were combined and evaporated. The residues were partitioned between saturated sodium hydrogen carbonate solution and ethyl acetate. The organic layer was separated, washed with water and brine. The organic solution was filtered through a hydrophobic frit and the filtrate was evaporated to afford two diastereoisomers.

Example 27 Compound 27 (First eluting) Diastereoisomer 1: (12 mg, 12%) as a white solid. $^1$H NMR (300 MHz, $d_6$-DMSO) δ 0.70 (d, J=6.5 Hz, 3H), 0.93 (d, J=6.5 Hz, 3H), 0.97 (d, J=6.9 Hz, 3H), 1.54 (d, J=6.9 Hz, 3H), 1.55-1.62 (m, 2H), 1.63 (d, J=6.7 Hz, 3H), 1.73-1.95 (m, 3H), 2.72-2.78 (m, 1H), 3.25-3.30 (m, 1H), 3.45-3.52 (m, 1H), 3.65-3.72 (m, 2H), 4.18-4.22 (m, 1H), 4.87 (d, J=12.2 Hz, 1H), 5.65-5.73 (m, 1H), 5.96 (q, J=6.7 Hz, 1H), 6.34 (dd, J=16.5, 5.5 Hz, 1H), 6.45 (d, J=16.5 Hz, 1H), 7.48 (d, J=8.3 Hz, 1H), 7.58 (d, J=8.7 Hz, 1H), 7.80 (s, 1H), 7.87 (d, J=8.5 Hz, 1H), 8.28 (d, J=8.5 Hz, 1H), 8.47 (d, J=8.3 Hz, 1H). LCMS (m/z) 523.3 [M+H], Tr=2.30 min.

Example 28 Compound 28 (Second Eluting) Diastereoisomer 2: (12 mg, 12%) as a white solid. $^1$H NMR (300 MHz, $d_6$-DMSO) 60.73 (d, J=6.7 Hz, 3H), 0.93 (d, J=6.5 Hz, 3H), 1.10 (d, J=6.9 Hz, 3H), 1.49 (d, J=7.1 Hz, 3H), 1.55-1.62 (m, 2H), 1.65 (d, J=6.9 Hz, 3H), 1.75-1.95 (m, 3H), 2.56-2.62 (m, 1H), 2.72-2.82 (m, 1H), 3.64-3.73 (m, 3H), 4.18-4.32 (m, 1H), 4.84 (d, J=12.1 Hz, 1H), 5.65-5.73 (m, 1H), 5.98 (q, J=6.7 Hz, 1H), 6.34 (dd, J=16.5, 5.2 Hz, 1H), 6.48 (d, J=16.5

Hz, 1H), 7.48 (d, J=8.5 Hz, 1H), 7.61 (d, J=8.5 Hz, 1H), 7.75 (s, 1H), 7.87 (d, J=8.5 Hz, 1H), 8.28 (d, J=8.3 Hz, 1H), 8.43 (d, J=8.0 Hz, 1H). LCMS (m/z) 523.3 [M+H], Tr=2.34 min.

Example 29

Compound 29

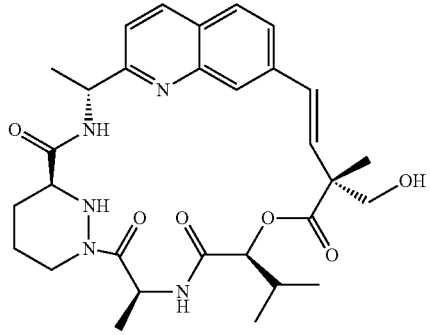 [SMILES: CC(C)[C@@H]1OC(=O)[C@@](C)(CO)/C=C/c2ccc3ccc(nc3c2)[C@@H](C)NC(=O)[C@@H]2CCCN(N2)C(=O)[C@H](C)NC1=O]

Compound 29a. (S)-1-[(S)-2-((S)-2-Hydroxy-3-methyl-butyrylamino)-propionyl]-hexahydro-pyridazine-3-carboxylic acid

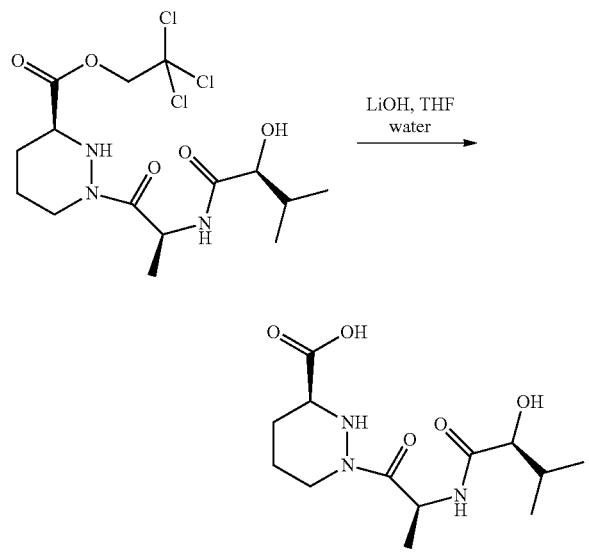

To (S)-1-[(S)-2-((S)-2-hydroxy-3-methyl-butyrylamino)-propionyl]-hexahydro-pyridazine-3-carboxylic acid 2,2,2-trichloro-ethyl ester 1e (502 mg, 1.16 mmol) suspended in tetrahydrofuran (15 mL) and water (3 mL) was added lithium hydroxide monohydrate (69 mg, 1.65 mmol). The reaction mixture was stirred for 45 minutes and then hydrochloric acid (2 M, 0.75 mL) was added. The reaction mixture was stirred for 5 minutes and then evaporated. The crude residue was used directly in the next step without further purification.

Compound 29b. (S)-1-[(S)-2-((S)-2-Amino-3-methyl-butyrylamino)-propionyl]-hexahydro-pyridazine-3-carboxylic acid (R)-1-(7-bromo-quinolin-2-yl)-ethyl amide

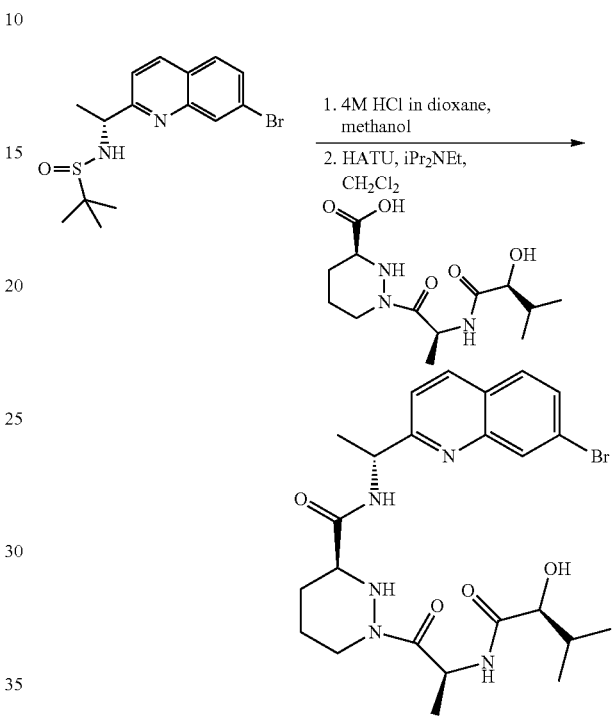

18c (533 mg, 1.50 mmol) was dissolved in hydrochloric acid in 1,4-dioxane (4 M, 7.5 mL) and methanol (7.5 mL). The reaction mixture was stirred for 2 h and then evaporated. The residue was passed through an SCX cartridge eluting with methanol and then 1 M ammonia in methanol. The basic fraction was collected and evaporated. The residue was dissolved in dichloromethane (30 mL) and 23 mL of this solution was added to freshly prepared 29a (350 mg, 1.16 mmol). The reaction vessel was cooled to 0° C. and 2-(1H-7-azabenzotriazol-1-yl)-1,1,3,3-tetramethyl uronium hexafluorophosphate methanaminium (616 mg, 1.62 mmol) and N,N-diisopropylethylamine (450 mg, 606 µL, 3.48 mmol) were added. The reaction mixture was allowed to warm to ambient temperature and stirred for 15 h. The mixture was diluted with dichloromethane and washed successively with saturated sodium bicarbonate solution, water and saturated ammonium chloride solution, dried over anhydrous sodium sulfate, filtered and evaporated. The residue was purified on silica eluting with ethyl acetate/methanol 1:0 to 19:1 to afford the title compound (205 mg, 33%) as a white foam. $^1$H NMR (300 MHz, CDCl$_3$) δ 0.85 (d, J=6.9 Hz, 3H), 1.01 (d, J=6.9 Hz, 3H), 1.41 (d, J=6.9 Hz, 3H), 1.58 (d, J=6.7 Hz, 3H), 1.60-1.81 (m, 2H), 2.04-2.16 (m, 1H), 2.20-2.29 (m, 1H), 3.69-3.79 (m, 1H), 3.26 (br s, 1H), 3.43-3.54 (m, 1H), 3.72 (heptet, J=6.4 Hz, 1H), 3.86 (d, J=11.8 Hz, 1H), 3.98 (d, J=3.1 Hz, 1H), 4.47-4.56 (m, 1H), 5.27 (app pentet, J=6.9 Hz, 1H), 5.46 (dq, J=8.0, 6.9 Hz, 1H), 7.13 (d, J=8.2 Hz, 1H), 7.39 (d, J=8.5 Hz, 1H), 7.65 (dd, J=8.5, 1.8 Hz, 1H), 7.70 (d, J=8.5 Hz, 1H), 8.10

(d, J=6.7 Hz, 1H), 8.14 (d, J=8.5 Hz, 1H), 8.43 (s, 1H). LCMS (m/z) 536.0 [M+H], Tr=2.21 min.

Compound 29c. (R)-4-Isopropyl-3-((E)-2-methyl-but-2-enoyl)-oxazolidin-2-one

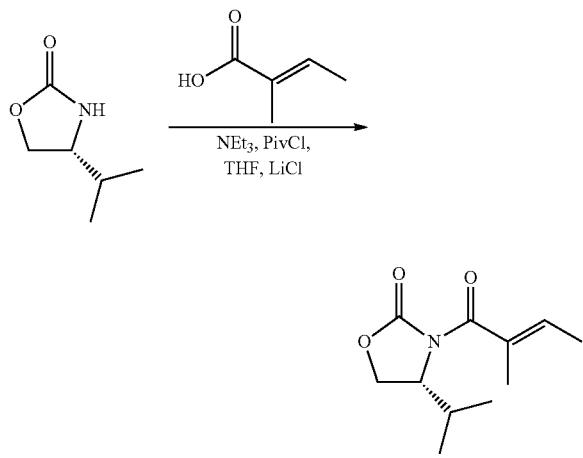

A cooled (−20° C.) solution of tiglic acid (2.005 g, 20.031 mmol) in anhydrous tetrahydrofuran (50 mL) was sequentially treated with triethylamine (6.1 mL, 44.068 mmol) and dropwise pivaloyl chloride (2.7 mL, 22.034 mmol). After stirring at −20° C. for 30 min, lithium chloride (1.019 g, 24.037 mmol) and (R)-(+)-4-isopropyl-2-oxazolidinone (2.587 g, 20.031 mmol) were added. The reaction mixture was allowed to slowly warm to room temperature, stirred for 3 days and was then quenched with saturated ammonium chloride. The aqueous layer was extracted with ethyl acetate (2×). The organics were combined, dried over anhydrous sodium sulfate, filtered and the volatiles were removed in vacuo. The residue was purified by silica gel chromatography using a 50 g Isolute cartridge eluted with a continuous gradient of iso-hexanes/ethyl acetate 1:0 to 4:1 to afford the title compound (3.307 g, 78%) as a colorless solid. $^1$H NMR (300 MHz, CDCl$_3$) δ 0.92 (d, J=6.9 Hz, 3H), 0.94 (d, J=7.1 Hz, 3H), 1.83 (d, J=6.9 Hz, 3H), 1.93 (s, 3H), 2.38 (d of heptet, J=6.9, 4.2 Hz, 1H), 4.19 (dd, J=8.9, 4.6 Hz, 1H), 4.33 (app t, J=8.9 Hz, 1H), 4.49-4.58 (m, 1H), 6.23 (q, J=7.1 Hz, 1H).

Compound 29d. (R)-4-Isopropyl-3-[(R)-2-methyl-2-(2-trimethylsilanyl-ethoxymethyl)-but-3-enoyl]-oxazolidin-2-one

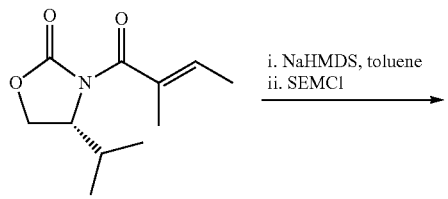

Residual moisture in 29c (458.9 mg, 2.172 mmol) was removed by azeotroping with anhydrous toluene. A cooled (−78° C.) solution of dried 29c in anhydrous toluene (10 mL) was treated dropwise with a solution of sodium bis(trimethylsilyl)amide in toluene (0.6 M, 5.4 mL, 3.258 mmol). After stirring the yellow solution at −78° C. for 35 min, 2-(trimethylsilyl)ethoxymethyl chloride (1.1 mL, 6.516 mmol) was added. After stirring at 0° C. for 3.5 h, the reaction was quenched with saturated ammonium chloride. The aqueous layer was extracted with dichloromethane (2×). The organics were combined, filtered through a phase separator and the volatiles were removed in vacuo. The residue was purified by silica gel chromatography using a 50 g Isolute cartridge eluted with a continuous gradient of iso-hexanes/ethyl acetate 1:0 to 9:1 to afford the title compound (543.3 mg, 73%) as a colorless oil and as a 5:1 mixture of diastereoisomers. $^1$H NMR (300 MHz, CDCl$_3$) δ 0.01 (s, 9H), 0.77-0.99 (m, 8H), 1.49 (s, 3H), 2.36 (d of heptet, J=6.9, 3.8 Hz, 1H), 3.42-3.60 (m, 3H), 4.15-4.31 (m, 3H), 4.49-4.57 (m, 1H), 5.00 (d, J=17.6 Hz, 1H), 5.10 (d, J=10.7, 1H), 6.19 (dd, J=17.8, 10.7 Hz, 1H). LCMS (m/z) 364.1 [M+Na], Tr=3.32 min.

Compound 29e. (R)-3-((R)-2-Hydroxymethyl-2-methyl-but-3-enoyl)-4-isopropyl-oxazolidin-2-one

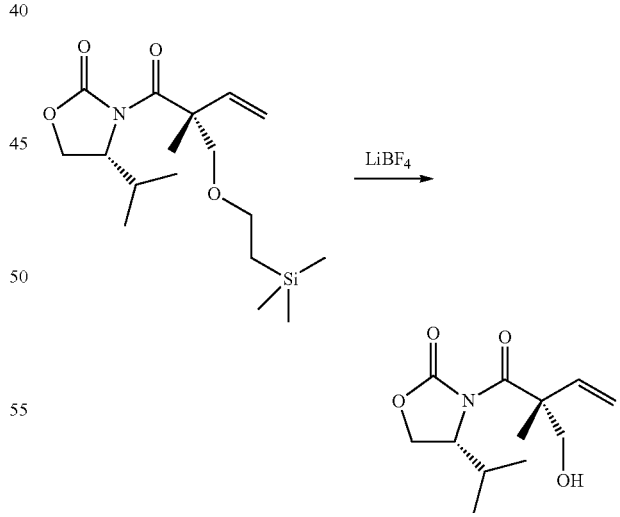

To a stirred solution of 29d (2.93 g, 8.58 mmol) in a mixture of acetonitrile (86 mL) and water (1.72 mL) was added lithium tetrafluoroborate (1 M in acetonitrile, 42.9 mL, 42.9 mmol). The mixture was heated at reflux under nitrogen for 5 h and allowed to cool to ambient temperature. More lithium tetrafluoroborate (1 M in acetonitrile, 8.6 mL, 8.6 mmol) was added and the mixture heated at reflux for a further 75 minutes and allowed to cool to ambient temperature. The mixture was diluted with water/diethyl ether (2:3, 100 mL) and the organic layer was separated and washed with water. The combined aqueous washes were back-extracted with diethyl ether and the combined organic extracts dried over anhydrous sodium sulfate, filtered and evaporated to give the title compound (1.89 g, 91%) as a yellow oil. $^1$H NMR (300 MHz, CDCl$_3$) δ 0.89 (d, J=6.9 Hz, 3H), 0.95 (d, J=6.9 Hz, 3H), 1.35 (s, 3H), 2.36-2.47 (m, 1H), 2.56-2.70 (br s, 1H), 3.47-3.54 (m, 1H), 3.91 (d, J=11.6 Hz, 1H), 4.22-4.31 (m, 2H), 4.47-4.53 (m, 1H), 4.97 (d, J=17.8 Hz, 1H), 5.17 (d, J=10.7 Hz, 1H), 6.09 (dd, J=17.8, 10.7 Hz, 1H). LCMS (m/z) 242.2 [M+H], Tr=1.82 min.

Compound 29f. (R)-3-[(R)-2-(tert-Butyl-dimethyl-silanyloxymethyl)-2-methyl-but-3-enoyl]-4-isopropyl-oxazolidin-2-one

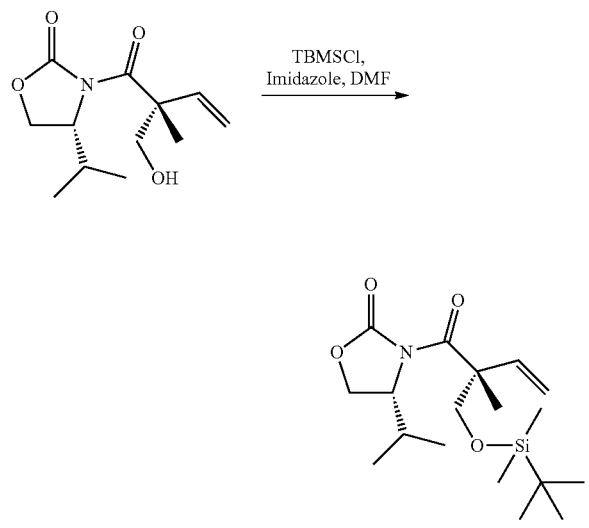

To a stirred solution of 29e (660 mg, 2.74 mmol) and tert-butyldimethylsilyl chloride (533 mg, 3.56 mmol) in N,N-dimethylformamide (10 mL) at 0° C. under nitrogen was added in one portion imidazole (821 mg, 12.1 mmol). The reaction was stirred at 0° C. for 15 minutes and then allowed to warm to ambient temperature and stirred for 5 h. The mixture was concentrated and then partitioned between saturated ammonium chloride solution and ether. The organic layer was separated and washed with water (3×), dried over anhydrous sodium sulfate, filtered and evaporated. The residue was purified on silica gel chromatography eluting with iso-hexanes/ethyl acetate 1:0 to 19:1 to afford the title compound (316 mg, 32%) as a colorless oil. $^1$H NMR (300 MHz, CDCl$_3$) δ 0.05 (s, 3H), 0.06 (s, 3H), 0.86-0.94 (m, 6H), 0.89 (s, 9H), 1.45 (s, 3H), 2.27-2.40 (m, 1H), 3.71 (d, J=9.6 Hz, 1H), 4.10-4.30 (m, 2H), 4.43 (d, J=9.6 Hz, 1H), 4.49-4.55 (m, 1H), 4.99 (d, J=17.8 Hz, 1H), 5.10 (d, J=9.6 Hz, 1H), 6.17 (dd, J=17.8, 10.9 Hz, 1H). LCMS (m/z) 356.2 [M+H], Tr=4.02 min Compound 29g. (R)-2-(tert-Butyl-dimethyl-silanyloxymethyl)-2-methyl-but-3-enoic acid

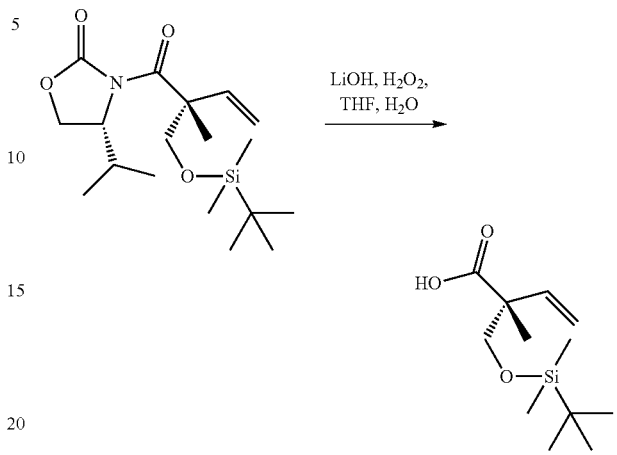

To a stirred mixture of 29f (310 mg, 0.872 mmol) in tetrahydrofuran (4.4 mL) and water (2.2 mL) at 0° C. was added hydrogen peroxide solution (30%, 494 mg, 449 μL, 4.36 mmol) followed by lithium hydroxide monohydrate (73 mg, 1.74 mmol). The reaction mixture was stirred at 0° C. for 5 minutes then allowed to warm to ambient temperature and stirred for 16 h. More tetrahydrofuran (1 mL) was added and the mixture cooled to 0° C. and lithium hydroxide monohydrate (37 mg, 0.87 mmol) was added. The reaction mixture was stirred at 0° C. for 40 minutes then allowed to warm to ambient temperature and stirred for 7 h. The reaction was then quenched with sodium metabisulfite and stirred for 30 minutes. The mixture was acidified to pH<3 with hydrochloric acid (2 M) and extracted with dichloromethane (3×). The combined organic extracts were dried over anhydrous magnesium sulfate, filtered and evaporated. The residue was purified on silica gel chromatography eluting with iso-hexanes/ethyl acetate 9:1 to afford the title compound (144 mg, 68%) as a colorless oil. $^1$H NMR (300 MHz, CDCl$_3$) δ 0.12 (s, 6H), 0.93 (s, 9H), 1.31 (s, 3H), 3.65 (d, J=9.6 Hz, 1H), 3.78 (d, J=9.6 Hz, 1H), 5.24 (d, J=17.6 Hz, 1H), 5.24 (d, J=10.9 Hz, 1H), 5.96 (dd, J=17.4, 10.9 Hz, 1H).

Compound 29h. (S)-1-{(S)-2-[(S)-3-Methyl-2-((R)-2-methyl-2-tert-butyl-dimethyl-silanyloxymethyl-but-3-enoylamino)-butyrylamino]-propionyl}-hexahydro-pyridazine-3-carboxylic acid (R)-1-(7-bromo-quinolin-2-yl)-ethyl amide

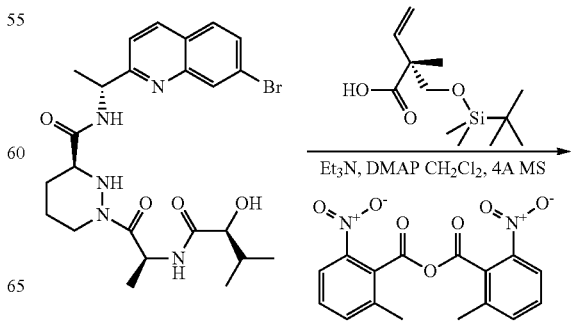

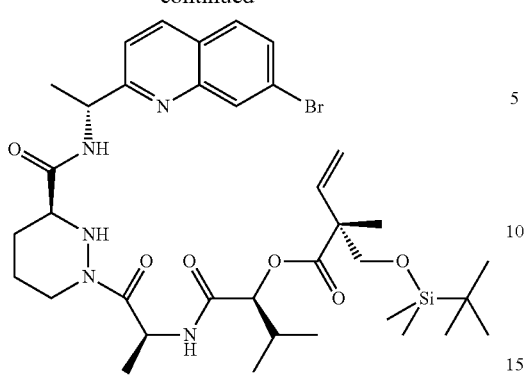

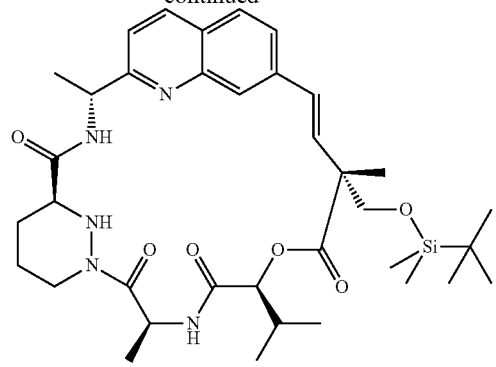

To a stirred solution 29b (504 mg, 0.944 mmol), 2-methyl-6-nitrobenzoic anhydride (649 mg, 1.89 mmol), 4-(dimethylamino)pyridine (46 mg, 0.378 mmol), triethylamine (238 mg, 328 µL, 2.36 mmol) and powdered 4 Å molecular sieves (~1 g) in dichloromethane (10 mL) was added a solution of 29g (346 mg, 1.42 mmol) in dichloromethane (4 mL). The reaction was stirred under nitrogen for 91 h and then more 2-methyl-6-nitrobenzoic anhydride (325 mg, 0.90 mmol), 4-(dimethylamino)pyridine (23 mg, 0.189 mmol) and a solution of 29g (173 mg, 0.71 mmol) in dichloromethane (2 mL) was added and the reaction mixture stirred for a further 23 h. The reaction mixture was filtered through Celite and cooled to 0° C. and ice-cold water was added. The organic layer was separated and washed sequentially with ice-cold saturated ammonium chloride solution, ice-cold saturated sodium bicarbonate solution and saturated brine, dried over anhydrous sodium sulfate, filtered and evaporated and purified on silica gel chromatography eluting with iso-hexanes/ethyl acetate 1:1 to 0:1 to afford the title compound (244 mg, 34%) as a beige oil. $^1$H NMR (300 MHz, CDCl$_3$) δ 0.05 (s, 3H), 0.06 (s, 3H), 0.88 (s, 9H), 0.93 (d, J=6.9 Hz, 3H), 0.94 (d, J=6.9 Hz, 3H), 1.37 (d, J=6.5 Hz, 3H), 1.42 (s, 3H), 1.61 (d, J=6.7 Hz, 3H), 1.54-1.71 (m, 2H), 1.91-2.01 (m, 1H), 2.23-2.35 (m, 2H), 2.57-2.68 (m, 1H), 3.39-3.50 (m, 1H), 3.65 (d, J=9.5 Hz, 1H), 3.73 (d, J=12.1 Hz, 1H), 3.89 (d, J=9.6 Hz, 1H), 4.51-4.60 (m, 1H), 5.02 (d, J=3.6 Hz, 1H), 5.21-5.43 (m, 4H), 6.04 (dd, J=17.4, 10.9 Hz, 1H), 6.86 (d, J=8.0 Hz, 1H), 7.42 (d, J=8.5 Hz, 1H), 7.61-7.71 (m, 2H), 8.02 (d, J=6.5 Hz, 1H), 8.12 (d, J=8.5 Hz, 1H), 8.36 (s, 1H). LCMS (m/z) 760.3, 762.3 [M+H], Tr=4.16 min.

Compound 29i

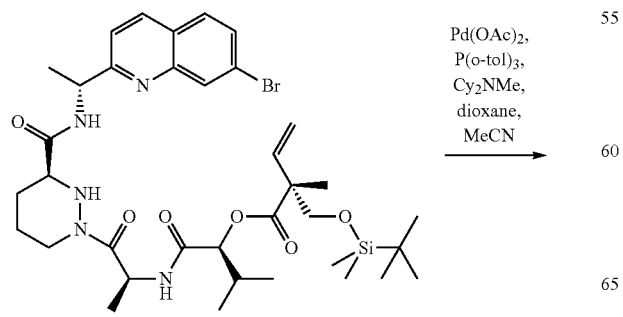

To solid palladium(II) acetate (14 mg, 0.060 mmol) and tri(o-tolyl)phosphine (20 mg, 0.060 mmol) was added a solution of 29h (49 mg, 0.060 mmol) in anhydrous 1,4-dioxane (18.4 mL), followed by N,N-dicyclohexylmethylamine (25 mg, 27 µL, 0.128 mmol) and anhydrous acetonitrile (0.2 mL). The mixture was heated at 120° C. in a microwave reactor for 25 minutes. Five batches of equivalent amount were reacted and combined and diluted with ethyl acetate, washed with saturated ammonium chloride solution (2×), brine, dried over anhydrous sodium sulfate, filtered and evaporated. The residue was purified on silica gel chromatography eluting with iso-hexanes/ethyl acetate 1:1 to 1:3 to afford the title compound (81 mg, 37%) as a yellow gum. LCMS (m/z) 680.3 [M+H], Tr=3.75 min Compound 29

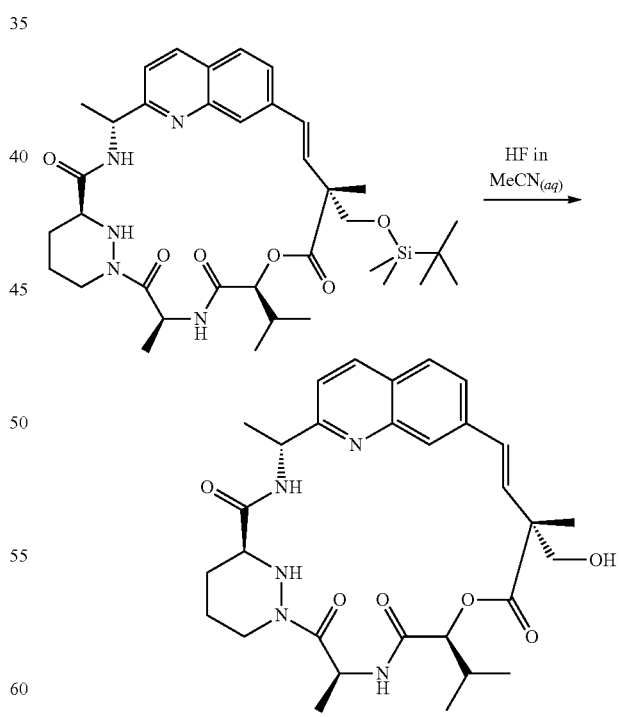

Compound 29i (40 mg, 0.059 mmol) was dissolved in acetonitrile (20 mL) and hydrofluoric acid (48% in water, 117 mg, 102 µL, 5.88 mmol) was added. The reaction mixture was stirred for 4 h and more hydrofluoric acid (48% in water, 117 mg, 102 µL, 5.88 mmol) was added and stirring continued for a further 3.5 h. Solid sodium bicarbonate was added and the mixture stirred for 5 minutes, filtered through a hydrophobic frit and the filtrate evaporated. The residue was purified by reverse phase preparative HPLC using a gradient of acetonitrile/water 1:4 to 7:3 to afford the title compound (10.0 mg, 30%) as a white solid. $^1$H NMR (300 MHz, CD$_3$OD) δ 1.01 (d, J=6.7 Hz, 3H), 1.06 (d, J=6.7 Hz, 3H), 1.48-1.78 (m, 2H), 1.56 (s, 3H), 1.60 (d, J=6.9 Hz, 3H), 1.66 (d, J=7.4H, 3H), 1.91-2.00 (m, 1H), 2.10-2.19 (m, 2H), 2.63-2.75 (m, 1H), 3.62 (dd, J=11.4, 2.7 Hz, 1H), 3.65 (d, J=10.9 Hz, 1H), 3.95 (d, J=10.9 Hz, 1H), 4.38-4.47 (m, 1H), 5.08 (q, J=6.6 Hz, 1H), 5.23 (d, J=9.2 Hz, 1H), 5.80 (q, J=7.2 Hz, 1H), 6.24 (d, J=16.5 Hz, 1H), 6.57 (d, J=16.5 Hz, 1H), 7.45 (d, J=8.5 Hz, 1H), 7.66 (dd, J=8.5, 1.3 Hz, 1H), 7.83 (s, 1H), 7.85 (d, J=8.5 Hz, 1H), 8.25 (d, J=8.5 Hz, 1H). LCMS (m/z) 566.3 [M+H], Tr=1.79 min.

Example 30

Compound 30

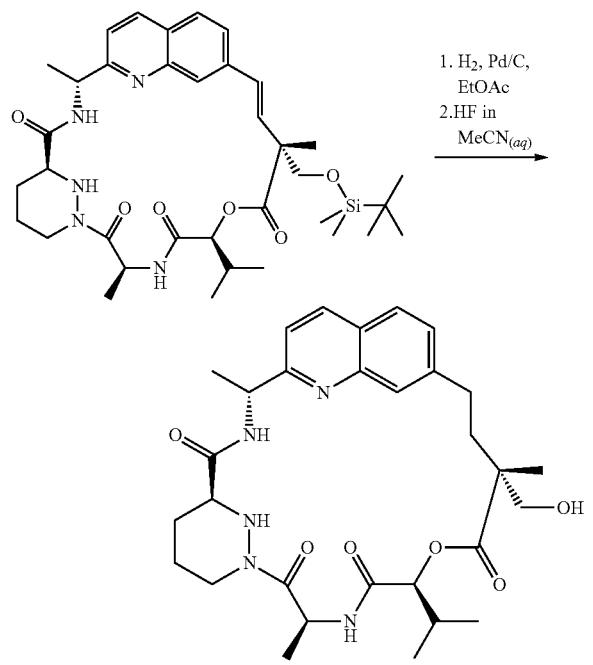

To a stirred solution of compound 29 (40 mg, 0.059 mmol) in ethyl acetate (6 mL) was added 10% palladium on carbon (12.5 mg, 0.012 mmol). The mixture was reacted under an atmosphere of hydrogen for 1 h and then the catalyst was filtered off. Fresh 10% palladium on carbon (12.5 mg, 0.012 mmol) was added to the filtrate and the stirred mixture reacted under an atmosphere of hydrogen for 1 h. The mixture was filtered through Celite and then evaporated. The residue was dissolved in ethyl acetate (6 mL) and fresh 10% palladium on carbon (12.5 mg, 0.012 mmol) was added and the stirred mixture reacted under an atmosphere of hydrogen for 2 h. The mixture was filtered through Celite and evaporated. The residue was dissolved in acetonitrile (20 mL) and hydrogen fluoride (48% in water, 117 mg, 102 µL, 2.82 mmol) was added. The reaction mixture was stirred for 2 h and more hydrogen fluoride (48% in water, 117 mg, 102 µL, 2.82 mmol) was added and stirred for a further 2 h. Solid sodium hydrogen carbonate was added and the mixture stirred for 5 min and then filtered through a hydrophobic frit. The mixture was evaporated and dissolved in ethyl acetate (6 mL) and 10% palladium on carbon (12.5 mg, 0.012 mmol) was added. The stirred mixture was reacted under a hydrogen atmosphere for 7 h and then filtered through Celite and evaporated. The residue was purified by two consecutive reverse phase preparative HPLCs using a gradient of acetonitrile/water 1:4 to 3:7 and then acetonitrile/water 1:4 to 1:1 modified with 0.1% formic acid to afford the title compound (3.1 mg, 9%) as a white solid. $^1$H NMR (300 MHz, CD$_3$OD) δ 1.04 (d, J=6.7 Hz, 3H), 1.09 (d, J=6.9 Hz, 3H), 1.41 (s, 3H), 1.48-1.75 (m, 2H), 1.58 (d, J=6.7 Hz, 3H), 1.60 (d, J=7.1H, 3H), 1.80-1.99 (m, 3H), 2.12-2.25 (m, 1H), 2.26-2.36 (m, 1H), 2.61-2.73 (m, 1H), 2.74-2.90 (m, 1H), 2.96-3.11 (m, 1H), 3.52 (d, J=10.9 Hz, 1H), 3.60 (dd, J=11.2, 2.3 Hz, 1H), 3.80 (d, J=10.9 Hz, 1H), 4.24-4.42 (m, 1H), 4.81-4.94 (m, 1H), 5.10 (q, J=6.7 Hz, 1H), 5.94 (d, J=7.2 Hz, 1H), 7.42 (d, J=8.5 Hz, 1H), 7.43 (dd, J=8.3, 1.6 Hz, 1H), 7.80 (d, J=8.5 Hz, 1H), 7.85 (s, 1H), 8.24 (d, J=8.5 Hz, 1H). LCMS (m/z) 568.2 [M+H], Tr=1.94 min.

Example 31

Compound 31

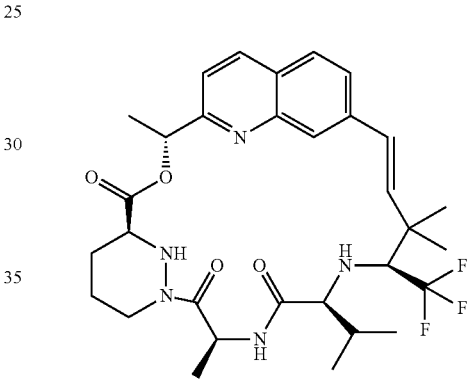

Compound 31a: (S)-3-Methyl-2-[2,2,2-trifluoro-ethylideneamino]-butyric acid methyl ester

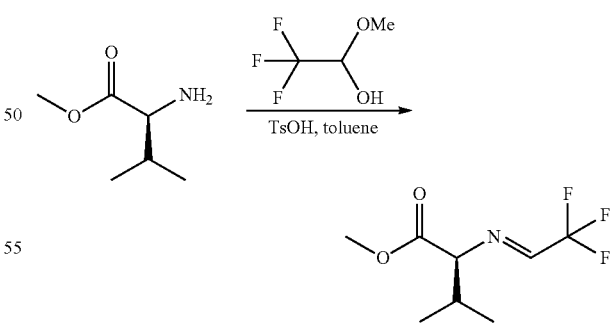

A solution of (S)-2-amino-3-methyl-butyric acid methyl ester hydrochloride (6.72 g, 40 mmol) in water (50 mL) was partitioned between saturated sodium hydrogen carbonate solution and dichloromethane. The organic layer was separated, washed with water and brine, dried over anhydrous magnesium sulfate, filtered and evaporated to afford (S)-2-amino-3-methyl-butyric acid methyl ester (40 mmol). A solution of (S)-2-amino-3-methyl-butyric acid methyl ester (40 mmol), 2,2,2-trifluoro-1-methoxy-ethanol (5.2 g, 3.8 mL, 40 mmol) and 4-toluenesulfonic acid hydrate (100 mg) in toluene (125 mL) was heated at reflux using a Dean-Stark apparatus for 3 h. The reaction mixture was cooled to room temperature and the solvent was evaporated. The residue was purified by silica gel chromatography using a gradient of iso-hexanes/ethyl acetate 10:1 to 5:1 to afford the title compound (4.79 g, 56%) as a colorless oil. ¹H NMR (300 MHz, CDCl₃) δ 0.94 (d, J=7.1 Hz, 3H), 0.97 (d, J=7.1 Hz, 3H), 2.32-2.44 (m, 1H), 3.73-3.77 (m, 4H), 7.67 (q, J=3.3 Hz, 1H).

Compound 31b: (S)-2-((S)-2,2-Dimethyl-1-trifluoromethyl-but-3-enylamino)-3-methyl-butyric acid methyl ester

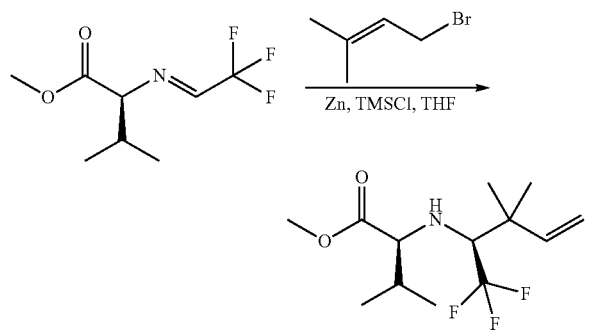

A solution of 31a (4.2 g, 20 mmol) and 3,3-dimethylallyl bromide (2.98 g, 2.3 mL, 20 mmol) in tetrahydrofuran (30 mL) was stirred at room temperature under nitrogen. Zinc granules (2.6 g, 40 mmol) and chlorotrimethylsilane (10 drops) were added and the reaction mixture was stirred at room temperature for 10 minutes and then heated at reflux for 2 h. The reaction mixture was cooled to room temperature. Saturated ammonium chloride solution was added and the mixture was extracted with diethyl ether. The organic layer was separated, washed with brine, dried over anhydrous magnesium sulfate, filtered and evaporated. The residue was purified by silica gel chromatography using a gradient of iso-hexanes/ethyl acetate 50:1 to 40:1 to afford the title compound (1.41 g, 25%) as a colorless oil. ¹H NMR (300 MHz, CDCl₃) δ 0.91 (d, J=6.7 Hz, 3H), 0.97 (d, J=6.7 Hz, 3H), 1.16 (s, 6H), 1.52-1.55 (m, 1H), 1.81-1.92 (m, 1H), 2.76-2.85 (m, 1H), 3.20 (dd, J=9.8, 7.1 Hz, 1H), 3.72 (s, 3H), 5.09 (d, J=17.4 Hz, 1H), 5.11 (d, J=10.8 Hz, 1H), 5.90 (dd, J=17.4, 10.8 Hz, 1H). LCMS (m/z) 282.1 [M+H], Tr=3.51 min.

Compound 31c: (S)-2-((S)-2,2-Dimethyl-1-trifluoromethyl-but-3-enylamino)-3-methyl-butyric acid

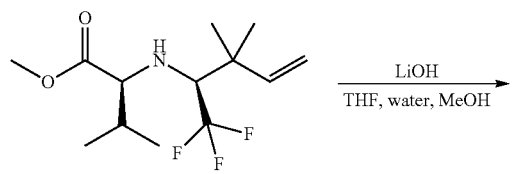

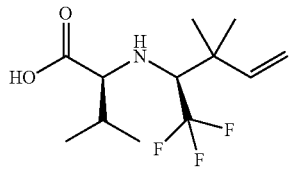

A solution of 31b (1.12 g, 4.0 mmol) in tetrahydrofuran (40 mL) was stirred at 0° C. under nitrogen. A solution of lithium hydroxide monohydrate (504 mg, 12.0 mmol) in water (8 mL) was added and the reaction mixture was stirred at 0° C. for 1 h and then at room temperature for 1 h. Methanol (5 mL) was added and the reaction mixture was stirred at room temperature for 22 h. Additional lithium hydroxide monohydrate (336 mg, 8.0 mmol) in water (2 mL) was added and the reaction mixture was stirred at room temperature for 24 h. The organic solvent was evaporated and the solution was acidified to pH 2 with 2 M hydrochloric acid and the mixture was extracted with ethyl acetate. The organic extracts were combined, washed with water and brine. The organic solution was filtered through a hydrophobic frit and the filtrate was evaporated to afford the title compound (770 mg, 72%) as a colorless oil. ¹H NMR (300 MHz, CDCl₃) δ 1.00 (d, J=6.7 Hz, 3H), 1.01 (d, J=6.9 Hz, 3H), 1.20 (s, 6H), 1.95-2.04 (m, 1H), 2.87 (q, J=7.8 Hz, 1H), 3.37 (d, J=5.8 Hz, 1H), 5.12 (d, J=17.2 Hz, 1H), 5.16 (d, J=10.7 Hz, 1H), 5.90 (dd, J=17.2, 10.7 Hz, 1H). LCMS (m/z) 268.2 [M+H], Tr=2.88 min.

Compound 31d: (S)-2-{(E)-(S)-4-[2-((R)-1-Acetoxyethyl)-quinolin-7-yl]-2,2-dimethyl-1-trifluoromethyl-but-3-enylamino}-3-methyl-butyric acid

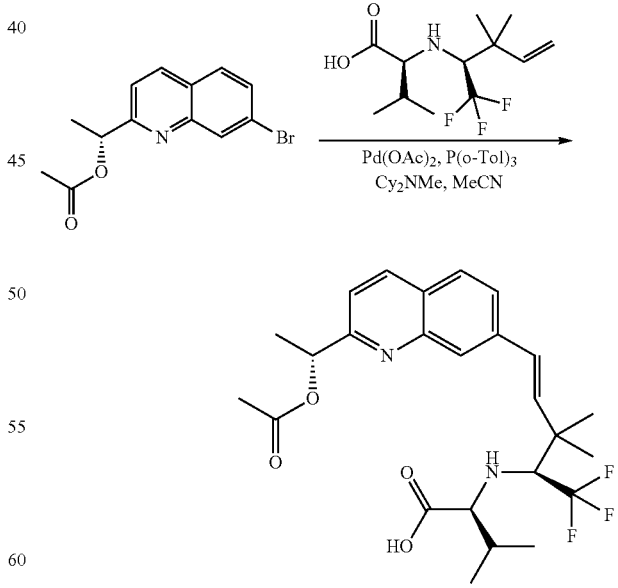

A solution of 31c (267 mg, 1.0 mmol) and 25d (294 mg, 1.0 mmol) in acetonitrile (10 mL) was stirred at room temperature under nitrogen. Palladium(II) acetate (45 mg, 0.2 mmol), tri(o-tolyl)phosphine (61 mg, 0.2 mmol) were added followed by N,N-dicyclohexylmethylamine (390 mg, 0.43 mL, 2.0 mmol) and the reaction mixture was heated at 120° C. in a microwave reactor for 30 minutes. The solvent was evaporated and the residue was partitioned between ethyl acetate and 1 M hydrochloric acid. The organic extracts were combined and washed with brine. The organic solution was filtered through a hydrophobic frit and the filtrate was evaporated to afford the crude product (640 mg, 1.0 mmol) as a yellow waxy solid which was used in the next step without further purification. LCMS (m/z) 481.1 [M+H], Tr=3.26 min.

Compound 31e: (S)-1-[(S)-2-((S)-2-{(E)-(S)-4-[2-((R)-1-Acetoxy-ethyl)-quinolin-7-yl]-2,2-dimethyl-1-trifluoromethyl-but-3-enylamino}-3-methyl-butyrylamino)-propionyl]-hexahydro-pyridazine-3-carboxylic acid 2,2,2-trichloro-ethyl ester organic solution was filtered through a hydrophobic frit and the filtrate was evaporated. The residue was purified by silica gel chromatography using a gradient of iso-hexanes/ethyl acetate 3:1 to 0:1 to afford the title compound (292 mg, 37% over 2 steps) as a white foam. $^1$H NMR (300 MHz, CDCl$_3$) δ 0.95 (d, J=7.1 Hz, 3H), 0.97 (d, J=7.1 Hz, 3H), 1.30 (d, J=6.7 Hz, 3H), 1.38 (s, 6H), 1.62-1.68 (m, 3H), 1.69 (d, J=6.7 Hz, 3H), 1.90-1.96 (m, 2H), 2.18 (s, 3H), 2.18-2.21 (m, 1H), 2.84-3.23 (m, 3H), 3.68-3.72 (m, 1H), 3.79 (d, J=11.1 Hz, 1H), 4.37-4.42 (m, 1H), 4.72 (d, J=11.8 Hz, 1H), 4.96 (d, J=11.8 Hz, 1H), 5.31-5.40 (m, 1H), 6.06 (q, J=6.7 Hz, 1H), 6.59 (ABq, Δδ$_{AB}$=0.07, J$_{AB}$=16.2 Hz, 2H), 7.05 (d, J=8.0 Hz, 1H), 7.42 (d, J=8.5 Hz, 1H), 7.66 (d, J=8.5 Hz, 1H), 7.76 (d,

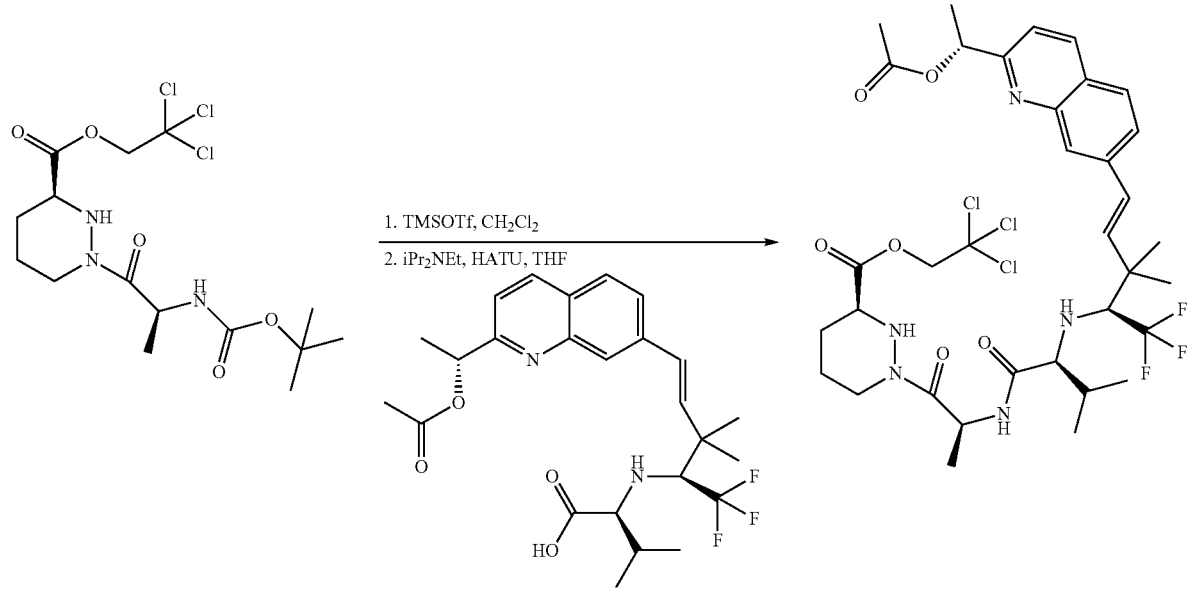 [SMILES: C[C@H](NC(=O)OC(C)(C)C)C(=O)N1CCC[C@@H](C(=O)OCC(Cl)(Cl)Cl)N1 ; CC(=O)O[C@H](C)c1ccc2ccc(/C=C/C(C)(C)[C@H](N[C@H](C(=O)O)C(C)C)C(F)(F)F)cc2n1 ; CC(=O)O[C@H](C)c1ccc2ccc(/C=C/C(C)(C)[C@H](N[C@H](C(=O)N[C@@H](C)C(=O)N3CCC[C@@H](C(=O)OCC(Cl)(Cl)Cl)N3)C(C)C)C(F)(F)F)cc2n1]

A solution of 1d (433 mg, 1.0 mmol) in dichloromethane (30 mL) was stirred at 0° C. under nitrogen. Trimethylsilyl trifluoromethanesulfonate (444 mg, 0.35 mL, 2.0 mmol) was added and the reaction mixture was stirred at 0° C. for 45 minutes. N,N-diisopropylethylamine (516 mg, 0.7 mL, 4.0 mmol) was added, the solvent was evaporated and the residue was dried affording crude (S)-1-((S)-2-amino-propionyl)-hexahydro-pyridazine-3-carboxylic acid 2,2,2-trichloro-ethyl ester (1.0 mmol), which was used in the next step. A mixture of crude (S)-1-((S)-2-amino-propionyl)-hexahydro-pyridazine-3-carboxylic acid 2,2,2-trichloro-ethyl ester (1.0 mmol), N,N-diisopropylethylamine (516 mg, 0.7 mL, 4.0 mmol) and crude 31d (1.0 mmol) in acetonitrile (30 mL) was stirred at 0° C. under nitrogen. 2-(1H-7-Azabenzotriazol-1-yl)-1,1,3,3-tetramethyl uronium hexafluorophosphate methanaminium (530 mg, 1.4 mmol) was added and the reaction mixture was stirred at 0° C. for 30 minutes and then at room temperature for 2 h. The solvent was evaporated and the residue was dissolved in ethyl acetate and the solution was washed with cold 1 M hydrochloric acid, water, saturated sodium hydrogen carbonate solution, water and brine. The J=8.5 Hz, 1H), 8.01 (s, 1H), 8.12 (d, J=8.5 Hz, 1H). LCMS (m/z) 794.2/796.2 [M+H], Tr=3.48 min.

Compound 31

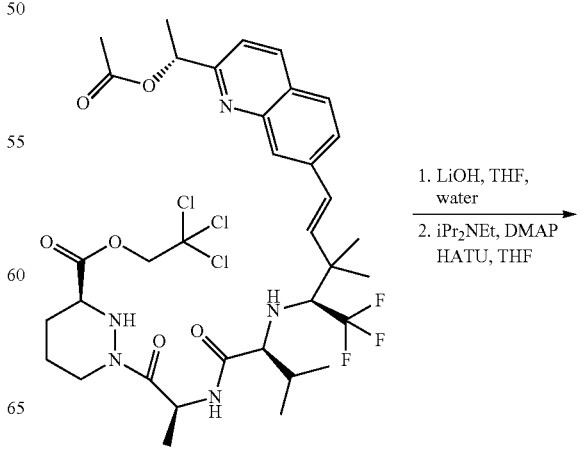

-continued

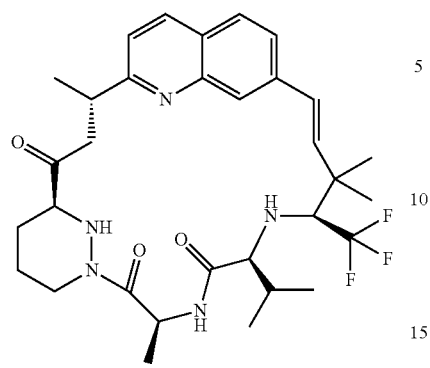

A solution of 31e (200 mg, 0.25 mmol) in tetrahydrofuran (10 mL) was stirred at 0° C. under nitrogen. A solution of lithium hydroxide monohydrate (53 mg, 1.25 mmol) in water (2 mL) was added and the reaction mixture was stirred at 0° C. for 5 h. 1 M Hydrochloric acid (1.25 mL, 1.25 mmol) was added and the solvent was evaporated. The residue was co-evaporated with tetrahydrofuran/toluene (1:1, 3×) and the residue was triturated with diethyl ether (2×) and the resulting solid was dried to afford (S)-1-[(S)-2-((S)-2-{(E)-(S)-4-[2-((R)-1-hydroxy-ethyl)-quinolin-7-yl]-2,2-dimethyl-1-trifluoromethyl-but-3-enylamino}-3-methyl-butyrylamino)-propionyl]-hexahydro-pyridazine-3-carboxylic acid (0.25 mmol) as a white solid which was used crude in the next reaction. LCMS (m/z) 622.3 [M+H], Tr=1.97 min. A suspension of crude (S)-1-[(S)-2-((S)-2-{(E)-(S)-4-[2-((R)-1-hydroxy-ethyl)-quinolin-7-yl]-2,2-dimethyl-1-trifluoromethyl-but-3-enylamino}-3-methyl-butyrylamino)-propionyl]-hexahydro-pyridazine-3-carboxylic acid (0.25 mmol) in tetrahydrofuran (250 mL) was stirred at 0° C. under nitrogen. N,N-Diisopropylethylamine (161 mg, 0.22 mL, 1.25 mmol) and 4-dimethylaminopyridine (20 mg) were added and the reaction mixture was stirred at 0° C. for 5 minutes. 2-(1H-7-Azabenzotriazol-1-yl)-1,1,3,3-tetramethyl uronium hexafluorophosphate methanaminium (133 mg, 0.35 mmol) was added and the reaction mixture was stirred at 0° C. for 30 minutes and then at room temperature for 3 h. Additional 2-(1H-7-azabenzotriazol-1-yl)-1,1,3,3-tetramethyl uronium hexafluorophosphate methanaminium (95 mg, 0.25 mmol) was added and the reaction mixture was stirred at room temperature for 18 h. The solvent was evaporated and the residue was suspended in ethyl acetate. Cold 1 M hydrochloric acid was added and the organic layer was separated, washed with water, saturated sodium hydrogen carbonate solution, water and brine. The organic solution was filtered through a hydrophobic frit and the filtrate was evaporated. The residue was purified by silica gel chromatography using a gradient of iso-hexanes/ethyl acetate 4:1 to 2:1 to afford the title compound (50 mg, 33% over 2 steps) as a white solid. $^1$H NMR (300 MHz, CD$_3$OD) δ 0.74 (d, J=6.7 Hz, 3H), 1.00 (d, J=6.7 Hz, 3H), 1.29 (s, 3H), 1.35 (s, 3H), 1.55-1.70 (m, 3H), 1.71 (d, J=6.7 Hz, 3H), 1.72 (d, J=6.5 Hz, 3H), 1.87-1.97 (m, 2H), 2.66-2.74 (m, 1H), 2.90 (d, J=9.4 Hz, 1H), 3.13 (q, J=7.8 Hz, 1H), 3.70-3.79 (m, 1H), 4.28-4.37 (m, 2H), 5.84 (q, J=7.1 Hz, 1H), 5.91 (q, J=6.7 Hz, 1H), 6.33 (d, J=16.2 Hz, 1H), 6.63 (d, J=16.2 Hz, 1H), 7.42 (d, J=8.7 Hz, 1H), 7.49 (dd, J=8.3, 1.6 Hz, 1H), 7.83 (d, J=8.5 Hz, 1H), 8.20-8.23 (m, 2H). LCMS (m/z) 604.3 [M+H], Tr=3.25 min.

Example 32

Compound 32

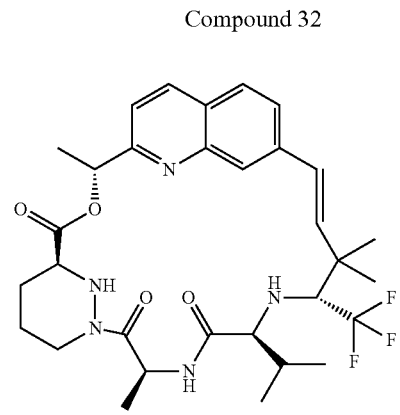

Compound 32a: (R)-3-Methyl-2-[2,2,2-trifluoro-ethylideneamino]-butyric acid methyl ester

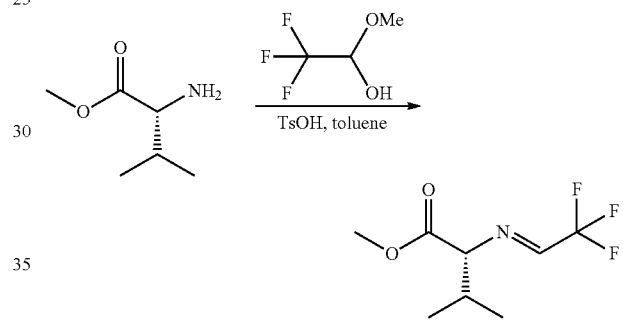

Compound 32a was prepared in the same manner as compound 31a using (R)-2-amino-3-methyl-butyric acid methyl ester hydrochloride instead of (S)-2-amino-3-methyl-butyric acid methyl ester hydrochloride in 64% yield. $^1$H NMR (300 MHz, CDCl$_3$) δ 0.94 (d, J=7.1 Hz, 3H), 0.97 (d, J=7.1 Hz, 3H), 2.32-2.44 (m, 1H), 3.73-3.77 (m, 4H), 7.67 (q, J=3.3 Hz, 1H).

Compound 32b: (R)-2-((R)-2,2-Dimethyl-1-trifluoromethyl-but-3-enylamino)-3-methyl-butyric acid methyl ester

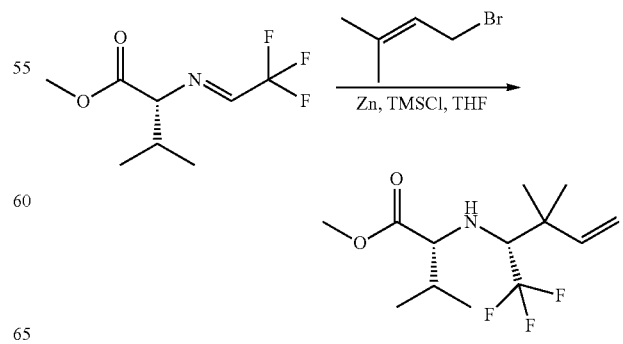

Compound 32b was prepared in the same manner as compound 31b using 32a instead of 31a in 30% yield. $^{1}$H NMR (300 MHz, CDCl$_3$) δ 0.91 (d, J=6.7 Hz, 3H), 0.97 (d, J=6.7 Hz, 3H), 1.16 (s, 6H), 1.52-1.55 (m, 1H), 1.81-1.92 (m, 1H), 2.76-2.85 (m, 1H), 3.20 (dd, J=9.8, 7.1 Hz, 1H), 3.72 (s, 3H), 5.09 (d, J=17.4 Hz, 1H), 5.11 (d, J=10.8 Hz, 1H), 5.90 (dd, J=17.4, 10.8 Hz, 1H). LCMS (m/z) 282.1 [M+H], Tr=3.51 min.

Compound 32c: (S)-2-((R)-2,2-dimethyl-1-trifluoromethyl-but-3-enylamino)-3-methyl-butyric acid

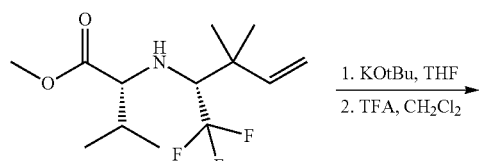

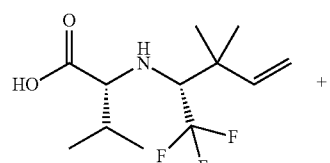

A solution of 32b (1.30 g, 4.6 mmol) in tetrahydrofuran (30 mL) was stirred at 0° C. under nitrogen. Potassium tert-butoxide (1.55 g, 13.8 mmol) was added and the reaction mixture was stirred at 0° C. and warmed to room temperature overnight. The volatiles were evaporated, 2 M hydrochloric acid was added and the mixture was extracted with ethyl acetate. The organic extracts were combined, washed with water and brine. The organic solution was filtered through a hydrophobic frit and the filtrate was evaporated to afford a mixture containing (R)-2-((R)-2,2-dimethyl-1-trifluoromethyl-but-3-enylamino)-3-methyl-butyric acid tert-butyl ester, (S)-2-((R)-2,2-dimethyl-1-trifluoromethyl-but-3-enylamino)-3-methyl-butyric acid tert-butyl ester, (R)-2-((R)-2,2-dimethyl-1-trifluoromethyl-but-3-enylamino)-3-methyl-butyric acid and (S)-2-((R)-2,2-dimethyl-1-trifluoromethyl-but-3-enylamino)-3-methyl-butyric acid (4.6 mmol) which was used crude in the next step. A solution of the mixture of (R)-2-((R)-2,2-dimethyl-1-trifluoromethyl-but-3-enylamino)-3-methyl-butyric acid tert-butyl ester, (S)-2-((R)-2,2-dimethyl-1-trifluoromethyl-but-3-enylamino)-3-methyl-butyric acid tert-butyl ester, (R)-2-((R)-2,2-dimethyl-1-trifluoromethyl-but-3-enylamino)-3-methyl-butyric acid and (S)-2-((R)-2,2-dimethyl-1-trifluoromethyl-but-3-enylamino)-3-methyl-butyric acid (4.6 mmol) in dichloromethane (10 mL) was stirred at 5° C. under nitrogen. Trifluoroacetic acid (5 mL) was added and the reaction mixture was stirred at room temperature for 20 h. Additional trifluoroacetic acid (5 mL) was added and the reaction mixture was stirred at room temperature for 48 h. The solvent was evaporated and the residue was co-evaporated with toluene (3×). The residue was partitioned between ethyl acetate and water. The organic extracts were combined, washed with water and brine. The organics were filtered through a hydrophobic frit and the filtrate was evaporated. The residue was purified by silica gel chromatography using a gradient of iso-hexanes/ethyl acetate 10:1 to 5:1 to afford (R)-2-((R)-2,2-dimethyl-1-trifluoromethyl-but-3-enylamino)-3-methyl-butyric acid (152 mg, 12%) as a colorless oil and the title compound (321 mg, 26%) as a colorless oil. $^{1}$H NMR (300 MHz, CDCl$_3$) δ 0.99 (d, J=6.7 Hz, 3H), 1.01 (d, J=6.7 Hz, 3H), 1.23 (s, 6H), 2.09-2.19 (m, 1H), 2.85 (q, J=8.0 Hz, 1H), 3.27 (d, J=4.0 Hz, 1H), 5.16 (d, J=17.2 Hz, 1H), 5.19 (d, J=10.8 Hz, 1H), 5.91 (dd, J=17.3, 10.8 Hz, 1H). LCMS (m/z) 268.1 [M+H], Tr=2.95 min.

Compound 32d: (S)-2-{(E)-(R)-4-[2-((R)-1-Acetoxy-ethyl)-quinolin-7-yl]-2,2-dimethyl-1-trifluoromethyl-but-3-enylamino}-3-methyl-butyric acid

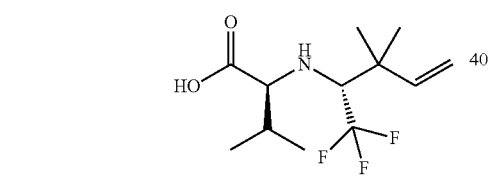

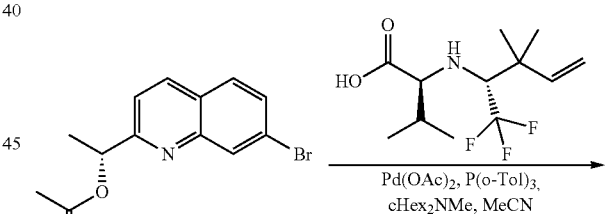

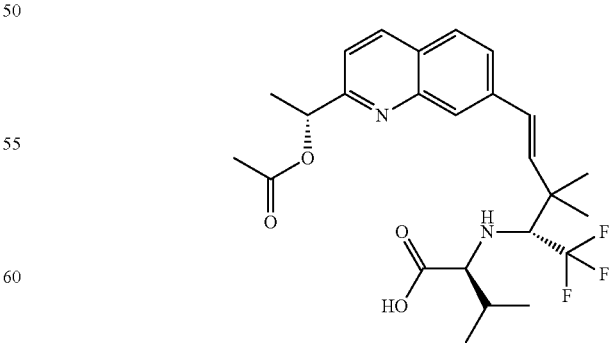

Compound 32d was prepared in the same manner as compound 31d using 32c instead of 31c and used crude in the next step. LCMS (m/z) 481.1 [M+H], Tr=3.15 min.

Compound 32e: (S)-1-[(S)-2-((S)-2-{(E)-(R)-4-[2-((R)-1-Acetoxy-ethyl)-quinolin-7-yl]-2,2-dimethyl-1-trifluoromethyl-but-3-enylamino}-3-methyl-butyrylamino)-propionyl]-hexahydro-pyridazine-3-carboxylic acid 2,2,2-trichloro-ethyl ester

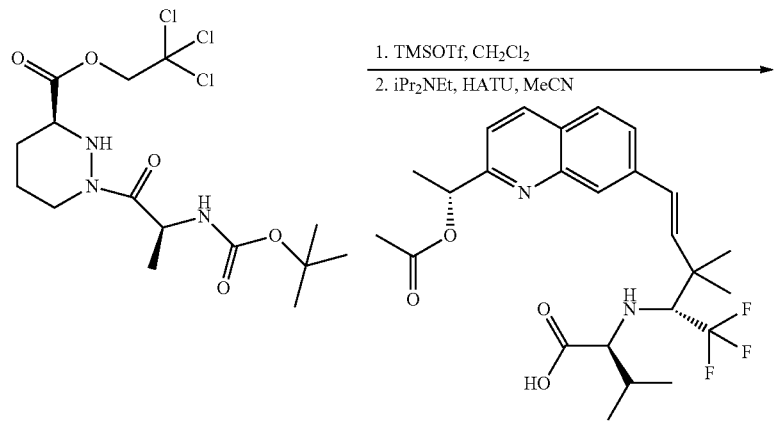

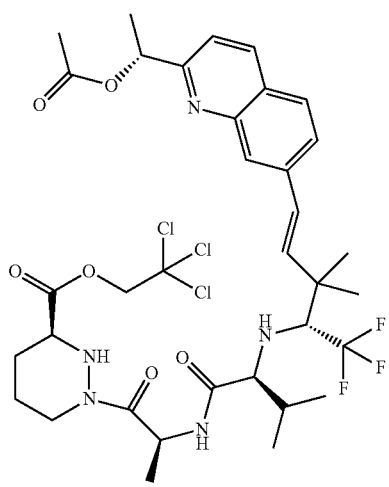

Compound 32e was prepared in the same manner as compound 31e using 32d instead of 32c in 58% yield. $^1$H NMR (300 MHz, CDCl$_3$) δ 0.90 (d, J=7.1 Hz, 3H), 0.92 (d, J=7.1 Hz, 3H), 1.31 (d, J=6.7 Hz, 3H), 1.38 (s, 6H), 1.69 (d, J=6.7 Hz, 3H), 1.69-1.79 (m, 3H), 1.89-2.02 (m, 2H), 2.18 (s, 3H), 2.18-2.21 (m, 1H), 2.83-3.12 (m, 3H), 3.66-3.73 (m, 1H), 3.83 (d, J=11.4 Hz, 1H), 4.42-4.48 (m, 1H), 4.72 (d, J=11.8 Hz, 1H), 4.95 (d, J=11.8 Hz, 1H), 5.27-5.34 (m, 1H), 6.06 (q, J=6.7 Hz, 1H), 6.56 (ABq, Δδ$_{AB}$=0.13, J$_{AB}$=16.3 Hz, 2H), 7.16 (d, J=7.6 Hz, 1H), 7.42 (d, J=8.5 Hz, 1H), 7.62 (d, J=8.5 Hz, 1H), 7.75 (d, J=8.5 Hz, 1H), 8.02 (s, 1H), 8.12 (d, J=8.5 Hz, 1H). LCMS (m/z) 794.2/796.1 [M+H], Tr=3.65 min.

Compound 32

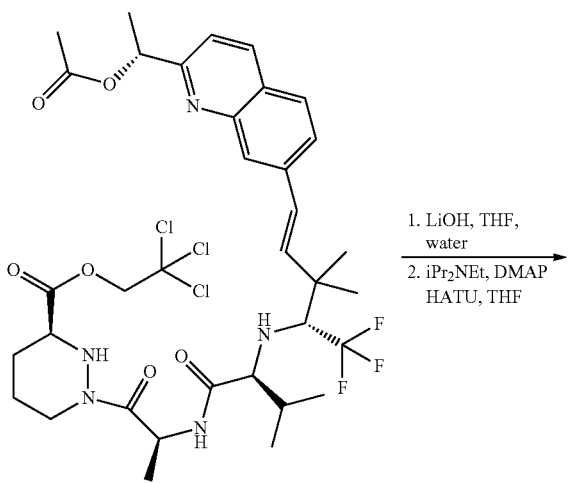

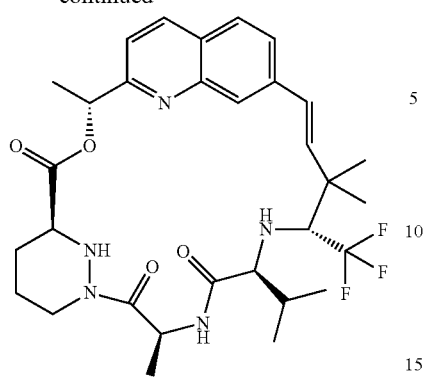

Compound 32 was prepared in the same manner as compound 31 using 32e instead of 31e in 35% as a white solid. $^1$H NMR (300 MHz, CD$_3$CN) δ 0.94 (d, J=6.9 Hz, 3H), 0.98 (d, J=6.7 Hz, 3H), 1.19 (d, J=6.7 Hz, 3H), 1.43 (s, 3H), 1.47 (s, 3H), 1.69 (d, J=6.7 Hz, 3H), 1.70-1.90 (m, 4H), 2.18-2.22 (m, 2H), 3.39-3.60 (m, 3H), 3.81-3.96 (m, 2H), 4.73-4.81 (m, 1H), 6.03-6.16 (m, 2H), 6.78 (ABq, Δδ$_{AB}$=0.10, J$_{AB}$=16.3 Hz, 2H), 7.39 (d, J=8.5 Hz, 1H), 7.52 (d, J=8.0 Hz, 1H), 7.87 (d, J=8.3 Hz, 1H), 7.98-8.05 (br s, 1H), 8.25 (d, J=8.5 Hz, 1H), 8.34 (s, 1H). LCMS (m/z) 604.3 [M+H], Tr=2.78 min.

Example 33

Compound 33

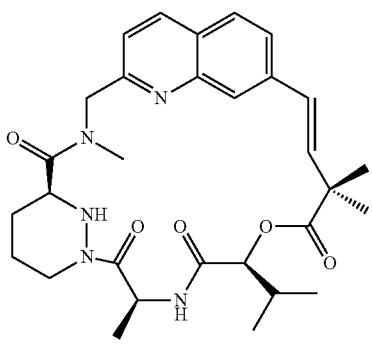

Compound 33a.
(7-Bromo-quinolin-2-ylmethyl)-methyl-carbamic acid tert-butyl ester

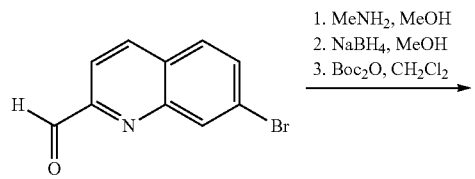

1. MeNH$_2$, MeOH
2. NaBH$_4$, MeOH
3. Boc$_2$O, CH$_2$Cl$_2$

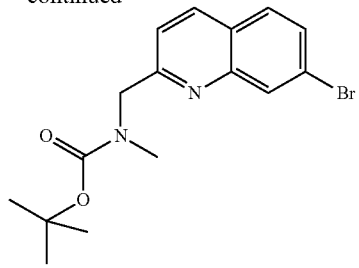

To a stirred slurry of 7-bromo-quinoline-2-carbaldehyde (236 mg, 1.00 mmol, prepared as in EP 239746) in methanol (5 mL) was added methylamine in methanol (2 M, 2.5 mL, 5.00 mmol). The reaction mixture was stirred for 20 h and then evaporated. The residue was suspended in methanol (5 mL) and sodium borohydride (57 mg, 1.50 mmol) was added portionwise. The reaction mixture was stirred for 1 h and then partitioned between dichloromethane and saturated ammonium chloride solution. The organic layer was separated and washed with saturated ammonium chloride solution and the aqueous extracts were extracted with dichloromethane and the combined organics dried over anhydrous sodium sulfate, filtered and evaporated. The residue was dissolved in dichloromethane (8 mL) and to the resulting stirred solution was added a solution of di-tert-butyl dicarbonate (327 mg, 1.50 mmol) in dichloromethane (2 mL). After stirring for 3 h the reaction mixture was diluted with dichloromethane and washed with saturated sodium bicarbonate solution (2×) and the aqueous layer was extracted with dichloromethane. The combined organic extracts were passed through a hydrophobic frit and evaporated. The residue was purified by silica gel chromatography eluting with a gradient of iso-hexanes/ethyl acetate 1:0 to 4:1 to afford the title compound (206 mg, 59%) as an orange oil and as a mixture of rotamers. $^1$H NMR (300 MHz, CDCl$_3$) δ 1.42-1.61 (m, 9H), 2.92 (s, 1.5H), 3.00 (s, 1.5H), 4.71 (s, 1H), 4.75 (s, 1H), 7.34-7.46 (m, 1H), 7.64 (d, J=8.5 Hz, 1H), 7.70 (d, J=8.5 Hz, 1H), 8.13 (d, J=5.8 Hz, 1H), 8.26 (s, 1H). LCMS (m/z) 351.1, 353.1 [M+H], Tr=3.13 min.

Compound 33b. (E)-4-{2-[(tert-Butoxycarbonyl-methyl-amino)-methyl]-quinolin-7-yl}-2,2-dimethyl-but-3-enoic acid methyl ester

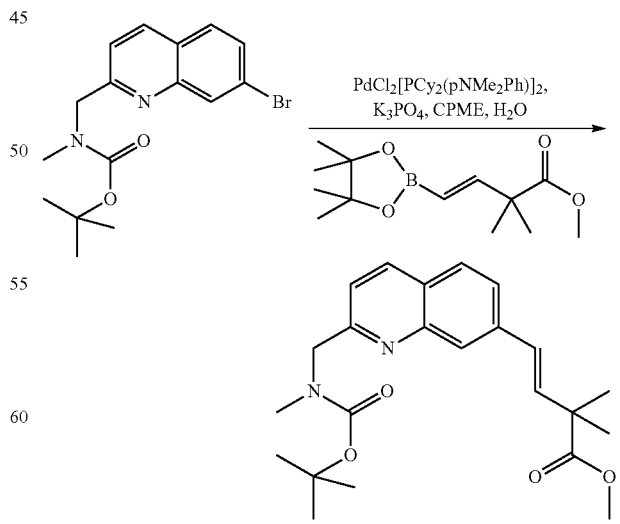

33a (206 mg, 0.586 mmol), 22d (171 mg, 0.674 mmol), bis[(dicyclohexyl)(4-dimethylaminophenyl)phosphine]palladium(II) chloride (24 mg, 0.029 mmol) and potassium phosphate tribasic (373 mg, 1.76 mmol) were suspended in cyclopentyl methyl ether (2 mL) and water (1 mL). The reaction mixture was stirred and heated at 80° C. for 2 h under nitrogen. More bis[(dicyclohexyl)(4-dimethylaminophenyl)phosphine]palladium(II) chloride (12 mg, 0.015 mmol) was added and the reaction mixture heated at 90° C. for 90 minutes. The reaction was allowed to cool and diluted with ethyl acetate and washed with water (2×). The aqueous layers were extracted with ethyl acetate and the combined organic extracts were washed with saturated brine, dried over anhydrous sodium sulfate, filtered and evaporated. The residue was purified by silica gel chromatography eluting with a gradient of iso-hexanes/ethyl acetate 1:0 to 7:3 to afford the title compound (178 mg, 76%) as a yellow gum and as a mixture of rotamers. $^1$H NMR (300 MHz, CDCl$_3$) δ 1.43-1.57 (m, 15H), 2.91 (s, 1.5H), 2.99 (s, 1.5H), 3.74 (s, 3H), 4.71 (s, 1H), 4.74 (s, 1H), 6.64 (app s, 2H), 7.27-7.39 (m, 1H), 7.63 (d, J=8.5 Hz, 1H), 7.76 (d, J=8.5 Hz, 1H), 7.90 (s, 1H), 8.10 (d, J=8.5 Hz, 1H). LCMS (m/z) 399.1 [M+H], Tr=3.02 min.

Compound 33c. (E)-4-{2-[({(S)-1-[(S)-2-((S)-2-Hydroxy-3-methyl-butyrylamino)-propionyl]-hexahydro-pyridazine-3-carbonyl}-methyl-amino)-methyl]-quinolin-7-yl}-2,2-dimethyl-but-3-enoic acid methyl ester

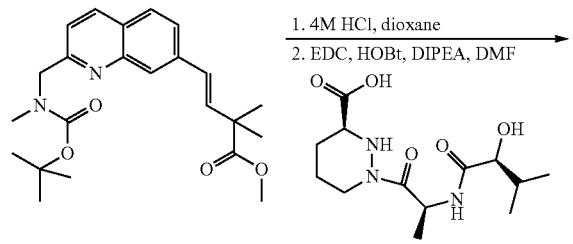

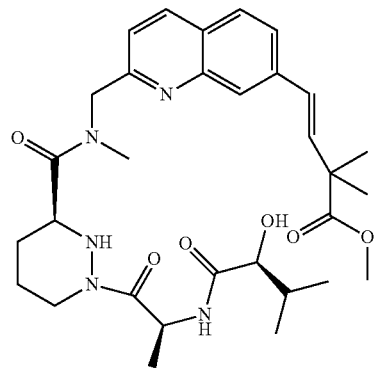

33b (134 mg, 0.336 mmol) was suspended in hydrogen chloride in 1,4-dioxane (4 M, 3.4 mL, 13.6 mmol) and the reaction mixture stirred for 2.5 h and then evaporated. To the residue was added a solution of 29a (106 mg, 0.353 mmol) in N,N-dimethylformamide (7 mL) followed by N,N-diisopropylethylamine (87 mg, 117 μL, 0.672 mmol), 1-hydroxybenzotriazole hydrate (63 mg, 0.470 mmol) and N-(3 dimethylaminopropyl)-N'-ethylcarbodiimide hydrochloride (90 mg, 0.470 mmol) and the reaction mixture was stirred for 16 h. The reaction mixture was diluted with ethyl acetate and washed successively with saturated sodium bicarbonate solution, water, saturated ammonium chloride solution, water and brine, dried over anhydrous sodium sulfate, filtered and evaporated. The residue was purified by silica gel chromatography eluting with a gradient of ethyl acetate/methanol 1:0 to 19:1 to afford the title compound (128 mg, 65%) as a colorless gum. $^1$H NMR (300 MHz, CDCl$_3$) δ 0.80-1.06 (m, 6H), 1.21-1.38 (m, 3H), 1.47 (s, 6H), 1.52-2.18 (m, 5H), 2.63-2.78 (m, 1H), 3.12 (s, 3H), 3.73 (s, 3H), 3.88-3.97 (m, 2H), 4.08-4.26 (m, 2H), 4.41-4.61 (m, 1H), 4.75-4.99 (m, 2H), 5.20-5.40 (m, 1H), 6.63 (app d, J=2.0 Hz, 2H), 7.22-7.34 (m, 1H), 7.59-7.69 (m, 1H), 7.72-7.78 (m, 1H), 7.90-7.97 (d, J=8.0 Hz, 1H), 8.08-8.20 (m, 1H). LCMS (m/z) 582.3 [M+H], Tr=2.35 min.

Compound 33

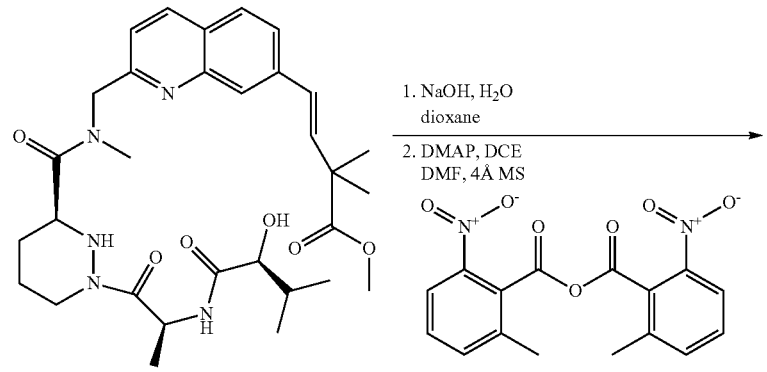

-continued

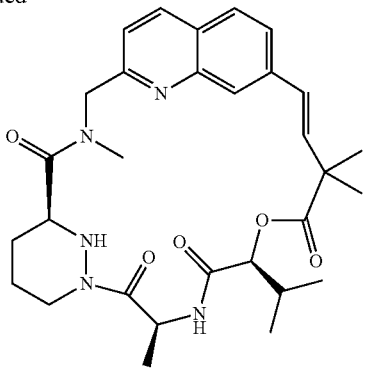

A stirred mixture of 33c (64 mg, 0.110 mmol) and 1M NaOH (0.88 mL, 0.88 mmol) in 1,4-dioxane (5.5 mL) was heated at reflux for 2.5 hours and then allowed to cool. The reaction mixture was neutralized to pH 7 with 2M hydrochloric acid and evaporated. The residue was azeotroped with tert-butanol/acetonitrile/toluene and then acetonitrile/toluene to give the crude acid.

To a stirred slurry of 2-methyl-6-nitrobenzoic acid (189 mg, 0.550 mmol), 4-(dimethylamino)pyridine (101 mg, 0.825 mmol) and powdered 4 Å molecular sieves (~2 g) in 1,2-dichloroethane (37 mL) under nitrogen at 50° C. was added a solution of the crude acid in N,N-dimethylformamide (5 mL) over 3 hours via syringe pump. The flask containing the original acid was washed with further N,N-dimethylformamide (1 mL) and this was added to the reaction mixture over 10 minutes. The reaction mixture was stirred at 50° C. for a further 2.5 hours and then allowed to cool. The mixture was filtered through celite and the filtrate washed successively with ice cold saturated ammonium chloride solution, ice cold saturated sodium bicarbonate solution and saturated brine, dried over sodium sulfate, filtered and evaporated. The residue was purified by preparative HPLC using a gradient of acetonitrile/water 1:4 to 7:3 to afford the title compound (3.9 mg, 6.5%) as a white solid. LCMS (m/z) 550.3 [M+H], Tr=2.35 min.

Examples 34 and 35

Compounds 34 and 35

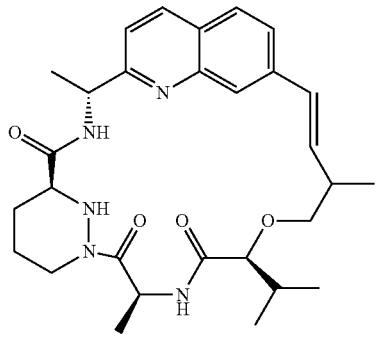 [SMILES: CC1/C=C/c2ccc3ccc(nc3c2)[C@@H](C)NC(=O)[C@@H]2CCCN(N2)C(=O)[C@H](C)NC(=O)[C@H](C(C)C)OC1]

Compound 34a. (S)-1-{(S)-2-[(S)-3-Methyl-2-(2-methyl-but-3-enyloxy)-butyrylamino]-propionyl}-hexahydro-pyridazine-3-carboxylic acid 2,2,2-trichloro-ethyl ester

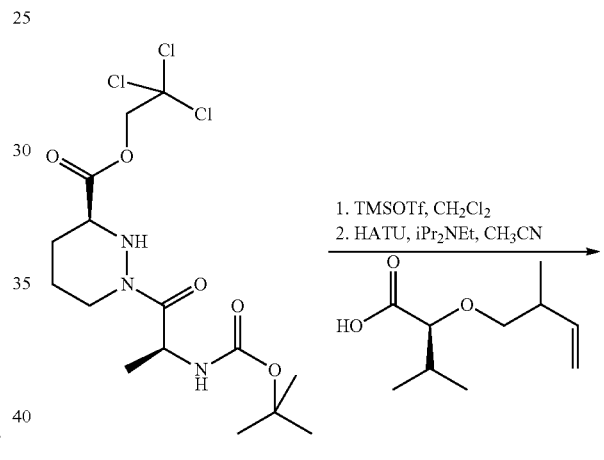

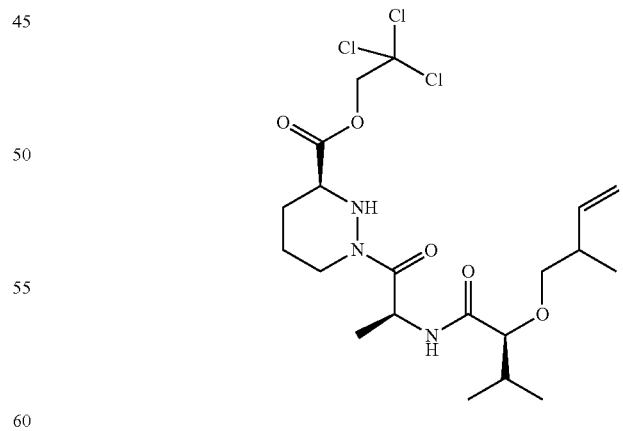

Compound 34a was prepared in the same manner as compound 27e using (S)-3-methyl-2-(2-methyl-but-3-enyloxy)-butyric acid instead of 27d in 72% yield and isolated as a 1:1 mixture of diastereosiomers. LCMS (m/z) 502.1/504.1 [M+H], Tr=3.32 min.

Compound 34b. (S)-1-{(S)-2-[(S)-3-Methyl-2-((E)-2-methyl-4-{2-[(R)-1-(2(R)-methyl-propane-2-sulfinylamino)-ethyl]-quinolin-7-yl}-but-3-enyloxy)-butyrylamino]-propionyl}-hexahydro-pyridazine-3-carboxylic acid 2,2,2-trichloro-ethyl ester Compound 34c. (S)-1-{(S)-2-[(S)-3-methyl-2-((E)-2-methyl-4-{2-[(R)-1-((R)-2-methyl-propane-2-sulfinylamino)-ethyl]-quinolin-7-yl}-but-3-enyloxy)-butyrylamino]-propionyl}-hexahydro-pyridazine-3-carboxylic acid methyl ester

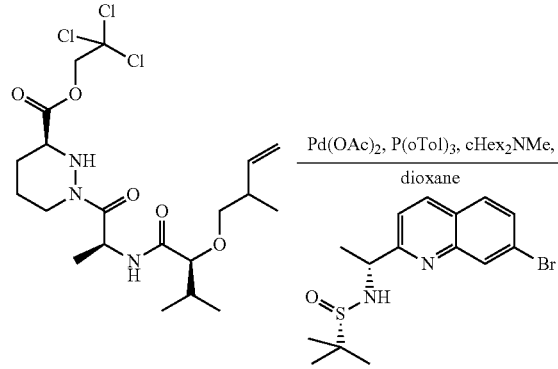

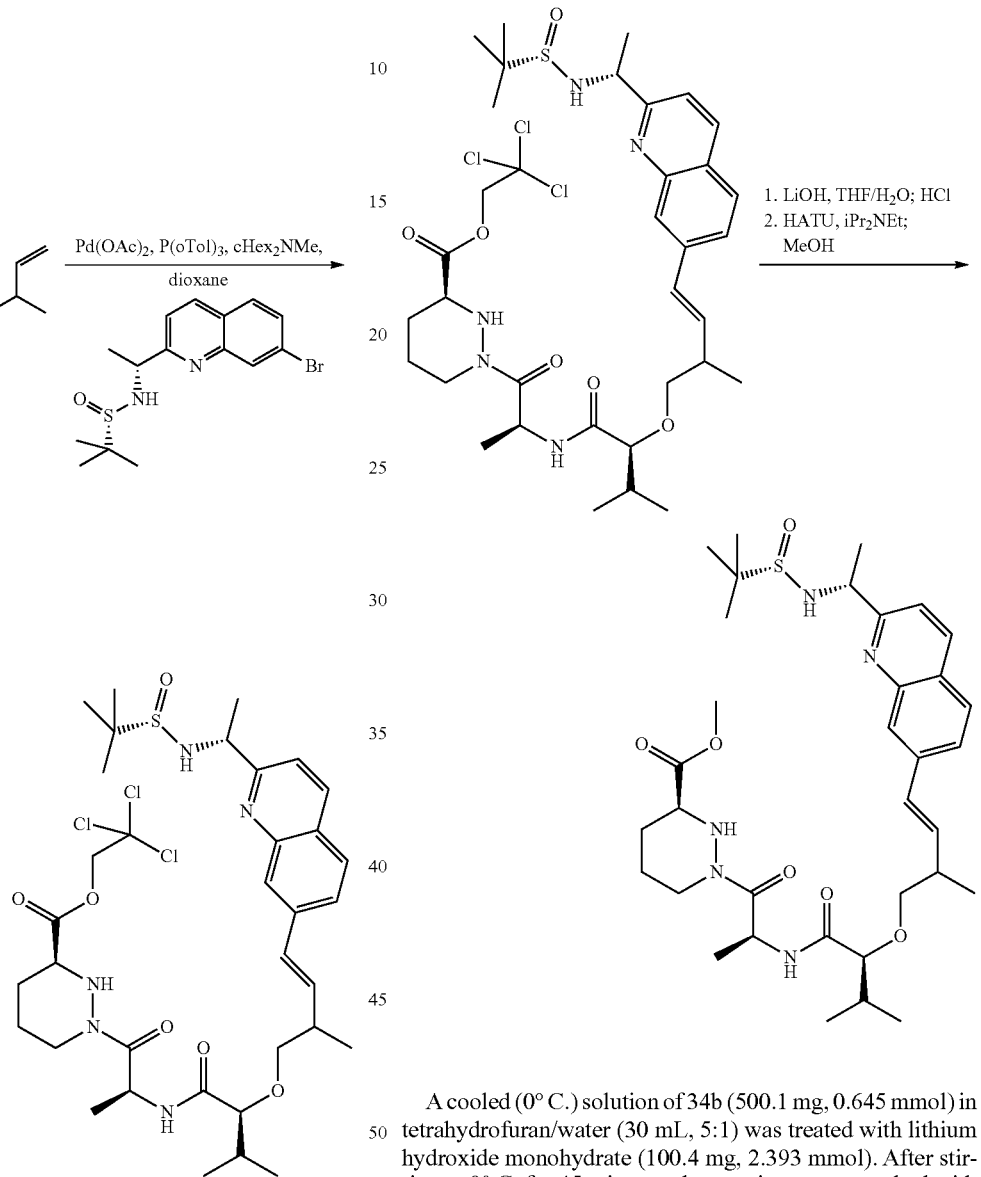

A solution of 34a (642.0 mg, 1.282 mmol), 18c (455.4 mg, 1.282 mmol), N,N-dicyclohexylmethylamine (0.83 mL, 3.846 mmol) in 1,4-dioxane (10 mL) was heated to 100° C. for 2 h. After cooling to room temperature, the volatiles were removed in vacuo and the residue was purified by silica gel chromatography using a 50 g Isolute cartridge eluted with a continuous gradient of iso-hexanes/ethyl acetate 1:0 to 0:1 to afford the title compound (500.1 mg, 50%) as an orange gum and as a 1:1 mixture of diastereoisomers. LCMS (m/z) 774.3/776.2 [M+H], Tr=3.31 min.

A cooled (0° C.) solution of 34b (500.1 mg, 0.645 mmol) in tetrahydrofuran/water (30 mL, 5:1) was treated with lithium hydroxide monohydrate (100.4 mg, 2.393 mmol). After stirring at 0° C. for 45 minutes, the reaction was quenched with hydrogen chloride solution (2 M, 1.2 mL) and the volatiles were removed in vacuo. The residual trichloroethanol was azeotroped off with toluene, toluene/methanol (2×), toluene then dried in high vacuo. The white solid was triturated with diethyl ether (2×) to provide crude (S)-1-{(S)-2-[(S)-3-methyl-2-((E)-2-methyl-4-{2-[(R)-1-((R)-2-methyl-propane-2-sulfinylamino)-ethyl]-quinolin-7-yl}-but-3-enyloxy)-butyrylamino]-propionyl}-hexahydro-pyridazine-3-carboxylic acid (LCMS (m/z) 644.4 [M+H], Tr=2.44 min) which was used without further purification. A cooled (0° C.) solution of crude (S)-1-{(S)-2-[(S)-3-methyl-2-((E)-2-methyl-4-{2-[(R)-1-((R)-2-methyl-propane-2-sulfinylamino)-ethyl]-quinolin-7-yl}-but-3-enyloxy)-butyrylamino]-propionyl}-hexahydro-pyridazine-3-carboxylic acid (0.645 mmol), N,N-diisopropylethylamine (0.56 mL, 3.225 mmol) and 4-dimethylaminopyridine (7.9 mg, 0.064 mmol) in dry tetrahydrofuran (210 mL) was treated with 2-(1H-7-azabenzotriazol-1-yl)-1,1,3,3-tetramethyl uronium hexafluorophosphate methanaminium (294.3 mg, 0.774 mmol). The reaction was allowed to slowly warm to room temperature. After 16 h, the reaction was quenched with anhydrous methanol (5 mL). The volatiles were removed in vacuo and the residue was purified by silica gel chromatography using a 50 g Isolute cartridge eluted with a continuous gradient of dichloromethane/methanol 1:0 to 9:1 to afford the title compound (482.0 mg) as an orange gum and as a 1:1 mixture of diastereoisomers. LCMS (m/z) 658.3 [M+H], Tr=2.68 min.

Compound 34d: (S)-1-{(S)-2-[(S)-3-Methyl-2-((E)-2-methyl-4-{2-[(R)-1-((R)-2-methyl-propane-2-sulfinylamino)-ethyl]-quinolin-7-yl}-but-3-enyloxy)-butyrylamino]-propionyl}-hexahydro-pyridazine-3-carboxylic acid

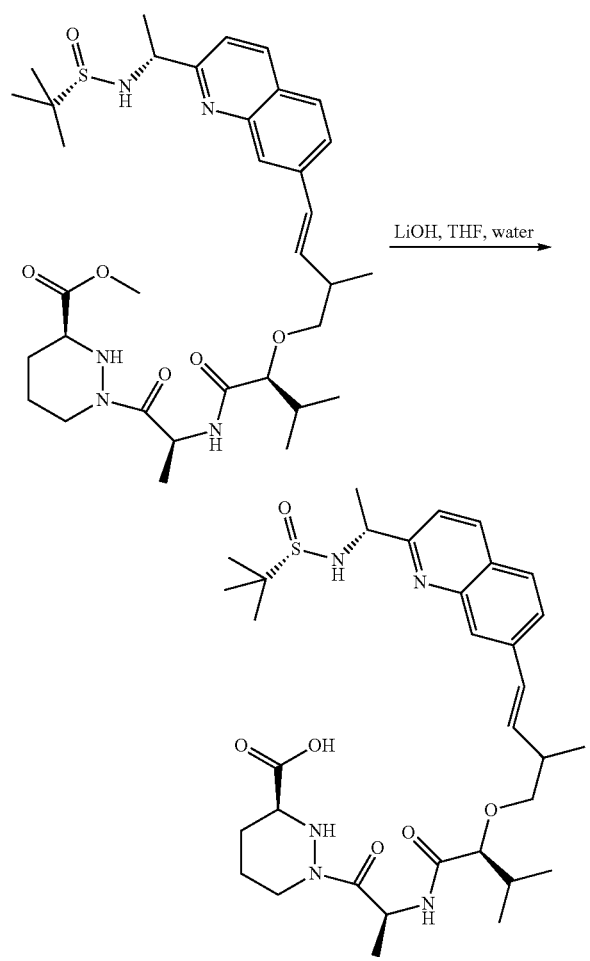

A solution of crude 34c (480 mg, 0.73 mmol) in tetrahydrofuran (15 mL) was stirred at 0° C. under nitrogen. A solution of lithium hydroxide monohydrate (92 mg, 2.2 mmol) in water (3 mL) was added and the reaction mixture was stirred at 0° C. for 1 h. 1 M Hydrochloric acid (2.2 mL, 2.2 mmol) was added and the volatiles were evaporated. The residue was co-evaporated with tetrahydrofuran/toluene (1:1, 3×) and then triturated with diethyl ether (2×) and dried to afford the title compound (0.73 mmol) as a pale yellow gum and as a 1:1 mixture of diastereoisomers. LCMS (m/z) 644.4 [M+H], Tr=2.44 min.

Compounds 34 and 35

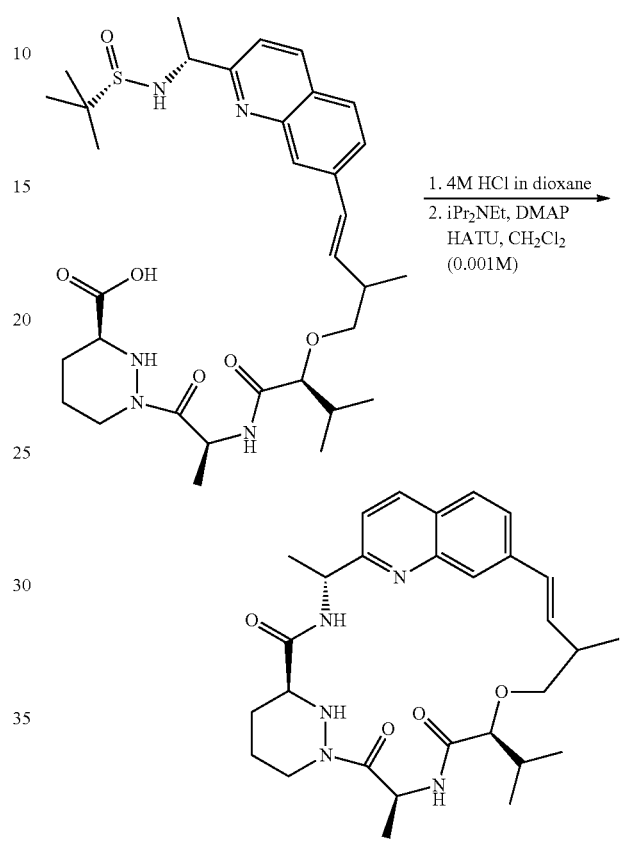

A solution of crude 34d (500 mg, 0.5 mmol) in 1,4-dioxane (10 mL) was stirred at room temperature under nitrogen. A solution of 4 M hydrogen chloride in 1,4-dioxane (1 mL) was added and the reaction mixture was stirred at room temperature for 30 minutes. The volatiles were evaporated and the residue was co-evaporated with tetrahydrofuran/toluene (1:1, 3×) and then triturated with diethyl ether (2×). The residue was dried to afford (S)-1-[(S)-2-((S)-2-{(E)-4-[2-((R)-1-amino-ethyl)-quinolin-7-yl]-2-methyl-but-3-enyloxy}-3-methyl-butyrylamino)-propionyl]-hexahydro-pyridazine-3-carboxylic acid hydrochloride as a dark yellow gum (0.5 mmol) and as a 1:1 mixture of diastereoisomers which was used crude in the next reaction. LCMS (m/z) 540.2 [M+H], Tr=1.57 min. A suspension of (S)-1-[(S)-2-((S)-2-{(E)-4-[2-((R)-1-amino-ethyl)-quinolin-7-yl]-2-methyl-but-3-enyloxy}-3-methyl-butyrylamino)-propionyl]-hexahydro-pyridazine-3-carboxylic acid hydrochloride (0.5 mmol) in dichloromethane (500 mL) was stirred at 0° C. under nitrogen. N,N-Diisopropylethylamine (387 mg, 0.52 mL, 3.0 mmol) and 4-dimethylaminopyridine (20 mg, 0.18 mmol) were added and the reaction mixture was stirred at 0° C. for 5 minutes. 2-(1H-7-Azabenzotriazol-1-yl)-11,1,3,3-tetramethyl uronium hexafluorophosphate methanaminium (380 mg, 1.0 mmol) was added and the reaction mixture was stirred at 0° C. for 2 h and then at room temperature for 72 h. The volatiles were evaporated. Ethyl acetate was added and the mixture was washed with cold 1 M hydrochloric acid, water, saturated sodium hydrogen carbonate solution, water and brine. The organic solution was filtered through a hydrophobic frit and the filtrate was evaporated. The residue was purified by silica gel chromatography using a gradient of iso-hexanes/ethyl acetate 1:3 to ethyl acetate then ethyl acetate to ethyl acetate/methanol 1:10. The residue was purified by reverse phase preparative HPLC eluting with acetonitrile (containing 0.1% formic acid)/water (containing 0.1% formic acid) 35:65. Fractions containing the pure diastereoisomers were combined and evaporated. The residues were partitioned between saturated sodium hydrogen carbonate solution and ethyl acetate. The organic layers were separated, washed with water and brine. The organic solutions were filtered through a hydrophobic frit and the filtrate was dried to afford two diastereoisomers.

Compound 34 (First Eluting) Diastereomer 1: (3 mg, 1%) as a white solid. $^1$H NMR (300 MHz, CD$_3$OD) δ 0.97 (d, J=6.7 Hz, 3H), 1.06 (d, J=6.7 Hz, 3H), 1.25 (d, J=6.9 Hz, 3H), 1.59 (d, J=6.7 Hz, 3H), 1.60-1.65 (m, 2H), 1.66 (d, J=7.1 Hz, 3H), 1.94-2.07 (m, 2H), 2.28-2.33 (m, 1H), 2.60-2.76 (m, 2H), 3.49 (d, J=8.5 Hz, 1H), 3.55-3.71 (m, 2H), 3.92 (dd, J=9.5, 4.4 Hz, 1H), 4.41-4.46 (m, 1H), 5.10 (q, J=6.5 Hz, 1H), 5.82 (q, J=7.1 Hz, 1H), 6.51 (dd, J=16.1, 5.8 Hz, 1H), 6.63 (d, J=16.1 Hz, 1H), 7.43 (d, J=8.5 Hz, 1H), 7.47 (d, J=8.5 Hz, 1H), 7.82 (d, J=8.3 Hz, 1H), 8.02 (s, 1H), 8.24 (d, J=8.5 Hz, 1H). LCMS (m/z) 522.2 [M+H], Tr=2.41 min.

Compound 35 (Second Eluting) Diastereomer 2: (3 mg, 1%) as a white solid. $^1$H NMR (300 MHz, CD$_3$OD) δ 0.93 (d, J=6.7 Hz, 3H), 1.06 (d, J=6.5 Hz, 3H), 1.07 (d, J=6.9 Hz, 3H), 1.51-1.55 (m, 1H), 1.59 (d, J=6.5 Hz, 3H), 1.68 (d, J=7.1 Hz, 3H), 1.69-1.73 (m, 1H), 1.94-1.99 (m, 2H), 2.29-2.34 (m, 1H), 2.65-2.75 (m, 2H), 3.38-3.43 (m, 2H), 3.57-3.62 (m, 1H), 3.96 (dd, J=9.0, 3.2 Hz, 1H), 4.40-4.46 (m, 1H), 5.10 (q, J=6.4 Hz, 1H), 5.84-5.89 (m, 1H), 6.38 (dd, J=16.1, 6.3 Hz, 1H), 6.65 (d, J=16.1 Hz, 1H), 7.42 (d, J=8.5 Hz, 1H), 7.46 (dd, J=8.5, 1.6 Hz, 1H), 7.82 (d, J=8.3 Hz, 1H), 8.05 (br s, 1H), 8.24 (d, J=8.5 Hz, 1H). LCMS (m/z) 522.2 [M+H], Tr=2.38 min.

Example 36

Compound 36

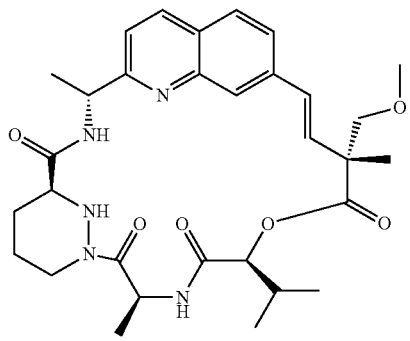 [SMILES: COC[C@@]1(C)/C=C/c2ccc3ccc(nc3c2)[C@@H](C)NC(=O)[C@@H]2CCCN(N2)C(=O)[C@H](C)NC(=O)[C@H](C(C)C)OC1=O]

Compound 36a. (S)-1-[(S)-2-((S)-2-Hydroxy-3-methyl-butyrylamino)-propionyl]-hexahydro-pyridazine-3-carboxylic acid [(R)-1-(7-bromo-quinolin-2-yl)-ethyl]-amide

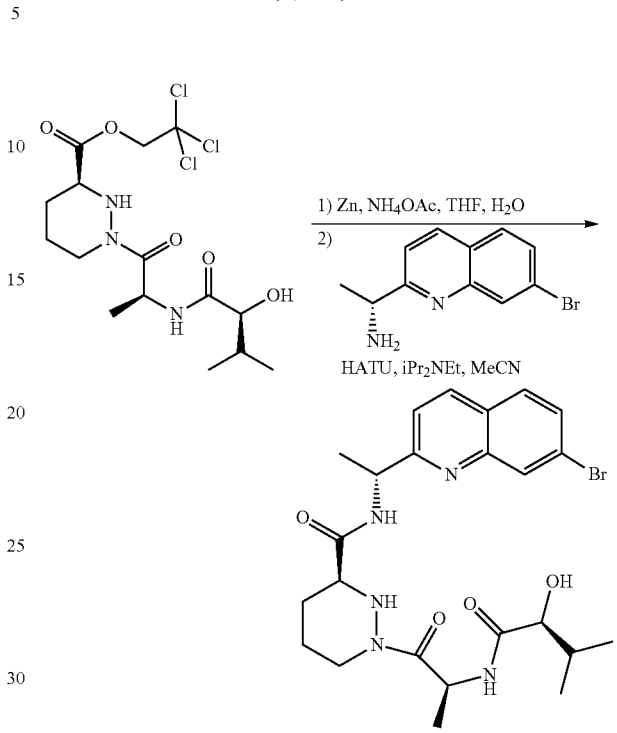

Zinc dust (1.3 g, 20.3 mmol) was added to a solution of (S)-1-[(S)-2-((S)-2-hydroxy-3-methyl-butyrylamino)-propionyl]-hexahydro-pyridazine-3-carboxylic acid 2,2,2-trichloro-ethyl ester (400 mg, 0.92 mmol) in tetrahydrofuran (20 mL). This suspension was treated with a solution of ammonium acetate (1.1 g, 13.9 mmol) in water (7 mL). After stirring at room temperature for 16 h, the zinc residues were filtered off and the volatiles were removed in vacuo. The residue was partitioned between ethyl acetate and saturated potassium hydrogen sulfate solution, the aqueous layer was extracted with ethyl acetate (2×), the organic layers were combined and the volatiles were removed in vacuo. The residual acetic acid was azeotroped off with toluene (3×10 mL) to give crude (S)-1-[(S)-2-((S)-2-hydroxy-3-methyl-butyrylamino)-propionyl]-hexahydro-pyridazine-3-carboxylic acid (280 mg, 99%) half of which (140 mg, 0.46 mmol) was combined with (R)-1-(7-bromo-quinolin-2-yl)-ethylamine hydrochloride (obtained from ASIBA Pharmatech, Inc.), (194 mg, 0.60 mmol) and N,N-diisopropylethylamine (0.400 mL, 2.3 mmol) in anhydrous acetonitrile (10 mL). This solution was then treated with 2-(1H-7-azabenzotriazol-1-yl)-1,1,3,3-tetramethyl uronium hexafluorophosphate methanaminium (227 mg, 0.60 mmol). After stirring at room temperature for 3 h, the volatiles were removed in vacuo. The residue was dissolved in ethyl acetate and subsequently washed with saturated ammonium chloride solution and sodium bicarbonate solution. The organics were combined and the volatiles were removed in vacuo. The residue was purified by silica gel chromatography using a 25 g Biotage cartridge eluted with a continuous gradient of iso-hexanes/acetone 1:0 to 1:1 to afford the title compound (136 mg, 55%) as a white solid. $^1$H NMR (300 MHz, CD$_3$OD) δ 0.83 (d, J=6.9 Hz, 3H), 0.98 (d, J=6.9 Hz, 3H), 1.38 (d, J=6.9 Hz, 3H), 1.60 (d, J=6.9 Hz, 3H), 1.65-1.75 (m, 3H), 1.87-1.96 (m, 1H), 2.02-2.12 (m, 2H), 2.87-3.00 (m, 1H), 3.55-3.62 (m, 1H), 3.81 (d, J=3.4 Hz, 1H), 4.24-4.34 (m, 1H), 5.18-5.28 (m, 1H), 5.31-5.40 (m, 1H), 7.57 (d, J=8.7 Hz, 1H), 7.69 (dd, J=8.7, 1.8 Hz, 1H), 7.85 (d, J=8.7 Hz, 1H), 8.26 (d, J=1.6 Hz, 1H), 8.33 (d, J=8.7 Hz, 1H). LCMS (m/z) 534.1, 536.1 [M+H], Tr=2.27 min.

Compound 36b.
(R)-2-Methoxymethyl-2-methyl-but-3-enoic acid

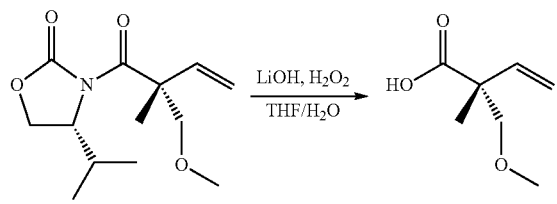

Compound 36b was prepared in the same manner as compound 29d using compound (R)-4-isopropyl-3-((R)-2-methoxymethyl-2-methyl-but-3-enoyl)-oxazolidin-2-one (the enantiomer of 58a, prepared as described in *Tet. Lett.* 2000, 41(33), 6429-6433) instead of 29c in 99% yield. ¹H NMR (300 MHz, CDCl₃) δ 1.36 (s, 3H), 3.41 (s, 3H), 3.43 (d, J=8.9 Hz, 1H), 3.61 (d, J=8.9 Hz, 1H), 5.20-5.30 (m, 2H), 6.00 (dd, J=17.6, 10.7 Hz, 1H).

Compound 36

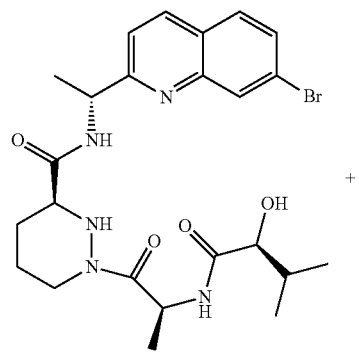

+

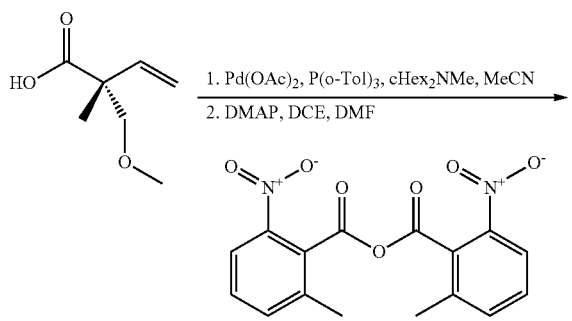

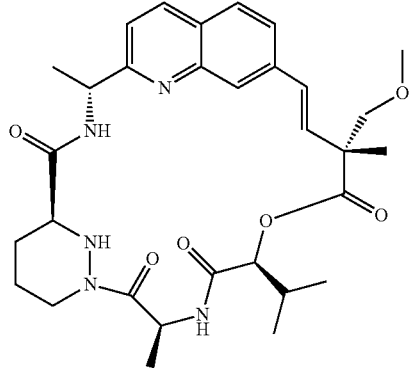

A solution of 36a (123 mg, 0.23 mmol), 36b (40 mg, 0.27 mmol), palladium(II) acetate (11 mg, 0.046 mmol), tris-(o-tolyl)phosphine (21 mg, 0.068 mmol) in anhydrous acetonitrile (3 mL) was treated with triethylamine (81 μL, 0.57 mmol). After stirring at 100° C. under microwave irradiation for 20 minutes, the reaction was cooled to room temperature and the volatiles were removed in vacuo. The residue was partitioned between dichloromethane and a saturated potassium hydrogen sulfate solution. The organics were combined and the volatiles were removed in vacuo. The residue was azeotroped with toluene (3×10 mL) to give crude (E)-(R)-4-{2-[(R)-1-({(S)-1-[(S)-2-((S)-2-hydroxy-3-methyl-butyrylamino)-1-oxo-propyl]-hexahydro-pyridazine-3-carbonyl}-amino)-ethyl]-quinolin-7-yl}-2-methoxymethyl-2-methyl-but-3-enoic acid which was dissolved in N,N-dimethylformamide (5 mL) and added via syringe pump over 6 h to a stirred slurry of 2-methyl-6-nitrobenzoic anhydride (161 mg, 0.47 mmol) and 4-dimethylaminopyridine (86 mg, 0.70 mmol) in 1,2-dichloroethane (35 mL) at 50° C. under nitrogen. The reaction was cooled down to room temperature and was subsequently washed with 5% citric acid solution and sodium bicarbonate solution. The organics were combined and the volatiles were removed in vacuo. The residue was purified by preparative reverse phase HPLC to afford the title compound (8 mg, 15%) as a white solid. ¹H NMR (300 MHz, CD₃OD) δ 1.01 (d, J=6.7 Hz, 3H), 1.06 (d, J=6.7 Hz, 3H), 1.56 (s, 3H), 1.60 (d, J=6.9 Hz, 3H), 1.68 (d, J=6.9 Hz, 3H), 1.69-1.75 (m, 1H), 1.91-1.99 (m, 1H), 2.10-2.30 (m, 2H), 3.36 (s, 2H), 3.41 (s, 3H), 3.49 (d, J=8.9 Hz, 1H), 3.58-3.68 (m, 1H), 3.80 (d, J=9.1 Hz, 1H), 4.38-4.48 (m, 1H), 5.03-5.13 (m, 1H), 5.19 (d, J=9.1 Hz, 1H), 5.74-5.85 (m, 1H), 6.41 (ABq, Δδ$_{AB}$=0.34, J$_{AB}$=16.4 Hz, 2H), 7.45 (d, J=8.5 Hz, 1H), 7.64 (d, J=8.5 Hz, 1H), 7.79 (s, 1H), 7.84 (d, J=8.5 Hz, 1H), 8.25 (d, J=8.5 Hz, 1H). LCMS (m/z) 580.2 [M+H], Tr=2.38 min.

Example 37

Compound 37

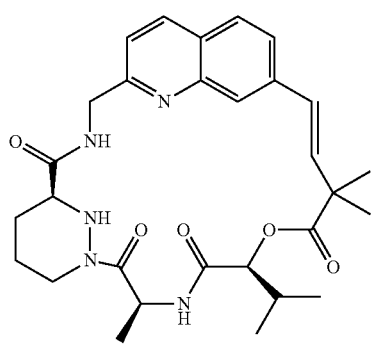 [SMILES: CC(C)[C@@H]1OC(=O)C(C)(C)/C=C/c2ccc3ccc(nc3c2)CNC(=O)[C@@H]2CCCN(N2)C(=O)[C@H](C)NC1=O]

Compound 37a. (7-Bromo-quinolin-2-ylmethyl)-(2,4-dimethoxy-benzyl)-amine

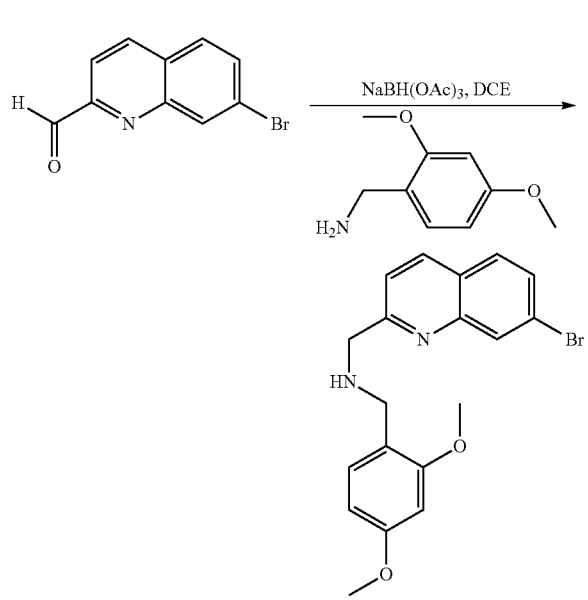

7-Bromo-quinoline-2-carbaldehyde (354 mg, 1.50 mmol, prepared as described in EP 239746) was dissolved in 1,2-dichloroethane (15 mL) and 2,4-dimethoxybenzylamine (251 mg, 225 µL, 1.50 mmol) was added and the reaction mixture stirred for 5 minutes before sodium triacetoxyborohydride (477 mg, 2.25 mmol) was added. After 3.5 h stirring the reaction mixture was quenched with saturated sodium hydrogen carbonate solution and ethyl acetate was added. The organic layer was separated and washed with sodium hydrogen carbonate and the combined aqueous layers were extracted with ethyl acetate. The organic extracts were washed with saturated brine, dried over anhydrous sodium sulfate, filtered and evaporated to give the crude, title compound as a yellow gum (571 mg) which was used without further purification. LCMS (m/z) 387.0, 389.0 [M+H], Tr=1.57 min.

Compound 37b. (7-Bromo-quinolin-2-ylmethyl)-carbamic acid tert-butyl ester

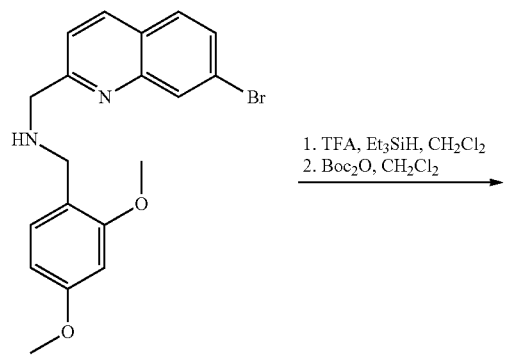

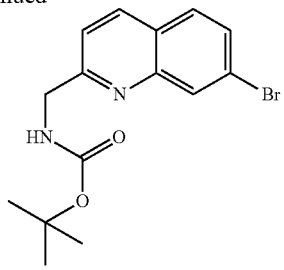

37a (290 mg, 0.75 mmol) was dissolved in dichloromethane (8 mL) and triethylsilane (1.6 mL) and trifluoroacetic acid (8 mL) were added. The reaction mixture was heated to reflux and stirred for 20 h and then allowed to cool. The mixture was evaporated and purified by SCX cartridge eluting with methanol and then methanolic ammonia and the basic fraction collected and evaporated. The residue was dissolved in dichloromethane (8 mL) and di-tert-butyl dicarbonate (245 mg, 1.13 mmol) added and the reaction mixture stirred for 17 h. Diluted with dichloromethane and washed with saturated sodium hydrogen carbonate solution (2×), the aqueous layer was back-extracted with dichloromethane and the combined organic extracts passed through a hydrophobic frit and evaporated. The residue was purified by silica gel chromatography using a gradient of iso-hexanes/ethyl acetate 1:0 to 4:1 to afford the title compound (150 mg, 59%) as a pale yellow solid. $^1$H NMR (300 MHz, CDCl$_3$) δ 1.52 (s, 9H), 4.65 (d, J=4.9 Hz, 2H), 5.90 (br s, 1H), 7.39 (d, J=8.5 Hz, 2H), 7.63 (dd, J=8.5, 1.9 Hz, 2H), 7.72 (d, J=8.5 HZ, 1H), 8.11 (d, J=8.5 Hz, 1H), 8.28 (s, 1H). LCMS (m/z) 337.0, 339.0 [M+H], Tr=2.79 min.

Compound 37c. (E)-4-[2-(tert-Butoxycarbonylamino-methyl)-quinolin-7-yl]-2,2-dimethyl-but-3-enoic acid methyl ester

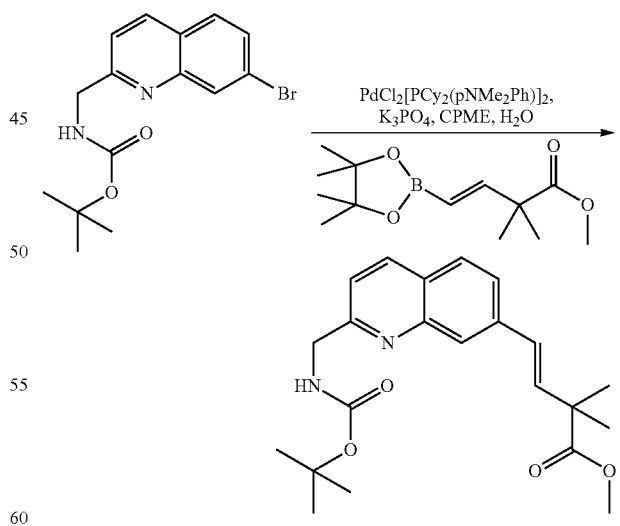

37b (296 mg, 0.878 mmol), 22d (256 mg, 1.01 mmol), bis[(dicyclohexyl)(4-dimethylaminophenyl)phosphine]palladium(II) chloride (36 mg, 0.044 mmol) and potassium phosphate tribasic (558 mg, 2.63 mmol) were suspended in cyclopentyl methyl ether (3 mL) and water (1.5 mL). The reaction mixture was stirred and heated at 80° C. for 3 h under nitrogen. The reaction was allowed to cool and diluted with ethyl acetate and washed with water (2×) and brine, dried over anhydrous sodium sulfate, filtered and evaporated. The residue was purified by silica gel chromatography using a gradient of iso-hexanes/ethyl acetate 1:0 to 7:3 to afford the title compound (257 mg, 76%) as a yellow solid. $^1$H NMR (300 MHz, CDCl$_3$) δ 1.49 (s, 6H), 1.52 (s, 9H), 3.75 (s, 3H), 4.63 (d, J=4.9 Hz, 2H), 5.96 (br s, 1H), 6.64 (s, 2H), 7.32 (d, J=8.5 Hz, 1H), 7.63 (dd, J=8.5, 1.3 Hz, 1H), 7.75 (d, J=8.5 Hz, 1H), 8.00 (s, 1H), 8.08 (d, J=8.5 Hz, 1H). LCMS (m/z) 385.1 [M+H], Tr=2.64 min.

Compound 37d. (E)-4-{2-[({(S)-1-[(S)-2-((S)-2-Hydroxy-3-methyl-butyrylamino)-propionyl]-hexahydro-pyridazine-3-carbonyl}-amino)-methyl]-quinolin-7-yl}-2,2-dimethyl-but-3-enoic acid methyl ester matography using a gradient of ethyl acetate/methanol 1:0 to 19:1 to afford the title compound (95 mg, 50%) as an off-white solid. $^1$H NMR (300 MHz, CDCl$_3$) δ 0.84 (d, J=6.9 Hz, 3H), 1.00 (d, J=6.9 Hz, 3H), 1.42 (d, J=6.9 Hz, 3H), 1.48 (s, 6H), 1.65-1.76 (m, 2H), 1.88-1.98 (m, 1H), 2.06-2.14 (m, 1H), 2.19-2.29 (m, 1H), 2.73-2.83 (m, 1H), 3.45-3.56 (m, 1H), 3.73 (s, 3H), 3.95 (d, J=3.1 Hz, 1H), 3.99 (d, J=11.6 Hz, 1H), 4.42-4.52 (m, 1H), 4.69-4.76 (m, 2H), 5.41-5.51 (m, 1H), 6.61-6.66 (m, 1H), 6.74 (d, J=16.3 Hz, 1H), 7.24-7.31 (m, 1H), 7.62-7.69 (m, 1H), 7.71-7.78 (m, 1H), 7.95-8.10 (m, 2H). LCMS (m/z) 568.3 [M+H], Tr=2.10 min.

Compound 37e. (E)-4-{2-[({(S)-1-[(S)-2-((S)-2-Hydroxy-3-methyl-butyrylamino)-propionyl]-hexahydro-pyridazine-3-carbonyl}-amino)-methyl]-quinolin-7-yl}-2,2-dimethyl-but-3-enoic acid

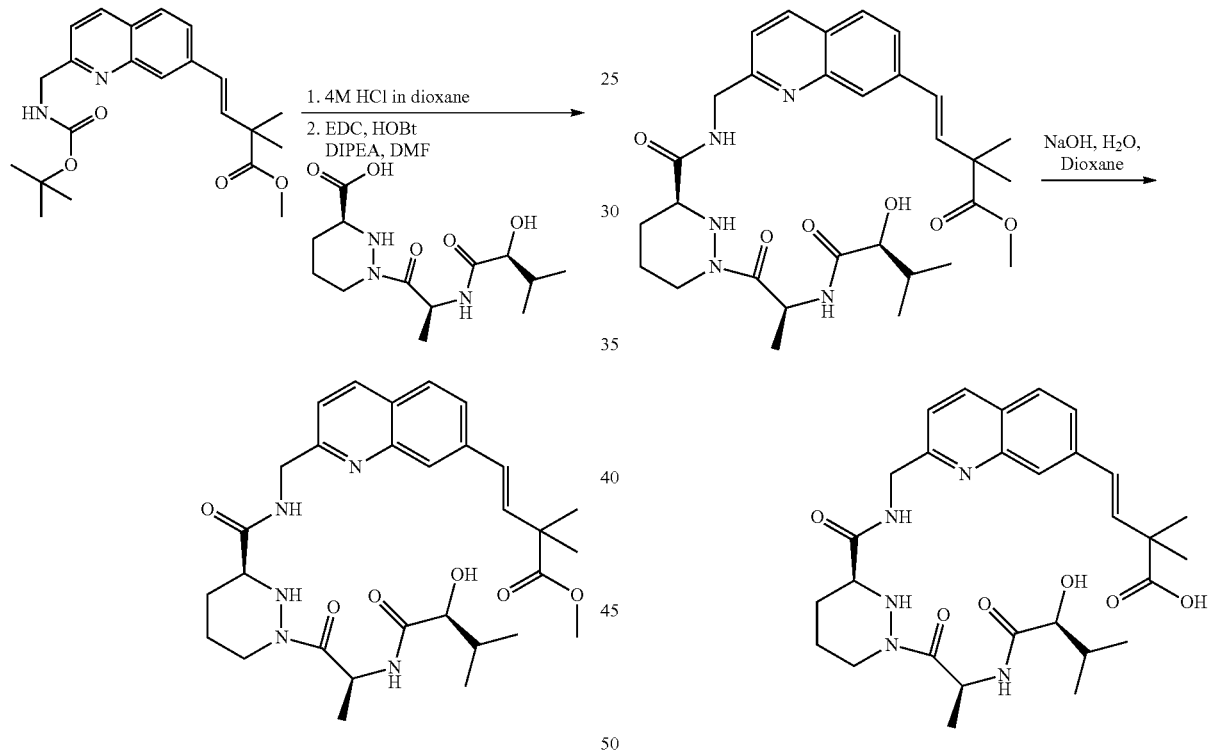

37c (128 mg, 0.333 mmol) was suspended in 4 M hydrogen chloride in 1,4-dioxane (3.3 mL) and the reaction mixture stirred for 2.5 h and then evaporated. To the residue was added a solution of 29a (105 mg, 0.350 mmol) in N,N-dimethylformamide (7 mL) followed by N,N-diisopropylethylamine (86 mg, 116 μL, 0.666 mmol). To the stirred solution was added 1-hydroxybenzotriazole hydrate (63 mg, 0.466 mmol) and N-(3 dimethylaminopropyl)-N'-ethylcarbodiimide hydrochloride (89 mg, 0.466 mmol) and the reaction mixture stirred for 16 h. The reaction mixture was diluted with ethyl acetate and washed successively with saturated sodium bicarbonate solution, water, saturated ammonium chloride solution, water and then brine, dried over anhydrous sodium sulfate, filtered and evaporated. The residue was purified by silica gel chro- A stirred mixture of 37d (95 mg, 0.167 mmol) and NaOH (1 M, 1.34 mL, 1.34 mmol) in 1,4-dioxane (8 mL) was heated at reflux for 70 minutes and then allowed to cool. The reaction mixture was acidified to pH 4 with hydrochloric acid (2 M) and evaporated. The residue was purified by reverse phase preparative HPLC using a gradient of acetonitrile/water 1:19 to 7:3 to afford the title compound (43 mg, 47%) as a white solid. $^1$H NMR (300 MHz, CDCl$_3$) δ 0.82 (d, J=6.8 Hz, 3H), 0.93-1.00 (m, 3H), 1.38 (d, J=8.2 Hz, 3H), 1.49 (s, 6H), 1.58-1.76 (m, 2H), 1.81-1.94 (m, 1H), 1.99-2.12 (m, 1H), 2.16-2.25 (m, 1H), 2.67-2.79 (m, 1H), 3.41-3.51 (m, 1H), 3.92-4.00 (m, 1H), 4.01-4.08 (d, J=11.6 Hz, 1H), 4.40-4.54 (m, 1H), 4.74 (d, J=4.5 Hz, 2H), 5.41-5.52 (m, 1H), 6.63-6.76 (m, 2H), 7.26-7.32 (m, 1H), 7.33-7.39 (m, 1H), 7.55-7.64 (m, 1H), 7.75 (d, J=8.5 Hz, 1H), 8.04-8.14 (m, 2H). LCMS (m/z) 554.2 [M+H], Tr=1.77 min.

Compound 37

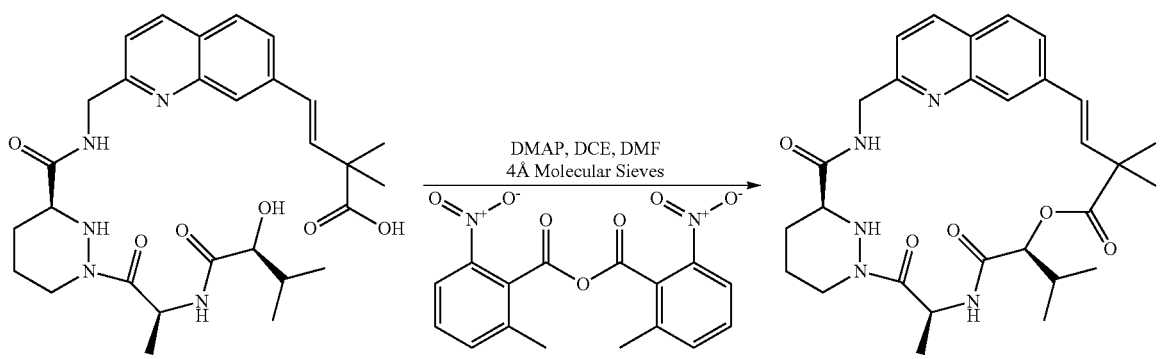

To a stirred slurry of 2-methyl-6-nitrobenzoic acid (134 mg, 0.388 mmol), 4-(dimethylamino)pyridine (71 mg, 0.583 mmol) and powdered 4 Å molecular sieves (~1 g) in 1,2-dichloroethane (26 mL) under nitrogen at 50° C. was added a solution of 37e (43 mg, 0.078 mmol) in N,N-dimethylformamide (3 mL) over 4 h via syringe pump. The flask containing the original acid was washed with further N,N-dimethylformamide (1 mL) and this was added to the reaction mixture over 10 minutes. After the end of addition, the reaction mixture was stirred at 50° C. for 3 h and then allowed to cool. The mixture was filtered through Celite and the filtrate washed successively with ice-cold saturated ammonium chloride solution, ice-cold saturated sodium bicarbonate solution and saturated brine, dried over anhydrous sodium sulfate, filtered and evaporated. The residue was purified by reverse phase preparative HPLC using a gradient of acetonitrile/water 1:4 to 4:1 modified with 0.1% formic acid and the product triturated with ether to afford the title compound (6.4 mg, 15%) as a white solid. $^1$H NMR (300 MHz, CD$_3$OD) δ 1.02 (d, J=6.7 Hz, 3H), 1.06 (d, J=6.9 Hz, 3H), 1.46 (s, 3H), 1.48 (d, J=7.3 Hz, 3H), 1.54 (s, 3H), 1.55-1.79 (m, 2H), 1.94-2.04 (m, 1H), 2.16-2.30 (m, 1H), 2.30-2.40 (m, 1H), 2.71-2.83 (m, 1H), 3.53-3.60 (m, 1H), 4.42-4.51 (m, 1H), 4.67, 4.75 (ABq, J$_{AB}$=18.4 Hz, 2H), 5.20 (d, J=8.9 Hz, 2H), 5.89 (q, J=7.2, 1H), 6.44 (d, J=16.2 Hz, 1H), 6.69 (d, J=16.2 Hz, 1H), 7.40 (d, J=8.5 Hz, 1H), 7.56 (d, J=8.5, 1.3 Hz, 1H), 7.85 (d, J=8.5 Hz, 1H), 7.92 (s, 1H), 8.23 (d, J=8.5 Hz, 1H). LCMS (m/z) 536.2 [M+H], Tr=2.47 min.

Example 38

Compound 38

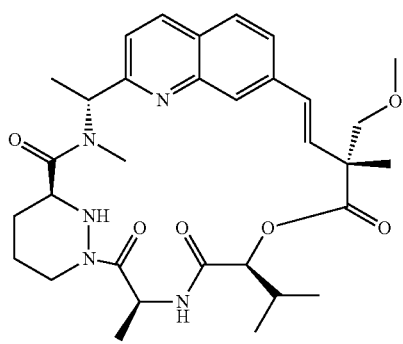 [SMILES: COC[C@@]1(C)/C=C/c2ccc3ccc(nc3c2)[C@@H](C)N(C)C(=O)[C@@H]2CCCN(N2)C(=O)[C@H](C)NC(=O)[C@H](C(C)C)OC1=O]

Compound 38a (R)-2-Methyl-propane-2-sulfinic acid [1-(7-bromo-quinolin-2-yl)-eth-(E)-ylidene]-amide

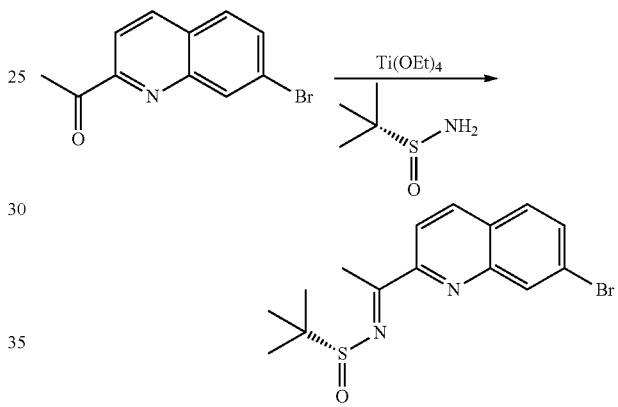

To a solution of 18a (1.42 g, 5.68 mmol) in THF (28 mL) was added titanium (IV) ethoxide (2.6 g, 2.35 mL, 11.4 mmol, tech. grade) followed by (R)-(+)-2-methyl-propanesulfinimide (825 mg, 6.82 mmol). The reaction mixture was stirred at 60° C. under nitrogen for 6 hours and allowed to cool. Brine was added followed by ethyl acetate and the suspension filtered through celite and the filter pad was washed with ethyl acetate. The ethyl acetate layer was separated, dried over sodium sulfate, filtered and evaporated. The residue was purified by silica gel chromatography using a gradient of isohexane/ethyl acetate 9:1 to 3:1 to give the title compound (448 mg, 22%) as an orange solid. $^1$H NMR (300 MHz, CDCl$_3$) δ 1.38 (s, 9H), 2.99 (s, 3H), 7.71 (m, 2H), 8.16 (d, J=8.6 Hz, 1H), 8.24 (d, J=8.6 Hz, 1H), 8.37 (s, 1H). LCMS (m/z) 352.9/354.9 [M+H], Tr 3.14 minutes.

Compound 38b (R)-2-Methyl-propane-2-sulfinic acid [(R)-1-(7-bromo-quinolin-2-yl)-ethyl]-amide

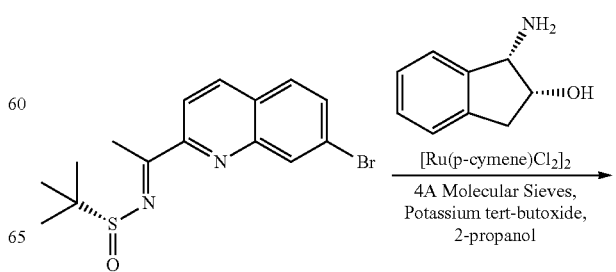

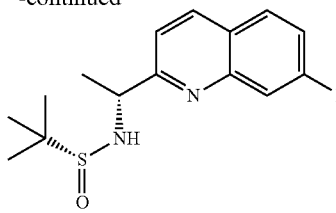

A mixture of (1S,2R)-(−)-cis-1-amino-2-indanol (19 mg, 0.13 mmol), [Ru(p-cymen) Cl₂]₂ (39 mg, 0.064 mmol) and powdered 4 Å Molecular Sieves (0.7 g) was suspended in anhydrous 2-propanol (3 mL) and stirred under nitrogen. The suspension was heated at 90° C. for 30 minutes. The reaction mixture was cooled to 40° C. and a solution 38a (448 mg, 1.27 mmol) in 2-propanol (9 mL) was added followed by a solution of potassium tert-butoxide (36 mg, 0.32 mmol) in 2-propanol (3 mL). The reaction mixture was stirred for 2 hours at 40° C. and then allowed to cool. The mixture was poured directly onto a silica gel cartridge and eluted with ethyl acetate. After concentration the residue was further purified by silica gel chromatography using a gradient of iso-hexane/ethyl acetate 1:1 to 0:1 to give the title compound (287 mg, 64%) as a brown gum. ¹H NMR (300 MHz, CDCl₃) δ 1.33 (s, 9H), 1.60 (d, J=6.7 Hz, 3H), 4.80 (m, 1H), 5.42 (br d, J=4.2 Hz, 1H), 7.42 (d, J=8.5 Hz, 1H), 7.62 (dd, J=8.5, 1.2 Hz, 1H), 7.68 (d, J=8.7 Hz, 1H), 8.12 (d, J=8.7 Hz, 1H), 8.25 (s, 1H). LCMS (m/z) 354.9/356.8 [M+H], Tr 2.49 min Compound 38c. 2-Methyl-propane-2-sulfinic acid (R)-[(R)-1-(7-bromo-quinolin-2-yl)-ethyl]-methyl-amide

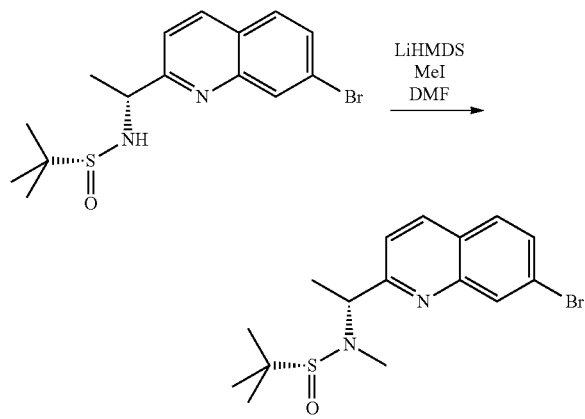

A cooled (−20° C.) solution of 38b (100 mg, 0.28 mmol, same as 18c) in N,N-dimethylformamide (5 mL) was treated with lithium bis(trimethylsilyl)amide (0.28 mL, 0.28 mmol, 1 M in hexane). After stirring at this temperature for 1 h, iodomethane (0.035 mL, 0.56 mmol) was added and the temperature raised to room temperature. After stirring at room temperature for 1 h, the reaction was quenched by addition of water (10 mL). The mixture was extracted with diethyl ether (3×20 mL). The organics were combined and the volatiles were removed in vacuo. The residue was purified by silica gel chromatography using a 10 g Biotage cartridge eluted with a continuous gradient of iso-hexanes/ethyl acetate 1:0 to 1:1 to afford the title compound (149 mg, 62%) as a white solid. ¹H NMR (300 MHz, CDCl₃) δ 1.25 (s, 9H), 1.74 (d, J=6.9 Hz, 3H), 2.53 (s, 3H), 4.81 (q, J=6.9 Hz, 1H), 7.55-7.70 (m, 3H), 8.11 (d, J=8.5 Hz, 1H), 8.27 (s, 1H). LCMS (m/z) 369.0, 371.0 [M+H], Tr=2.91 min.

Compound 38d. (S)-1-[(S)-2-((S)-2-Hydroxy-3-methyl-butyrylamino)-propionyl]-hexahydro-pyridazine-3-carboxylic acid [(R)-1-(7-bromo-quinolin-2-yl)-ethyl]-methyl-amide

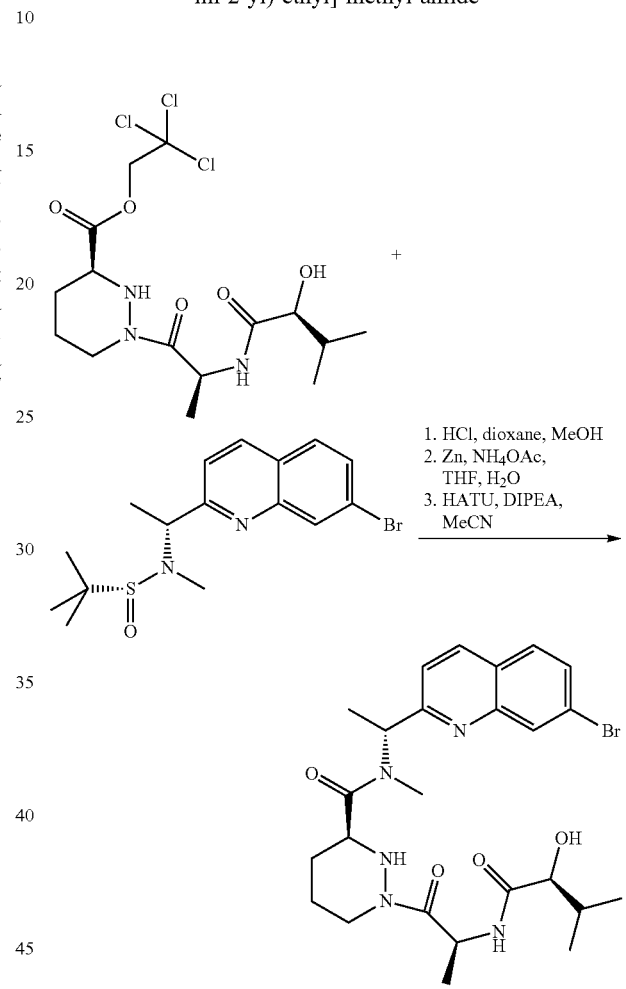

A solution of 38c (450 mg, 1.22 mmol) in methanol (10 mL) was treated with hydrochloric acid in 1,4-dioxane (4 M, 5 mL). After stirring at room temperature for 2 h, the volatiles were removed in vacuo. The residual solvent was azeotroped off with toluene (3×10 mL) to give crude [(R)-1-(7-bromo-quinolin-2-yl)-ethyl]-methyl-amine hydrochloride.

Zinc dust (1.30 g, 20.32 mmol) was added to a solution of (S)-1-[(S)-2-((S)-2-hydroxy-3-methyl-butyrylamino)-propionyl]-hexahydro-pyridazine-3-carboxylic acid 2,2,2-trichloro-ethyl ester (400 mg, 0.92 mmol) in tetrahydrofuran (20 mL). This suspension was treated with a solution of ammonium acetate (1.10 g, 13.9 mmol) in water (7 mL). After stirring at room temperature for 16 h, zinc residues were filtered off and the volatiles were removed in vacuo. The residue was partitioned between ethyl acetate and saturated potassium hydrogen sulfate solution, the aqueous layer was extracted with ethyl acetate (2×), the organic layers were combined and the volatiles were removed in vacuo. The residual acetic acid was azeotroped off with toluene (3×10 mL) to give crude (S)-1-[(S)-2-((S)-2-hydroxy-3-methyl-butyrylamino)-propionyl]-hexahydro-pyridazine-3-carboxylic acid which was combined with crude [(R)-1-(7-bromo-quinolin-2-yl)-ethyl]-methyl-amine hydrochloride in anhydrous acetonitrile (15 mL) and N,N-diisopropylethylamine (0.801 mL, 4.60 mmol). This solution was then treated with 2-(1H-7-azabenzotriazol-1-yl)-1,1,3,3-tetramethyl uronium hexafluorophosphate methanaminium (464 mg, 1.22 mmol). After stirring at room temperature for 2 h, the volatiles were removed in vacuo. The residue was dissolved in ethyl acetate and subsequently washed with saturated ammonium chloride solution and sodium bicarbonate solution. The organics were combined and the volatiles were removed in vacuo. The residue was purified by silica gel chromatography using a 25 g Biotage cartridge eluted with a continuous gradient of iso-hexanes/acetone 1:0 to 0:1 to afford the title compound (318 mg, 58%) as a white solid. $^1$H NMR (300 MHz, CD$_3$OD) δ 0.85 (d, J=6.9 Hz, 3H), 1.00 (d, J=6.9 Hz, 3H), 1.33 (d, J=6.9 Hz, 3H), 1.69 (d, J=6.9 Hz, 3H), 1.72-2.15 (m, 6H), 2.98 (s, 3H), 2.85-2.95 (m, 1H), 3.80-3.90 (m, 1H), 4.30-4.40 (m, 1H), 5.25-5.35 (m, 1H), 5.95-6.10 (m, 1H), 7.45-7.78 (m, 1H), 7.65-7.72 (m, 1H), 7.80-7.90 (m, 1H), 8.18-8-38 (m, 2H). LCMS (m/z) 548.1, 550.1 [M+H], Tr=2.60 min.

Compound 38

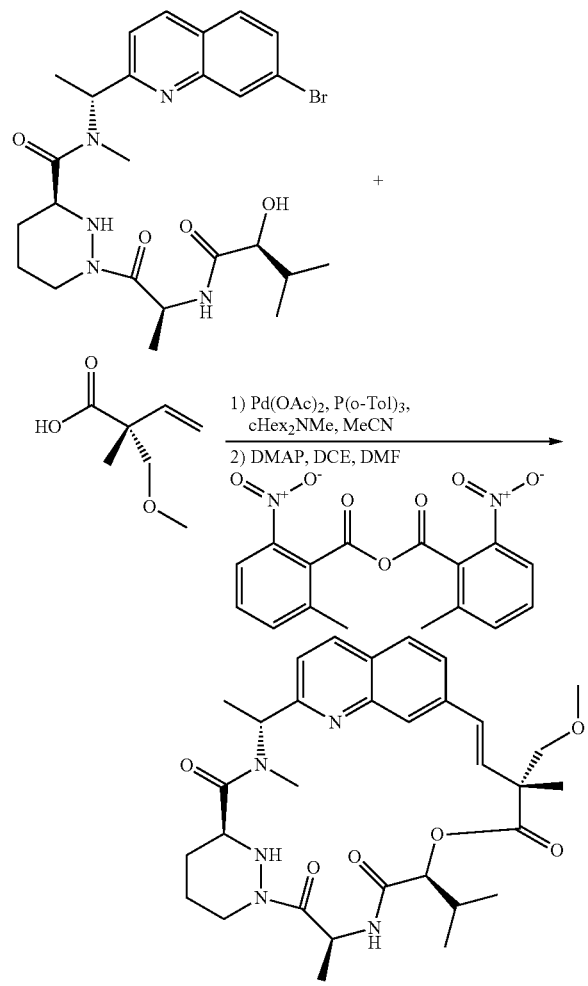

Compound 38 was prepared in the same manner as compound 36 using 38d instead of (36a (123 mg, 0.23 mmol) in 4% yield. $^1$H NMR (300 MHz, CD$_3$OD) δ 1.00 (d, J=6.7 Hz, 3H), 1.01 (d, J=6.7 Hz, 3H), 1.52-1.59 (m, 6H), 1.73 (d, J=7.4 Hz, 3H), 1.76-1.88 (m, 2H), 1.89-1.99 (m, 2H), 2.09-2.21 (m, 1H), 2.71-2.84 (m, 1H), 3.29 (s, 3H), 3.40 (s, 3H), 3.44 (d, J=8.7 Hz, 1H), 3.79 (d, J=8.9 Hz, 1H), 4.13-4.22 (m, 1H), 4.39-4.47 (m, 1H), 5.05 (d, J=9.1 Hz, 1H), 5.83-5.97 (m, 2H), 6.38 (ABq, Δδ$_{AB}$=0.24, J$_{AB}$=16.5 Hz, 2H), 7.45 (d, J=8.5 Hz, 1H), 7.64-7.73 (m, 2H), 7.79 (d, J=8.5 Hz, 1H), 8.19 (d, J=8.5 Hz, 1H). LCMS (m/z) 594.2 [M+H], Tr=2.48 min.

Examples 39 and 40

Compound 39 and 40

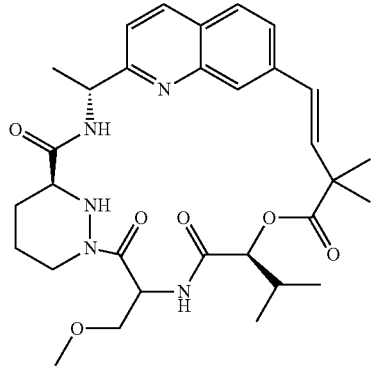 [SMILES: COCC1NC(=O)[C@H](C(C)C)OC(=O)C(C)(C)/C=C/c2ccc3ccc(nc3c2)[C@@H](C)NC(=O)[C@@H]2CCCN(N2)C1=O]

Compound 39a. [(R)-1-(7-Bromo-quinolin-2-yl)-ethyl]-carbamic acid tert-butyl ester

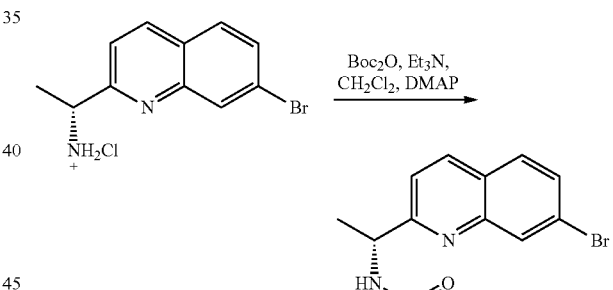

To a solution of (R)-1-(7-bromo-quinolin-2-yl)-ethylamine hydrochloride (obtained from ASIBA Pharmatech Inc.), (3.5 g, 12.2 mmol) in anhydrous dichloromethane at 0° C. and under an atmosphere of nitrogen was added triethylamine (5.1 mL, 36.5 mmol), 4-dimethylaminopyridine (297 mg, 2.4 mmol) and di-tert-butyl dicarbonate (4.0 g, 18.3 mmol). The reaction was warmed to room temperature and stirred for 2 h. The reaction was cooled to 0° C. and quenched with hydrochloric acid (1 M). The organic layer was separated, washed with brine, dried through a hydrophobic frit and concentrated in vacuo. The product was purified by silica gel chromatography using iso-hexanes/ethyl acetate 6:1 to afford the title compound (3 g, 70%) as a yellow solid. $^1$H NMR (300 MHz, CDCl$_3$) δ 1.49 (s, 9H), 1.55 (d, J=6.9 Hz, 3H), 4.93-5.10 (m, 1H), 6.01-6.20 (m, 1H), 7.38 (d, J=8.5 Hz, 1H), 7.62

(dd, J=8.7, 1.8 Hz, 1H), 7.69 (d, J=8.7 Hz, 1H), 8.11 (d, J=8.5 Hz, 1H), 8.29 (s, 1H). LCMS (m/z) 353.0 [M+H], Tr=3.02 min.

Compound 39b. (E)-4-[2-((R)-1-tert-Butoxycarbonylamino-ethyl)-quinolin-7-yl]-2,2-dimethyl-but-3-enoic acid methyl ester

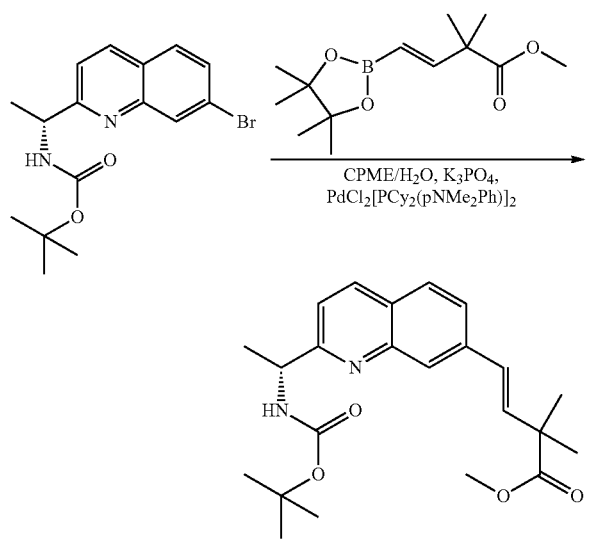

To a solution 39a (1 g, 2.86 mmol) in cyclopentylmethyl ether (14 mL) and water (7 mL), at room temperature, was added 22d (840 mg, 3.43 mmol), potassium phosphate tribasic (1.8 g, 8.57 mmol) and bis[(dicyclohexyl)(4-dimethylaminophenyl)phosphine]palladium(II) chloride (116 mg, 0.14 mmol). The reaction was heated to 80° C. for 2 h. The reaction was cooled, diluted with ethyl acetate and washed with brine (2×). The organic layer was dried through a hydrophobic frit and concentrated in vacuo. The product was purified by silica gel chromatography using iso-hexanes/ethyl acetate 2:1 to afford the title compound (1.1 g, 96%) as a viscous oil. $^1$H NMR (300 MHz, CDCl$_3$) δ 1.43-1.52 (m, 15H), 1.56 (d, J=6.7 Hz, 3H), 3.75 (s, 3H), 4.92-5.09 (m, 1H), 6.16-6.32 (m, 1H), 6.64 (s, 2H), 7.30 (d, J=8.5 Hz, 1H), 7.62 (dd, J=8.5, 1.6 Hz, 1H), 7.75 (d, J=8.5 Hz, 1H), 8.02 (s, 1H), 8.08 (d, J=8.5 Hz, 1H). LCMS (m/z) 399.3 [M+H], Tr=2.75 min.

Compound 39c. (E)-4-[2-((R)-1-tert-Butoxycarbonylamino-ethyl)-quinolin-7-yl]-2,2-dimethyl-but-3-enoic acid

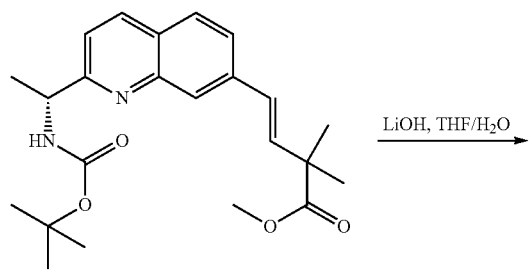

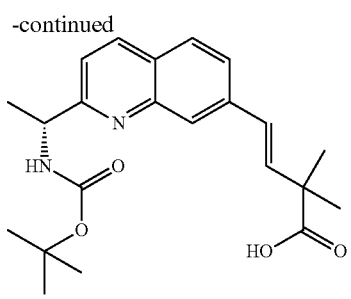

To a solution of 39b (1.1 g, 2.76 mmol) in tetrahydrofuran (24 mL) and water (5 mL) was added lithium hydroxide monohydrate (580 mg, 13.8 mmol). The reaction was heated to 40° C. for 20 h. The reaction was cooled to room temperature and acidified to pH 5 with aqueous hydrochloric acid (2 M). The mixture was evaporated to dryness and dichloromethane and acetonitrile added. This suspension was filtered through a hydrophobic frit and the filtrate concentrated in vacuo to afford the title compound (800 mg, 76%) as a yellow solid. $^1$H NMR (300 MHz, CDCl$_3$) δ 1.46 (s, 9H), 1.51 (s, 6H), 1.56 (d, J=6.7 Hz, 3H), 4.91-5.14 (m, 1H), 6.35-6.52 (m, 1H), 6.66, 6.72 (ABq, J=16.2 Hz, 2H), 7.31 (d, J=8.5 Hz, 1H), 7.57 (d, J=8.0 Hz, 1H), 7.70 (d, J=8.3 Hz, 1H), 7.99-8.17 (m, 2H). LCMS (m/z) 385.3 [M+H], Tr=2.21 min.

Compound 39d: (S)-1-(2-tert-Butoxycarbonylamino-3-methoxy-propionyl)-hexahydro-pyridazine-3-carboxylic acid 2,2,2-trichloro-ethyl ester

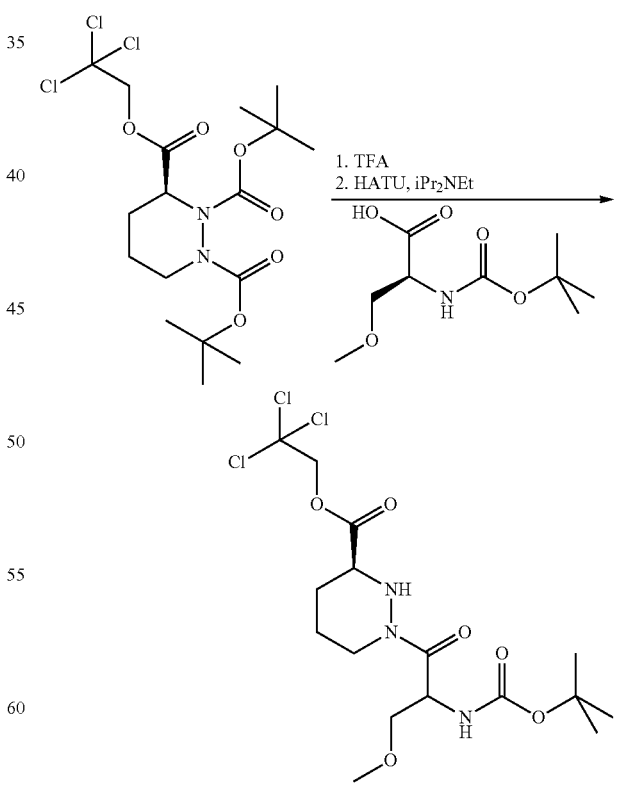

Compound 39d was prepared (starting from bis-N-Boc TCE ester prepared as described in *Angew. Chem. Intl. Ed. English,* 1999, 38, 2443.) in the same manner as intermediate 1d using N-α-Boc-O-methyl serine (1 g, 4.56 mmol) instead of L-N-Boc-alanine to afford the title compound as a clear viscous oil (1.5 g, 71%) and as a 1:1 mixture of two diastereoisomers. LCMS (m/z) 462.7 [M+H], Tr=2.71 min.

Compound 39e. (S)-1-[2-((S)-2-Hydroxy-3-methyl-butyrylamino)-3-methoxy-propionyl]-hexahydro-pyridazine-3-carboxylic acid 2,2,2-trichloro-ethyl ester

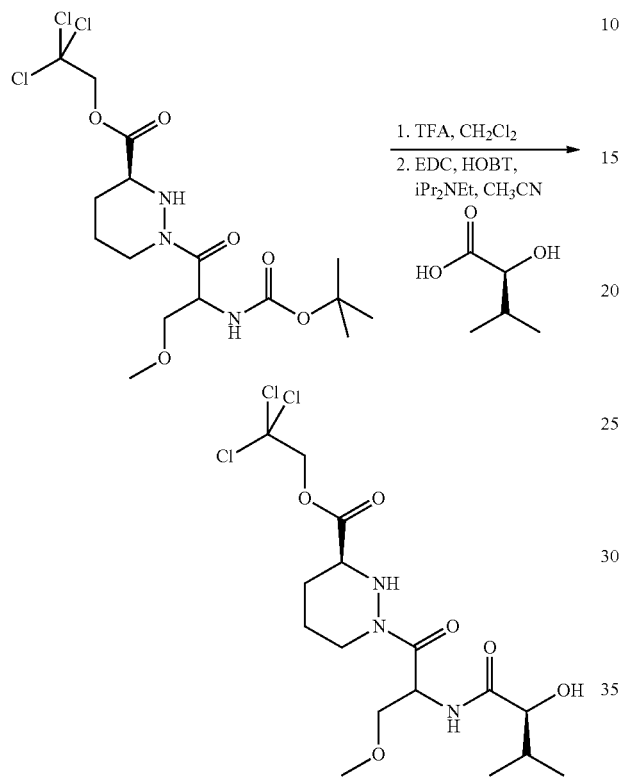

To a solution of 39d (1.0 g, 2.16 mmol) in anhydrous dichloromethane (7 mL) at room temperature and under an atmosphere of nitrogen was added trifluoroacetic acid (1.7 mL). The reaction was stirred at room temperature for 1.5 h and concentrated in vacuo. The ensuing residue was co-evaporated from toluene (3×) to yield a viscous light brown oil. This was dissolved in anhydrous acetonitrile (22 mL) and cooled to 0° C. before adding (S)-2-hydroxy-3-methyl-butyric acid (255 mg, 2.2 mmol), hydroxybenzotriazole monohydrate (497 mg, 3.3 mmol), 1-ethyl-3-(3-dimethylaminopropyl)carbodiimide (623 mg, 3.3 mmol) and N,N-diisopropylethylamine (1.9 mL, 10.8 mmol). The reaction mixture was warmed to ambient temperature and stirred for 72 h. The reaction was diluted with ethyl acetate and washed with hydrochloric acid (1 M), saturated sodium bicarbonate and brine. The organic layer was dried through a hydrophobic frit and concentrated in vacuo. The residue was purified by silica gel chromatography using iso-hexanes/acetone 3:2 to give the title compound (750 mg, 75% over 2 steps) as a clear viscous oil and as a 1:1 mixture of two diastereoisomers. LCMS (m/z) 462.0 [M+H], Tr=2.24 min.

Compound 39f. (S)-1-[2-((S)-2-{(E)-4-[2-((R)-1-tert-Butoxycarbonylamino-ethyl)-quinolin-7-yl]-2,2-dimethyl-but-3-enoyloxy}-3-methyl-butyrylamino)-3-methoxy-propionyl]-hexahydro-pyridazine-3-carboxylic acid 2,2,2-trichloro ethyl ester

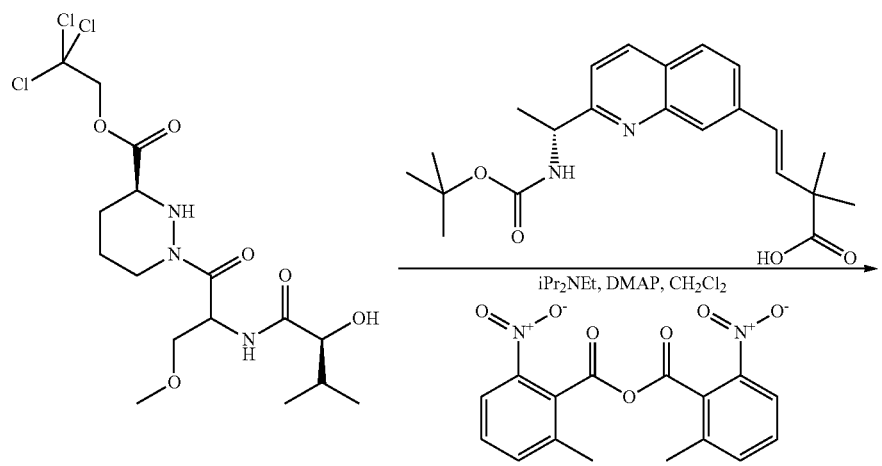

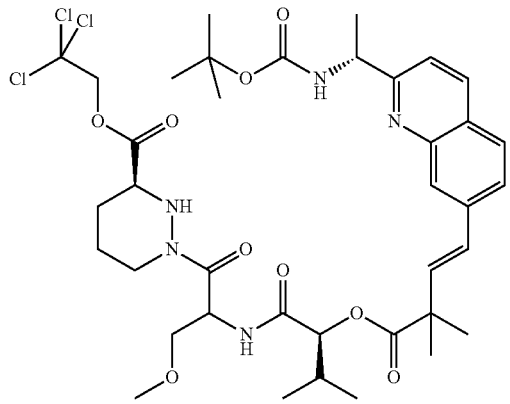

To a solution of 39b (300 mg, 0.78 mmol) in anhydrous dichloromethane (5 mL) at room temperature and under an atmosphere of nitrogen was added N,N-diisopropylethylamine (0.28 mL, 1.56 mmol), 4-dimethylaminopyridine (200 mg, 1.64 mmol) and 2-methyl-6-nitrobenzoic anhydride (323 mg, 0.94 mmol) followed by a solution of 39e (433 mg, 0.94 mmol) in anhydrous dichloromethane (2.5 mL). The reaction was stirred for 2 h after which it was diluted with ethyl acetate and washed with water and brine. The organic layer was dried through a hydrophobic frit and concentrated in vacuo. The residue was purified by silica gel chromatography using iso-hexanes/ethyl acetate 1:2 to give the title compound (211 mg, 33%) as a clear viscous oil and as a 1:1 mixture of two diastereoisomers. LCMS (m/z) 828.3 [M+H], Tr=3.48 min.

Compounds 39 and 40

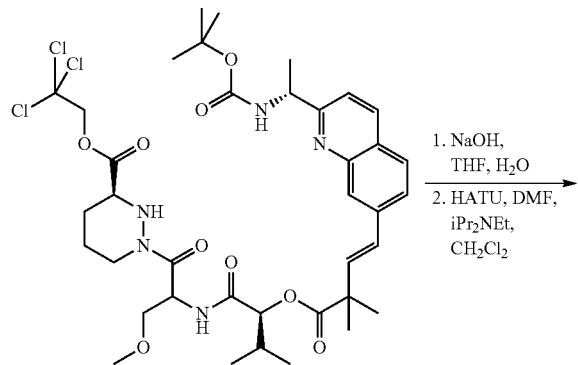

1. NaOH, THF, H$_2$O
2. HATU, DMF, iPr$_2$NEt, CH$_2$Cl$_2$

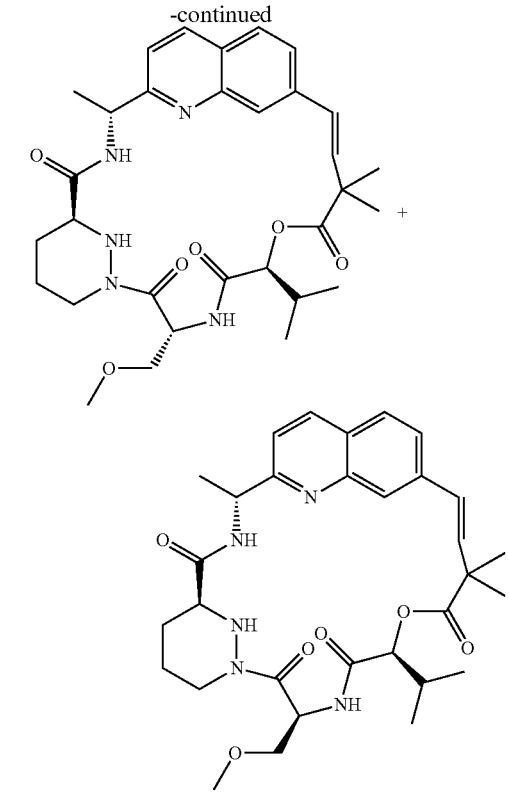

To a solution of 39f (200 mg, 0.24 mmol) in anhydrous tetrahydrofuran (3 mL) at 0° C. was added a 0.4 M aqueous solution of sodium hydroxide (0.7 mL, 0.29 mmol). The reaction was stirred at 0° C. for 1 h before being acidified to pH 5 with hydrochloric acid (2 M) and concentrated in vacuo. The resulting residue was partitioned between dichloromethane and water and the organic layer separated, dried through a hydrophobic frit and concentrated in vacuo. The residue was dissolved in anhydrous 1,4-dioxane (1 mL) and at room temperature was added a 4 M solution of hydrochloric acid in dioxane (0.3 mL, 1.2 mmol). The reaction was stirred for 1.5 h, concentrated in vacuo and the resulting solid triturated with diethyl ether to afford a light yellow solid. The solid was dissolved in anhydrous N,N-dimethylformamide (3 mL) and N,N-diisopropylethylamine (0.21 mL, 1.2 mmol) and this solution was added to a pre-stirred solution of 2-(1H-7-azabenzotriazol-1-yl)-1,1,3,3-tetramethyl uronium hexafluorophosphate methanaminium (137 mg, 0.4 mmol) in anhydrous dichloromethane (80 mL) at 0° C. and under an atmosphere of nitrogen. Following the addition, the reaction was stirred at room temperature for 2 h before being concentrated in vacuo. The ensuing residue was dissolved in ethyl acetate and washed with hydrochloric acid (0.5 M), saturated sodium bicarbonate and brine. The organic layer was dried through a hydrophobic frit and concentrated in vacuo. The residue was purified by reverse phase preparatory HPLC to afford two diastereoisomers as white solids.

Compound 39. (Second eluting) Diastereoisomer 1 (7 mg, 5%). $^1$H NMR (300 MHz, CD$_3$OD) δ 1.06 (d, J=6.7 Hz, 3H), 1.09 (d, J=6.7 Hz, 3H), 1.48 (s, 3H), 1.57 (d, J=6.7 Hz, 3H), 1.59 (s, 3H), 1.51-1.65 (m, 1H), 1.69-2.11 (m, 4H), 2.19-2.37 (m, 1H), 2.72-2.86 (m, 1H), 2.91 (s, 3H), 3.40-3.58 (m, 3H), 3.80-3.90 (m, 1H), 4.33-4.45 (m, 1H), 5.11-5.22 (m, 3H), 5.57-5.63 (m, 1H), 6.54, 6.71 (ABq, J=15.9 Hz, 2H), 7.44 (d, J=8.5 Hz, 1H), 7.54 (d, J=8.5 Hz, 1H), 7.85 (d, J=8.5 Hz, 1H), 7.96 (s, 1H), 8.24 (d, J=8.5 Hz, 1H). LCMS (m/z) 580.2 [M+H], Tr=2.58 min.

Compound 40 (First eluting) Diastereomer 2. (3 mg, 2%); $^1$H NMR (300 MHz, CD$_3$OD) δ 1.00 (d, J=6.7 Hz, 3H), 1.05 (d, J=6.7 Hz, 3H), 1.43 (s, 3H), 1.54 (s, 3H), 1.57 (d, J=6.7 Hz, 3H), 1.53-1.75 (m, 1H), 1.91-2.02 (m, 1H), 2.12-2.24 (m, 1H), 2.25-2.36 (m, 1H), 2.64-2.76 (m, 1H), 3.46 (s, 3H), 3.59-3.70 (m, 1H), 3.87 (d, J=6.0 Hz, 2H), 4.41-4.50 (m, 1H), 5.12 (q, J=6.7 Hz, 1H), 5.18 (d, J=11.6 Hz, 1H), 5.27 (d, J=8.5 Hz, 1H), 6.09 (t, J=6.3 Hz, 1H), 6.41, 6.61 (ABq, J=16.3 Hz, 2H), 7.43 (d, J=8.5 Hz, 1H), 7.58 (dd, J=8.5, 1.5 Hz, 1H), 7.83 (d, J=8.5 Hz, 1H), 8.03 (s, 1H), 8.24 (d, J=8.5 Hz, 1H). LCMS (m/z) 580.2 [M+H], Tr=2.62 min.

Example 41

Compound 41

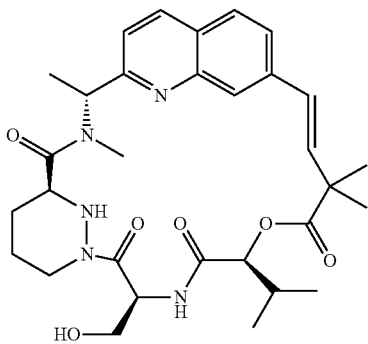 [SMILES: CC(C)[C@@H]1OC(=O)C(C)(C)/C=C/c2ccc3ccc(nc3c2)[C@@H](C)N(C)C(=O)[C@@H]2CCCN(N2)C(=O)[C@H](CO)NC1=O]

Compound 41a. [(R)-1-(7-Bromo-quinolin-2-yl)-ethyl]-methyl-carbamic acid tert-butyl ester

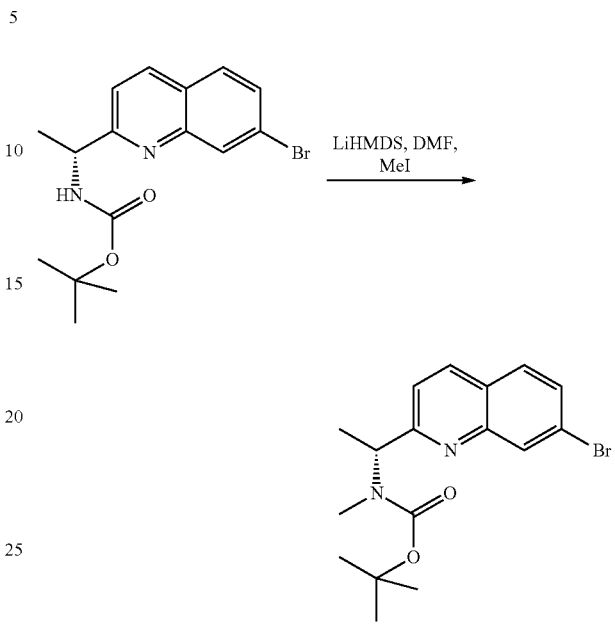

To a solution 39a (500 mg, 1.4 mmol) in anhydrous N,N-dimethylformamide (5 mL), at −20° C. and under an atmosphere of nitrogen, was added dropwise lithium bis(trimethylsilyl)amide (1.0 M in THF, 1.7 mL, 1.71 mmol) over 10 minutes. Following the addition the reaction was stirred at −20° C. for 45 minutes and then iodomethane (0.18 mL, 2.85 mmol) was added. The reaction was warmed to room temperature and stirred for 1 h before quenching with saturated aqueous ammonium chloride and extracting with diethyl ether (2×). The combined organics were washed with 5% aqueous lithium chloride solution, dried through a hydrophobic frit and concentrated in vacuo. The product was purified by silica gel chromatography using iso-hexanes/ethyl acetate 6:1 to afford the title compound (500 mg, 96%) as a viscous oil. $^1$H NMR (300 MHz, CDCl$_3$) δ 1.50 (s, 9H), 1.68 (d, J=6.9 Hz, 3H), 2.72 (br s, 3H), 5.34-5.92 (m, 1H), 7.41 (d, J=8.5 Hz, 1H), 7.62 (dd, J=8.5, 1.8 Hz, 1H), 7.68 (d, J=8.7 Hz, 1H), 8.08 (d, J=8.7 Hz, 1H), 8.29 (d, J=1.6 Hz, 1H). LCMS (m/z) 367.0 [M+H], Tr=3.61 min.

Compound 41b. (E)-4-{2-[(R)-1-(tert-Butoxycarbonyl-methyl-amino)-ethyl]-quinolin-7-yl}-2,2-dimethyl-but-3-enoic acid methyl ester

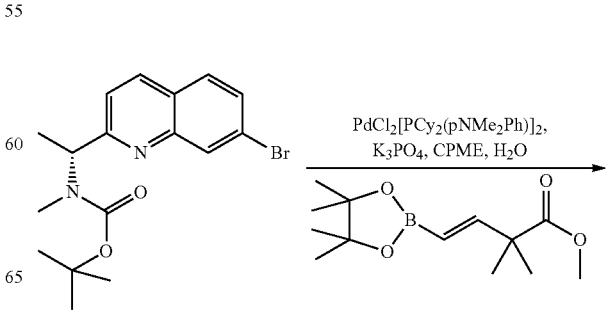

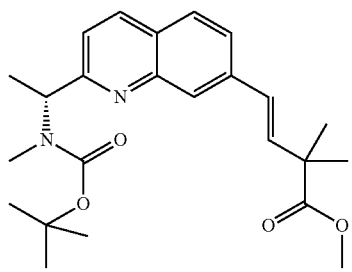

Compound 41b was prepared in the same manner as compound 39b using 41a instead of 39a in 80% yield. $^1$H NMR (300 MHz, CDCl$_3$) δ 1.50 (s, 9H), 1.56 (s, 6H), 1.69 (d, J=7.1 Hz, 3H), 2.72 (br s, 3H), 3.74 (s, 3H), 5.28-6.01 (m, 1H), 6.64 (s, 2H), 7.33 (d, J=8.3 Hz, 1H), 7.61 (dd, J=8.7, 1.6 Hz, 1H), 7.74 (d, J=8.3 Hz, 1H), 8.01-8.08 (m, 2H). LCMS (m/z) 413.2 [M+H], Tr=3.42 min.

Compound 41c. (E)-4-{2-[(R)-1-(tert-Butoxycarbonyl-methyl-amino)-ethyl]-quinolin-7-yl}-2,2-dimethyl-but-3-enoic acid

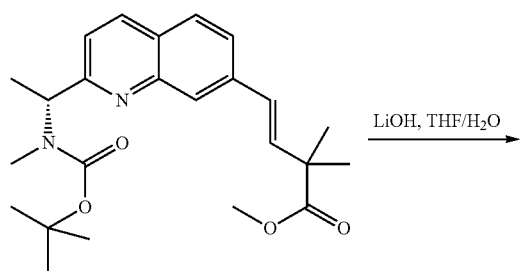

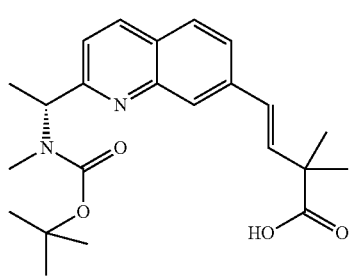

Compound 41c was prepared in the same manner as compound 39c using 41b instead of (E)-4-[2-((R)-1-tert-butoxy-carbonylamino-ethyl)-quinolin-7-yl]-2,2-dimethyl-but-3-enoic acid methyl ester in 99% yield. $^1$H NMR (300 MHz, CDCl$_3$) δ 1.49 (s, 9H), 1.52 (s, 6H), 1.69 (d, J=7.1 Hz, 3H), 2.73 (br s, 3H), 5.29-5.84 (m, 1H), 6.66, 6.70 (ABq, J=16.3 Hz, 2H), 7.34 (d, J=108.9 Hz, 1H), 7.59-7.66 (m, 1H), 7.74 (d, J=8.5 Hz, 1H), 8.00-8.09 (m, 2H). LCMS (m/z) 399.1 [M+H], Tr=2.75 min.

Compound 41d. (S)-1-[(S)-2-tert-Butoxycarbonylamino-3-(tert-butyl-diphenyl-silanyloxy)-propionyl]-hexahydro-pyridazine-3-carboxylic acid 2,2,2-trichloro-ethyl ester

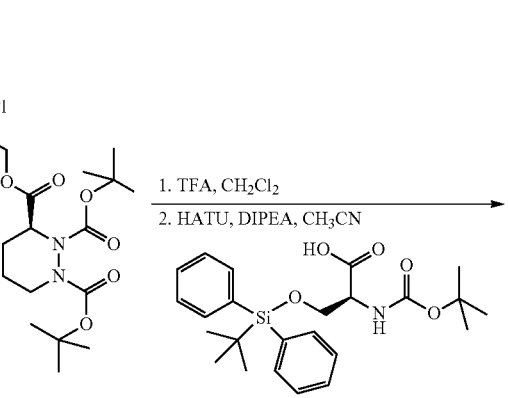

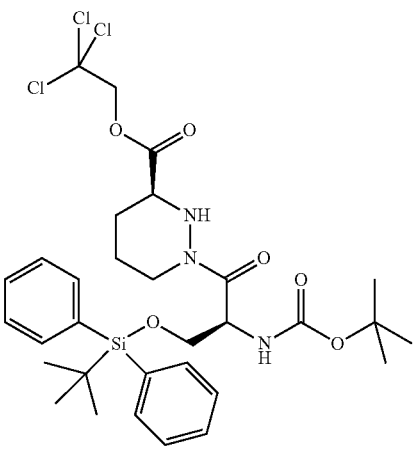

To (S)-tetrahydro-pyridazine-1,2,3-tricarboxylic acid 1,2-di-tert-butyl ester 3-(2,2,2-trichloro-ethyl) ester (prepared according to the procedure described in *Angew. Chem. Int. Ed. English* 1999, 38, 2443.), (5.0 g, 10.8 mmol) in anhydrous dichloromethane (33 mL) at 0° C. and under an atmosphere of nitrogen was added trifluoroacetic acid (33 mL, 432 mmol). The solution was warmed to room temperature and stirred for 16 h. The reaction was concentrated in vacuo and the residue co-evaporated from toluene (3×). The resulting brown viscous oil was dissolved in anhydrous acetonitrile (5 mL) and added to a solution of (S)-2-tert-butoxycarbonylamino-3-(tert-butyl-diphenyl-silanyloxy)-propionic acid (2.39 g, 5.4 mmol, prepared as in PCT Int. Appl. 2006, WO 2006004880 A2), N,N-diisopropylethylamine (3.76 mL, 21.6 mmol) and O-(benzotriazol-1-yl)-N,N,N',N'-tetramethyluronium hexafluorophosphate (2.05 g, 5.4 mmol) in anhydrous acetonitrile (25 mL) that had been previously stirred at 0° C. for 20 minutes. The reaction was warmed to room temperature and stirred for 16 h before being concentrated in vacuo. The residue was purified by silica gel chromatography using isohexanes/ethyl acetate 4:1 to give the title compound (1.8 g, 49%) as a clear viscous oil. $^1$H NMR (300 MHz, CDCl$_3$) δ 1.08 (s, 9H), 1.46 (s, 9H), 1.53-1.67 (m, 1H), 1.80-2.01 (m, 2H), 2.82-2.96 (m, 1H), 3.19-3.32 (m, 1H), 3.62 (d, J=10.9 Hz, 1H), 3.80-3.97 (m, 3H), 4.23-4.34 (m, 1H), 4.61 (d, J=12.0 Hz, 1H), 4.90 (d, J=12.0 Hz, 1H), 5.18-5.27 (m, 1H), 5.51-5.63 (m, 1H), 7.35-7.49 (m, 6H), 7.58-7.70 (m, 4H). LCMS (m/z) 686.2 [M+H], Tr=4.32 min.

Compound 41e. (S)-1-[(S)-3-(tert-Butyl-diphenyl-silanyloxy)-2-((S)-2-hydroxy-3-methyl-butyrylamino)-propionyl]-hexahydro-pyridazine-3-carboxylic acid 2,2,2-trichloro-ethyl ester

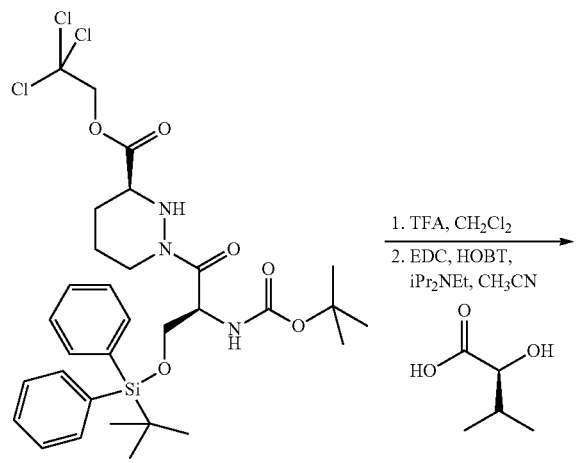

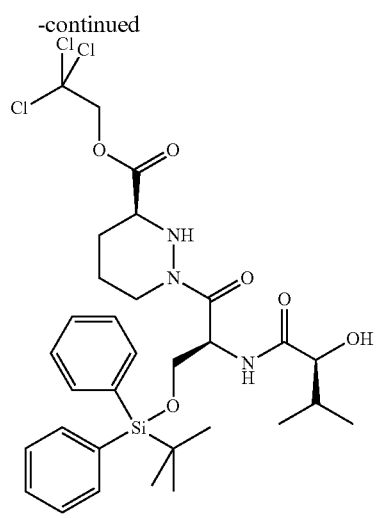

Compound 41e was prepared in the same manner as compound 39e using (S)-1-[(S)-2-tert-butoxycarbonylamino-3-(tert-butyl-diphenyl-silanyloxy)-propionyl]-hexahydro-pyridazine-3-carboxylic acid 2,2,2-trichloro-ethyl ester instead of (S)-1-((S)-2-tert-butoxycarbonylamino-3-methoxy-propionyl)-hexahydro-pyridazine-3-carboxylic acid 2,2,2-trichloro-ethyl ester in 50% yield. $^1$H NMR (300 MHz, CDCl$_3$) δ 0.90 (d, J=6.7 Hz, 3H), 1.07-1.09 (m, 12H), 1.42-1.71 (m, 2H), 1.80-1.91 (m, 1H), 1.93-2.02 (m, 1H), 2.07-2.15 (m, 1H), 2.72 (d, J=5.9 Hz, 1H), 2.86-3.02 (m, 1H), 3.17-3.28 (m, 1H), 3.60 (d, J=10.5 Hz, 1H), 3.90-3.99 (m, 3H), 4.18-4.29 (m, 1H), 4.62, 4.91 (ABq, J=11.9 Hz, 2H), 5.42-5.50 (m, 1H), 7.35-7.51 (m, 7H) 7.58-7.71 (m, 4H). LCMS (m/z) 686.2 [M+H], Tr=3.93 min.

Compound 41f

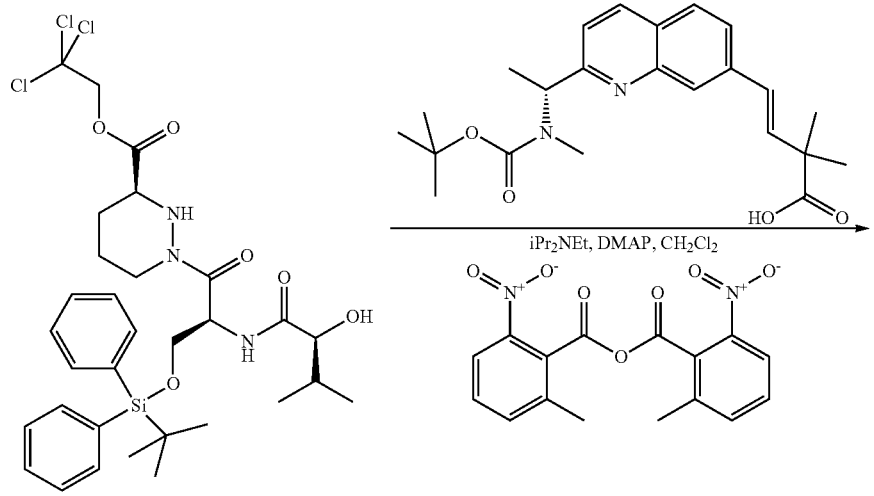

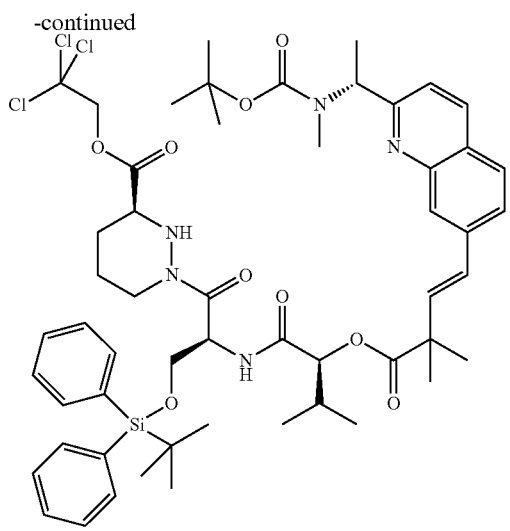

Compound 41f was prepared in the same manner as compound 39f using (E)-4-{2-[(R)-1-(tert-butoxycarbonyl-methyl-amino)-ethyl]-quinolin-7-yl}-2,2-dimethyl-but-3-enoic acid and (S)-1-[(S)-3-(tert-butyl-diphenyl-silanyloxy)-2-((S)-2-hydroxy-3-methyl-butyrylamino)-propionyl]-hexahydro-pyridazine-3-carboxylic acid 2,2,2-trichloro-ethyl ester instead of (E)-4-[2-((R)-1-tert-butoxycarbonylamino-ethyl)-quinolin-7-yl]-2,2-dimethyl-but-3-enoic acid and (S)-1-[(S)-2-((S)-2-hydroxy-3-methyl-butyrylamino)-3-methoxy-propionyl]-hexahydro-pyridazine-3-carboxylic acid 2,2,2-trichloro-ethyl ester in 32% yield. $^1$H NMR (300 MHz, CDCl$_3$) δ 0.98-1.05 (m, 6H), 1.07 (s, 9H), 1.50 (s, 9H), 1.52-1.60 (m, 2H), 1.57 (s, 3H), 1.61 (s, 3H), 1.68 (d, J=6.9 Hz, 3H), 1.72-1.93 (m, 2H), 2.31-2.46 (m, 1H), 2.63-3.01 (m, 5H), 3.47 (d, J=11.2 Hz, 1H), 3.87 (dd, J=10.3, 2.7 Hz, 1H), 4.04 (dd, J=10.3, 3.4 Hz, 1H), 4.11-4.23 (m, 1H), 4.60, 4.88 (ABq, J=12.0 Hz, 2H), 5.21 (d, J=3.6 Hz, 1H), 5.38-5.44 (m, 1H), 6.72, 6.76 (ABq, J=16.3 Hz, 2H), 7.31-7.49 (m, 8H), 7.56-7.62 (m, 2H), 7.64-7.71 (m, 4H), 7.99-8.06 (m, 2H). LCMS (m/z) 1066.5 [M+H], Tr=4.94 min.

Compound 41g

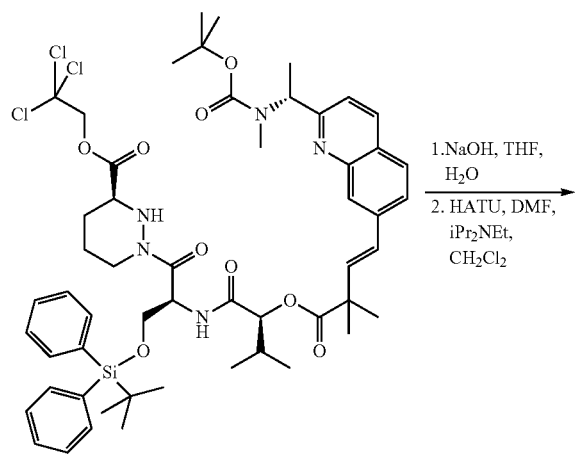

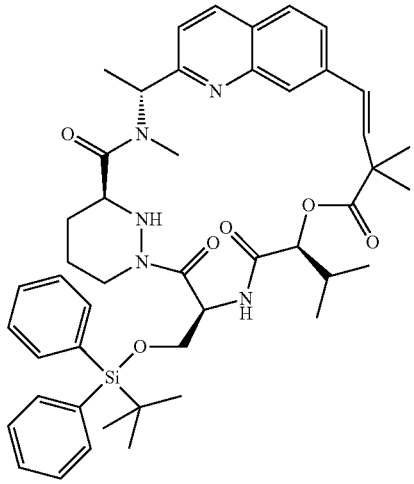

Compound 41g was prepared in the same manner as compound 39 using 41f instead of (S)-1-[(S)-2-((S)-2-{(E)-4-[2-((R)-1-tert-butoxycarbonylamino-ethyl)-quinolin-7-yl]-2,2-dimethyl-but-3-enoyloxy}-3-methyl-butyrylamino)-3-methoxy-propionyl]-hexahydro-pyridazine-3-carboxylic acid 2,2,2-trichloro ethyl ester in 77% yield. $^1$H NMR (300 MHz, CDCl$_3$) δ 0.95-1.04 (m, 6H), 1.46 (s, 3H), 1.53 (s, 3H), 1.54-1.61 (m, 12H), 1.65-2.01 (m, 4H), 2.19-2.37 (m, 1H), 2.61 (s, 3H), 2.65-2.78 (m, 1H), 3.57-3.76 (m, 2H), 3.79 (d, J=12.0 Hz, 1H), 4.03-4.10 (m, 1H), 4.52-4.63 (m, 1H), 4.89 (d, J=8.5 Hz, 1H), 5.93 (q, J=7.1 Hz, 1H), 5.98-6.07 (m, 1H), 6.28, 6.47 (ABq, J=16.4 Hz, 2H), 6.56-6.63 (m, 1H), 7.21-7.54 (m, 7H), 7.61-7.75 (m, 7H), 8.02 (d, J=8.3 Hz, 1H). LCMS (m/z) 818.4 [M+H], Tr=4.22 min.

Compound 41

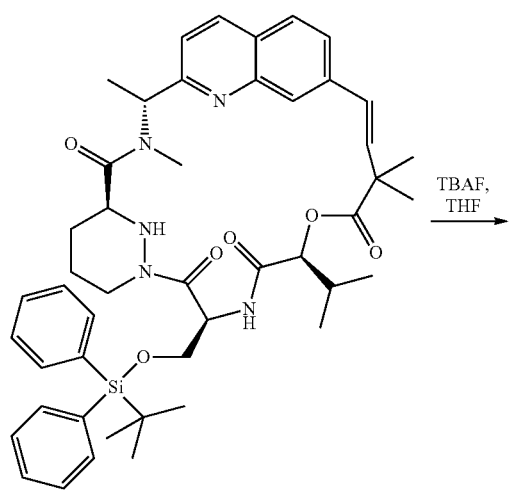

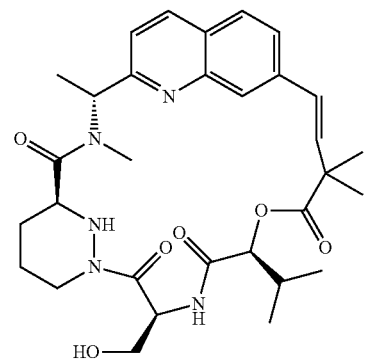

To a solution of compound 41g (190 mg, 0.23 mmol) in anhydrous tetrahydrofuran (1 mL), at room temperature and under an atmosphere of nitrogen, was added tetrabutylammonium fluoride (1 M in THF, 1.2 mL, 1.2 mmol). The reaction was stirred for 45 minutes before being diluted with ethyl acetate and washed with saturated aqueous ammonium chloride. The organic layer was dried through a hydrophobic frit and concentrated in vacuo. The product was purified by silica gel chromatography using iso-hexanes/acetone 1:1 to give the title compound (35 mg, 27%) as a white solid. $^1$H NMR (300 MHz, CD$_3$OD) δ 0.98 (d, J=6.7 Hz, 3H), 1.01 (d, J=6.5 Hz, 3H), 1.42 (s, 3H), 1.52 (s, 3H), 1.72 (d, J=7.4 Hz, 3H), 1.72-1.97 (m, 4H), 2.09-2.25 (m, 1H), 2.71-2.86 (m, 1H), 3.30 (s, 3H), 3.96 (d, J=6.3 Hz, 2H), 4.18-4.30 (m, 1H), 4.42-4.53 (m, 2H), 5.08 (d, J=8.7 Hz, 1H), 5.88 (q, J=7.4 Hz, 1H), 6.06 (t, J=6.0 Hz, 1H), 6.40, 6.49 (ABq, J=16.5 Hz, 2H), 7.44 (d, J=8.7 Hz, 1H), 7.64 (dd, J=8.5, 1.3 Hz, 1H), 7.78 (d, J=8.5 Hz, 1H), 7.89 (s, 1H), 8.19 (d, J=8.7 Hz, 1H). LCMS (m/z) 580.2 [M+H], Tr=2.14 min.

Example 42

Compound 42

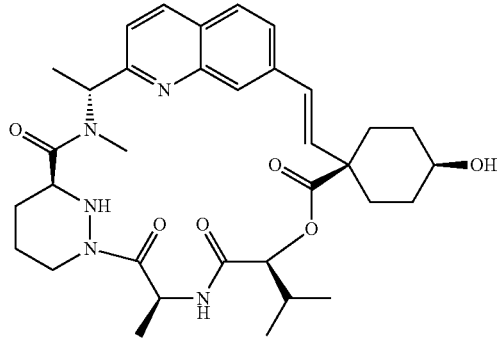 [SMILES: CC(C)[C@@H]1OC(=O)[C@]2(/C=C/c3ccc4ccc(nc4c3)[C@@H](C)N(C)C(=O)[C@@H]3CCCN(N3)C(=O)[C@H](C)NC1=O)CC[C@H](O)CC2]

Compound 42a.
4-Oxo-1-vinyl-cyclohexanecarboxylic acid

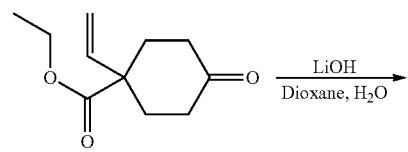

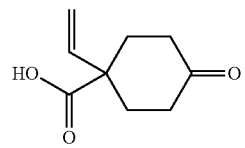

A solution of the commercially available 4-oxo-1-vinyl-cyclohexanecarboxylic acid ethyl ester (provided by Small Molecules Inc.), (1.20 g, 6.11 mmol) in 1,4-dioxane (20 mL) was treated with a solution of lithium hydroxide monohydrate (734 mg, 30.6 mmol) in water (10 mL). After stirring at 50° C. for 2 h, the volatiles were removed in vacuo. The residue was partitioned between water and diethyl ether. The aqueous layer was acidified to pH 1 by addition of saturated potassium hydrogen sulfate solution and was extracted with ethyl acetate (3×). The organic layer was dried over anhydrous magnesium sulfate, filtered and the volatiles were removed in vacuo to afford the title compound (1.00 g, 97%) as a clear gum. $^1$H NMR (300 MHz, CDCl$_3$) δ 1.92-2.08 (m, 2H), 2.36-2.59 (m, 6H), 5.34 (d, J=17.5 Hz, 1H), 5.35 (d, J=10.5 Hz, 1H), 5.97 (dd, J=17.5, 10.5 Hz, 1H), 11.30 (br s, 1H).

Compound 42b. 1-((E)-2-{2-[(R)-1-(tert-Butoxycarbonyl-methyl-amino)-ethyl]-quinolin-7-yl}-vinyl)-4-oxo-cyclohexanecarboxylic acid

Compound 42c. 1-((E)-2-{2-[(R)-1-(tert-Butoxycarbonyl-methyl-amino)-ethyl]-quinolin-7-yl}-vinyl)-4-cis-hydroxy-cyclohexanecarboxylic acid

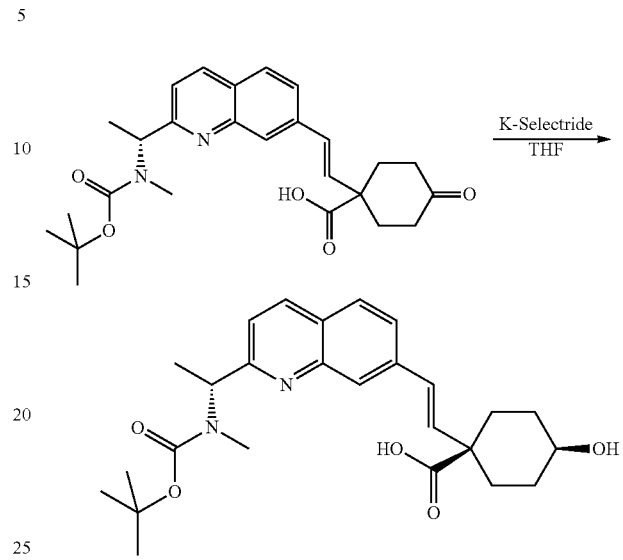

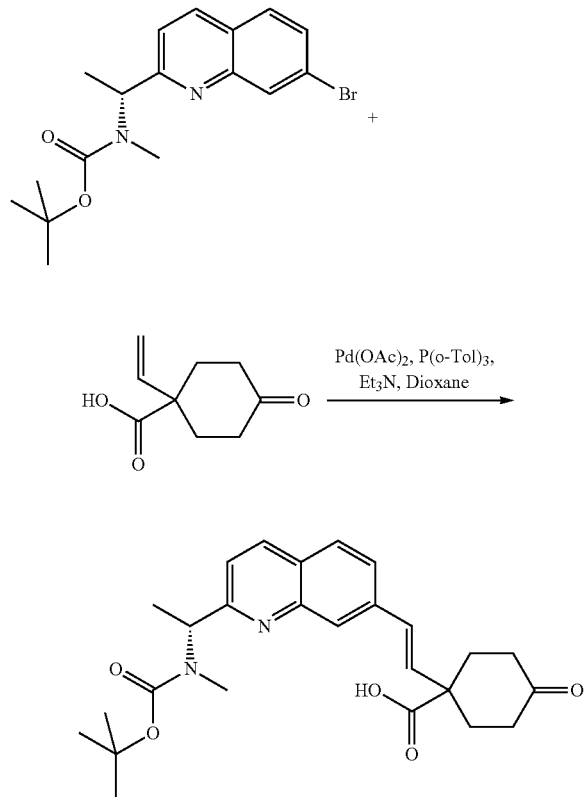

A solution of [(R)-1-(7-bromo-quinolin-2-yl)-ethyl]-methyl-carbamic acid tert-butyl ester (200 mg, 0.55 mmol), 4-oxo-1-vinyl-cyclohexanecarboxylic acid (138 mg, 0.82 mmol), palladium(II) acetate (25 mg, 0.11 mmol), tri-(o-tolyl)phosphine (50 mg, 0.16 mmol) in anhydrous 1,4-dioxane (2 mL) was treated with triethylamine (267 µL, 1.91 mmol). After stirring at 100° C. under microwave irradiation for 30 minutes, the reaction was cooled to room temperature and the volatiles were removed in vacuo. The residue was partitioned between ethyl acetate and a 5% citric acid solution, the aqueous layer was extracted with ethyl acetate (2 x), the organics were combined and the volatiles were removed in vacuo. The residue was purified by silica gel chromatography using a 25 g Biotage cartridge eluted with a continuous gradient of iso-hexanes/ethyl acetate 1:0 to 1:1 to afford the title compound (235 mg, 94%) as a white solid. $^1$H NMR (300 MHz, CDCl$_3$) δ 1.48 (s, 9H), 1.68 (d, J=7.1 Hz, 3H), 2.07-2.22 (m, 2H), 2.44-2.70 (m, 6H), 2.75 (br s, 3H), 5.61 (br s, 1H), 6.68 (ABq, Δδ$_{AB}$=0.31, J$_{AB}$=16.3 Hz, 2H), 7.36 (d, J=8.5 Hz, 1H), 7.60 (d, J=8.5 Hz, 1H), 7.75 (d, J=8.5 Hz, 1H), 8.05-8.12 (m, 2H). LCMS (m/z) 453.1 [M+H], Tr=2.48 min.

A cooled (−50° C.) solution of 1-((E)-2-{2-[(R)-1-(tert-butoxycarbonyl-methyl-amino)-ethyl]-quinolin-7-yl}-vinyl)-4-oxo-cyclohexanecarboxylic acid (235 mg, 0.52 mmol) in anhydrous tetrahydrofuran (15 mL) was treated with potassium tri-sec-butylborohydride (1.56 mL, 1.56 mmol, 1 M in tetrahydrofuran). The temperature was raised to −30° C. After stirring for 20 minutes, the reaction was quenched by addition of a saturated ammonium chloride solution (10 mL). The temperature was raised to room temperature, the pH adjusted to pH 2 by addition of citric acid then extracted with ethyl acetate (3×). The organics were combined and the volatiles were removed in vacuo. The residue was purified by silica gel chromatography using a 25 g Biotage cartridge eluted with a continuous gradient of iso-hexanes/ethyl acetate 1:0 to 0:1 to afford the title compound (185 mg, 78%) as a white solid. $^1$H NMR (300 MHz, CDCl$_3$) δ 1.48 (s, 9H), 1.52-1.62 (m, 4H), 1.67 (d, J=6.9 Hz, 3H), 1.95-2.05 (m, 2H), 2.42-2.55 (m, 2H), 2.73 (br s, 3H), 3.73 (br s, 1H), 5.57 (br s, 1H), 6.58 (ABq, Δδ$_{AB}$=0.29, J$_{AB}$=16.3 Hz, 2H), 7.34 (d, J=8.5 Hz, 1H), 7.58 (d, J=8.5 Hz, 1H), 7.72 (d, J=8.5 Hz, 1H), 8.01-8.10 (m, 2H). LCMS (m/z) 455.1 [M+H], Tr=2.31 min.

Compound 42d. 1-((E)-2-{2-[(R)-1-(tert-Butoxycarbonyl-methyl-amino)-ethyl]-quinolin-7-yl}-vinyl)-4-cis-(tert-butyl-dimethyl-silanyloxy)-cyclohexanecarboxylic acid

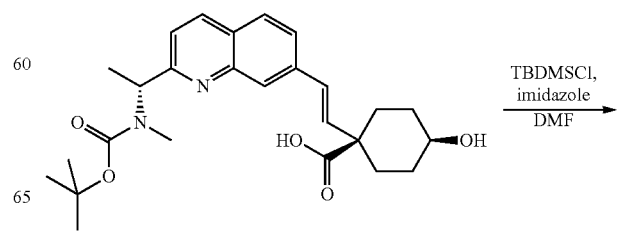

-continued

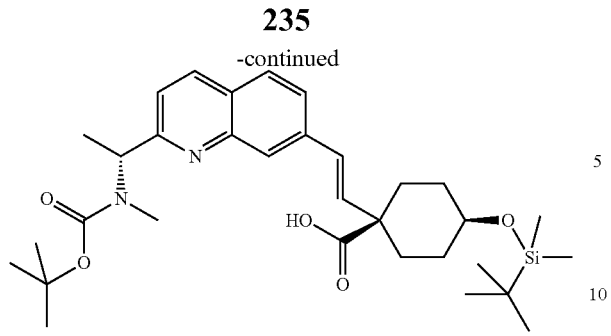

A solution of 1-((E)-2-{2-[(R)-1-(tert-butoxycarbonyl-methyl-amino)-ethyl]-quinolin-7-yl}-vinyl)-4-cis-hydroxy-cyclohexanecarboxylic acid (185 mg, 0.41 mmol) and imidazole (138 mg, 2.03 mmol) in anhydrous in N,N-dimethylformamide (5 mL) was treated with tert-butyldimethylsilyl chloride (153 mg, 1.02 mmol). After stirring for 16 h, the reaction was quenched by addition of a potassium carbonate solution (10 mL). After stirring for 3 h, the pH was adjusted to pH 3 by addition of potassium hydrogen sulfate solution then extracted with ethyl acetate (3×). The organics were combined and the volatiles were removed in vacuo. The residue was purified by silica gel chromatography using a 25 g Biotage cartridge eluted with a continuous gradient of iso-hexanes/ethyl acetate 1:0 to 7:3 to afford the title compound (142 mg, 61%) as a white solid. $^1$H NMR (300 MHz, CDCl$_3$) δ 0.08 (s, 6H), 0.91 (s, 9H), 1.49 (s, 9H), 1.53-1.64 (m, 4H), 1.67 (d, J=6.9 Hz, 3H), 1.80-1.92 (m, 2H), 2.38-2.51 (m, 2H), 2.72 (br s, 3H), 3.70 (br s, 1H), 5.59 (br s, 1H), 6.58 (ABq, Δδ$_{AB}$=0.30, J$_{AB}$=16.3 Hz, 2H), 7.33 (d, J=8.5 Hz, 1H), 7.58 (dd, J=8.5, 1.3 Hz, 1H), 7.71 (d, J=8.5 Hz, 1H), 8.00-8.06 (m, 2H). LCMS (m/z) 569.2 [M+H], Tr=4.37 min.

Compound 42e. (S)-1-((S)-2-{(S)-2-[1-((E)-2-{7-[(R)-1-(tert-Butoxycarbonyl-methyl-amino)-ethyl]-quinolin-2-yl}-vinyl)-4-cis-(tert-butyl-dimethyl-silanyloxy)-cyclohexanecarbonyloxy]-3-methyl-butyrylamino}-propionyl)-hexahydro-pyridazine-3-carboxylic acid 2,2,2-trichloro-ethyl ester -continued

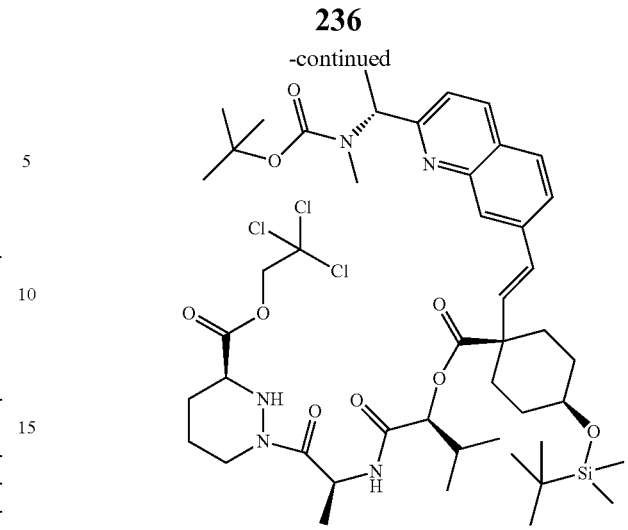

A solution of 1-((E)-2-{2-[(R)-1-(tert-butoxycarbonyl-methyl-amino)-ethyl]-quinolin-7-yl}-vinyl)-4-cis-(tert-butyl-dimethyl-silanyloxy)-cyclohexanecarboxylic acid (142 mg, 0.25 mmol), (S)-1-[(S)-2-((S)-2-hydroxy-3-methyl-butyrylamino)-propionyl]-hexahydro-pyridazine-3-carboxylic acid 2,2,2-trichloro-ethyl ester (108 mg, 0.25 mmol), triethylamine (0.087 mL, 0.62 mmol) and 4-dimethylaminopyridine (15 mg, 0.12 mmol) in anhydrous dichloromethane (10 mL) was treated with 2-methyl-6-nitrobenzoic anhydride (146 mg, 0.42 mmol). After stirring for 60 h, the reaction was quenched by addition of a sodium bicarbonate solution (10 mL), the aqueous layer was extracted with dichloromethane (2×), the organics were combined and the volatiles were removed in vacuo. The residue was purified by silica gel chromatography using a 25 g Biotage cartridge eluted with a continuous gradient of iso-hexanes/ethyl acetate 1:0 to 1:1 to afford the title compound (105 mg, 43%) as a white solid. $^1$H NMR (300 MHz, CD$_3$OD) δ 0.10 (s, 6H), 0.93 (s, 9H), 1.01 (d, J=6.9 Hz, 3H), 1.02 (d, J=6.9 Hz, 3H), 1.27 (d, J=6.9 Hz, 3H), 1.40-1.50 (m, 9H), 1.68 (d, J=6.9 Hz, 3H), 1.72-1.81 (m, 4H), 1.82-1.94 (m, 4H), 1.95-2.10 (m, 2H), 2.25-2.32 (m, 2H), 2.37-2.44 (m, 1H), 2.46-2.57 (m, 2H), 2.80 (br s, 3H), 3.52-3.70 (m, 1H), 3.74-3.85 (m, 2H), 4.73-4.80 (m, 1H), 5.01 (d, J=4.7 Hz, 1H), 5.30-5.45 (m, 2H), 6.70 (ABq, Δδ$_{AB}$=0.28, J$_{AB}$=16.3 Hz, 2H), 7.37 (d, J=8.5 Hz, 1H), 7.73-7.85 (m, 2H), 7.97 (s, 1H), 8.22 (d, J=8.5 Hz, 1H).

Compound 42

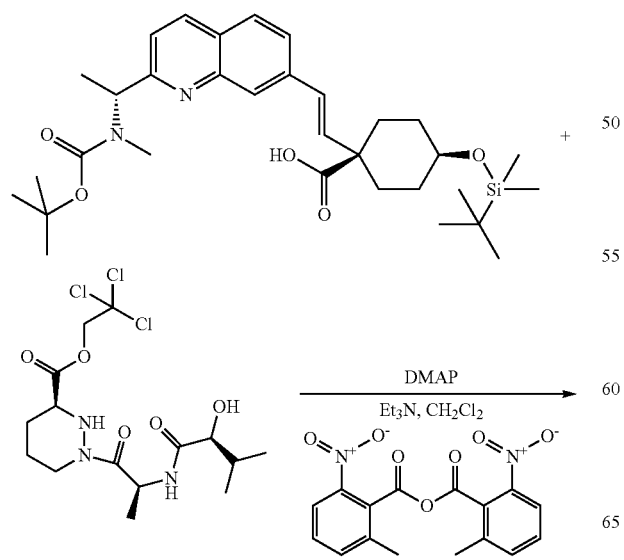

+

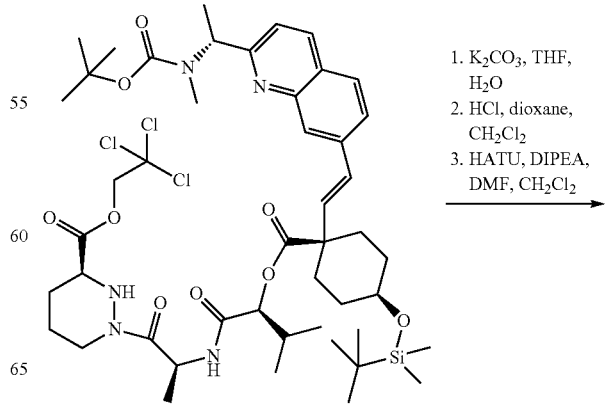

1. K$_2$CO$_3$, THF, H$_2$O
2. HCl, dioxane, CH$_2$Cl$_2$
3. HATU, DIPEA, DMF, CH$_2$Cl$_2$

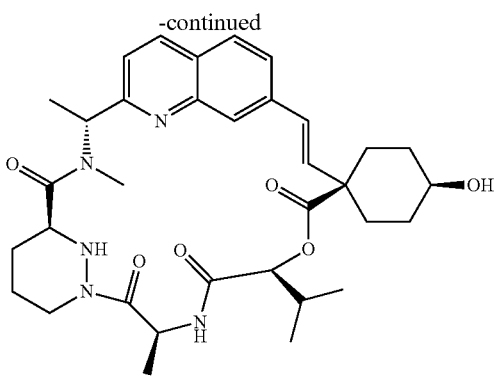

A solution of (S)-1-((S)-2-{(S)-2-[1-((E)-2-{7-[(R)-1-(tert-butoxycarbonyl-methyl-amino)-ethyl]-quinolin-2-yl}-vinyl)-4-cis-(tert-butyl-dimethyl-silanyloxy)-cyclohexanecarbonyloxy]-3-methyl-butyrylamino}-propionyl)-hexahydro-pyridazine-3-carboxylic acid 2,2,2-trichloroethyl ester (105 mg, 0.11 mmol) in tetrahydrofuran (10 mL) was treated with a solution of potassium carbonate (221 mg, 1.60 mmol) in water (5 mL). After stirring at room temperature for 3 h, the pH was adjusted to pH 3 by addition of dilute hydrochloric acid then extracted with ethyl acetate (3×). The organics were combined and the volatiles were removed in vacuo. The residue was dissolved in dichloromethane (10 mL) and treated with hydrochloric acid in 1,4-dioxane (4 M, 5 mL). After stirring at room temperature for 1 h, the volatiles were removed in vacuo. The residual solvent was azeotroped off with toluene (3×15 mL) to give crude (S)-1-{(S)-2-[(S)-2-(4-cis-hydroxy-1-{(E)-2-[7-((R)-1-methylamino-ethyl)-quinolin-2-yl]-vinyl}-cyclohexanecarbonyloxy)-3-methyl-butyrylamino]-propionyl}-hexahydro-pyridazine-3-carboxylic acid. This residue was dissolved in N,N-dimethylformamide (4 mL) and N,N-diisopropylethylamine (0.093 mL, 0.53 mmol) and added via syringe pump over 1 h to a stirred solution of 2-(1H-7-azabenzotriazol-1-yl)-1,1,3,3-tetramethyl uronium hexafluorophosphate methanaminium (61 mg, 0.16 mmol) in dichloromethane (50 mL) at room temperature under nitrogen. The reaction was quenched by addition of a sodium bicarbonate solution (10 mL), the aqueous layer was extracted with dichloromethane (2×), The organics were combined and the volatiles were removed in vacuo. The residue was purified by preparative reverse phase HPLC to afford the title compound (13 mg, 19%) as a white solid. $^1$H NMR (300 MHz, CD$_3$OD) δ 1.02 (d, J=6.7 Hz, 3H), 1.06 (d, J=6.7 Hz, 3H), 1.27-1.48 (m, 3H), 1.54 (d, J=7.1 Hz, 3H), 1.72 (d, J=7.6 Hz, 3H), 1.78-2.05 (m, 5H), 2.11-2.25 (m, 1H), 2.28-2.40 (m, 1H), 2.50-2.62 (m, 1H), 2.71-2.84 (m, 1H), 3.27 (s, 3H), 3.52-3.80 (m, 3H), 4.11-4.24 (m, 1H), 4.38-4.51 (m, 1H), 5.16 (d, J=9.1 Hz, 1H), 5.86-5.98 (m, 2H), 6.36 (ABq, Δδ$_{AB}$=0.17, J$_{AB}$=16.5 Hz, 2H), 7.44 (d, J=8.7 Hz, 1H), 7.64-7.72 (m, 2H), 7.78 (d, J=8.5 Hz, 1H), 8.18 (d, J=8.7 Hz, 1H). LCMS (m/z) 620.5 [M+H], Tr=2.09 min.

Examples 43 and 44

Compounds 43 and 44

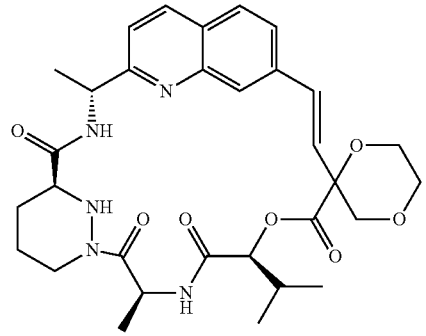 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)COCCO2]

Compound 43a. [1,4]Dioxane-2-carboxylic acid methyl ester

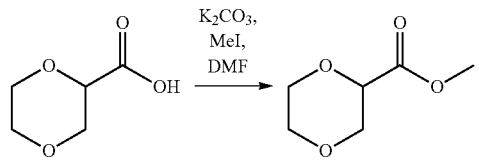

A solution of [1,4]dioxane-2-carboxylic acid (supplied by Enamine Ltd.), (2.90 g, 22.0 mmol) in N,N-dimethylformamide (15 mL) was stirred at room temperature. Potassium carbonate (6.07 g, 44.0 mmol) was added and the suspension was stirred at 5° C. Iodomethane (6.25 g, 2.75 mL, 44.0 mmol) was added dropwise and the reaction mixture was stirred at room temperature for 24 h. Water and brine were added and the mixture was extracted with diethyl ether. The aqueous layer was saturated with sodium chloride and the mixture was extracted with ethyl acetate (3×). The organic extracts were combined, dried over anhydrous magnesium sulfate, filtered and evaporated. The residue was purified by silica gel chromatography using a gradient of pentane/diethyl ether 4:1 to 1:1 to afford the title compound (3.06 g, 95%) as a volatile, pale yellow oil. $^1$H NMR (300 MHz, CDCl$_3$) δ 3.68-3.78 (m, 4H), 3.81 (s, 3H), 3.97-4.05 (m, 2H), 4.29 (dd, J=8.5, 3.1 Hz, 1H). LCMS (m/z) 169.2 [M+Na], Tr=0.69 min.

Compound 43b.
2-(1-Hydroxy-ethyl)-[1,4]dioxane-2-carboxylic acid methyl ester

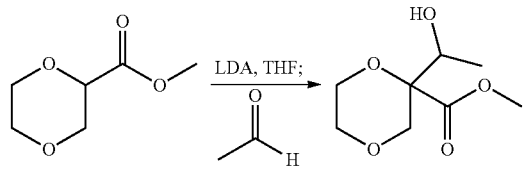

A solution of N,N-diisopropylamine (1.67 g, 2.3 mL, 16.5 mmol) in anhydrous tetrahydrofuran (10 mL) was stirred at −78° C. under nitrogen. n-Butyllithium (6.6 mL, 16.5 mmol, 2.5 M solution in hexane) was added dropwise and the reaction mixture was stirred at −78° C. for 30 minutes. A solution of [1,4]dioxane-2-carboxylic acid methyl ester (1.61 g, 11 mmol) in tetrahydrofuran (10 mL) was added and the reaction mixture was stirred at −78° C. for 30 minutes. Acetaldehyde (1.45 g, 1.8 mL, 33 mmol) was added in one portion. The cooling bath was removed and the reaction mixture was stirred at room temperature for 30 minutes. The reaction mixture was cooled to 5° C. and ice-cold 1 M hydrochloric acid was added to acidify the reaction mixture to pH 2. Sodium chloride was added to saturate the solution and the mixture was extracted with diethyl ether (4×). The organic extracts were combined and washed with brine. The organic solution was filtered through a hydrophobic frit and the filtrate was evaporated. The residue was purified by silica gel chromatography using a gradient of pentane/diethyl ether 1:1 to 0:1 to afford the title compound (1.49 g, 71%), as an oil, and as a 3:1 mixture of diastereoisomers. LCMS (m/z) 213.2 [M+H], Tr=0.62 min.

Compound 43c. 2-[1-(Toluene-4-sulfonyloxy)-ethyl]-[1,4]dioxane-2-carboxylic acid methyl ester

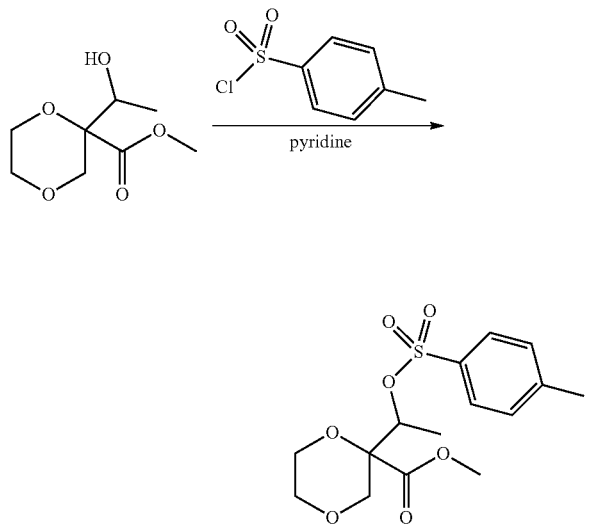

A solution of 2-(1-hydroxy-ethyl)-[1,4]dioxane-2-carboxylic acid methyl ester (1.49 g, 7.8 mmol) in pyridine (8 mL) was stirred at room temperature. 4-Toluenesulfonyl chloride (1.50 g, 7.8 mmol) was added and the reaction mixture was stirred at room temperature for 18 h. The majority of the pyridine was evaporated, 1 M hydrochloric acid was added to acidify the mixture to pH 2 and the mixture was extracted with ethyl acetate. The organic extracts were combined and washed with brine. The organic solution was filtered through a hydrophobic frit and the filtrate was evaporated. The residue was purified by silica gel chromatography using a gradient of pentane/diethyl ether 3:1 to 0:1 to afford the title compound (1.70 g, 63%) as a yellow gum and as a 3:1 mixture of diastereoisomers. LCMS (m/z) 367.0 [M+Na], Tr=2.44 min.

Compound 43d. 2-Vinyl-[1,4]dioxane-2-carboxylic acid methyl ester

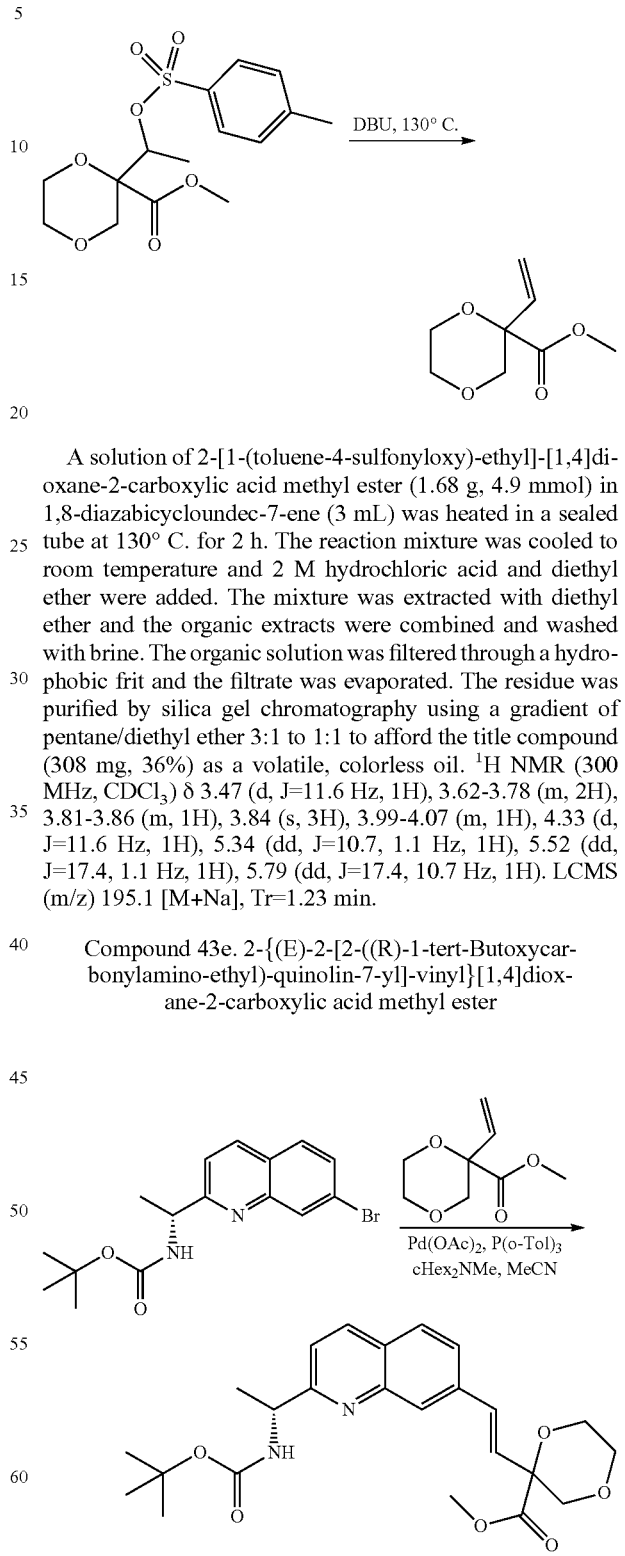

A solution of 2-[1-(toluene-4-sulfonyloxy)-ethyl]-[1,4]dioxane-2-carboxylic acid methyl ester (1.68 g, 4.9 mmol) in 1,8-diazabicycloundec-7-ene (3 mL) was heated in a sealed tube at 130° C. for 2 h. The reaction mixture was cooled to room temperature and 2 M hydrochloric acid and diethyl ether were added. The mixture was extracted with diethyl ether and the organic extracts were combined and washed with brine. The organic solution was filtered through a hydrophobic frit and the filtrate was evaporated. The residue was purified by silica gel chromatography using a gradient of pentane/diethyl ether 3:1 to 1:1 to afford the title compound (308 mg, 36%) as a volatile, colorless oil. $^1$H NMR (300 MHz, CDCl$_3$) δ 3.47 (d, J=11.6 Hz, 1H), 3.62-3.78 (m, 2H), 3.81-3.86 (m, 1H), 3.84 (s, 3H), 3.99-4.07 (m, 1H), 4.33 (d, J=11.6 Hz, 1H), 5.34 (dd, J=10.7, 1.1 Hz, 1H), 5.52 (dd, J=17.4, 1.1 Hz, 1H), 5.79 (dd, J=17.4, 10.7 Hz, 1H). LCMS (m/z) 195.1 [M+Na], Tr=1.23 min.

Compound 43e. 2-{(E)-2-[2-((R)-1-tert-Butoxycarbonylamino-ethyl)-quinolin-7-yl]-vinyl}[1,4]dioxane-2-carboxylic acid methyl ester A solution of [(R)-1-(7-bromo-quinolin-2-yl)-ethyl]-carbamic acid tert-butyl ester (316 mg, 0.9 mmol), 2-vinyl-[1,4] dioxane-2-carboxylic acid methyl ester (154 mg, 0.9 mmol), palladium(II) acetate (41 mg, 0.18 mmol), tri(o-tolyl)phosphine (54 mg, 0.18 mmol) and N,N-dicyclohexylmethylamine (351 mg, 0.38 mL, 1.8 mmol) in acetonitrile (8 mL) was heated at 120° C. in a microwave reactor for 30 minutes. The reaction mixture was filtered and the solvent was evaporated. The residue was dissolved in dichloromethane; brine and ice-cold 1 M hydrochloric acid were added to acidify the mixture to pH 2. The organic layer was separated and washed with brine. The organic solution was filtered through a hydrophobic frit and the filtrate was evaporated. The residue was purified by silica gel chromatography using a gradient of iso-hexanes/ethyl acetate 7:3 to 6:4 to afford the title compound (157 mg, 40%) as a yellow gum and as a 1:1 mixture of diastereoisomers. LCMS (m/z) 443.1 [M+H], Tr=2.34 min.

Compound 43f. 2-{(E)-2-[2-((R)-1-tert-Butoxycarbonylamino-ethyl)-quinolin-7-yl]-vinyl}-[1,4]dioxane-2-carboxylic acid

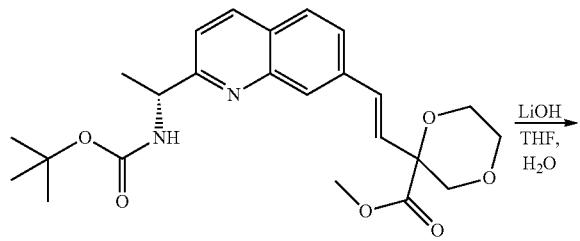

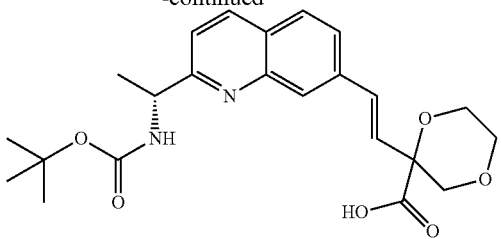

A solution of 2-{(E)-2-[2-((R)-1-tert-butoxycarbonylamino-ethyl)-quinolin-7-yl]-vinyl}-[1,4]dioxane-2-carboxylic acid methyl ester (157 mg, 0.35 mmol) in tetrahydrofuran (6 mL) was stirred at 5° C. under nitrogen. A solution of lithium hydroxide monohydrate (30 mg, 0.71 mmol) in water (1.5 mL) was added and the reaction mixture was stirred at room temperature for 18 h. The majority of the organic solvent was evaporated. The solution was acidified to pH 2 with 2 M hydrochloric acid and the mixture was extracted with dichloromethane. The organic extracts were combined and washed with brine. The organic solution was filtered through a hydrophobic frit and the filtrate was evaporated to afford the title compound (149 mg, 100%) as a pale yellow foam and as a 1:1 mixture of diastereoisomers. LCMS (m/z) 429.1 [M+H], Tr=1.87 min.

Compound 43g. (S)-1-{(S)-2-[(S)-2-(2-{(E)-2-[2-((R)-1-tert-Butoxycarbonylamino-ethyl)-quinolin-7-yl]-vinyl}-[1,4]dioxane-2-carbonyloxy)-3-methyl-butyrylamino]-propionyl}-hexahydro-pyridazine-3-carboxylic acid 2,2,2-trichloro-ethyl ester

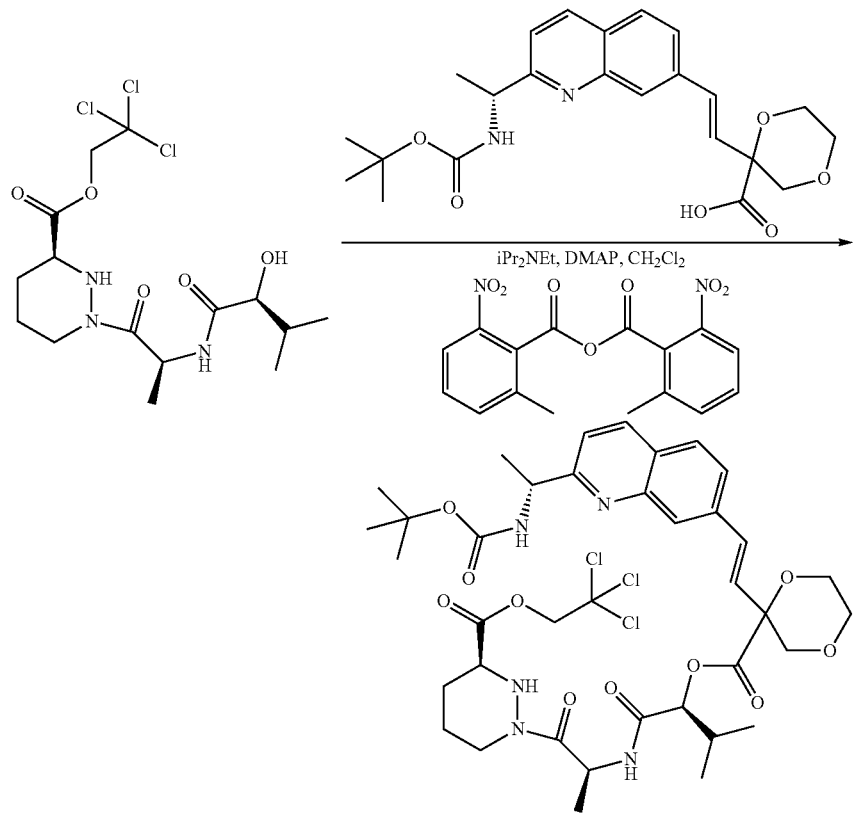

A solution of 2-{(E)-2-[2-((R)-1-tert-butoxycarbonylamino-ethyl)-quinolin-7-yl]-vinyl}-[1,4]dioxane-2-carboxylic acid (50 mg, 0.1 mmol), [(S)-1-[(S)-2-((S)-2-hydroxy-3-methyl-butyrylamino)-propionyl]-hexahydro-pyridazine-3-carboxylic acid 2,2,2-trichloro-ethyl ester (44 mg, 0.1 mmol), N,N-diisopropylethylamine (32 mg, 0.043 mL, 0.25 mmol), 4-dimethylaminopyridine (6 mg, 0.05 mmol) and 2-methyl-6-nitrobenzoic anhydride (58 mg, 0.17 mmol) in dichloromethane (5 mL) was stirred at room temperature under nitrogen for 18 h. The reaction mixture was diluted with dichloromethane and the solution was washed with ice-cold saturated ammonium chloride solution, ice-cold saturated sodium hydrogen carbonate solution and brine. The organic solution was filtered through a hydrophobic frit and the filtrate was evaporated. The residue was purified by silica gel chromatography using a gradient of iso-hexanes/ethyl acetate 1:1 to 1:3 to afford the title compound (47 mg, 55%) as a white solid and as a 1:1 mixture of diastereoisomers. LCMS (m/z) 842.2/844.0 [M+H], Tr=3.25 and 3.31 min.

Compounds 43 and 44

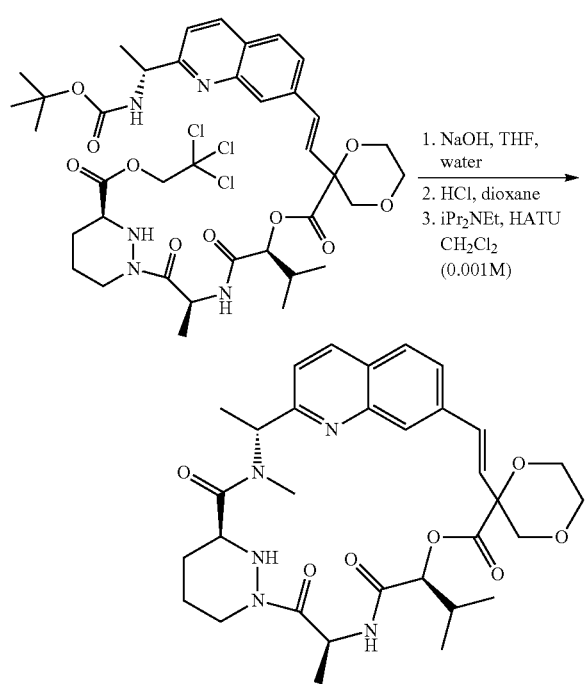

A solution of (S)-1-{(S)-2-[(S)-2-(2-{(E)-2-[2-((R)-1-tert-butoxycarbonylamino-ethyl)-quinolin-7-yl]-vinyl}-[1,4]dioxane-2-carbonyloxy)-3-methyl-butyrylamino]-propionyl}-hexahydro-pyridazine-3-carboxylic acid 2,2,2-trichloro-ethyl ester (69 mg, 0.081 mmol) in tetrahydrofuran (4 mL) was stirred at 0° C. under nitrogen. An ice-cold aqueous solution of sodium hydroxide (0.1 M, 0.82 mL, 0.082 mmol) was added and the reaction mixture was stirred at 0° C. for 20 minutes. Cold 1 M hydrochloric acid was added to acidify the mixture to pH 2 and the solvent was evaporated. The residue was co-evaporated with tetrahydrofuran/toluene (1:1, 3×) and the residue was triturated with diethyl ether (2×) and the resulting solid was dried to afford (S)-1-{(S)-2-[(S)-2-(2-{(E)-2-[2-((R)-1-tert-butoxycarbonylamino-ethyl)-quinolin-7-yl]-vinyl}-[1,4]dioxane-2-carbonyloxy)-3-methyl-butyrylamino]-propionyl}-hexahydro-pyridazine-3-carboxylic acid (0.081 mmol) as a yellow solid and as a 1:1 mixture of diastereoisomers which was used crude in the next reaction. LCMS (m/z) 712.3 [M+H], Tr=2.46 min.

A mixture of crude (S)-1-{(S)-2-[(S)-2-(2-{(E)-2-[2-((R)-1-tert-butoxycarbonylamino-ethyl)-quinolin-7-yl]-vinyl}-[1,4]dioxane-2-carbonyloxy)-3-methyl-butyrylamino]-propionyl}-hexahydro-pyridazine-3-carboxylic acid (0.081 mmol) in 4 M hydrogen chloride in 1,4-dioxane (2 mL) was stirred at room temperature for 1 h. The solvent was evaporated and the residue was co-evaporated with diethyl ether (2×) and the resulting solid was dried to afford (S)-1-{(S)-2-[(S)-2-(2-{(E)-2-[2-((R)-1-amino-ethyl)-quinolin-7-yl]-vinyl}-[1,4]dioxane-2-carbonyloxy)-3-methyl-butyrylamino]-propionyl}-hexahydro-pyridazine-3-carboxylic acid hydrochloride (0.081 mmol) as an off-white solid and as a 1:1 mixture of diastereoisomers which was used crude in the next reaction. LCMS (m/z) 612.1 [M+H], Tr=1.38 min.

A suspension of crude (S)-1-{(S)-2-[(S)-2-(2-{(E)-2-[2-((R)-1-amino-ethyl)-quinolin-7-yl]-vinyl}-[1,4]dioxane-2-carbonyloxy)-3-methyl-butyrylamino]-propionyl}-hexahydro-pyridazine-3-carboxylic acid hydrochloride (0.081 mmol) in dichloromethane (75 mL) was stirred at 0° C. under nitrogen. A solution of N,N-diisopropylethylamine (42 mg, 0.324 mmol) in dichloromethane (6 mL) was added and the resulting solution was stirred at 0° C. 2-(1H-7-Azabenzotriazol-1-yl)-1,1,3,3-tetramethyl uronium hexafluorophosphate methanaminium (62 mg, 0.162 mmol) was added and the reaction mixture was stirred at 0° C. for 30 minutes and then at room temperature for 1 h. The majority of the solvent was evaporated and the solution (~20 mL) was washed with ice-cold 1 M hydrochloric acid and brine. The organic solution was filtered through a hydrophobic frit and the filtrate was evaporated. The residue was purified by silica gel chromatography using a gradient of iso-hexanes/ethyl acetate 1:4 to 0:1 to afford a 1:1 mixture of diastereoisomers. The mixture was purified by reverse phase preparative HPLC eluting with acetonitrile/water 3:7 to afford the two separate diastereoisomers.

Compound 43 (First eluting) Diastereoisomer 1: (4.0 mg, 8%) as a white solid. ¹H NMR (300 MHz, CD₃OD) δ 1.06 (d, J=6.7 Hz, 3H), 1.12 (d, J=6.7 Hz, 3H), 1.56-1.60 (m, 7H), 1.68-1.73 (m, 1H), 1.95-2.00 (m, 1H), 2.20-2.35 (m, 2H), 2.69-2.78 (m, 1H), 3.55-3.85 (m, 5H), 4.03-4.12 (m, 1H), 4.43-4.48 (m, 1H), 4.57 (d, J=11.6 Hz, 1H), 5.12 (q, J=6.7 Hz, 1H), 5.24 (d, J=10.4 Hz, 1H), 5.39 (d, J=8.5 Hz, 1H), 5.83 (q, J=7.2 Hz, 1H), 6.29 (d, J=16.3 Hz, 1H), 6.97 (d, J=16.3 Hz, 1H), 7.49 (d, J=8.5 Hz, 1H), 7.61 (dd, J=8.5, 1.3 Hz, 1H), 7.86-7.90 (m, 2H), 8.28 (d, J=8.5 Hz, 1H). LCMS (m/z) 594.2 [M+H], Tr=2.14 min.

Compound 44 (Second eluting) Diastereoisomer 2: (4.6 mg, 10%) as a white solid. ¹H NMR (300 MHz, CD₃OD) δ 1.08 (d, J=6.5 Hz, 3H), 1.10 (d, J=6.5 Hz, 3H), 1.49-1.54 (m, 1H), 1.59 (d, J=6.7 Hz, 3H), 1.64 (d, J=7.1 Hz, 3H), 1.66-1.71 (m, 1H), 1.90-1.96 (m, 1H), 2.20-2.28 (m, 2H), 2.63-2.71 (m, 1H), 3.55-3.93 (m, 6H), 4.40-4.47 (m, 2H), 4.98 (d, J=12.0 Hz, 1H), 5.09 (q, J=6.7 Hz, 1H), 5.20 (d, J=8.9 Hz, 1H), 5.79 (q, J=7.1 Hz, 1H), 6.10 (d, J=16.3 Hz, 1H), 6.88 (d, J=16.3 Hz, 1H), 7.47 (d, J=8.5 Hz, 1H), 7.62 (dd, J=8.5, 1.6 Hz, 1H), 7.85-7.88 (m, 2H), 8.26 (d, J=8.5 Hz, 1H). LCMS (m/z) 594.2 [M+H], Tr=2.17 min.

Examples 45 and 46

Compounds 45 and 46

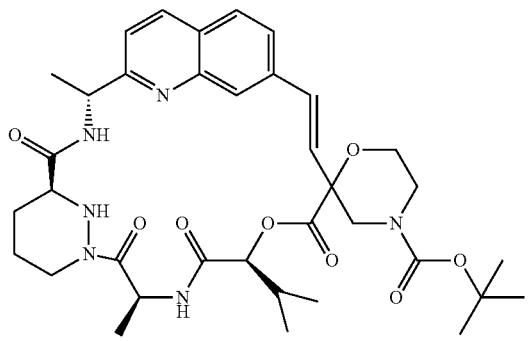 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)CN(C(=O)OC(C)(C)C)CCO2]

Compound 45a. Morpholine-2,4-dicarboxylic acid 4-tert-butyl ester 2-methyl ester

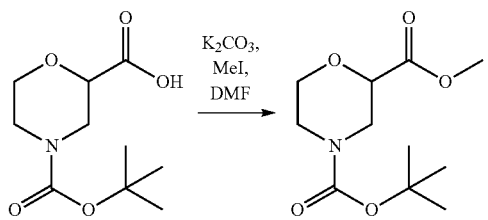 [SMILES: CC(C)(C)OC(=O)N1CCOC(C(=O)O)C1 ; COC(=O)C1CN(C(=O)OC(C)(C)C)CCO1]

A solution of morpholine-2,4-dicarboxylic acid 4-tert-butyl ester (supplied by NeoMPS, Inc.), (5.78 g, 25.0 mmol) in N,N-dimethylformamide (30 mL) was subsequently treated with potassium carbonate (4.14 g, 30.0 mmol) and iodomethane (7.10 g, 3.1 mL, 50.0 mmol). After stirring at room temperature for 18 h, the reaction mixture was diluted with water and the aqueous layer was extracted with ethyl acetate. The organic extracts were combined, washed with water (4x) and brine then filtered through a hydrophobic frit and the volatiles were removed in vacuo. The residue was purified by silica gel chromatography using a gradient of iso-hexanes/ethyl acetate 3:1 to 1:3 to afford the title compound (4.83 g, 79%) as a white solid. $^1$H NMR (300 MHz, CDCl$_3$) δ 1.49 (s, 9H), 3.06-3.15 (m, 2H), 3.56-3.64 (m, 1H), 3.75-3.79 (m, 1H), 3.81 (s, 3H), 4.00-4.14 (m, 3H). LCMS (m/z) 268.1 [M+Na], Tr=1.94 min.

Compound 45b. 2-(1-Hydroxy-ethyl)-morpholine-2,4-dicarboxylic acid 4-tert-butyl ester 2-methyl ester

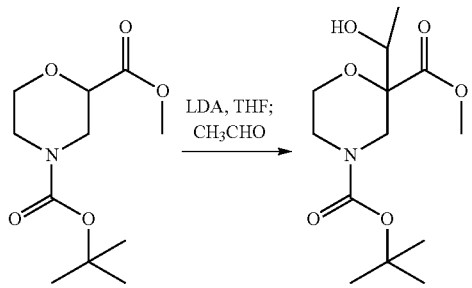 [SMILES: COC(=O)C1CN(C(=O)OC(C)(C)C)CCO1 ; COC(=O)C1(C(C)O)CN(C(=O)OC(C)(C)C)CCO1]

A cooled (−78° C.) solution of N,N-diisopropylamine (1.3 mL, 9.092 mmol, dried over calcium hydride) in anhydrous tetrahydrofuran (10 mL) was treated with a solution of n-butyllithium in hexanes (3.4 mL, 8.524 mmol, 2.5 M). After stirring at −78° C. for 30 minutes, the mixture was treated with a solution of morpholine-2,4-dicarboxylic acid 4-tert-butyl ester 2-methyl ester (1.394 g, 5.683 mmol) in anhydrous tetrahydrofuran (10 mL). After stirring at −78° C. for 20 minutes, the mixture was treated with acetaldehyde (0.96 mL, 17.05 mmol). After stirring at room temperature for 1 h, the reaction was quenched at 0° C. with hydrochloric acid (1 M, 40 mL). The aqueous layer was extracted with dichloromethane (2x). The organics were combined, filtered through a phase separator and the volatiles were removed in vacuo. The residue was purified by silica gel chromatography using a 50 g Isolute cartridge eluted with a continuous gradient of iso-hexanes/ethyl acetate 1:0 to 3:2 to afford the title compound (1.476 g, 90%) as a yellow oil and as a 2:1 mixture of diastereoisomers.

Compound 45c. 2-(1-Trifluoromethanesulfonyloxy-ethyl)-morpholine-2,4-dicarboxylic acid 4-tert-butyl ester 2-methyl ester

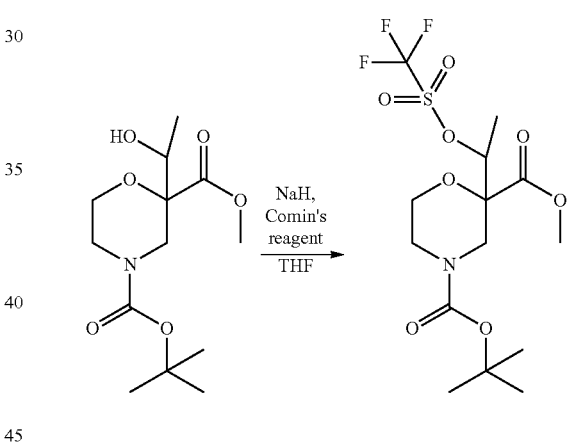

A cooled (−78° C.) suspension of sodium hydride (262 mg, 6.542 mmol, 60% in mineral oil) in anhydrous tetrahydrofuran (10 mL) was treated with a solution of 2-(1-hydroxy-ethyl)-morpholine-2,4-dicarboxylic acid 4-tert-butyl ester 2-methyl ester (1.262 g, 4.361 mmol) in anhydrous tetrahydrofuran (10 mL). The light yellow suspension was stirred at −78° C. for 15 minutes and then treated with a solution of N-(5-chloro-2-pyridyl)bis(trifluoromethanesulfonimide) (3.425 g, 8.722 mmol) in anhydrous tetrahydrofuran (10 mL). After stirring at room temperature for 1.5 h, the reaction was quenched with a saturated solution of ammonium chloride. The aqueous layer was extracted with dichloromethane (2x). The organics were combined, filtered through a phase separator and the volatiles were removed in vacuo. The residue was purified by silica gel chromatography using a 50 g Isolute cartridge eluted with a continuous gradient of iso-hexanes/ethyl acetate 1:0 to 4:1 to afford the title compound (1.384 g, 75%) as a light yellow oil and as a 2:1 mixture of diastereoisomers.

Compound 45d.
2-Vinyl-morpholine-2,4-dicarboxylic acid 4-tert-butyl ester 2-methyl ester

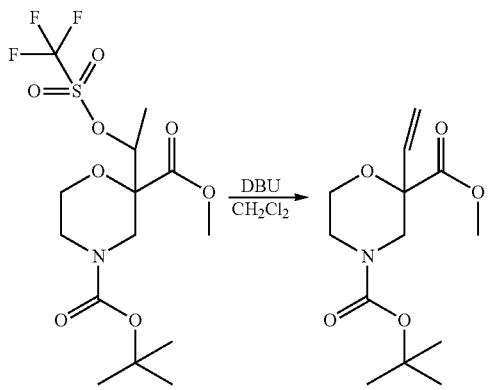

A warm (35° C.) solution of 2-(1-trifluoromethanesulfonyloxy-ethyl)-morpholine-2,4-dicarboxylic acid 4-tert-butyl ester 2-methyl ester (1.384 g, 3.284 mmol) in dichloromethane (40 mL) was treated with 1,8-diazabicyclo[5.4.0]undec-7-ene (2.5 mL, 16.422 mmol). After stirring at 35° C. for 2 h, the reaction was cooled to 0° C. and quenched with hydrochloric acid (1 M, 50 mL). The aqueous layer was extracted with dichloromethane. The organics were combined, filtered through a phase separator and the volatiles were removed in vacuo to provide the title compound as an orange oil which was used without further purification in the next step. $^1$H NMR (300 MHz, CDCl$_3$) δ 1.49 (s, 9H), 3.13-3.29 (m, 2H), 3.60-3.73 (m, 1H), 3.79 (s, 3H), 3.83-3.92 (m, 2H), 4.24 (d, J=13.1 Hz, 1H), 5.37 (d, J=10.9 Hz, 1H), 5.55 (d, J=17.4 Hz, 1H), 5.84 (dd, J=17.4, 10.9 Hz, 1H).

Compound 45e.
2-Vinyl-morpholine-2,4-dicarboxylic acid 4-tert-butyl ester

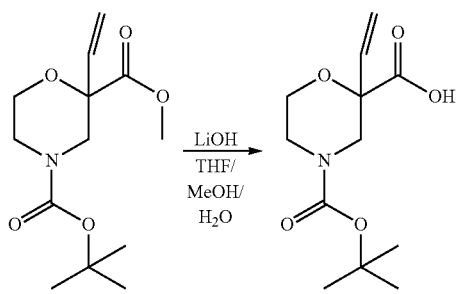

A solution of crude 2-vinyl-morpholine-2,4-dicarboxylic acid 4-tert-butyl ester 2-methyl ester (3.284 mmol) in tetrahydrofuran/methanol/water (50 mL, 2:2:1) was treated with lithium hydroxide monohydrate (413.3 mg, 9.852 mmol). After stirring at room temperature for 2 h, the volatiles were removed in vacuo and the residue was cooled to 0° C. and quenched with hydrochloric acid (1 M). The aqueous layer was extracted with dichloromethane (2×). The combined organics were filtered through a phase separator and the volatiles were removed in vacuo to provide the title compound (761.4 mg, 90% over 2 steps) as colorless needles. $^1$H NMR (300 MHz, CDCl$_3$) δ 1.48 (s, 9H), 3.31-3.42 (m, 1H), 3.45-3.61 (m, 2H), 3.87-3.94 (m, 2H), 4.02 (d, J=13.6 Hz, 1H), 5.44 (d, J=10.7 Hz, 1H), 5.60 (d, J=17.4 Hz, 1H), 5.85 (dd, J=17.4, 10.7 Hz, 1H).

Compound 45f. 2-((E)-2-{2-[(R)-1-({(S)-1-[(S)-2-((S)-2-Hydroxy-3-methyl-butyrylamino)-propionyl]-hexahydro-pyridazine-3-carbonyl}-amino)-ethyl]-quinolin-7-yl}-vinyl)-morpholine-2,4-dicarboxylic acid 4-tert-butyl ester A solution of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (95 mg, 0.178 mmol), 2-vinyl-morpholine-2,4-dicarboxylic acid 4-tert-butyl ester (45.7 mg, 0.178 mmol), tri(o-tolyl)phosphine (11 mg, 0.036 mmol) and triethylamine (0.08 mL, 0.534 mmol) in 1,4-dioxane (5 mL) was degassed by bubbling nitrogen through for 5 minutes then warmed to 50° C. and treated with tris(dibenzylideneacetone)dipalladium(0) (16.3 mg, 0.018 mmol). After stirring at 100° C. for 50 minutes the reaction was cooled to room temperature, filtered through a pad of Celite, which was rinsed with ethyl acetate. The volatiles were removed in vacuo to provide crude title compound as an orange foam that was used without further purification. LCMS (m/z) 711.3 [M+H], Tr=2.14 min.

Compound 45 and 46

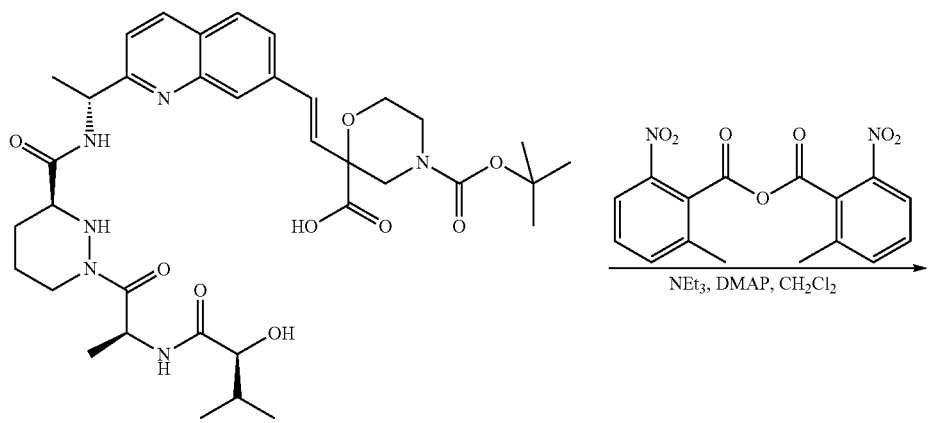

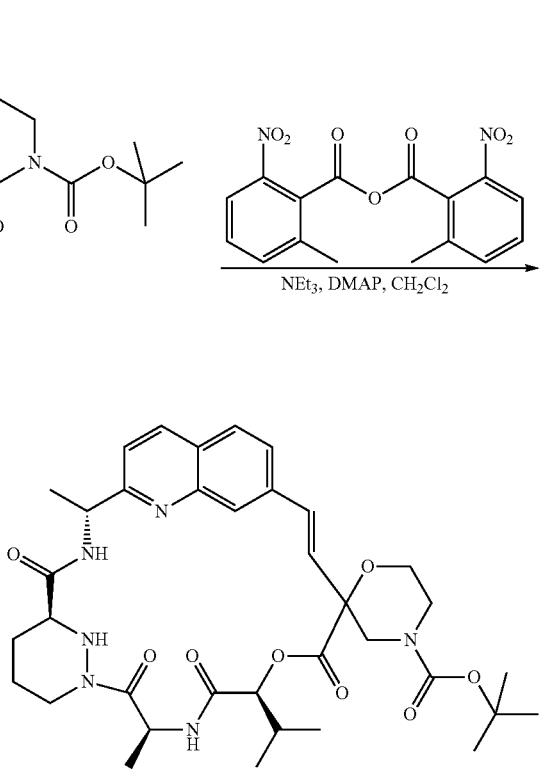

A solution of crude 2-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-morpholine-2,4-dicarboxylic acid 4-tert-butyl ester (0.178 mmol), 4-dimethylaminopyridine (21.7 mg, 0.178 mmol) and triethylamine (0.08 mL, 0.534 mmol) in dry dichloromethane (150 mL) was treated with 2-methyl-6-nitrobenzoic anhydride (122.6 mg, 0.356 mmol). After stirring at room temperature for 1.5 h, more 2-methyl-6-nitrobenzoic anhydride (122.6 mg, 0.356 mmol) was added. After stirring at room temperature for 16 h, more triethylamine (0.2 mL) and 4-dimethylaminopyridine (217 mg, 1.780 mmol) were added. After stirring at room temperature for 4 h, the volatiles were removed in vacuo. The residue was partitioned between dichloromethane and a saturated solution of sodium bicarbonate. The aqueous layer was extracted with dichloromethane. The organics were combined, filtered through a phase separator and the volatiles were removed in vacuo. The residue was purified by silica gel chromatography using a 25 g Isolute cartridge eluted with a continuous gradient of isohexanes/ethyl acetate 1:0 to 0:1 then by reverse phase preparative HPLC eluting with a continuous gradient of water/acetonitrile 95:5 to 0:1 to afford the title compound as two separate isomers.

Compound 45 (Second eluting) Diastereomer 1 (1.9 mg, 1.5%) as a white solid. $^1$H NMR (300 MHz, CD$_3$OD) δ 1.06 (d, J=6.7 Hz, 6H), 1.47-1.54 (m, 10H), 1.55-1.77 (m, 8H), 1.90-2.00 (m, 1H), 2.16-2.31 (m, 2H), 2.62-2.74 (m, 1H), 3.04-3.18 (m, 2H), 3.54-3.62 (m, 1H), 3.68-3.80 (m, 1H), 3.83-3.93 (m, 1H), 3.94-4.03 (m, 1H), 4.38-4.47 (m, 1H), 4.57-4.67 (m, 1H), 5.03 (d, J=12.0 Hz, 1H), 5.10 (q, J=6.7 Hz, 1H), 5.19 (d, J=8.7 Hz, 1H), 5.80 (q, J=7.3 Hz, 1H), 6.18 (d, J=16.3 Hz, 1H), 6.93 (d, J=16.3 Hz, 1H), 7.47 (d, J=8.5 Hz, 1H), 7.62 (dd, J=8.5, 1.3 Hz, 1H), 7.87 (d, J=8.5 Hz, 1H), 7.90 (s, 1H), 8.27 (d, J=8.5 Hz, 1H). LCMS (m/z) 693.3 [M+H], Tr=2.68 min.

Compound 46 (First eluting) Diastereomer 2 (0.8 mg, 1%) as a white solid. $^1$H NMR (300 MHz, CD$_3$OD) δ 0.97-1.06 (m, 6H), 1.40 (d, J=6.7 Hz, 3H), 1.43-1.58 (m, 13H), 1.65-1.74 (m, 1H), 1.97-2.07 (m, 1H), 2.18-2.37 (m, 2H), 3.42-3.49 (m, 1H), 3.74-4.03 (m, 4H), 5.16 (q, J=7.1 Hz, 1H), 5.27-5.33 (m, 1H), 5.35 (q, J=6.7 Hz, 1H), 6.58 (d, J=16.3 Hz, 1H), 6.78 (d, J=7.1 Hz, 1H), 7.20 (d, J=16.0 Hz, 1H), 7.44 (d, J=8.5 Hz, 1H), 7.70 (d, J=8.5 Hz, 1H), 7.74-7.81 (m, 1H), 7.99 (s, 1H), 8.06 (d, J=7.6 Hz, 1H), 8.13 (d, J=8.5 Hz, 1H). LCMS (m/z) 693.5 [M+H], Tr=3.39 min.

Example 47

Compound 47

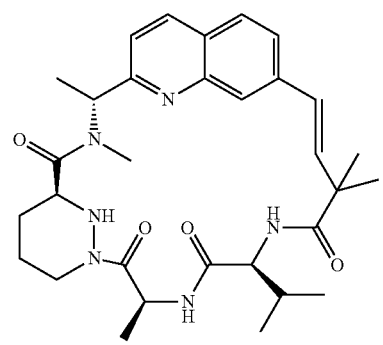 [SMILES: CC(C)[C@@H]1NC(=O)C(C)(C)/C=C/c2ccc3ccc(nc3c2)[C@@H](C)N(C)C(=O)[C@@H]2CCCN(N2)C(=O)[C@H](C)NC1=O]

Compound 47a. (S)-1-{(S)-2-[(S)-2-((E)-4-{2-[(R)-1-(tert-Butoxycarbonyl-methyl-amino)-ethyl]-quinolin-7-yl}-2,2-dimethyl-but-3-enoyloxy)-3-methyl-butyrylamino]-propionyl}-hexahydro-pyridazine-3-carboxylic acid 2,2,2-trichloro-ethyl ester

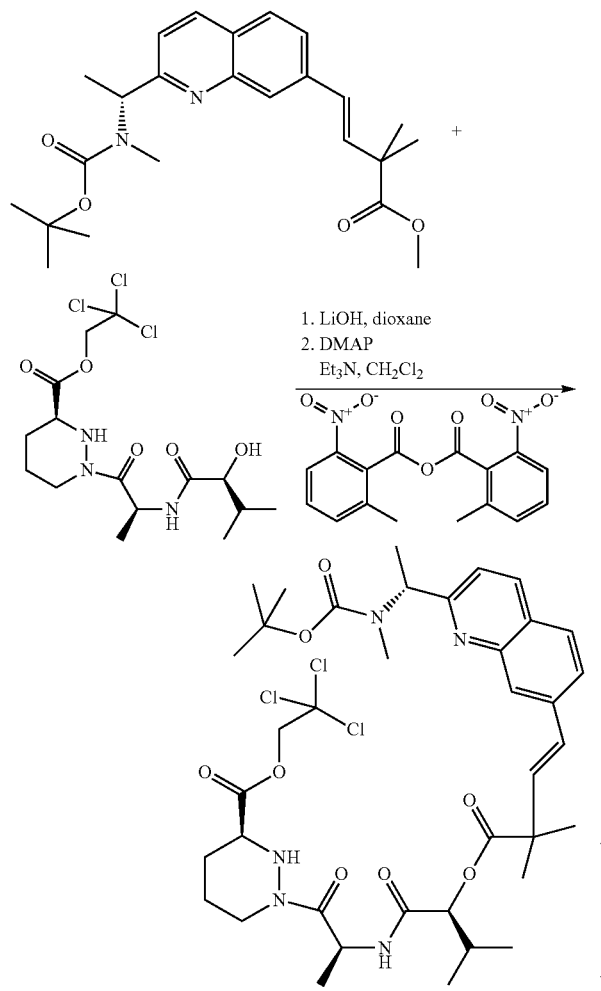

A solution of (E)-4-{2-[(R)-1-(tert-butoxycarbonyl-methyl-amino)-ethyl]-quinolin-7-yl}-2,2-dimethyl-but-3-enoic acid methyl ester (193 mg, 0.47 mmol) in 1,4-dioxane (10 mL) was treated with a solution of lithium hydroxide monohydrate (112 mg, 4.7 mmol) in water (5 mL). After stirring at 50° C. for 1 h, the volatiles were removed in vacuo. The residue was partitioned between water and diethyl ether. The aqueous layer was acidified to pH 2 by addition of hydrochloric acid then extracted with ethyl acetate (3×). The organics were combined and the volatiles were removed in vacuo. The residue was dissolved in dichloromethane (10 mL) and was treated with 4-dimethylaminopyridine (57 mg, 0.47 mmol), 2-methyl-6-nitrobenzoic anhydride (275 mg, 0.80 mmol), and triethylamine (0.197 mL, 1.41 mmol). After stirring for 30 min (S)-1-[(S)-2-((S)-2-hydroxy-3-methyl-butyrylamino)-propionyl]-hexahydro-pyridazine-3-carboxylic acid 2,2,2-trichloro-ethyl ester (203 mg, 0.47 mmol) was added. After stirring for 16 h, the reaction was quenched by addition of a sodium bicarbonate solution (10 mL), the aqueous layer was extracted with dichloromethane (2×), the organics were combined and the volatiles were removed in vacuo. The residue was purified by silica gel chromatography using a 25 g Biotage cartridge eluted with a continuous gradient of isohexanes/acetone 1:0 to 3:1 to afford the title compound (260 mg, 68%) as a white solid. $^1$H NMR (300 MHz, CD$_3$OD) δ 0.97-1.05 (m, 6H), 1.29 (d, J=6.9 Hz, 3H), 1.44 (br s, 9H), 1.55 (s, 3H), 1.57 (s, 3H), 1.68 (d, J=6.9 Hz, 3H), 1.71-2.00 (m, 4H), 2.02-2.30 (m, 3H), 2.80 (br s, 3H), 3.56 (br s, 1H), 3.78-3.83 (m, 1H), 4.75-4.82 (m, 1H), 4.93-5.01 (m, 2H), 5.35-5.45 (m, 1H), 6.65-6.82 (m, 2H), 7.36 (d, J=8.5 Hz, 1H), 7.72-7.83 (m, 2H), 7.98 (s, 1H), 8.21 (d, J=8.5 Hz, 1H). LCMS (m/z) 814.1 [M+H], Tr=3.97 min.

Compound 47

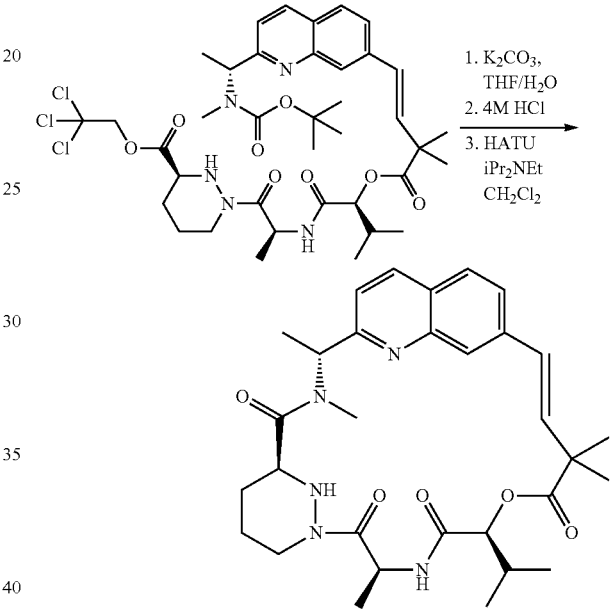

A solution of (S)-1-{(S)-2-[(S)-2-((E)-4-{2-[(R)-1-(tert-butoxycarbonyl-methyl-amino)-ethyl]-quinolin-7-yl}-2,2-dimethyl-but-3-enoyloxy)-3-methyl-butyrylamino]-propionyl}-hexahydro-pyridazine-3-carboxylic acid 2,2,2-trichloro-ethyl ester (260 mg, 0.32 mmol) in tetrahydrofuran (30 mL) was prepared and a solution of potassium carbonate (663 mg, 4.80 mmol) in water (15 mL) was added. The reaction was stirred at room temperature for 1.5 h. The reaction mixture was acidified to pH 3 with hydrochloric acid (1 M) then extracted with ethyl acetate (3×20 mL). The combined extracts were dried over anhydrous sodium sulfate, filtered and evaporated. The residue was dried under vacuum for 1 h before dissolving in dichloromethane (30 mL) and treating with hydrogen chloride in 1,4-dioxane (4 M, 15 mL). It was stirred for 1 h at room temperature then evaporated. Residual water was azeotroped off with toluene (2×20 mL) to yield a white solid (251 mg). The white solid was dissolved in anhydrous N,N-dimethylformamide (10 mL) and N,N-diisopropylethylamine (279 µL, 1.6 mmol) was added. This solution was then added via a syringe pump to a stirred solution of 2-(1H-7-azabenzotriazol-1-yl)-1,1,3,3-tetramethyl uronium hexafluorophosphate methanaminium (183 mg, 0.48 mmol) in anhydrous dichloromethane (150 mL) over 1 h. The reaction mixture was washed with saturated sodium bicarbonate solution (30 mL), filtered through a phase separator and evaporated. The residue was purified by reverse phase preparative HPLC to yield the title product (54 mg, 30%) as a white solid. $^1$H NMR (300 MHz, CDCl$_3$) δ 0.97 (s, 3H), 0.99 (s, 3H), 1.44 (s, 3H), 1.50-1.55 (m, 6H), 1.56-2.03 (m, 4H), 1.68 (d, J=7.4 Hz, 3H), 2.20-2.34 (m, 1H), 2.64-2.79 (m, 1H), 3.14 (s, 3H), 3.90-4.01 (m, 1H), 4.50-4.61 (m, 1H), 4.85 (d, J=8.5 Hz, 3H), 5.88-6.15 (m, 1H), 6.30 (d, J=16.5 Hz, 1H), 6.38 (d, J=8.0 Hz, 1H), 6.53 (d, J=16.3 Hz, 1H), 6.61-6.87 (m, 1H), 7.28 (d, J=8.5 Hz, 1H), 7.52 (d, J=8.3 Hz, 1H), 7.68 (d, J=8.5 Hz, 1H), 7.87 (s, 1H), 8.05 (d, J=8.5 Hz, 1H). LCMS (m/z) 564.2 [M+H], Tr=2.54 min.

Example 48

Compound 48

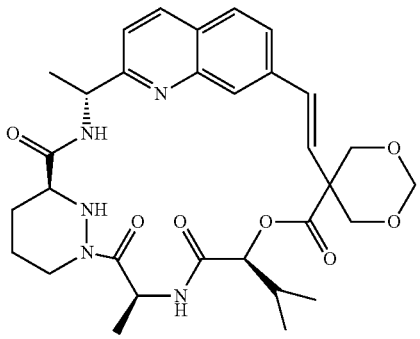 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)COCOC2]

Compound 48a. Ethyl 2,2-bis(hydroxymethyl)-3-oxobutanoate

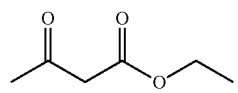

To a stirred solution of ethyl acetoacetate (150 g, 1.2 mol) in formaldehyde (210 mL, 2.8 mol, 40% aq.) and dioxane (550 mL) was added dropwise triethylamine (1.0 M in tetrahydrofuran, 57 mL, 0.06 mol) at 0° C. The temperature was raised up to 35-40° C. and the mixture was stirred for 1 h. The reaction mixture was diluted with water (400 mL), and the side products were extracted with toluene (3×600 mL). The aqueous phase was evaporated at 35° C. to one fourth of the initial volume and extracted with ethyl acetate (3×900 mL). The extracts were dried over sodium sulfate and evaporated to get the crude product (75 g) as yellow oil, which was used directly to the next step without purification.

Compound 48b. Ethyl 5-acetyl-1,3-dioxane-5-carboxylate

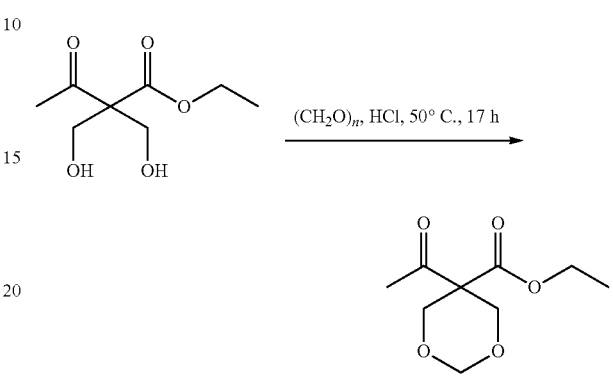

A solution of ethyl 2,2-bis(hydroxymethyl)-3-oxobutanoate (75 g, 0.39 mol) and 40% formaldehyde (360 mL) in concentrated hydrochloric acid (360 mL) was heated at 50° C. for 17 h. The two-phase solution was cooled to room temperature and extracted with ethyl acetate (2×200 mL). The combined organic phases were washed with water, dried over magnesium sulfate, and evaporated to give a residue, which was purified by flash column chromatography eluting with a continuous gradient of petroleum ether/ethyl acetate 15:1 to 9:1 to afford the title compound (33 g, 14%, 2 steps) as a colorless oil. $^1$H NMR (400 MHz, CDCl$_3$) δ 1.25 (m, 3H), 2.31 (s, 3H), 4.25-4.19 (m, 4H), 4.35 (d, J=12.0 Hz, 2H), 4.77 (d, J=6.0 Hz, 1H), 4.82 (d, J=6.0 Hz, 1H).

Compound 48c. Ethyl 5-(1-hydroxyethyl)-1,3-dioxane-5-carboxylate

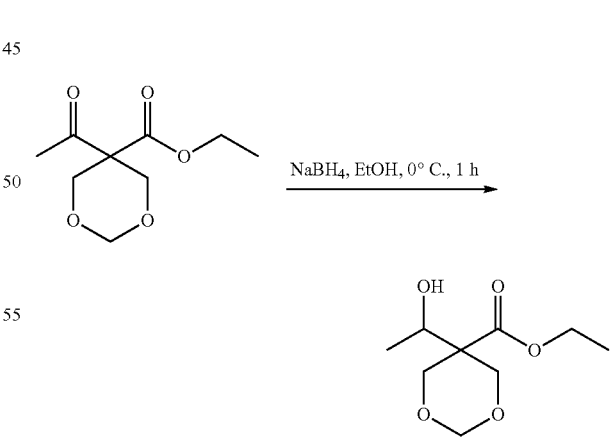

Ethyl 5-acetyl-1,3-dioxane-5-carboxylate (2) (22.3 g, 0.11 mol) was dissolved in ethanol (100 mL) and sodium borohydride (2.08 g, 0.055 mol) was added at 0° C. in portions. The mixture was stirred at the same temperature for 1 h. The excess of sodium borohydride was destroyed with acetone and the solution was extracted with ethyl acetate (3×600 mL).

The combined organic extracts were concentrated in vacuo to give the title compound (18.9 g, 84%) as colorless oil.

Compound 48d. Ethyl 5-(1-(tosyloxy)ethyl)-1,3-dioxane-5-carboxylate

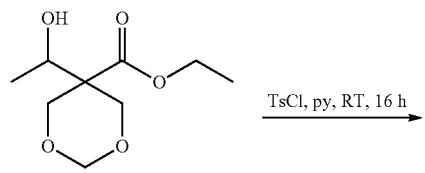

To a mixture of ethyl 5-(1-hydroxyethyl)-1,3-dioxane-5-carboxylate (16.8 g, 83 mmol) in dry pyridine (40 mL) at 0° C. was added 4-toluenesulfonyl chloride (19.1 g, 99 mmol). The mixture was stirred at rt for 16 h. Water (40 mL) was added, and the mixture was extracted with ethyl acetate (2×400 mL). The organic layer was washed with brine (3×). After concentrated in vacuo, the crude product was purified by silica gel chromatography eluting with petroleum ether/ethyl acetate 25:1 to 5:1 to provide the title compound (22.7 g, 76%) as a colorless oil. $^1$H NMR (400 MHz, CDCl$_3$) δ 1.26 (m, 3H), 1.34 (d, J=6.8 Hz, 3H), 2.45 (s, 3H), 3.80 (d, J=11.6 Hz, 1H), 3.87 (d, J=11.6 Hz, 1H), 4.02 (d, J=11.6 Hz, 1H), 4.08 (d, J=12.0 Hz, 1H), 4.20-4.17 (m, 2H), 5.03-4.98 (m, 1H), 7.34 (d, J=8.0 Hz, 2H), 7.79 (d, J=8.8 Hz, 2H).

Compound 48e. 5-Vinyl-[1,3]dioxane-5-carboxylic acid ethyl ester

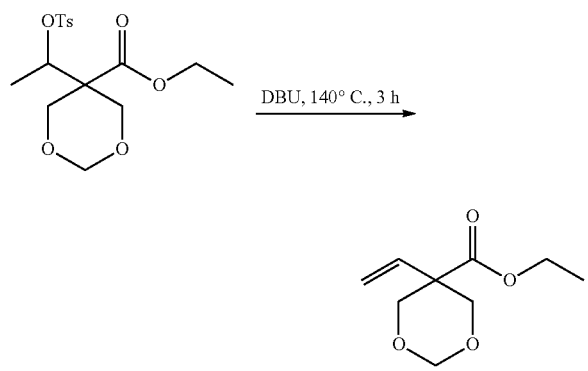

A mixture of ethyl 5-(1-(tosyloxy)ethyl)-1,3-dioxane-5-carboxylate (20.7 g, 58 mmol) and DBU (25 mL) was heated at 140° C. for 3 h. After being cooled to rt, the reaction mixture was poured into ether (300 mL), and the organic layer was washed with brine (3×). The ether layer was dried over sodium sulfate, and concentrated in vacuo. The residue was purified by silica gel chromatography eluting with petroleum ether/ether 30:1 to 20:1 to give a crude product, which was distilled under reduced pressure (45-49° C./0.3 mbar) to afford the title compound (3.6 g, 33%) as colorless oil. $^1$H NMR (400 MHz, CDCl$_3$) δ 1.29 (t, J=11.0 Hz, 3H), 3.70 (d, J=11.6 Hz, 2H), 4.25 (t, J=7.2 Hz, 2H), 4.44 (t, J=11.2 Hz, 2H), 4.71 (d, J=8.0 Hz, 1H), 4.95 (d, J=6.0 Hz, 1H), 5.24 (m, 1H), 5.27 (m, 1H), 5.65 (m, 1H). This $^1$H spectral data is in good agreement with that reported for the synthesis of the title compound, the which is described in Borremans, F. et al. *Bull. Soc. Chim. Belg.* 1976, 85, 681-696.

Compound 48f. 5-Vinyl-[1,3]dioxane-5-carboxylic acid

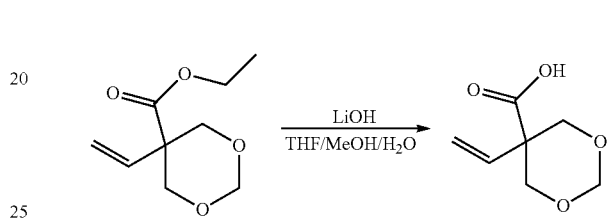

A solution of 5-vinyl-[1,3]dioxane-5-carboxylic acid ethyl ester (397.7 mg, 2.136 mmol) in tetrahydrofuran/methanol/water (15 mL, 2:2:1) was treated with lithium hydroxide monohydrate (269 mg, 6.408 mmol). After stirring at room temperature for 1.5 h, the volatiles were removed in vacuo and the residue was cooled to 0° C. and quenched with hydrochloric acid (1 M). The aqueous layer was saturated with sodium chloride, extracted with dichloromethane (3×). The combined organics were filtered through a phase separator and the volatiles were removed in vacuo to provide the title compound (320.3 mg, 95%) as a colourless solid. $^1$H NMR (300 MHz, CDCl$_3$) δ 3.72 (d, J=11.6 Hz, 2H), 4.50 (d, J=11.4 Hz, 2H), 4.73 (d, J=6.2 Hz, 1H), 5.02 (d, J=6.0 Hz, 1H), 5.27-5.39 (m, 2H), 5.69 (dd, J=17.6, 10.9 Hz, 1H).

Compound 48g. 5-((E)-2-{2-[(R)-1-({(S)-1-[(S)-2-((S)-2-Hydroxy-3-methyl-butyrylamino)-propionyl]-hexahydro-pyridazine-3-carbonyl}-amino)-ethyl]-quinolin-7-yl}-vinyl)-[1,3]dioxane-5-carboxylic acid

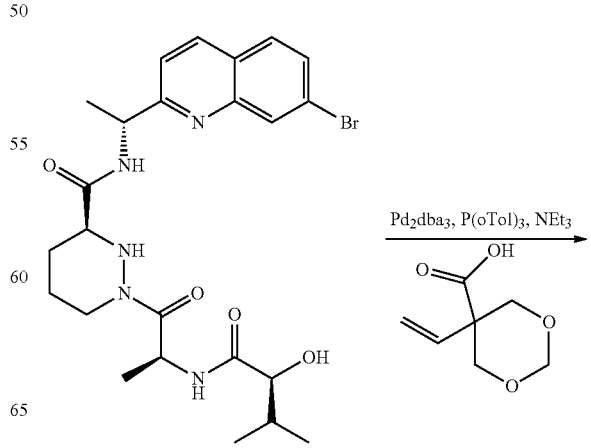

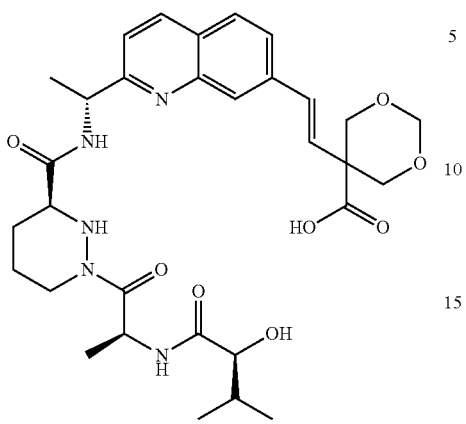

A solution of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (398.4 mg, 0.745 mmol), 5-vinyl-[1,3]dioxane-5-carboxylic acid (117.9 mg, 0.745 mmol), tri(o-tolyl)phosphine (45.3 mg, 0.149 mmol) and triethylamine (0.32 mL, 2.235 mmol) in 1,4-dioxane (15 mL) was degassed by bubbling nitrogen through for 5 minutes then warmed to 50° C. and treated with tris(dibenzylideneacetone)dipalladium(0) (68.2 mg, 0.074 mmol). After stirring at 100° C. for 40 minutes the reaction was cooled to room temperature, filtered through a pad of Celite, which was rinsed with ethyl acetate. The volatiles were removed in vacuo to provide crude title compound as an orange foam that was used without further purification. LCMS (m/z) 612.2 [M+H], Tr=1.70 min.

Compound 48

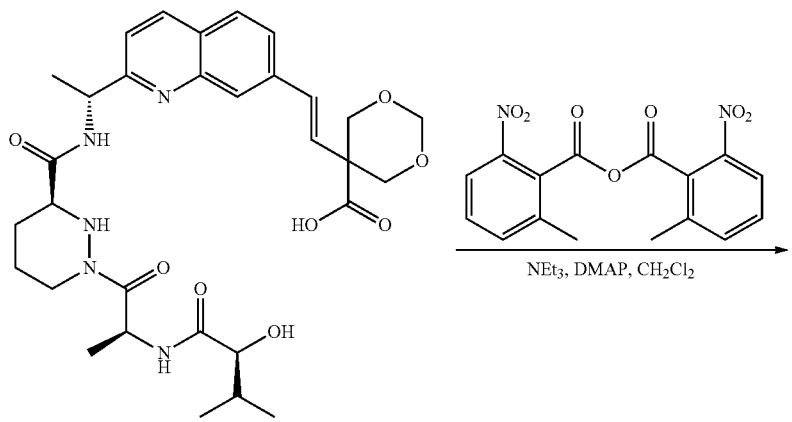

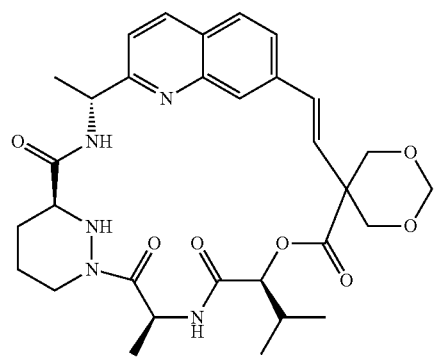

A solution of crude 5-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-[1,3]dioxane-5-carboxylic acid (0.745 mmol) in dry dichloromethane (18 mL) was added via syringe pump to a solution of 2-methyl-6-nitrobenzoic anhydride (385.0 mg, 1.117 mmol), 4-dimethylaminopyridine (273.0 mg, 2.235 mmol) in dry dichloromethane (230 mL) containing 4 Å molecular sieves over 3 h. After the end of the addition, the reaction was stirred at room temperature for 40 minutes then filtered and the volatiles were partially removed in vacuo. The organics were washed with pH 4 citrate buffer, a saturated solution of sodium bicarbonate and filtered on a phase separator. The volatiles were removed in vacuo and the residue was purified by silica gel chromatography using a 25 g Isolute cartridge eluted with a continuous gradient of iso-hexanes/acetone 1:0 to 1:1 to provide the title compound at 90% purity (133.8 mg, 30% yield). A third of this material was purified by reverse phase preparative HPLC eluting with a continuous gradient of water/acetonitrile 95:5 to 0:1 to afford the title compound (8.1 mg) as a white solid. $^1$H NMR (300 MHz, CD$_3$OD) δ 1.06 (d, J=6.7 Hz, 3H), 1.11 (d, J=6.7 Hz, 3H), 1.47-1.80 (m, 8H), 2.12-2.31 (m, 2H), 2.65-2.77 (m, 1H), 3.59-3.66 (m, 1H), 3.85 (d, J=11.4 Hz, 1H), 3.92 (d, J=11.4 Hz, 1H), 4.39-4.53 (m, 2H), 4.63-4.71 (m, 1H), 4.98 (d, J=6.2 Hz, 1H), 5.08 (q, J=6.9 Hz, 1H), 5.35 (d, J=9.1 Hz, 1H), 5.82 (q, J=7.3 Hz, 1H), 6.15 (d, J=16.5 Hz, 1H), 6.63 (d, J=16.5 Hz, 1H), 7.47 (d, J=8.5 Hz, 1H), 7.69 (dd, J=8.5, 1.8 Hz, 1H), 7.75 (s, 1H), 7.86 (d, J=8.5 Hz, 1H), 8.26 (d, J=8.5 Hz, 1H). LCMS (m/z) 594.1 [M+H], Tr=2.60 min.

Example 49

Compound 49

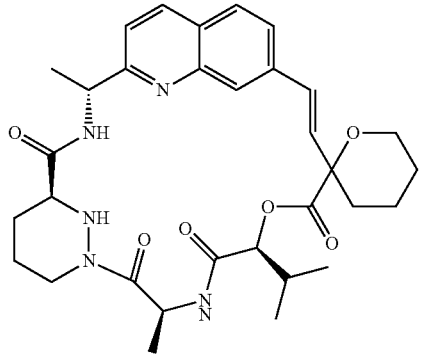

Compound 49a.
2-(1-Hydroxy-ethyl)-tetrahydro-pyran-2-carboxylic acid methyl ester

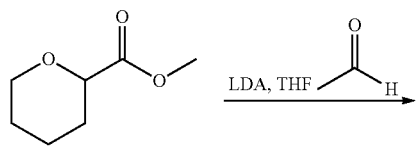

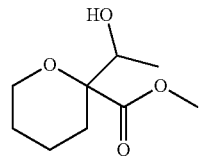

A solution of N,N-diisopropylamine (909 mg, 1.25 mL, 9 mmol) in tetrahydrofuran (4 mL) was stirred at −78° C. under nitrogen. n-Butyllithium (3.6 mL, 9 mmol, 2.5 M solution in hexane) was added dropwise and the reaction mixture was stirred at −78° C. for 30 minutes. A solution of tetrahydro-pyran-2-carboxylic acid methyl ester (864 mg, 6 mmol) in tetrahydrofuran (8 mL) was added and the reaction mixture was stirred at −78° C. for 20 minutes. Acetaldehyde (792 mg, 1.0 mL, 18 mmol) was added in one portion. The cooling bath was removed and the reaction mixture was stirred at room temperature for 1 h. The reaction mixture was cooled to 0° C. and ice-cold hydrochloric acid (2 M) was added to acidify the reaction mixture to pH 2. Sodium chloride was added to saturate the aqueous phase and the mixture was extracted with diethyl ether. The organic extracts were combined and washed with brine. The organic solution was filtered through a hydrophobic frit and the filtrate was evaporated. The residue was purified by silica gel chromatography using a gradient of pentane/diethyl ether 1:1 to 0:1 to afford the title compound (1.28 g) as an oil and as a 2:1 mixture of diastereoisomers. LCMS (m/z) 189.3 [M+H], Tr=1.23 min.

Compound 49b.
2-Vinyl-tetrahydro-pyran-2-carboxylic acid methyl ester

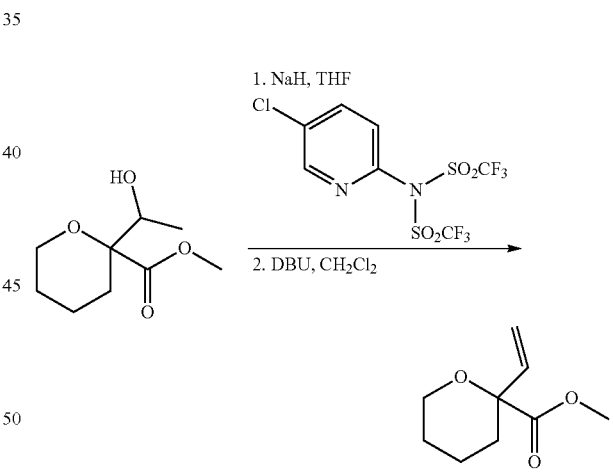

A suspension of sodium hydride (200 mg, 5 mmol, 60% dispersion in oil) in tetrahydrofuran (6 mL) was stirred at −78° C. under nitrogen. A solution of 2-(1-hydroxy-ethyl)-tetrahydro-pyran-2-carboxylic acid methyl ester (620 mg, 3.3 mmol) in tetrahydrofuran 3 mL) was added and the reaction mixture was stirred at −78° C. for 15 minutes. A solution of N-(5-chloro-2-pyridyl)bis(trifluoromethanesulfonimide) (2.60 g, 6.6 mmol) in tetrahydrofuran (10 mL) was added and the reaction mixture was stirred at −78° C. for 30 minutes. The reaction mixture was warmed to room temperature and then stirred at room temperature for 1 h. The reaction mixture was cooled to 5° C. and saturated ammonium chloride solution was cautiously added. The reaction mixture was extracted with diethyl ether. The organics were combined and washed with brine. The organic solution was filtered through a hydrophobic frit and the filtrate was evaporated. The residue was purified by silica gel chromatography using a gradient of pentane/diethyl ether 10:1 to 5:1 to afford 2-(1-trifluoromethanesulfonyloxy-ethyl)-tetrahydro-pyran-2-carboxylic acid methyl ester (2.12 g, 3.3 mmol) as an oil and as a 2:1 mixture of diastereoisomers which was used immediately in the next step. LCMS (m/z) 321.0 [M+H], Tr=2.88 min.

A solution of 2-(1-trifluoromethanesulfonyloxy-ethyl)-tetrahydro-pyran-2-carboxylic acid methyl ester (2.12 g, 3.3 mmol) in dichloromethane (5 mL) was stirred at room temperature under nitrogen. 1,8-Diazabicycloundec-7-ene (2.0 g, 2 mL, 13.2 mmol) was added and the reaction mixture was stirred at room temperature for 18 h. The reaction mixture was cooled to 0° C. and acidified to pH 2 with ice cold hydrochloric acid (2 M). The mixture was extracted with dichloromethane. The organic extracts were combined and washed with brine. The organic solution was filtered through a hydrophobic frit and the filtrate was evaporated. The residue was purified by silica gel chromatography using a gradient of pentane/diethyl ether 10:1 to 5:1 to afford the title compound (466 mg, 75% over two steps) as an oil. $^1$H NMR (300 MHz, CDCl$_3$) δ 1.55-1.80 (m, 5H), 2.21-2.29 (m, 1H), 2.68-2.77 (m, 1H), 3.79 (s, 3H), 3.91-3.98 (m, 1H), 5.26 (dd, J=10.7, 0.9 Hz, 1H), 5.41 (dd, J=17.4, 1.1 Hz, 1H), 5.87 (dd, J=17.4, 10.7 Hz, 1H). LCMS (m/z) 193.2 [M+H], Tr=2.01 min.

Compound 49c. (S)-1-{(S)-2-[(S)-2-(2-{(E)-2-[2-((R)-1-tert-Butoxycarbonylamino-ethyl)-quinolin-7-yl]-vinyl}-tetrahydro-pyran-2-carbonyloxy)-3-methyl-butyrylamino]-propionyl}-hexahydro-pyridazine-3-carboxylic acid 2,2,2-trichloroethyl ester

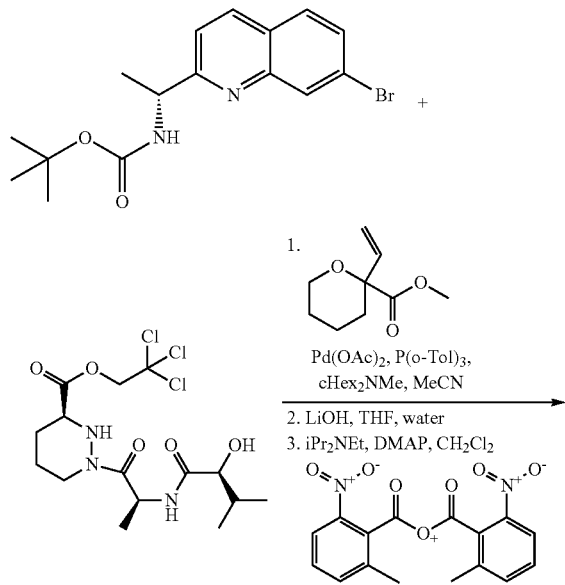

-continued

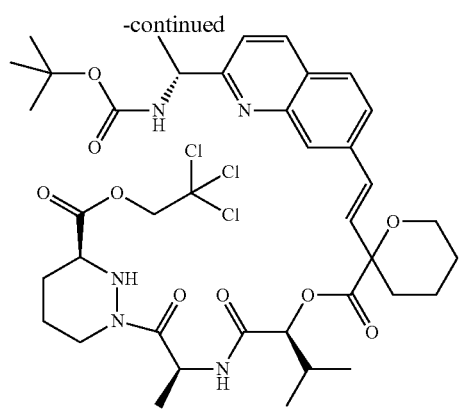

A solution of [(R)-1-(7-bromo-quinolin-2-yl)-ethyl]-carbamic acid tert-butyl ester (320 mg, 0.9 mmol), 2-vinyl-tetrahydro-pyran-2-carboxylic acid methyl ester (330 mg, 0.9 mmol), tris(dibenzylideneacetone)dipalladium(0) (82 mg, 0.09 mmol), tri(o-tolyl)phosphine (54 mg, 0.18 mmol) and N,N-dicyclohexylmethylamine (526 mg, 0.58 mL, 2.7 mmol) in acetonitrile (4 mL) was heated at 120° C. in a microwave reactor for 30 minutes. The reaction mixture was filtered and the solvent was evaporated. The residue was dissolved in ethyl acetate and the solution was washed with ice-cold hydrochloric acid (1 M). The aqueous layer was extracted with ethyl acetate and the organic extracts were combined and washed with brine. The organic solution was filtered through a hydrophobic frit and the filtrate was evaporated to afford 2-{(E)-2-[2-((R)-1-tert-butoxycarbonylamino-ethyl)-quinolin-7-yl]-vinyl}-tetrahydro-pyran-2-carboxylic acid methyl ester (130 mg, 21%) as an oil LCMS (m/z) 441.1 [M+H], Tr=2.75 min.

A solution of 2-{(E)-2-[2-((R)-1-tert-butoxycarbonylamino-ethyl)-quinolin-7-yl]-vinyl}-tetrahydro-pyran-2-carboxylic acid methyl ester (130 mg, 0.3 mmol) in tetrahydrofuran (6 mL) was stirred at 5° C. under nitrogen. A solution of lithium hydroxide monohydrate (25 mg, 0.6 mmol) in water (1.5 mL) was added and the reaction mixture was stirred at room temperature for 18 h. The majority of the organic solvent was evaporated. The solution was acidified to pH 2 with ice-cold hydrochloric acid (2 M) and the mixture was extracted with dichloromethane. The organic extracts were combined and washed with brine. The organic solution was filtered through a hydrophobic frit and the filtrate was evaporated to afford 2-{(E)-2-[2-((R)-1-tert-butoxycarbonylamino-ethyl)-quinolin-7-yl]-vinyl}-tetrahydro-pyran-2-carboxylic acid (135 mg, 0.3 mmol) as a yellow gum which was used crude in the next step. LCMS (m/z) 427.1 [M+H], Tr=2.17 min.

A solution of 2-{(E)-2-[2-((R)-1-tert-butoxycarbonylamino-ethyl)-quinolin-7-yl]-vinyl}-tetrahydro-pyran-2-carboxylic acid (135 mg, 0.3 mmol), N,N-diisopropylethylamine (96 mg, 0.133 mL, 0.75 mmol), 4-dimethylaminopyridine (80 mg, 0.66 mmol) and 2-methyl-6-nitrobenzoic anhydride (193 mg, 0.56 mmol) in dichloromethane (5 mL) was stirred at 0° C. under nitrogen. A solution of (S)-1-[(S)-2-((S)-2-hydroxy-3-methyl-butyrylamino)-propionyl]-hexahydro-pyridazine-3-carboxylic acid 2,2,2-trichloro-ethyl ester (142 mg, 0.33 mmol) in dichloromethane (2 mL) was added and the reaction mixture was stirred at room temperature for 6 h. The reaction mixture was diluted with dichloromethane and the solution was washed with ice-cold saturated sodium hydrogen carbonate solution, water, ice-cold hydrochloric acid (1 M), water and brine. The organic solution was filtered through a hydrophobic frit and the filtrate was evaporated. The residue was purified by silica gel chromatography using a gradient of iso-hexanes/ethyl acetate 3:1 to 1:3 to afford the title compound (44 mg, 17%) as a white solid and as a 1:1 mixture of two diastereoisomers. LCMS (m/z) 840.2, 842.0 [M+H], Tr=3.75 min.

Compound 49

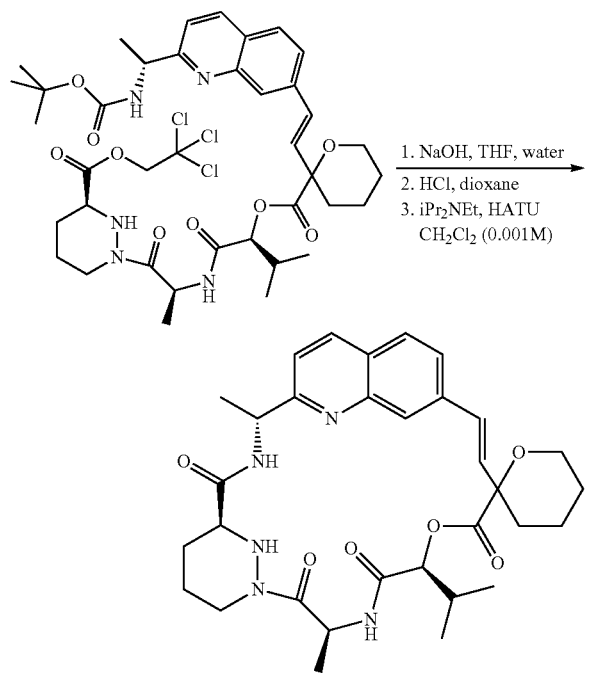

A solution of (S)-1-{(S)-2-[(S)-2-(2-{(E)-2-[2-((R)-1-tert-butoxycarbonylamino-ethyl)-quinolin-7-yl]-vinyl}-tetrahydro-pyran-2-carbonyloxy)-3-methyl-butyrylamino]-propionyl}-hexahydro-pyridazine-3-carboxylic acid 2,2,2-trichloroethyl ester (42 mg, 0.05 mmol) in tetrahydrofuran (2 mL) was stirred at 0° C. under nitrogen. An ice-cold aqueous solution of sodium hydroxide (0.1 M, 0.5 mL, 0.05 mmol) was added and the reaction mixture was stirred at 0° C. for 30 minutes. Additional sodium hydroxide solution (0.1 M, 1.0 mL, 0.1 mmol) was added and the reaction mixture was stirred at 0° C. for 1 h. Additional sodium hydroxide solution (0.1 M, 1.0 mL, 0.1 mmol) was added and the reaction mixture was stirred at 0° C. for 90 minutes. Cold hydrochloric acid (1 M) was added to acidify the mixture to pH 2 and the solvent was evaporated. The residue was co-evaporated with tetrahydrofuran/toluene (1:1, 3×) and the residue was triturated with diethyl ether (2×) and the resulting solid was dried to afford (S)-1-{(S)-2-[(S)-2-(2-{(E)-2-[2-((R)-1-tert-butoxycarbonylamino-ethyl)-quinolin-7-yl]-vinyl}-tetrahydro-pyran-2-carbonyloxy)-3-methyl-butyrylamino]-propionyl}-hexahydro-pyridazine-3-carboxylic acid (0.05 mmol) as a yellow solid and as a 1:1 mixture of diastereoisomers which was used crude in the next reaction. LCMS (m/z) 710.3 [M+H], Tr=2.80 min.

A mixture of crude (S)-1-{(S)-2-[(S)-2-(2-{(E)-2-[2-((R)-1-tert-butoxycarbonylamino-ethyl)-quinolin-7-yl]-vinyl}-tetrahydro-pyran-2-carbonyloxy)-3-methyl-butyrylamino]-propionyl}-hexahydro-pyridazine-3-carboxylic acid (0.05 mmol) in hydrochloric acid (4 M in 1,4-dioxane, 2 mL) was stirred at room temperature for 1 h. The solvent was evaporated and the residue was co-evaporated with diethyl ether (2×) and the resulting solid was dried to afford (S)-1-{(S)-2-[(S)-2-(2-{(E)-2-[2-((R)-1-amino-ethyl)-quinolin-7-yl]-vinyl}-tetrahydro-pyran-2-carbonyloxy)-3-methyl-butyrylamino]-propionyl}-hexahydro-pyridazine-3-carboxylic acid hydrochloride (0.05 mmol) as an off-white solid and as a 1:1 mixture of diastereoisomers which was used crude in the next reaction. LCMS (m/z) 610.1 [M+H], Tr=1.60 min.

A suspension of crude (S)-1-{(S)-2-[(S)-2-(2-{(E)-2-[2-((R)-1-amino-ethyl)-quinolin-7-yl]-vinyl}-tetrahydro-pyran-2-carbonyloxy)-3-methyl-butyrylamino]-propionyl}-hexahydro-pyridazine-3-carboxylic acid hydrochloride (0.05 mmol) in dichloromethane (45 mL) was stirred at 0° C. under nitrogen. A solution of N,N-diisopropylethylamine (26 mg, 0.2 mmol) in dichloromethane (5 mL) was added and the resulting solution was stirred at 0° C. 2-(1H-7-Azabenzotriazol-1-yl)-1,1,3,3-tetramethyl uronium hexafluorophosphate methanaminium (38 mg, 0.1 mmol) was added and the reaction mixture was stirred at 0° C. for 30 minutes and then at room temperature for 1 h. The reaction mixture was cooled to 0° C. and the solution was washed with ice-cold hydrochloric acid (1 M) and brine. The organic solution was filtered through a hydrophobic frit and the filtrate was evaporated. The residue was triturated with diethyl ether and the residue was dried. The residue purified by silica gel chromatography using a gradient of iso-hexanes/acetone 2:1. The residue was triturated with iso-hexanes/diethyl ether 1:1 and the resulting solid was dried to afford the title compound (6.0 mg, 21%) as a white solid and as a 1:1 mixture of diastereoisomers. LCMS (m/z) 592.2 [M+H], Tr=2.51 min and (m/z) 592.2 [M+H], Tr=2.61 min.

Examples 50 and 51

Compounds 50 and 51

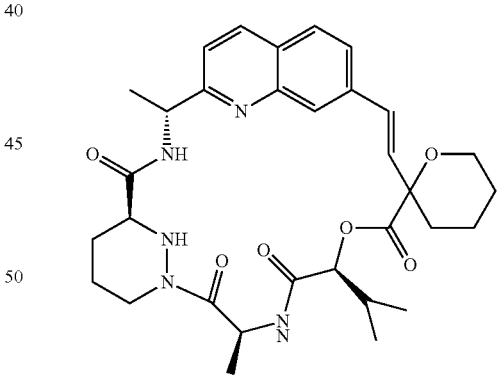

Compound 50a. Tetrahydro-pyran-3-carboxylic acid benzyl ester

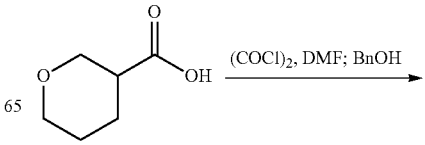

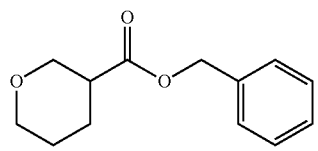

A cooled (0° C.) solution of tetrahydro-pyran-3-carboxylic acid (2.831 g, 21.752 mmol) in dichloromethane (60 mL) and N,N-dimethylformamide (5 drops) was treated with oxalyl chloride (2.0 mL, 23.927 mmol). After stirring at room temperature for 2 h, benzyl alcohol (2.5 mL, 23.927 mmol) was added. After stirring at room temperature for 2 h and standing overnight, the volatiles were removed in vacuo and the residue was purified by silica gel chromatography using a 50 g Isolute cartridge eluted with a continuous gradient of iso-hexanes/ethyl acetate 1:0 to 4:1 to afford the title compound (4.587 g, 96%) as a white solid. $^1$H NMR (300 MHz, CDCl$_3$) δ 1.58-1.88 (m, 3H), 2.03-2.13 (m, 1H), 2.62-2.72 (m, 1H), 3.47 (ddd, J=11.4, 9.6, 3.4 Hz, 1H), 3.63 (dd, J=11.4, 9.1 Hz, 1H), 3.85 (app dt, J=11.1, 3.8 Hz, 1H), 4.06 (ddd, J=11.4, 4.0, 1.6 Hz, 1H), 5.12, 5.17 (ABq, J$_{AB}$=12.5 Hz, 2H), 7.31-7.46 (m, 5H).

Compound 50b.
3-(1-Hydroxy-ethyl)-tetrahydro-pyran-3-carboxylic acid benzyl ester

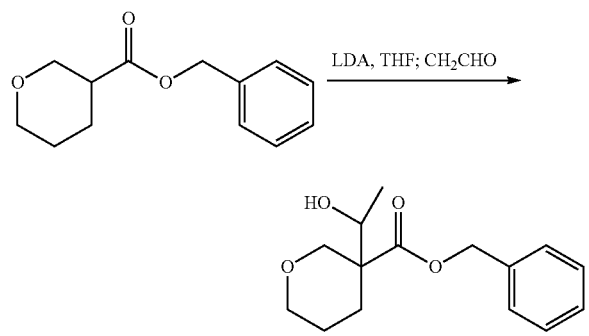

A cooled (−78° C.) solution of N,N-diisopropylamine (4.7 mL, 33.316 mmol, dried over calcium hydride) in anhydrous tetrahydrofuran (60 mL) was treated with a solution of n-butyllithium in hexanes (12.5 mL, 31.234 mmol, 2.5 M). After stirring at −78° C. for 25 minutes, the mixture was treated with a solution of tetrahydro-pyran-3-carboxylic acid benzyl ester (4.587 g, 20.823 mmol) in anhydrous tetrahydrofuran (20 mL). After stirring at −78° C. for 15 minutes, the mixture was treated with acetaldehyde (3.5 mL, 62.469 mmol). After stirring at room temperature for 45 minutes, the reaction was quenched at 0° C. with hydrochloric acid (2 M, 50 mL). The aqueous layer was saturated with sodium chloride, extracted with dichloromethane (2 x). The organics were combined, filtered through a phase separator and the volatiles were removed in vacuo. The residue was purified by silica gel chromatography using a 100 g Isolute cartridge eluted with a continuous gradient of iso-hexanes/ethyl acetate 1:0 to 3:2 to afford the title compound (2.212 g, 40%) as a yellow oil and as a 3:1 mixture of diastereoisomers. LCMS (m/z) 287.0 [M+Na], Tr=2.00 min.

Compound 50c. 3-(1-Trifluoromethanesulfonyloxy-ethyl)-tetrahydro-pyran-3-carboxylic acid benzyl ester

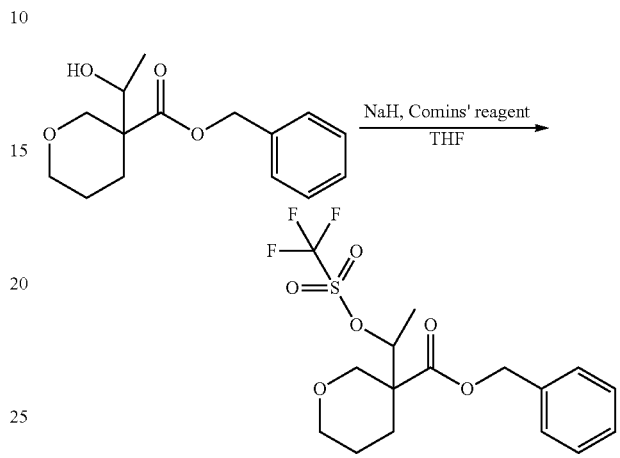

A cooled (−78° C.) suspension of sodium hydride (502.1 mg, 12.552 mmol, 60% in mineral oil) in anhydrous tetrahydrofuran (20 mL) was slowly treated with a solution of 3-(1-hydroxy-ethyl)-tetrahydro-pyran-3-carboxylic acid benzyl ester (2.212 g, 8.368 mmol) in anhydrous tetrahydrofuran (20 mL). The light yellow suspension was stirred at −78° C. for 15 minutes and then treated with a solution of N-(5-chloro-2-pyridyl)bis(trifluoromethanesulfonimide) (6.572 g, 16.736 mmol) in anhydrous tetrahydrofuran (20 mL). After stirring at room temperature for 3 h, more sodium hydride (502.1 mg, 12.552 mmol, 60% in mineral oil) was added. After stirring at room temperature for 2 h, more sodium hydride (502.1 mg, 12.552 mmol, 60% in mineral oil) was added. After stirring at room temperature for 30 minutes, the reaction was quenched at −20° C. with hydrochloric acid (2 M, 50 mL). The aqueous layer was extracted with dichloromethane (3×). The organics were combined, filtered through a phase separator and the volatiles were removed in vacuo to afford the title compound in a mixture which was used without further purification. LCMS (m/z) 397.0 [M+H], Tr=2.48 min.

Compound 50d.
3-Vinyl-tetrahydro-pyran-3-carboxylic acid benzyl ester

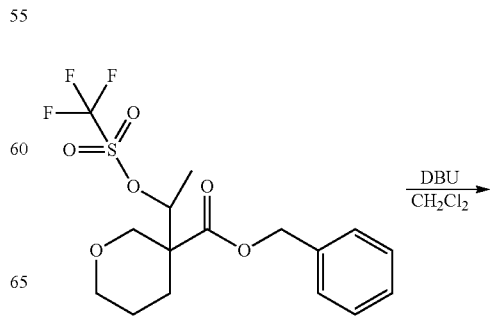

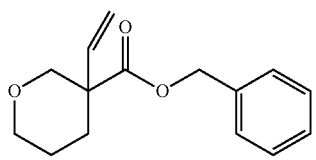

A solution of 3-(1-trifluoromethanesulfonyloxy-ethyl)-tetrahydro-pyran-3-carboxylic acid benzyl ester (8.368 mmol) in dichloromethane (100 mL) was treated with 1,8-diazabicyclo[5.4.0]undec-7-ene (5.0 mL, 33.472 mmol). After stirring at room temperature for 2.5 h, the volatiles were removed in vacuo and the residue was purified by silica gel chromatography using a 100 g Isolute cartridge eluted with a continuous gradient of iso-hexanes/ethyl acetate 1:0 to 4:1 to afford the title compound (809.5 mg, 39% over two steps) as a colorless oil. $^1$H NMR (300 MHz, CDCl$_3$) δ 1.58-1.80 (m, 3H), 2.29-2.40 (m, 1H), 3.42-3.54 (m, 2H), 3.81 (app dt, J=10.5, 4.2 Hz, 1H), 4.27 (dd, J=11.4, 1.8 Hz, 1H), 5.13-5.27 (m, 4H), 5.77 (dd, J=17.4, 10.9 Hz, 1H), 7.31-7.42 (m, 5H).

Compound 50e.
3-Vinyl-tetrahydro-pyran-3-carboxylic acid

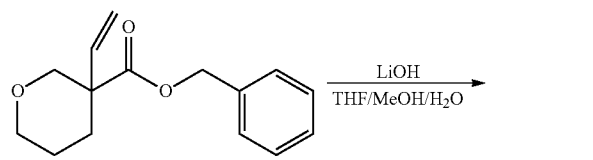

A solution of 3-vinyl-tetrahydro-pyran-3-carboxylic acid benzyl ester (809.5 mg, 3.286 mmol) in tetrahydrofuran/methanol/water (25 mL, 2:2:1) was treated with lithium hydroxide monohydrate (413.6 mg, 9.859 mmol). After stirring at room temperature for 2 h, more lithium hydroxide monohydrate (413.6 mg 9.859 mmol) was added. After stirring at room temperature for 2 h, the volatiles were removed in vacuo and the residue was cooled to 0° C. and quenched with hydrochloric acid (1 M). The aqueous layer was saturated with sodium chloride, extracted with dichloromethane (3×). The combined organics were filtered through a phase separator and the volatiles were removed in vacuo. The residue was purified by silica gel chromatography using a 25 g Isolute cartridge eluted with a continuous gradient of iso-hexanes/ethyl acetate 1:0 to 1:1 to afford crude title compound which was dissolved in diethyl ether. Organics were extracted with a saturated solution of sodium bicarbonate. The aqueous layer was acidified with hydrochloric acid (2 M) to pH ~2, saturated with sodium chloride and extracted with dichloromethane (2×) to provide the title compound (377.1 mg, 73%) as a white solid. $^1$H NMR (300 MHz, CDCl$_3$) δ 1.59-1.90 (m, 3H), 2.27-2.38 (m, 1H), 3.39-3.55 (m, 2H), 3.87 (app dt, J=11.2, 4.0 Hz, 1H), 4.26 (dd, J=11.4, 2.0 Hz, 1H), 5.22-5.32 (m, 2H), 5.79 (dd, J=17.8, 10.7 Hz, 1H).

Compound 50f. 3-((E)-2-{2-[(R)-1-({(S)-1-[(S)-2-((S)-2-Hydroxy-3-methyl-butyrylamino)-propionyl]-hexahydro-pyridazine-3-carbonyl}-amino)-ethyl]-quinolin-7-yl}-vinyl)-tetrahydro-pyran-3-carboxylic acid

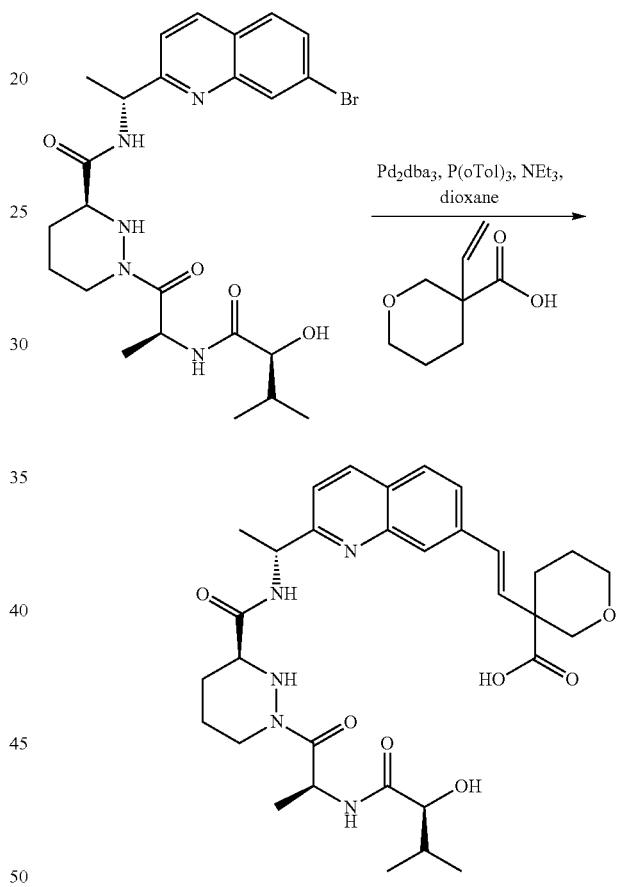

A solution of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (600 mg, 1.122 mmol), 3-vinyl-tetrahydro-pyran-3-carboxylic acid (175.3 mg, 1.122 mmol), tri(o-tolyl)phosphine (68.3 mg, 0.224 mmol) and triethylamine (0.47 mL, 3.366 mmol) in 1,4-dioxane (15 mL) was degassed by bubbling nitrogen through for 5 minutes then warmed to 50° C. and treated with tris(dibenzylideneacetone)dipalladium(0) (102.7 mg, 0.112 mmol). After stirring at 100° C. for 45 minutes the reaction was cooled to room temperature, filtered through a pad of Celite, which was rinsed with ethyl acetate. The volatiles were removed in vacuo to provide crude title compound as an orange foam that was used without further purification. LCMS (m/z) 610.2 [M+H], Tr=1.97 min.

Compounds 50 and 51

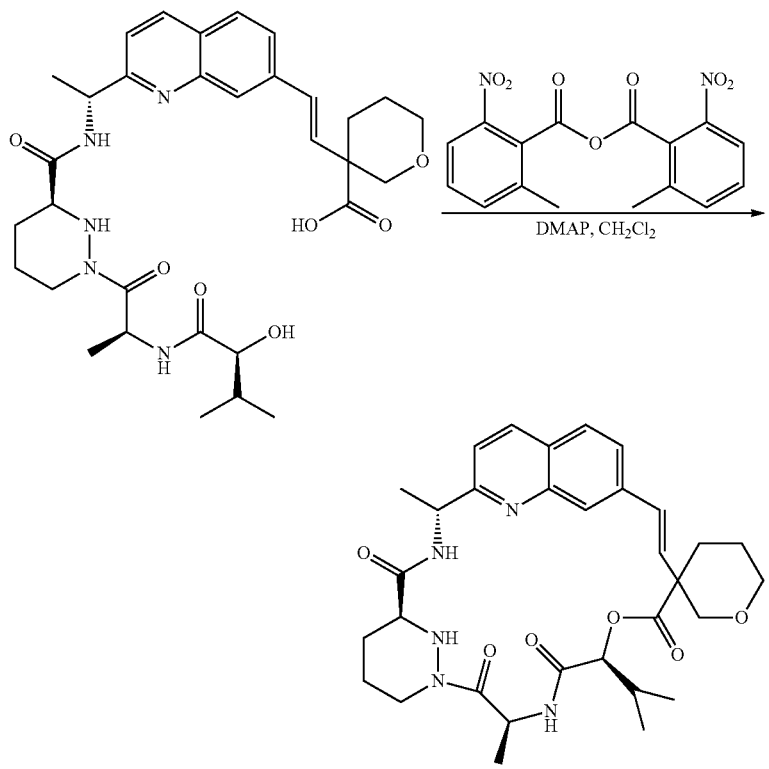

A solution of crude 3-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-tetrahydro-pyran-3-carboxylic acid (1.122 mmol) in dry dichloromethane (20 mL) was added via syringe pump to a solution of 2-methyl-6-nitrobenzoic anhydride (772.6 mg, 2.244 mmol), 4-dimethylaminopyridine (548.2 mg, 4.488 mmol) in dry dichloromethane (350 mL) containing 4 Å molecular sieves over 4 h. After the end of the addition, the reaction was stirred at room temperature for 3 days then filtered and the volatiles were partially removed in vacuo. The organics were washed with pH 4 citrate buffer, a saturated solution of sodium bicarbonate and filtered on a phase separator. The volatiles were removed in vacuo and the residue was purified by silica gel chromatography using a 50 g Isolute cartridge eluted with a continuous gradient of isohexanes/acetone 1:0 to 2:3 to provide two fractions that were further purified by reverse preparative HPLC eluting with water/acetonitrile 95:5 to 0:1 to afford two separate, single isomers 1 and 2.

Compound 50 (First eluting) Diastereomer 1 (50.1 mg, 7.5%) as a white solid. $^1$H NMR (300 MHz, CD$_3$OD) δ 1.0 (d, J=6.4 Hz, 3H), 1.09 (d, J=6.7 Hz, 3H), 1.47-1.72 (m, 9H), 1.73-1.88 (m, 2H), 1.91-2.02 (m, 1H), 2.11-2.32 (m, 2H), 2.35-2.45 (m, 1H), 2.65-2.78 (m, 1H), 3.46-3.67 (m, 3H), 3.84-3.94 (m, 1H), 4.39-4.54 (m, 2H), 5.03-5.16 (m, 2H), 5.34 (d, J=9.1 Hz, 1H), 5.81 (q, J=7.3 Hz, 1H), 6.23 (d, J=16.5 Hz, 1H), 6.62 (d, J=16.5 Hz, 1H), 7.46 (d, J=8.5 Hz, 1H), 7.66 (dd, J=8.5, 1.3 Hz, 1H), 7.75 (s, 1H), 7.85 (d, J=8.5 Hz, 1H), 8.26 (d, J=8.5 Hz, 1H). LCMS (m/z) 592.2 [M+H], Tr=2.31 min.

Compound 51 (Second eluting) Diastereomer 2 (28.8 mg, 4.3%) as a white solid. $^1$H NMR (300 MHz, CD$_3$OD) δ 1.06 (d, J=6.7 Hz, 3H), 1.09 (d, J=6.7 Hz, 3H), 1.60 (d, J=6.7 Hz, 3H), 1.65 (d, J=7.3 Hz, 3H), 1.68-1.79 (m, 3H), 1.88-2.00 (m, 2H), 2.12-2.29 (m, 2H), 2.55-2.76 (m, 2H), 3.49-3.67 (m, 3H), 3.84-3.93 (m, 1H), 4.29 (dd, J=11.2, 1.6 Hz, 1H), 4.39-4.48 (m, 1H), 5.08 (q, J=6.7 Hz, 1H), 5.28 (d, J=8.7 Hz, 1H), 5.82 (q, J=7.1 Hz, 1H), 6.20 (d, J=16.7 Hz, 1H), 6.62 (d, J=16.7 Hz, 1H), 7.46 (d, J=8.5 Hz, 1H), 7.66 (dd, J=8.5, 1.6 Hz, 1H), 7.79 (s, 1H), 7.85 (d, J=8.5 Hz, 1H), 8.25 (d, J=8.5 Hz, 1H). LCMS (m/z) 592.1 [M+H], Tr=2.27 min.

Example 52

Compound 52

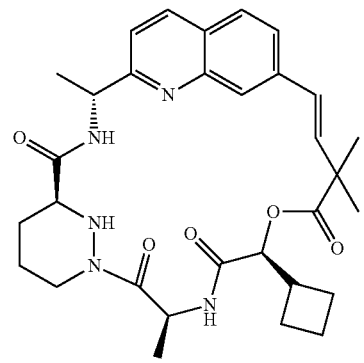 [SMILES: C[C@@H]1NC(=O)[C@H](C2CCC2)OC(=O)C(C)(C)/C=C/c2ccc3ccc(nc3c2)[C@@H](C)NC(=O)[C@@H]2CCCN(N2)C1=O]

Compound 52a. (S)-Cyclobutyl-hydroxy-acetic acid

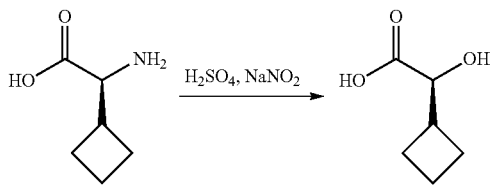 [SMILES: N[C@H](C(=O)O)C1CCC1 ; O=C(O)[C@@H](O)C1CCC1]

A cooled (0° C.) solution of cyclobutyl-L-glycine (572.8 mg, 4.435 mmol) in aqueous sulfuric acid (0.5 M, 18 mL) was treated with a solution of sodium nitrite (1.836 g, 26.610 mmol) in water (10 mL). After stirring at room temperature for 19 h, the solution was saturated with sodium chloride and extracted with tetrahydrofuran (3×). The organics were filtered through a hydrophobic frit and the volatiles were removed in vacuo. The solid residue was then extracted with ethyl acetate, the organics were filtered through a hydrophobic frit and the volatiles were removed in vacuo to afford the title compound (235.9 mg, 41%) as an orange gum which was used without further purification. $^1$H NMR (300 MHz, CDCl$_3$) δ 1.76-2.23 (m, 6H), 2.66-2.82 (m, 1H), 4.18 (d, J=5.8 Hz, 1H).

Compound 52b. (S)-1-[(S)-2-((S)-2-Cyclobutyl-2-hydroxy-acetylamino)-propionyl]-hexahydro-pyridazine-3-carboxylic acid [(R)-1-(7-bromo-quinolin-2-yl)-ethyl]-amide

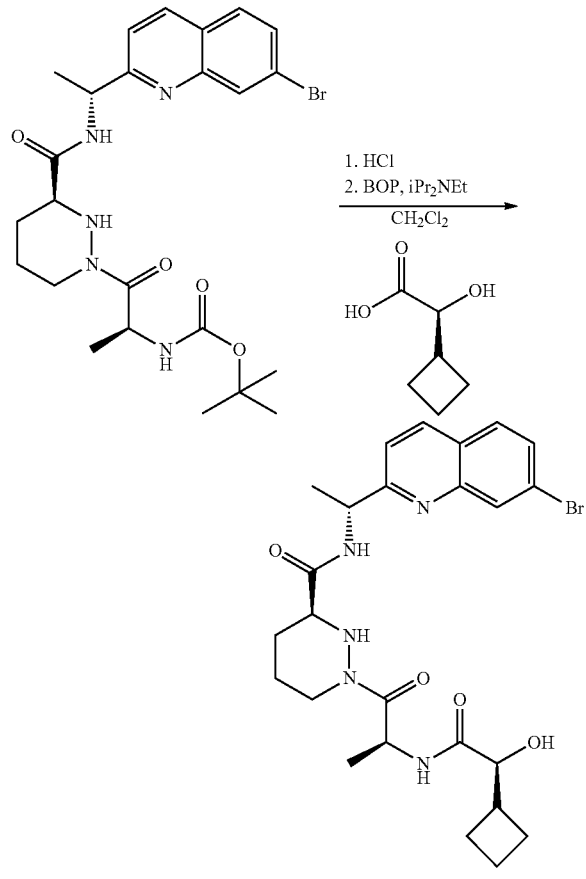

A cooled (0° C.) solution of (S)-2-{(S)-3-[(R)-1-(7-bromo-quinolin-2-yl)-ethylcarbamoyl]-tetrahydro-pyridazin-1-yl}-1-methyl-2-oxo-ethyl)-carbamic acid tert-butyl ester 53a (1.065 g, 1.994 mmol) in dichloromethane (15 mL) was treated with a solution of hydrogen chloride (3 mL, 11.964 mmol, 4 M in 1,4-dioxane). After stirring at room temperature for 2 h, a solution of hydrogen chloride (3 mL, 11.964 mmol, 4 M in 1,4-dioxane) was added. After stirring for 2 h, the volatiles were removed in vacuo. Residual water was azeotroped off with toluene to provide (S)-1-((S)-2-amino-propionyl)-hexahydro-pyridazine-3-carboxylic acid [(R)-1-(7-bromo-quinolin-2-yl)-ethyl]-amide hydrochloride as a white solid which was then combined with (S)-cyclobutyl-hydroxy-acetic acid (235.9 mg, 1.812 mmol) and dry dichloromethane (20 mL). This suspension was cooled to 0° C. and subsequently treated with N,N-diisopropylethylamine (0.95 mL, 5.436 mmol) and (benzotriazol-1-yloxy)tris(dimethylamino)phosphonium hexafluorophosphate (961.7 mg, 2.174 mmol). The reaction was slowly warmed to room temperature. After stirring for 17 h the reaction was quenched at 0° C. with hydrochloric acid (2 M). The aqueous layer was extracted with dichloromethane. The organics were washed with a saturated solution of sodium bicarbonate. The basic aqueous layer was extracted with dichloromethane. The organics were combined, filtered through a phase separator and the volatiles were removed in vacuo. The residue was purified by silica gel chromatography using a 50 g Isolute cartridge eluted with a continuous gradient of iso-hexanes/acetone 1:0 to 1:1 to afford the title compound (427.5 mg, 39%) as an orange foam. $^1$H NMR (300 MHz, CDCl$_3$) δ 1.40 (d, J=8.0 Hz, 3H), 1.59 (d, J=6.4 Hz, 3H), 1.63-2.10 (m, 10H), 2.21-2.32 (m, 1H), 2.58-2.78 (m, 2H), 3.41-3.54 (m, 1H), 4.01 (app t, J=5.8 Hz, 1H), 4.52 (d, J=13.8 Hz, 1H), 5.28 (app pentet, J=6.9 Hz, 1H), 5.41 (app pentet, J=8.0 Hz, 1H), 7.00 (d, J=8.2 Hz, 1H), 7.40 (d, J=8.5 Hz, 1H), 7.65 (dd, J=8.5, 1.8 Hz, 1H), 7.71 (d, J=8.5 Hz, 1H), 8.06 (d, J=7.1 Hz, 1H), 8.16 (d, J=8.5 Hz, 1H), 8.44 (s, 1H). LCMS (m/z) 547.0, 549.0 [M+H], Tr=2.39 min.

Compound 52c. (E)-4-{2-[(R)-1-({(S)-1-[(S)-2-((S)-2-Cyclobutyl-2-hydroxy-acetylamino)-propionyl]-hexahydro-pyridazine-3-carbonyl}-amino)-ethyl]-quinolin-7-yl}-2,2-dimethyl-but-3-enoic acid

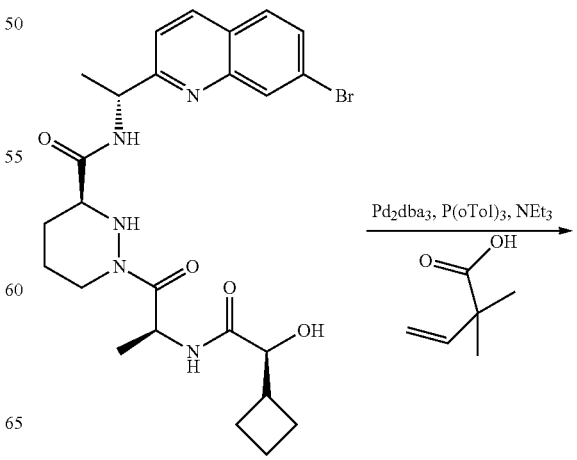

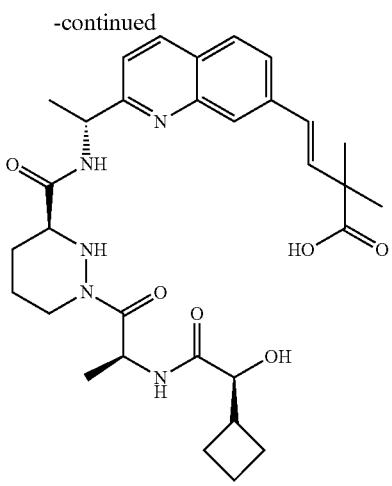

A solution of (S)-1-[(S)-2-((S)-2-cyclobutyl-2-hydroxy-acetylamino)-propionyl]-hexahydro-pyridazine-3-carboxylic acid [(R)-1-(7-bromo-quinolin-2-yl)-ethyl]-amide (427.5 mg, 0.782 mmol), 2,2-dimethyl-but-3-enoic acid (89.3 mg, 0.782 mmol), tri(o-tolyl)phosphine (47.6 mg, 0.156 mmol) and triethylamine (0.33 mL, 2.346 mmol) in 1,4-dioxane (10 mL) was degassed by bubbling nitrogen through for 5 minutes then warmed to 50° C. and treated with tris(dibenzylideneacetone)dipalladium(0) (71.6 mg, 0.078 mmol). After stirring at 100° C. for 1.5 h, tris(dibenzylideneacetone)dipalladium(0) (71.6 mg, 0.078 mmol) and tri(o-tolyl)phosphine (47.6 mg, 0.156 mmol) were added. After stirring for 40 minutes at 100° C., the reaction was cooled to room temperature, filtered through a pad of Celite, which was rinsed with ethyl acetate. The volatiles were removed in vacuo to provide crude title compound as an orange foam that was used without further purification. LCMS (m/z) 580.2 [M+H], Tr=2.01 min.

Compound 52

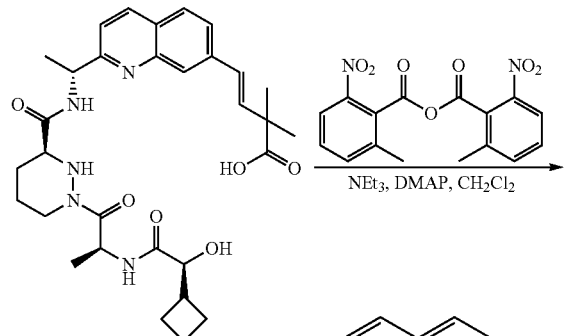

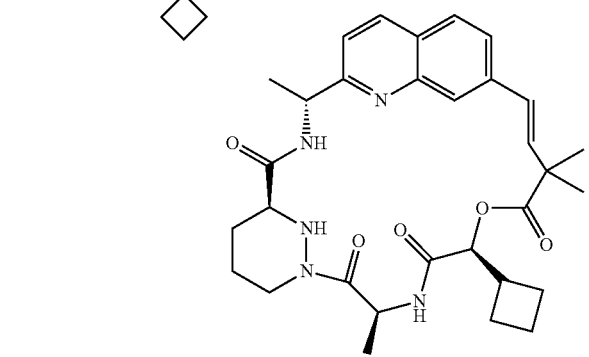

A solution of crude (E)-4-{2-[(R)-1-({(S)-1-[(S)-2-((S)-2-cyclobutyl-2-hydroxy-acetylamino)-propionyl]-hexahydro-pyridazine-3-carbonyl}-amino)-ethyl]-quinolin-7-yl}-2,2-dimethyl-but-3-enoic acid (0.782 mmol) in dry dichloromethane (20 mL) was added via syringe pump to a solution of 2-methyl-6-nitrobenzoic anhydride (538.4 mg, 1.564 mmol), 4-dimethylaminopyridine (382.1 mg, 3.128 mmol) in dry dichloromethane (280 mL) containing 4 Å molecular sieves over 4 h. After the end of the addition, the reaction was stirred at room temperature for 30 minutes then filtered and the volatiles were partially removed in vacuo. The organics were washed with pH 4 citrate buffer, a saturated solution of sodium bicarbonate and filtered on a phase separator. The volatiles were removed in vacuo and the residue was purified by silica gel chromatography using a 50 g Isolute cartridge eluted with a continuous gradient of iso-hexanes/acetone 1:0 to 1:1 and then by reverse phase preparative HPLC eluting with a continuous gradient of water/acetonitrile 95:5 to 0:1 to afford the title compound (48.6 mg, 11%) as a white solid. $^1$H NMR (300 MHz, CD$_3$OD) δ 1.43 (s, 3H), 1.47-1.75 (m, 12H), 1.89-2.12 (m, 6H), 2.24-2.33 (m, 1H), 2.69 (app dt, J=12.9, 3.1 Hz, 1H), 2.84 (app sextet, J=8.0 Hz, 1H), 3.60 (dd, J=11.6, 2.9 Hz, 1H), 4.38-4.47 (m, 1H), 5.10 (q, J=6.7 Hz, 1H), 5.53 (d, J=8.0 Hz, 1H), 5.81 (q, J=7.1 Hz, 1H), 6.38 (d, J=16.3 Hz, 1H), 6.57 (d, J=16.3 Hz, 1H), 7.44 (d, J=8.5 Hz, 1H), 7.61 (dd, J=8.5, 1.6 Hz, 1H), 7.81-7.87 (m, 2H), 8.25 (d, J=8.5 Hz, 1H). LCMS (m/z) 562.1 [M+H], Tr=2.68 min.

Example 53

Compound 53

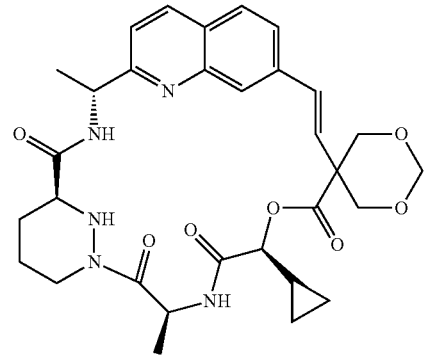 [SMILES: C[C@@H]1NC(=O)[C@H](C2CC2)OC(=O)C2(/C=C/c3ccc4ccc(nc4c3)[C@@H](C)NC(=O)[C@@H]3CCCN(N3)C1=O)COCOC2]

Compound 53a. ((S)-2-{(S)-3-[(R)-1-(7-Bromo-quinolin-2-yl)-ethylcarbamoyl]-tetrahydro-pyridazin-1-yl}-1-methyl-2-oxo-ethyl)-carbamic acid tert-butyl ester

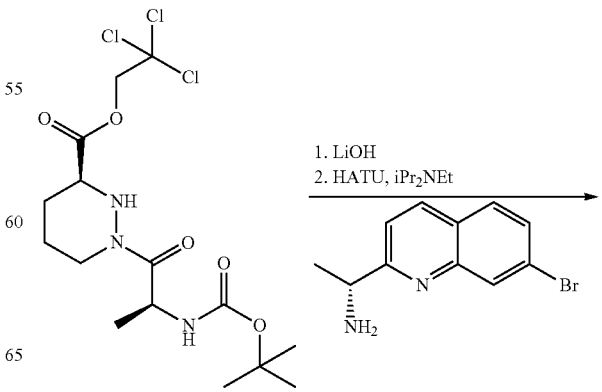

1. LiOH
2. HATU, iPr$_2$NEt

-continued

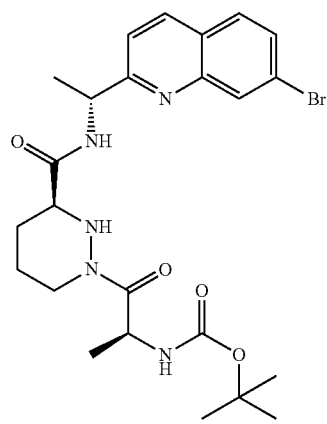

A cooled (0° C.) solution of (S)-1-((S)-2-tert-butoxycarbonylamino-propionyl)-hexahydro-pyridazine-3-carboxylic acid 2,2,2-trichloro-ethyl ester (3.007 g, 6.948 mmol) in tetrahydrofuran/water (60 mL, 5:1) was treated with lithium hydroxide monohydrate (874.4 mg, 20.844 mmol). After stirring at 0° C. for 40 minutes the reaction was quenched with hydrochloric acid (1 M, 50 mL). The aqueous layer was extracted with ethyl acetate (2x). The organics were combined, dried over anhydrous sodium sulfate, filtered and the volatiles were removed in vacuo. Residual trichlorethanol was azeotroped off with toluene (3x) to provide (S)-1-((S)-2-tert-butoxycarbonylamino-propionyl)-hexahydro-pyridazine-3-carboxylic acid as a white solid which was then combined with (R)-1-(7-bromo-quinolin-2-yl)-ethylamine hydrochloride (1.998 g, 6.948 mmol) and suspended in anhydrous acetonitrile (60 mL) and tetrahydrofuran (10 mL). The suspension was cooled to 0° C. and subsequently treated with N,N-diisopropylethylamine (6 mL, 34.740 mmol) and 1-[bis(dimethylamino)methylene]-1H-1,2,3-triazolo[4,5-b]pyridinium 3-oxide hexafluorophosphate (3.699 g, 9.727 mmol). After slowly warming to room temperature and stirring for 16 h, the reaction was quenched at 0° C. with hydrochloric acid (1 M, 70 mL). The aqueous layer was extracted with ethyl acetate (2x). The organics were combined, washed with a saturated solution of sodium bicarbonate, dried over anhydrous sodium sulfate, filtered and the volatiles were removed in vacuo. The residue was purified by silica gel chromatography using a 100 g Isolute cartridge eluted with a continuous gradient of iso-hexanes/ethyl acetate 1:0 to 1:4 to afford the title compound (3.702 g, 99%) as a white foam. $^1$H NMR (300 MHz, CDCl$_3$) δ 1.38 (d, J=6.9 Hz, 3H), 1.43 (s, 9H), 1.47-1.55 (m, 2H), 1.58 (d, J=6.9 Hz, 3H), 1.60-1.78 (m, 2H), 2.22-2.31 (m, 1H), 2.65-2.78 (m, 1H), 3.39-3.52 (m, 1H), 4.55 (d, J=13.4 Hz, 1H), 5.18-5.34 (m, 2H), 5.36-5.45 (m, 1H), 7.37 (d, J=8.5 Hz, 1H), 7.65 (dd, J=8.5, 1.6 Hz, 1H), 7.70 (d, J=8.5 Hz, 1H), 8.04 (d, J=6.5 Hz, 1H), 8.14 (d, J=8.5 Hz, 1H), 8.36 (s, 1H). LCMS (m/z) 536.1, 537.1 [M+H], Tr=2.58 min.

Compound 53b. (S)-1-[(S)-2-(2-Cyclopropyl-2-hydroxy-acetylamino)-propionyl]-hexahydro-pyridazine-3-carboxylic acid [(R)-1-(7-bromo-quinolin-2-yl)-ethyl]-amide

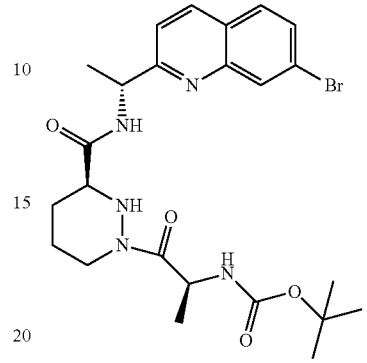

((S)-2-{(S)-3-[(R)-1-(7-Bromo-quinolin-2-yl)-ethylcarbamoyl]-tetrahydro-pyridazin-1-yl}-1-methyl-2-oxo-ethyl)-carbamic acid tert-butyl ester, (1.07 g, 2.00 mmol) was suspended in dichloromethane (20 mL) and the mixture was cooled to 0° C. with stirring. 4 M Hydrogen chloride in 1,4-dioxane (11 mL) was added and the reaction mixture stirred for 90 minutes and then evaporated. Residual water was azeotroped off with toluene and the residue was suspended in dichloromethane (20 mL) and cyclopropyl-hydroxy-acetic acid (255 mg, 2.20 mmol) was added. The mixture was cooled to 0° C. with stirring and N,N-diisopropylethylamine (775 mg, 1.05 mL, 6.00 mmol) was added followed by (benzotriazol-1-yloxy)tris(dimethylamino)phosphonium hexafluorophosphate (1.06 g, 2.40 mmol). The reaction was allowed to warm to ambient temperature and stirred for 18 h. 1M Hydrochloric acid was added and the organic layer was washed with saturated sodium bicarbonate solution, passed through a hydrophobic frit and evaporated. The residue was purified by silica gel chromatography eluting with a gradient of ethyl acetate/methanol 1:0 to 9:1 to afford the title compound (328 mg) as a white foam. The original aqueous extracts were re-extracted with dichloromethane/methanol (9:1, 2x) and the organic extracts dried over anhydrous sodium sulfate, filtered and evaporated. The residue purified by silica gel chromatography eluting with a gradient of ethyl acetate/methanol 1:0 to 17:3 to afford the title compound (378 mg) as a white foam. The two foams were combined (706 mg, 66%). $^1$H NMR (300 MHz, CDCl$_3$) δ 0.46-0.73 (m, 4H), 1.04-1.18 (m, 1H), 1.49-1.59 (m, 6H), 1.53-1.78 (m, 2H), 1.95-2.04 (m, 1H), 2.25-2.34 (m, 1H), 2.64-2.82 (m, 1H), 3.44-3.55 (m, 2H), 3.60-3.84 (m, 1H), 4.50-4.60 (m, 1H), 5.23-5.33 (m, 1H), 5.48-

5.55 (m, 1H), 7.36-7.41 (m, 1H), 7.62-7.73 (m, 2H), 8.13-8.19 (m, 2H), 8.47-8.51 (m, 1H). LCMS (m/z) [M+H] 532.0, 534.0 Tr=2.07 min. LCMS (m/z) 532.0, 533.9 [M+H], Tr=2.12 min.

Compound 53

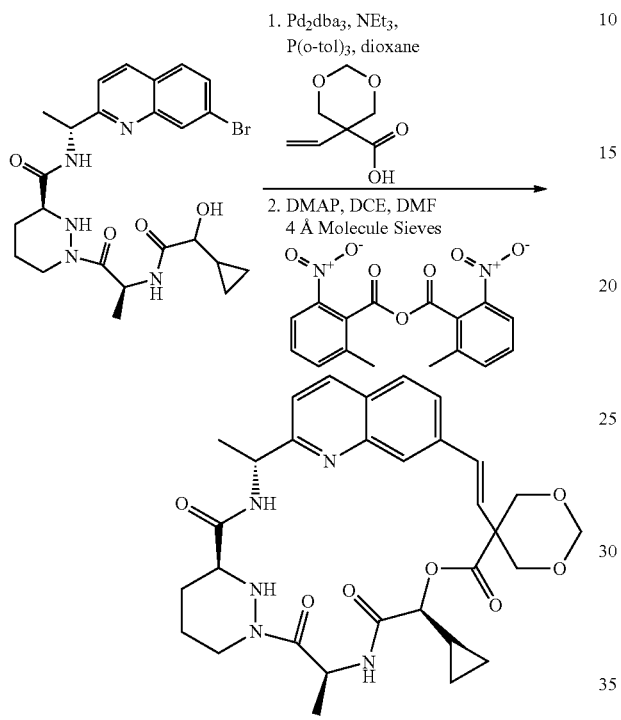

A solution of (S)-1-[(S)-2-(2-cyclopropyl-2-hydroxy-acetylamino)-propionyl]-hexahydro-pyridazine-3-carboxylic acid [(R)-1-(7-bromo-quinolin-2-yl)-ethyl]-amide (592 mg, 1.11 mmol), 5-vinyl[1,3]dioxane-5-carboxylic acid (176 mg, 1.11 mmol), triethylamine (343 mg, 472 μL, 3.39 mmol) and tri(o-tolyl)phosphine (67 mg, 0.22 mmol) in 1,4-dioxane (15 mL) was degassed with nitrogen for 5 minutes and then warmed to 50° C. under nitrogen with stirring. Tris(dibenzylideneacetone)dipalladium(0) (101 mg, 0.11 mmol) was added and the mixture was heated to reflux for 20 minutes and then allowed to cool to room temperature. The suspension was filtered through Celite and the filtrate evaporated to give crude 5-((E)-2-{2-[(R)-1-({(S)-1-[(S)-2-(2-cyclopropyl-2-hydroxy-acetylamino)-propionyl]-hexahydro-pyridazine-3-carbonyl}-amino)-ethyl]-quinolin-7-yl}-vinyl)-[1,3]dioxane-5-carboxylic acid.

To a stirred mixture of powdered 4 Å molecular sieves, 2-methyl-6-nitrobenzoic anhydride (764 mg, 2.22 mmol) and 4-(dimethylamino)-pyridine (542 mg, 4.44 mmol) in dichloromethane (375 mL) was added a solution of crude 5-((E)-2-{2-[(R)-1-({(S)-1-[(S)-2-(2-cyclopropyl-2-hydroxy-acetylamino)-propionyl]-hexahydro-pyridazine-3-carbonyl}-amino)-ethyl]-quinolin-7-yl}-vinyl)-[1,3]dioxane-5-carboxylic acid in dichloromethane (20 mL) over 5 h via syringe pump. The flask originally containing the crude acid was washed with further dichloromethane (5 mL) and this was added to the reaction mixture over ca. 5 minutes. The reaction mixture was stirred for 16 h and then filtered through Celite and evaporated to ~100 mL, washed successively with ice-cold saturated ammonium chloride solution, ice-cold saturated sodium bicarbonate solution, saturated brine and then filtered through a hydrophobic frit. The residue was purified by silica gel chromatography eluting with a gradient of iso-hexanes/acetone 1:0 to 1:1 and then by reverse phase preparative HPLC using a gradient of acetonitrile/water 1:9 to 3:2 modified with 0.1% formic acid to give the title compound (39 mg, 6%) as a yellow solid. $^1$H NMR (300 MHz, CD$_3$OD) δ 0.52-0.76 (m, 4H), 1.30-1.40 (m, 1H), 1.49-1.76 (m, 2H), 1.60 (d, J=6.9 Hz, 3H), 1.64 (d, J=7.1 Hz, 3H), 1.93-2.02 (m, 1H), 2.21-2.30 (m, 1H), 2.66-2.77 (m, 1H), 3.59-3.66 (m, 1H), 3.85, 3.96 (ABq, J$_{AB}$=11.4 Hz, 2H), 4.41-4.51 (m, 2H), 4.63-4.70 (m, 1H), 4.82 (d, J=6.2 Hz, 1H), 4.98 (d, J=6.0 Hz, 1H), 5.04-5.13 (m, 2H), 5.83-5.91 (m, 1H), 6.17 (d, J=16.7 Hz, 1H), 6.66 (d, J=16.7 Hz, 1H), 7.47 (d, J=8.5 Hz, 1H), 7.68 (dd, J=8.5, 1.5 Hz, 1H), 7.83 (s, 1H), 7.86 (d, J=8.5 Hz, 1H), 8.26 (d, J=8.5 Hz, 1H). LCMS (m/z) 592.2 [M+H], Tr=2.04 min.

Example 54

Compound 54

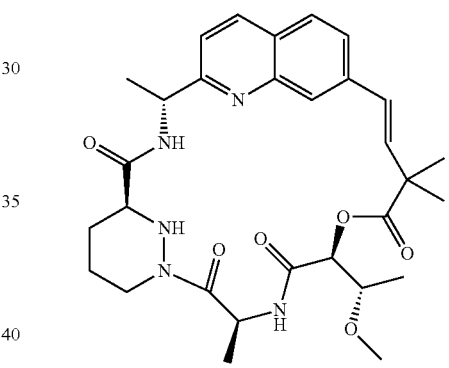

Compound 54a.
(2S,3S)-2-Hydroxy-3-methoxy-butyric acid

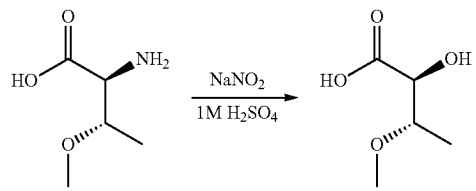

A solution of methyl L-allo-threonine (900 mg, 6.75 mmol) in 1 M sulphuric acid (10 mL) was prepared and cooled to 0° C., before adding a solution of sodium nitrite (693 mg, 10 mmol) in water (2.25 mL) dropwise over 10 minutes. The reaction mixture was stirred at 0° C. for 15 h. Solid ammonium chloride was added to saturate the solution, which was then extracted with diethyl ether (3×25 mL). The extracts were combined and dried over anhydrous sodium sulfate, filtered and evaporated to give the title product (193 mg, 21%) as a colorless oil. $^1$H NMR (300 MHz, CDCl$_3$) δ 1.29 (d, J=6.5 Hz, 3H), 3.48 (s, 3H), 3.71-3.81 (m, 1H), 4.35 (d, J=4.7 Hz, 1H).

Compound 54b. (S)-1-[(S)-2-((2S,3S)-2-Hydroxy-3-methoxy-butyrylamino)-propionyl]-hexahydro-pyridazine-3-carboxylic acid [(R)-1-(7-bromo-quinolin-2-yl)-ethyl]-amide

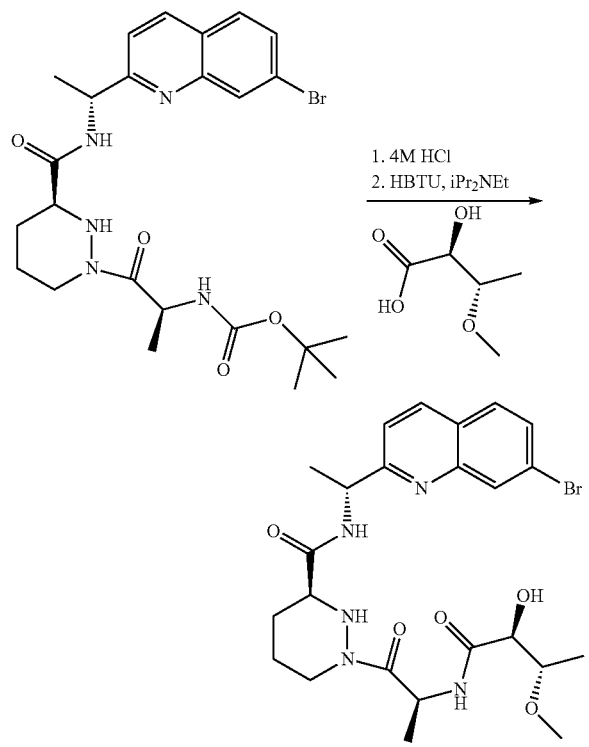

A solution of ((S)-2-{(S)-3-[(R)-1-(7-bromo-quinolin-2-yl)-ethylcarbamoyl]-tetrahydro-pyridazin-1-yl}-1-methyl-2-oxo-ethyl)-carbamic acid tert-butyl ester (838 mg, 1.44 mmol) in dichloromethane (20 mL) was treated with hydrogen chloride in 1,4-dioxane (4 M, 1.44 mL, 5.76 mmol) and stirred for 2 h at room temperature. The solution was evaporated to dryness. The residue was dissolved in dichloromethane (20 mL) and (2S,3S)-2-hydroxy-3-methoxy-butyric acid (193 mg, 1.44 mmol) was added followed by N,N-diisopropylethylamine (1.0 mL, 5.76 mmol) and O-(benzotriazol-1-yl)-N,N,N',N'-tetramethyluronium hexafluorophosphate (819 mg, 2.16 mmol). The solution was stirred at room temperature for 20 h and then evaporated to dryness. The residue was purified by silica gel chromatography eluting with a gradient of acetone/ethyl acetate 1:9 to 1:1 to yield the title compound (243 mg, 31%) as a white gum. $^1$H NMR (300 MHz, CDCl$_3$) δ 1.14 (d, J=6.2 Hz, 3H), 1.33-1.50 (m, 6H), 1.58 (d, J=6.7 Hz, 3H), 2.20-2.30 (m, 1H), 2.66-2.79 (m, 1H), 3.26-3.63 (m, 3H), 3.37 (s, 3H), 3.90 (d, J=11.8 Hz, 1H), 4.20 (d, J=5.1 Hz, 1H), 4.46-4.56 (m, 1H), 5.20-5.31 (m, 1H), 5.36-5.49 (m, 1H), 7.41 (d, J=8.5 Hz, 1H), 7.61-7.70 (m, 2H), 8.15 (d, J=8.5 Hz, 1H), 8.41 (s, 1H). LCMS (m/z) 550.0, 552.0 [M+H], Tr=2.05 min.

Compound 54c. (E)-4-{2-[(R)-1-({(S)-1-[(S)-2-((2S,3S)-2-Hydroxy-3-methoxy-butyrylamino)-propionyl]-hexahydro-pyridazine-3-carbonyl}-amino)-ethyl]-quinolin-7-yl}-2,2-dimethyl-but-3-enoic acid

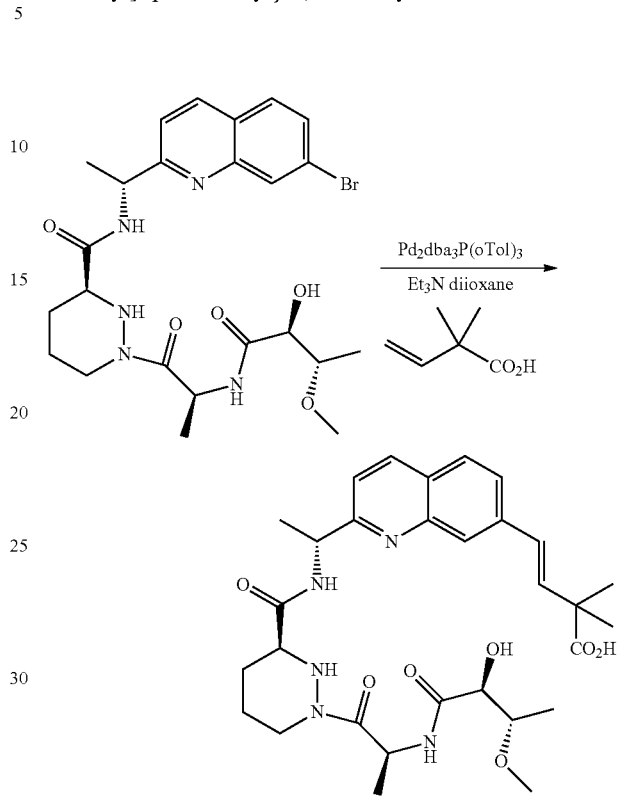

A solution of (S)-1-[(S)-2-((2S,3S)-2-hydroxy-3-methoxy-butyrylamino)-propionyl]-hexahydro-pyridazine-3-carboxylic acid [(R)-1-(7-bromo-quinolin-2-yl)-ethyl]-amide (243 mg, 0.44 mmol) and 2,2-dimethylbut-3-enoic acid (50 mg, 0.44 mmol) in 1,4-dioxane was prepared and triethylamine (183 μL, 1.32 mmol) was added. The reaction mixture was purged with nitrogen for 5 minutes then tris(dibenzylideneacetone)dipalladium(0) (40 mg, 0.044 mmol) was added. The reaction mixture was heated at 100° C. under a nitrogen atmosphere for 1.5 h. The reaction was filtered through hyflo supercel, washing through with ethyl acetate. The filtrate was evaporated in vacuo to yield the crude title compound as a yellow gum. LCMS (m/z) 584.2 [M+H], Tr=1.77 min.

Compound 54

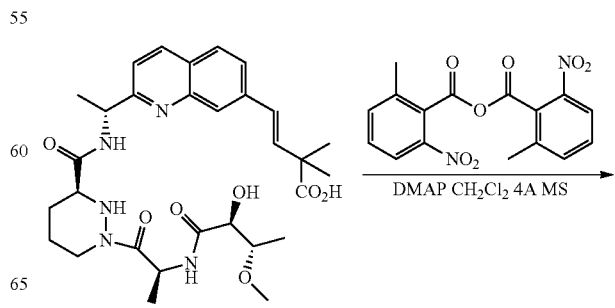

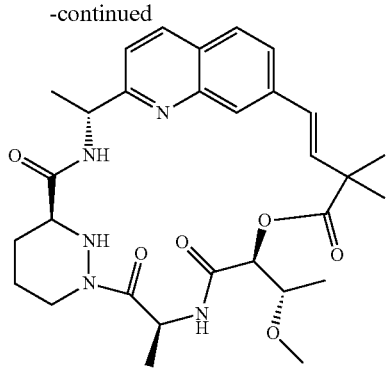

A solution of 2-methyl-6-nitrobenzoic anhydride (389 mg, 1.13 mmol) in anhydrous dichloromethane (160 mL) was prepared and 4 Å molecular sieves and 4-(dimethylamino)pyridine (275 mg, 2.25 mmol) were added. A solution of crude (E)-4-{2-[(R)-1-({(S)-1-[(S)-2-((2S,3S)-2-hydroxy-3-methoxy-butyrylamino)-propionyl]-hexahydro-pyridazine-3-carbonyl}-amino)-ethyl]-quinolin-7-yl}-2,2-dimethyl-but-3-enoic acid (ca. 0.44 mmol) in dichloromethane (11 mL) was added over 5.5 h via syringe pump. After the end of addition, the reaction mixture was stirred for a further 30 minutes at room temperature. The solution was filtered and washed with saturated aqueous sodium bicarbonate solution (70 mL). The organics were filtered through a phase separating cartridge and evaporated to give a yellow gum (0.97 g) which was purified by silica gel chromatography eluting with a gradient of ethyl acetate/acetone 1:0 to 4:1 to yield a colorless gum (133 mg) which was purified by reverse phase preparative HPLC eluting acetonitrile/water 9:11 to yield the title product (15.5 mg, 6%) as a white solid. $^1$H NMR (300 MHz, CD$_3$OD) δ 1.23 (d, J=6.3 Hz, 3H), 1.44 (s, 3H), 1.53 (s, 3H), 1.58 (d, J=6.9 Hz, 3H), 1.61 (d, J=7.4 Hz, 3H), 1.34-1.84 (m, 2H), 1.91-2.01 (m, 2H), 2.25-2.36 (m, 1H), 2.63-2.77 (m, 1H), 3.43 (s, 3H), 2.54-3.67 (m, 1H), 2.73-3.83 (m, 1H), 4.40-4.50 (m, 1H), 4.07-5.16 (m, 1H), 5.56 (d, J=5.6 Hz, 1H), 5.86 (q, J=7.1 Hz, 1H), 6.45, 6.60 (ABq, J$_{AB}$=16.1 Hz, 2H), 7.44 (d, J=8.5 Hz, 1H), 7.59 (m, 1H), 7.84 (d, J=8.3 Hz, 1H), 7.93 (s, 1H), 8.25 (d, J=8.5 Hz, 1H). LCMS (m/z) 566.1 [M+H], Tr=2.32 min.

Example 55

Compound 55

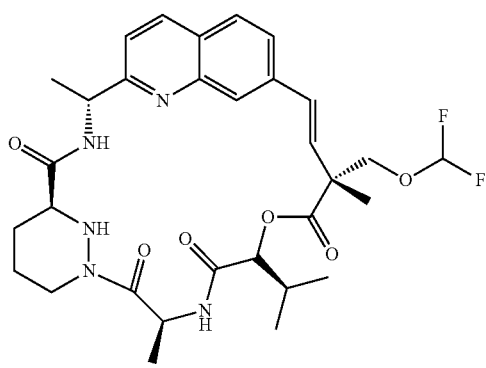

Compound 55a.
(R)-2-Hydroxymethyl-2-methyl-but-3-enoic acid methyl ester

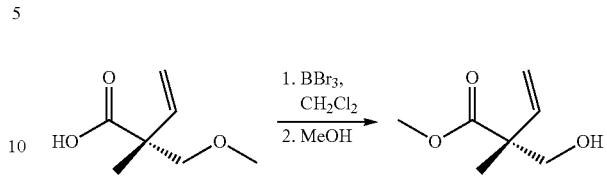

A solution of (R)-2-methoxymethyl-2-methyl-but-3-enoic acid (600 mg, 4.2 mmol) in dichloromethane (40 mL) was stirred at 0° C. under nitrogen. Boron tribromide (1 M in dichloromethane, 16.8 mL, 16.8 mmol) was added and the reaction mixture was stirred at 0° C. for 90 minutes. Methanol (20 mL) was cautiously added and the reaction mixture was warmed to room temperature over 30 minutes and then stirred at room temperature for 30 minutes. The solvent was evaporated and the residue was purified by silica gel chromatography using a gradient of pentane/diethyl ether 3:1 to 1:1 to afford the title compound (540 mg, 90%) as a clear oil. $^1$H NMR (300 MHz, CDCl$_3$) δ 1.35 (s, 3H), 2.33 (m, 1H), 3.62 (m, 1H), 3.75 (s, 3H), 3.75-3.80 (m, 1H), 5.21 (dd, J=17.4, 0.5 Hz, 1H), 5.24 (dd, J=10.7, 0.5 Hz, 1H), 5.98 (dd, J=17.4, 10.7 Hz, 1H). LCMS (m/z) 145.1 [M+H], Tr=1.16 min.

Compound 55b.
(R)-2-Difluoromethoxymethyl-2-methyl-but-3-enoic acid methyl ester

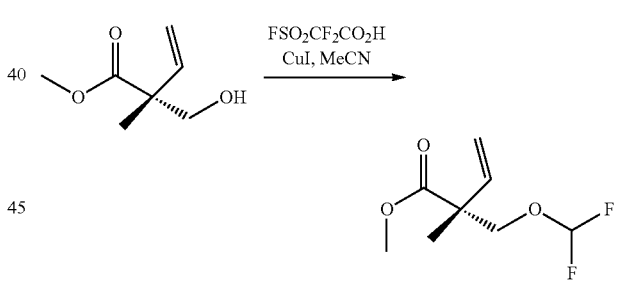

A solution of (R)-2-hydroxymethyl-2-methyl-but-3-enoic acid methyl ester (288 mg, 2.0 mmol) in acetonitrile (8 mL) was stirred at room temperature under nitrogen. Copper(I) iodide (80 mg, 0.4 mmol) was added followed by difluorofluorosulfonyl-acetic acid (356 mg, 0.2 mL, 2.0 mmol) and the reaction mixture was heated at reflux for 30 minutes. The reaction mixture was cooled to room temperature, water was added and the mixture was extracted with ethyl acetate. The organic extracts were combined and washed with brine. The organic solution was filtered through a hydrophobic frit and the filtrate was evaporated. The residue was purified by silica gel chromatography using a gradient of pentane/diethyl ether 10:1 to 5:1 to afford the title compound (195 mg, 50%) as a clear oil. $^1$H NMR (300 MHz, CDCl$_3$) δ 1.40 (s, 3H), 3.75 (s, 3H), 3.86 (d, J=9.4 Hz, 1H), 4.10 (d, J=9.4 Hz, 1H), 5.24 (d, J=17.4 Hz, 1H), 5.24 (dd, J=10.9 Hz, 1H), 5.95 (dd, J=17.4, 10.9 Hz, 1H), 6.22 (t, J=74.3 Hz, 1H).

Compound 55c.
(R)-2-Difluoromethoxymethyl-2-methyl-but-3-enoic acid

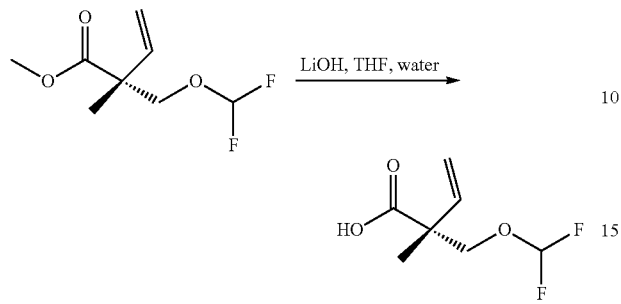

A solution of (R)-2-difluoromethoxymethyl-2-methyl-but-3-enoic acid methyl ester (159 mg, 0.8 mmol) in tetrahydrofuran (6 mL) was stirred at 5° C. under nitrogen. A solution of lithium hydroxide monohydrate (100 mg, 2.4 mmol) in water (1.5 mL) was added and the reaction mixture was stirred at 5° C. for 1 h and then at room temperature for 20 h. Water was added and the mixture was acidified to pH 2 with hydrochloric acid (2 M) and the mixture was extracted with diethyl ether. The organic extracts were combined and washed with brine. The organic solution was filtered through a hydrophobic frit and the filtrate was evaporated to afford the title compound (133 mg, 92%) as a clear oil. $^1$H NMR (300 MHz, d$_6$-DMSO) δ1.24 (s, 3H), 3.80 (d, J=9.4 Hz, 1H), 4.02 (d, J=9.4 Hz, 1H), 5.19 (dd, J=10.6 Hz, 1H), 5.20 (d, J=17.6 Hz, 1H), 5.91 (dd, J=17.6, 10.6 Hz, 1H), 6.68 (t, J=75.6 Hz, 1H), 12.5-13.0 (br s, 1H). LCMS (m/z) 179.1 [M–H], Tr=1.79 min.

Compound 55

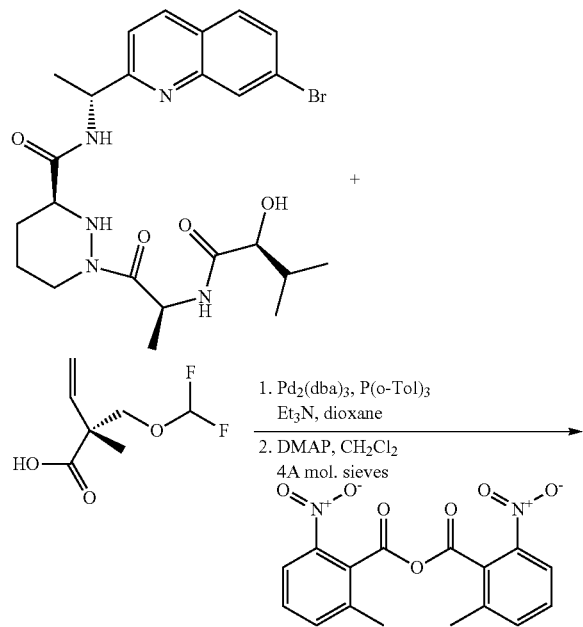

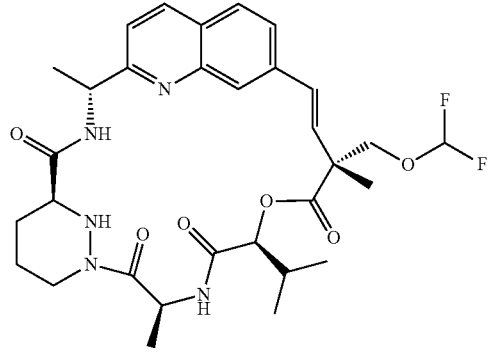

A solution of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (160 mg, 0.3 mmol), (R)-2-difluoromethoxymethyl-2-methyl-but-3-enoic acid (54 mg, 0.3 mmol), tri(o-tolyl)phosphine (18 mg, 0.06 mmol) and triethylamine (91 mg, 0.125 mL, 0.9 mmol) in 1,4-dioxane (6 mL) was stirred at 50° C. under nitrogen. Tris(dibenzylideneacetone)dipalladium(0) (27 mg, 0.03 mmol) was added and the reaction mixture was heated at reflux for 40 minutes. The reaction mixture was cooled to room temperature and the mixture was filtered through a hydrophobic frit and the filtrate was evaporated to afford crude (E)-(R)-2-difluoromethoxymethyl-4-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-2-methyl-but-3-enoic acid (0.3 mmol) which was used in the next step. LCMS (m/z) 634.2 [M+H], Tr=2.04 min.

A mixture of powdered 4 Å molecular sieves (200 mg), 4-dimethylaminopyridine (146 mg, 1.2 mmol), and 2-methyl-6-nitrobenzoic anhydride (206 mg, 0.6 mmol) in dichloromethane (200 mL) was stirred at room temperature under nitrogen. A solution of crude (E)-(R)-2-difluoromethoxymethyl-4-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-2-methyl-but-3-enoic acid (0.3 mmol) in dichloromethane (4 mL) was added via syringe pump over 4 h and the reaction mixture was stirred at room temperature for 18 h. The reaction mixture was filtered through Celite and the filtrate was evaporated to a volume of approximately 50 mL. The solution was washed with ice-cold saturated ammonium chloride solution, ice-cold saturated sodium hydrogen carbonate solution and brine. The organic solution was filtered through a hydrophobic frit and the filtrate was evaporated. The residue was purified by silica gel chromatography using a gradient of iso-hexanes/ethyl acetate 1:2 0:1 and then by reverse phase preparative HPLC eluting with a gradient of acetonitrile/water 1:4 to 1:0 to afford the title compound (21 mg, 11%) as a white solid. $^1$H NMR (300 MHz, CD$_3$OD) δ 1.01 (d, J=6.7 Hz, 3H), 1.06 (d, J=6.7 Hz, 3H), 1.60 (d, J=6.7 Hz, 3H), 1.61 (s, 3H), 1.66 (d, J=7.1 Hz, 3H), 1.66-1.70 (m, 2H), 1.93-1.98 (m, 1H), 2.13-2.26 (m, 2H), 2.64-2.73 (m, 1H), 3.55-3.67 (m, 1H), 3.94 (d, J=9.6 Hz, 1H), 4.26 (d, J=9.6 Hz, 1H), 4.40-4.45 (m, 1H), 5.04 (d, J=12.0 Hz, 1H), 5.08 (q, J=6.7 Hz, 1H), 5.23 (d, J=9.2 Hz, 1H), 5.81 (q, J=7.1 Hz, 1H), 6.24 (d, J=16.5 Hz, 1H), 6.45 (t, J=75.4 Hz, 1H), 6.63 (d, J=16.5 Hz, 1H), 7.46 (d, J=8.5 Hz, 1H), 7.66 (dd, J=8.5, 1.5 Hz, 1H), 7.80 (br s, 1H), 7.86 (d, J=8.5 Hz, 1H), 8.26 (d, J=8.5 Hz, 1H). LCMS (m/z) 616.2 [M+H], Tr=2.58 min.

Example 56

Compound 56

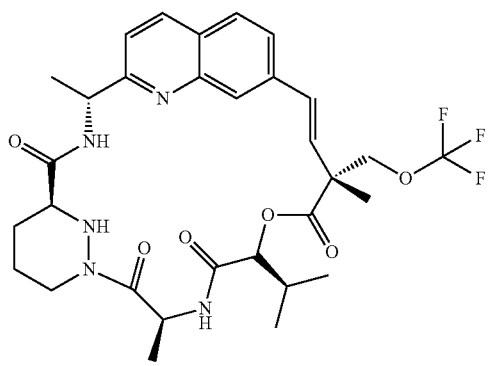

Compound 56a.
(R)-2-Methyl-2-trifluoromethoxymethyl-but-3-enoic acid

Zinc bis(trifluoromethylsulfonyl)imide (750 mg, 1.2 mmol) and (1-(trifluoromethyl)-1,2-benziodoxol-3(1H)-one (758 mg, 2.4 mmol) were added to a stirred solution of (R)-2-hydroxymethyl-2-methyl-but-3-enoic acid methyl ester (288 mg, 2.0 mmol) in dry deuterochloroform (4 mL) under nitrogen. The reaction mixture was stirred at room temperature under nitrogen in a sealed flask for 5 days. The resulting suspension was diluted with dichloromethane and the supernatant was separated and evaporated. Dichloromethane (5 mL) was added to the residue and the supernatant solution was purified by silica gel chromatography using a gradient of pentane/diethyl ether 10:1 to 5:1 to afford crude (R)-2-methyl-2-trifluoromethoxymethyl-but-3-enoic acid methyl ester (98 mg) as a clear oil which was used in the next step.

A solution of crude (R)-2-methyl-2-trifluoromethoxymethyl-but-3-enoic acid methyl ester (98 mg) in tetrahydrofuran (4 mL) was stirred at 5° C. under nitrogen. A solution of lithium hydroxide monohydrate (63 mg, 1.5 mmol) in water (1 mL) was added and the reaction mixture was stirred at 5° C. for 1 h and then at room temperature for 3 days. Water was added and the mixture was acidified to pH 2 with hydrochloric acid (2 M) and the mixture was extracted with diethyl ether. The organic extracts were combined and washed with brine. The organic solution was filtered through a hydrophobic frit and the filtrate was evaporated to afford the crude title compound (95 mg) as a clear oil which was used in the next step. LCMS (m/z) 197.1 [M–H], Tr=2.16 min.

Compound 56

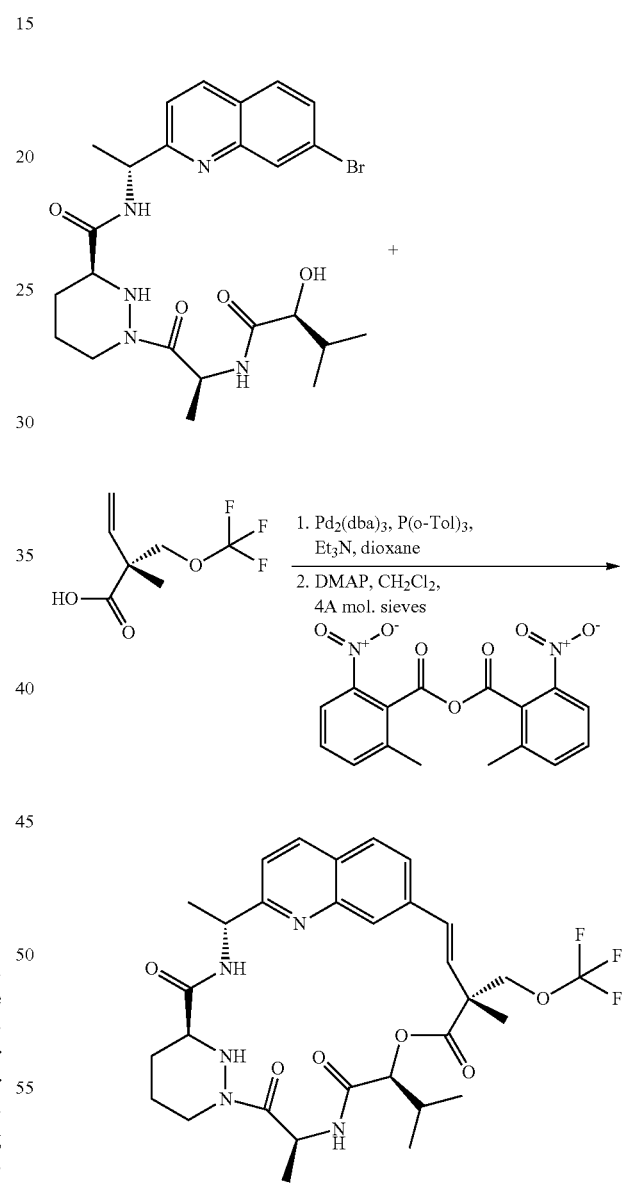

A solution of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (212 mg, 0.4 mmol), crude (R)-2-methyl-2-trifluoromethoxymethyl-but-3-enoic acid (95 mg), tri(o-tolyl)phosphine (24 mg, 0.08 mmol) and triethylamine (121 mg, 0.17 mL, 1.2 mmol) in 1,4-dioxane (10 mL) was stirred at 50° C. under nitrogen. Trs(dibenzylideneacetone)dipalladium(0) (36 mg, 0.04 mmol) was added and the reaction mixture was heated at reflux for 40 minutes. The reaction mixture was cooled to room temperature and the mixture was filtered through a hydrophobic frit and the filtrate was evaporated to afford crude (E)-(R)-4-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-2-methyl-2-trifluoromethoxymethyl-but-3-enoic acid which was used in the next step. LCMS (m/z) 652.1 [M+H], Tr=2.17 min.

A mixture of powdered 4 Å molecular sieves (200 mg), 4-dimethylaminopyridine (195 mg, 1.6 mmol), and 2-methyl-6-nitrobenzoic anhydride (275 mg, 0.8 mmol) in dichloromethane (200 mL) was stirred at room temperature under nitrogen. A solution of crude (E)-(R)-4-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-2-methyl-2-trifluoromethoxymethyl-but-3-enoic acid in dichloromethane (5 mL) was added via syringe pump over 4 h and the reaction mixture was stirred at room temperature for 18 h. The reaction mixture was filtered through Celite and the filtrate was evaporated to a volume of approximately 50 mL. The solution was washed with ice-cold saturated ammonium chloride solution, ice-cold saturated sodium hydrogen carbonate solution and brine. The organic solution was filtered through a hydrophobic frit and the filtrate was evaporated. The residue was purified by silica gel chromatography using a gradient of iso-hexanes/ethyl acetate 1:2 to 0:1 then by reverse phase preparative HPLC eluting with a gradient of acetonitrile/water 1:4 to 1:0 to afford the title compound (4.3 mg, 0.3% over 4 steps) as a white solid. ¹H NMR (300 MHz, CD₃OD) δ 1.01 (d, J=6.7 Hz, 3H), 1.07 (d, J=6.7 Hz, 3H), 1.60 (d, J=6.7 Hz, 3H), 1.63 (s, 3H), 1.66 (d, J=7.1 Hz, 3H), 1.66-1.70 (m, 2H), 1.93-1.97 (m, 1H), 2.14-2.27 (m, 2H), 2.64-2.73 (m, 1H), 3.58-3.67 (m, 1H), 4.10 (d, J=9.1 Hz, 1H), 4.37-4.42 (m, 1H), 4.45 (d, J=9.1 Hz, 1H), 5.03 (d, J=12.0 Hz, 1H), 5.09 (q, J=6.7 Hz, 1H), 5.24 (d, J=8.9 Hz, 1H), 5.81 (q, J=7.1 Hz, 1H), 6.23 (d, J=16.5 Hz, 1H), 6.64 (d, J=16.5 Hz, 1H), 7.47 (d, J=8.5 Hz, 1H), 7.67 (dd, J=8.5, 1.5 Hz, 1H), 7.82 (br s, 1H), 7.87 (d, J=8.5 Hz, 1H), 8.26 (d, J=8.5 Hz, 1H). LCMS (m/z) 634.1 [M+H], Tr=2.85 min.

Example 57

Compound 57

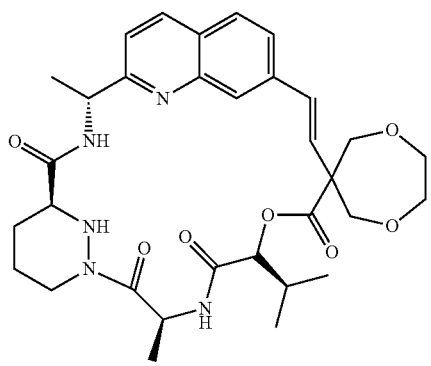

Compound 57a. 6-Nitromethyl-[1,4]dioxepan-6-ol

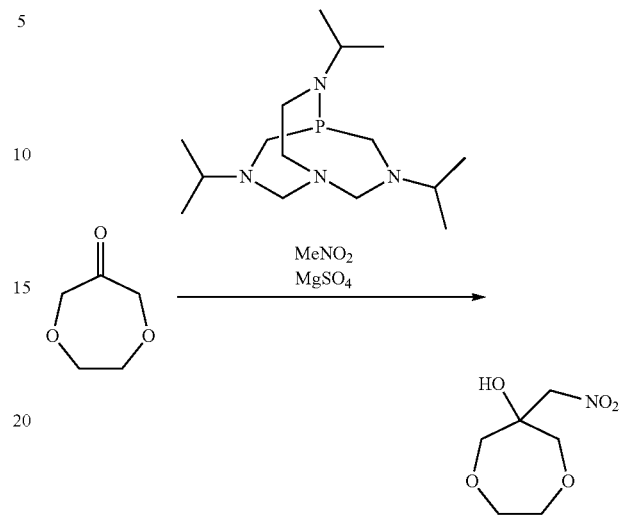

To magnesium sulfate (2.05 g, 17.0 mmol) under nitrogen was added nitromethane (4 mL) and the mixture was vigorously stirred. A solution of [1,4]ioxepan-6-one (899 mg, 7.74 mmol, prepared as described in PCT Int. Appl. 2010139717) in nitromethane (2 mL) was added and the mixture was stirred at room temperature for 5 minutes. A solution of 2,8,9-triisopropyl-2,5,8,9-tetraaza-1-phosphabicyclo[3,3,3]undecane (231 mg, 250 μL, 0.77 mmol) in nitromethane (2 mL) was added and the mixture was heated at 40° C. for 19 h. The cooled reaction mixture was directly loaded on silica and purified by silica gel chromatography using a gradient of pentane/diethyl ether 1:1 to 1:3 to give the title compound (798 mg, 58%). as a yellow oil. ¹H NMR (300 MHz, CDCl₃) δ 3.27 (s, 1H), 3.77-3.93 (m, 4H), 3.85 (s, 4H), 4.58 (s, 2H).

Compound 57b. 6-Nitromethylene-[1,4]dioxepane

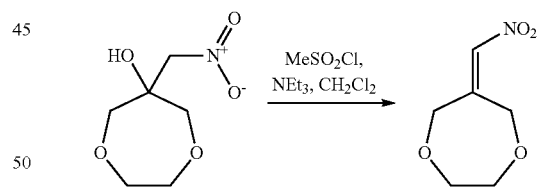

A stirred mixture of 6-nitromethyl-[1,4]dioxepan-6-ol (0.74 g, 4.18 mmol) and triethylamine (1.86 g, 2.56 mL, 18.4 mmol) in dichloromethane (20 mL), under nitrogen, was cooled to −78° C. and methanesulfonyl chloride (1.43 g, 970 μL, 12.5 mmol) was added dropwise. The reaction mixture was stirred for 30 minutes and then quenched with saturated ammonium chloride solution. The mixture was removed from the cooling bath and allowed to warm to ambient temperature. The organic layer was separated and the aqueous layer was extracted with dichloromethane. The combined organic extracts were dried over anhydrous sodium sulfate, filtered and evaporated. The residue was purified by silica gel chromatography using a gradient of pentane/diethyl ether 3:1 to 1:1 to give the title compound (512 mg, 77%) as a yellow oil. ¹H NMR (300 MHz, CDCl₃) δ 3.81-3.90 (m, 4H), 4.36 (d, J=0.5 Hz, 2H), 5.04 (d, J=2.5 Hz, 2H), 7.02 (t, J=2.5 Hz, 1H). LCMS (m/z) 182.1.0 [M+Na], Tr=1.04 min.

Compound 57c.
6-Nitromethyl-6-vinyl-[1,4]dioxepane

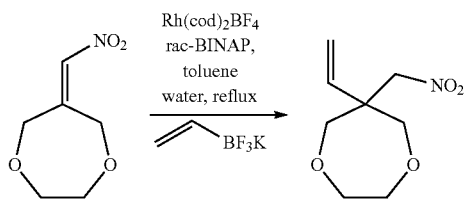

A mixture of toluene (13 mL) and water (3.25 mL) was deoxygenated by bubbling nitrogen through for 20 minutes. It was then added to 6-nitromethylene-[1,4]dioxepane (512 mg, 3.22 mmol). 2,2'-Bis(diphenylphosphino)-1,1'-binaphthalene (218 mg, 0.35 mmol) and potassium vinyltrifluoroborate (1.73 g, 12.9 mmol) were added and the mixture was deoxygenated by bubbling nitrogen through for 5 minutes. Bis(1,5-cyclooctadiene)rhodium(I) tetrafluoroborate (131 mg, 0.32 mmol) was added and the reaction mixture was stirred and heated at reflux under nitrogen for 4.5 h. The mixture was allowed to cool and was partitioned between diethyl ether and water. The aqueous layer was separated and extracted with diethyl ether and the combined organics extracts were dried over anhydrous sodium sulfate, filtered and evaporated. The residue was purified by silica gel chromatography using a gradient of iso-hexanes/diethyl ether 3:1 to 13:7 to give the title compound (155 mg, 26%) as a pale brown oil. $^1$H NMR (300 MHz, CDCl$_3$) δ 3.77-3.93 (m, 8H), 4.64 (s, 2H), 5.22 (d, J=17.9 Hz, 1H), 5.30 (d, J=11.2 Hz, 1H), 5.79 (dd, J=17.8, 11.2 Hz, 1H). LCMS (m/z) 210.1 [M+Na], Tr=1.51 min.

Compound 57d.
6-Vinyl-[1,4]dioxepane-6-carboxylic acid

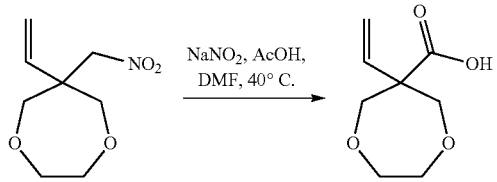

To a stirred solution of 6-nitromethyl-6-vinyl-[1,4]dioxepane (214 mg, 1.14 mmol) in N,N-dimethylformamide (5 mL) under nitrogen was added acetic acid (684 mg, 652 µL, 11.4 mmol) and sodium nitrite (237 mg, 3.43 mmol). The mixture was heated at 40° C. for 23 h and allowed to cool. The mixture was acidified to pH 1 with hydrochloric acid (2 M) and the aqueous layer was extracted with diethyl ether (3×). The combined organic extracts were washed with water, dried over anhydrous magnesium sulfate, filtered, evaporated. Residual N,N-dimethylformamide was azeotroped off with toluene to give the title compound (79 mg, 40%) as a yellow gum. The original aqueous layer was saturated with sodium chloride and extracted with diethyl ether (3×) and the combined organic extracts were washed with water, dried over anhydrous magnesium sulfate, filtered and evaporated. Residual N,N-dimethylformamide was azeotroped off with toluene to give the title compound (22 mg, 11%) as a yellow gum. The two gums were finally combined (101 mg, 51%). $^1$H NMR (300 MHz, CDC$_3$) δ 3.76-3.93 (m, 4H), 3.88 (d, J=12.5 Hz, 2H), 4.35 (d, J=12.7 Hz, 2H), 5.26 (d, J=17.8 Hz, 1H), 5.27 (d, J=10.9 Hz, 1H), 5.79 (dd, J=17.4, 10.9 Hz, 1H). LCMS (m/z) 195.2 [M+Na], Tr=0.96 min.

Compound 57e. 6-((E)-2-{2-[(R)-1-({(S)-1-[(S)-2-((S)-2-Hydroxy-3-methyl-butyrylamino)-propionyl]-hexahydro-pyridazine-3-carbonyl}-amino)-ethyl]-quinolin-7-yl}-vinyl)-[1,4]dioxepane-6-carboxylic acid

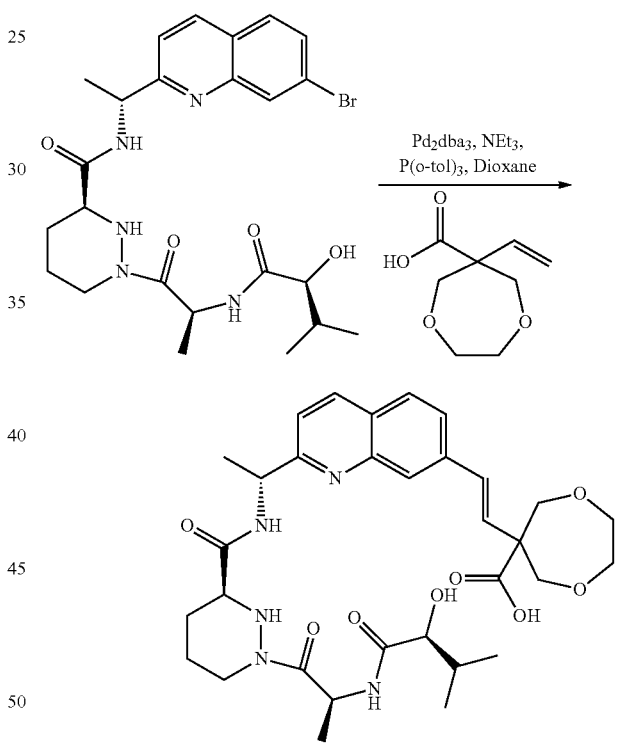

A mixture of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (68 mg, 0.128 mmol), 6-vinyl-[1,4]dioxepane-6-carboxylic acid (22 mg, 0.128 mmol), triethylamine (39 mg, 54 µL, 0.384 mmol) and tri(o-tolyl)phosphine (8 mg, 0.026 mmol) in 1,4-dioxane (2 mL) was deoxygenated by bubbling nitrogen through for 5 minutes and then warmed to 50° C. under nitrogen with stirring. Tris(dibenzylideneacetone)dipalladium(0) (12 mg, 0.013 mmol) was added and the mixture was refluxed for 40 minutes and then allowed to cool. The suspension was filtered and the filtrate was evaporated to give crude title compound which was used directly in the next stage. LCMS (m/z) 626.2 [M+H], Tr=1.67 min.

Compound 57

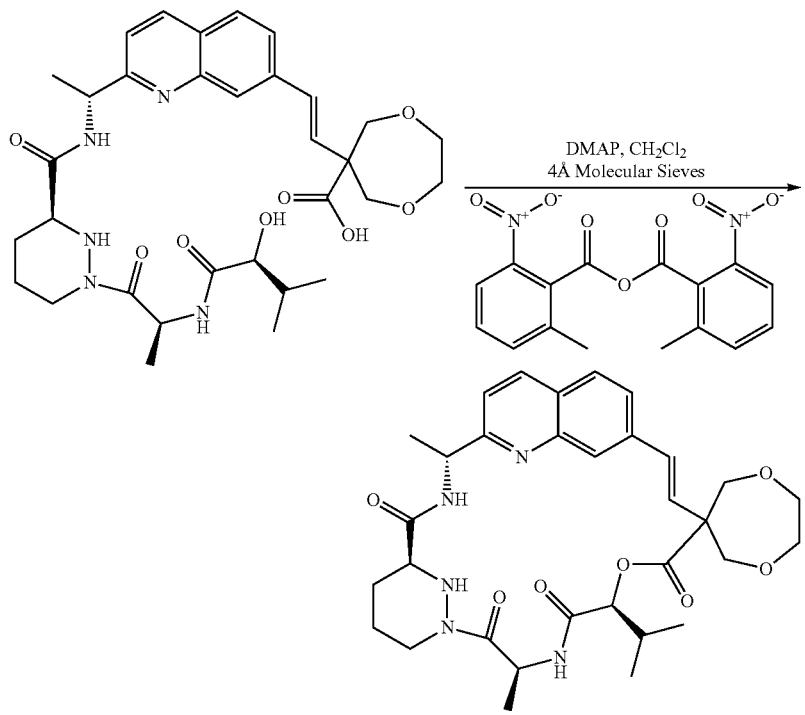

To a stirred mixture of powdered 4 Å molecular sieves (~1 g), 2-methyl-6-nitrobenzoic anhydride (88 mg, 0.256 mmol) and 4-(dimethylamino)-pyridine (63 mg, 0.512 mmol) in dichloromethane (38 mL), under nitrogen, was added a solution of crude 6-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-[1,4]dioxepane-6-carboxylic acid (0.128 mmol) in dichloromethane (5 mL) over 2.5 h via syringe pump. The flask originally containing the crude acid was washed with dichloromethane (1 mL) and added to the reaction mixture over ca. 10 minutes. The reaction mixture was stirred for 1 h and then filtered through Celite and washed successively with ice-cold saturated ammonium chloride solution, ice-cold saturated sodium bicarbonate solution, saturated brine and then dried over anhydrous sodium sulfate, filtered and evaporated. The residue was purified by reverse phase preparative HPLC using a gradient of acetonitrile/water 1:9 to 7:3 containing 0.1% formic acid, to give, after trituration with diethyl ether, the title compound (6.5 mg, 8% over 2 steps) as a white solid. $^1$H NMR (300 MHz, CD$_3$OD) δ 1.04 (d, J=6.7 Hz, 3H), 1.08 (d, J=6.7 Hz, 3H), 1.53-1.73 (m, 2H), 1.60 (d, J=6.7 Hz, 3H), 1.66 (d, J=7.4 Hz, 3H), 1.90-2.00 (m, 1H), 2.10-2.28 (m, 2H), 2.63-2.75 (m, 1H), 3.57-3.65 (m, 1H), 3.76-3.91 (m, 5H), 4.13 (d, J=12.5 Hz, 1H), 4.38 (d, J=12.7 Hz, 1H), 4.38-4.46 (m, 1H), 4.53 (d, J=12.7 Hz, 1H), 5.07 (q, J=6.7 Hz, 1H), 5.35 (d, J=9.2 Hz, 1H), 5.76-5.86 (m, 1H), 6.30 (d, J=16.5 Hz, 1H), 6.49 (d, J=16.5 Hz, 1H), 7.46 (d, J=8.5 Hz, 1H), 7.68-7.73 (m, 2H), 7.85 (d, J=8.9 Hz, 1H), 8.19 (br s, 1H), 8.25 (d, J=8.5 Hz, 1H). LCMS (m/z) 608.2 [M+H], Tr=2.12 min.

Example 58

Compound 58

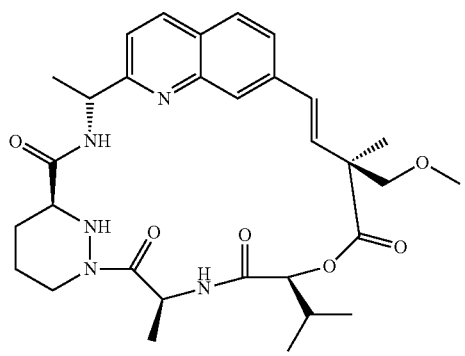

Compound 58a. (S)-4-Isopropyl-3-((S)-2-methoxymethyl-2-methyl-but-3-enoyl)-oxazolidin-2-one

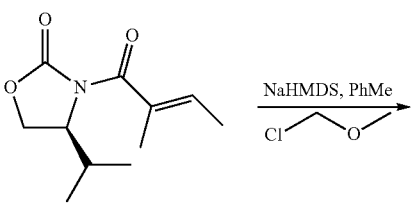

-continued

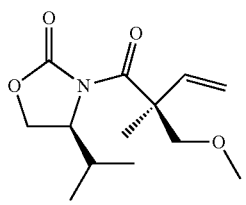

To a solution of (S)-4-isopropyl-3-((E)-2-methyl-but-2-enoyl)-oxazolidin-2-one (prepared according to the method reported in Example 29c but using the opposite enantiomer of the oxazolidinone), (4.44 g, 21 mmol), in anhydrous toluene (40 mL) under nitrogen at −78° C. was added dropwise a solution of Sodium bis(trimethylsily)amide in toluene (0.6 M, 54 mL, 32 mmol). When addition was completed, the reaction mixture was left to stir at −78° C. for another minutes. Chloromethyl methyl ether (3.38 g, 42 mmol) was slowly added. Stirring was maintained at −60° C. for 30 minutes and then for 1 h as the temperature was allowed to rise to 0° C. Saturated ammonium chloride solution (230 mL) was added and the mixture was left to stir at room temperature for 10 minutes. The aqueous layer was extracted with ethyl acetate (2×) and the combined organic layers were washed with brine, dried over anhydrous sodium sulfate and filtered. The filtrate was evaporated. The crude residue was purified by silica gel chromatography using a Biotage KP-Sil 100 g cartridge eluting with a gradient of iso-hexanes/ethyl acetate 1:0 to 9:1 to give the title product (2.55 g, 48%) as a colorless oil. $^1$H NMR (300 MHz, CDCl$_3$) δ 0.80-1.00 (m, 6H), 1.50 (s, 3H), 2.25-2.45 (m, 1H), 3.35 (s, 3H), 3.46 (d, J=8.7 Hz, 1H), 4.16-4.23 (m, 2H), 4.28 (app t, J=8.2 Hz, 1H), 4.45-4.60 (m, 1H), 5.01 (d, J=17.6 Hz, 1H), 5.12 (d, J=10.7 Hz, 1H), 6.19 (dd, J=17.6, 10.7 Hz, 1H). LCMS (m/z) 255.3 [M+H], Tr=2.58 min.

Compound 58b.
(S)-2-Methoxymethyl-2-methyl-but-3-enoic acid

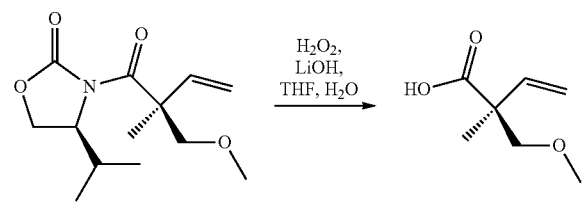

To a stirred solution of (S)-4-isopropyl-3-((R)-2-methoxymethyl-2-methyl-but-3-enoyl)-oxazolidin-2-one (1.5 g, 5.87 mmol) in tetrahydrofuran (30 mL) and water (15 mL) at 0° C., was added hydrogen peroxide (30% solution, 3 mL, 29.35 mmol) and lithium hydroxide monohydrate (0.59 g, 11.75 mmol). The reaction mixture was stirred at 0° C. for 3 h then was treated with saturated sodium metabisulfite and the pH of the solution was adjusted to 1 with dropwise addition of hydrochloric acid (10 M). The aqueous layer was extracted with ethyl acetate (2×) and the combined organic layers were washed with brine, dried over anhydrous sodium sulfate and filtered. The filtrate was evaporated. The crude residue was purified by silica gel chromatography using a Biotage KP-Sil 50 g cartridge, eluting with a gradient of iso-hexanes/ethyl acetate 1:0 to 3:1 to give the title product (0.546 g, 65%) as a colorless oil. $^1$H NMR (300 MHz, CDCl$_3$) δ 1.36 (s, 3H), 3.42 (s, 3H), 3.45 (d, J=8.9 Hz, 1H), 3.62 (d, J=8.9 Hz, 1H), 5.20-5.30 (m, 2H), 6.01 (dd, J=17.6, 10.7 Hz, 1H), 9.80-11.80 (br. s, 1H).

Compound 58c. (E)-(S)-4-[2-((R)-1-tert-Butoxycarbonylamino-ethyl)-quinolin-7-yl]-2-methoxymethyl-2-methyl-but-3-enoic acid

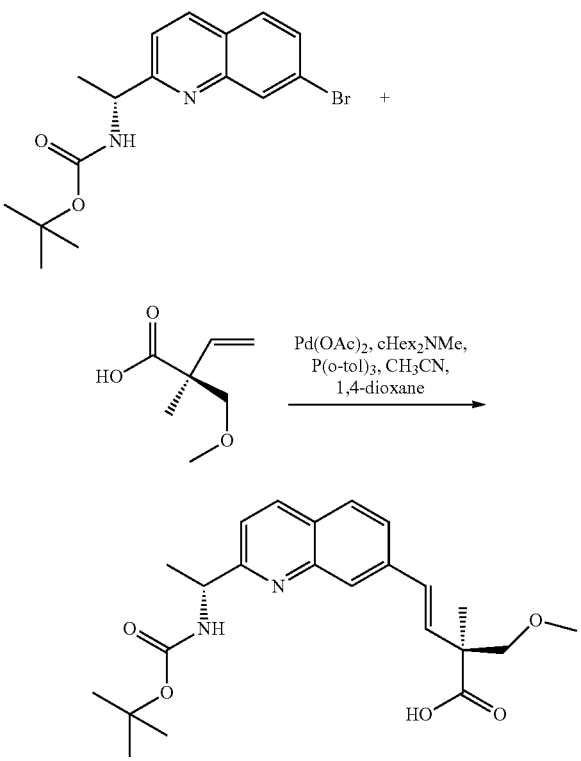

To a vial charged with [(R)-1-(7-bromo-quinolin-2-yl)-ethyl]-carbamic acid tert-butyl ester (706 mg, 2 mmol), (S)-2-methoxymethyl-2-methyl-but-3-enoic acid (290 mg, 2 mmol), tri-(o-tolyl)phosphine (610 mg, 2 mmol) and N,N-dicyclohexyl-methyl-amine (0.85 mL, 4 mmol), was added acetonitrile (2 mL) and 1,4-dioxane (6 mL). The vial was purged with nitrogen. Palladium(II) acetate (450 mg, 2 mmol) was added. The vial was sealed and irradiated by microwave at 130° C. for 1 h. The mixture was then treated with saturated solution of potassium hydrogen sulfate. The aqueous layer was extracted with ethyl acetate (2×) and the combined organic layers were washed with brine, dried over anhydrous sodium sulfate and filtered. The filtrate was evaporated. The crude residue was purified by silica gel chromatography using a Biotage KP-Sil 100 g cartridge eluting with a gradient of ethyl acetate/methanol 1:0 to 41:9 to give the title product (0.176 g, 21%) as an amber oil. $^1$H NMR (300 MHz, CDCl$_3$) δ 1.45 (s, 9H), 1.54 (s, 3H), 1.57 (d, J=6.5 Hz, 3H), 3.47 (s, 3H), 3.62 (d, J=8.7 Hz, 1H), 3.77 (d, J=8.7 Hz, 1H), 4.90-5.10 (m, 1H), 6.60-6.85 (m, 2H), 7.34 (d, J=8.4 Hz, 1H), 7.61 (d, J=8.4 Hz, 1H), 7.75 (d, J=8.4 Hz, 1H), 8.06-8.17 (m, 2H). LCMS (m/z) 415.3 [M+H], Tr=2.11 min.

Compound 58d. (S)-1-[(S)-2-((S)-2-{(E)-(S)-4-[2-((R)-1-tert-Butoxycarbonylamino-ethyl)-quinolin-7-yl]-2-methoxymethyl-2-methyl-but-3-enoyloxy}-3-methyl-butyrylamino)-propionyl]-hexahydro-pyridazine-3-carboxylic acid 2,2,2-trichloro-ethyl ester

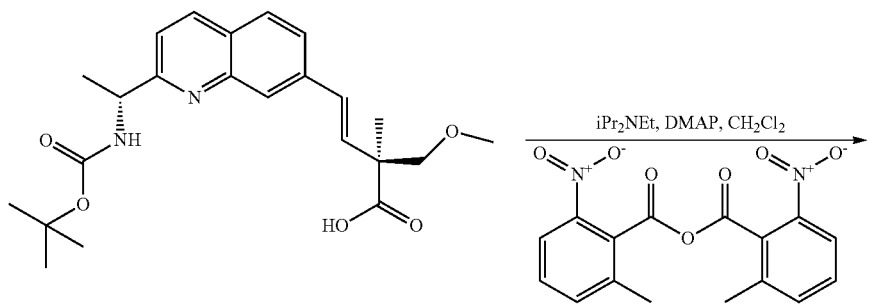

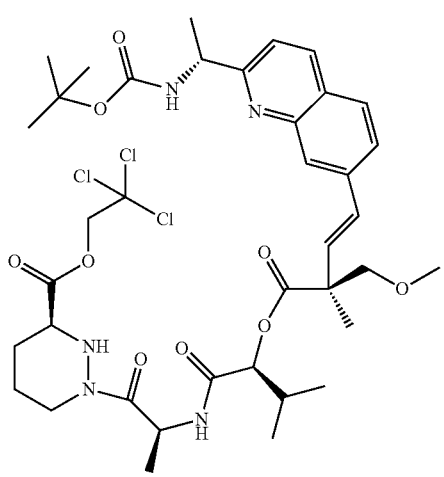

Compound 58

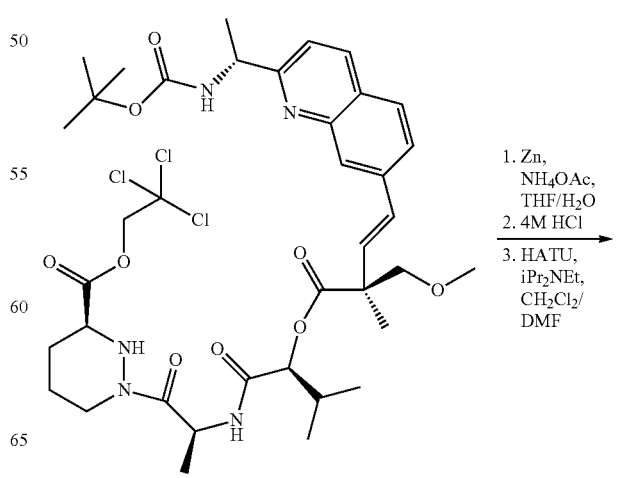

To a solution of (E)-(S)-4-[2-((R)-1-tert-butoxycarbonylamino-ethyl)-quinolin-7-yl]-2-methoxymethyl-2-methyl-but-3-enoic acid (176 mg, 0.34 mmol) in dichloromethane (2 mL), was added (S)-1-[(S)-2-((S)-2-hydroxy-3-methyl-butyrylamino)-propionyl]-hexahydro-pyridazine-3-carboxylic acid 2,2,2-trichloro-ethyl ester (205 mg, 0.47 mmol), 4-dimethylaminopyridine (116 mg, 0.95 mmol), N,N-diisopropylethylamine (123 mg, 0.95 mmol) and 2-methyl-6-nitrobenzoic anhydride (164 mg, 0.47 mmol). The reaction mixture was stirred at room temperature for 18 h, was then treated with saturated solution of sodium hydrogen carbonate, extracted with dichloromethane (2×) and the combined organic layers were washed with brine, dried over anhydrous sodium sulfate and filtered. The filtrate was evaporated. The crude residue was purified by silica gel chromatography using a Biotage KP-Sil 50 g cartridge eluting with a gradient of iso-hexanes/ethyl acetate 9:1 to 0:1 to give the title product (0.22 g, 78%) as a yellow solid. $^1$H NMR (300 MHz, CDCl$_3$) δ 0.85-1.10 (m, 6H), 1.20-1.70 (m, 23H), 2.05-2.20 (m, 1H), 2.30-2.45 (m, 1H), 3.44 (s, 3H), 3.60-3.95 (m, 4H), 4.15-4.32 (m, 1H), 4.68-4.70 (m, 1H), 4.90-5.05 (m, 2H), 5.20-5.45 (m, 1H), 6.10-6.28 (m, 1H), 6.60-6.85 (m, 2H), 7.10-7.20 (m, 1H), 7.28 (d, J=8.4 Hz, 1H), 7.66-7.74 (m, 2H), 8.00 (d, J=4.0 Hz, 1H), 8.05 (d, J=8.4 Hz, 1H). LCMS (m/z) 828.5 [M+H], Tr=3.48 min.

-continued

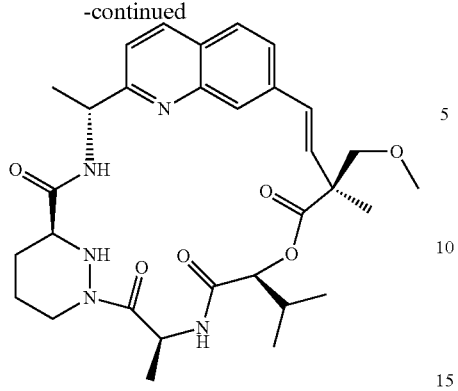

To a solution of (S)-1-[(S)-2-((S)-2-{(E)-(S)-4-[2-((R)-1-tert-butoxycarbonylamino-ethyl)-quinolin-7-yl]-2-methoxymethyl-2-methyl-but-3-enoyloxy}-3-methyl-butyrylamino)-propionyl]-hexahydro-pyridazine-3-carboxylic acid 2,2,2-trichloro-ethyl ester (0.22 g, 0.265 mmol) in tetrahydrofuran (3 mL), was added zinc powder (190 mg, 2.92 mmol) and a solution of ammonium acetate (153 mg, 1.99 mmol) in water (1.5 mL). The resulting mixture was stirred for 24 h. The mixture was filtered through a pad of Celite and the filtrate was washed with saturated potassium hydrogen sulfate. The aqueous layer was extracted with ethyl acetate. The combined organic layers were washed with brine, dried over anhydrous sodium sulfate and filtered. The filtrate was evaporated and then co-evaporated with toluene to give an amber oil which was treated with hydrogen chloride in 1,4-dioxane (4 M, 4 mL) After stirring for 1 h volatiles were evaporated to give a crude solid which was dissolved in anhydrous dichloromethane (20 mL) and anhydrous N,N-dimethylformamide (1 mL). N,N-Diisopropylethylamine (66 mg, 0.515 mmol) and 2-(1H-7-azabenzotriazol-1-yl)-1,1,3,3-tetramethyl uronium hexafluorophosphate methanaminium (59 mg, 0.155 mmol) were added. The mixture was stirred for 1.5 h then water was added and the organic layer was filtered through a phase separator frit. The organic filtrate was evaporated and then co-evaporated with toluene to give an amber oil. The crude residue was purified by silica gel chromatography using a Biotage KP-Sil 10 g cartridge eluting with a gradient of iso-hexanes/ethyl acetate 9:1 to 0:1 then by reverse phase preparative HPLC eluting with a gradient of water/acetonitrile 13:7 to 13:12 over 30 minutes to give the title compound.

Compound 58 (2.83 mg, 4.8%) as white solid. $^1$H NMR (300 MHz, CD$_3$OD) δ 1.02 (d, J=6.7 Hz, 3H), 1.08 (d, J=6.7 Hz, 3H), 1.48 (s, 3H), 1.50-1.80 (m, 7H), 1.91-2.03 (m, 1H), 2.11-2.22 (m, 1H), 2.24-2.34 (m, 1H), 2.65-2.78 (m, 1H), 3.39 (s, 3H), 3.43 (d, J=8.5 Hz, 1H), 3.54-3.67 (m, 1H), 3.99 (d, J=8.5 Hz, 1H), 4.40-4.50 (m, 1H), 5.02-5.20 (m, 2H), 5.30 (d, J=8.9 Hz, 1H), 5.82 (q, J=7.1 Hz, 1H), 6.31 (d, J=16.5 Hz, 1H), 6.64 (d, J=16.5 Hz, 1H), 7.46 (d, J=8.5 Hz, 1H), 7.64 (dd, J=8.2, 1.5 Hz, 1H), 7.79 (s, 1H), 7.85 (d, J=8.5 Hz, 1H), 8.26 (d, J=8.5 Hz, 1H). LCMS (m/z) 580.2 [M+H], Tr=2.45 min.

Example 59

Compound 59

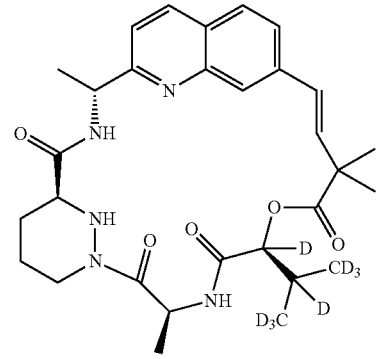 [SMILES: [2H]C([2H])([2H])C([2H])(C([2H])([2H])[2H])[C@]1([2H])OC(=O)C(C)(C)/C=C/c2ccc3ccc(nc3c2)[C@@H](C)NC(=O)[C@@H]2CCCN(N2)C(=O)[C@H](C)NC1=O]

Compound 59a

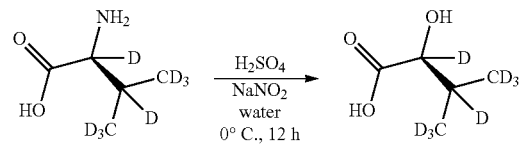 [SMILES: [2H]C([2H])([2H])C([2H])(C([2H])([2H])[2H])[C@]([2H])(N)C(=O)O ; "H2SO4" ; "NaNO2water0° C., 12 h" ; [2H]C([2H])([2H])C([2H])(C([2H])([2H])[2H])[C@]([2H])(O)C(=O)O]

To a solution of L-valine-d$_8$ (CAS Number: 35045-72-8; C/DIN Isotopes Inc.) (1 g, 8 mmol) in 1M sulfuric acid (16 ml, 1M aqueous solution), cooled to 0° C., was added a solution of sodium nitrite (1.1 g, 16 mmol) in water (8 ml). The temperature was maintained below 5° C. during the addition, and the mixture was stirred at such overnight. The solution was then saturated with ammonium sulfate, extracted with diethyl ether (3×25 ml), dried over sodium sulfate and evaporated under reduced pressure giving the title compound (0.68 g, 67%) as a colorless oil that crystallized on standing. $^1$H NMR (400 MHz, CD$_3$OD): 6 no signal. LCMS (m/z) 125.0 [M−H], Tr=0.65 min.

Compound 59b

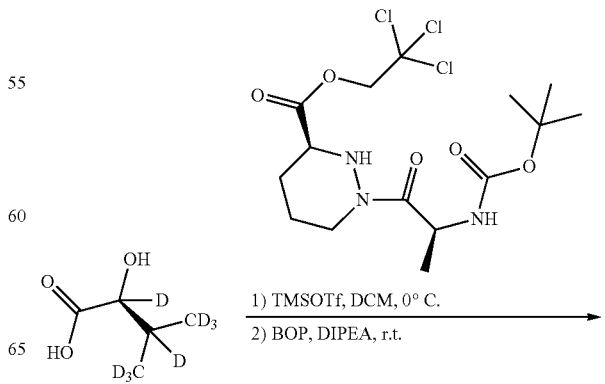

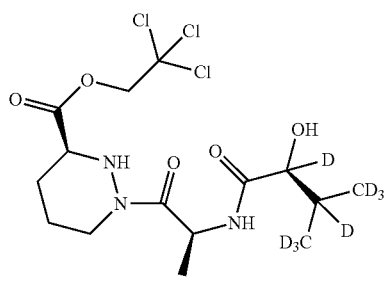

A solution of 1d (866 mg, 2 mmol) in dichloromethane (30 mL) was cooled in an ice water bath. Trimethylsilyl trifluoromethanesulfonate (667 mg, 3 mmol) was added dropwise at 0° C. under argon, and the resulting solution was stirred at room temperature for 30 minutes. The reaction mixture was evaporated to dryness and the resulting crude residue (LCMS (m/z) 332.2/334.3 [M+H]' Tr=2.06 min) was dissolved in anhydrous dichloromethane (20 mL) and cooled to 0° C. To this was added 59a (252 mg, 2.2 mmol), N,N-diisopropylethylamine (0.86 mL, 5 mmol), and (benzotriazol-1-yloxy)tris(dimethylamino)phosphonium hexafluorophosphate (1062 mg, 2.4 mmol). The reaction was allowed to warm to room temperature and stirred for 8 hours. The mixture was evaporated to dryness and the residue was dissolved in ethyl acetate (100 mL) and washed with 10% citric acid (100 mL), saturated $NaHCO_3$ (100 mL), and brine (100 mL). The organic layer was dried over $MgSO_4$, one volume equivalent of hexane was added and this solution was filtered through a 5 cm layer of silica gel, silica gel layer was washed with 50 mL of ethyl acetate/hexane mixture (1/1). The desired product was washed out with ethyl acetate (100 mL), concentrated under reduced pressure and co-distilled with dichloromethane. 59b (878 mg, quantitative yield) was isolated after drying under high vacuum for one day. $^1$H NMR (400 MHz, $CD_3OD$) δ 5.50-5.42 (m, 1H), 5.03 (d, J=12.1 Hz, 1H), 4.85 (d, J=11.9 Hz, 1H), 4.16-4.10 (m, 1H), 3.88-3.85 (m, 1H), 3.75-3.41 (m, 2H), 2.16-2.07 (m, 1H), 2.00-1.83 (m, 2H), 1.81-1.69 (m, 1H), 1.32 (d, J=6.8 Hz, 3H). LCMS (m/z) 440.1/442.1 [M+H]' Tr=2.32 min.

Compound 59c

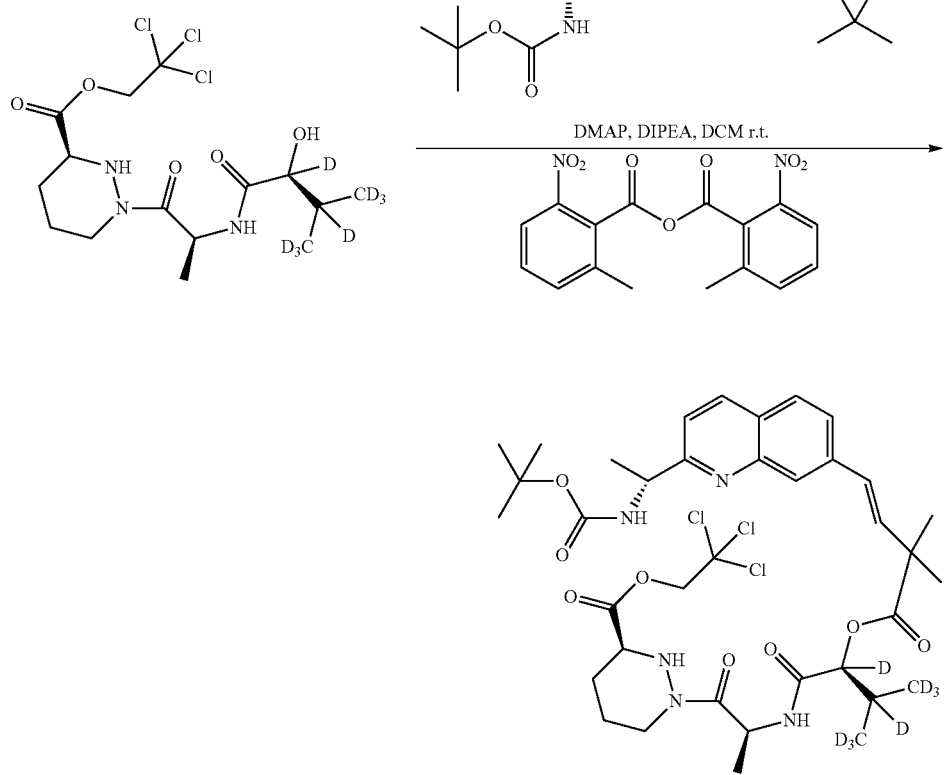

Into an oven-dried, argon purged flask were placed 2-methyl-6-nitrobenzoic anhydride (344 mg, 1 mmol), 4-dimethylaminopyridine (128 mg, 1.05 mmol), Boc-protected quinoline carboxylic acid (192 mg, 0.50 mmol), and anhydrous dichloromethane (20 mL). Into the resulting solution was added N,N-diisopropylethylamine (0.26 mL, 1.50 mmol) and this reaction mixture was stirred at room temperature for 10 minutes. 59b (331 mg, 0.75 mmol) was added dropwise via syringe as a solution in anhydrous dichloromethane (10 mL). After stirring for 12 hours at room temperature, the reaction mixture was transferred to a separatory funnel and washed with water (20 mL, 10 mL of brine was added to support the separation). The aqueous phase was extracted with dichloromethane (20 mL). Combined organic extracts were washed with brine (20 mL) and dried over magnesium sulfate, filtered and concentrated under reduced pressure. The residue was purified by silica gel chromatography (gradient from 0-40% ethyl acetate+methanol (4/1) in iso-hexanes) to afford 59c (391 mg, 97%) as a white solid after evaporation. $^1$H NMR (400 MHz, CD$_3$OD) δ 8.28 (d, J=8.5 Hz, 1H), 7.97 (s, 1H), 7.87 (d, J=8.5 Hz, 1H), 7.81 (d, J=8.5 Hz, 1H), 7.52 (d, J=8.5 Hz, 1H), 6.90-6.71 (m, 2H), 5.49-5.34 (m, 2H), 5.50-4.98 (m, 2H), 4.87-4.79 (m, 2H), 4.17-4.10 (m, 1H), 4.90-4.80 (m, 2H), 2.15-2.06 (m, 1H), 1.99-1.85 (m, 2H), 1.82-1.72 (m, 1H), 1.72-1.62 (m, 1H), 1.58 (d, J=5.8 Hz, 3H), 1.52 (d, J=7.1 Hz, 3H), 1.47 (s, 9H), 1.32 (dd, J=13.9, 6.9 Hz, 6H). LCMS (m/z) 806.2/808.1 [M+H]' Tr=2.82 min.

Compound 59

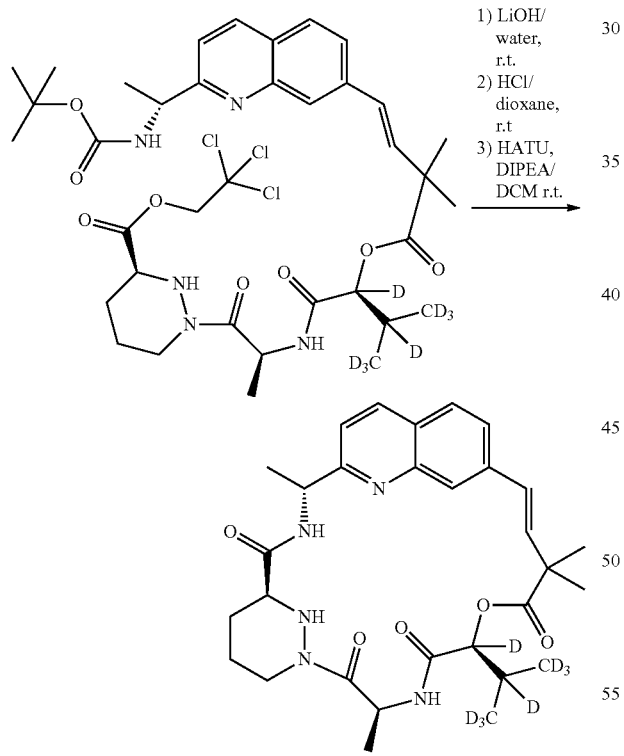

1) LiOH/water, r.t.
2) HCl/dioxane, r.t
3) HATU, DIPEA/DCM r.t.

To 59c (390 mg, 0.48 mmol) in tetrahydrofuran (20 mL) was added a solution of lithium hydroxide (13 mg, 0.53 mmol) in water (10 mL). After stirring at room temperature for 2 hour, 1M hydrochloric acid was added (0.55 mL of 1M solution in water, 0.55 mmol) and the reaction mixture was concentrated under reduced pressure and the residue partitioned between dichloromethane (50 mL) and water (50 mL). The organic layer was collected, concentrated under reduced pressure and dried under high vacuum for one day. The residue was treated with 4M hydrogen chloride in 1,4-dioxane (10 mL, 40 mmol) at room temperature under argon for 4 hours. Reaction mixture was concentrated under reduced pressure. This residue was dissolved in N,N-dimethylformamide (5 mL) and the obtained solution was added into an argon purged flask containing 2-(1H-7-azabenzotriazol-1-yl)-11,1,3,3-tetramethyl uronium hexafluorophosphate methanaminium (276 mg, 0.73 mmol), N,N-diisopropylethylamine (312 mg, 2.42 mmol) and dichloromethane (200 mL). The reaction mixture was re-purged with argon and stirred at room temperature for 2 hours. The obtained reaction mixture was washed with water (100 ml) and brine (100 mL), dried over magnesium sulfate, filtered and concentrated under reduced pressure. The residue was purified by silica gel chromatography (gradient from 0-40% ethyl acetate+methanol (4/1) in iso-hexanes) to afford 59 (137 mg, 51%) as a white solid after evaporation. $^1$H NMR (400 MHz, CD$_3$OD) δ 8.27 (d, J=8.5 Hz, 1H), 7.86 (d, J=8.4 Hz, 1H), 7.80 (s, 1H), 7.64 (dd, J=8.5, 1.6 Hz, 1H), 7.46 (d, J=8.5 Hz, 1H), 6.56 (d, J=16.3 Hz, 1H), 6.38 (d, J=16.3 Hz, 1H), 5.82 (q, J=7.3 Hz, 1H), 5.11 (q, J=6.7 Hz, 1H), 4.45 (dd, J=13.0, 3.5 Hz, 1H), 3.62 (dd, J=11.8, 2.8 Hz, 1H), 2.72 (td, J=13.0, 3.3 Hz, 1H), 2.40-2.65 (m, 1H), 2.02-1.94 (m, 1H), 1.77-1.68 (m, 2H), 1.65 (d, J=7.3 Hz, 3H), 1.60 (d, J=6.7 Hz, 3H), 1.55 (s, 3H), 1.44 (s, 3H). LCMS (m/z) 558.4 [M+H]' Tr=2.41.

Example 60

Compound 60

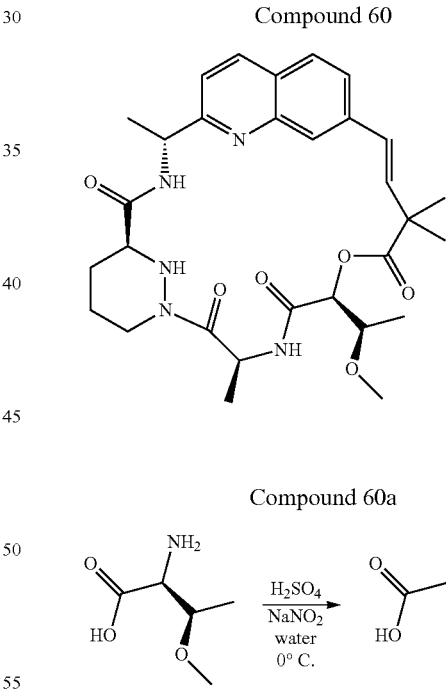

Compound 60a

To a solution of (2S,3R)-2-amino-3-methoxybutanoic acid (CAS Number: 4144-02-9; Ark Pharm, Inc.) (1 g, 7.5 mmol) in 1M sulfuric acid (15 ml, 1M aqueous solution), cooled to 0° C., was added a solution of sodium nitrite (1.0 g, 15 mmol) in water (8 ml). The temperature was maintained below 50° C. during the addition, and the mixture was stirred at such overnight. The solution was then saturated with ammonium sulfate, extracted with diethyl ether (5×25 ml), dried over sodium sulfate and evaporated under reduced pressure giving 60a (0.27 g, 67%) as a colorless oil that crystallized on standing. $^1$H NMR (400 MHz, CDCl$_3$): δ 4.14 (d, J=3.6 Hz, 1H), 3.81 (qd, J=6.4, 3.6 Hz, 1H), 3.41 (s, 3H), 1.25 (d, J=6.4 Hz, 3H). LCMS (m/z) 132.9 [M−H], Tr=0.39 min.

Compound 60b

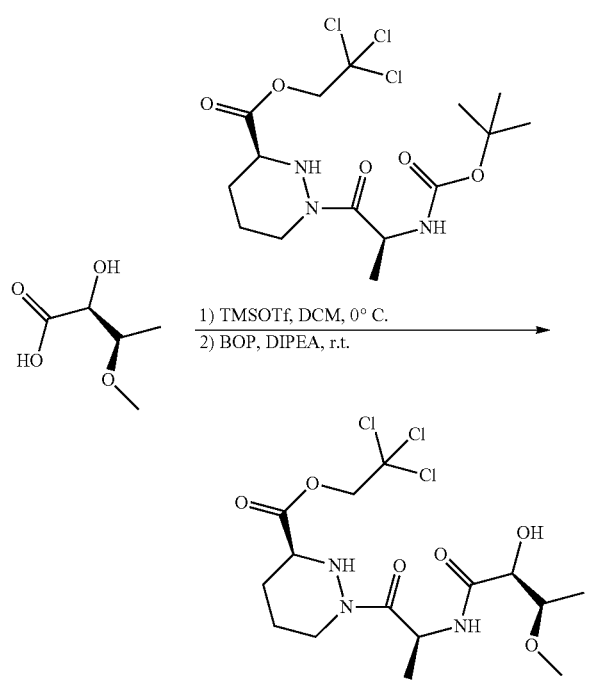

A solution of 1d (517 mg, 1.19 mmol) in dichloromethane (20 mL) was cooled in an ice water bath. Trimethylsilyl trifluoromethanesulfonate (398 mg, 1.79 mmol) was added dropwise at 0° C. under argon, and the resulting solution was stirred at room temperature for 30 minutes. The reaction mixture was evaporated to dryness and the resulting crude residue (LCMS (m/z) 332.2/334.3 [M+H]' Tr=2.06 min) was dissolved in anhydrous dichloromethane (20 mL) and cooled to 0° C. To this was added 60a (192 mg, 1.43 mmol), N,N-diisopropylethylamine (0.51 mL, 2.98 mmol), and (benzotriazol-1-yloxy)tris(dimethylamino)phosphonium hexafluorophosphate (633 mg, 1.43 mmol). The reaction was allowed to warm to room temperature and stirred for 8 hours. The mixture was evaporated to dryness and the residue was dissolved in ethyl acetate (100 mL) and washed with 10% citric acid (100 mL), saturated NaHCO$_3$ (100 mL), and brine (100 mL). The organic layer was dried over MgSO$_4$, one volume equivalent of hexane was added and this solution was filtered through a 5 cm layer of silica gel, silica gel layer was washed with 50 mL of ethyl acetate/hexane mixture (1/1). The desired product was washed out with ethyl acetate (100 mL), concentrated under reduced pressure and co-distilled with dichloromethane. The 60b (537 mg, quantitative yield) was isolated after drying under high vacuum for one day. $^1$H NMR (400 MHz, CD$_3$OD): δ 5.53 (q, J=6.9 Hz, 1H), 5.10 (d, J=12.1 Hz, 1H), 4.92 (d, J=12.2 Hz, 1H), 3.96 (d, J=2.6 Hz, 1H), 3.94 (dd, J=7.1, 4.7 Hz, 1H), 3.86 (qd, J=6.4, 2.5 Hz, 1H), 3.81-3.60 (m, 2H), 3.42 (s, 3H), 2.34-2.14 (m, 1H), 2.09-1.90 (m, 2H), 1.87-1.76 (m, 1H), 1.41 (d, J=6.9 Hz, 3H), 1.32 (d, J=6.4 Hz, 3H). LCMS (m/z) 448.1/450.0[M+H]' Tr=2.11 min.

Compound 60c

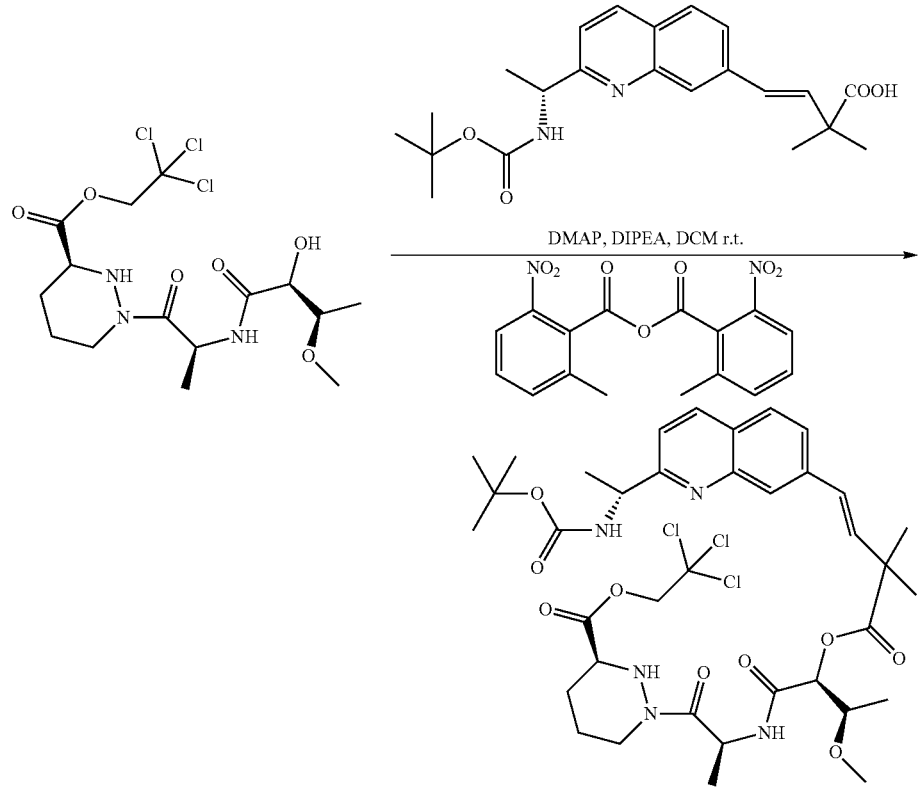

Into an oven-dried, argon purged flask were placed 2-methyl-6-nitrobenzoic anhydride (172 mg, 0.5 mmol), 4-dimethylaminopyridine (64 mg, 0.50 mmol), N-Boc protected (R,E)-4-(2-(1-(tert-butoxycarbonylamino)ethyl)quinolin-7-yl)-2,2 dimethylbut-3-enoic acid (96 mg, 0.25 mmol), and anhydrous dichloromethane (10 mL). Into the resulting solution was added N,N-diisopropylethylamine (0.13 mL, 0.75 mmol) and this reaction mixture was stirred at room temperature for 10 minutes. 60b (168 mg, 0.38 mmol) was added dropwise via syringe as a solution in anhydrous dichloromethane (10 mL). After stirring for 12 hours at room temperature, the reaction mixture was transferred to a separatory funnel and washed with water (20 mL, 10 mL of brine was added to support the separation). The aqueous phase was extracted with dichloromethane (20 mL). Combined organic extracts were washed with brine (20 mL) and dried over magnesium sulfate, filtered and concentrated under reduced pressure. The residue was purified by silica gel chromatography (gradient from 0-40% ethyl acetate+methanol (4/1) in iso-hexanes) to afford 60c (149 mg, 73%) as a white solid after evaporation. $^1$H NMR (400 MHz, CD$_3$OD): δ 8.35 (d, J=8.6 Hz, 1H), 8.07-8.01 (m, 1H), 7.93 (d, J=8.5 Hz, 1H), 7.88 (d, J=8.4 Hz, 1H), 7.58 (d, J=8.5 Hz, 1H), 6.98-6.77 (m, 2H), 5.48 (q, J=6.5, 6.1 Hz, 1H), 5.20 (d, J=4.0 Hz, 1H), 5.06 (d, J=12.1 Hz, 1H), 4.88 (d, J=12.1 Hz, 1H), 4.25-4.15 (m, 1H), 3.99-3.85 (m, 2H), 3.80-3.55 (m, 2H), 3.46 (s, 3H), 2.20-2.09 (m, 1H), 2.07-1.94 (m, 1H), 1.92-1.80 (m, 1H), 1.80-1.71 (m, 1H), 1.68-1.64 (m, 6H), 1.59 (d, J=7.1 Hz, 3H), 1.54 (s, 9H), 1.37 (d, J=7.0 Hz, 3H), 1.29 (d, J=6.4 Hz, 3H). LCMS (m/z) 814.1/816.1 [M+H]' Tr=2.64 min.

Compound 60

To 60c (139 mg, 0.17 mmol) in tetrahydrofuran (10 mL) was added a solution of lithium hydroxide (4.5 mg, 0.19 mmol) in water (5 mL). After stirring at room temperature for 2 hour, 1M hydrochloric acid was added (0.20 mL of 1M solution in water, 0.20 mmol) and the reaction mixture was concentrated under reduced pressure and the residue partitioned between dichloromethane (50 mL) and water (50 mL). The organic layer was collected, concentrated under reduced pressure and dried under high vacuum for one day. The residue was treated with 4M hydrogen chloride in 1,4-dioxane (5 mL, 20 mmol) at room temperature under argon for 4 hours. Reaction mixture was concentrated under reduced pressure. This residue was dissolved in N,N-dimethylformamide (5 mL) and the obtained solution was added into an argon purged flask containing 2-(1H-7-azabenzotriazol-1-yl)-1,1,3,3-tetramethyl uronium hexafluorophosphate methanaminium (98 mg, 0.26 mmol), N,N-diisopropylethylamine (110 mg, 0.86 mmol) and dichloromethane (100 mL). The reaction mixture was re-purged with argon and stirred at room temperature for 2 hours. The obtained reaction mixture was washed with water (50 ml) and brine (50 mL), dried over magnesium sulfate, filtered and concentrated under reduced pressure. The residue was purified by silica gel chromatography (gradient from 0-60% ethyl acetate+methanol (4/1) in iso-hexanes) to afford 60 (32 mg, 33%) as a white solid after evaporation. $^1$H NMR (400 MHz, CD$_3$OD): δ 8.24 (d, J=8.5 Hz, 1H), 7.83 (d, J=8.4 Hz, 1H), 7.81 (s, 1H), 7.61 (dd, J=8.4, 1.6 Hz, 1H), 7.43 (d, J=8.5 Hz, 1H), 6.54 (d, J=16.3 Hz, 1H), 6.37 (d, J=16.3 Hz, 1H), 5.78 (q, J=7.2 Hz, 1H), 5.44 (d, J=8.2 Hz, 1H), 5.08 (q, J=6.7 Hz, 1H), 4.41 (dd, J=13.5, 3.4 Hz, 1H), 3.77-3.63 (m, 1H), 3.59 (dd, J=11.8, 2.9 Hz, 1H), 3.41 (s, 3H), 2.68 (td, J=12.9, 3.1 Hz, 1H), 2.31-2.24 (m, 1H), 1.99-1.91 (m, 1H), 1.72-1.64 (m, 2H), 1.61 (d, J=7.2 Hz, 3H), 1.57 (d, J=6.7 Hz, 3H), 1.53 (s, 3H), 1.42 (s, 3H), 1.26 (d, J=6.4 Hz, 3H). LCMS (m/z) 566.3 [M+H]' Tr=2.42 min.

Example 61

Compound 61

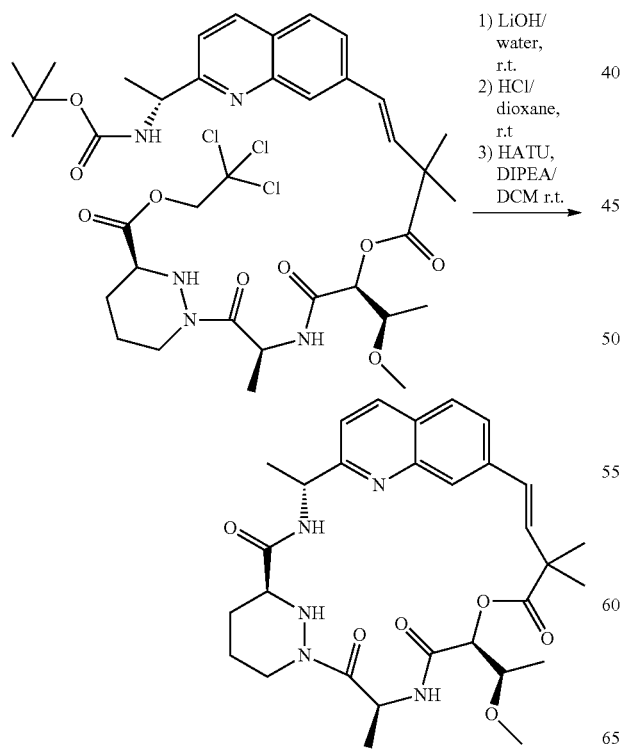

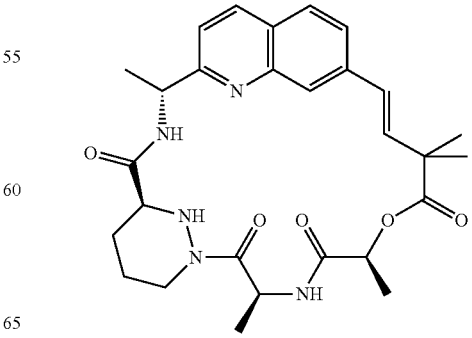

Compound 61a

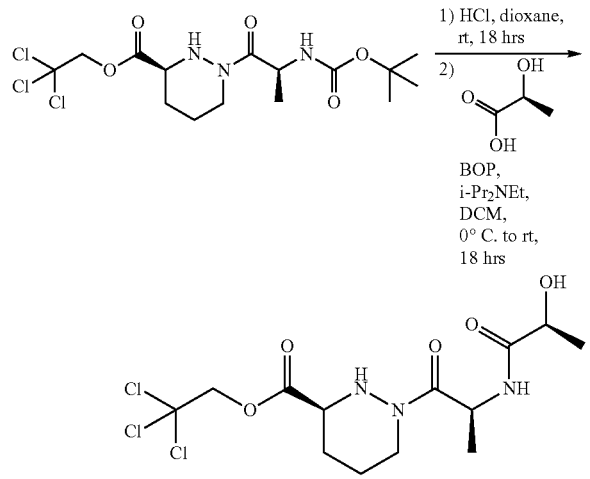

To 1d (500.3 mg, 1.16 mmol) was added an HCl solution (1.2 mL, 4 M in dioxane, 1 M). After stirring for 18 hours, the reaction was concentrated in vacuo to afford the free dipetide as an amorphous, pale yellow solid.

To L-(+)-lactic acid (252.3 mg, 2.80 mmol) in DMF (10 mL, 0.3 M) was added TMSCl (0.35 mL, 2.77 mmol), followed by i-Pr₂NEt (1.0 mL, 5.74 mmol). After 3 hours, HATU (1.08 g, 2.84 mmol) was added. After 10 minutes, the free dipeptide was added in DMF (11.5 mL, 1 M). After 60 minutes, the reaction was concentrated in vacuo to 5 mL, diluted with EtOAc (10 mL) and washed with water (10 mL). The aqueous was extracted with EtOAc (2×10 mL) and the combined organics were washed with 5% aq. LiCl (5×20 mL) and brine (20 mL), dried over MgSO₄, and concentrated in vacuo. The compound was purified via column chromatography (0-100% EtOAc/hexane) to afford 61a (346.6 g, 74%) as a white foam. ¹H NMR (400 MHz, CDCl₃): δ 7.22 (d, J=8.1 Hz, 1H), 5.36 (p, J=6.9 Hz, 1H), 4.95 (d, J=11.9 Hz, 1H), 4.72 (d, J=11.9 Hz, 1H), 4.34 (d, J=12.1 Hz, 1H), 4.23 (q, J=6.8 Hz, 1H), 3.70 (m, 1H), 3.16 (m, 1H), 2.91 (m, 1H), 2.18 (m, 1H), 1.94 (m, 1H), 1.72 (m, 2H), 1.49 (dd, J=7.1, 3.4 Hz, 2H), 1.43 (t, J=7.0 Hz, 3H), 1.34 (d, J=6.9 Hz, 3H). LCMS (m/z) 477.85 [M+H].

To the N-Boc (R,E)-4-(2-(1-(tert-butoxycarbonylamino)ethyl)quinolin-7-yl)-2,2 dimethylbut-3-enoic acid (150.9 mg, 0.390 mmol), 61a (191.6 mg, 0.468 mmol), and DMAP (115.3 mg, 0.936 mmol) in DCM (2.2 mL, 0.1 M) at 0° C. under Ar was added i-Pr$_2$NEt (0.16 mL, 0.936 mmol) followed by 2-methyl-6-nitrobenzoic anhydride (278.6 mg, 0.780 mmol). The reaction was warmed to rt and, after 60 minutes, was diluted with DCM (10 mL), washed with sat. NH$_4$Cl$_{(aq)}$ (15 mL). The aqueous was extracted with DCM (2×15 mL). The combined organics were washed with H$_2$O (50 mL), dried over MgSO$_4$, and concentrated in vacuo. The compound was purified via column chromatography (0-75% EtOAc/hexane) to afford 61b (214.8 mg, 71%) as a yellow oil. $^1$H NMR (400 MHz, CDCl$_3$): δ 8.11 (d, J=7.4 Hz, 1H), 8.04 (m, 2H), 7.72 (d, J=8.8 Hz, 1H), 7.65 (d, J=8.4 Hz, 1H), 6.70 (dd, J=20.5, 10.7 Hz, 4H), 5.22 (m, 2H), 4.94 (dd, J=11.8, 8.2 Hz, 3H), 4.71 (d, J=11.9 Hz, 2H), 4.32 (m, 1H), 3.68 (m, 2H), 2.82 (m, 3H), 2.16 (m, 1H), 1.89 (m, 1H), 1.68 (m, 2H), 1.54 (s, 6H), 1.51 (d, J=7.5 Hz, 6H), 1.47 (s, 9H), 1.42 (d, J=6.8 Hz, 3H), 1.29 (m, 3H). LCMS (m/z) 770.17 [M+H].

Compound 61

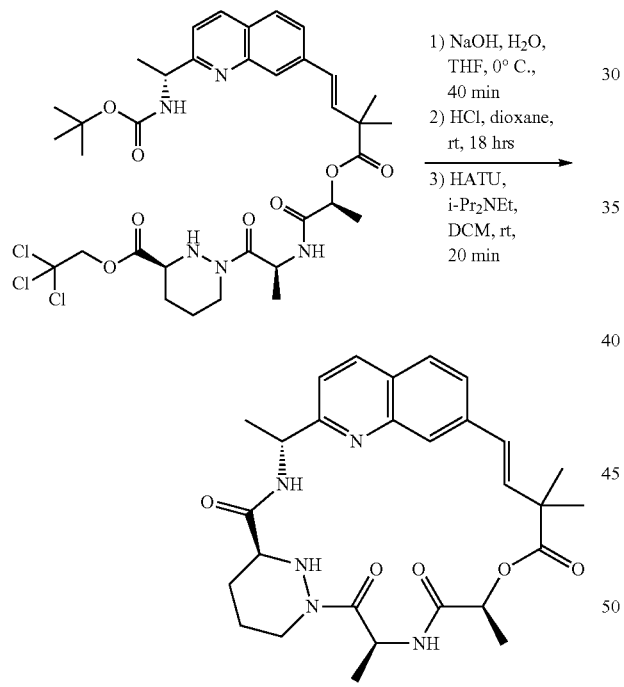

To 61b (214.8 mg, 0.279 mmol) in THF (2.8 mL, 0.1 M) at 0° C. was added 0.3 M NaOH$_{(aq)}$ (0.93 mL, 0.249 mmol). After 40 minutes, the reaction was quenched with 1 M HCl$_{(aq)}$ (0.29 mL) to ~pH 4. The mixture was then diluted with EtOAc (15 mL), washed with water (3×5 mL) and brine (10 mL), dried over MgSO$_4$, and concentrated in vacuo to afford a yellow foam (190.1 mg). The crude material was dissolved in dioxane (1 mL) and an HCl solution (3 mL, 4 M in dioxane) was added. After 18 hours, the suspension was concentrated in vacuo to a yellow solid (175.3 mg). The crude material in DMF (5 mL) was diluted with DCM (750 mL, 0.0003 M) and i-Pr$_2$NEt (0.30 mL, 1.62 mmol) was added, followed by HATU (151.9 mg, 0.400 mmol). After 20 minutes, the mixture was washed with 5% LiCl$_{(aq)}$ (2×500 mL) and brine (500 mL), dried over MgSO$_4$, and concentrated in vacuo to an orange residue. The impurities were triturated with DCM/tBME to afford 61 (68.0 mg, 47%) as a yellow residue. $^1$H NMR (400 MHz, CDCl$_3$): δ 8.98 (s, 1H), 8.25 (s, 1H), 8.11 (s, 1H), 7.74 (d, J=7.0 Hz, 2H), 7.45 (s, 2H), 6.69 (d, J=15.4 Hz, 2H), 6.43 (d, J=16.1 Hz, 1H), 5.80 (m, 1H), 5.41 (m, 1H), 4.57 (d, J=8.9 Hz, 2H), 4.15 (s, 1H), 3.77 (m, 1H), 3.66 (m, 4H), 3.55 (m, 2H), 3.08 (m, 2H), 2.58 (m, 1H), 1.97 (d, J=14.1 Hz, 1H), 1.56 (m, 6H), 1.44 (m, 6H). LCMS (m/z) 522.23 [M+H]. Rt=4.75 min.

Example 62

Compound 62

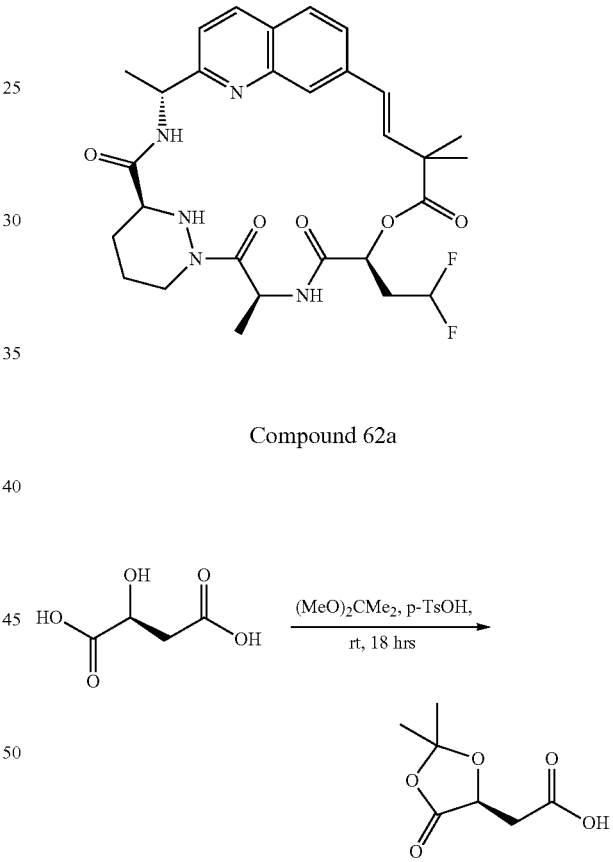

Compound 62a

To L-(−)-malic acid (10 g, 74.6 mol) and p-toluenesulfonic acid monohydrate (172.5 mg, 7.46 mmol) was added 2,2-dimethoxypropane (75 mL, 1 M). After 18 hours, water (50 mL) and NaHCO$_3$ (72.3 mg) were added, and the mixture was extracted with DCM (3×100 mL). The combined organics were dried over MgSO$_4$ and concentrated in vacuo to a yellow oil. The material was purified via crystallization with Et$_2$O/hexane to afford 62a (11.2 g, 88%) as a white solid. $^1$H NMR (400 MHz, CDCl$_3$): δ 4.72 (dd, J=6.6, 3.9 Hz, 1H), 3.00 (dd, J=17.3, 3.9 Hz, 1H), 2.86 (dd, J=17.3, 6.6 Hz, 1H), 1.63 (s, 3H), 1.57 (s, 3H).

Compound 62b

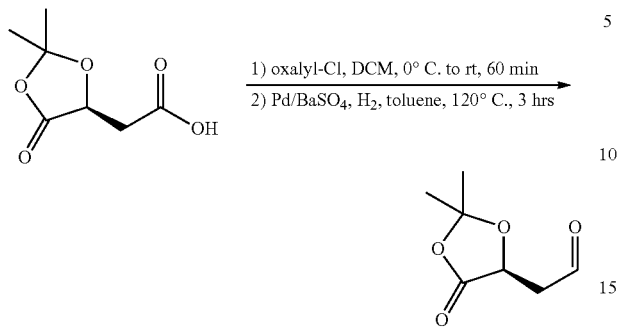

To 62a (385.9 g, 2.21 mmol) in DCM (22 mL, 0.1 M) at 0° C. was added oxalyl chloride (0.23 mL, 2.66 mmol) followed by a drop of DMF. The reaction was warmed to rt and stirred for 60 minutes. The reaction was then concentrated in vacuo to afford pale yellow needles. The crude was dissolved in toluene (22 mL, 0.1 M) and Pd/BaSO₄ (111.9 mg) was added. The mixture was purged with H₂ and refluxed for 3 hours. The reaction was then cooled to rt, filtered through celite, rinsed with EtOAc, and concentrated in vacuo to afford 62b (160 mg, 47%) as a yellow oil. $^1$H NMR (400 MHz, CDCl₃): δ 9.78 (s, 1H), 4.79 (dd, J=7.0, 3.5 Hz, 1H), 3.09 (dd, J=18.3, 3.5 Hz, 1H), 2.92 (dd, J=18.3, 7.0 Hz, 1H), 1.63 (s, 3H), 1.58 (s, 3H).

Compound 62c

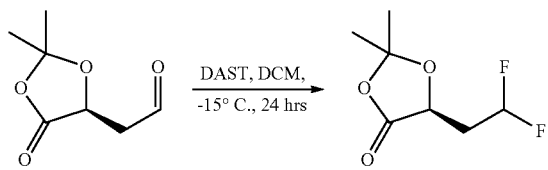

To 62b (1 g, 5.55 mmol) in DCM (11 mL, 0.5 M) at −15° C. was added DAST (0.88 mL, 6.66 mmol) and the reaction was allowed to warm to rt slowly. After 14 hours, the reaction was slowly quenched with cold sat. NaHCO₃$_{(aq)}$ (10 mL), the phases were separated, and the aqueous was extracted with DCM (2×15 mL). The combined organics were dried over MgSO4 and concentrated in vacuo to afford 62c (956.2 mg, 92%) as a yellow-orange oil. $^1$H NMR (400 MHz, CDCl₃): δ 6.01 (tdd, J=56.1, 5.4, 4.1 Hz, 1H), 4.53 (ddd, J=8.4, 4.0, 0.8 Hz, 1H), 2.52-2.36 (m, 1H), 2.32-2.15 (m, 1H), 1.65-1.60 (m, 3H), 1.56-1.53 (m, 3H). $^{19}$F NMR (376 MHz, CDCl₃) δ −117.10-−119.71 (m).

Compound 62d

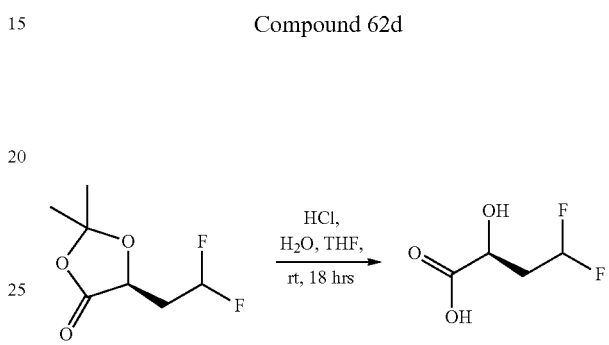

To 62c (956.2 mg, 5.31 mmol) in THF (5 mL, 1 M) was added 1 M HCl$_{(aq)}$ (5 mL, 1 M). After 18 hours, the reaction was saturated with NaCl, and extracted Et₂O (2×20 mL) and THF (15 mL). The combined organics were dried over MgSO₄ and concentrated in vacuo to afford 62d (654.8 mg, 88%) as a clear oil. $^1$H NMR (400 MHz, CDCl₃): δ 6.06 (tdd, J=56.4, 5.5, 4.2 Hz, 1H), 4.48-4.39 (m, 1H), 2.51-2.33 (m, 1H), 2.33-2.12 (m, 1H). $^{19}$F NMR (376 MHz, CDCl₃) δ −117.40-−120.28 (m).

Compound 62e

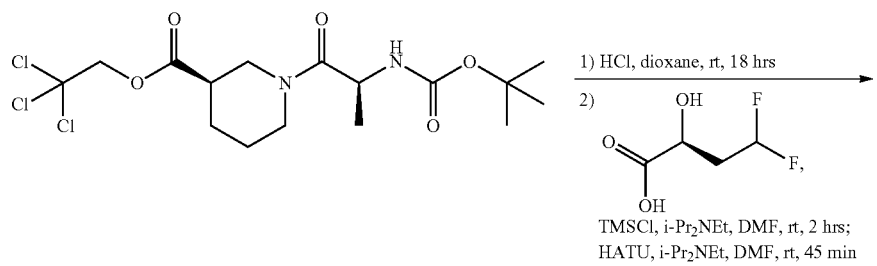

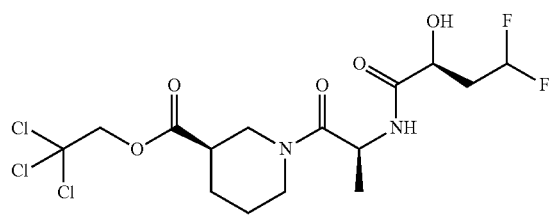

To 1d (2.75 g, 6.37 mmol) in dioxane (2 mL) was added an HCl solution (6.5 mL, 25.5 mmol, 4 M in dioxane). After stirring for 18 hours, the reaction was concentrated in vacuo to afford the free dipetide as an amorphous, pale yellow solid.

To 62d (654.8 mg, 4.67 mmol) in DMF (16 mL, 0.3 M) was added TMSCl (0.59 mL, 4.67 mmol), followed by i-Pr$_2$NEt (2.0 mL, 11.7 mmol). After 2 hours, the free dipetide was added in DMF (6 mL, 1 M) followed by i-Pr$_2$NEt (4.0 mL, 23.4 mmol) and HATU (2.66 g, 7.01 mmol). After 45 minutes, the reaction was concentrated in vacuo to 5 mL, diluted with sat. NaHCO$_{3(aq)}$ (50 mL) and extracted with EtOAc (3×50 mL). The combined organics were washed with 5% LiCl$_{(aq)}$ (4×50 mL) and brine (100 mL), dried over MgSO$_4$, and concentrated in vacuo. The compound was purified via column chromatography (50-100% EtOAc/hexane) to afford 62e (1.24 g, 59%) as a tan foam. $^1$H NMR (400 MHz, CDCl$_3$): δ 6.06 (m, 1H), 5.36 (p, J=7.2 Hz, 1H), 4.95 (d, J=12.0 Hz, 1H), 4.72 (d, J=11.8 Hz, 1H), 4.32 (m, 2H), 3.85 (m, 1H), 3.70 (m, 1H), 2.94 (m, 1H), 2.39 (m, 1H), 2.16 (m, 2H), 1.94 (m, 1H), 1.74 (m, 2H), 1.34 (d, J=6.9 Hz, 3H). $^{19}$F NMR (376 MHz, CDCl$_3$) δ −117.56 (dt, J=56.4, 16.5 Hz). LCMS (m/z) 456.03 [M+H].

To N-Boc (R,E)-4-(2-(1-(tert-butoxycarbonylamino)ethyl)quinolin-7-yl)-2,2 dimethylbut-3-enoic acid (98.7 mg, 0.220 mmol), 62e (115.3 mg, 0.264 mmol), and DMAP (66.1 mg, 0.528 mmol) in DCM (2.2 mL, 0.1 M) under Ar was added i-Pr$_2$NEt (0.10 mL, 0.528 mmol) followed by 2-methyl-6-nitrobenzoic anhydride (115.9 mg, 0.330 mmol). After 60 minutes, the reaction was diluted with DCM (10 mL), washed with sat. NH$_4$Cl$_{(aq)}$ (10 mL). The aqueous was extracted with DCM (10 mL). The combined organics were washed with H$_2$O (15 mL), dried over MgSO$_4$, and concentrated in vacuo. The compound was purified via column chromatography (20-100% EtOAc/hexane) to afford 62f (159.0 mg, 89%) as an pale yellow foam. $^1$H NMR (400 MHz, CDCl$_3$): δ 8.02 (d, J=15.5 Hz, 1H), 7.78-7.60 (m, 3H), 7.18 (s, 1H), 6.71 (m, 2H), 5.93 (tt, J=55.9, 4.4 Hz, 1H), 5.37 (dd, J=7.5, 4.3 Hz, 1H), 5.23 (m, 1H), 4.91 (d, J=11.9 Hz, 1H), 4.69 (d, J=11.9 Hz, 1H), 4.25 (d, J=9.7 Hz, 1H), 3.76 (d, J=11.0 Hz, 1H), 3.64 (m, 1H), 2.84 (m 1H), 2.48 (m, 1H), 2.15 (m, 2H), 1.88 (dt, J=3.8, 2.8 Hz, 2H), 1.67 (dq, J=12.4, 6.4 Hz, 6H), 1.55 (d, J=7.0 Hz, 9H), 1.44 (s, 12H). $^{19}$F NMR (376 MHz, cdcl$_3$) δ −115.88 (ddt, J=55.4, 33.0, 17.6 Hz). LCMS (m/z) 822.19 [M+H].

Compound 62f

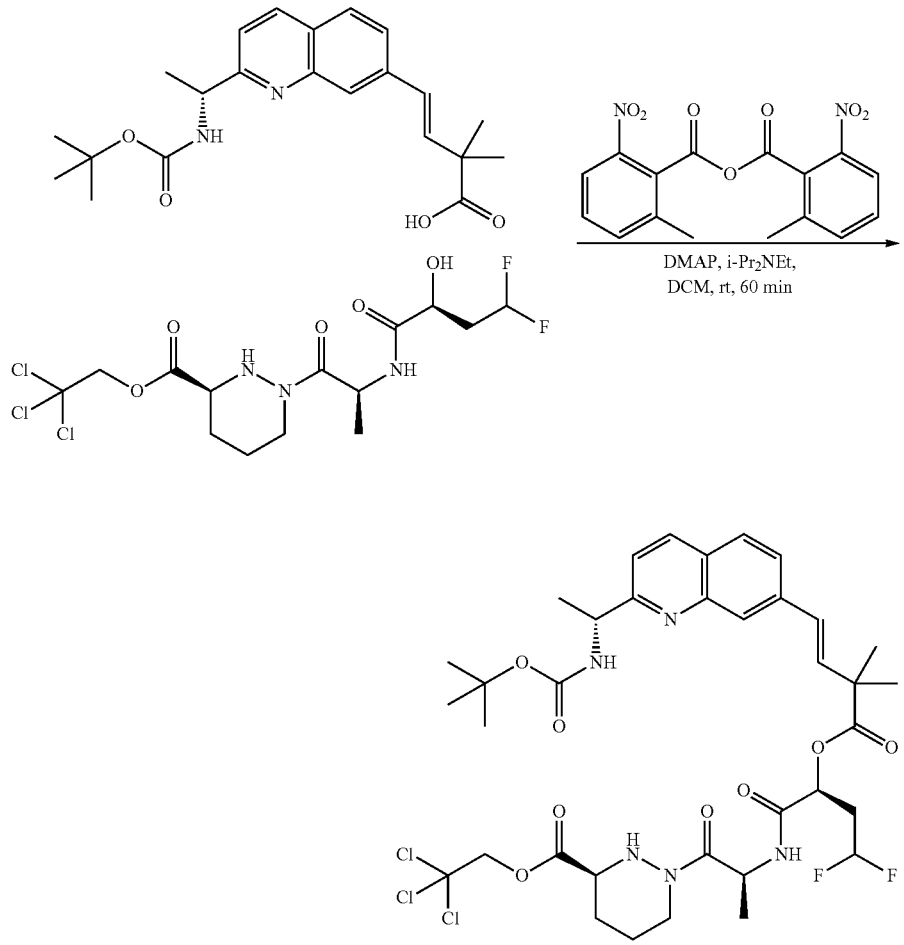

Compound 62

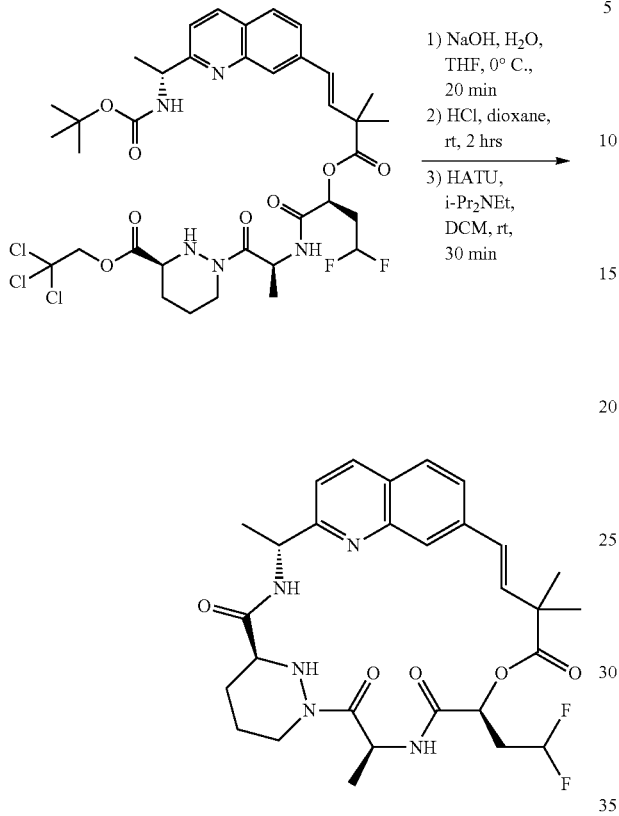

MHz, CDCl$_3$) δ −117.00 (ddt, J=61.8, 56.0, 14.9 Hz). LCMS (m/z) 690.33 [M+H]. Tr=5.178 min.

Example 63

Compound 63

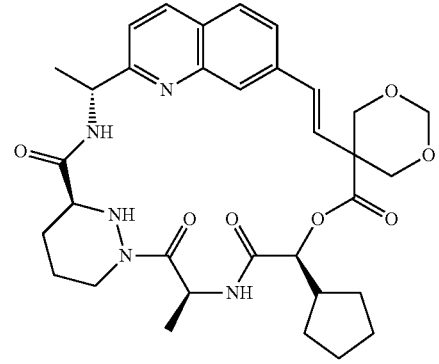 [SMILES: C[C@@H]1NC(=O)[C@H](C2CCCC2)OC(=O)C2(/C=C/c3ccc4ccc(nc4c3)[C@@H](C)NC(=O)[C@@H]3CCCN(N3)C1=O)COCOC2]

Compound 63a

To 62f (158.0 mg, 0.194 mmol) in THF (2.0 mL, 0.1 M) at 0° C. was added 0.3 M NaOH$_{(aq)}$ (0.65 mL, 0.194 mmol). After 20 minutes, the reaction was quenched with 1 M HCl$_{(aq)}$ (0.2 mL) to ~pH 4. The mixture was then diluted with EtOAc (20 mL), washed with water (3×5 mL) and brine (5 mL), dried over MgSO$_4$, and concentrated in vacuo to afford a yellow residue (153.9 mg). The crude material was dissolved in dioxane (1 mL) and an HCl solution (1 mL, 4 M in dioxane) was added. After 2 hours, the suspension was concentrated in vacuo to a yellow solid (202.5 mg). The crude material in DMF (2 mL, 0.1 M) was diluted with DCM (650 mL, 0.0003 M) and i-Pr$_2$NEt (0.17 mL, 0.982 mmol) was added, followed by HATU (89.9 mg, 0.232 mmol). After 30 minutes, the mixture was washed with 5% LiCl (2×300 mL), sat. NaHCO$_3$ (300 mL), and brine (300 mL), dried over MgSO$_4$, and concentrated in vacuo. The crude material was purified by prep HPLC (Gemini, 30-90% MeCN/H$_2$O) to afford 62 (39.2 mg, 36%) as an off-white solid. $^1$H NMR (400 MHz, CDCl$_3$): δ 9.02 (s, 1H), 8.09 (d, J=18.2 Hz, 2H), 7.76 (s, 1H), 7.45 (s, 1H), 6.70 (d, J=16.0 Hz, 2H), 6.43 (d, J=7.9 Hz, 1H), 6.30 (d, J=15.8 Hz, 1H), 5.99 (d, J=55.2 Hz, 1H), 5.74 (s, 1H), 5.48 (s, 1H), 5.23 (s, 1H), 5.11 (s, 1H), 4.92 (s, 1H), 4.56 (d, J=12.9 Hz, 1H), 3.55 (m, 2H), 2.58 (t, J=11.7 Hz, 2H), 2.40 (m, 4H), 1.67 (m, 6H), 1.58 (m, 5H), 1.49 (m, 9H). $^{19}$F NMR (376

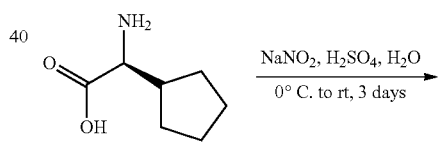

To (S)-2-amino-2-cyclopentylacetic acid (1 g, 6.98 mmol) in 1 M H$_2$SO$_4$ (14 mL, 0.5 M) at 0° C. was added 2 M NaNO$_{2(aq)}$ (11.5 mL, 10.5 mmol) slowly and the reaction was warmed to rt. After 48 hours, the reaction was cooled back to 0° C., more 2 M NaNO$_2$ (10 mL, 9.11 mmol), and the reaction was warmed to rt. After 3 days, the reaction was extracted with EtOAc (3×50 mL), dried over Na$_2$SO$_4$ and concentrated in vacuo to afford 63a (925 mg, 83%) as a white solid. $^1$H NMR (400 MHz, d$_6$-DMSO): δ 3.79 (d, J=5.9 Hz, 1H), 2.18-2.04 (m, 1H), 1.63-1.33 (m, 8H).

Compound 63b

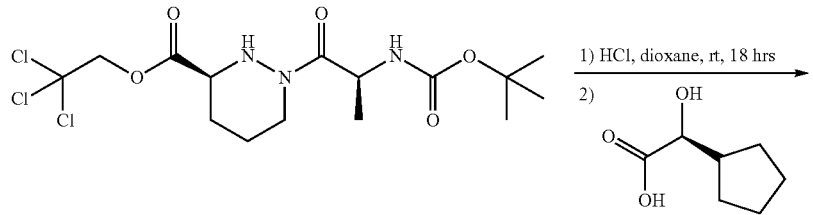

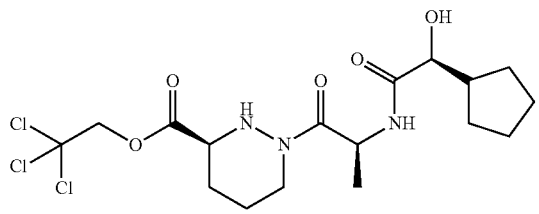

To 1d (4 g, 9.24 mmol) in dioxane (5 mL) was added an HCl solution (34 mL, 0.25 M, 4 M in dioxane). After stirring for 18 hours, the reaction was concentrated in vacuo to afford the free dipeptide (3.69 g) as an amorphous, pale yellow solid. To 63a (501.5 mg, 3.48 mmol), dipeptide (1.28 g, 3.48 mmol), and i-Pr$_2$NEt (0.61 mL, 3.48 mmol) in DCM (35 mL, 0.05 M) at 0° C. was added (benzotriazol-1-yloxy)tris(dimethylamino)phosphonium hexafluorophosphate (1.25 g, 4.17 mmol) and the reaction was warmed to room temperature. After 24 hours, the reaction was concentrated in vacuo. The residue was diluted with EtOAc (200 mL), washed with 10% citric acid (2×100 mL), sat. NaHCO$_3$ (2×100 mL), and brine (200 mL), dried over Na$_2$SO$_4$, and concentrated in vacuo. Purification by column chromatography equipped with an ELSD (0-100% EtOAc/hexane) afforded 63b (458.3 mg, 20%) as a golden orange oil. $^1$H NMR (400 MHz, CDCl$_3$): δ 6.95 (s, 1H), 5.35 (p, J=6.8 Hz, 1H), 4.94 (d, J=12.0 Hz, 1H), 4.69 (d, J=12.0 Hz, 1H), 4.30 (d, J=10.2 Hz, 1H), 4.07 (d, J=4.7 Hz, 1H), 3.69 (d, J=7.0 Hz, 1H), 2.92 (m, 1H), 2.20 (m, 1H), 1.91 (m, 1H), 1.72 (m, 3H), 1.55 (m, 8H), 1.32 (d, J=6.8 Hz, 3H). LCMS (m/z) 458.20 [M+H].

Compound 63c

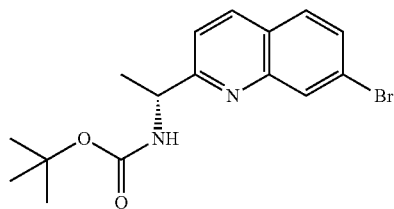

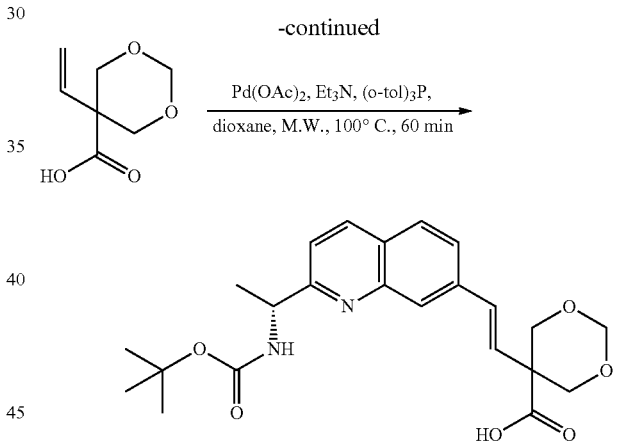

To 39a (636 mg, 1.81 mmol) and 48f (286 mg, 1.81 mmol) in dioxane (14.5 mL, 0.125 M) was added palladium (II) acetate (61.5 mg, 0.272 mmol), tris(2-methylphenyl)phosphine (168 mg, 0.543 mmol), triethylamine (0.71 mL, 5.43 mmol). The mixture was heated in a microwave reactor to 100° C. for 60 minutes. The reaction was filtered through celite, rinsed with ethyl acetate, and concentrated in vacuo. The crude material was suspended in Et$_2$O (15 mL) and extracted with sat. NaHCO$_{3(aq)}$ (9×30 mL). The combined aqueous were acidified to ~pH 4 using 1 M HCl$_{(aq)}$, extracted with EtOAc (3×500 mL), dried over MgSO$_4$, and concentrated in vacuo to afford the title compound (457 mg, 59%) as a yellow foam. $^1$H NMR (400 MHz, CDCl$_3$) δ 8.16 (m, 2H), 7.78 (s, 1H), 7.68 (s, 1H), 7.42 (s, 1H), 6.90 (d, J=16.6 Hz, 1H), 6.38 (m, 2H), 5.01 (d, J=5.7 Hz, 2H), 4.85 (d, J=6.1 Hz, 1H), 4.58 (m, 2H), 3.95 (m, 2H), 1.58 (s, 3H), 1.43 (s, 9H). LCMS (m/z) 429.00 [M+H].

Compound 63d

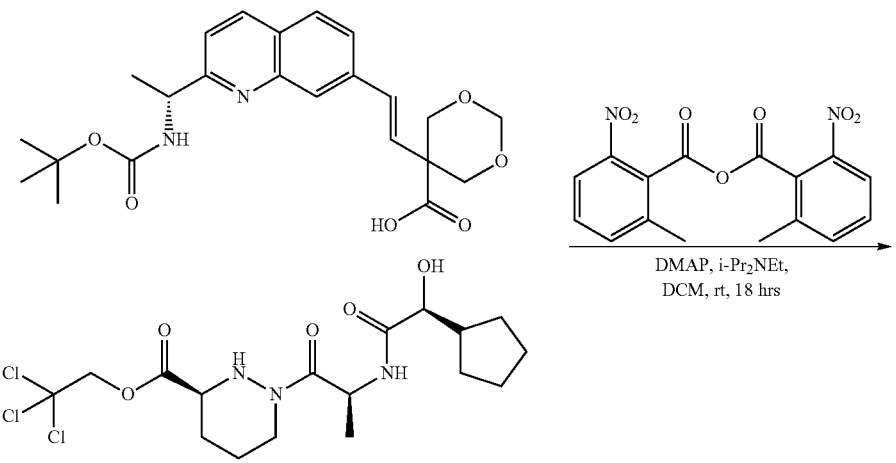

To N-Boc protected 1,3-dioxane carboxylic acid 63c (149.7 mg, 0.35 mmol), compound 63b (189.3 mg, 0.42 mmol), and DMAP (104.5 mg, 0.84 mmol) in DCM (3.5 mL, 0.1 M) under Ar was added i-Pr$_2$NEt (0.15 mL, 0.84 mmol) followed by 2-methyl-6-nitrobenzoic anhydride (181.6 mg, 0.525 mmol). After 18 hours, the reaction was diluted with DCM (10 mL), washed with water (3×10 mL), dried over MgSO$_4$, and concentrated in vacuo to a yellow foam that was purified via column chromatography (0-100% EtOAc/hexane) to afford 63d (192.0 mg, 51%) as an off-white foam. $^1$H NMR (400 MHz, CDCl$_3$): δ 8.04 (s, 1H), 7.96 (s, 1H), 7.71 (s, 1H), 7.54 (s, 1H), 7.29 (d, J=7.4 Hz, 2H), 6.74 (d, J=16.7 Hz, 1H), 6.17 (d, J=16.2 Hz, 2H), 5.35 (d, J=4.3 Hz, 1H), 5.32 (d, J=7.1 Hz, 1H), 5.16 (d, J=5.9 Hz, 1H), 4.97 (d, J=6.1 Hz, 1H), 4.92 (d, J=12.0 Hz, 1H), 4.75 (d, J=5.9 Hz, 1H), 4.68 (m, 3H), 4.31 (d, J=12.6 Hz, 1H), 3.73 (m, 5H), 2.85 (m, 2H), 2.13 (m, 1H), 1.76 (m, 4H), 1.58 (m, 12H), 1.45 (s, 9H), 1.27 (d, J=6.9 Hz, 3H). LCMS (m/z) 868.15 [M+H].

Compound 63

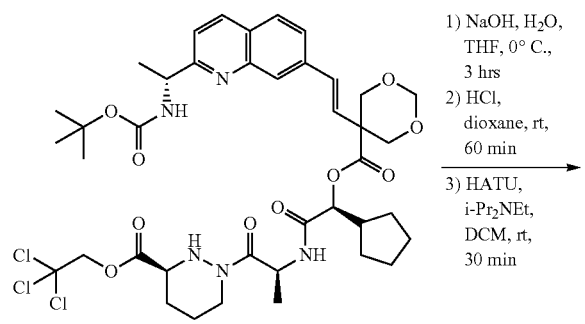

1) NaOH, H$_2$O, THF, 0° C., 3 hrs
2) HCl, dioxane, rt, 60 min
3) HATU, i-Pr$_2$NEt, DCM, rt, 30 min

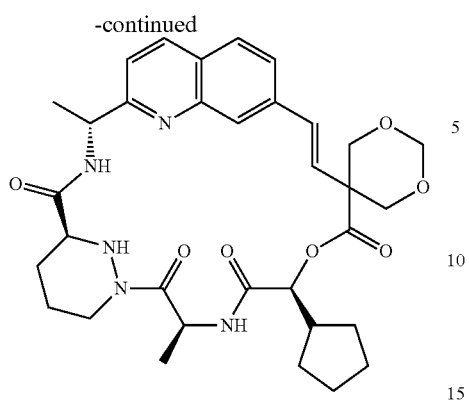

To 63c (192.0 mg, 0.219 mmol) in THF (2.2 mL, 0.1 M) at 0° C. was added 0.3 M NaOH$_{(aq)}$ (0.55 mL, 0.6.56 mmol). The reaction was monitored by LCMS hourly, with additions of 0.3 M NaOH$_{(aq)}$. The reaction was shown to be complete after 3 hours and was quenched with 1 M HCl$_{(aq)}$ (0.34 mL) to ~pH 4. The mixture was then diluted with EtOAc (15 mL), washed with water (3×5 mL), dried over MgSO$_4$, and concentrated in vacuo to afford a yellow foam (171.4 mg). The crude material was dissolved in dioxane (1 mL) and an HCl solution (3 mL, 4 M in dioxane) was added. After 60 min, the suspension was concentrated in vacuo to a yellow solid (193.1 mg). The crude material in DMF (1 mL) was diluted with DCM (100 mL) and i-Pr$_2$NEt (0.22 mL, 1.23 mmol) was added, followed by HATU (113.8 mg, 0.295 mmol). After 30 minutes, the mixture was washed with 5% LiCl (3×100 mL), sat. NaHCO$_3$ (100 mL), and brine (100 mL), dried over MgSO$_4$, and concentrated in vacuo to an orange residue. The crude material was purified by column chromatography (25-100% EtOAc/hexane) to afford 63 (46.0 mg, 26%) as a whitish residue. $^1$H NMR (400 MHz, CDCl$_3$): δ 9.04 (d, J=5.7 Hz, 1H), 8.16-8.03 (m, 4H), 7.72 (d, J=8.4 Hz, 2H), 7.48 (d, J=8.3 Hz, 2H), 7.24 (s, 1H), 6.76 (d, J=16.4 Hz, 2H), 6.48 (d, J=8.5 Hz, 1H), 6.14 (d, J=16.5 Hz, 1H), 5.90-5.79 (m, 1H), 5.15 (m, 2H), 5.00 (d, J=5.8 Hz, 1H), 4.81 (d, J=6.0 Hz, 1H), 4.57 (m, 4H), 3.91 (dd, J=44.8, 11.5 Hz, 3H), 3.56 (m, 2H), 2.57 (m, 2H), 2.43 (m, 2H), 1.62 (m, 8H). LCMS (m/z) 620.48 [M+H]. Rt=2.60 min.

Example 64

Compound 64

Example 64

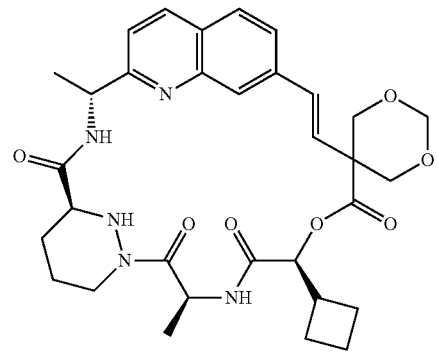 [SMILES: C[C@@H]1NC(=O)[C@H](C2CCC2)OC(=O)C2(/C=C/c3ccc4ccc(nc4c3)[C@@H](C)NC(=O)[C@@H]3CCCN(N3)C1=O)COCOC2]

Compound 64a

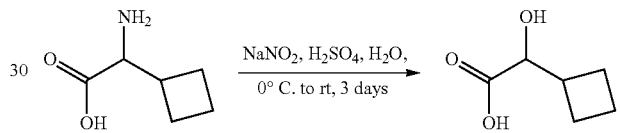

To 2-amino-2-cyclobutylacetic acid (1 g, 6.04 mmol) in 1 M H$_2$SO$_{4(aq)}$ (12 mL, 0.5 M) at 0° C. was added 2 M NaNO$_{2(aq)}$ (15 mL, 30.19 mmol) slowly and the reaction was allowed to warm to rt slowly. After 3 days, $^1$H NMR showed no starting material and the reaction was extracted with EtOAc (3×50 mL). The combined organics were dried over Na$_2$SO$_4$ and concentrated in vacuo to afford 64a (495.0 g, 44%) as a yellow solid. $^1$H NMR (400 MHz, d$_6$-DMSO): δ 3.78 (d, J=8.5 Hz, 1H), 2.62 (m, 1H), 1.94 (m, 4H).

Compound 64b

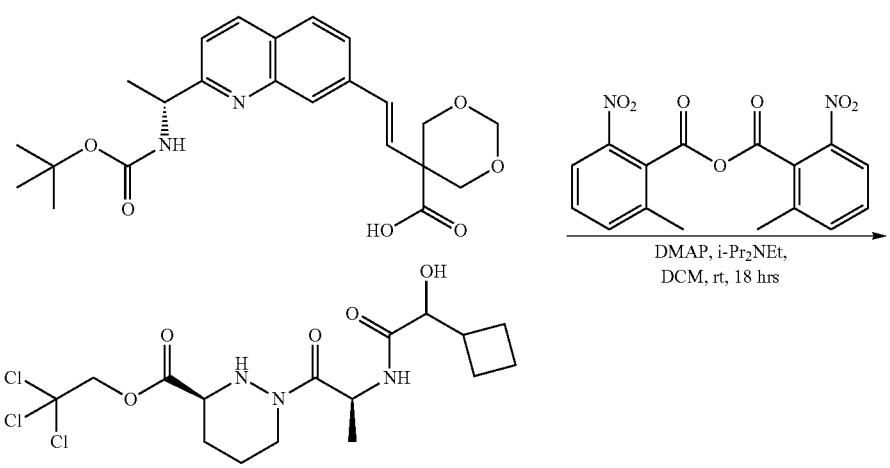

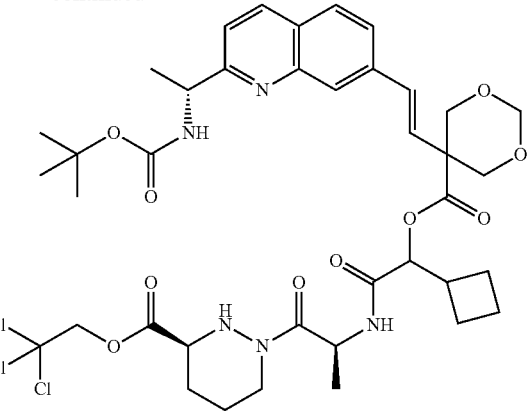

To N-Boc protected quinolinyl 1,3-dioxane carboxylic acid 63c (105.3 mg, 0.245 mmol), and a tripeptide (prepared using 64a from the method described for 1e) (129.9 mg, 0.294 mmol), and DMAP (73.5 mg, 0.588 mmol) in DCM (3 mL, 0.1 M) under argon was added i-Pr$_2$NEt (0.10 mL, 0.588 mmol) followed by 2-methyl-6-nitrobenzoic anhydride (127.0 mg, 0.268 mmol). After 18 hours, the reaction was diluted with DCM (10 mL), washed with water (3×5 mL), dried over MgSO$_4$, and concentrated in vacuo to a brown foam that was purified via column chromatography (0-100% EtOAc/hexane) to afford 64b (201.3 mg, 85%) as an off-white foam. $^1$H NMR (400 MHz, CDCl$_3$): δ 8.06 (s, 1H), 7.98 (s, 1H), 7.73 (s, 1H), 7.54 (s, 1H), 7.31 (s, 1H), 6.76 (m, 1H), 6.18 (m, 1H), 5.32 (m, 2H), 5.17 (dd, J=17.5, 5.9 Hz, 1H), 4.90 (m, 2H), 4.74 (m, 4H), 4.38 (m, 1H), 3.79 (m, 5H), 3.00 (m, 1H), 2.86 (d, J=10.3 Hz, 1H), 2.14 (m, 2H), 1.88 (m, 8H), 1.62 (m, 4H), 1.53 (s, 3H), 1.46 (s, 9H). LCMS (m/z) 856.16 [M+H].

Compound 64

To 64b (201.3 mg, 0.235 mmol) in THF (2.5 mL, 0.1 M) at 0° C. was added 0.3 M NaOH$_{(aq)}$ (0.58 mL, 0.177 mmol). The reaction was monitored by LCMS hourly, with additions of 0.3 M NaOH$_{(aq)}$. The reaction was shown to be complete after 90 minutes and was quenched with 1 M HCl$_{(aq)}$ (0.26 mL) to ~pH 4. The mixture was then diluted with EtOAc (15 mL), washed with water (3×5 mL), dried over MgSO$_4$, and concentrated in vacuo to afford a white foam. The crude material was dissolved in dioxane (1 mL) and an HCl solution (3 mL, 4 M in dioxane) was added. After 60 min, the suspension was concentrated in vacuo to a yellow solid. The crude material in DMF (0.5 mL) was diluted with DCM (100 mL) and i-Pr$_2$NEt (0.22 mL, 1.26 mmol) was added followed, by HATU (119.6 mg, 0.302 mmol). After 30 minutes, the mixture was washed with 5% LiCl$_{(aq)}$ (3×100 mL), sat. NaHCO$_3$ (100 mL), and brine (100 mL), dried over MgSO$_4$, and concentrated in

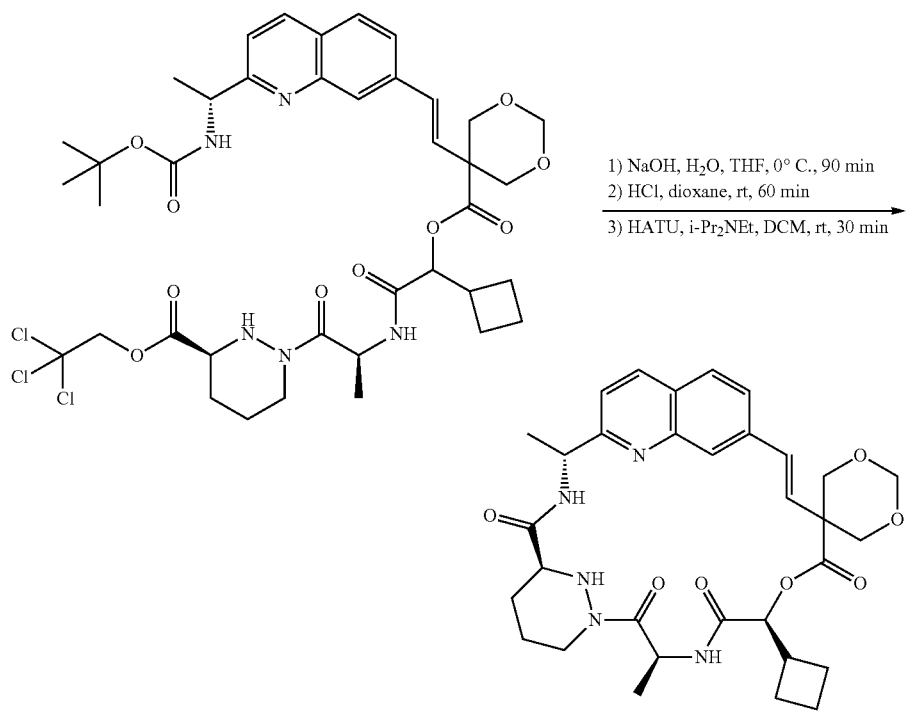

1) NaOH, H$_2$O, THF, 0° C., 90 min
2) HCl, dioxane, rt, 60 min
3) HATU, i-Pr$_2$NEt, DCM, rt, 30 min vacuo. The crude material was purified by prep HPLC (Synergi Polar-RP, 40-55% MeCN/H$_2$O) to afford 64 (3.5 mg, 2%) as a whitish residue. $^1$H NMR (400 MHz, CDCl$_3$): δ 9.48 (s, 1H), 8.60 (s, 1H), 8.52 (s, 1H), 7.96 (s, 2H), 7.66 (d, J=8.6 Hz, 1H), 6.85 (d, J=16.7 Hz, 1H), 6.35 (d, J=16.6 Hz, 1H), 6.20 (d, J=8.6 Hz, 1H), 5.53 (m, 1H), 5.30 (m, 1H), 4.94 (dd, J=7.2, 3.2 Hz, 2H), 4.87 (d, J=5.9 Hz, 1H), 4.48 (m, J=9.8 Hz, 3H), 4.06 (d, J=11.2 Hz, 1H), 3.94 (d, J=11.1 Hz, 1H), 3.76 (m, 2H), 2.68 (m, 1H), 2.54 (m, 1H), 1.92 (m, 13H), 1.64 (m, 6H). LCMS (m/z) 606.46 [M+H]. Tr=3.57 min (Gemini 5u C18 110 Å, 50×4.60 mm 5 micron column, 10 min, 2 ml/min, 5-100% acetonitrile/water, 0.1% TFA modifier).

Example 65

Compound 65

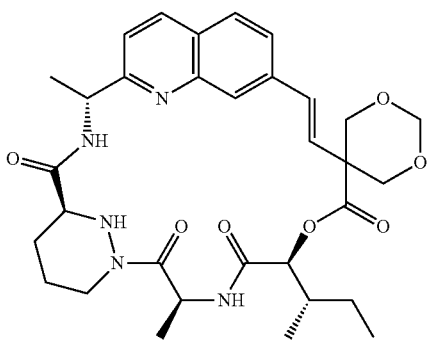 [SMILES: CC[C@H](C)[C@@H]1OC(=O)C2(/C=C/c3ccc4ccc(nc4c3)[C@@H](C)NC(=O)[C@@H]3CCCN(N3)C(=O)[C@H](C)NC1=O)COCOC2]

Compound 65a

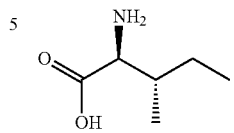

To L-isoleucine (2 g, 15.2 mmol) in 1 M H$_2$SO$_{4(aq)}$ (30 mL, 0.5 M) at 0° C. was added 2 M NaNO$_{2(aq)}$ (11.5 mL, 22.9 mmol) slowly and the reaction was allowed to warm to rt slowly. After 7 days, the reaction was saturated with (NH$_4$)$_2$SO$_4$, extracted with EtOAc (3×50 mL), dried over Na$_2$SO$_4$ and concentrated in vacuo to afford 65a (1.25 g, 57%) as a white solid. $^1$H NMR (400 MHz, d$_6$-DMSO): δ 3.77 (d, J=4.9 Hz, 1H), 1.66 (m, 1H), 1.40 (m, 1H), 1.15 (1H), 0.84 (dd, J=15.0, 7.2 Hz, 6H).

Compound 65b

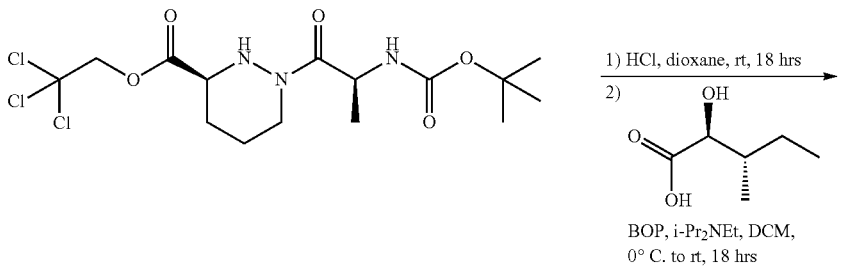

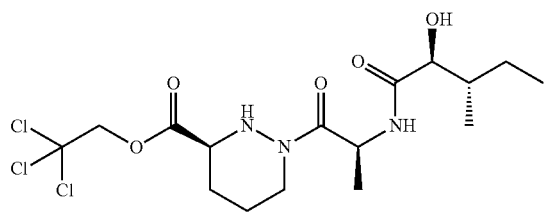

To 1d (5.88 g, 13.6 mmol) was added an HCl solution (13.6 mL, 1 M, 4 M in dioxane). After stirring for 18 hours, the reaction was concentrated in vacuo to afford the free dipeptide as an amorphous, pale yellow solid. To 65a (492.4 mg, 3.78 mmol), dipeptide (1.39 g, 3.78 mmol), and i-Pr₂NEt (0.66 mL, 3.787 mmol) in DCM (40 mL, 0.1 M) at 0° C. was added (benzotriazol-1-yloxy)tris(dimethylamino)phosphonium hexafluorophosphate (1.38 g, 4.54 mmol) and the reaction was slowly warmed to room temperature. After 18 hours, the reaction was concentrated in vacuo. The residue was diluted with EtOAc (200 mL), washed with 10% citric acid (200 mL), sat. NaHCO₃ (200 mL), and brine (200 mL), dried over Na₂SO₄, and concentrated in vacuo. Purification by column chromatography equipped with an ELSD (0-100% EtOAc/hexane) afforded 65b (856.8 mg, 51%) as a white solid. ¹H NMR (400 MHz, CDCl₃): δ 7.18 (s, 1H), 5.39 (m, 1H), 4.95 (d, J=11.9 Hz, 1H), 4.71 (d, J=11.9 Hz, 1H), 4.34 (m, 1H), 4.00 (d, J=3.4 Hz, 1H), 3.70 (m, 1H), 2.93 (m, 1H), 2.18 (m 1H), 1.89 (m, 1H), 1.73 (t, J=9.7 Hz, 2H), 1.42 (m, 1H), 1.34 (d, J=6.9 Hz, 3H), 1.24 (t, J=8.7, 5.6 Hz, 3H), 1.19 (m, 1H), 1.00 (d, J=6.9 Hz, 3H). LCMS (m/z) 46.00 [M+H].

To the N-Boc protected quinolinyl 1,3-dioxane carboxylic acid 63c (74.9 mg, 0.175 mmol), 65b (96.2 mg, 0.175 mmol), and DMAP (52.7 mg, 0.420 mmol) in DCM (1.8 mL, 0.1 M) under Ar was added i-Pr₂NEt (0.07 mL, 0.420 mmol) followed by 2-methyl-6-nitrobenzoic anhydride (93.1 mg, 0.263 mmol). After 18 hours, the reaction was diluted with DCM (10 mL), washed with water (3×5 mL), dried over MgSO₄, and concentrated in vacuo to afford 65c as a yellow foam (185.8 mg, 99%). ¹H NMR (400 MHz, CDCl₃): δ 8.22 (s, 1H), 8.06 (d, J=8.4 Hz, 1H), 7.98 (s, 1H), 7.73 (d, J=8.4 Hz, 1H), 7.31 (d, J=8.4 Hz, 1H), 6.75 (d, J=16.7 Hz, 1H), 6.55 (s, 2H), 6.18 (d, J=16.2 Hz, 1H), 5.34 (m, 2H), 4.98 (m, 2H), 4.73 (m, 4H), 4.33 (d, J=14.7 Hz, 1H), 3.85 (dd, J=27.7, 11.0 Hz, 2H), 2.18 (dt, J=15.3, 8.4 Hz, 1H), 1.53 (d, J=6.6 Hz, 3H), 1.47 (s, 9H), 1.33 (d, J=6.8 Hz, 2H), 1.29 (d, J=6.8 Hz, 3H), 0.98 (d, J=6.8 Hz, 3H), 0.92 (t, J=7.6 Hz, 3H). LCMS (m/z) 856.51 [M+H].

Compound 65c

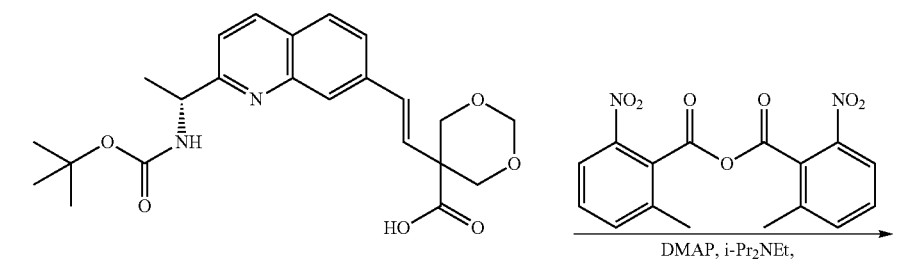

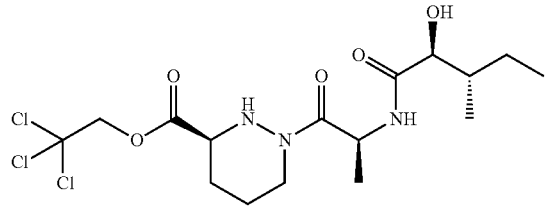

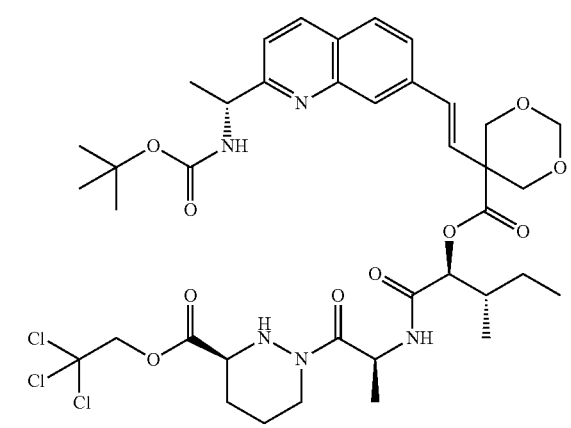

Compound 65

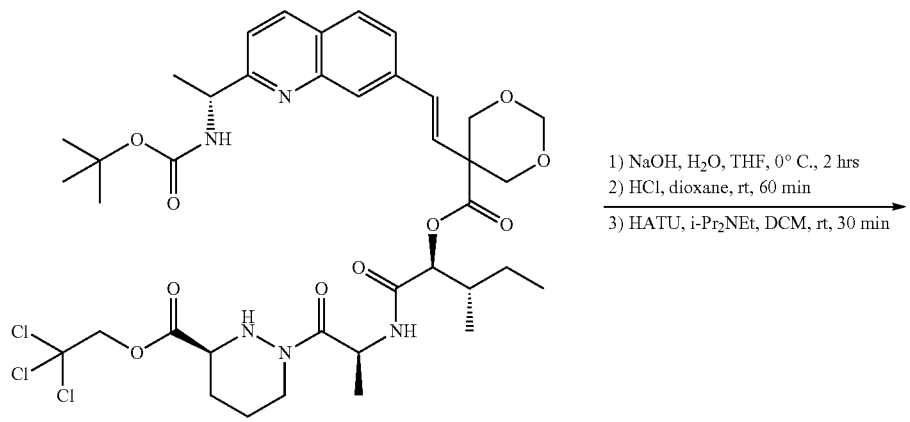

To 65c (150 mg, 0.175 mmol) in THF (1.8 mL, 0.1 M) at 0° C. was added 0.3 M NaOH$_{(aq)}$ (0.44 mL, 0.131 mmol). The reaction was monitored by LCMS ever 30 minutes, with additions of 0.3 M NaOH$_{(aq)}$. The reaction was shown to be complete after 2 hours and was quenched with 1 M HCl$_{(aq)}$ (0.40 mL) to ~pH 4. The mixture was then diluted with EtOAc (15 mL), washed with water (3×5 mL) and brine (5 mL), dried over MgSO$_4$, and concentrated in vacuo to afford a yellow foam (116.8 mg). The crude material was dissolved in dioxane (1 mL) and an HCl solution (3 mL, 4 M in dioxane) was added. After 60 min, the suspension was concentrated in vacuo to an orange solid. The crude material in DMF (1 mL) was diluted with DCM (100 mL) and i-Pr$_2$NEt (0.22 mL, 1.26 mmol) was added, followed by HATU (305.2 mg, 0.803 mmol). After 30 minutes, the mixture was washed with 5% LiCl$_{(aq)}$ (3×100 mL), sat. NaHCO$_{3(aq)}$ (100 mL), and brine (100 mL), dried over MgSO$_4$, and concentrated in vacuo to an orange residue. The crude material was purified by column chromatography (20-100% MeCN/H$_2$O). The residue was dissolved in EtOAc (20 mL) and washed with 5% LiCl (10× 10 mL) to afford 65 (24.2 mg, 13%) as a whitish residue. $^1$H NMR (400 MHz, CDCl$_3$): δ 9.09 (s, 1H), 8.11 (s, 1H), 7.75 (s, 1H), 7.52 (s, 1H), 7.3 (s, 1H), 6.73 (d, J=16.5 Hz, 2H), 6.33 (d, J=8.6 Hz, 1H), 6.14 (d, J=16.2 Hz, 1H), 5.85 (s, 1H), 5.11 (s, 2H), 5.02 (d, J=5.9 Hz, 1H), 4.80 (d, J=6.2 Hz, 1H), 4.65 (d, J=11.3 Hz, 1H), 4.56 (d, J=11.6 Hz, 2H), 3.95 (d, J=11.5 Hz, 1H), 3.83 (d, J=11.3 Hz, 1H), 3.56 (m, 1H), 2.56 (m, 1H), 1.96 (m, 1H), 1.61 (m, 10H), 1.26 (t, J=7.1 Hz, 3H), 1.01 (d, J=5.8 Hz, 3H). LCMS (m/z) 608.47 [M+H]. Tr=3.67 min.

Example 66

Compound 66

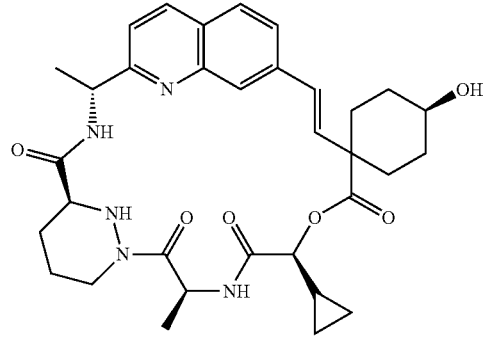

Compound 66a

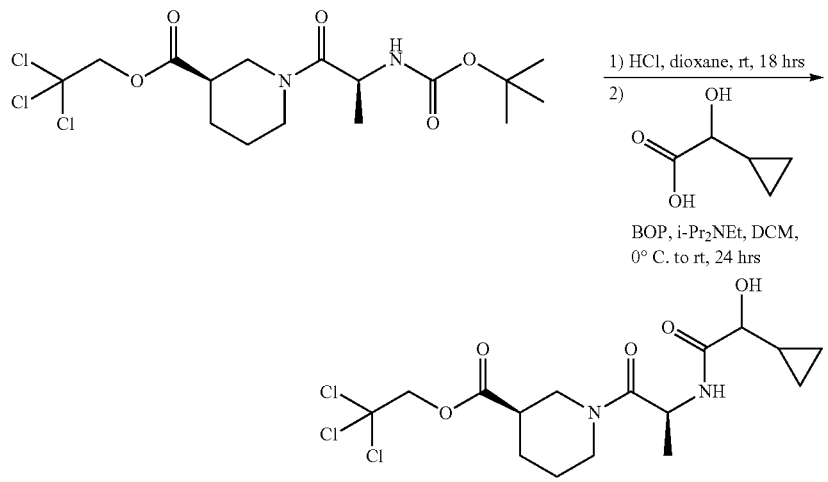

To 1d (4 g, 9.24 mmol) in dioxane (5 mL) was added an HCl solution (34 mL, 0.25 M, 4 M in dioxane). After stirring for 18 hours, the reaction was concentrated in vacuo to afford the free dipeptide (3.69 g) as an amorphous, pale yellow solid. To α-hydroxy cyclopropyl acetic acid (obtained from ArkPharm, Inc.), (493.5 mg, 4.09 mmol), dipeptide (1000 mg, 2.72 mmol), and i-Pr$_2$NEt (0.48 mL, 2.72 mmol) in DCM (45 mL, 0.05 M) at 0° C. was added (benzotriazol-1-yloxy)tris(dimethylamino)phosphonium hexafluorophosphate (981.1 mg, 3.27 mmol) and the reaction was slowly warmed to room temperature. After 24 hours, the reaction was concentrated in vacuo. The residue was diluted with EtOAc (100 mL), washed with 10% citric acid (5×50 mL), sat. NaHCO$_{3(aq)}$ (2×50 mL), and brine (100 mL), dried over Na$_2$SO$_4$, and concentrated in vacuo. Purification by column chromatography equipped with an ELSD (0-100% EtOAc/hexane) afforded 66a (425.8 mg, 36%) as a white foam. $^1$H NMR (400 MHz, CDCl$_3$): δ 7.14 (m, 1H), 5.37 (m, 1H), 4.95 (d, J=12.0 Hz, 1H), 4.72 (dd, J=12.0, 2.8 Hz, 1H), 4.33 (m, 1H), 3.86 (m, 1H), 3.70 (m, 1H), 3.48 (dd, J=12.0, 8.2 Hz, 1H), 2.93 (m, 1H), 2.86 (d, J=10.3 Hz, 1H), 2.19 (m, 1H), 1.94 (m, 1H), 1.73 (m, 2H), 1.35 (m, 3H), 1.09 (m, 1H), 0.67 (m, 1H), 0.54 (m, 3H). LCMS (m/z) 430.12 [M+H].

Compound 66b

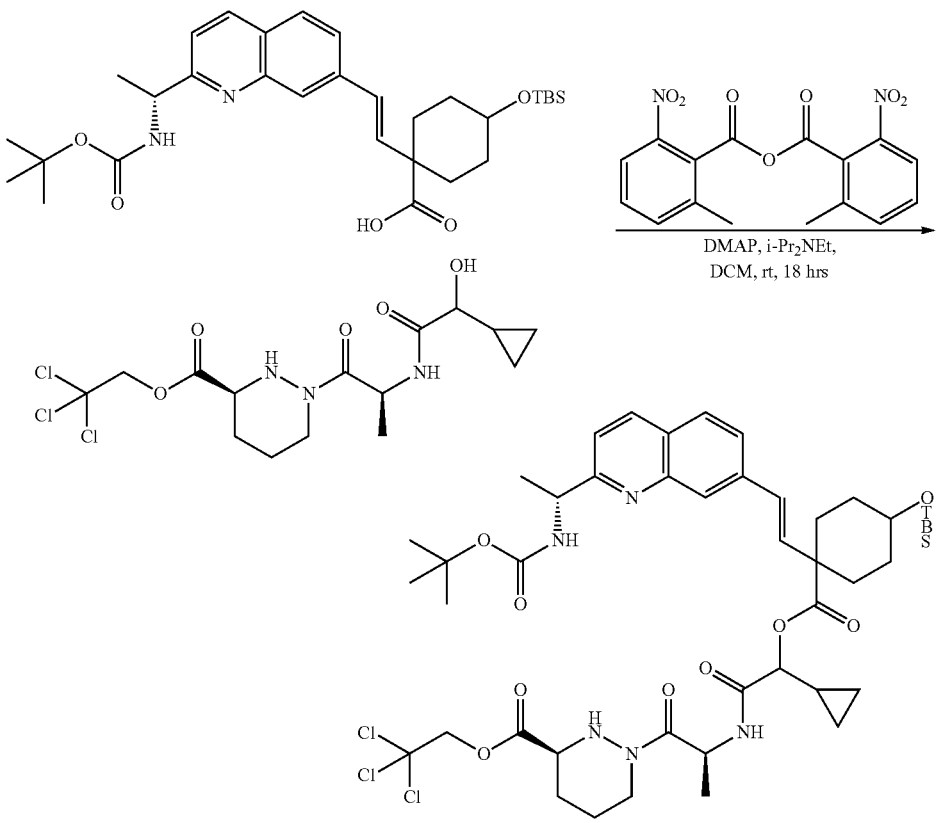

To the indicated N-Boc quinolinyl carboxylate 74c (242.1 mg, 0.451 mmol), 66a (238.4 mg, 0.451 mmol), and DMAP (132.3 mg, 1.08 mmol) in DCM (4.6 mL, 0.1 M) under Ar was added i-Pr$_2$NEt (0.19 mL, 1.08 mmol) followed by 2-methyl-6-nitrobenzoic anhydride (235.6 mg, 0.676 mmol). After 18 hours, the reaction was diluted with DCM (10 mL), washed with water (3×10 mL), dried over MgSO$_4$, and concentrated in vacuo to a yellow foam that was purified via column chromatography (0-100% EtOAc/hexane) to afford 66b (313.7 mg, 66%) as a pale golden oil. $^1$H NMR (400 MHz, CDCl$_3$): δ 8.05 (d, J=8.3 Hz, 1H), 7.97 (s, 1H), 7.70 (d, J=8.3 Hz, 1H), 7.62 (d, J=8.2 Hz, 1H), 7.27 (s, 1H), 7.08 (m, 1H), 6.76 (d, J=16.6 Hz, 1H), 6.43 (d, J=16.3 Hz, 1H), 6.19 (m, 1H), 5.25 (m, J=15.1 Hz, 1H), 4.92 (m, 2H), 4.81 (dd, J=14.1, 6.4 Hz, 1H), 4.70 (dd, J=12.7, 10.3 Hz, 1H), 4.29 (m, 1H), 3.66 (m, 3H), 2.49 (m, 1H), 2.09 (m, 2H), 1.80 (m, 2H), 1.68 (m, 4H), 1.52 (d, J=6.2 Hz, 3H), 1.47 (s, 9H), 1.29 (m, 3H), 1.12 (s, 1H), 0.57 (m, 4H). LCMS (m/z) 968.24 [M+H].

To 66b (313.7 mg, 0.324 mmol) in THF (3.2 mL, 0.1 M) at 0° C. was added 0.3 M NaOH (0.81 mL, 0.243 mmol). The reaction was monitored by LCMS ever 30 minutes, with additions of 0.3 M NaOH. The reaction was shown to be complete after 60 minutes and was quenched with 1 M HCl (0.36 mL) to ~pH 4. The mixture was then diluted with EtOAc (15 mL), washed with water (3×5 mL), dried over MgSO$_4$, and concentrated in vacuo to afford a pale yellow foam (283.7 mg). The crude material was dissolved in dioxane (1 mL) and an HCl solution (3 mL, 4 M in dioxane) was added. After 60 min, the suspension was concentrated in vacuo to a pale yellow solid (275.5 mg). The crude material in DMF (1.5 mL) was diluted with DCM (100 mL) and i-Pr$_2$NEt (0.30 mL, 1.69 mmol) was added, followed by HATU (157.2 mg, 0.405 mmol). After 30 minutes, the mixture was washed with 5% LiCl$_{(aq)}$ (3×100 mL), sat. NaHCO$_3$ (100 mL), and brine (100 mL), dried over MgSO$_4$, and concentrated in vacuo. The crude material was purified by prep HPLC (Synergi Polar-RP, 35% MeCN/H$_2$O) and lyophilized to afford 66 (3.4 mg, 1%) as a white solid. $^1$H NMR (400 MHz, CDCl$_3$): δ 8.54 (s, 1H), 8.10 (s, 1H), 7.73 (d, J=7.3 Hz, 2H), 7.43 (s, 1H), 6.72 (dd, J=19.3, 8.7 Hz, 1H), 6.48 (dd, J=24.9, 16.4 Hz, 1H), 5.89 (m, 1H), 5.17 (t, J=6.2 Hz, 1H), 4.72 (m, 1H), 4.57 (m, 1H), 3.70 (m, 2H), 3.52 (m, 2H), 2.54 (m, 6H), 2.02 (m, 3H), 1.62 (m, 10H), 1.30 (m, 3H), 0.88 (m, 1H), 0.60 (m, 4H). LCMS (m/z) 604.60 [M+H]. Tr=2.23 min (Gemini 5u C18 110 Å, 50×4.60 mm 5 micron column, 5 min, 2 ml/min, 5-100% acetonitrile/water, 0.1% TFA modifier).

Compound 66

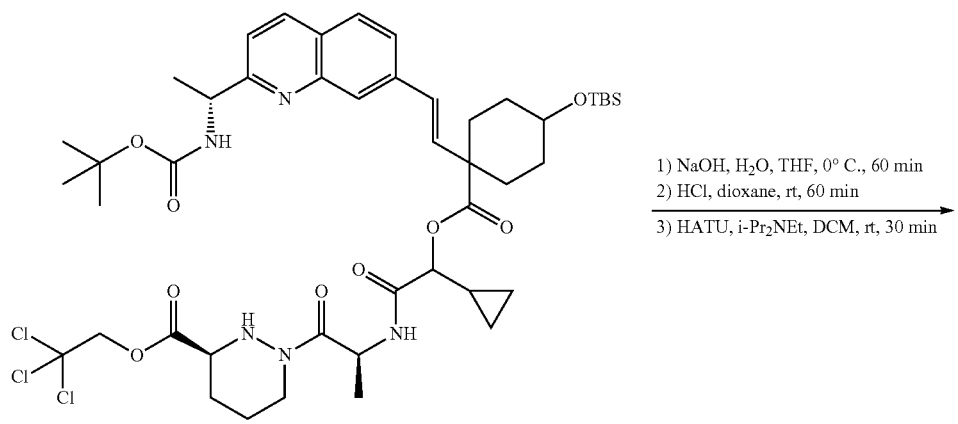

1) NaOH, H$_2$O, THF, 0° C., 60 min
2) HCl, dioxane, rt, 60 min
3) HATU, i-Pr$_2$NEt, DCM, rt, 30 min

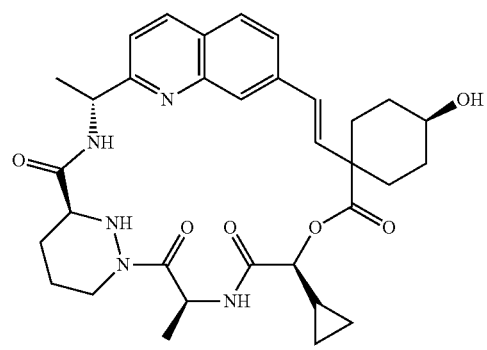

Example 67

Compound 67

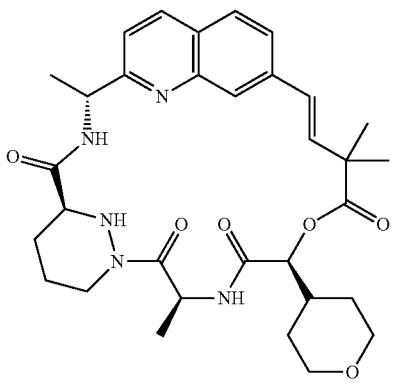 [SMILES: C[C@@H]1NC(=O)[C@H](C2CCOCC2)OC(=O)C(C)(C)/C=C/c2ccc3ccc(nc3c2)[C@@H](C)NC(=O)[C@@H]2CCCN(N2)C1=O]

Compound 67a

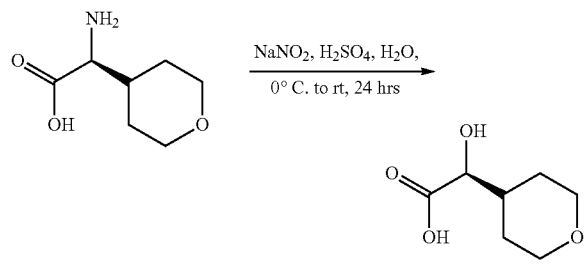

To (S)-2-amino-2-(tetrahydro-2H-pyran-4-yl)acetic acid (obtained from AstaTech, Inc.), (1.01 g, 6.35 mmol) in 1 M $H_2SO_{4(aq)}$ (12.5 mL, 0.5 M) at 0° C. was added 2 M $NaNO_{2(aq)}$ (9.5 mL, 19.0 mmol) slowly and the reaction was allowed to warm to rt slowly. After 24 hours, $^1H$ NMR showed no starting material and the reaction was extracted with EtOAc (3×50 mL). The combined organics were dried over $Na_2SO_4$ and concentrated in vacuo to afford 67a (868.8 g, 85%) as an off-white solid. $^1H$ NMR (400 MHz, $d_6$-DMSO): δ 3.84 (m, 2H), 3.76 (d, J=5.1 Hz, 1H), 3.24 (m, 2H), 1.81 (m, 1H), 1.39 (m, 4H).

Compound 67b

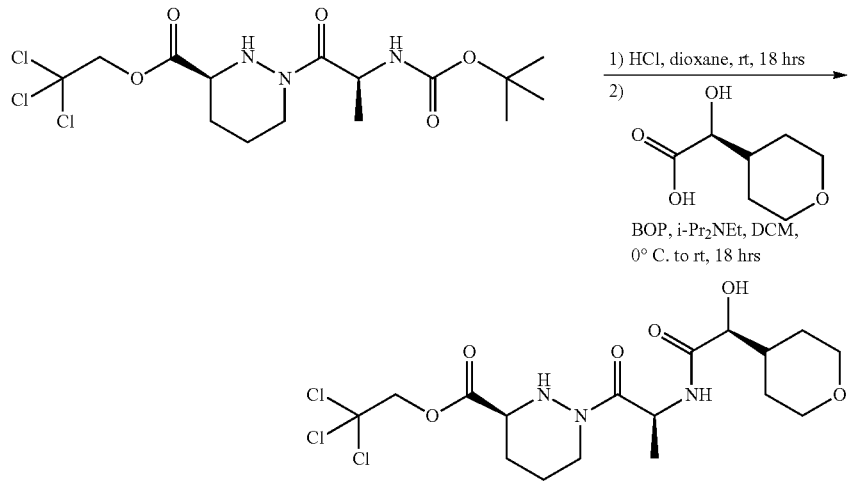

To 1d (5 g, 11.6 mmol) in dioxane (5 mL) was added an HCl solution (45 mL, 0.25 M, 4 M in dioxane). After stirring for 18 hours, the reaction was concentrated in vacuo to afford the free dipeptide (4.71 g) as an amorphous, pale yellow solid.

To 67a (300.9 mg, 1.87 mmol), dipeptide (447.9 mg, 1.25 mmol), and i-$Pr_2NEt$ (0.27 mL, 1.56 mmol) in DCM (16 mL, 0.1 M) at 0° C. was added (benzotriazol-1-(benzyloxy)tris(dimethylamino)phosphonium hexafluorophosphate (827.9 mg, 1.87 mmol) and the reaction was slowly warmed to room temperature. After 18 hours, the reaction was concentrated in vacuo. The residue was diluted with EtOAc (100 mL), washed with 10% citric acid (3×100 mL), sat. $NaHCO_{3(aq)}$ (100 mL), and brine (100 mL), dried over $Na_2SO_4$, and concentrated in vacuo. Purification by column chromatography equipped with an ELSD (0-100% EtOAc/hexane) afforded 67b (171.3 mg, 23%) as an off-white foam. $^1H$ NMR (400 MHz, $CDCl_3$): δ 7.15 (d, J=7.9 Hz, 1H), 5.38 (p, J=6.8 Hz, 1H), 4.95 (d, J=11.9 Hz, 1H), 4.71 (d, J=11.9 Hz, 1H), 4.31 (d, J=14.2 Hz, 1H), 3.99 (m, 3H), 3.94 (d, J=3.8 Hz, 1H), 3.70 (m, 1H), 3.39 (m, 2H), 2.94 (m, 1H), 2.19 (m, 1H), 1.98 (m, 2H), 1.75 (dd, J=19.3, 10.0 Hz, 2H), 1.64 (ddd, J=24.9, 12.7, 4.6 Hz, 2H), 1.55 (t, J=8.4 Hz, 2H), 1.39 (m, 1H), 1.33 (d, J=6.8 Hz, 3H). LCMS (m/z) 474.26 [M+H].

Compound 67c

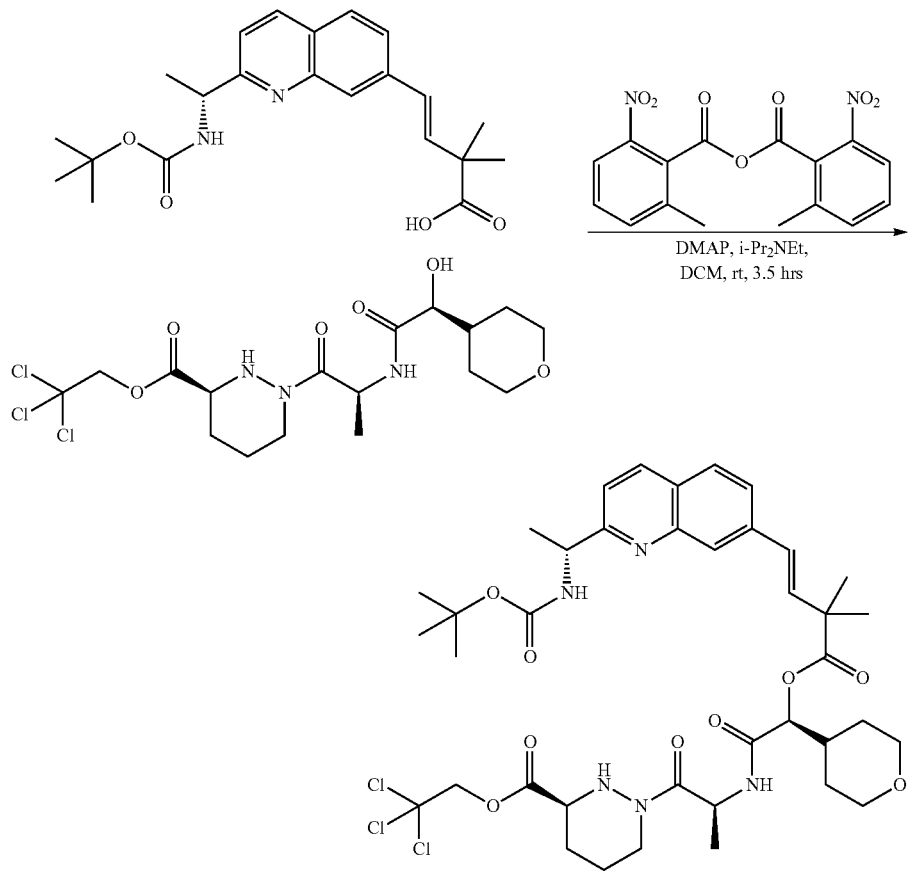

To (R,E)-4-(2-(1-(tert-butoxycarbonylamino)ethyl)quinolin-7-yl)-2,2 dimethylbut-3-enoic acid (136.9 mg, 0.361 mmol), 67b (171.3 mg, 0.361 mmol), and DMAP (106.1 mg, 866 mmol) in DCM (3.5 mL, 0.1 M) under Ar was added i-Pr$_2$NEt (0.15 mL, 866 mmol) followed by 2-methyl-6-nitrobenzoic anhydride (189.2 mg, 0.541 mmol). After 2.5 hours, more 2-methyl-6-nitrobenzoic anhydride (50.8) was added. After another hour, the reaction was diluted with DCM (10 mL), washed with water (3×5 mL), dried over MgSO$_4$, and concentrated in vacuo to afford 67c as an off-white foam (324.4 mg, 90%). $^1$H NMR (400 MHz, CDCl$_3$): δ 8.22 (d, J=5.9 Hz, 2H), 8.05 (d, J=8.3 Hz, 1H), 8.02 (s, 1H), 7.71 (s, 1H), 7.66 (d, J=8.8 Hz, 1H), 7.28 (s, 1H), 7.12 (s, 1H), 6.70 (d, J=14.1 Hz, 1H), 6.52 (d, J=6.4 Hz, 2H), 6.22 (s, 1H), 5.14 (d, J=3.7 Hz, 1H), 4.94 (m, 2H), 4.70 (d, J=12.1 Hz, 1H), 3.96 (s, 2H), 3.73 (m, 1H), 3.37 (t, J=12.1 Hz, 2H), 2.29 (m, 1H), 2.19 (m, 1H), 1.89 (m, 1H), 1.57 (d, J=6.1 Hz, 6H), 1.52 (m, 6H), 1.48 (m, 15H), 1.28 (d, J=6.7 Hz, 3H). LCMS (m/z) 840.67 [M+H].

Compound 67

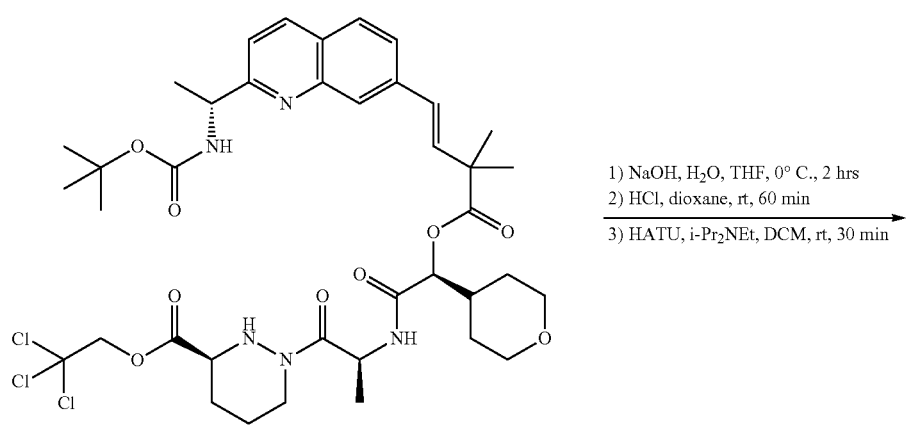

1) NaOH, H$_2$O, THF, 0° C., 2 hrs
2) HCl, dioxane, rt, 60 min
3) HATU, i-Pr$_2$NEt, DCM, rt, 30 min

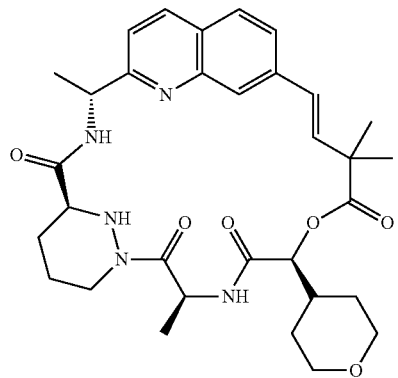

To 67c (273.5 mg, 0.325 mmol) in THF (3.4 mL, 0.1 M) at 0° C. was added 0.3 M aq. NaOH (8.2 mL, 0.244 mmol). The reaction was monitored by LCMS hourly, with additions of 0.3 M aq. NaOH. The reaction was shown to be complete after 2 hours and was quenched with 1 M aq. HCl (0.77 mL) to ~pH 4. The mixture was then diluted with EtOAc (15 mL), washed with water (3×5 mL) and brine (5 mL), dried over MgSO$_4$, and concentrated in vacuo to afford a yellow foam (251.0 mg). The crude material was dissolved in dioxane (1 mL) and HCl (3 mL, 4 M in dioxane) was added. After 60 min, the suspension was concentrated in vacuo to a yellow solid (266.8 mg). The crude material in DMF (1 mL) was diluted with DCM (100 mL) and i-Pr$_2$NEt (0.28 mL, 1.63 mmol) was added, followed by HATU (148.9 g, 0.325 mmol). After 30 minutes, the mixture was washed with 5% aq. LiCl (3×100 mL), sat. NaHCO$_{3(aq)}$ (100 mL), and brine (100 mL), dried over MgSO$_4$, and concentrated in vacuo to an orange residue. The crude material was purified by column chromatography (25-100% EtOAc/hexane) to afford 67 (38.4 mg, 18%) as a pale yellow residue. $^1$H NMR (400 MHz, CDCl$_3$): δ 9.07 (s, 1H), 8.13 (d, J=7.1 Hz, 1H), 8.05 (s, 1H), 7.74 (d, J=8.1 Hz, 1H), 7.47 (d, J=7.4 Hz, 1H), 7.28 (s, 1H), 6.65 (d, J=16.0 Hz, 1H), 6.43-6.26 (m, 1H), 5.79 (m, 1H), 5.36 (m, 1H), 5.23 (m, 1H), 5.11 (m, 1H), 4.99 (d, J=7.6 Hz, 1H), 4.54 (dd, J=13.5, 2.5 Hz, 1H), 3.96 (d, J=11.1 Hz, 2H), 3.84 (dd, J=33.2, 14.1 Hz, 1H), 3.64 (d, J=11.9 Hz, 1H), 3.51 (t, J=11.5 Hz, 1H), 3.33 (m, 3H), 2.57 (td, J=13.1, 2.5 Hz, 1H), 2.43 (d, J=14.1 Hz, 1H), 2.33 (m, 1H), 2.21 (m, 1H), 1.96 (d, J=12.9 Hz, 1H), 1.70 (m, 4H), 1.63 (s, 6H), 1.60 (m, 6H), 1.53 (s, 3H), 1.48 (s, 2H), 1.44 (s, 3H). LCMS (m/z) 592.37 [M+H]. Tr=2.45 min.

Example 68

Compound 68

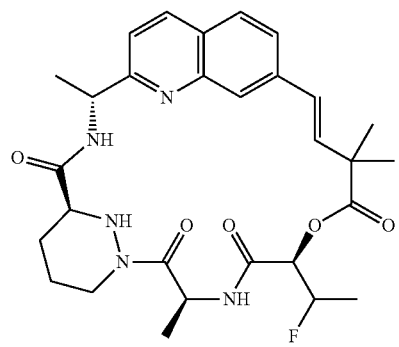 [SMILES: CC(F)[C@@H]1OC(=O)C(C)(C)/C=C/c2ccc3ccc(nc3c2)[C@@H](C)NC(=O)[C@@H]2CCCN(N2)C(=O)[C@H](C)NC1=O]

Compound 68a

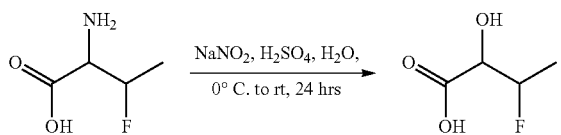

To 2-amino-3-fluorobutanoic acid (obtained from Fluorochem, Ltd.), (509.4 mg, 4.13 mmol) in 1 M H$_2$SO$_{4(aq)}$ (8.5 mL, 0.5 M) at 0° C. was added 2 M NaNO$_{2(aq)}$ (6.0 mL, 12.4 mmol) slowly and the reaction was allowed to warm to rt slowly. After 24 hours, $^1$H NMR showed trace starting material and the reaction was extracted with EtOAc (3×25 mL). The combined organics were dried over Na$_2$SO$_4$ and concentrated in vacuo to afford 68a (437.2 g, 87%) as a white solid. $^1$H NMR (400 MHz, d$_6$-DMSO): δ 5.07-4.65 (m, 1H), 4.07 (ddd, J=33.7, 23.1, 3.1 Hz, 1H), 1.28 (ddd, J=24.7, 18.4, 6.4 Hz, 3H). $^{19}$F NMR (376 MHz, DMSO): δ−180.63 (dqd, J=48.5, 24.3, 14.9 Hz), −186.54 (ddq, J=48.3, 31.5, 24.1 Hz).

Compound 68b

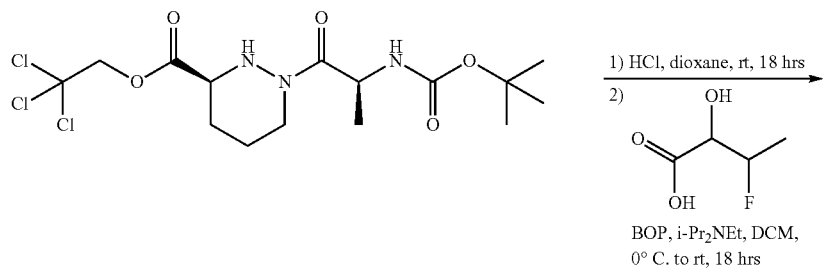

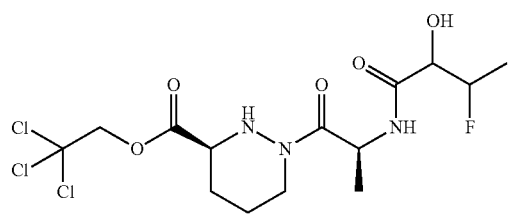

To 1d (5 g, 11.6 mmol) in dioxane (5 mL) was added an HCl solution (45 mL, 0.25 M, 4 M in dioxane). After stirring for 18 hours, the reaction was concentrated in vacuo to afford the free dipeptide (4.71 g) as an amorphous, pale yellow solid. To 68a (225.3 mg, 1.84 mmol), dipeptide (671.2 mg, 1.84 mmol), and i-Pr$_2$NEt (0.32 mL, 1.84 mmol) in DCM (20 mL, 0.1 M) at 0° C. was added (benzotriazol-1-yloxy)tris(dimethylamino)phosphonium hexafluorophosphate (1.2130 g, 2.76 mmol) and the reaction was slowly warmed to room temperature. After 18 hours, the reaction was concentrated in vacuo. The residue was diluted with EtOAc (100 mL), washed with 10% citric acid (3×100 mL), sat. NaHCO$_{3(aq)}$ (100 mL), and brine (100 mL), dried over Na$_2$SO$_4$, and concentrated in vacuo. Purification by column chromatography equipped with an ELSD (0-100% EtOAc/hexane) afforded 68b (318.9 mg, 32%) as a white foam. $^1$H NMR (400 MHz, CDCl$_3$): δ 5.39 (m, 1H), 5.07 (m 1H), 4.95 (d, J=11.9 Hz, 1H), 4.70 (dd, J=11.9, 4.2 Hz, 1H), 4.31 (m, 1H), 4.10 (ddd, J=13.9, 10.0, 5.5 Hz, 1H), 3.70 (d, J=6.4 Hz, 1H), 2.91 (m, 1H), 2.87 (d, J=10.3 Hz, 1H), 2.20 (m, 1H), 1.91 (m, 1H), 1.72 (m, 1H), 1.36 (m, 8H). $^{19}$F NMR (376 MHz, CDCl$_3$): δ −181.98−−182.68 (m), −186.38−−187.09 (m), −187.09−−187.99 (m). LCMS (m/z) 437.82 [M+H].

Compound 68c

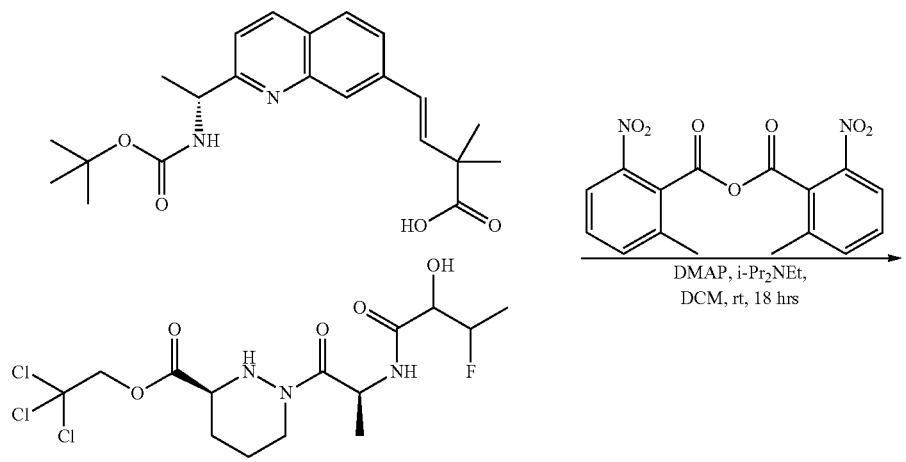

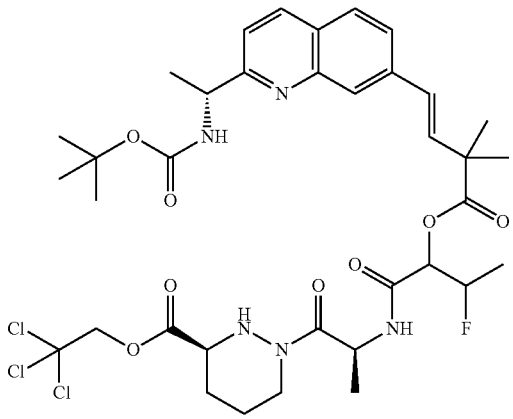

To the indicated N-Boc-quinolinyl carboxylate (211.3 mg, 0.538 mmol), 68b (235.0 mg, 0.538 mmol), and DMAP (156.9 mg, 1.29 mmol) in DCM (5.4 mL, 0.1 M) under Ar was added i-Pr₂NEt (0.23 mL, 1.29 mmol) followed by 2-methyl-6-nitrobenzoic anhydride (279.5 mg, 0.807 mmol). After 18 hours, the reaction was diluted with DCM (15 mL), washed with water (3×5 mL), dried over MgSO₄, and concentrated in vacuo to afford 68c as a pale yellow foam (455.7 mg, 90%). ¹H NMR (400 MHz, CDCl₃): δ 8.10 (d, J=8.7 Hz, 1H), 8.03 (m, 1H), 7.68 (d, J=21.0 Hz, 2H), 7.27 (s, 1H), 6.74 (d, J=7.5 Hz, 2H), 6.21 (m, 1H), 5.27 (d, J=15.8 Hz, 2H), 5.12 (m, 1H), 4.93 (d, J=12.0 Hz, 1H), 4.70 (dd, J=11.9, 2.9 Hz, 1H), 4.28 (m, 1H), 3.69 (m, 1H), 2.86 (d, J=10.2 Hz, 1H), 2.65 (d, J=9.3 Hz, 1H), 2.16 (M, 1H), 1.89 (M, 1H), 1.63 (s, 2H), 1.61 (d, J=3.7 Hz, 3H), 1.54 (d, J=10.1 Hz, 9H), 1.47 (s, 10H), 1.29 (m, 8H).

Compound 68

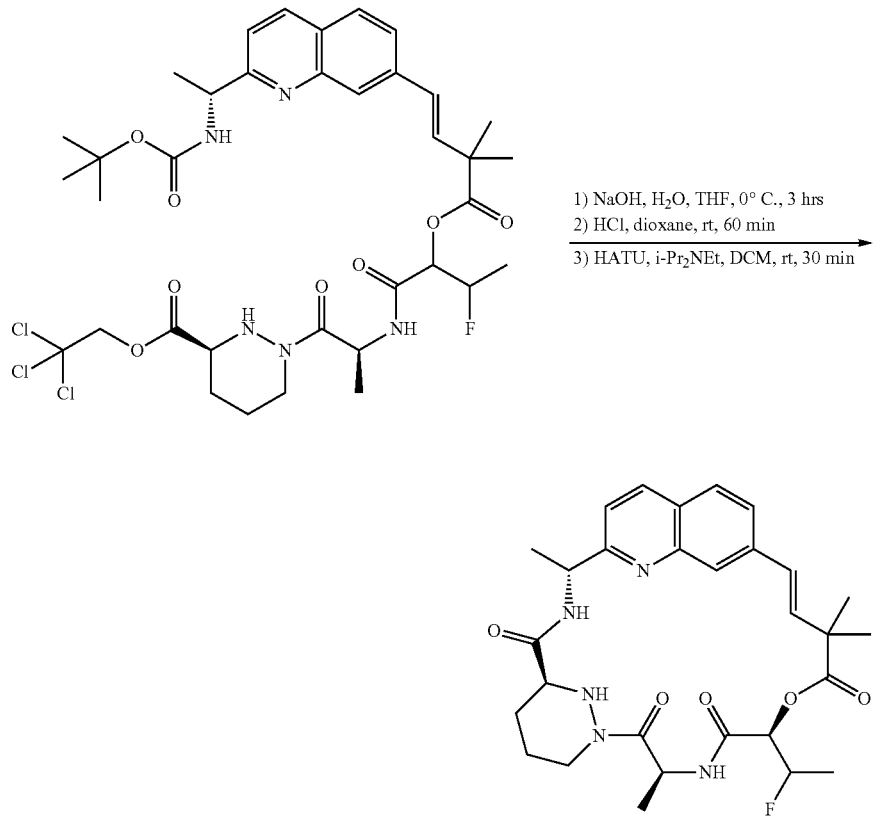

To 68c (455.7 mg, 0.567 mmol) in THF (5.4 mL, 0.1 M) at 0° C. was added 0.3 M aq. NaOH (1.3 mL, 0.426 mmol). The reaction was monitored by LCMS hourly, with additions of 0.3 M aq. NaOH. The reaction was shown to be complete after 3 hours and was quenched with 1 M aq. HCl (0.75 mL) to ~pH 4. The mixture was then diluted with EtOAc (15 mL), washed with water (3×5 mL) and brine (2×5 mL), dried over MgSO$_4$, and concentrated in vacuo to afford a pale yellow foam (388.7 mg). The crude material was dissolved in dioxane (1.5 mL) and an HCl solution (3 mL, 4 M in dioxane) was added. After 60 min, the suspension was concentrated in vacuo to a yellow solid (464.1 mg). The crude material in DMF (1.5 mL) was diluted with DCM (100 mL) and i-Pr$_2$NEt (0.51 mL, 2.90 mmol) was added, followed by HATU (265.6 mg, 0.695 mmol). After 30 minutes, the mixture was washed with 5% LiCl$_{(aq)}$ (3×100 mL), sat. NaHCO$_{3(aq)}$ (100 mL), and brine (100 mL), dried over MgSO$_4$, and concentrated in vacuo to an orange residue. The crude material was purified by prep HPLC (Synergi Polar-RP, 50% MeCN/H$_2$O) and lyophilized to afford 68 (25.3 mg, 7%) as a white solid. $^1$H NMR (400 MHz, CDCl$_3$): δ 9.01 (d, J=9.8 Hz, 1H), 8.22 (s, 1H), 8.10 (s, 1H), 7.74 (d, J=8.2 Hz, 1H), 7.46 (d, J=7.6 Hz, 1H), 6.97 (m, 1H), 6.70 (m, 2H), 6.48 (d, J=15.7 Hz, 1H), 5.86 (m, 1H), 5.37 (m, 1H), 5.18 (m, 1H), 4.55 (d, J=11.9 Hz, 1H), 3.83 (m, 1H), 3.57 (m, 1H), 3.27 (m, 1H), 2.52 (m, 1H), 1.95 (m, 1H), 1.68 (d, J=22.6 Hz, 6H), 1.59 (s, 6H), 1.55 (s, 2H), 1.48 (s, 6H), 1.43-1.21 (m, 3H). $^{19}$F NMR (376 MHz, CDCl$_3$) δ −184.47--185.27 (m), −187.78--188.41 (m). LCMS (m/z) 554.42 [M+H]. Tr=2.49.

Example 69

Compound 69

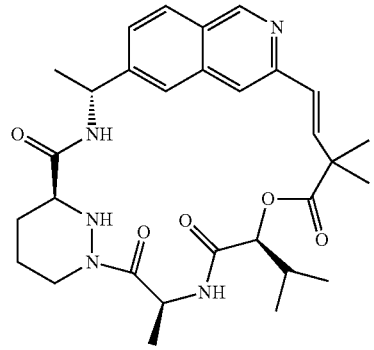 [SMILES: CC(C)[C@@H]1OC(=O)C(C)(C)/C=C/c2cc3cc(ccc3cn2)[C@@H](C)NC(=O)[C@@H]2CCCN(N2)C(=O)[C@H](C)NC1=O]

Compound 69a

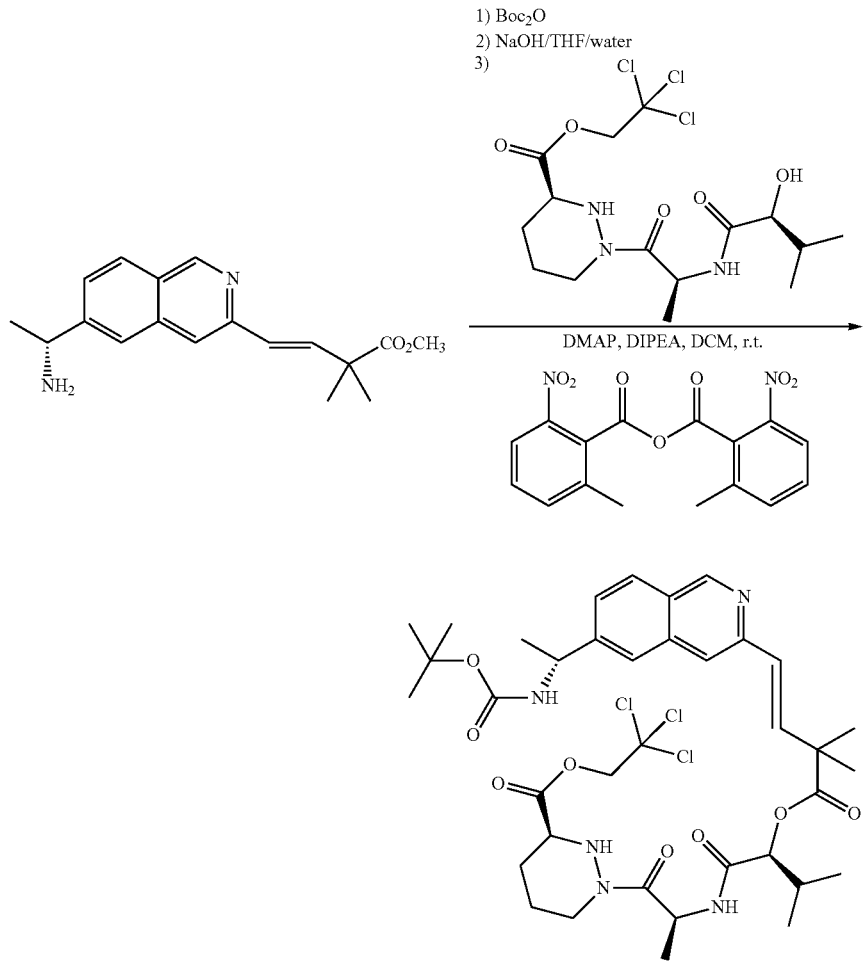

Beginning from 18e (192 mg, 0.50 mmol), N-Boc amine protection and subsequent ester hydrolysis with NaOH/THF/water gave, after acidification with 1N HCl and concentration to a crude residue, the intermediate carboxylic acid in quantitative yield. The resulting material was carried forward directly into amide formation where 2-methyl-6-nitrobenzoic anhydride (344 mg, 1 mmol), 4-dimethylaminopyridine (128 mg, 1.05 mmol), and the N-Boc protected isoquinolinyl acid were stirred in anhydrous dichloromethane (20 mL). Into the resulting solution was added N,N-diisopropylethylamine (0.26 mL, 1.50 mmol) and this reaction mixture was stirred at room temperature for 10 minutes. Following the procedure described for Example 58, 1e (331 mg, 0.75 mmol) was added dropwise in anhydrous dichloromethane (10 mL). After stirring for 12 hours at room temperature, the reaction mixture was transferred to a separatory funnel and washed with water (20 mL, 10 mL of brine was added to support the separation). The aqueous phase was extracted with dichloromethane (20 mL). Combined organic extracts were washed with brine (20 mL) and dried over magnesium sulfate, filtered and concentrated under reduced pressure. The residue was purified by silica gel chromatography (gradient from 0-40% ethyl acetate+methanol (4/1) in iso-hexanes) to afford 69a (391 mg, 97%) as a white solid after evaporation. LCMS (m/z) 798.1 [M+H]' Tr=2.82 min (Gemini 5u C18 110 Å, 50×4.60 mm 5 micron column, 3.5 min, 2 ml/min, 5-100% acetonitrile/water, 0.1% acetic acid modifier gradient).

Compound 69

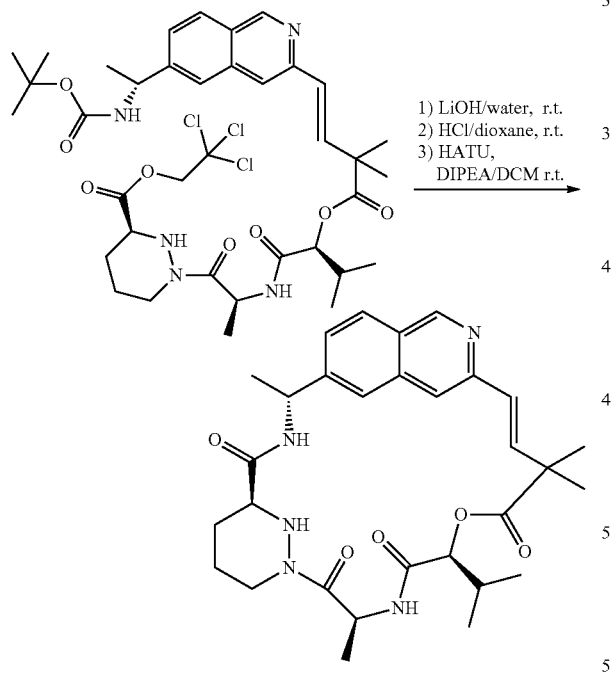

To 69a (390 mg, 0.48 mmol) in tetrahydrofuran (20 mL) was added a solution of lithium hydroxide (13 mg, 0.53 mmol) in water (10 mL). After stirring at room temperature for 2 hour, 1M hydrochloric acid was added (0.55 mL of 1M solution in water, 0.55 mmol) and the reaction mixture was concentrated under reduced pressure and the residue partitioned between dichloromethane (50 mL) and water (50 mL). The organic layer was collected, concentrated under reduced pressure and dried under high vacuum for one day. The residue was treated with 4M hydrogen chloride in 1,4-dioxane (10 mL, 40 mmol) at room temperature under argon for 4 hours. Reaction mixture was concentrated under reduced pressure. This residue was dissolved in N,N-dimethylformamide (5 mL) and the obtained solution was added into an argon purged flask containing 2-(1H-7-azabenzotriazol-1-yl)-11,1,3,3-tetramethyl uronium hexafluorophosphate methanaminium (276 mg, 0.73 mmol), N,N-diisopropylethylamine (312 mg, 2.42 mmol) and dichloromethane (200 mL). The reaction mixture was re-purged with argon and stirred at room temperature for 2 hours. The obtained reaction mixture was washed with water (100 ml) and brine (100 mL), dried over magnesium sulfate, filtered and concentrated under reduced pressure. The residue was purified by silica gel chromatography (gradient from 0-40% ethyl acetate+methanol (4/1) in iso-hexanes) to afford 69 (4 mg, 3%) as a white solid after evaporation. $^1$H NMR (400 MHz, CD$_3$CN): δ 9.12 (s, 1H), 7.93 (d, J=6.4 Hz, 1H), 7.60, (s, 1H), 7.43 (s, 1H), 7.27 (m, 1H), 7.03 (d, J=12 Hz, 1H), 6.83 (d, J=12, 1H), 5.65 (d, J=3 Hz, 1H), 4.96 (m, 2H), 4.30 (d, J=9.3 Hz, 1H), 3.21 (m, 1H), 2.91 (bm, 1H), 2.32 (m, 1H), 1.94-1.75 (cm, 3H), 1.64 (s, 3H), 1.62-1.48 (m, 4H), 1.46-1.35 (m, 2H), 1.01 (d, J=6.7 Hz, 3H), 0.91 (d, J=6.7 Hz, 3H). LCMS (m/z) 550.4 [M+H]' Tr=1.81 min.

Example 70

Compound 70

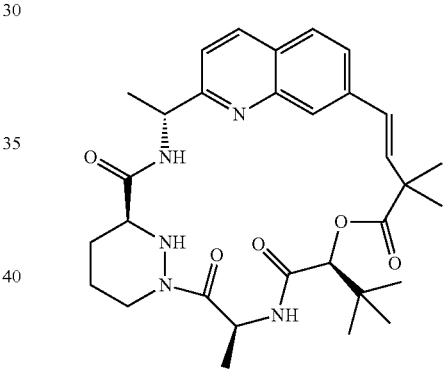

Compound 70a

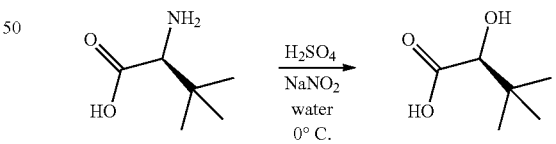

To a solution of 3,3-dimethyl butanoic acid (1 g, 7.5 mmol) in 1M sulfuric acid (15 ml, 1M aqueous solution), cooled to 0° C., was added a solution of sodium nitrite (1.0 g, 15 mmol) in water (8 ml). The temperature was maintained below 50° C. during the addition, and the mixture was stirred at such overnight. The solution was then saturated with ammonium sulfate, extracted with diethyl ether (5×25 ml), dried over sodium sulfate and evaporated under reduced pressure giving the title compound (0.27 g, 67%) as a colorless oil that crystallized on standing. $^1$H NMR (400 MHz, CDC$_3$) 3.41 (s, 1H), 1.25 (s, 9H). LCMS (m/z) 133.2 [M+H], Tr=0.39 min (Gemini 5u C18 110 Å, 50×4.60 mm 5 micron column, 3.5 min, 2 ml/min, 5-100% acetonitrile/water, 0.1% acetic acid modifier gradient).

Compound 70b

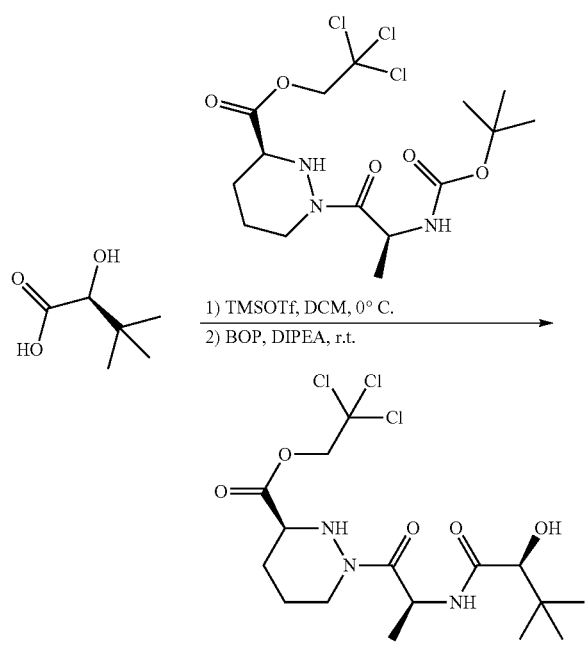

A solution of 1d (517 mg, 1.19 mmol) in dichloromethane (20 mL) was cooled in an ice water bath. Trimethylsilyl trifluoromethanesulfonate (398 mg, 1.79 mmol) was added dropwise at 0° C. under argon, and the resulting solution was stirred at room temperature for 30 minutes. The reaction mixture was evaporated to dryness and the resulting crude residue (LCMS (m/z) 332.2/334.3 [M+H]' Tr=2.06 min) was dissolved in anhydrous dichloromethane (20 mL) and cooled to 0° C. To this was added 70a (192 mg, 1.43 mmol), N,N-diisopropylethylamine (0.51 mL, 2.98 mmol), and (benzotriazol-1-yloxy)tris(dimethylamino)phosphonium hexafluorophosphate (633 mg, 1.43 mmol). The reaction was allowed to warm to room temperature and stirred for 8 hours. The mixture was evaporated to dryness and the residue was dissolved in ethyl acetate (100 mL) and washed with 10% citric acid (100 mL), saturated $NaHCO_3$ (100 mL), and brine (100 mL). The organic layer was dried over $MgSO_4$, one volume equivalent of hexane was added and this solution was filtered through a 5 cm layer of silica gel, silica gel layer was washed with 50 mL of ethyl acetate/hexane mixture (1/1). The desired product was washed out with ethyl acetate (100 mL), concentrated under reduced pressure and co-distilled with dichloromethane. The 70b compound (537 mg, quantitative yield) was isolated after drying under high vacuum for one day. $^1$H NMR (400 MHz, $CD_3OD$): δ 5.52 (q, J=6.9 Hz, 1H), 5.11 (d, J=12.1 Hz, 1H), 4.91 (d, J=12.2 Hz, 1H), 3.94 (d, J=2.6 Hz, 1H), 3.84 (dd, J=7.1, 4.7 Hz, 1H), 3.84 (m, 1H), 3.80-3.58 (m, 2H), 3.41 (s, 3H), 2.33-2.13 (m, 1H), 2.09-1.92 (m, 2H), 1.86-1.75 (m, 1H), 1.42 (d, J=6.9 Hz, 3H), 1.32 (s, 9H). LCMS (m/z) 446.0[M+H]' Tr=2.11 min.

Compound 70c

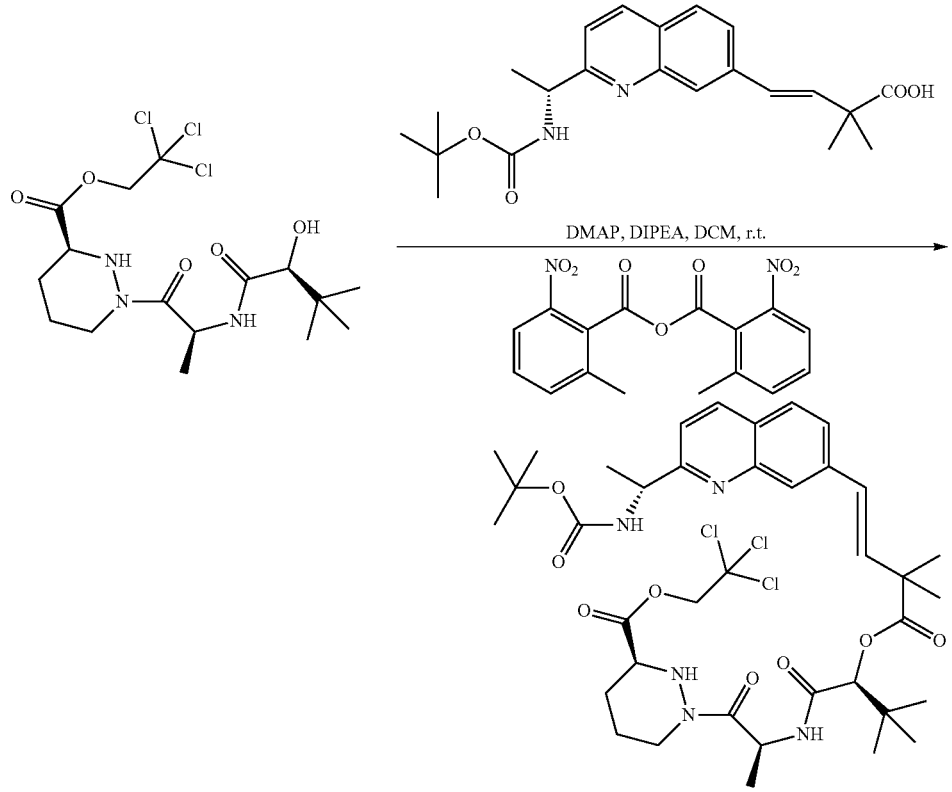

Into an oven-dried, argon purged flask were placed 2-methyl-6-nitrobenzoic anhydride (172 mg, 0.5 mmol), 4-dimethylaminopyridine (64 mg, 0.50 mmol), the indicated N-Boc-quinolinyl carboxylate (96 mg, 0.25 mmol), and anhydrous dichloromethane (10 mL). Into the resulting solution was added N,N-diisopropylethylamine (0.13 mL, 0.75 mmol) and this reaction mixture was stirred at room temperature for 10 minutes. 70b (168 mg, 0.38 mmol) was added dropwise via syringe as a solution in anhydrous dichloromethane (10 mL). After stirring for 12 hours at room temperature, the reaction mixture was transferred to a separatory funnel and washed with water (20 mL, 10 mL of brine was added to support the separation). The aqueous phase was extracted with dichloromethane (20 mL). Combined organic extracts were washed with brine (20 mL) and dried over magnesium sulfate, filtered and concentrated under reduced pressure. The residue was purified by silica gel chromatography (gradient from 0-40% ethyl acetate+methanol (4/1) in iso-hexanes) to afford 70c (149 mg, 73%) as a white solid after evaporation. $^1$H NMR (400 MHz, CD$_3$OD): δ 8.35 (d, J=8.6 Hz, 1H), 8.07-8.01 (m, 1H), 7.93 (d, J=8.5 Hz, 1H), 7.88 (d, J=8.4 Hz, 1H), 7.58 (d, J=8.5 Hz, 1H), 6.98-6.77 (m, 2H), 5.48 (q, J=6.5, 6.1 Hz, 1H), 5.20 (d, J=4.0 Hz, 1H), 5.06 (d, J=12.1 Hz, 1H), 4.88 (d, J=12.1 Hz, 1H), 4.25-4.15 (m, 1H), 3.99-3.85 (m, 2H), 3.80-3.55 (m, 2H), 3.46 (s, 3H), 2.20-2.09 (m, 1H), 2.07-1.94 (m, 1H), 1.92-1.80 (m, 1H), 1.80-1.71 (m, 1H), 1.68-1.64 (m, 6H), 1.59 (d, J=7.1 Hz, 3H), 1.54 (s, 9H), 1.37 (d, J=7.0 Hz, 3H), 1.29 (d, J=6.4 Hz, 3H). LCMS (m/z) 812.3 [M+H]' Tr=2.64 min (Gemini 5u C18 110 Å, 50×4.60 mm 5 micron column, 3.5 min, 2 mL/min, 5-100% acetonitrile/water, 0.1% acetic acid modifier gradient).

Compound 70

To 70c (139 mg, 0.17 mmol) in tetrahydrofuran (10 mL) was added a solution of lithium hydroxide (4.5 mg, 0.19 mmol) in water (5 mL). After stirring at room temperature for 2 h, 1M hydrochloric acid was added (0.20 mL of 1M solution in water, 0.20 mmol) and the reaction mixture was concentrated under reduced pressure and the residue partitioned between dichloromethane (50 mL) and water (50 mL). The organic layer was collected, concentrated under reduced pressure and dried under high vacuum for one day. The residue was treated with 4M hydrogen chloride in 1,4-dioxane (5 mL, 20 mmol) at room temperature under argon for 4 hours. Reaction mixture was concentrated under reduced pressure. This residue was dissolved in N,N-dimethylformamide (5 mL) and the obtained solution was added into an argon purged flask containing 2-(1H-7-azabenzotriazol-1-yl)-11,1,3,3-tetramethyl uronium hexafluorophosphate methanaminium (98 mg, 0.26 mmol), N,N-diisopropylethylamine (110 mg, 0.86 mmol) and dichloromethane (100 mL). The reaction mixture was re-purged with argon and stirred at room temperature for 2 hours. The obtained reaction mixture was washed with water (50 ml) and brine (50 mL), dried over magnesium sulfate, filtered and concentrated under reduced pressure. The residue was purified by HPLC to afford compound 70 (20 mg, 21%) as a white solid after lyophilization. $^1$H NMR (400 MHz, CDCl$_3$): δ 9.05 (s, 1H), 8.05 (bs, 1H), 7.69 (s, 1H), 7.24 (s, 1H), 7.61 (dd, J=8.4, 1.6 Hz, 1H), 7.43 (d, J=8.5 Hz, 1H), 6.62 (d, J=12.3 Hz, 1H), 6.33 (d, J=12.3 Hz, 1H), 6.14 (m, 1H), 5.86 (bs, 1H), 5.08 (m, 1H), 4.53 (s, 1H), 4.12 (d, J=6.1 Hz, 1H), 3.57-3.49 (m, 2H), 2.02-1.92 (bm, 2H), 1.68 (m, 1H), 1.72-1.45 (cm, 8H), 1.07 (s, 9H), 0.91 (m, 3H). LCMS (m/z) 564.3 [M+H]' Tr=2.42 min.

Example 71

Compound 71

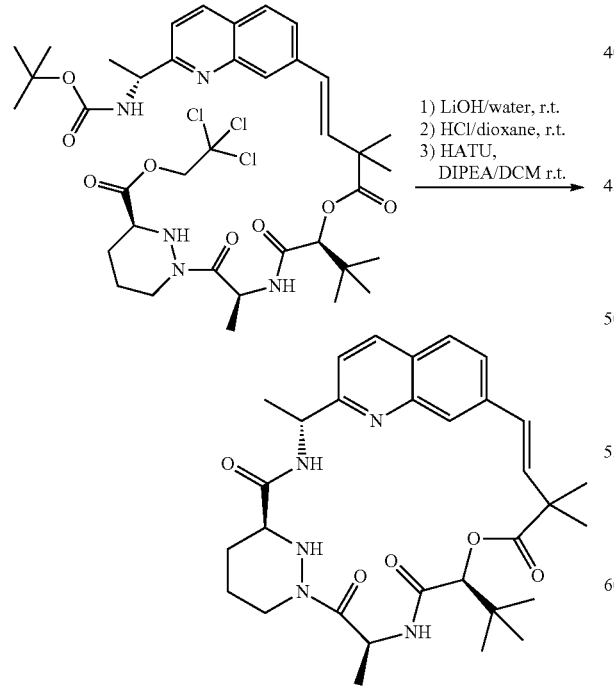
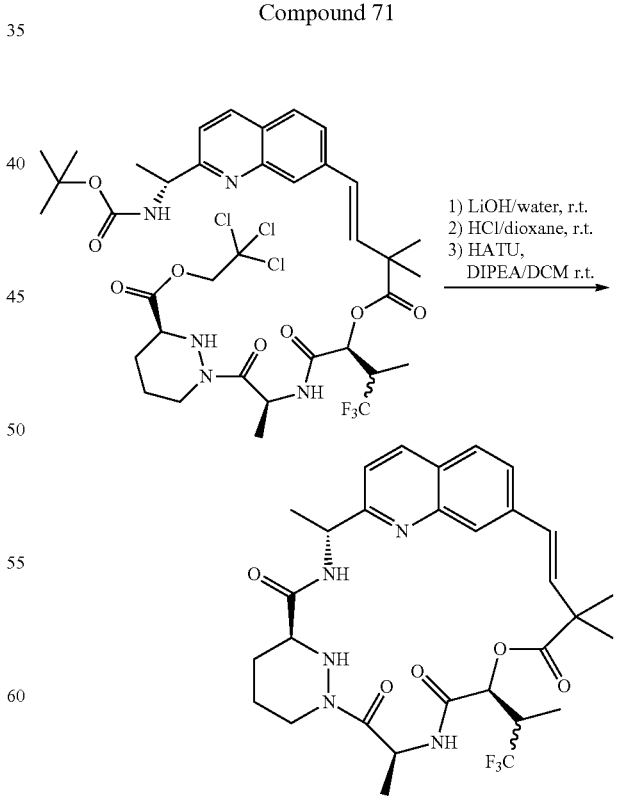

Following the synthetic sequence described in Example 70, the indicated N-Boc-protected quinolnyl seco-acid was prepared in 5% yield beginning from 1 gram commercially available 4,4,4-trifluoro-DL-valine obtained from Apollo Scientific, Inc.

To this compound (139 mg, 0.17 mmol) in tetrahydrofuran (10 mL) was added a solution of lithium hydroxide (4.5 mg, 0.19 mmol) in water (5 mL). After stirring at room temperature for 2 hour, 1M hydrochloric acid was added (0.20 mL of 1M solution in water, 0.20 mmol) and the reaction mixture was concentrated under reduced pressure and the residue partitioned between dichloromethane (50 mL) and water (50 mL). The organic layer was collected, concentrated under reduced pressure and dried under high vacuum for one day. The residue was treated with 4M hydrogen chloride in 1,4-dioxane (5 mL, 20 mmol) at room temperature under argon for 4 hours. Reaction mixture was concentrated under reduced pressure. This residue was dissolved in N,N-dimethylformamide (5 mL) and the obtained solution was added into an argon purged flask containing 2-(1H-7-azabenzotriazol-1-yl)-1,1,3,3-tetramethyl uronium hexafluorophosphate methanaminium (98 mg, 0.26 mmol), N,N-diisopropylethylamine (110 mg, 0.86 mmol) and dichloromethane (100 mL). The reaction mixture was re-purged with argon and stirred at room temperature for 2 hours. The obtained reaction mixture was washed with water (50 ml) and brine (50 mL), dried over magnesium sulfate, filtered and concentrated under reduced pressure. The residue was purified by HPLC on C18 column with acetonitrile/water eluent to afford 71 as the latest eluting of three isomers (7 mg, 8%) as a white solid after evaporation. $^1$H NMR (400 MHz, CD$_3$CN): δ 7.86 (s, 1H), 7.72 (s, 1H), 7.61 (d, J=5.8 Hz, 1H), 7.43 (d, J=5.8 Hz, 1H), 7.31 (m, 1H), 6.50 (d, J=12.2 Hz, 1H), 6.34 (d, J=12.2 Hz, 1H), 5.60 (m, 2H), 5.08 (m, 1H), 4.38 (m, 1H), 4.18 (d, J=9.1 Hz, 1H), 3.52 (m, 1H), 2.91 (m, 1H), 2.59 (m, 1H), 1.94-1.48 (cm, 10H), 1.42 (s, 3H), 1.38 (cm, 5H). LCMS (m/z) 604.3 [M+H]' Tr=2.42 min.

Example 72

Compound 72

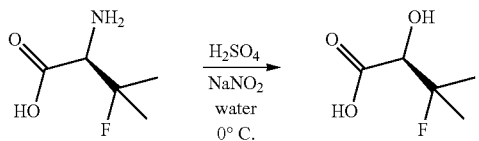

To a solution of 2-amino-3-fluoro-3-methyl butanoic acid obtained from Sigma-Aldrich Inc. (1 g, 7.5 mmol) in 1M sulfuric acid (15 ml, 1M aqueous solution), cooled to 0° C., was added a solution of sodium nitrite (1.0 g, 15 mmol) in water (8 ml). The temperature was maintained below 50° C. during the addition, and the mixture was stirred at such overnight. The solution was then saturated with ammonium sulfate, extracted with diethyl ether (5×25 ml), dried over sodium sulfate and evaporated under reduced pressure giving the title compound (0.4 g, 37%) as a colorless oil that crystallized on standing. $^1$H NMR (400 MHz, CDCl$_3$): δ 4.34 (d, 1H), 1.35 (d, 6H). LCMS (m/z) 137.4 [M+H], Tr=0.79 min.

Compound 72b

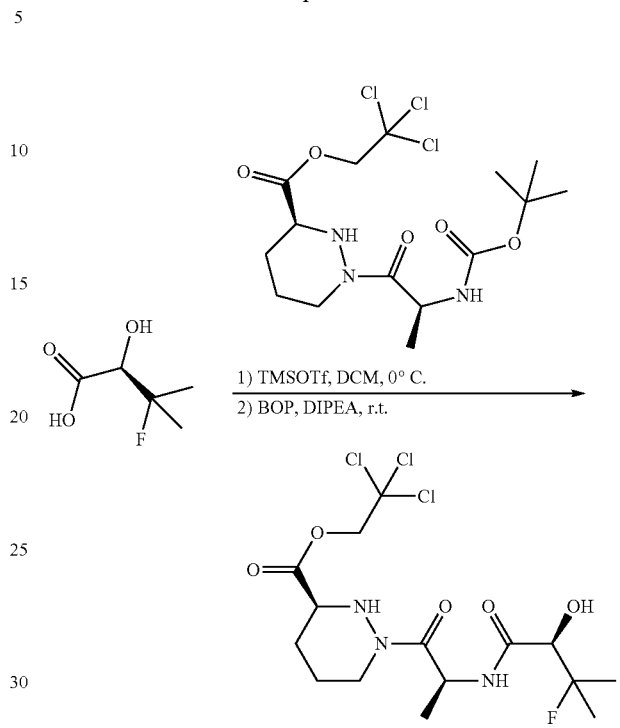

A solution of 1d (517 mg, 1.19 mmol) in dichloromethane (20 mL) was cooled in an ice water bath. Trimethylsilyl trifluoromethanesulfonate (398 mg, 1.79 mmol) was added dropwise at 0° C. under argon, and the resulting solution was stirred at room temperature for 30 minutes. The reaction mixture was evaporated to dryness and the resulting crude residue (LCMS (m/z) 332.2/334.3 [M+H]' Tr=2.06 min) was dissolved in anhydrous dichloromethane (20 mL) and cooled to 0° C. To this was added 72a (192 mg, 1.43 mmol), N,N-diisopropylethylamine (0.51 mL, 2.98 mmol), and (benzotriazol-1-yloxy)tris(dimethylamino)phosphonium hexafluorophosphate (633 mg, 1.43 mmol). The reaction was allowed to warm to room temperature and stirred for 8 hours. The mixture was evaporated to dryness and the residue was dissolved in ethyl acetate (100 mL) and washed with 10% citric acid (100 mL), saturated NaHCO$_3$ (100 mL), and brine (100 mL). The organic layer was dried over MgSO$_4$, one volume equivalent of hexane was added and this solution was filtered through a 5 cm layer of silica gel, silica gel layer was washed with 50 mL of ethyl acetate/hexane mixture (1/1). The desired product was washed out with ethyl acetate (100 mL), concentrated under reduced pressure and co-distilled with dichloromethane. 72b (400 mg, 80%) was isolated after drying under high vacuum for one day. $^1$H NMR (400 MHz, CD$_3$OD): δ 5.53 (q, J=6.9 Hz, 1H), 5.10 (d, J=12.1 Hz, 1H), 4.92 (d, J=12.2 Hz, 1H), 3.96 (d, J=2.6 Hz, 1H), 3.94 (dd, J=7.1, 4.7 Hz, 1H), 3.86 (qd, J=6.4, 2.5 Hz, 1H), 3.81-3.60 (m, 2H), 3.42 (s, 3H), 2.34-2.14 (m, 1H), 2.09-1.90 (m, 2H), 1.87-1.76 (m, 1H), 1.41 (d, J=6.9 Hz, 3H), 1.32 (d, J=6.4 Hz, 3H). LCMS (m/z) 450.1 [M+H]' Tr=2.11 min.

Compound 72c

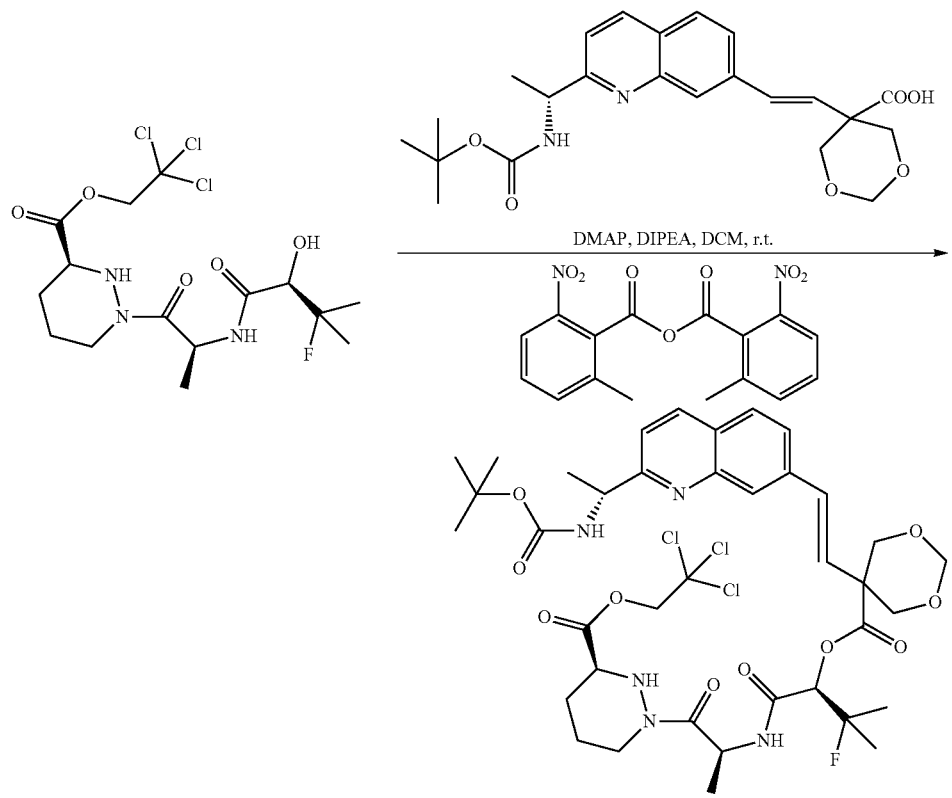

Following the procedure described in Example 70, into an oven-dried, argon purged flask were placed 2-methyl-6-nitrobenzoic anhydride (172 mg, 0.5 mmol), 4-dimethylaminopyridine (64 mg, 0.50 mmol), the N-Boc protected quinoline 1,3-dioxane carboxylic acid 63c (96 mg, 0.25 mmol), and anhydrous dichloromethane (10 mL). Into the resulting solution was added N,N-diisopropylethylamine (0.13 mL, 0.75 mmol) and this reaction mixture was stirred at room temperature for 10 minutes. Compound 72b (168 mg, 0.38 mmol) was added via syringe as a solution in anhydrous dichloromethane (10 mL). After stirring for 2 hours at room temperature, the reaction mixture was transferred to a separatory funnel and washed with water (20 mL, 10 mL of brine was added to support the separation). The aqueous phase was extracted with dichloromethane (20 mL). Combined organic extracts were washed with brine (20 mL) and dried over magnesium sulfate, filtered and concentrated under reduced pressure. The residue was purified by silica gel chromatography (gradient from 0-40% ethyl acetate+methanol (4/1) in iso-hexanes) to afford the 72c (149 mg, 73%) as a white solid after evaporation. $^1$H NMR (400 MHz, CD$_3$OD): δ 8.35 (d, J=8.6 Hz, 1H), 8.07-8.01 (m, 1H), 7.93 (d, J=8.5 Hz, 1H), 7.88 (d, J=8.4 Hz, 1H), 7.58 (d, J=8.5 Hz, 1H), 6.98-6.77 (m, 2H), 5.48 (q, J=6.5, 6.1 Hz, 1H), 5.20 (d, J=4.0 Hz, 1H), 5.06 (d, J=12.1 Hz, 1H), 4.88 (d, J=12.1 Hz, 1H), 4.25-4.15 (m, 1H), 3.99-3.85 (m, 2H), 3.80-3.55 (m, 2H), 3.46 (s, 3H), 2.20-2.09 (m, 1H), 2.07-1.94 (m, 1H), 1.92-1.80 (m, 1H), 1.80-1.71 (m, 1H), 1.68-1.64 (m, 6H), 1.59 (d, J=7.1 Hz, 3H), 1.54 (s, 9H), 1.37 (d, J=7.0 Hz, 3H), 1.29 (d, J=6.4 Hz, 3H). LCMS (m/z) 860.1/862.5 [M+H].' Tr=2.64 min.

Compound 72

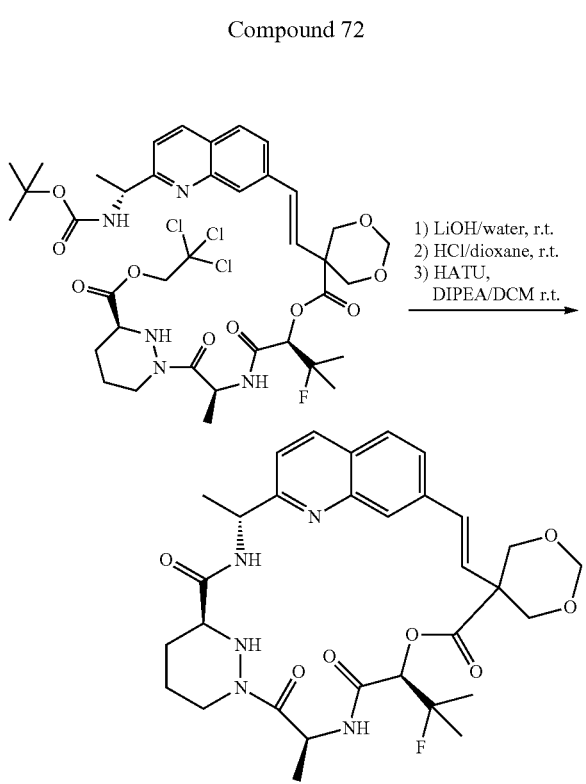

To 72c (139 mg, 0.17 mmol) in tetrahydrofuran (10 mL) was added a solution of lithium hydroxide (4.5 mg, 0.19 mmol) in water (5 mL). After stirring at room temperature for 2 hour, 1M hydrochloric acid was added (0.20 mL of 1M solution in water, 0.20 mmol) and the reaction mixture was concentrated under reduced pressure and the residue partitioned between dichloromethane (50 mL) and water (50 mL). The organic layer was collected, concentrated under reduced pressure and dried under high vacuum for one day. The residue was treated with 4M hydrogen chloride in 1,4-dioxane (5 mL, 20 mmol) at room temperature under argon for 4 hours. Reaction mixture was concentrated under reduced pressure. This residue was dissolved in N,N-dimethylformamide (5 mL) and the obtained solution was added into an argon purged flask containing 2-(1H-7-azabenzotriazol-1-yl)-1,1,3,3-tetramethyl uronium hexafluorophosphate methanaminium (98 mg, 0.26 mmol), N,N-diisopropylethylamine (110 mg, 0.86 mmol) and dichloromethane (100 mL). The reaction mixture was re-purged with argon and stirred at room temperature for 2 hours. The obtained reaction mixture was washed with water (50 ml) and brine (50 mL), dried over magnesium sulfate, filtered and concentrated under reduced pressure. The residue was purified by silica gel chromatography (gradient from 0-60% ethyl acetate+methanol (4/1) in iso-hexanes) to afford the title compound (32 mg, 33%) as a white solid after evaporation. $^1$H NMR (400 MHz, CD$_3$OD): δ 8.26 (s, 1H), 7.83 (d, J=8.2 Hz, 1H), 7.83 (d, J=8.2 Hz, 1H), 7.51 (m, 2H), 6.71 (d, J=12.3 Hz, 1H), 6.19 (d, J=12.3 Hz, 1H), 5.86 (q, J=7.2 Hz, 1H), 5.48 (d, J=8.2 Hz, 1H), 5.08 (m, 2H), 4.41 (m, 1H), 3.77-3.62 (m, 1H), 3.59 (m, 1H), 2.68 (m, 1H), 2.31-2.24 (m, 1H), 1.99-1.91 (m, 1H), 1.72-1.54 (cm, 8H), 1.42 (s, 3H), LCMS (m/z) 612.1 [M+H]' Tr=2.22 min.

Example 73

Compound 73

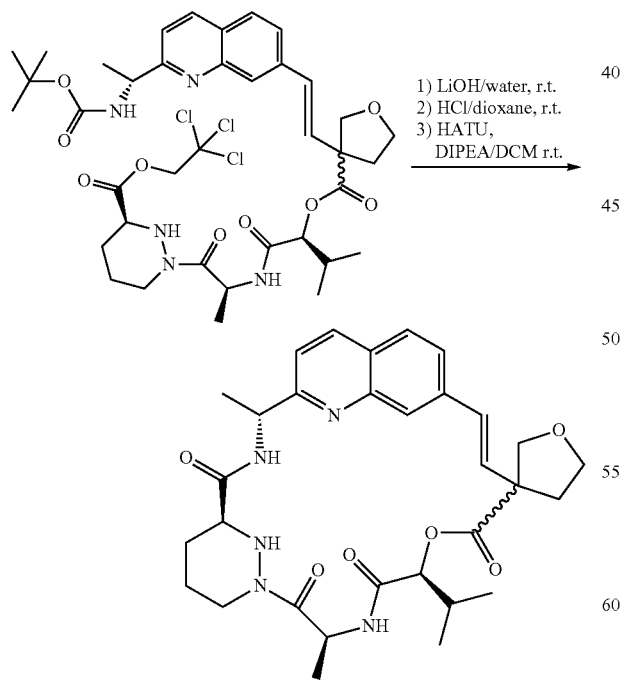

Following the synthetic sequence described in Example 43, instead using 1.5 g methyl-oxolane-3-carboxylate (C.A.S. #53662-85-4) supplied by Enamine, Ltd., the indicated bis-protected seco-acid above was prepared in 110 mg quantity (1.2% yield). This intermediate was then carried through the standard multistep synthetic sequence reported in Example 70 to afford Compound 73, where 4 mg was obtained after final HPLC purification as the a diasteromer mixture. $^1$H NMR (400 MHz, CD$_3$CN): δ 8.81 (m, 1H), 8.15 (d, J=6.1 Hz, 1H), 7.73 (d, J=6.2 Hz, 1H), 7.60 (m, 1H), 7.35 (m, 1H), 7.06 (m, 1H), 6.48-6.33 (m, 2H), 5.62 (m, 1H), 5.08 (m, 1H), 4.95 (m, 1H), 4.30 (m, 2H), 4.08 (m, 2H), 3.90-3.69 (cm, 4H), 3.56 (m, 2H), 3.39 (m, 2H), 2.68 (cm, 3H), 2.31-2.24 (m, 2H), 1.55-1.35 (cm, 7H), 0.92-0.82 (cm, 7H). LCMS (m/z) 578.2 [M+H], Tr=2.11 min.

Examples 74, 75, 76, and 77

Compounds 74, 75, 76, and 77

Compounds 74 and 75

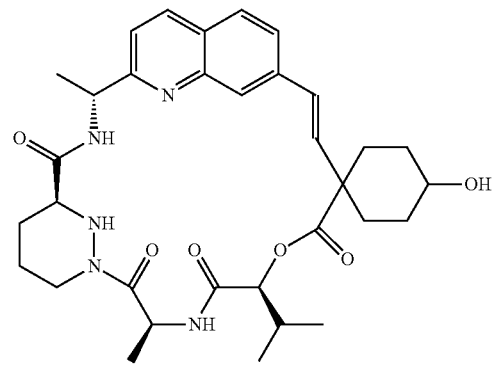

Compounds 76 and 77

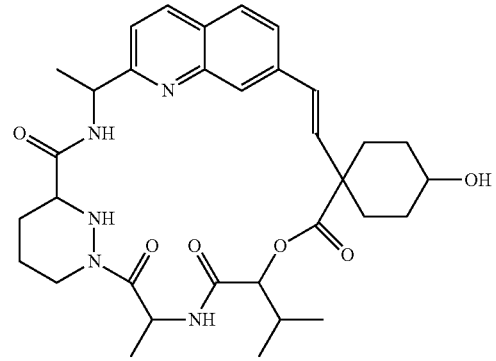

Intermediate 74a

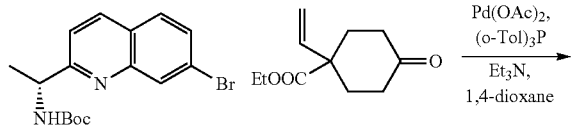

-continued

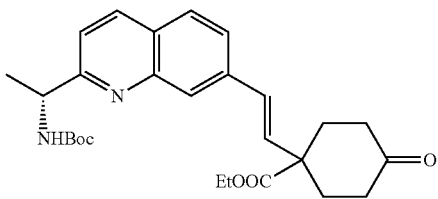

To a mixture of the bromide 39a (556 mg, 1.583 mmol), ethyl-4-oxo-1-vinylcyclohexanecarboxylate (obtained from Small Molecules, Inc.), (559 mg, 2.849 mmol), Pd(OAc)$_2$ (70 mg, 0.312 mmol), and (o-Tol)$_3$P (100 mg, 0.329 mmol) in 1,4-dioxane (5 mL) was added NEt$_3$ (0.72 mL, 5.166 mmol) and the resulting mixture was heated at 100° C. for 30 min in a microwave reactor. The mixture was concentrated and treated with water and ethyl acetate (~50 mL each). After the mixture was filtered through celite pad, the two fractions in the filtrate were separated. After the aqueous fraction was extracted with ethyl acetate (×1), two organic fractions were washed with water (×1), combined, dried (MgSO$_4$), and concentrated. The residue was purified by CombiFlash using hexanes-ethyl acetate as eluents to obtain 479 mg (65%) of the product 74a. $^1$H NMR (400 MHz, Chloroform-d): δ 8.07 (d, J=8.3 Hz, 1H), 8.01 (s, 1H), 7.75 (d, J=8.5 Hz, 1H), 7.58 (d, J=8.3 Hz, 1H), 7.31 (d, J=8.5 Hz, 1H), 6.74 (d, J=16.1 Hz, 1H), 6.47 (d, J=16.3 Hz, 1H), 6.16 (s, 1H), 4.27 (q, J=7.1 Hz, 2H), 2.76-2.56 (m, 2H), 2.57-2.38 (m, 4H), 2.18-2.00 (m, 2H), 1.47 (s, 9H), 1.32 (t, J=7.1 Hz, 3H). LCMS (m/z) 467.0 [M+H], Tr=2.33 min.

Compound 74b

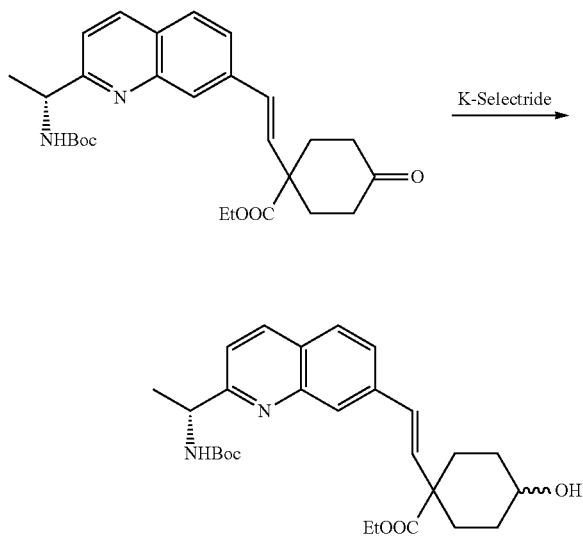

A solution of 74a (237 mg, 0.508 mmol) in THF (5 mL) was stirred at −60° C. bath as 1.0 M K-selectride in THF (0.61 mL) was added. After the reaction mixture was slowly warmed to 0° C. over 30 min, the mixture was diluted with ethyl acetate and washed with water (×2). After the aqueous fractions were extracted with ethyl acetate (×1), two organic fractions were combined, dried (MgSO$_4$), and concentrated. The residue was purified by CombiFlash using hexanes-ethyl acetate as eluents to obtain 192 mg (81%) 74b as a ~4:1 mixture. LCMS (m/z) 469.0 [M+H], Tr=2.20 min.

Compound 74c

A mixture of 74b (192 mg, 0.410 mmol) and LiOH (87.7 mg, 2.090 mmol) in THF (2 mL), MeOH (2 mL), and water (2 mL) was stirred at 50° C. bath for 3 h. The mixture was concentrated to ~1/3 volume, diluted with water, neutralized with 1 N HCl (2.2 mL), and extracted with ethyl acetate (×2). The extracts were washed with water (×1), combined, dried (MgSO$_4$), and concentrated. A solution of the residue, imidazole (115 mg, 1.689 mmol), and TBSCI (79 mg, 0.524 mmol) in DMF was stirred at 35° C. bath for 1.5 h before addition of additional imidazole (102 mg, 1.498 mmol), and TBSCI (77 mg, 0.511 mmol) were added. The resulting mixture was stirred at 35° C. for 17 h, concentrated, and diluted with ethyl acetate before washing with 5% LiCl solution (×2). After the aqueous fractions were extracted with ethyl acetate (×1), two organic fractions were combined, dried (MgSO$_4$), and concentrated. The residue was dissolved in THF (2 mL), MeOH (2 mL), and water (2 mL), and stirred with K$_2$CO$_3$ (226 mg, 1.635 mmol) at rt for 30 min. The solution was concentrated to ~1/2 volume, diluted with water, and acidified with 1 N HCl (~3.5 mL) before extraction with ethyl acetate (×2). The extracts were washed with water (×1), combined, dried (MgSO$_4$), and concentrated. The residue was purified by CombiFlash using hexanes-ethyl acetate as eluents to obtain 193 mg (85%) of the product 74c as an apparent ~4:1 isomer mixture. LCMS (m/z) 555.1 [M+H], Tr=2.60 min.

Compound 74d

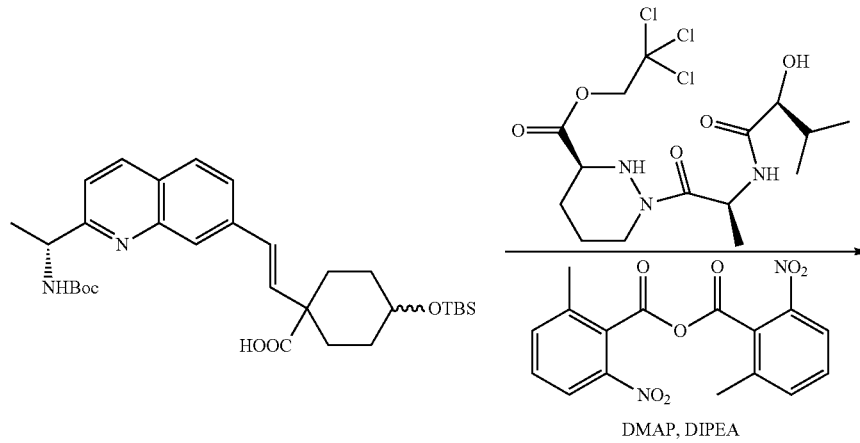

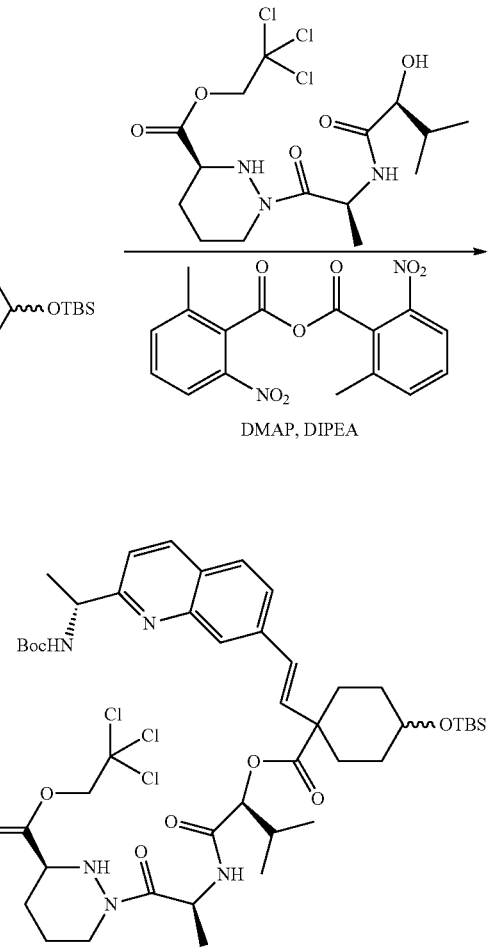

A mixture of the acid 74c (131 mg, 0.236 mmol), the compound 1e (125 mg, 0.289 mmol), Shiina reagent (98 mg, 0.285 mmol), and DMAP (72 mg, 0.589 mmol) was dissolved in CH$_2$Cl$_2$ (3 mL) at rt. After 3 min, DIPEA (0.1 mL, 0.574 mmol) was added and the resulting mixture was stirred at rt for 16.5 h. The mixture was diluted with ethyl acetate, and washed with water (×2). After the aqueous fractions were extracted with ethyl acetate (×1), two organic fractions were combined, dried (MgSO$_4$), and concentrated. The residue was purified by CombiFlash using hexanes-ethyl acetate as eluents to obtain 90 mg (39%) of 74d as a mixture. LCMS (m/z) 968.2 [M+H], Tr=3.04 min.

Compounds 74, 75, 76, and 77

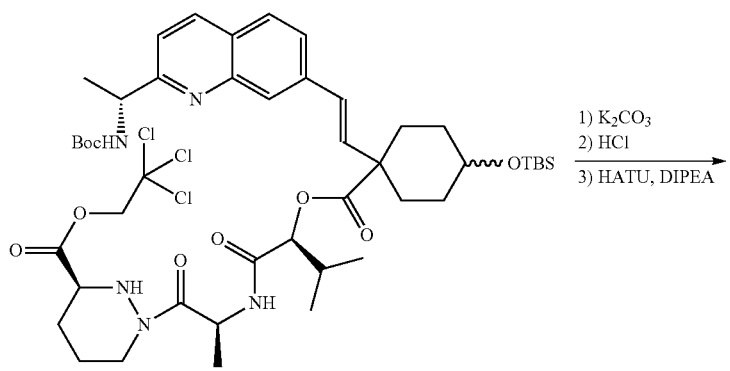

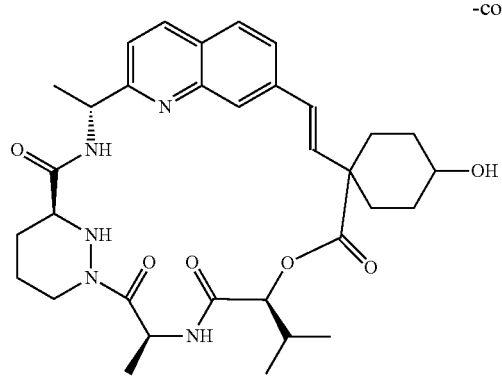

Compounds 74 and 75

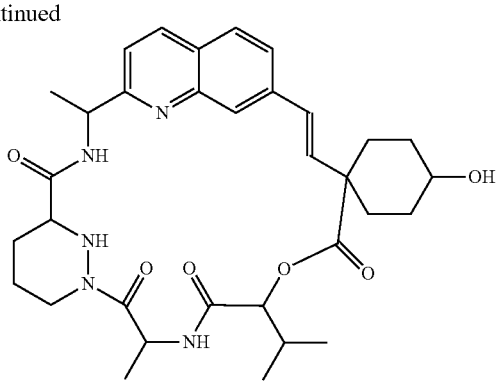

Compounds 76 and 77

A mixture of 74d (90 mg, 0.093 mmol) in THF (1 mL), MeOH (1 mL), and water (1 mL) was added K$_2$CO$_3$ (89 mg, 0.644 mmol) at 0° C. The mixture was stirred at 0° C. for 2.5 h, 64 h at freezer, at rt for 3 h, and at 30° C. for 1.5 h. The mixture was diluted with saturated NaCl solution and extracted with ethyl acetate (×2). After the aqueous fractions were extracted with ethyl acetate (×1), two organic fractions were combined, dried (MgSO$_4$), concentrated, and dried in vacuum. The residue was dissolved in 4 N HCl in dioxane (3 mL) and stirred at rt for 45 min before concentration and drying in vacuum for 2 h to obtain the crude hydroxy amino acid. A suspension of HATU (177 mg, 0.466 mmol) in CH$_2$Cl$_2$ (100 mL) was stirred at rt as a solution of the crude hydroxylamino acid and DIPEA (0.13 mL, 0.746 mmol) in DMF (7.5 mL) was added over 5 min. After 1.5 h at rt, the mixture was concentrated and the residue was diluted with ethyl acetate before washing with 5% LiCl solution (×2), 0.1 N HCl (×1), and water (×1). After the aqueous fractions were extracted with ethyl acetate (×1), two organic fractions were combined, dried (MgSO$_4$), and concentrated. The residue was separated by preparative HPLC using a 21.2×250 mm 10 micron C18 Phenomenex Gemini semi-preparative column and acetonitrile/water (containing 0.1% TFA modifier) as mobile phase at a flow rate of 20 mL/min with a 50 minute gradient consisting of 0 min-5 min: 20% acetonitrile; 5 min-48 min: 20% acetonitrile to 80% acetonitrile; 48 min-50 min: 80% acetonitrile to obtain four separate product fractions. Each fraction was then separately concentrated to remove MeCN, neutralized with NaHCO$_3$ solution, diluted with water, and extracted with ethyl acetate (×2). The separated extracts were concentrated to obtain 4.6 mg (8%) of 74, 1.1 mg (2%) of 75, 10.5 mg (19%) of 76, and 2.3 mg (4%) of 77.

Compounds 74-77 represent stereoisomers of the compound:

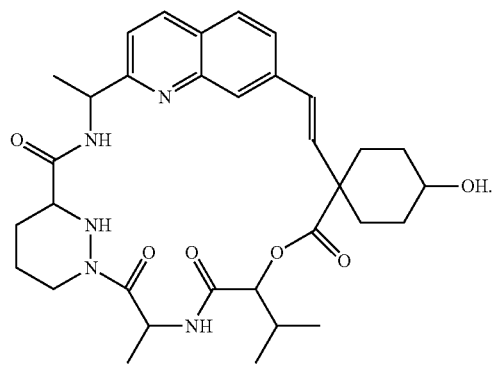 [SMILES: CC1NC(=O)C(C(C)C)OC(=O)C2(/C=C/c3ccc4ccc(nc4c3)C(C)NC(=O)C3CCCN(N3)C1=O)CCC(O)CC2]

Contemplated stereoisomers include:

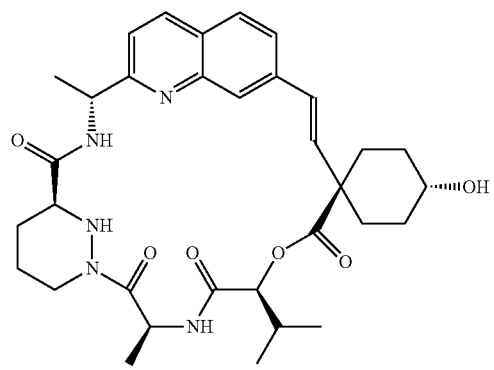

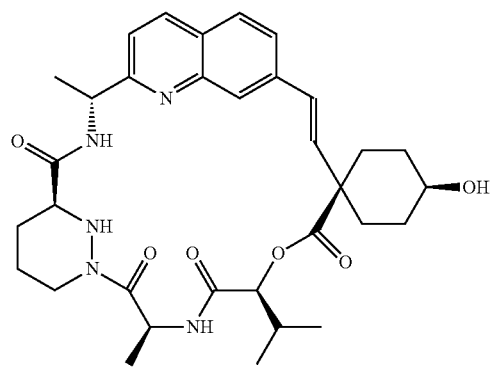

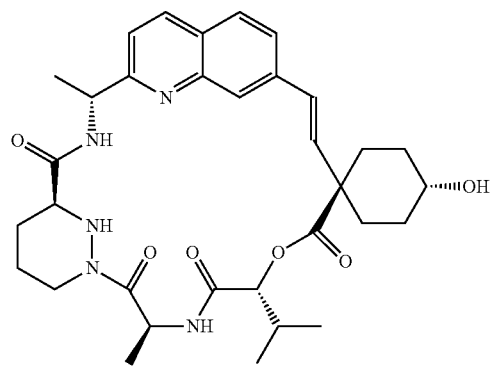

365

-continued

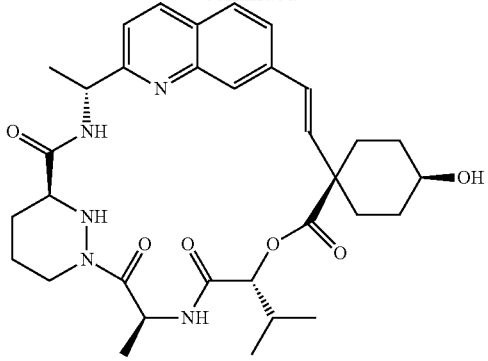

Compound 74: First eluting isomer. ¹H NMR (400 MHz, Methanol-d₄): δ 8.23 (d, J=8.5 Hz, 1H), 7.82 (d, J=8.4 Hz, 1H), 7.77 (d, J=1.7 Hz, 1H), 7.62 (dd, J=8.4, 1.7 Hz, 1H), 7.43 (d, J=8.5 Hz, 1H), 6.61 (d, J=16.4 Hz, 1H), 6.29 (d, J=16.4 Hz, 1H), 5.79 (q, J=7.2 Hz, 1H), 5.23 (d, J=8.6 Hz, 1H), 5.06 (q, J=6.6 Hz, 1H), 4.41 (dd, J=13.2, 4.3 Hz, 1H), 3.88 (s, 1H), 3.57 (dd, J=11.7, 2.8 Hz, 1H), 2.68 (td, J=13.0, 3.3 Hz, 1H), 2.25 (d, J=11.2 Hz, 1H), 2.21-2.06 (m, 3H), 2.00-1.88 (m, 3H), 1.84-1.63 (m, 5H), 1.60 (d, J=7.3 Hz, 3H), 1.57 (d, J=6.8 Hz, 3H), 1.61-1.47 (m, 1H), 1.28 (s, 1H), 1.05 (d, J=6.8 Hz, 3H), 1.00 (d, J=6.7 Hz, 3H). LCMS (m/z) 606.3 [M+H], Tr=2.03 min.

Compound 75: Second eluting isomer. ¹H NMR (400 MHz, Methanol-d₄): δ 8.23 (d, J=8.5 Hz, 1H), 7.81 (d, J=8.5 Hz, 1H), 7.76 (d, J=1.7 Hz, 1H), 7.60 (dd, J=8.4, 1.6 Hz, 1H), 7.42 (d, J=8.5 Hz, 1H), 6.53 (d, J=16.3 Hz, 1H), 6.25 (d, J=16.3 Hz, 1H), 5.80 (q, J=7.2 Hz, 1H), 5.28 (d, J=8.6 Hz, 1H), 5.06 (q, J=6.7 Hz, 1H), 4.41 (d, J=13.8 Hz, 1H), 3.60 (m, 2H), 2.76-2.62 (m, 1H), 2.57 (d, J=14.1 Hz, 1H), 2.33 (dd, J=13.0, 3.9 Hz, 1H), 2.29-2.10 (m, 2H), 1.94 (m, 3H), 1.78-1.38 (m, 3H), 1.61 (d, J=7.3 Hz, 3H), 1.57 (d, J=6.7 Hz, 3H), 1.28 (s, 4H), 1.07 (d, J=6.8 Hz, 3H), 1.04 d, J=6.8 Hz, 3H). LCMS (m/z) 606.3 [M+H], Tr=2.02 min.

Compound 76: Third eluting isomer. ¹H NMR (400 MHz, Methanol-d₄): δ 9.43 (d, J=6.2 Hz, 1H), 8.24 (d, J=8.5 Hz, 1H), 8.02-7.94 (m, 1H), 7.84 (d, J=8.4 Hz, 1H), 7.57 (dd, J=8.4, 1.6 Hz, 1H), 7.43 (d, J=8.5 Hz, 1H), 6.86 (d, J=16.3 Hz, 1H), 6.33 (d, J=16.3 Hz, 1H), 5.85 (q, J=7.2 Hz, 1H), 5.19 (d, J=9.0 Hz, 1H), 5.15 (m, 1H), 4.49-4.38 (m, 1H), 3.83 (s, 1H), 3.41 (dd, J=11.8, 2.8 Hz, 1H), 2.79 (td, J=12.8, 3.2 Hz, 1H), 2.39 (dd, J=13.2, 3.4 Hz, 1H), 2.21 (m, 1H), 2.18-2.06 (m, 3H), 2.06-1.91 (m, 2H), 1.76 (m, 2H), 1.68 (m, 2H), 1.44-1.61 (m, 1H), 1.56 (d, J=6.7 Hz, 3H), 1.28 (s, 1H), 1.22 (d, J=7.2 Hz, 3H), 1.04 (d, J=6.9 Hz, 3H), 1.02 (d, J=6.7 Hz, 3H). LCMS (m/z) 606.3 [M+H], Tr=2.10 min.

Compound 77: Fourth eluting isomer. ¹H NMR (400 MHz, Methanol-d₄): δ 9.45 (d, J=6.3 Hz, 1H), 8.25 (d, J=8.4 Hz, 1H), 8.00 (d, J=1.6 Hz, 1H), 7.84 (d, J=8.4 Hz, 1H), 7.55 (dd, J=8.4, 1.6 Hz, 1H), 7.44 (d, J=8.5 Hz, 1H), 6.78 (d, J=16.3 Hz, 1H), 6.36 (d, J=16.3 Hz, 1H), 5.88 (q, J=7.2 Hz, 1H), 5.45 (d, J=12.0 Hz, 1H), 5.24 (d, J=8.9 Hz, 1H), 5.17 (q, J=6.6 Hz, 1H), 4.51-4.39 (m, 1H), 3.71-3.54 (m, 1H), 3.51-3.38 (m, 1H), 2.85-2.72 (m, 1H), 2.63 (d, J=13.5 Hz, 1H), 2.43 (m, 2H), 2.24 (m, 1H), 1.98 (m, 3H), 1.77-1.59 (m, 2H), 1.57 (d, J=6.7 Hz, 3H), 1.54 (d, J=3.6 Hz, 1H), 1.41 (q, J=13.0 Hz, 1H), 1.35-1.26 (m, 2H), 1.26 (d, J=7.2 Hz, 3H), 1.07 (d, J=6.8 Hz, 3H), 1.06 (d, J=6.8 Hz, 3H). LCMS (m/z) 606.3 [M+H], Tr=2.11 min.

366

Examples 78 and Example 79

Compounds 78 and 79

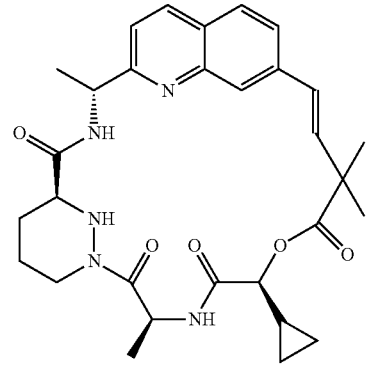 [SMILES: C[C@@H]1NC(=O)[C@H](C2CC2)OC(=O)C(C)(C)/C=C/c2ccc3ccc(nc3c2)[C@@H](C)NC(=O)[C@@H]2CCCN(N2)C1=O]

Compound 78a

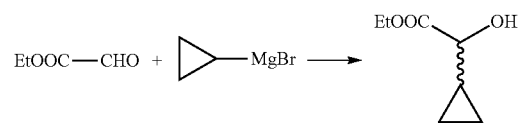

A solution of 50% ethyl glyoxalate in toluene (5.15 mL, 26 mmol) in THF (50 mL) was stirred at −20-−30° C. bath as 0.5 M cyclopropylmagnesium bromide in THF (50 mL) was added over 10 min. After 2 h at −30° C. bath, the reaction mixture was quenched with water (250 mL) and extracted with ethyl acetate (×3). The extracts were washed with water (×1), combined, dried (MgSO₄), and concentrated. The residue was purified by CombiFlash using hexanes-ethyl acetate as eluents to obtain 882 mg (17%) of 78a with 72% purity. ¹H NMR (400 MHz, Chloroform-d): δ 4.27 (q, J=7.2 Hz, 2H), 3.77 (d, J=6.6 Hz, 1H), 1.56 (s, 1H), 1.32 (t, J=7.1 Hz, 3H), 1.15-1.03 (m, 1H), 0.59-0.46 (m, 3H), 0.46-0.38 (m, 1H).

Compound 78b

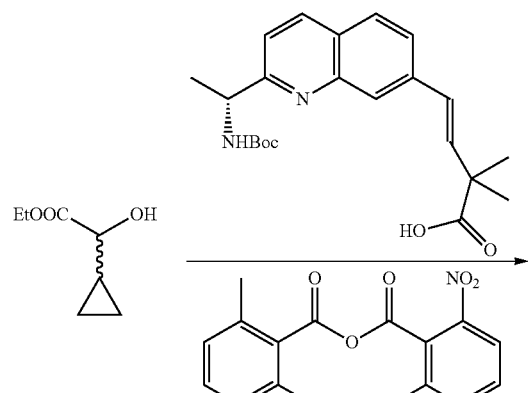

DMAP, DIEA

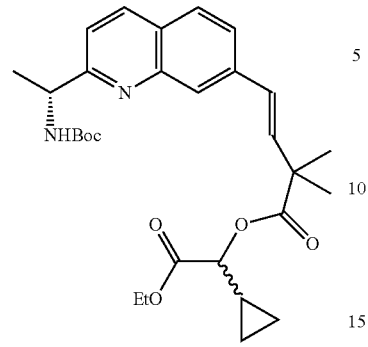

A solution of the indicated acid (100 mg, 0.260 mmol), the alcohol (75 mg, 0.375 mmol, 72% purity), and DMAP (79 mg, 0.647 mmol) in CH$_2$Cl$_2$ (5 mL) were added Shiina reagent (180 mg, 0.523 mmol) and DIEA (0.24 mL, 1.378 mmol) at rt. After 16.5 h at rt, the mixture was concentrated and the residue was dissolved in ethyl acetate before washing with dilute citric acid solution (×1) and NaHCO$_3$ solution (×1). After the aqueous fractions were extracted with ethyl acetate (×1), two organic fractions were combined, dried (MgSO$_4$), and concentrated. The residue was purified by CombiFlash using hexanes-ethyl acetate as eluents to obtain 76 mg (57%) of the product 78b as a diasteromer mixture. $^1$H NMR (400 MHz, Chloroform-d): δ 8.05 (d, J=8.4 Hz, 1H), 7.99 (s, 1H), 7.72 (d, J=8.4 Hz, 1H), 7.61 (dd, J=8.5, 1.7 Hz, 1H), 7.28 (d, J=8.6 Hz, 1H), 6.69 (d, J=16.3 Hz, 1H), 6.63 (d, J=16.2 Hz, 1H), 6.22 (s, 1H), 5.09-4.87 (m, 1H), 4.49 (d, J=7.9 Hz, 1H), 4.21 (p, J=7.0 Hz, 2H), 1.53 (d, J=7.3 Hz, 3H), 1.51 (s, 3H), 1.49 (s, 3H), 1.47 (s, 9H), 1.30 (m, 1H), 1.26 (t, J=7.1 Hz, 3H), 0.72-0.52 (m, 3H), 0.51-0.41 (m, 1H). LCMS (m/z) 511.0 [M+H], Tr=2.49 min.

Compound 78c

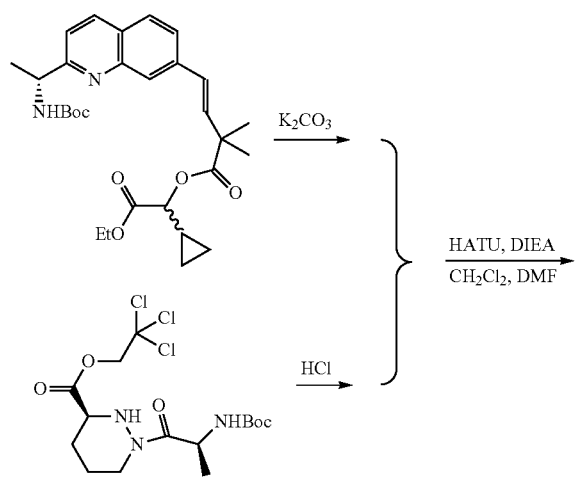

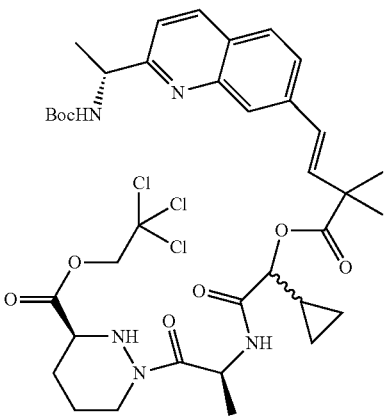

To a solution of the ethyl ester reactant 78b (76 mg, 0.149 mmol) in THF (2 mL), MeOH (2 mL), and water (2 mL) was added K$_2$CO$_3$ (104 mg, 0.752 mmol) at 0° C. After stirring at 0° C. for 1.5 h and at rt for 10.5 h, the mixture was acidified using 1 N HCl (1.6 mL), diluted with water, and extracted with ethyl acetate (×2). After the aqueous fractions were extracted with ethyl acetate (×1), two organic fractions were combined, dried (MgSO$_4$), and concentrated. The residue was purified by CombiFlash using hexanes-ethyl acetate as eluents to obtain 49 mg (68%) of the intermediate product with ~15% of impurity. LCMS (m/z) 483.0 [M+H]. A solution of the dipeptide (48 mg, 0.111 mmol) in 4 N HCl in dioxane (2 mL) was stirred at rt for 1 h. After the mixture was concentrated and the residue was co-evaporated with toluene, A solution of the residue, the previously obtained acid (49 mg), and HATU (80 mg, 0.210 mmol) in CH$_2$Cl$_2$ (3 mL) and DMF (1 mL) was stirred at rt as DIEA (0.1 mL, 0.574 mmol) was added. After 30 min at rt, the mixture was diluted with EA and washed with 5% LiCl solution (×2), citric acid solution (×1), saturated NaHCO$_3$, (×1), and saturated NaCl solution (×1). After the aqueous fractions were extracted with ethyl acetate (×1), two organic fractions were combined, dried (MgSO$_4$), and concentrated. The residue was purified by CombiFlash using hexanes-ethyl acetate as eluents to obtain 64 mg (79%) of the product 78c as a diasteromer mix. $^1$H NMR (400 MHz, Chloroform-d): δ 8.05 (d, J=8.4 Hz, 1H), 8.00 (s, 1H), 7.71 (d, J=8.3 Hz, 1H), 7.67-7.60 (m, 1H), 7.28 (d, J=8.5 Hz, 1H), 7.03 (dd, J=16.5, 7.6 Hz, 1H), 6.71 (dd, J=16.2, 3.8 Hz, 1H), 6.64 (d, J=16.2 Hz, 1H), 6.21 (s, 1H), 5.37-5.20 (m, 1H), 4.97 (s, 1H), 4.92 (d, J=11.9 Hz, 1H), 4.77 (dd, J=7.8, 3.2 Hz, 1H), 4.69 (dd, J=11.9, 3.7 Hz, 1H), 4.36-4.18 (m, 1H), 3.81 (t, J=8.9 Hz, 1H), 3.65 (m, 1H), 2.84 (br, 1H), 2.14 (m, 1H), 1.88 (m, 1H), 1.77-1.59 (m, 2H), 1.55 (s, 3H), 1.53 (s, 3H), 1.51 (d, J=8.2 Hz, 3H), 1.46 (s, 9H), 1.24 (m, 4H), 0.65 (m, 1H), 0.50 (m, 3H). LCMS (m/z) 796.0 [M+H], Tr=2.50 min.

Compound 78 and Compound 79

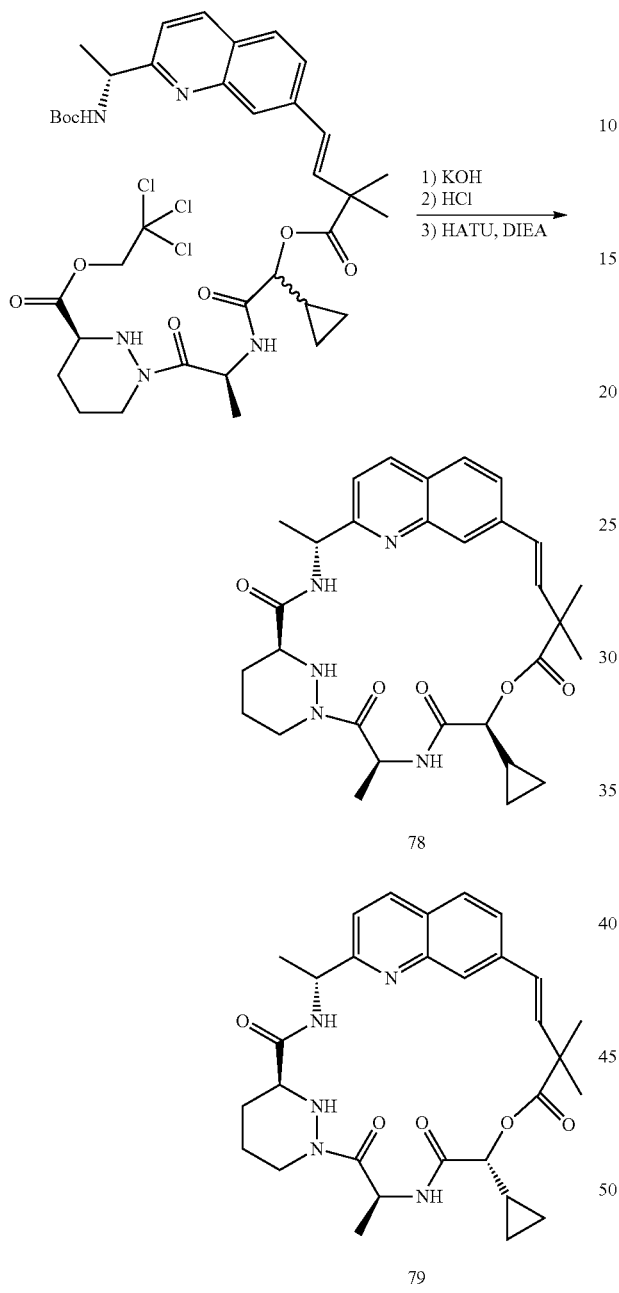

A mixture of the reactant (64 mg, 0.080 mmol) in THF (1 mL) and water (1 mL) was stirred at 0° C. as 1N KOH (0.09 mL) was added. After stirring at 0° C. for 1.25 h, the mixture was acidified using 1 N HCl (0.1 mL), diluted with water, and extracted with ethyl acetate (×2). After the aqueous fractions were extracted with ethyl acetate (×1), two organic fractions were combined, dried (MgSO₄), and concentrated. The residue was dissolved in 4 N HCl in dioxane (2 mL) and stirred at rt for 1 h. After the mixture was concentrated and the residue was co-evaporated with toluene, a solution of the residue and HATU (155 mg, 0.408 mmol) in DMF (2.5 mL) and CH$_2$Cl$_2$ (25 mL) was stirred at 0° C. as DIEA (0.12 mL, 0.689 mmol) was added. After 30 min, the solution was concentrated, diluted with ethyl acetate before washing with 5% LiCl solution (×2), citric acid solution (×1), and saturated NaHCO$_3$ solution (×1). After the aqueous fractions were extracted with ethyl acetate (×1), two organic fractions were combined, dried (MgSO$_4$), and concentrated. The residue was separated by preparative HPLC to obtain 2 fractions. Each fraction was separately concentrated to remove MeCN, neutralized with NaHCO$_3$ solution, diluted with water, and extracted with ethyl acetate (×2). The extracts were combined, dried (MgSO$_4$), and concentrated to obtain 11.9 mg (23%) of 78 and 11.0 mg (22%) of 79.

Compound 78: $^1$H NMR (400 MHz, Methanol-d$_4$): δ 8.63 (d, J=7.2 Hz, 1H), 8.23 (d, J=8.5 Hz, 1H), 7.85 (s, 1H), 7.82 (d, J=8.4 Hz, 1H), 7.57 (dd, J=8.5, 1.7 Hz, 1H), 7.42 (d, J=8.5 Hz, 1H), 6.56 (d, J=16.2 Hz, 1H), 6.35 (d, J=16.2 Hz, 1H), 5.87-5.72 (m, 1H), 5.14-5.01 (m, 1H), 4.89 (d, J=8.9 Hz, 1H), 4.43 (dd, J=13.8, 4.4 Hz, 1H), 3.57 (dd, J=11.8, 2.9 Hz, 1H), 2.69 (td, J=13.0, 3.3 Hz, 1H), 2.34-2.21 (m, 1H), 1.94 (d, J=13.4 Hz, 1H), 1.76-1.61 (m, 1H), 1.59 (d, J=7.2 Hz, 3H), 1.56 (d, J=6.7 Hz, 3H), 1.51 (s, 3H), 1.40 (s, 3H), 1.30 (m, 2H), 0.69-0.57 (m, 3H), 0.56-0.42 (m, 1H). LCMS (m/z) 548.3 [M+H], Tr=2.25 min.

Compound 79: $^1$H NMR (400 MHz, Methanol-d$_4$): δ 9.27 (d, J=6.2 Hz, 1H), 8.24 (s, 1H), 8.21 (d, J=8.5 Hz, 1H), 8.02 (d, J=6.7 Hz, 1H), 7.80 (d, J=8.3 Hz, 1H), 7.46 (dd, J=8.3, 1.7 Hz, 1H), 7.41 (d, J=8.4 Hz, 1H), 6.72 (d, J=16.0 Hz, 1H), 6.57 (d, J=16.1 Hz, 1H), 5.91-5.76 (m, 1H), 5.13 (m, 1H), 4.73 (d, J=8.9 Hz, 1H), 4.43 (dd, J=8.8, 4.0 Hz, 1H), 3.55 (dd, J=11.9, 2.9 Hz, 1H), 2.69 (td, J=13.1, 3.3 Hz, 1H), 2.32 (dd, J=13.4, 3.4 Hz, 1H), 1.93 (d, J=13.2 Hz, 1H), 1.68 (qt, J=13.4, 4.4 Hz, 1H), 1.57 (d, J=6.9, Hz, 3H), 1.56 (d, J=6.9, Hz, 3H), 1.54 (s, 3H), 1.53-1.45 (m, 1H), 1.42 (s, 3H), 1.28 (s, 1H), 0.78-0.59 (m, 3H), 0.50 (m, 1H). LCMS (m/z) 548.3 [M+H], Tr=2.33 min.

Example 80

Compound 80

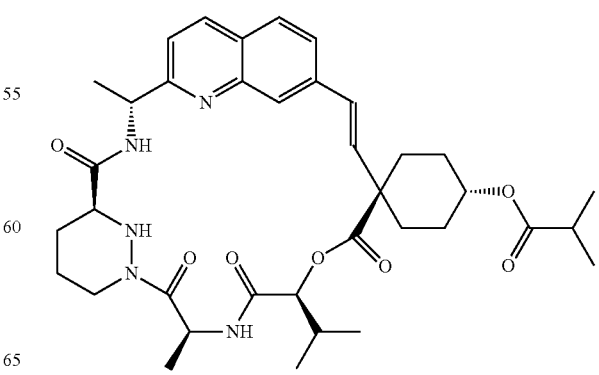

Compound 80

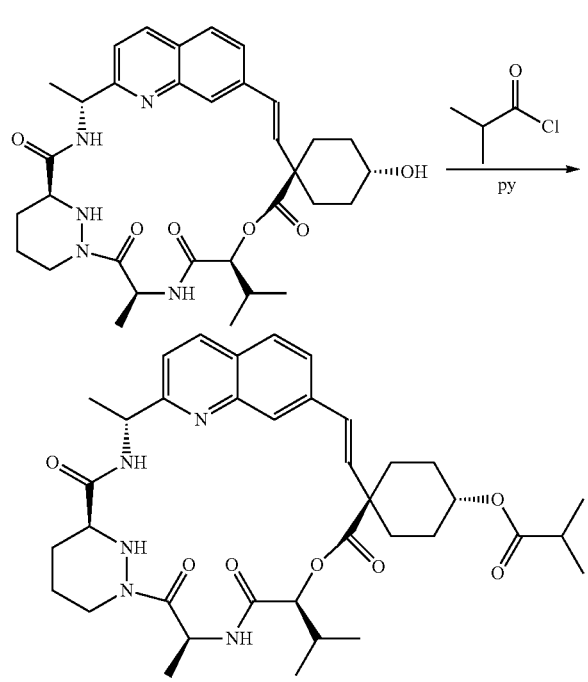

To a solution of 74 (7.13 mg, 0.012 mmol) in pyridine (0.15 mL) was added isobutyryl chloride (0.05 mL) at rt. After 1 h at rt, the mixture was diluted with ethyl acetate, washed with citric acid solution (×1) and saturated NaHCO$_3$ solution (×1). After the aqueous fractions were extracted with EA (×1), two organic fractions were combined, dried (MgSO$_4$), and concentrated. The residue was purified by CombiFlash using hexanes-ethyl acetate as eluents to obtain 6.4 mg (80%) of the product 80. $^1$H NMR (400 MHz, Methanol-d$_4$): δ 8.83 (d, J=7.5 Hz, 1H), 8.23 (d, J=8.5 Hz, 1H), 7.83 (d, J=8.5 Hz, 1H), 7.79 (s, 1H), 7.64 (dd, J=8.4, 1.7 Hz, 1H), 7.43 (d, J=8.5 Hz, 1H), 6.61 (d, J=16.4 Hz, 1H), 6.30 (d, J=16.4 Hz, 1H), 5.80 (q, J=7.1 Hz, 1H), 5.26 (d, J=8.5 Hz, 1H), 5.07 (q, J=6.7 Hz, 1H), 4.96 (s, 1H), 4.41 (dd, J=13.5, 4.1 Hz, 1H), 3.62-3.54 (m, 1H), 2.68 (td, J=13.2, 3.4 Hz, 1H), 2.60 (p, J=7.0 Hz, 1H), 2.33 (d, J=13.4 Hz, 1H), 2.25 (d, J=12.0 Hz, 1H), 2.21-2.09 (m, 2H), 2.05-1.76 (m, 7H), 1.76-1.63 (m, 1H), 1.60 (d, J=7.2 Hz, 3H), 1.57 (d, J=6.7 Hz, 3H), 1.56-1.46 (m, 1H), 1.20 (d, J=7.0 Hz, 6H), 1.06 (d, J=6.8 Hz, 3H), 1.02 (d, J=6.7 Hz, 3H). LCMS (m/z) 676.3 [M+H], Tr=1.35 min.

Example 81

Compound 81

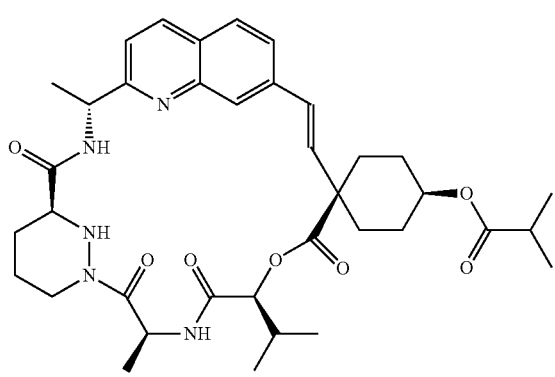 [SMILES: CC(C)C(=O)O[C@H]1CC[C@]2(/C=C/c3ccc4ccc(nc4c3)[C@@H](C)NC(=O)[C@@H]3CCCN(N3)C(=O)[C@H](C)NC(=O)[C@H](C(C)C)OC2=O)CC1]

Compound 81

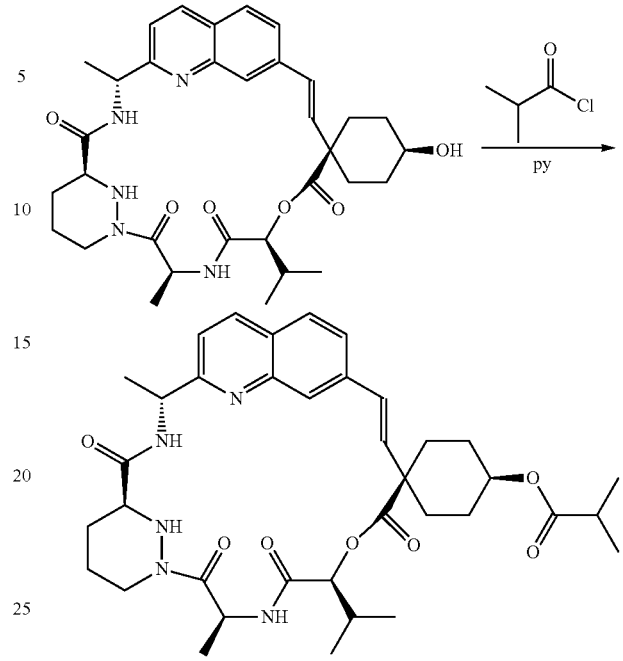

To a solution of the 75 (6.6 mg, 0.011 mmol) in pyridine (0.15 mL) was added isobutyryl chloride (0.05 mL) at rt. After 1 h at rt, the mixture was diluted with ethyl acetate, washed with citric acid solution (×1) and saturated NaHCO$_3$ solution (×1). After the aqueous fractions were extracted with ethyl acetate (×1), two organic fractions were combined, dried (MgSO$_4$), and concentrated. The residue was purified by CombiFlash using hexanes-ethyl acetate as eluents to obtain 5.1 mg (69%) of the product. $^1$H NMR (400 MHz, Methanol-d$_4$): δ 8.27 (d, J=8.5 Hz, 1H), 7.83 (d, J=8.2 Hz, 1H), 7.79 (s, 1H), 7.64 (d, J=8.3 Hz, 1H), 7.46 (d, J=8.5 Hz, 1H), 6.58 (d, J=16.3 Hz, 1H), 6.29 (d, J=16.4 Hz, 1H), 5.81 (p, J=7.4 Hz, 1H), 5.28 (d, J=8.4 Hz, 1H), 5.08 (q, J=6.8 Hz, 1H), 4.77 (m, 1H), 4.42 (d, J=15.0 Hz, 1H), 3.58 (d, J=11.6, 3.2 Hz, 1H), 2.68 (td, J=12.8, 3.2 Hz, 1H), 2.56 (m, 1H), 2.52 (hept, J=7.0 Hz, 1H), 2.35 (d, J=13.1 Hz, 1H), 2.30-2.11 (m, 2H), 2.10-1.88 (m, 3H), 1.75 (td, J=13.6, 2.8 Hz, 1H), 1.71-1.40 (m, 5H), 1.61 (d, J=7.5 Hz, 3H), 1.59 (d, J=6.9 Hz, 3H), 1.14 (d, J=7.0, Hz, 6H), 1.08 (d, J=6.8 Hz, 3H), 1.03 (d, J=6.7 Hz, 3H). LCMS (m/z) 676.5 [M+H], Tr=1.20 min.

Example 82

Compound 82

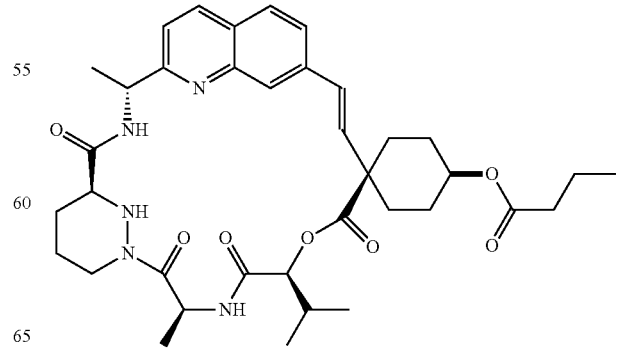

373
Compound 82

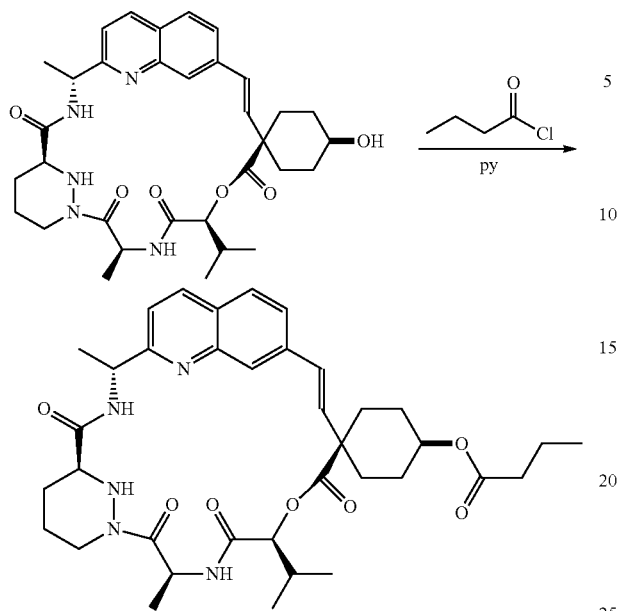

To a solution of the 75 (7.0 mg, 0.012 mmol) in pyridine (0.15 mL) was added n-butyryl chloride (0.05 mL) at rt. After 1 h at rt, the mixture was diluted with ethyl acetate, washed with 10% citric acid solution (×1) and saturated NaHCO$_3$ solution (×1). After the aqueous fractions were extracted with ethyl acetate (×1), two organic fractions were combined, dried (MgSO$_4$), and concentrated. The residue was purified by CombiFlash using hexanes-ethyl acetate as eluents to obtain 5.7 mg (73%) of the product 82. $^1$H NMR (400 MHz, Methanol-d$_4$): δ 8.23 (d, J=8.5 Hz, 1H), 7.82 (d, J=8.5 Hz, 1H), 7.77 (s, 1H), 7.61 (dd, J=8.4, 1.7 Hz, 1H), 7.43 (d, J=8.5 Hz, 1H), 6.56 (d, J=16.4 Hz, 1H), 6.26 (d, J=16.3 Hz, 1H), 5.80 (q, J=7.2 Hz, 1H), 5.28 (d, J=8.6 Hz, 1H), 5.06 (q, J=6.6 Hz, 1H), 4.77 (m, 1H), 4.47-4.34 (m, 1H), 3.58 (dd, J=12.8, 2.8 Hz, 1H), 2.68 (td, J=12.8, 3.2 Hz, 1H), 2.58 (d, J=13.9 Hz, 1H), 2.41-2.31 (m, 1H), 2.28 (t, J=7.3 Hz, 2H), 2.24-2.11 (m, 1H), 2.10-1.88 (m, 3H), 1.80-1.38 (m, 9H), 1.61 (d, J=7.3 Hz, 3H), 1.57 (d, J=6.8 Hz, 3H), 1.07 (d, J=6.8 Hz, 3H), 1.03 (d, J=6.7 Hz, 3H), 0.94 (t, J=7.4 Hz, 3H). LCMS (m/z) 676.4 [M+H], Tr=1.19 min.

Example 83
Compound 83

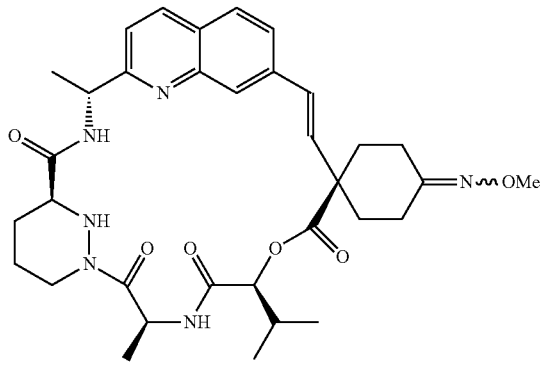

374
Compound 83a

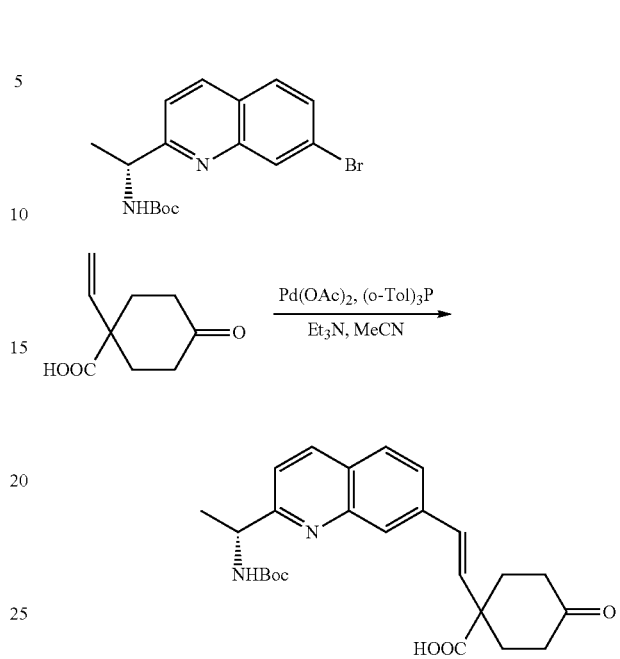

To a mixture of the [(R)-1-(7-bromo-quinolin-2-yl)-ethyl]-carbamic acid tert-butyl ester 39a (1160 mg, 3.303 mmol), the vinyl acid (833 mg, 4.953 mmol), Pd(OAc)$_2$ (149 mg, 0.664 mmol), and (o-Tol)$_3$P (203 mg, 0.667 mmol) in dioxane (18 mL) was added NEt$_3$ (1.65 mL, 11.838 mmol) and the resulting mixture was heated at 100° C. for 30 min in a microwave reactor. The mixture was filtered through celite pad, and the filtrate was diluted with ethyl acetate before washing with water (×2). After the aqueous fractions were extracted with ethyl acetate (×1), two organic fractions were washed with water (×1), combined, dried (MgSO$_4$), and concentrated. The residue was purified by CombiFlash using hexanes-ethyl acetate as eluents to obtain 1033 mg (71%) of the product 83a. $^1$H NMR (400 MHz, Chloroform-d): δ 8.23 (s, 1H), 8.14 (br d, 1H), 7.76 (d, J=8.5 Hz, 1H), 7.61 (d, J=8.3 Hz, 1H), 7.39 (br, 1H), 6.87 (d, J=16.3 Hz, 1H), 6.60 (d, J=16.2 Hz, 1H), 6.49 (s, 1H), 5.04 (s, 1H), 2.81-2.58 (m, 4H), 2.49 (m, 2H), 2.13 (m, 2H), 1.55 (br, 3H), 1.40 (s, 9H). LCMS (m/z) 439.0 [M+H], Tr=0.87 min.

Compound 83b

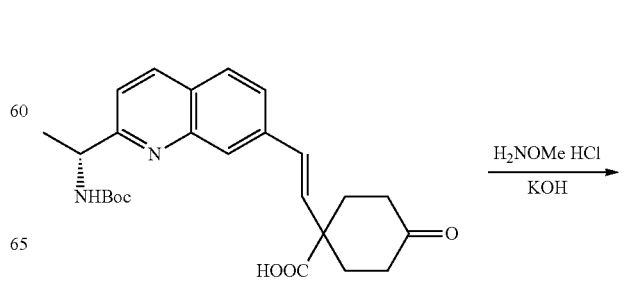

-continued

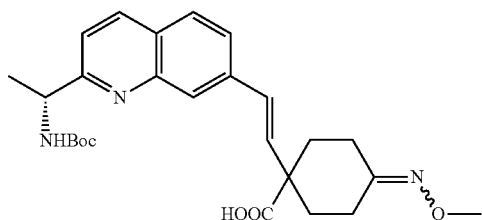

A solution of the 83a (150 mg, 0.342 mmol) in MeOH (2 mL) and water (2 mL) was stirred at rt as methoxylamine hydrochloride (70 mg, 0.838 mmol) and 1 N KOH (0.7 mL) were added. After 1 h at rt, the mixture was diluted with ethyl acetate and washed with 10% citric acid (×1) and water (×1). After the aqueous fractions were extracted with ethyl acetate (×1), two organic fractions were washed with water (×1), combined, dried (MgSO₄), and concentrated. The residue was purified by CombiFlash using hexanes-EA as eluents to obtain 144 mg (90%) of the product 83b. LCMS (m/z) 468.0 [M+H], Tr=0.98 min.

A mixture of the acid 83b (144 mg, 0.308 mmol), 1e (162 mg, 0.374 mmol), Shiina reagent (276 mg, 0.802 mmol), and DMAP (107 mg, 0.876 mmol) was dissolved in CH₂Cl₂ (5 mL) at rt. After 3 min, DIEA (0.15 mL, 0.861 mmol) was added and the resulting mixture was stirred at rt for 16 h. The mixture was diluted with ethyl acetate, and washed with water (×2). After the aqueous fractions were extracted with ethyl acetate (×1), two organic fractions were combined, dried (MgSO₄), and concentrated. The residue was purified by CombiFlash using hexanes-ethyl acetate as eluents to obtain 161 mg (59%) of the product 83c as an isomer mixture. LCMS (m/z) 881.3 [M+H], Tr=1.37 min.

Compound 83c

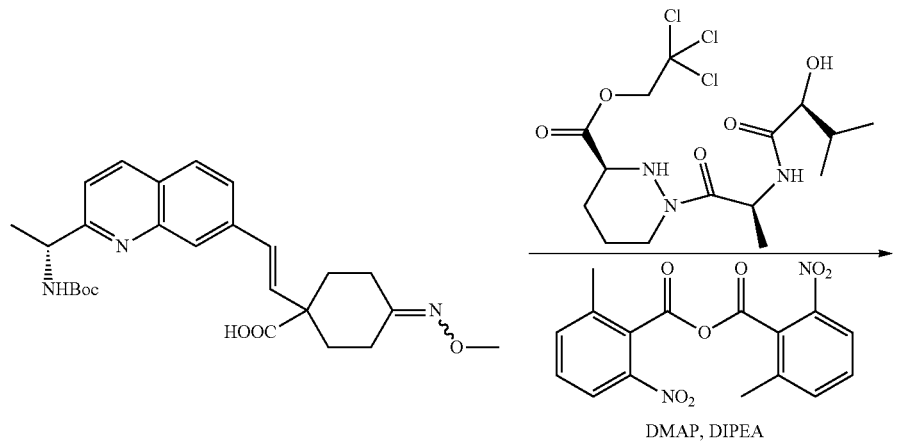

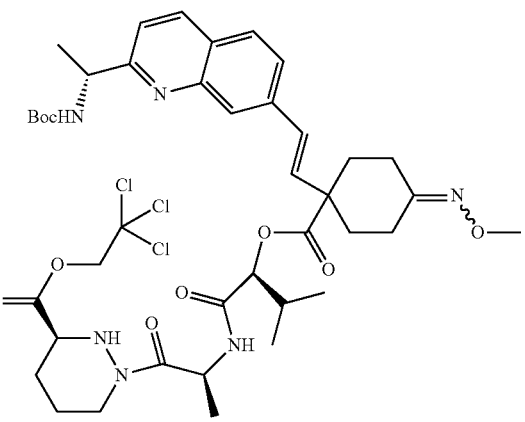

Compound 83

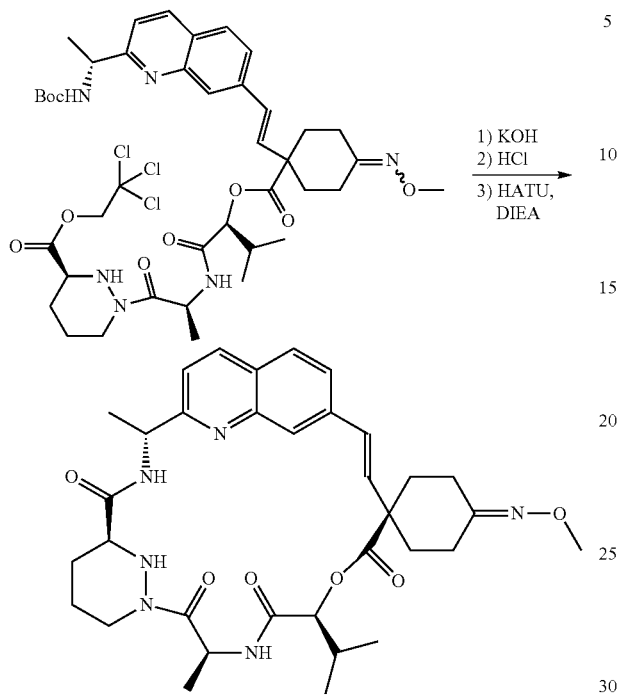

Example 84

Compound 84

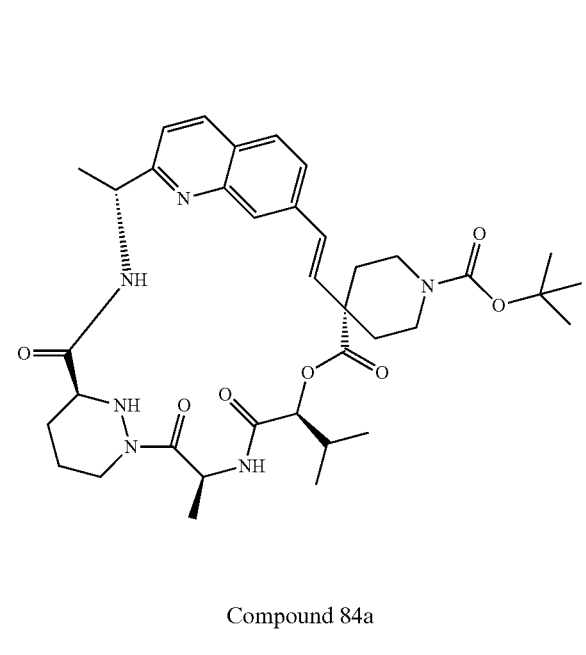

Compound 84a

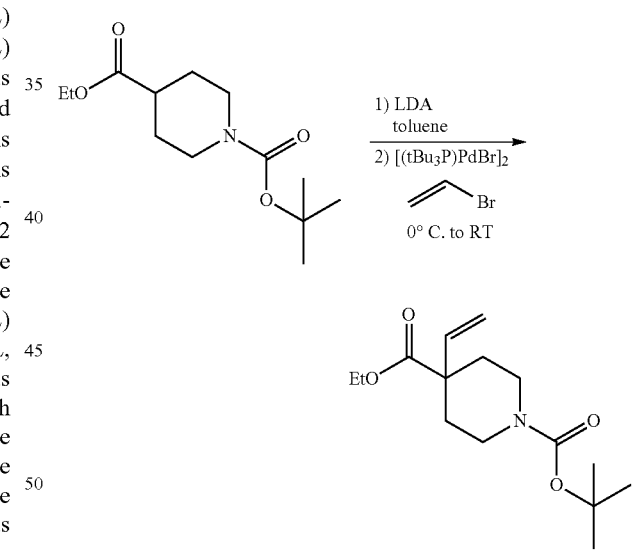

A mixture of the 83c (161 mg, 0.182 mmol) in THF (2 mL) and water (2 mL) was stirred at 0° C. as 1 N KOH (0.19 mL) was added. After stirring at 0° C. for 1 h, the mixture was acidified using 1 N HCl (0.20 mL), diluted with water, and extracted with ethyl acetate (×2). After the aqueous fractions were extracted with ethyl acetate (×1), two organic fractions were combined, dried ($MgSO_4$), and concentrated. The residue was stirred in $CH_2Cl_2$ (2 mL) and 4 N HCl in dioxane (2 mL) at rt for 1 h. After the mixture was concentrated and the residue was co-evaporated with toluene (×2), a solution of the residue and HATU (150 mg, 0.394 mmol) in DMF (2.5 mL) and $CH_2Cl_2$ (50 mL) was stirred at 0° C. as DIEA (0.2 mL, 1.148 mmol) was added. After 1.5 h at 0° C., the solution was concentrated, diluted with ethyl acetate before washing with 5% LiCl solution (×2). After the aqueous fractions were extracted with ethyl acetate (×1), two organic fractions were combined, dried ($MgSO_4$), and concentrated. The residue was purified by CombiFlash using hexanes-ethyl acetate as eluents. The partially purified product was further purified by preparative HPLC to obtain 17.2 mg (23%) of compound 83 as one isomer. $^1$H NMR (400 MHz, Methanol-$d_4$): δ 9.40 (d, J=5.9 Hz, 1H), 8.87 (d, J=7.5 Hz, 1H), 8.22 (d, J=8.5 Hz, 1H), 7.81 (d, J=8.5 Hz, 1H), 7.78 (s, 1H), 7.61 (dd, J=8.5, 1.7 Hz, 1H), 7.43 (d, J=8.5 Hz, 1H), 6.60 (d, J=16.4 Hz, 1H), 6.29 (d, J=16.4 Hz, 1H), 5.81 (q, J=7.2 Hz, 1H), 5.30 (d, J=8.6 Hz, 1H), 5.12-5.01 (m, 1H), 4.40 (dd, J=13.8, 4.2 Hz, 1H), 3.79 (s, 3H), 3.56 (dd, J=11.6, 2.9 Hz, 1H), 3.18 (dt, J=15.0, 4.3 Hz, 1H), 2.68 (td, J=13.0, 3.2 Hz, 1H), 2.61-2.50 (m, 1H), 2.48-2.11 (m, 5H), 2.06-1.86 (m, 2H), 1.83-1.62 (m, 3H), 1.60 (d, J=7.3 Hz, 3H), 1.57 (d, J=6.8 Hz, 3H), 1.51 (dd, J=13.3, 9.6 Hz, 1H), 1.06 (d, J=6.8 Hz, 3H), 1.01 (d, J=6.6 Hz, 3H). LCMS (m/z) 633.5 [M+H], Tr=1.05 min.

1-tert-butyl 4-ethyl 4-vinylpiperidine-1,4-dicarboxylate 84a was prepared according to the reported method for enolate arylation reported by Bercot, E. A. et al. in *Organic Letters*, 2008, 10, p. 5251-5254 using 1-tert-butyl 4-ethyl piperidine-1,4-dicarboxylate in 12% yield.

$^1$H NMR (400 MHz, Chloroform-d): δ 5.76 (dd, J=17.5, 10.7 Hz, 1H), 5.19-5.02 (m, 2H), 4.14 (q, J=7.1 Hz, 2H), 3.80-3.59 (m, 2H), 3.02 (ddd, J=13.8, 10.2, 3.3 Hz, 2H), 2.10 (dtt, J=13.6, 3.2, 1.6 Hz, 2H), 1.56 (ddd, J=13.7, 10.1, 4.1 Hz, 2H), 1.41 (s, 9H), 1.22 (t, J=7.1 Hz, 3H). LCMS [M+H]$^+$=184.05 (−Boc). Tr=2.43 min

Compound 84

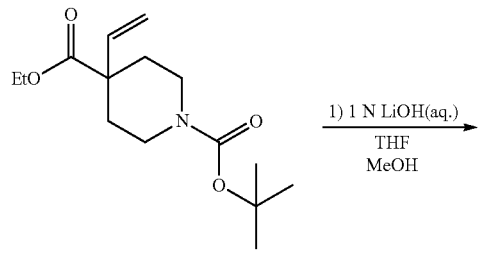

1) 1 N LiOH(aq.)
THF
MeOH

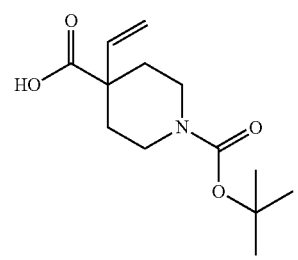

+

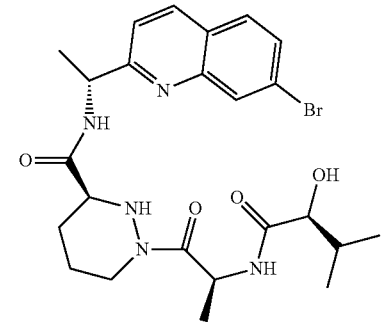

2) Pd(OAc)₂
(p-Tol)₃P
TEA
CH₃CN
100 C.

3) Shiina conditions

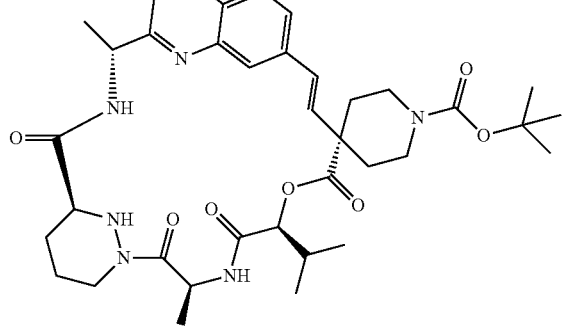

1-tert-butyl 4-ethyl piperidine-1,4-dicarboxylate (282 mg) was hydrolyzed to its acid, and this was then followed by the Heck reaction and subsequent Shiina reaction to form 84 (129 mg) following the method reported in Example 36. $^1$H NMR (400 MHz, Methanol-$d_4$): δ 9.41 (d, J=6.2 Hz, 1H), 8.28-8.18 (m, 1H), 8.00 (s, 1H), 7.57 (d, J=8.5 Hz, 1H), 7.43 (d, J=8.5 Hz, 1H), 6.84 (d, J=16.3 Hz, 1H), 6.34 (d, J=16.3 Hz, 1H), 5.86 (q, J=7.3 Hz, 1H), 5.44 (d, J=12.2 Hz, 1H), 5.23 (d, J=8.9 Hz, 1H), 5.15 (t, J=6.4 Hz, 1H), 4.43 (d, J=13.2 Hz, 1H), 3.96-3.80 (m, 2H), 2.79 (d, J=12.7 Hz, 1H), 2.47-2.15 (m, 4H), 1.95 (m, 1H), 1.80 (m, 2H), 1.55 (d, J=6.7 Hz, 4H), 1.46 (s, 9H), 1.32-1.16 (m, 10H), 1.04 (dd, J=8.3, 6.7 Hz, 6H). LCMS [M+H]⁺=691.30; Tr=2.02 min.

Example 85

Compound 85

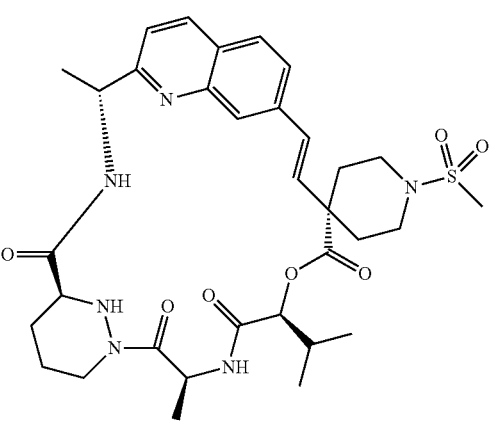

Compound 85a

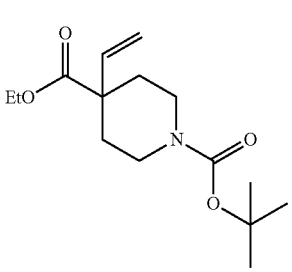

4N HCl in dioxane
DCM
RT/1 h

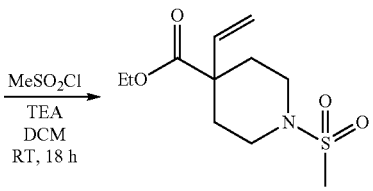

MeSO₂Cl
TEA
DCM
RT, 18 h

Following the procedure reported in Example 84, the N-Boc group of 1-tert-butyl 4-ethyl 4-vinylpiperidine-1,4-dicarboxylate 84a (450 mg) was removed via treatment with 4N HCl in dioxane/DCM at RT for 1 h to give ethyl 4-vinylpiperidine-4-carboxylate. Ethyl 4-vinylpiperidine-4-carboxylate reacted with MsCl with TEA in DCM at RT for 18 h to give ethyl 1-(methylsulfonyl)-4-vinylpiperidine-4-carboxylate 85a (409 mg, 98% yield). LCMS [M+H]⁺=249.90 (-Boc); Tr=1.96 min.

Compound 85

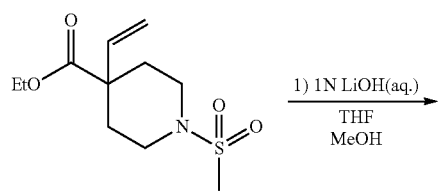

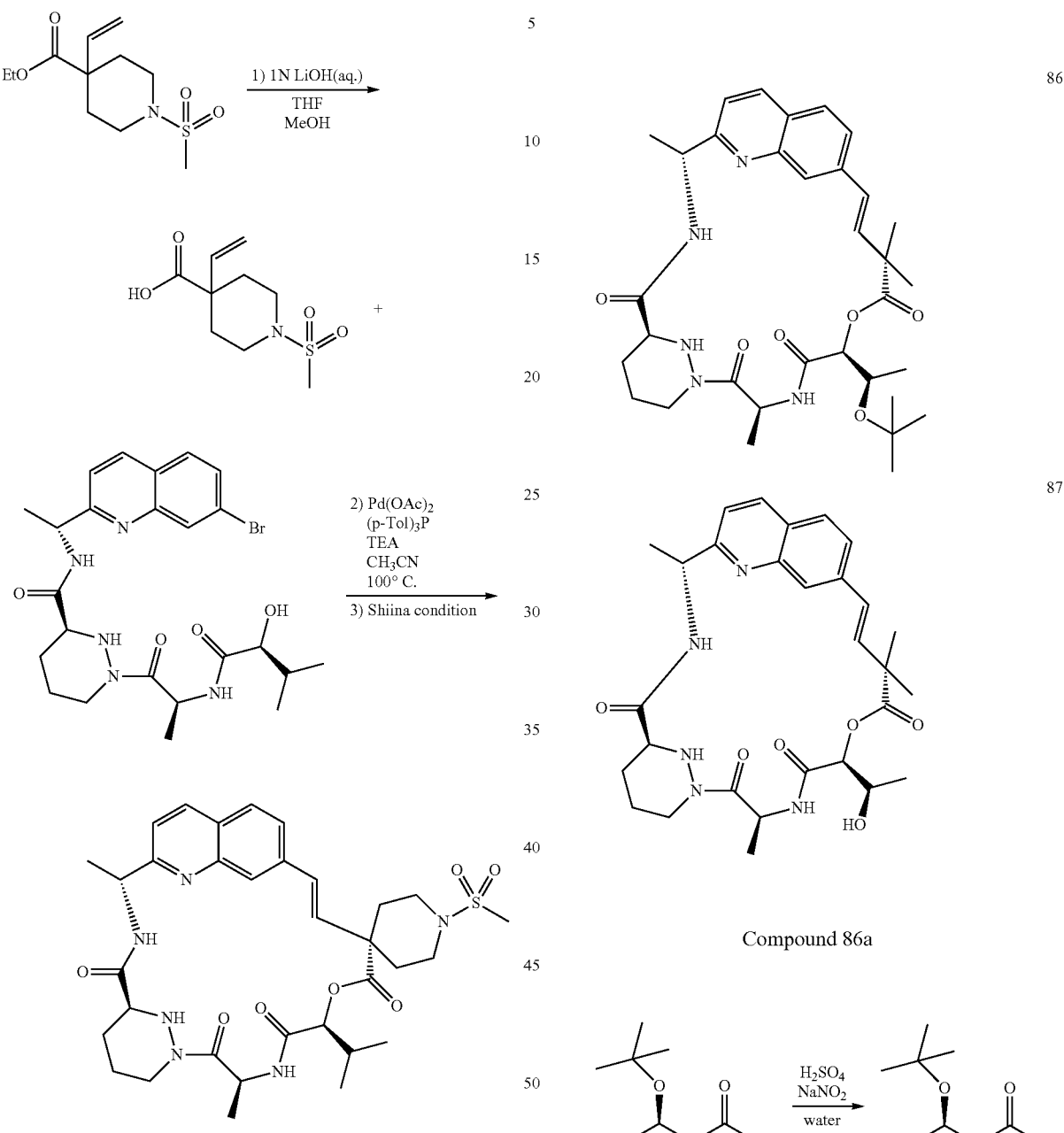

Compound 85a (409 mg) was hydrolyzed to its acid, and the material submitted Heck coupling, and Shiina-mediated lactonization reaction was used to form 85 (34 mg) in a manner like that reported in Example 84. $^1$H NMR (400 MHz, Methanol-$d_4$): δ 8.22 (d, J=8.5 Hz, 1H), 7.85-7.74 (m, 2H), 7.70-7.58 (m, 1H), 7.42 (d, J=8.5 Hz, 1H), 6.45 (dd, J=132.8, 16.3 Hz, 2H), 5.79 (q, J=7.1 Hz, 1H), 5.28 (d, J=8.5 Hz, 1H), 5.05 (q, J=6.5 Hz, 1H), 4.39 (d, J=13.2 Hz, 1H), 4.06 (s, 3H), 3.70 (dd, J=18.6, 5.4 Hz, 1H), 3.64 (s, 2H), 3.60-3.51 (m, 1H), 3.04-2.84 (m, 2H), 2.73-2.60 (m, 1H), 2.53 (d, J=13.7 Hz, 1H), 2.34 (d, J=13.7 Hz, 1H), 2.30-2.09 (m, 2H), 2.04-1.82 (m, 3H), 1.64 (dd, J=10.8, 6.5 Hz, 1H), 1.57 (dd, J=10.6, 7.0 Hz, 6H), 1.49 (dd, J=9.7, 5.2 Hz, 1H), 1.45-1.18 (m, 2H), 1.02 (dd, J=17.8, 6.7 Hz, 6H). LCMS [M+H]$^+$=669.49; Tr=0.95 min.

Example 86 and Example 87

Compounds 86 and 87

Compound 86a

The reactant t-butyl-L-threonine (supplied by Sigma-Aldrich, Inc.) (1 g, 5.7 mmol) in the solution of water (7 mL)/acetone (14 mL)/sulfuric acid (7.2 mL) was cooled to 0° C. A solution of sodium nitrite (1.18 g, 17.1 mmol) in water (5 mL) was added dropwise. The mixture was stirred and warmed to rt overnight. After acetone was removed via rotary evaporation, the residue was extracted with EtOAc twice and washed with brine. The organic layer was dried through (MgSO$_4$), and concentrated. The residue purified by CombiFlash on silica gel column using MeOH/DCM. It gave 674 mg (67% yield) of (2S,3R)-3-tert-butoxy-2-hydroxybutanoic acid 86a.

¹H NMR (400 MHz, Chloroform-d): δ 4.18-4.02 (m, 1H), 2.40 (m, 1H), 1.32-1.25 (m, 12H).

Compound 86b

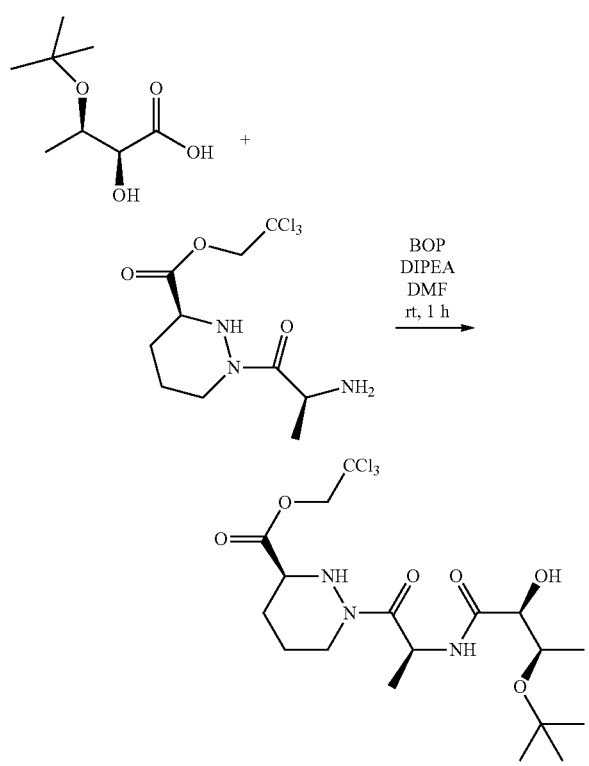

(2S,3R)-3-tert-butoxy-2-hydroxybutanoic acid 86a (337 mg, 1.9 mmol) was reacted with the indicated dipeptide resulting from N-Boc removal from 1d as described in the synthesis of 1e (1.2 eq) with DIPEA (2 mL), BOP (924 mg, 2.09 mmol) in DMF at 0° C. for 30 min, and then at RT for 30 min. It was quenched with 3% LiCl aq. The solution was extracted with EtOAc twice and washed with brine. The organic layer was dried through (MgSO₄), and concentrated. The residue purified by CombiFlash on silica gel column using MeOH/DCM. To obtain 599 mg (64% yield) desired tripeptide 86b. LCMS [M+H]⁺=489.88 (100%), Tr=1.05 min.

Compound 86

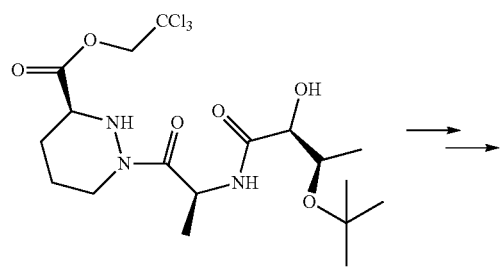

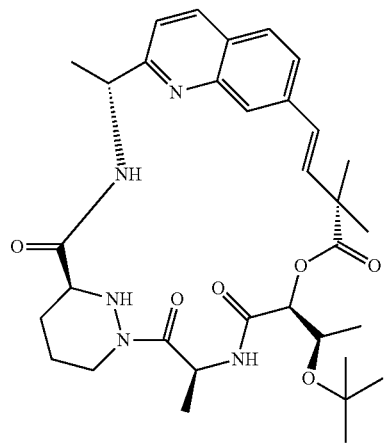

313 mg tripeptide 86b was converted to final compound 86 using a synthetic sequence identical to that reported in Example 84, yielding 7 mg 86. ¹H NMR (400 MHz, Methanol-d₄): δ 8.80 (d, J=8.5 Hz, 1H), 8.22 (d, J=8.5 Hz, 1H), 7.88 (s, 1H), 7.80 (m, 1H), 7.55 (m, 1H), 7.42 (d, J=8.5 Hz, 1H), 6.57-6.35 (dd, J=132.8, 16.3 Hz, 2H), 5.79 (q, J=7.1 Hz, 1H), 5.28 (d, J=8.5 Hz, 1H), 5.05 (q, J=6.5 Hz, 1H), 4.39 (d, J=13.2 Hz, 1H), 4.06 (m, 1H), 3.60 (dd, J=18.6, 5.4 Hz, 1H), 2.78 (s, 9H), 2.70-2.63 (m, 1H), 2.27 (d, J=13.7 Hz, 1H), 1.90 (d, J=13.7 Hz, 1H), 1.68-1.63 (m, 1H), 1.57 (dd, J=10.6, 7.0 Hz, 6H), 1.50 (s, 3H), 1.40 (s, 3H), 1.23 (m, 12H). LCMS [M+H]⁺=608.25; Tr=1.17 min.

Compound 87

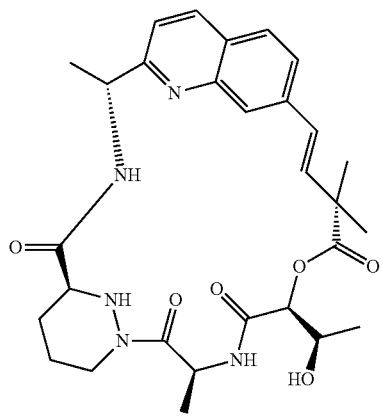

17 mg of 87 was the obtained as by-product during the synthesis of 86 reported above. ¹H NMR (400 MHz, Methanol-d₄): δ 8.94 (d, J=8.5 Hz, 1H), 8.22 (d, J=8.5 Hz, 1H), 7.81-7.77 (m, 2H), 7.58 (m, 1H), 7.40 (d, J=8.5 Hz, 1H), 6.54-6.31 (dd, J=132.8, 16.3 Hz, 2H), 5.76 (q, J=7.1 Hz, 1H), 5.33 (d, J=8.5 Hz, 1H), 5.05 (q, J=6.5 Hz, 1H), 4.40 (d, J=13.2 Hz, 1H), 4.06 (m, 1H), 3.60 (dd, J=18.6, 5.4 Hz, 1H), 2.70-2.63 (m, 1H), 2.27 (d, J=13.7 Hz, 1H), 1.90 (d, J=13.7 Hz, 1H), 1.68-1.63 (m, 1H), 1.57 (dd, J=10.6, 7.0 Hz, 6H), 1.50 (s, 3H), 1.40 (s, 3H), 1.23 (m, 12H). LCMS [M+H]⁺=552.31; Tr=0.90 min.

Example 88

Compound 88

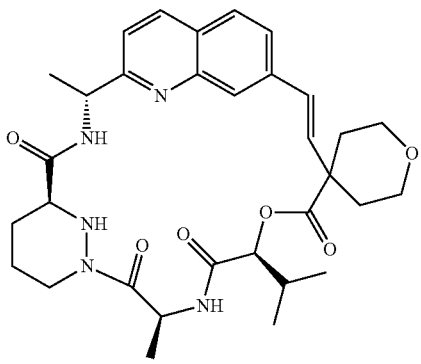 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)CCOCC2]

Compound 88a: 1,2-Dichloro-ethyne

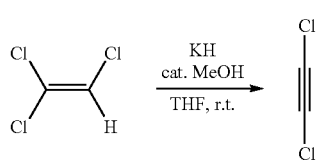

Into an oven dried, argon purged flask were placed oil-free potassium hydride (from 1740 mg of ca. 30% dispersion in mineral oil, ca. 13 mmol), anhydrous tetrahydrofuran (10 mL) and hexane (1 mL). The flask was repurged with argon and trichloroethylene (900 µL, 1.32 g, 10 mmol) was added followed by dry methanol (10 µL, 7.9 mg, 0.25 mmol). This mixture was stirred at room temperature for two hours. After this time, hexane (10 mL) was added and the resulting solution was immediately used in the subsequent step.

Compound 88b:
4-Chloroethynyl-tetrahydro-pyran-4-carboxylic acid methyl ester

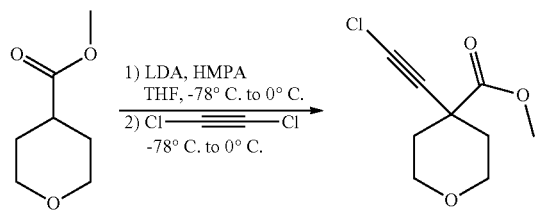

Into an oven dried, argon purged flask tetrahydrofuran (50 mL) was added and the solution was cooled with an ice bath. A 1.8 M solution of lithium diisopropylamide (7.2 mL, 13 mmol) in tetrahydrofuran/heptane/ethylbenzene was added. The resulting solution was cooled to −78° C., and treated dropwise with methyl tetrahydro-2H-pyran-4-carboxylate (Sigma-Aldrich) (1.20 mL. 1.30 g, 9 mmol) followed by hexamethylphosphoramide (1.56 mL, 1.61 g, 9 mmol). The resulting solution was warmed to 0° C., stirred for 20 min., cooled to −78° C., and treated dropwise with pre-cooled (0° C.) solution of 1,2-dichloro-ethyne (ca. 10 mmol). The reaction mixture was stirred at −78° C. for 30 min and then allowed to warm to room temperature. After 4 hours at room temperature, the reaction mixture was poured into crushed ice and extracted with diethyl ether (200 mL) (5 mL of brine was added to support the separation). The organic phase was separated and washed with water (200 mL). This water phase was extracted with diethyl ether (100 mL). The combined organic fractions were washed with brine (100 mL), dried over magnesium sulfate, filtered through a 2 cm layer of silica gel (silica gel layer was washed with 50 mL of ethyl acetate), and then concentrated under reduced pressure. The crude product was subjected to silica gel chromatography (gradient from 0-15% ethyl acetate in iso-hexanes) to afford the title compound (1.22 g, 67%) as a colorless oil. R$_f$=0.48, 30% ethyl acetate in iso-hexanes, phosphomolybdic acid in ethanol. LCMS (m/z) 203.2/205.3 [M+H]' Tr=3.12 min (Gemini 5u C18 110 Å, 50×4.60 mm 5 micron column, 3.5 min, 2 ml/min, 5-100% acetonitrile/water, 0.1% acetic acid modifier gradient). ¹H NMR (400 MHz, CDCl₃): δ 3.79-3.65 (m, 4H), 3.72 (s, 3H), 1.97 (m, 2H), 1.78 (m, 2H).

Compound 88c:
4-Ethynyl-tetrahydro-pyran-4-carboxylic acid methyl ester

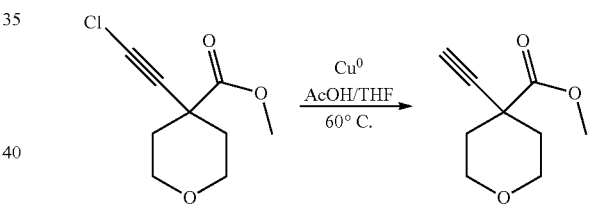

4-Chloroethynyl-tetrahydro-pyran-4-carboxylic acid methyl ester (1.01 g, 5 mmol) and copper powder (1.6 g, 25 mmol) were suspended in tetrahydrofuran (100 mL). Acetic acid (15 mL) was added and the reaction mixture was heated to 60° C. for 3 hours. After this time, the reaction mixture was poured onto water (copper powder was filtered off with the use of the filtration paper) and extracted with diethyl ether (3×50 mL). The combined organic extracts were washed with saturated solution of ammonium chloride (3×50 mL), with saturated solution of sodium bicarbonate (2×50 mL) and with water (50 mL). This water phase was extracted with diethyl ether (50 mL). Combined organic extracts were washed with brine (50 mL) and dried over magnesium sulfate, filtered through a 2 cm layer of silica gel (silica gel layer was washed with 50 mL of ethyl acetate), and concentrated under reduced pressure. After drying under high vacuum for one day, the title compound was isolated (0.84 g, quantitative yield) as a colorless oil. R$_f$=0.37, 30% ethyl acetate in iso-hexanes, phosphomolybdic acid in ethanol. LCMS (m/z) 169.0 [M+H]' Tr=2.43 min (Gemini 5u C18 110 Å, 50×4.60 mm 5 micron column, 3.5 min, 2 ml/min, 5-100% acetonitrile/water, 0.1% acetic acid modifier gradient). $^1$H NMR (400 MHz, CDCl$_3$): δ 3.80-3.67 (m, 4H), 3.73 (s, 3H), 2.34 (s, 1H), 1.98 (m, 2H), 1.80 (m, 2H).

Compound 88d

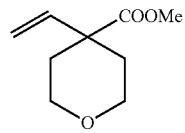

+

To a mixture of methyl 4-vinyltetrahydro-2H-pyran-4-carboxylate (prepared following the hydrogenation of 88c with Lindlar's catalyst), (0.726 g, 4.27 mmol), triethylamine (1.29 g, 12.81 mmol) and the [(R)-1-(7-bromo-quinolin-2-yl)-ethyl]-carbamic acid tert-butyl ester 39a (1.5 g, 4.27 mmol) in anhydrous dioxane (30 mL) were added palladium acetate (0.19 g, 0.85 mmol) and tri-o-tolyphosphine (0.26 g, 0.85 mmol). The reaction mixture was heated to 100° C. for 2 hours and diluted with EtOAc (100 mL). The crude was washed with water and dried over Na$_2$SO$_4$. After concentration, the residue was purified by silica gel chromatography using a gradient of iso-hexanes/ethyl acetate 1:0 to 0:1 to afford 88a (1.1 g, 59%). LCMS (m/z) 441.2 [M+H]. Tr=2.21 min.

Compound 88e

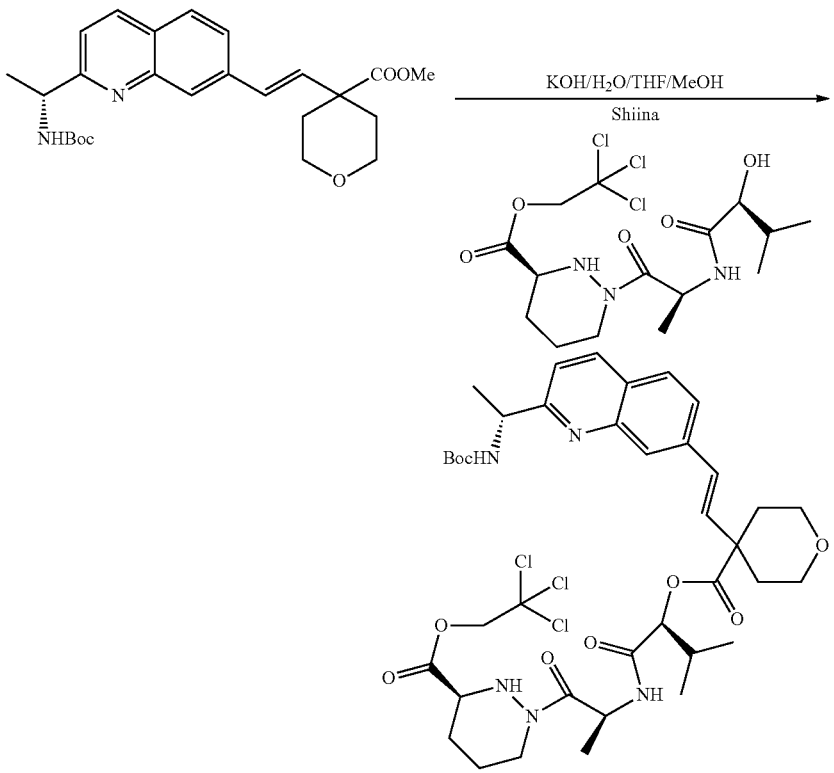

-continued

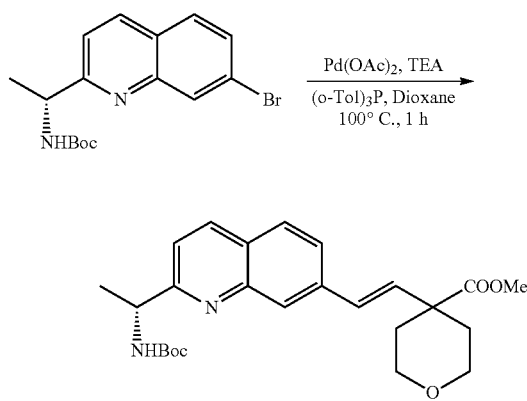

To a solution of 88d (1.0 g, 2.27 mmol) in THF (10 mL) and MeOH (5 ml) was added 1 N KOH in water (11.4 mL). The reaction mixture was stirred at 50° C. for 2 hours and was acidified by adding 1 N HCl in water (11.4 mL). After extracted with EtOAc (2×100 mL), dried over Na$_2$SO$_4$ and concentrated, the crude acid was used without further purification. The crude acid above (0.328 g, 0.77 mmol), 1e (0.398, 0.92 mmol), 4-DMAP (0.225 g, 1.85 mmol), DIPEA (0.239 g, 1.85 mmol) and Shiina reagent (0.632 g, 1.84 mmol) were dissolved in DCM (10 mL). The reaction mixture was stirred at room temperature for overnight. After concentration, the crude was diluted with EtOAc (100 mL), washed with sat. NH$_4$Cl and dried over Na$_2$SO$_4$. After concentration, the residue was purified by silica gel chromatography using a gradient of iso-hexanes/ethyl acetate 1:0 to 0:1 to afford 88e (0.55 g, 85%). LCMS (m/z) 841.2 [M+H]. Tr=2.56 min.

389

Compound 88

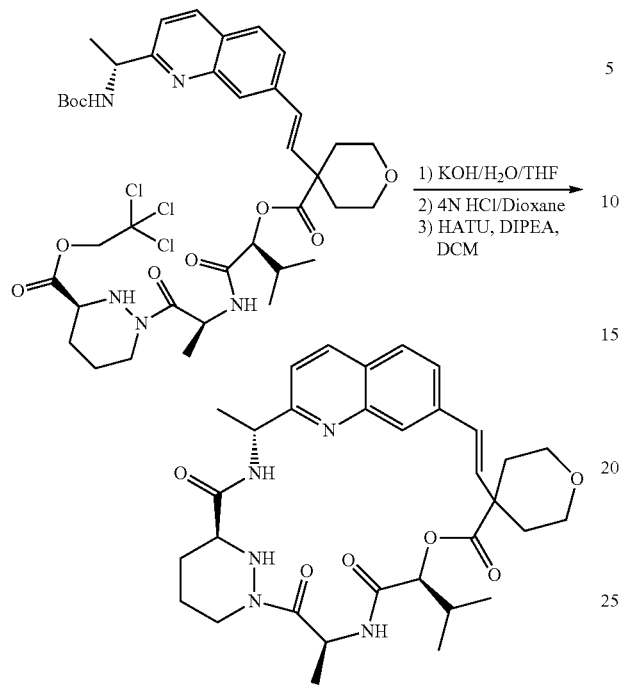

To a solution of 88e (0.70 g, 0.83 mmol) in THF (10 mL) was added 1 N KOH in water (0.83 mL). The reaction mixture was vigorously stirred at room temperature for 20 minutes and was acidified by adding 1 N HCl in water (0.83 mL). After concentration, the crude was dissolved in 4 N HCl/dioxane (2 ml) and stirred for 1 hour. After concentration and co-evaporated with toluene (3×), the crude above was dissolved in DCM (800 mL). N,N-diisopropylethylamine (0.54 g, 4.2 mmol), DMAP (catalytic amount) and 2-(1H-7-azabenzotriazol-1-yl)-1,1,3,3-tetramethyl uronium hexafluorophosphate methanaminium (0.63 g, 1.66 mmol). The reaction mixture was stirred at room temperature for 1 hour. After concentration, the crude was purified by prep-HPLC to obtain 88 (0.22 g, 45%) as a white solid. $^1$H NMR (400 MHz, Methanol-$d_4$): δ 8.81 (d, J=7.7 Hz, 1H), 8.54-8.30 (m, 1H), 8.11-7.78 (m, 2H), 7.68 (dd, J=8.5, 1.7 Hz, 1H), 7.53 (d, J=8.5 Hz, 1H), 6.62 (d, J=16.3 Hz, 1H), 6.34 (d, J=16.3 Hz, 1H), 5.78 (m, 1H), 5.21 (dd, J=8.1, 1.0 Hz, 1H), 5.09 (q, J=6.7 Hz, 1H), 4.38 (d, J=13.2 Hz, 1H), 3.92 (ddq, J=19.0, 12.0, 4.0, 3.4 Hz, 2H), 3.71-3.40 (m, 3H), 2.69 (m, 1H), 2.38 (m, 1H), 2.17 (m, 3H), 2.08-1.74 (m, 4H), 1.76-1.44 (m, 7H), 1.00 (dd, J=24.1, 6.7 Hz, 6H). LCMS (m/z) 592.3 [M+H]. Tr=2.15 min.

Example 89

Compound 89

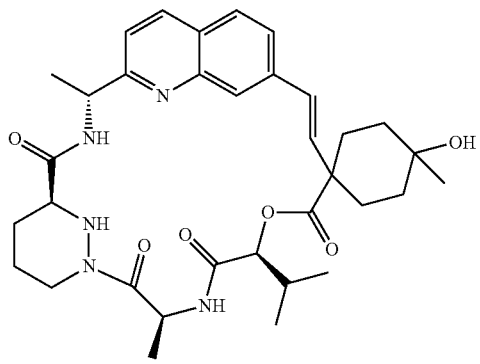 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)CCC(C)(O)CC2]

390

Compound 89a

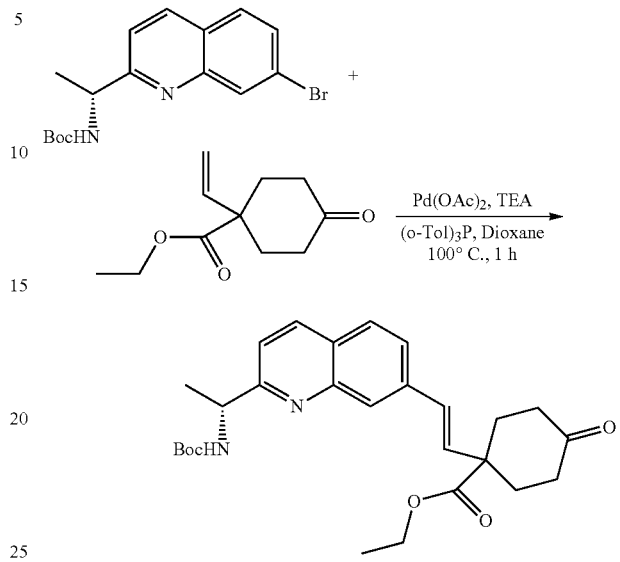

To a mixture of [(R)-1-(7-bromo-quinolin-2-yl)-ethyl]-carbamic acid tert-butyl ester 39a, (0.50 g, 1.42 mmol), triethylamine (0.43 g 4.26 mmol) and the vinyl cyclohexanone ethoxy ester obtained from Small Molecules, Inc. (0.279 g, 1.42 mmol) in anhydrous dioxane (15 mL) were added palladium acetate (0.063 g, 0.28 mmol) and tri-o-tolyphosphine (0.085 g, 0.28 mmol). The reaction mixture was heated to 100° C. for 3 hours and diluted with EtOAc (50 mL). The crude mixture was washed with water and dried over $Na_2SO_4$. After concentration, the residue was purified by silica gel chromatography using a gradient of iso-hexanes/ethyl acetate 1:0 to 0:1 to afford 89a (0.30 g, 45%). LCMS (m/z) 467.2 [M+H]. Tr=2.39 min.

Compound 89b

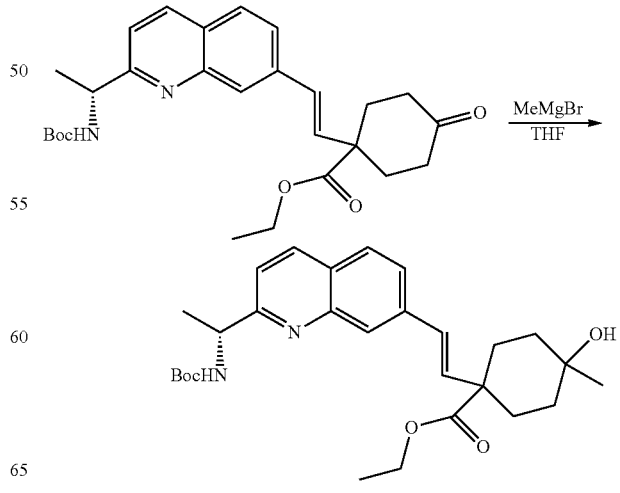

To a solution of 89a (0.3 g, 0.64 mmol) in anhydrous THF (5 mL), cooled to −78° C., was added methyl magnesium bromide (3.0 M solution in ether, 0.43 mL) dropwise. The mixture was stirred at −780° C. for 1 h. The reaction mixture was diluted with EtOAc (30 mL) and quenched with sat. NH$_4$Cl (2 mL). After layers separation, the organic layer was dried over Na$_2$SO$_4$ and concentrated. the crude residue was purified by silica gel chromatography using iso-hexanes/ethyl acetate 1:0 to 1:1 to give the tile compound 89b (0.17 g, 56%) as a mixture of 1:1 cis/trans mixture. LCMS (m/z) 483.3 [M+H]. Tr=2.36 min.

Compound 89c

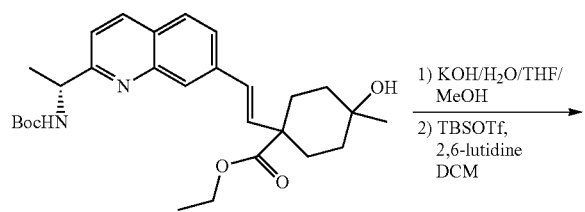

-continued

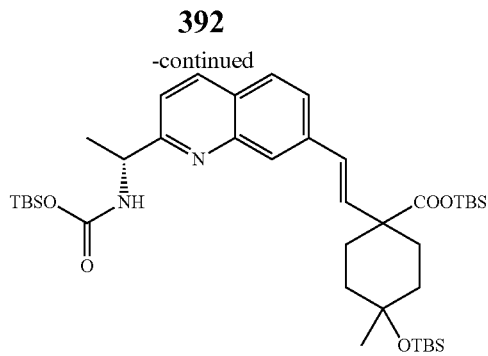

To a solution of 89b (0.17 g, 0.353 mmol) in THF (2 mL) and methanol (1 mL) was added a solution of 1N KOH in water (1.76 mL). The reaction mixture was stirred at room temperature for 1 hour. 1 N HCl (1.76 mL) was added to the reaction mixture. After concentration, the crude was under high vacuum over night. The crude above and 2,6-lutidine (0.227 g, 2.12 mmol) were dissolved in DCM (5 mL). The reaction mixture was cooled to 0° C., TBSOTf (0.280 g, 1.06 mmol) was added drop wise to the reaction mixture. After stirred at room temperature for 1 hour and concentrated, the crude was purified by silica gel chromatography using iso-hexanes/ethyl acetate 1:0 to 1:1 to give the 89c (0.150 g, 58%). LCMS (m/z) 741.4 [M+H]. Tr=3.56 min.

Compound 89d

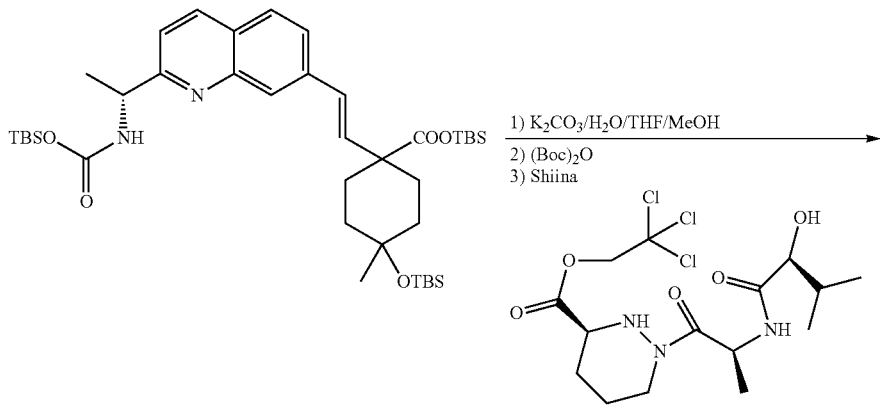

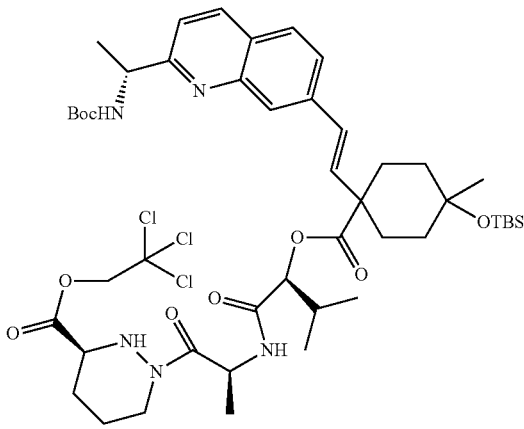

A solution of 89c (0.15 g, 0.20 mmol) in tetrahydrofuran (1 mL) and methanol (1 ml) was prepared and a 1M aq. solution of potassium carbonate (0.8 mL) was added. The reaction mixture was stirred at room temperature for 1 hour. Di-tert-butyl dicarbonate (0.44 g, 0.20 mmol) was added to the reaction solution. Then, the reaction mixture was stirred at room temperature for an additional 1 h, and acidified to pH=4 by adding 1 N HCl in water. After concentration and co-evaporated with toluene (3×) to give the crude acid. The crude acid above, 1e (0.104 g, 0.24 mmol), DMAP (0.06 g, 0.48 mmol), DIPEA (0.02 g, 0.48 mmol) and shiina reagent (0.138 g, 0.40 mmol) were dissolved in DCM (10 mL). The reaction mixture was stirred at room temperature for overnight. After concentration, the crude was diluted with EtOAc (100 mL), washed with sat. $NH_4Cl$ and dried over $Na_2SO_4$. After concentration, the residue was purified by silica gel chromatography using a gradient of iso-hexanes/ethyl acetate 1:0 to 0:1 to 89d (0.07 g, 35%). LCMS (m/z) 983.5 [M+H]. Tr=2.98 min.

To a solution of 89d (0.06 g, 0.061 mmol) in THF (1 mL) was added 1 N KOH in water (0.061 mL). The reaction mixture was vigorously stirred at room temperature for 20 minutes and was acidified by adding 1 N HCl in water (0.1 mL). After concentration, the crude was dissolved in 4 N HCl/dioxane (3 ml) and stirred for 1 hour at room temperature. After concentration and co-evaporated with toluene (3×), the crude above was dissolved in DCM (20 mL). N,N-diisopropylethylamine (0.039 g, 0.31 mmol), DMAP (catalytic amount) and 2-(1H-7-azabenzotriazol-11-yl)-1,1,3,3-tetramethyl uronium hexafluorophosphate methanaminium (0.028 g, 0.073 mmol). The reaction mixture was stirred at room temperature for 1 hour. After concentration, the crude was purified by prep-HPLC to obtain 89 (0.006 g, 16%) as a single compound. The other isomer was not pure. $^1$H NMR (400 MHz, Methanol-$d_4$): δ 8.93 (d, J=8.6 Hz, 1H), 8.18 (d, J=8.6 Hz, 1H), 8.14-8.02 (m, 2H), 7.86 (d, J=8.5 Hz, 1H), 7.04 (d, J=16.5 Hz, 1H), 6.81 (d, J=16.5 Hz, 1H), 5.27 (dd, J=27.9, 7.0 Hz, 2H), 4.00 (s, 1H), 3.58 (dd, J=9.0, 3.7 Hz, 1H), 3.06 (d, J=39.1 Hz, 1H), 2.32-1.77 (m, 11H), 1.81-1.50 (m, 5H), 1.43 (s, 3H), 1.32 (d, J=6.9 Hz, 4H), 0.95 (d, J=6.9 Hz, 3H), 0.80 (d, J=6.8 Hz, 3H). LCMS (m/z) 620.3 [M+H]. Tr=2.12 min.

Compound 89

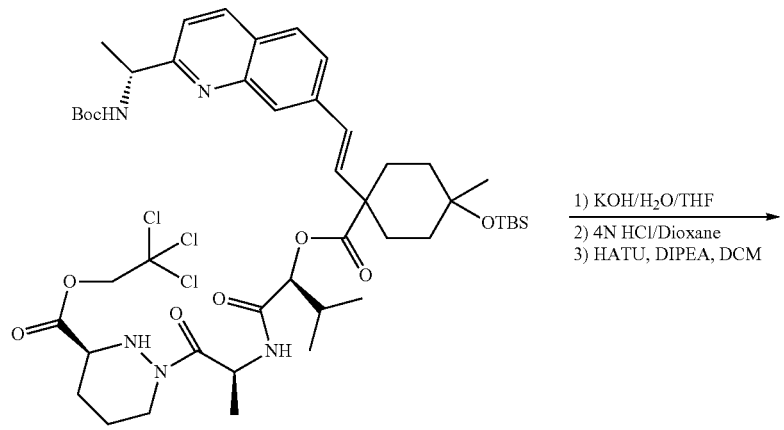

1) KOH/$H_2$O/THF
2) 4N HCl/Dioxane
3) HATU, DIPEA, DCM

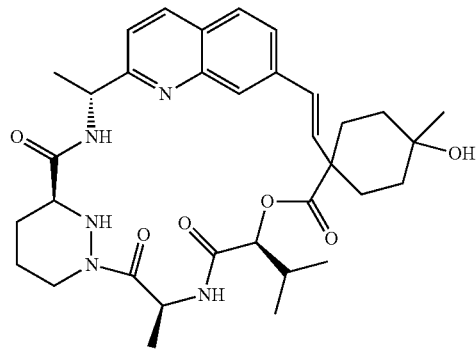

Examples 90 and 91

Compound 90 and Compound 91

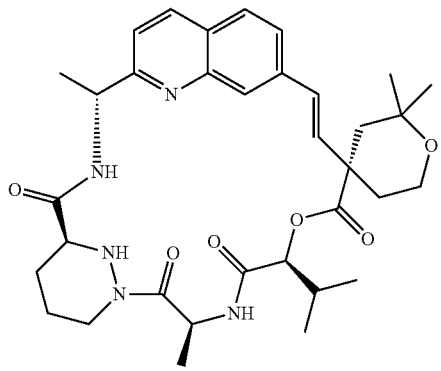

Compound 90

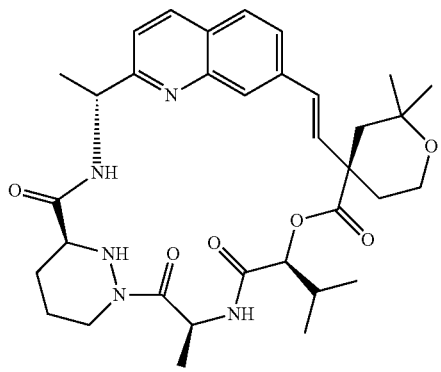

Compound 91

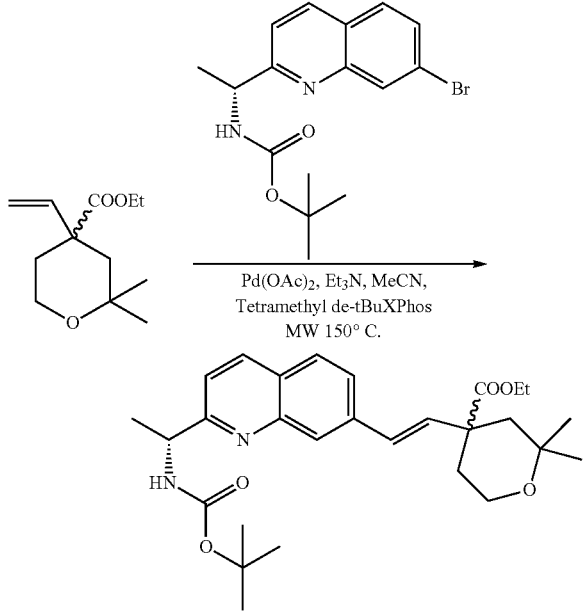

Compound 90a

To a solution of (R)-tert-butyl 1-(7-bromoquinolin-2-yl)ethylcarbamate 39a (740 mg, 2.1 mmol) in anhydrous acetonitrile (25 mL) was added palladium(II) acetate (95 mg, 0.42 mmol), the indicated olefinic dimethylpyran ethoxycarboxylic ester (670 mg, 3.16 mmol), 2-di-tert-butylphosphino-3,4,5,6-tetramethyl-2',4',6'-triisopropyl-1,1'-biphenyl (202 mg, 0.42 mmol) and triethylamine (630 mg, 6.3 mmol) then the mixture was heated in the microwave at 150° C. for 2 hours. The reaction mixture was filtered through Celite and the filter pad was washed with tetrahydrofuran (20 mL). The filtrate was evaporated then water (50 mL) was added and the organics extracted with ethyl acetate (2×50 mL). The combined organics were dried over sodium sulfate, filtered and concentrated under reduced pressure to give a crude residue. This was subjected to silica gel chromatography (gradient from 0-70% ethyl acetate in iso-hexanes) to afford 90a (170 mg, 17%) as a white solid. $^1$H NMR (400 MHz, CDCl$_3$): δ 8.04 (d, J=8.4 Hz, 1H), 7.96 (s, 1H), 7.71 (d, J=8.5 Hz, 1H), 7.53 (d, J=8.5 Hz, 1H), 7.27 (d, J=8.4 Hz, 1H), 6.60 (d, J=16.3 Hz, 1H), 6.35 (d, J=16.3 Hz, 1H), 6.20-6.10 (m, 1H), 5.01-4.89 (m, 1H), 4.25-4.09 (m, 2H), 3.91-3.69 (m, 2H), 2.41-2.14 (m, 2H), 1.80-1.61 (m, 2H), 1.56 (s, 3H), 1.45 (s, 9H), 1.32-1.21 (m, 6H), 1.15 (s, 3H). LCMS (m/z) 483.2 [M+H], Tr=4.28 min.

Compound 90b

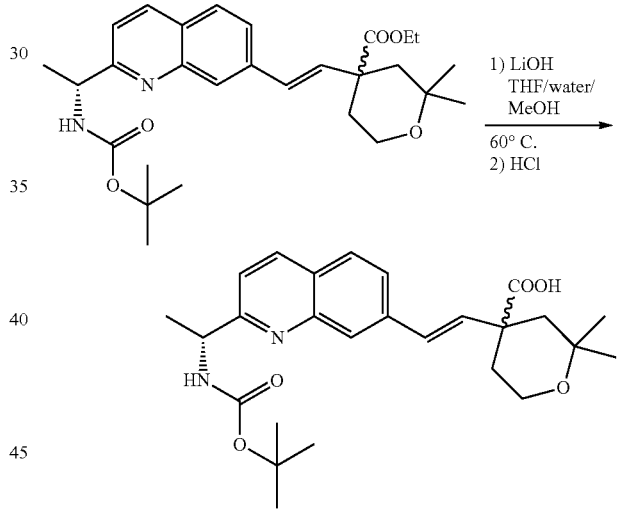

A solution of 90a (160 mg, 0.33 mmol) in tetrahydrofuran/water/methanol (10 mL, 4:1:1) was treated with lithium hydroxide (12 mg, 0.50 mmol). After stirring at 60° C. for 6 hours, the reaction was concentrated down under reduced pressure. The residue was dissolved in water (20 mL), 1 M hydrochloric acid (0.5 mL, 0.5 mmol) was added and the mixture was quickly extracted with dichloromethane (2×50 mL). The organics were combined, washed with brine, dried over sodium sulfate and filtered. The filtrate was evaporated to afford 90b (110 mg, 73%) as a white solid. $^1$H NMR (400 MHz, CDCl$_3$): δ 8.03 (d, J=8.2 Hz, 1H), 7.96 (s, 1H), 7.70 (d, J=8.5 Hz, 1H), 7.58 (d, J=8.5 Hz, 1H), 7.22 (d, J=8.2 Hz, 1H), 6.62 (d, J=16.3 Hz, 1H), 6.35 (d, J=16.3 Hz, 1H), 6.17-6.15 (m, 1H), 5.21-4.94 (m, 1H), 3.92-3.72 (m, 2H), 2.43-2.15 (m, 2H), 1.82-1.63 (m, 2H), 1.61 (s, 3H), 1.42 (s, 9H), 1.24 (s, 3H), 1.15 (s, 3H). LCMS (m/z) 455.2 [M+H], Tr=3.35 min (Gemini 5u C18 110 Å, 50×4.60 mm 5 micron column, 6 min, 2 ml/min, 5-100% acetonitrile/water, 0.1% acetic acid modifier gradient).

Compound 90c

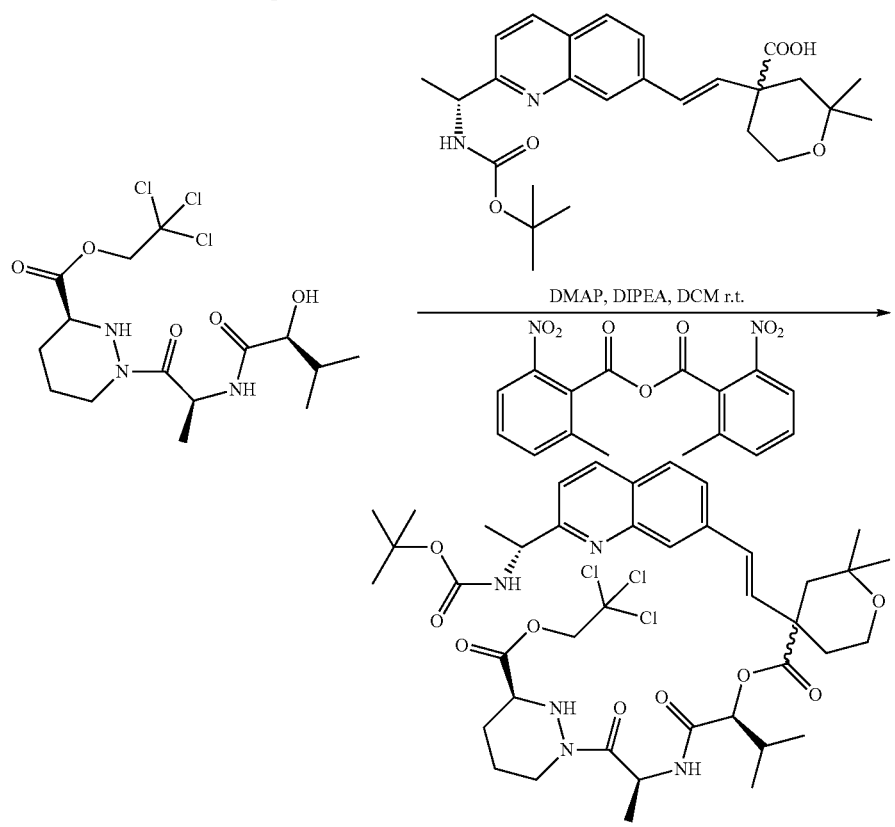

Into an oven-dried, argon purged flask were placed 2-methyl-6-nitrobenzoic anhydride (125 mg, 0.36 mmol), 4-dimethylaminopyridine (62 mg, 0.51 mmol), 90b (110 mg, 0.24 mmol), and anhydrous dichloromethane (10 mL). Into the resulting solution was added N,N-diisopropylethylamine (66 mg, 0.51 mmol) and this reaction mixture was stirred at room temperature for 10 minutes. 1e (157 mg, 0.36 mmol) was added dropwise via syringe as a solution in anhydrous dichloromethane (5 mL). After stirring for 12 hours at room temperature, the reaction mixture was transferred to a separatory funnel and washed with water (20 mL, 10 mL of brine was added to support the separation). The aqueous phase was extracted with dichloromethane (20 mL). Combined organic extracts were washed with brine (20 mL) and dried over magnesium sulfate, filtered and concentrated under reduced pressure. The residue was purified by silica gel chromatography (gradient from 0-40% ethyl acetate+methanol (4/1) in iso-hexanes) to afford 90c (201 mg, 96%) as a white solid after evaporation. $^1$H NMR (400 MHz, CD$_3$OD): δ 8.28 (d, J=8.4 Hz, 1H), 7.98 (s, 1H), 7.88 (d, J=8.2 Hz, 1H), 7.78 (d, J=9.4 Hz, 1H), 7.53 (d, J=8.4 Hz, 1H), 6.93-6.81 (m, 1H), 6.67-6.51 (m, 1H), 5.51-5.34 (m, 2H), 5.03 (d, J=12.1 Hz, 2H), 4.86 (d, J=12.1 Hz, 2H), 4.13 (q, J=7.1 Hz, 1H), 3.91-3.83 (m, 3H), 2.49-2.33 (m, 2H), 2.30-2.20 (m, 1H), 2.17-2.07 (m, 3H), 2.02-1.85 (m, 2H), 1.83-1.65 (m, 2H), 1.53 (d, J=7.1 Hz, 3H), 1.47 (s, 9H), 1.34 (d, J=6.9 Hz, 3H), 1.04 (d, J=6.9 Hz, 6H), 0.88 (d, J=6.8 Hz, 6H). LCMS (m/z) 868.2/870.2 [M+H]' Tr=3.22 min (Gemini 5u C18 110 Å, 50×4.60 mm 5 micron column, 3.5 min, 2 ml/min, 5-100% acetonitrile/water, 0.1% acetic acid modifier gradient).

Compounds 90 and 91

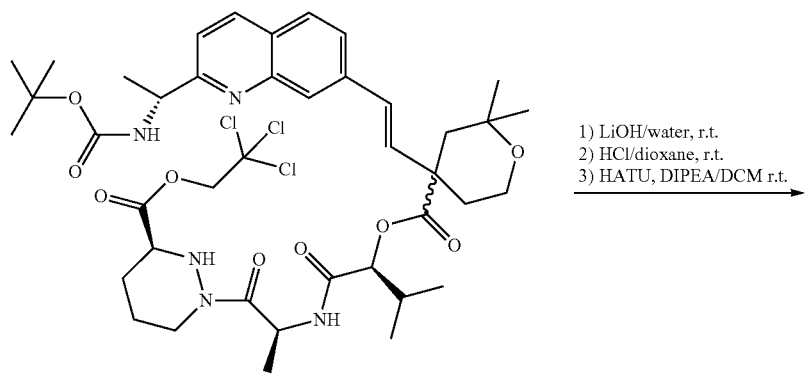

1) LiOH/water, r.t.
2) HCl/dioxane, r.t.
3) HATU, DIPEA/DCM r.t.

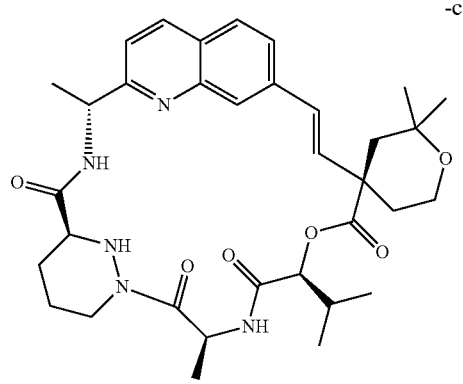

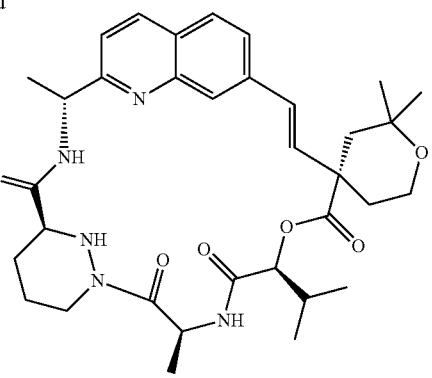

To 90c (195 mg, 0.22 mmol) in tetrahydrofuran (10 mL) was added a solution of lithium hydroxide (6 mg, 0.53 mmol) in water (5 mL). After stirring at room temperature for 2 hour, 1M hydrochloric acid was added (0.25 mL of 1M solution in water, 0.25 mmol) and the reaction mixture was concentrated under reduced pressure and the residue partitioned between dichloromethane (50 mL) and water (50 mL). The organic layer was collected, concentrated under reduced pressure and dried under high vacuum for one day. The residue was treated with 4M hydrogen chloride in 1,4-dioxane (5 mL, 20 mmol) at room temperature under argon for 4 hours. Reaction mixture was concentrated under reduced pressure. This residue was dissolved in N,N-dimethylformamide (5 mL) and the obtained solution was added into an argon purged flask containing 2-(1H-7-azabenzotriazol-1-yl)-11,1,3,3-tetramethyl uronium hexafluorophosphate methanaminium (128 mg, 0.34 mmol), N,N-diisopropylethylamine (144 mg, 1.12 mmol) and dichloromethane (100 mL). The reaction mixture was re-purged with argon and stirred at room temperature for 2 hours. The obtained reaction mixture was washed with water (100 ml) and brine (100 mL), dried over magnesium sulfate, filtered and concentrated under reduced pressure. The residue was purified by silica gel chromatography (gradient from 0-40% ethyl acetate in iso-hexanes) to afford firstly Compound 90 (27 mg, 19%) and then Compound 91 (17 mg, 12%) white solids after evaporation.

Compound 90: $^1$H NMR (400 MHz, CD$_3$OD): δ 9.08 (d, J=8.6 Hz, 1H), 8.48 (s, 1H), 8.27 (d, J=8.6 Hz, 1H), 8.03 (s, 1H), 7.97 (dd, J=8.5, 1.5 Hz, 1H), 6.91-6.69 (m, 2H), 5.92-5.73 (m, 1H), 5.36-5.22 (m, 1H), 4.42-4.26 (m, 1H), 4.01-3.83 (m, 2H), 3.83-3.73 (m, 1H), 3.71-3.62 (m, 1H), 3.55-3.42 (m, 1H), 2.53-2.41 (m, 1H), 2.33-2.26 (m, 1H), 2.13-2.05 (m, 1H), 2.00-1.87 (m, 2H), 1.81 (d, J=7.2 Hz, 3H), 1.79-1.61 (m, 4H), 1.44-1.38 (m, 2H), 1.33 (s, 3H), 1.30-1.24 (m, 3H), 1.22 (s, 3H), 1.11-1.02 (m, 3H), 0.99 (d, J=6.8 Hz, 3H). LCMS (m/z) 620.4 [M+H]' Tr=3.45 min Compound 91: $^1$H NMR (400 MHz, CD$_3$OD): δ 8.27 (d, J=8.5 Hz, 1H), 7.86 (d, J=8.5 Hz, 1H), 7.83 (s, 1H), 7.64 (dd, J=8.4, 1.7 Hz, 1H), 7.47 (d, J=8.5 Hz, 1H), 6.63 (d, J=16.2 Hz, 1H), 6.24 (d, J=16.3 Hz, 1H), 5.82 (q, J=7.2 Hz, 1H), 5.24 (d, J=8.3 Hz, 1H), 5.16-5.05 (m, 1H), 4.53-4.40 (m, 1H), 3.91-3.82 (m, 2H), 3.67-3.57 (m, 1H), 2.72 (td, J=12.9, 3.3 Hz, 1H), 2.54-2.44 (m, 1H), 2.40 (dd, J=13.8, 1.9 Hz, 1H), 2.34-2.16 (m, 1H), 2.02-1.92 (m, 1H), 1.90-1.79 (m, 1H), 1.78-1.70 (m, 2H), 1.68-1.52 (m, 2H), 1.64 (d, J=7.2 Hz, 3H), 1.61 (d, J=6.7 Hz, 3H), 1.31 (s, 3H), 1.20 (s, 3H), 1.12 (d, J=6.8 Hz, 3H), 1.08 (d, J=6.6 Hz, 3H). LCMS (m/z) 620.4 [M+H]' Tr=3.47 min (Gemini 5u C18 110 Å, 50×4.60 mm 5 micron column, 6 min, 2 ml/min, 5-100% acetonitrile/water, 0.1% acetic acid modifier gradient).

Example 92

Compound 92

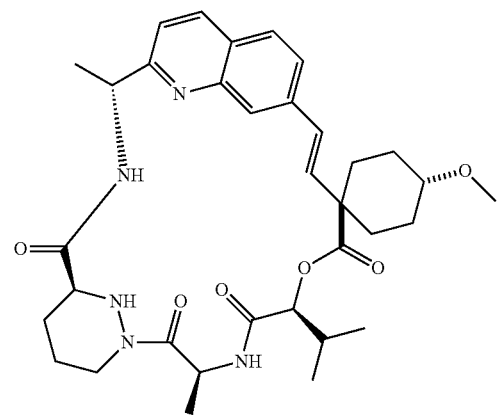 [SMILES: CO[C@H]1CC[C@@]2(/C=C/c3ccc4ccc(nc4c3)[C@@H](C)NC(=O)[C@@H]3CCCN(N3)C(=O)[C@H](C)NC(=O)[C@H](C(C)C)OC2=O)CC1]

Compound 92a

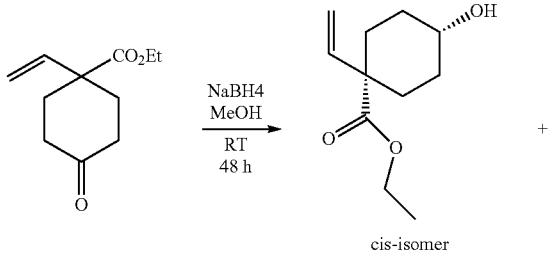

401

-continued

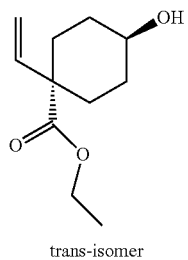

trans-isomer

The commercially supplied ethyl-4-oxo-1-vinylcyclohexanecarboxylate (provided by Small Molecules, Inc.), (3.0 g, 15.29 mmol) in MeOH (80 mL) in a flask equipped with a dropping funnel was added a MeOH (80 mL) solution of NaBH$_4$ (697 mg, 18.35 mmol) dropwise at 0° C. It was stirred at 0° C. for 10 min, and RT for 48 h. After quenched with sat'd NH$_4$Cl solution, it was extracted with EtOAc and washed with brine once. The organic layer was dried through (Na$_2$SO$_4$), and concentrated. The cis and trans isomers were separated by CombiFlash on silica gel column using EtOAC/Hexane as eluents. On TLC with EA/HEX=1/3, Rf of trans=0.5, Rf of cis=0.4. Yield: trans-isomer 92a was 425 mg, cis-isomer was 864 mg, mix of cis/trans was 468 mg. Total yield of (cis+trans) was 1.76 g, 59%.

For trans-isomer 92a: $^1$H NMR (400 MHz, Chloroform-d): δ 5.84-5.71 (m, 1H), 5.23-5.11 (m, 2H), 4.11 (q, J=7.5 Hz, 2H), 3.79 (tq, J=6.8, 3.6 Hz, 1H), 1.90 (ddd, J=11.7, 8.2, 4.2 Hz, 4H), 1.71 (ddt, J=11.9, 7.8, 3.7 Hz, 2H), 1.61-1.50 (m, 2H), 1.22 (t, J=7.1 Hz, 3H).

For cis-isomer: $^1$H NMR (400 MHz, Chloroform-d): δ 5.78 (dd, J=17.5, 10.6 Hz, 1H), 5.13-5.00 (m, 2H), 4.15 (q, J=7.1 Hz, 2H), 3.61 (dt, J=13.2, 6.4 Hz, 1H), 2.38-2.22 (m, 2H), 1.89 (dt, J=10.7, 5.2 Hz, 2H), 1.47-1.29 (m, 4H), 1.24 (t, J=7.1 Hz, 3H).

Compound 92b

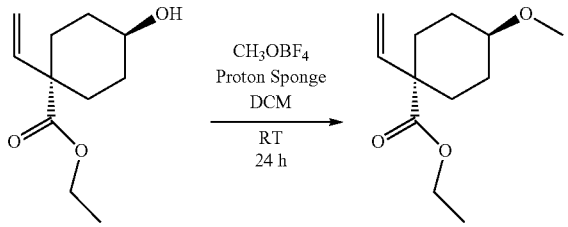

402

The reactant 92a (1R,4R)-ethyl 4-hydroxy-1-vinylcyclohexanecarboxylate (425 mg, 2.13 mmol) in DCM (10 mL) was added with CH$_3$OBF$_4$ (1.66 g, 10.7 mmol) and Proton Spronge (2.3 g, 10.7 mmol) and stirred at RT for 24 h. After filtrated through a pile of Celite, the filtrate was washed with sat'd NaHCO$_3$ solution. The organic layer was dried through (Na$_2$SO$_4$), and concentrated and purified by CombiFlash on silica gel column using EtOAC/Hexane as eluents. It gave 223 mg (49% yield) of (1R,4R)-ethyl 4-methoxy-1-vinyl-cyclohexanecarboxylate 92b. $^1$H NMR (400 MHz, Chloroform-d): δ 5.87-5.68 (m, 1H), 5.20-4.99 (m, 2H), 4.23-3.95 (m, 2H), 3.36-3.19 (m, 4H), 1.87 (pd, J=13.5, 5.6 Hz, 4H), 1.75-1.54 (m, 4H), 1.29-1.14 (m, 3H).

Compound 92c

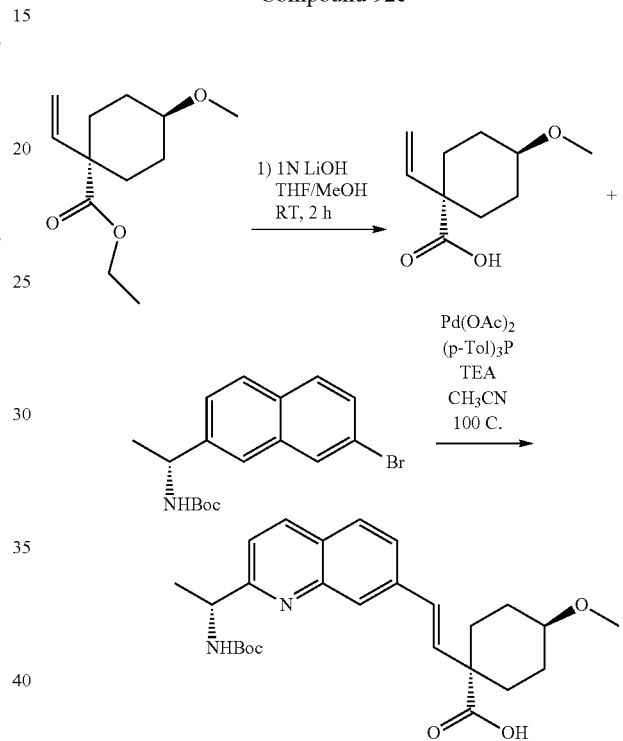

Proceeding from 223 mg (1.05 mmol) 92b, Heck reaction to form (1R,4R)-ethyl 1-((E)-2-(7-((R)-1-(tert-butoxycarbonylamino)ethyl)naphthalen-2-yl)vinyl)-4-methoxycyclohexanecarboxylate was done in the same manner as in Example 74, instead using ethyl 4-oxo-1-vinylcyclohexanecarboxylate, to give 424 mg (89% yield) intermediate compound 92c. LCMS [M+H]$^+$=455.10

Compound 92

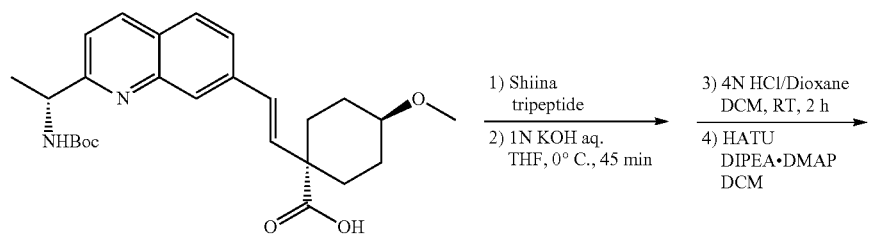

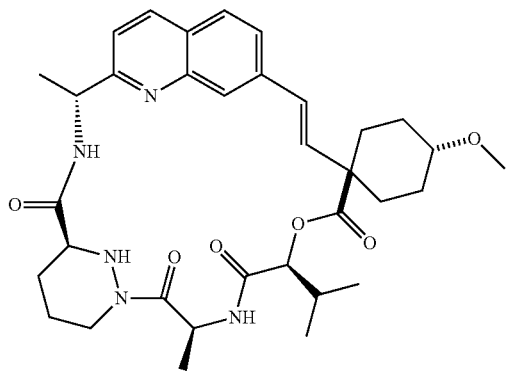

Compound 92 was prepared using a multistep synthesis beginning from 424 mg (0.92 mmol) 92c where esterification with 1e, selective hydrolysis and then N-Boc removal provided an intermediate which furnished macrocycle 92 (36 mg) in 6.2% overall yield after treatment with HATU/DIPEA in DCM/DMF using the lactonization and final purification method reported in Example 90. $^1$H NMR (400 MHz, Methanol-$d_4$): δ 8.21 (d, J=8.5 Hz, 1H), 7.80 (d, J=8.4 Hz, 1H), 7.75 (d, J=1.7 Hz, 1H), 7.59 (dd, J=8.5, 1.7 Hz, 1H), 7.41 (d, J=8.5 Hz, 1H), 6.40 (dd, J=124.5, 16.3 Hz, 2H), 5.78 (q, J=7.2 Hz, 1H), 5.23 (d, J=8.6 Hz, 1H), 5.09-4.99 (m, 1H), 4.45-4.34 (m, 1H), 3.60-3.51 (m, 1H), 3.44 (s, 1H), 3.33 (s, 3H), 2.66 (td, J=13.0, 3.3 Hz, 1H), 2.29-2.09 (m, 3H), 2.05-1.78 (m, 6H), 1.74-1.62 (m, 2H), 1.62-1.39 (m, 8H), 1.26 (m, 3H), 1.02 (dd, J=19.3, 6.7 Hz, 6H). LCMS [M+H]$^+$=620.63.

Example 93

Compound 93

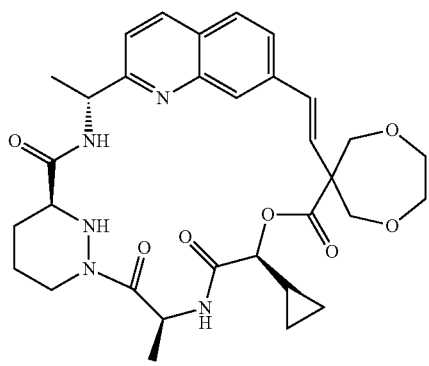 [SMILES: C[C@@H]1NC(=O)[C@H](C2CC2)OC(=O)C2(/C=C/c3ccc4ccc(nc4c3)[C@@H](C)NC(=O)[C@@H]3CCCN(N3)C1=O)COCCOC2]

Compound 93a. (S)-4-Benzyl-3-(2-cyclopropyl-acetyl)-oxazolidin-2-one

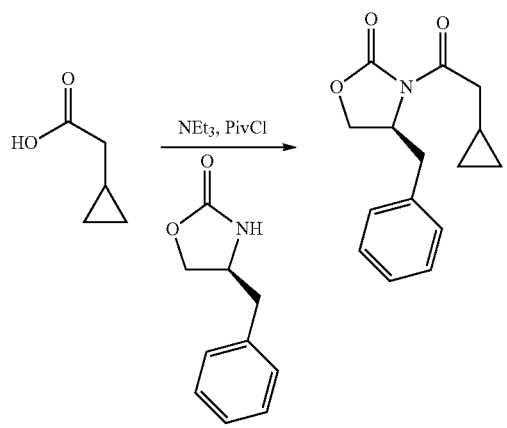

A cooled (−40° C.) solution of cyclopropylacetic acid (5.13 g, 51.250 mmol) in anhydrous tetrahydrofuran (150 mL) was subsequently treated with triethylamine (21.4 mL, 153.75 mmol) and trimethylacetyl chloride (6.9 mL, 56.375 mmol). After stirring at −40° C. for 1 h, the mixture was treated with (S)-4-benzyl-oxazolidin-2-one (9.99 g, 56.375 mmol) and lithium chloride (2.39 g, 56.375 mmol). The mixture was allowed to slowly warm to room temperature and after stirring at room temperature for 22 h, the reaction was partitioned between dichloromethane and half-saturated ammonium chloride. The aqueous layer was extracted with dichloromethane. The organics were combined, filtered through a phase separator and the volatiles were removed in vacuo. The residue was purified by silica gel chromatography using a 100 g Isolute cartridge eluted with a continuous gradient of iso-hexanes/ethyl acetate 1:0 to 9:1 to afford the title compound (11.63 g, 87%) as a colorless oil. $^1$H NMR (300 MHz, CDCl$_3$) δ 0.19-0.32 (m, 2H), 0.56-0.69 (m, 2H), 1.10-1.24 (m, 1H), 2.76-2.87 (m, 2H), 2.96 (dd, J=16.9, 6.9 Hz, 1H), 3.34 (dd, J=13.2, 3.3 Hz, 1H), 4.15-4.29 (m, 2H), 4.66-4.77 (m, 1H), 7.20-7.40 (m, 5H). LCMS (m/z) 282.1 [M+Na], Tr=2.78 min.

Compound 93b. (S)-4-Benzyl-3-((S)-2-cyclopropyl-2-hydroxy-acetyl)-oxazolidin-2-one

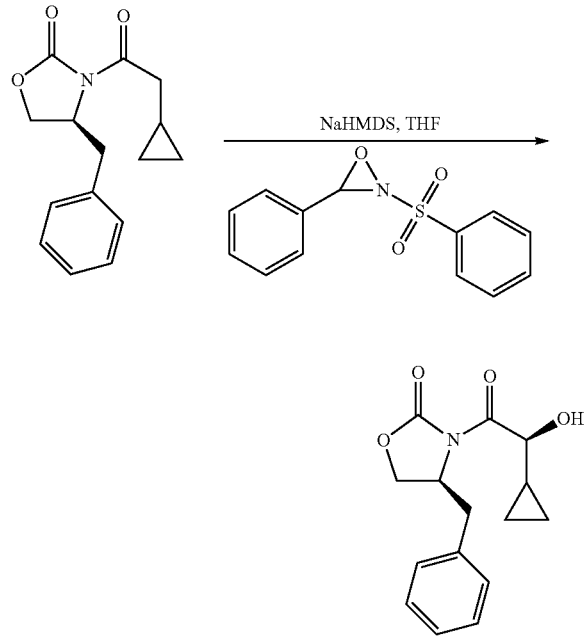

A cooled (−78° C.) solution of sodium bis(trimethylsilyl) amide (0.6 M in toluene, 65 mL, 38.918 mmol) was diluted with anhydrous tetrahydrofuran (100 mL) and treated with a solution of (S)-4-benzyl-3-(2-cyclopropyl-acetyl)-oxazolidin-2-one (9.174 g, 35.380 mmol) in anhydrous tetrahydrofuran (50 mL). After stirring at −78° C. for 45 min, the mixture was treated with a solution of 2-benzenesulfonyl-3-phenyl-oxaziridine (11.064 g, 42.456 mmol) in anhydrous tetrahydrofuran (50 mL). After stirring at −78° C. for 55 min, the reaction was quenched with acetic acid (10.1 mL, 176.9 mmol) and allowed to warm to room temperature. The mixture was quenched with sodium bicarbonate solution (300 mL) and poured over dichloromethane/iso-hexanes (3:1, 400 mL). The aqueous layer was extracted with dichloromethane and the organics were combined, washed with saturated sodium thiosulfate, hydrochloric acid (1 M, 300 mL), water and filtered through a phase separator. The volatiles were removed in vacuo and the residue was purified by silica gel chromatography using a 100 g Isolute cartridge eluted with a continuous gradient of iso-hexanes/ethyl acetate 1:0 to 7:3 followed by silica gel chromatography using a 100 g Isolute cartridge eluted with a continuous gradient of iso-hexanes/ethyl acetate 1:0 to 4:1 to afford the title compound (7.922 g, 81%) as a colorless oil. $^1$H NMR (300 MHz, CDCl$_3$) δ 0.42-0.65 (m, 4H), 1.25-1.38 (m, 1H), 2.88 (dd, J=13.4, 9.6 Hz, 1H), 3.35 (dd, J=13.4, 3.4 Hz, 1H), 3.44 (d, J=8.2 Hz, 1H), 4.25-4.37 (m, 2H), 4.67-4.72 (m, 1H), 4.80 (dd, J=8.0, 6.0 Hz, 1H), 7.21-7.41 (m, 5H). LCMS (m/z) 298.1 [M+Na], Tr=2.27 min.

Compound 93c. (S)-4-Benzyl-3-((S)-2-cyclopropyl-2-triisopropylsilanyloxy-acetyl)-oxazolidin-2-one

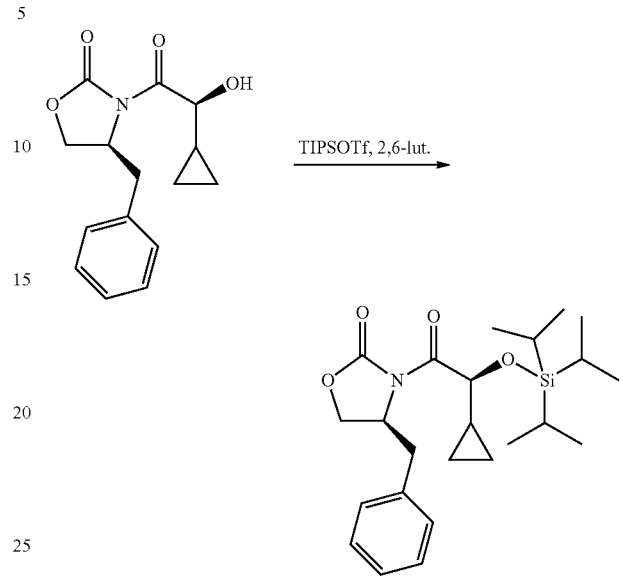

A cooled (0° C.) solution of (S)-4-benzyl-3-((S)-2-cyclopropyl-2-hydroxy-acetyl)-oxazolidin-2-one (4.137 g, 15.026 mmol) in dichloromethane (60 mL) was subsequently treated with 2,6-lutidine (3.5 mL, 30.052 mmol) and triisopropylsilyl trifluoromethanesulfonate (6.1 mL, 22.539 mmol). After stirring at room temperature for 1 h, the reaction was quenched with pH 4 buffer (phthalate). The aqueous layer was extracted with dichloromethane. The organics were combined, filtered through a phase separator and the volatiles were removed in vacuo. The residue was purified by silica gel chromatography using a 100 g Isolute cartridge eluted with a continuous gradient of iso-hexanes/diethyl ether 1:0 to 9:1 to afford the title compound (5.28 g, 81%) as a colorless oil. $^1$H NMR (300 MHz, CDCl$_3$) δ 0.40-0.49 (m, 2H), 0.53-0.62 (m, 1H), 0.63-0.71 (m, 1H), 1.02-1.18 (m, 21H), 1.20-1.34 (m, 1H), 2.66 (dd, J=13.1, 10.5 Hz, 1H), 3.49 (dd, J=13.1, 3.4 Hz, 1H), 4.17-4.27 (m, 2H), 4.63-4.73 (m, 1H), 5.58 (d, J=5.1 Hz, 1H), 7.24-7.40 (m, 5H).

Compound 93d. (S)-Cyclopropyl-hydroxy-acetic acid

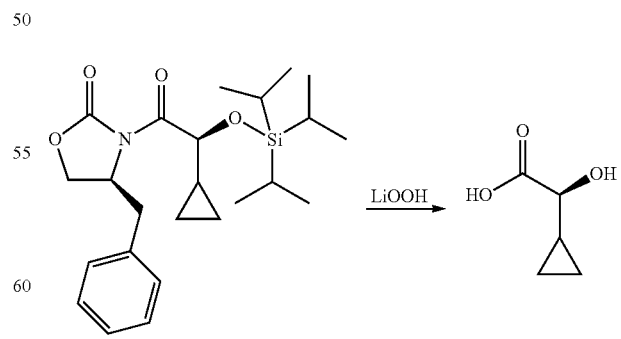

A cooled (0° C.) solution of (S)-4-benzyl-3-((S)-2-cyclopropyl-2-triisopropylsilanyloxy-acetyl)-oxazolidin-2-one (2.260 g, 5.235 mmol) in tetrahydrofuran/water (60 mL, 5:1) was subsequently treated with hydrogen peroxide (30% aqueous, 2.7 mL, 26.173 mmol) and lithium hydroxide monohydrate (439.2 mg, 10.470 mmol). After stirring at 0° C. for 4 h, the reaction was quenched with concentrated hydrochloric acid (~8 mL) and sodium metabisulfite (9.9 g). The aqueous layer was extracted with tetrahydrofuran/ethyl acetate (2×). The organics were combined, filtered through a phase separator and the volatiles were removed in vacuo. The residue was purified by silica gel chromatography using a 25 g Isolute cartridge eluted with a continuous gradient of dichloromethane/methanol 1:0 to 9:1 to afford the title compound (298.3 mg, 49%) as colorless needles. $^1$H NMR (300 MHz, CDCl$_3$) δ 0.45-0.71 (m, 4H), 1.14-1.29 (m, 1H), 3.87 (d, J=6.9 Hz, 1H).

Compound 93e. ((S)-2-{(S)-3-[(R)-1-(7-Bromo-quinolin-2-yl)-ethylcarbamoyl]-tetrahydro-pyridazin-1-yl}-1-methyl-2-oxo-ethyl)-carbamic acid tert-butyl ester

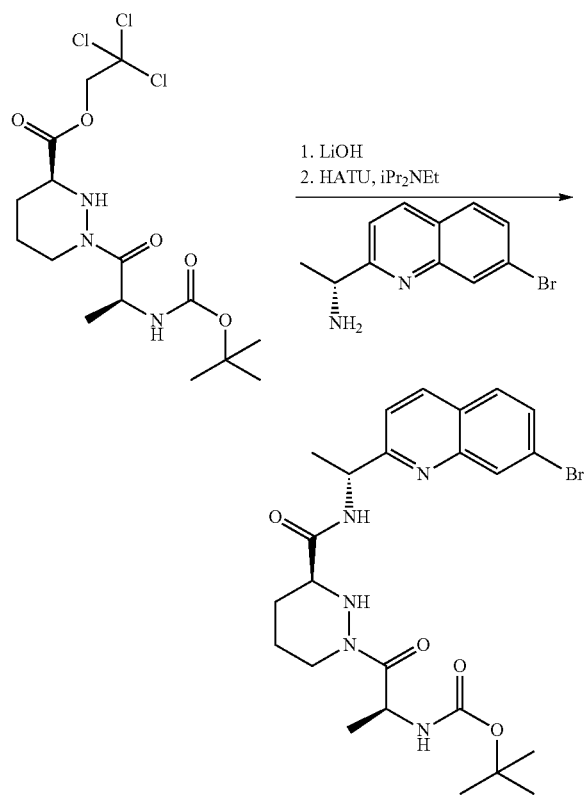

A cooled (0° C.) solution of (S)-1-((S)-2-tert-butoxycarbonylamino-propionyl)-hexahydro-pyridazine-3-carboxylic acid 2,2,2-trichloro-ethyl ester (3.007 g, 6.948 mmol) in tetrahydrofuran/water (60 mL, 5:1) was treated with lithium hydroxide monohydrate (874.4 mg, 20.844 mmol). After stirring at 0° C. for 40 minutes the reaction was quenched with hydrochloric acid (1 M, 50 mL). The aqueous layer was extracted with ethyl acetate (2×). The organics were combined, dried over anhydrous sodium sulfate, filtered and the volatiles were removed in vacuo. Residual trichlorethanol was azeotroped off with toluene (3×) to provide (S)-1-((S)-2-tert-butoxycarbonylamino-propionyl)-hexahydro-pyridazine-3-carboxylic acid as a white solid which was then combined with (R)-1-(7-bromo-quinolin-2-yl)-ethylamine hydrochloride (1.998 g, 6.948 mmol) and suspended in anhydrous acetonitrile (60 mL) and tetrahydrofuran (10 mL). The suspension was cooled to 0° C. and subsequently treated with N,N-diisopropylethylamine (6 mL, 34.740 mmol) and 1-[bis(dimethylamino)methylene]-1H-1,2,3-triazolo[4,5-b]pyridinium 3-oxide hexafluorophosphate (3.699 g, 9.727 mmol). After slowly warming to room temperature and stirring for 16 h, the reaction was quenched at 0° C. with hydrochloric acid (1 M, 70 mL). The aqueous layer was extracted with ethyl acetate (2×). The organics were combined, washed with a saturated solution of sodium bicarbonate, dried over anhydrous sodium sulfate, filtered and the volatiles were removed in vacuo. The residue was purified by silica gel chromatography using a 100 g Isolute cartridge eluted with a continuous gradient of iso-hexanes/ethyl acetate 1:0 to 1:4 to afford the title compound (3.702 g, 99%) as a white foam. $^1$H NMR (300 MHz, CDCl$_3$) δ 1.38 (d, J=6.9 Hz, 3H), 1.43 (s, 9H), 1.47-1.55 (m, 2H), 1.58 (d, J=6.9 Hz, 3H), 1.60-1.78 (m, 2H), 2.22-2.31 (m, 1H), 2.65-2.78 (m, 1H), 3.39-3.52 (m, 1H), 4.55 (d, J=13.4 Hz, 1H), 5.18-5.34 (m, 2H), 5.36-5.45 (m, 1H), 7.37 (d, J=8.5 Hz, 1H), 7.65 (dd, J=8.5, 1.6 Hz, 1H), 7.70 (d, J=8.5 Hz, 1H), 8.04 (d, J=6.5 Hz, 1H), 8.14 (d, J=8.5 Hz, 1H), 8.36 (s, 1H). LCMS (m/z) 536.1, 537.1 [M+H], Tr=2.58 min.

Compound 93f. (S)-1-[(S)-2-((S)-2-Cyclopropyl-2-hydroxy-acetylamino)-propionyl]-hexahydro-pyridazine-3-carboxylic acid [(R)-1-(7-bromo-quinolin-2-yl)-ethyl]-amide

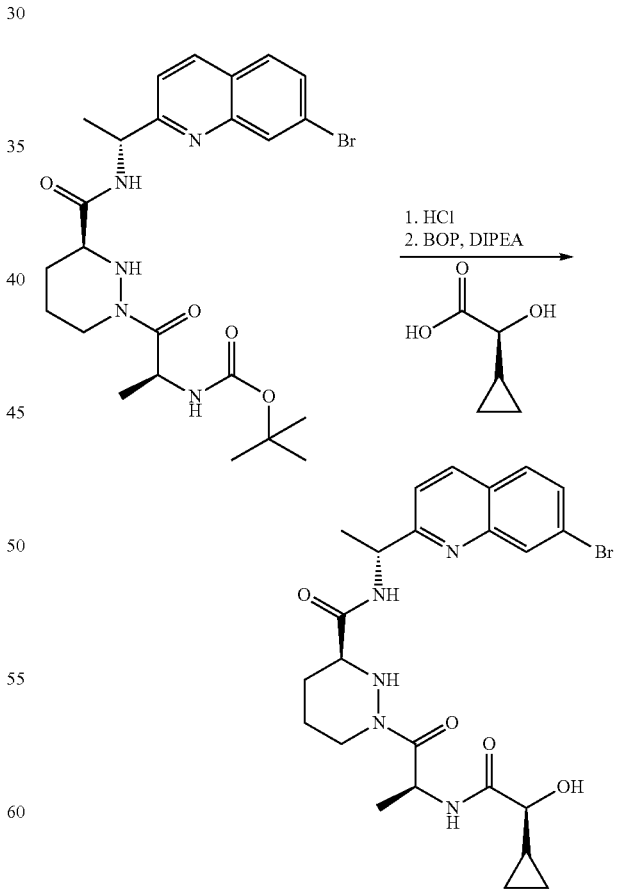

A cooled (0° C.) solution of (S)-2-{(S)-3-[(R)-1-(7-bromo-quinolin-2-yl)-ethylcarbamoyl]-tetrahydro-pyridazin-1-yl}-1-methyl-2-oxo-ethyl)-carbamic acid tert-butyl ester (802.2 mg, 1.501 mmol) in dichloromethane (20 mL) was treated with a solution of hydrogen chloride (1.9 mL, 7.505 mmol, 4 M in 1,4-dioxane). After stirring at room temperature for 3 h, the volatiles were removed in vacuo. Residual water was azeotroped off with toluene to provide (S)-1-((S)-2-amino-propionyl)-hexahydro-pyridazine-3-carboxylic acid [(R)-1-(7-bromo-quinolin-2-yl)-ethyl]-amide hydrochloride as a white solid which was then combined with (S)-cyclopropyl-hydroxy-acetic acid (174.3 mg, 1.501 mmol) and dry acetonitrile (20 mL). This suspension was cooled to 0° C. and subsequently treated with N,N-diisopropylethylamine (0.79 mL, 4.503 mmol) and (benzotriazol-1-yloxy)tris(dimethylamino)phosphonium hexafluorophosphate (796.6 mg, 1.801 mmol). The reaction was slowly warmed to room temperature. After stirring for 16 h the reaction was quenched at 0° C. with hydrochloric acid (1 M, 40 mL) and diluted with dichloromethane. The aqueous layer was extracted with dichloromethane. The organics were washed with a saturated solution of sodium bicarbonate. The basic aqueous layer was extracted with dichloromethane. The organics were combined, filtered through a phase separator and the volatiles were removed in vacuo. The residue was purified by silica gel chromatography using a 50 g Isolute cartridge eluted with a continuous gradient of dichloromethane/methanol 1:0 to 95:5 to afford the title compound (393.0 mg, 49%) as a white solid. $^1$H NMR (300 MHz, CDCl$_3$) δ 0.43-0.72 (m, 4H), 1.03-1.15 (m, 1H), 1.47 (d, J=6.7 Hz, 3H), 1.59 (d, J=6.7 Hz, 3H), 1.64-1.78 (m, 2H), 1.93-2.03 (m, 1H), 2.23-2.33 (m, 1H), 2.65-2.77 (m, 1H), 3.44-3.58 (m, 2H), 3.62-3.75 (m, 2H), 3.80 (d, J=11.8 Hz, 1H), 4.49-4.59 (m, 1H), 5.28 (app pentet, J=6.7 Hz, 1H), 5.49 (app pentet, J=7.8 Hz, 1H), 7.20 (d, J=8.2 Hz, 1H), 7.40 (d, J=8.5 Hz, 1H), 7.64 (dd, J=8.7, 1.8 Hz, 1H), 7.70 (d, J=8.5 Hz, 1H), 8.15 (d, J=8.5 Hz, 1H), 8.48 (s, 1H). LCMS (m/z) 534.0 [M+H], Tr=2.07 min.

Compound 93g. 6-((E)-2-{2-[(R)-1-({(S)-1-[(S)-2-((S)-2-Cyclopropyl-2-hydroxy-acetylamino)-propionyl]-hexahydro-pyridazine-3-carbonyl}-amino)-ethyl]-quinolin-7-yl}-vinyl)-[1,4]dioxepane-6-carboxylic acid

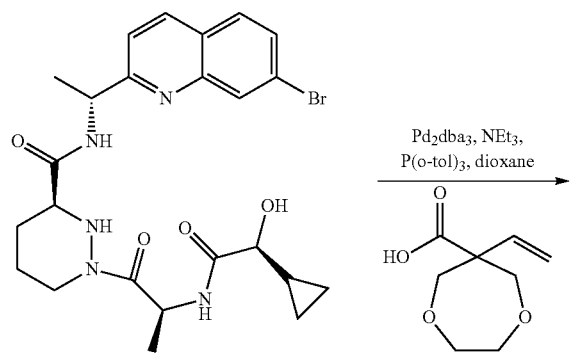

A solution of (S)-1-[(S)-2-((S)-2-cyclopropyl-2-hydroxy-acetylamino)-propionyl]-hexahydro-pyridazine-3-carboxylic acid [(R)-1-(7-bromo-quinolin-2-yl)-ethyl]-amide (244 mg, 0.459 mmol), 6-vinyl-[1,4]dioxepane-6-carboxylic acid 57d (79 mg, 0.459 mmol), triethylamine (140 mg, 192 μL, 1.38 mmol) and tri(o-tolyl)phosphine (28 mg, 0.092 mmol) in 1,4-dioxane (9 mL) was degassed with nitrogen for 5 min and then warmed to 50° C. under nitrogen with stirring. Tris(dibenzylideneacetone)dipalladium(0) (42 mg, 0.046 mmol) was added and the mixture was heated to 80° C. for 45 min and then allowed to cool. The suspension was filtered and evaporated to give crude title compound which was used in the next stage without further purification. LCMS (m/z) 624.2 [M+H], Tr=1.58 min.

Compound 93

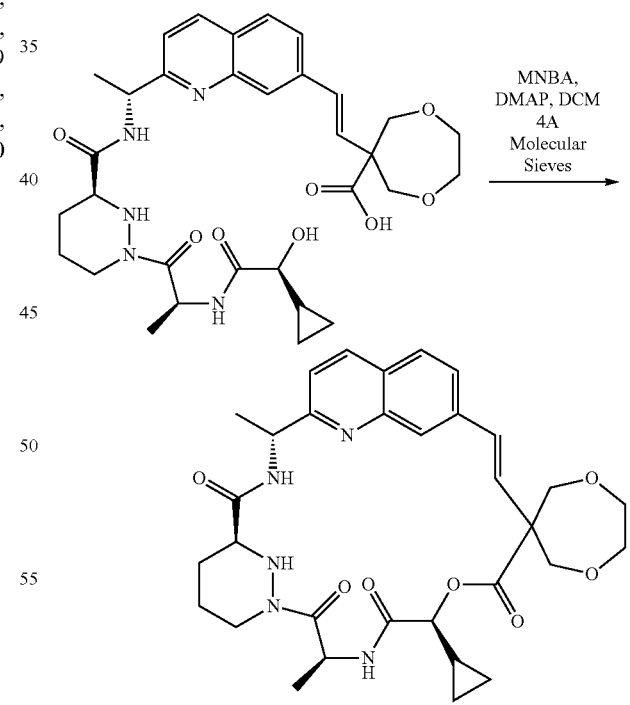

To a stirred mixture of powdered 4 Å molecular sieves (~1 g), 2-methyl-6-nitrobenzoic anhydride (316 mg, 0.918 mmol) and 4-(dimethylamino)-pyridine (224 mg, 1.84 mmol) in dichloromethane (138 mL), under nitrogen, was added a solution of 93g in dichloromethane (10 mL) over 3 h via syringe pump. The flask originally containing the crude acid was washed with dichloromethane (1 mL) and this was added to the reaction mixture over ca. 20 min. After the end of the addition, the reaction mixture was stirred for 1.5 h, filtered through Celite and washed successively with ice-cold saturated ammonium chloride solution, ice-cold saturated sodium bicarbonate solution, saturated brine and filtered through a hydrophobic frit and evaporated. The residue was purified by silica gel chromatography using a gradient of iso-hexanes/acetone 1:1 to 1:3 followed by reverse phase preparative HPLC using a gradient of acetonitrile/water 1:9 to 7:3 to give, after trituration with diethyl ether, the title compound (21 mg, 8% over 2 steps) as a white solid. $^1$H NMR (300 MHz, CD$_3$OD) δ 0.49-0.74 (m, 4H), 1.27-1.41 (m, 1H), 1.48-1.78 (m, 2H), 1.60 (d, J=6.9 Hz, 3H), 1.65 (d, J=7.3 Hz, 3H), 1.91-2.01 (m, 1H), 2.20-2.29 (m, 2H), 2.65-2.76 (m, 1H), 3.57-3.94 (m, 5H), 4.17 (d, J=12.7 Hz, 1H), 4.36 (d, J=12.7 Hz, 1H), 4.39-4.48 (m, 1H), 4.53 (d, J=12.7 Hz, 1H), 5.03-5.12 (m, 3H), 5.84 (q, J=7.1 Hz, 1H), 6.33 (d, J=16.5 Hz, 1H), 6.52 (d, J=16.5 Hz, 1H), 7.47 (d, J=8.5 Hz, 1H), 7.70 (dd, J=8.5, 1.6 Hz, 1H), 7.78 (br s, 1H), 7.86 (d, J=8.5 Hz, 1H), 8.26 (d, J=8.5 Hz, 1H). LCMS (m/z) 606.2 [M+H], Tr=2.08 min.

Example 94

Compound 94

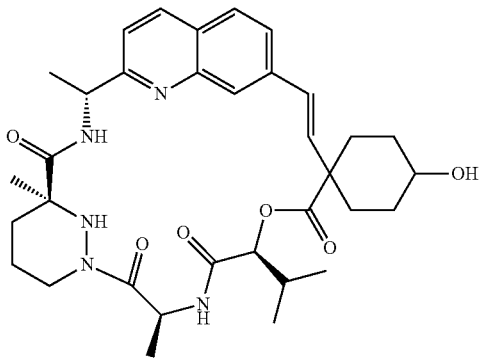 [SMILES: CC(C)[C@@H]1OC(=O)C2(/C=C/c3ccc4ccc(nc4c3)[C@@H](C)NC(=O)[C@]3(C)CCCN(N3)C(=O)[C@H](C)NC1=O)CCC(O)CC2]

Compound 94a.
3-Methyl-tetrahydro-pyridazine-1,2,3-tricarboxylic acid 1,2-di-tert-butyl ester 3-methyl ester

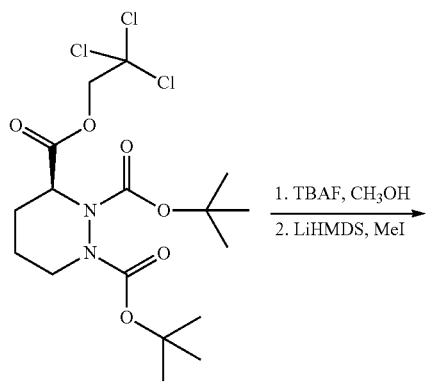

To a solution of (S)-tetrahydro-pyridazine-1,2,3-tricarboxylic acid 1,2-di-tert-butyl ester 3-(2,2,2-trichloro-ethyl) ester (5.0 g, 10.8 mmol) in tetrahydrofuran/methanol (50 mL, 1:1) containing 3 Å molecular sieves at 0° C. was added tetra n-butylammonium fluoride (22 mL, 22 mmol, 1 M in tetrahydrofuran). After stirring at room temperature for 24 h, the mixture was filtered through a pad of Celite and the filtrate was evaporated. The residue was partitioned between diethyl ether and saturated sodium hydrogen carbonate solution. The aqueous layer was extracted with diethyl ether. The organic extracts were combined and the solution was filtered through a hydrophobic frit and the solvent was evaporated. The residue was purified by silica gel chromatography eluting with iso-hexanes/ethyl acetate 20:1 to 3:2 to afford (S)-tetrahydro-pyridazine-1,2,3-tricarboxylic acid 1,2-di-tert-butyl ester 3-methyl ester (3.0 g, 82%) as a colorless oil and as a mixture of rotamers. LCMS (m/z) 345.1 [M+H], Tr=2.78 min. A solution of (S)-tetrahydro-pyridazine-1,2,3-tricarboxylic acid 1,2-di-tert-butyl ester 3-methyl ester (3.0 g, 8.72 mmol) in tetrahydrofuran (20 mL) at −78° C. was treated with lithium bis(trimethylsilyl)amide (13 mL, 13.0 mmol, 1 M in tetrahydrofuran). After stirring at −78° C. for 1 h, the mixture was treated with iodomethane (1.4 mL, 22.5 mmol). The reaction mixture was stirred at −78° C. for 1 h, then at 0° C. for 1 h and at room temperature for 1 h. The reaction mixture was re-cooled to 0° C. and quenched with water. The aqueous phase was extracted with dichloromethane (2×) and the organic solution was passed through a hydrophobic frit and the solvent was evaporated. The residue was purified by silica gel chromatography eluting with a gradient of iso-hexanes/ethyl acetate 4:1 to 0:1 to afford the title compound (1.62 g, 52%) as a colorless oil. $^1$H NMR (300 MHz, CDCl$_3$) δ 1.41-1.52 (m, 18H), 1.53-1.67 (m, 4H), 1.71-1.99 (m, 3H), 3.17-3.51 (m, 1H), 3.70-3.81 (m, 3H), 3.90-4.21 (m, 1H). LCMS (m/z) 359.0 [M+H], Tr=2.90 min.

Compound 94b. 3-[(R)-1-(7-Bromo-quinolin-2-yl)-ethylcarbamoyl]-3-methyl-tetrahydro-pyridazine-1,2-dicarboxylic acid di-tert-butyl ester

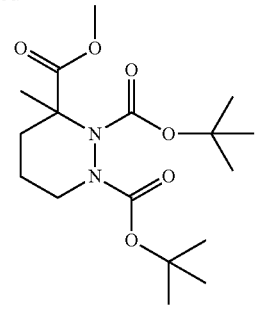

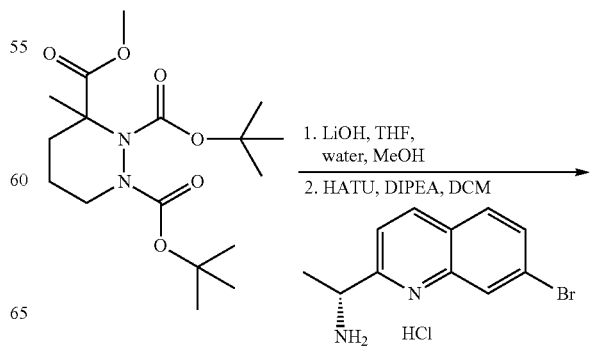

Compound 94c. ((S)-2-{3-[(R)-1-(7-Bromo-quinolin-2-yl)-ethylcarbamoyl]-3-methyl-tetrahydro-pyridazin-1-yl}-1-methyl-2-oxo-ethyl)-carbamic acid tert-butyl ester

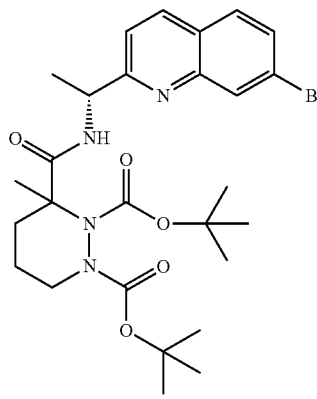

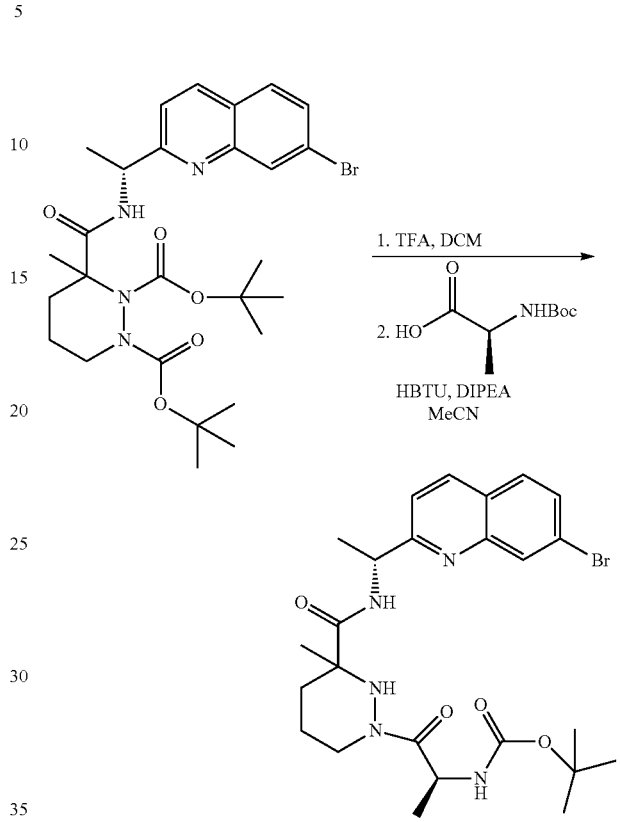

To a solution of 3-methyl-tetrahydro-pyridazine-1,2,3-tricarboxylic acid 1,2-di-tert-butyl ester 3-methyl ester (1.62 g, 4.52 mmol) in tetrahydrofuran/water/methanol (50 mL, 5:1:1) at 0° C. was added lithium hydroxide hydrate (2.2 g, 52.3 mmol). The reaction mixture was stirred at 0° C. for 1 h and then at room temperature for 1 h. The reaction mixture was heated at 40° C. for 19 h then cooled to room temperature and the solvent was evaporated. The residue was partitioned between ethyl acetate and water and the mixture was acidified to pH 5 with hydrochloric acid (1 M). The organic phase was separated and the aqueous phase was extracted with ethyl acetate. The combined organic extracts were dried over anhydrous magnesium sulfate, filtered and the solvent was evaporated. The residue was dissolved in toluene and the solvent was evaporated to give 3-methyl-tetrahydro-pyridazine-1,2,3-tricarboxylic acid 1,2-di-tert-butyl ester as a yellow oil (1.47 g, 95%). LCMS (m/z) 343.1 [M−H], Tr=2.36 min. To a solution of 3-methyl-tetrahydro-pyridazine-1,2,3-tricarboxylic acid 1,2-di-tert-butyl ester (1.37 g, 4.0 mmol) in dichloromethane (30 mL) at 0° C. was added (R)-1-(7-bromo-quinolin-2-yl)-ethylamine hydrochloride (1.30 g, 4.5 mmol) and N,N-diisopropylethylamine (2.8 mL, 16.0 mmol) followed by (dimethylamino)-N,N-dimethyl(3H-[1,2,3]triazolo[4,5-b]pyridin-3-yloxy)methaniminium hexafluorophosphate (1.81 g, 4.76 mmol). The reaction mixture was stirred at 0° C. for 30 min and then at room temperature for 2 h. The reaction mixture was diluted with dichloromethane and washed with water. The layers were separated and the aqueous layer was extracted with dichloromethane. The combined organic extracts were passed through a hydrophobic frit and the solvent was evaporated. The residue was purified by silica gel chromatography eluting with a gradient of iso-hexanes/ethyl acetate 20:1 to 0:1 to afford the title compound (929 mg, 40%) as a yellow foam and as a mixture of diastereoisomers. LCMS (m/z) 577.3, 579.2 [M+H], Tr=3.72 min.

To a solution of 3-[(R)-1-(7-bromo-quinolin-2-yl)-ethylcarbamoyl]-3-methyl-tetrahydro-pyridazine-1,2-dicarboxylic acid di-tert-butyl ester (925 mg, 1.6 mmol) in dichloromethane (10 mL) at 0° C. was added trifluoroacetic acid (3 mL). The reaction mixture was stirred at 0° C. for 30 min and then at room temperature for 36 h. The reaction mixture was concentrated at reduced pressure and the residue was co-evaporated with toluene (3×) to give 3-methyl-hexahydro-pyridazine-3-carboxylic acid [(R)-1-(7-bromo-quinolin-2-yl)-ethyl]-amide bis-trifluoroacetate salt (1.6 mmol) as a light brown foam. LCMS (m/z) 377.3, 379.2 [M+H], Tr=1.18 min. To a solution of (S)-2-tert-butoxycarbonylamino-propionic acid (303 mg, 1.6 mmol) in anhydrous acetonitrile (12 mL) at 0° C. was added O-(benzotriazol-1-yl)-N,N,N',N'-tetramethyluronium hexafluorophosphate (915 mg, 2.41 mmol) and N,N-diisopropylethylamine (1.5 mL, 8.42 mmol). The reaction mixture was stirred at 0° C. for 15 min and then treated with a solution of [(R)-1-(7-bromo-quinolin-2-yl)-ethyl]-amide bis-trifluoroacetate salt (1.6 mmol) in anhydrous acetonitrile (8 mL). The reaction mixture was allowed to warm to room temperature and was stirred for 16 h. The solvent was evaporated and the residue was partitioned between dichloromethane and water. The organic layer was separated and the aqueous layer was extracted with dichloromethane. The combined organic extracts were passed through a hydrophobic frit and the solvent was evaporated. The residue was purified by silica gel chromatography eluting with a gradient of iso-hexanes/ethyl acetate 20:1 to 0:1 to afford the title compound (857 mg, 40% over 2 steps) as a brown oil and as a mixture of diastereoisomers. LCMS (m/z) 548.0, 550.0 [M+H], Tr=2.68 min.

Compound 94d. 1-[(S)-2-((S)-2-Hydroxy-3-methyl-butyrylamino)-propionyl]-3-methyl-hexahydro-pyridazine-3-carboxylic acid [(R)-1-(7-bromo-quinolin-2-yl)-ethyl]-amide rated. The residue was purified by silica gel chromatography eluting with a gradient of ethyl acetate/methanol 1:0 to 20:1 to afford the title compound (745 mg, 39% over 2 steps) as a white foam and as a 1:4 mixture of diastereoisomers. LCMS (m/z) 548.0, 550.0 [M+H], Tr=2.21 min.

Compound 94e

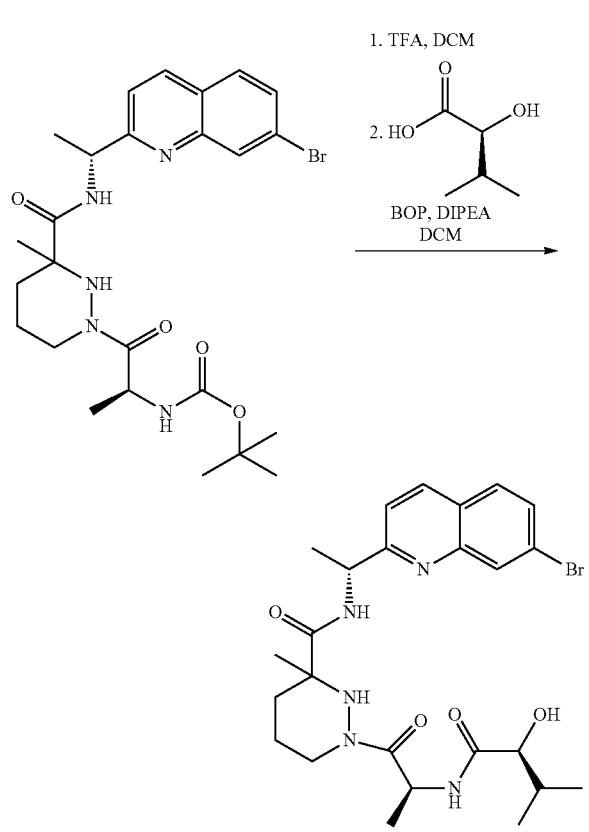

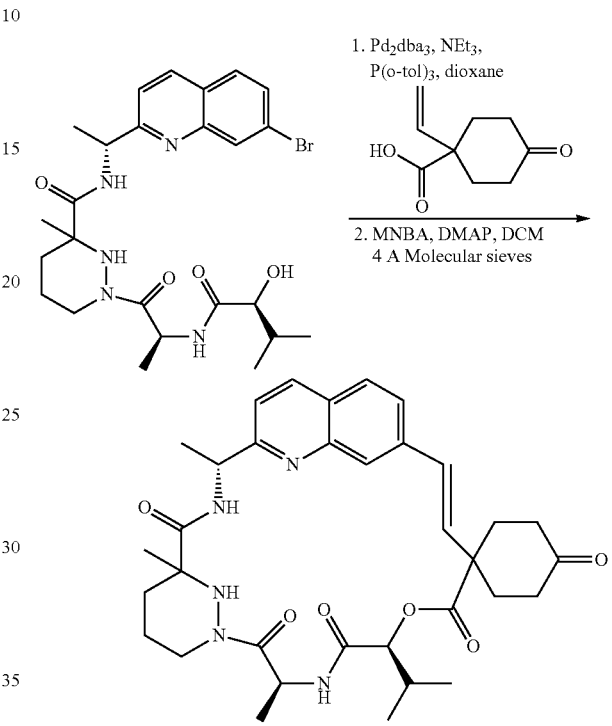

To a solution of ((S)-2-{3-[(R)-1-(7-bromo-quinolin-2-yl)-thylcarbamoyl]-3-methyl-tetrahydro-pyridazin-1-yl}-1-methyl-2-oxo-ethyl)-carbamic acid tert-butyl ester (1.92 g, 3.5 mmol) in dichloromethane (15 mL) at 0° C. was added trifluoroacetic acid (3 mL). The reaction mixture was allowed to warm to room temperature and then stirred for 4 h. The reaction mixture was concentrated and the residue was co-evaporated with toluene (3×) to give 1-((S)-2-amino-propionyl)-3-methyl-hexahydro-pyridazine-3-carboxylic acid [(R)-1-(7-bromo-quinolin-2-yl)-ethyl]-amide trifluoroacetate salt (3.5 mmol) as a brown oil. LCMS (m/z) 448.0, 450.0 [M+H], Tr=1.22 min. 1-((S)-2-Amino-propionyl)-3-methyl-hexahydro-pyridazine-3-carboxylic acid [(R)-1-(7-bromo-quinolin-2-yl)-ethyl]-amide trifluoroacetate salt (3.5 mmol) was dissolved in dichloromethane (20 mL) and the solution was cooled to 0° C. (S)-2-Hydroxy-3-methyl-butyric acid (458 mg, 3.8 mmol), N,N-diisopropylethylamine (5 mL, 28.0 mmol) and (benzotriazol-1-yloxy)tris(dimethylamino) phosphonium hexafluorophosphate (1.86 g, 4.2 mmol) were added. The reaction mixture was allowed to warm to room temperature and was stirred for 16 h. The solvent was evaporated and the residue was dissolved in ethyl acetate. The organic solution was washed with citric acid (10%), saturated sodium hydrogen carbonate solution and brine, dried over anhydrous magnesium sulfate and the solvent was evapo- A stirred solution of 1-[(S)-2-((S)-2-hydroxy-3-methyl-butyrylamino)-propionyl]-3-methyl-hexahydro-pyridazine-3-carboxylic acid [(R)-1-(7-bromo-quinolin-2-yl)-ethyl]-amide (164 mg, 0.3 mmol), 4-oxo-1-vinyl-cyclohexanecarboxylic acid (50 mg, 0.3 mmol), tri(o-tolyl) phosphine (18 mg, 0.06 mmol) and triethylamine (91 mg, 0.13 mL, 0.9 mmol) in 1,4-dioxane (10 mL) was degassed with nitrogen for 15 min. The solution was heated to 50° C. and tris(dibenzylideneacetone)dipalladium(0) (28 mg, 0.03 mmol) was added. The reaction mixture was heated at 80° C. for 1 h. The reaction mixture was cooled to room temperature and the mixture was filtered through a hydrophobic frit and the filtrate was evaporated to afford crude 1-((E)-2-{2-[(R)-1-({1-[(S)-2-((S)-2-hydroxy-3-methyl-butyrylamino)-propionyl]-3-methyl-hexahydro-pyridazine-3-carbonyl}-amino)-ethyl]-quinolin-7-yl}-vinyl)-4-oxo-cyclohexanecarboxylic acid (0.3 mmol) as a yellow gum and as a mixture of diastereoisomers. LCMS (m/z) 636.2 [M+H], Tr=1.65 min. A solution of 2-methyl-6-nitrobenzoic anhydride (206 mg, 0.6 mmol) and 4-(dimethylamino)-pyridine (146 mg, 1.2 mmol) in dichloromethane (200 mL) containing 4 Å molecular sieves (200 mg) was stirred at room temperature under nitrogen. A solution of crude 1-((E)-2-{2-[(R)-1-({1-[(S)-2-((S)-2-hydroxy-3-methyl-butyrylamino)-propionyl]-3-methyl-hexahydro-pyridazine-3-carbonyl}-amino)-ethyl]-quinolin-7-yl}-vinyl)-4-oxo-cyclohexanecarboxylic acid (0.3 mmol) in dichloromethane (5 mL) was added dropwise over 4 h and the reaction mixture was stirred at room temperature for 18 h. The reaction mixture was filtered through Celite and the solution was partially evaporated to a volume of ~30 mL. The solution was washed with ice-cold saturated ammonium chloride solution, ice-cold saturated sodium bicarbonate solution and brine. The organic solution was filtered through a hydrophobic frit and the filtrate was evaporated. The residue was purified by silica gel chromatography eluting with a gradient of iso-hexanes/ethyl acetate 1:1 to 0:1 to afford the title compound (77 mg, 41%) as a white solid and as a mixture of diastereoisomers. LCMS (m/z) 618.2 [M+H], Tr=2.38 min.

Compound 94

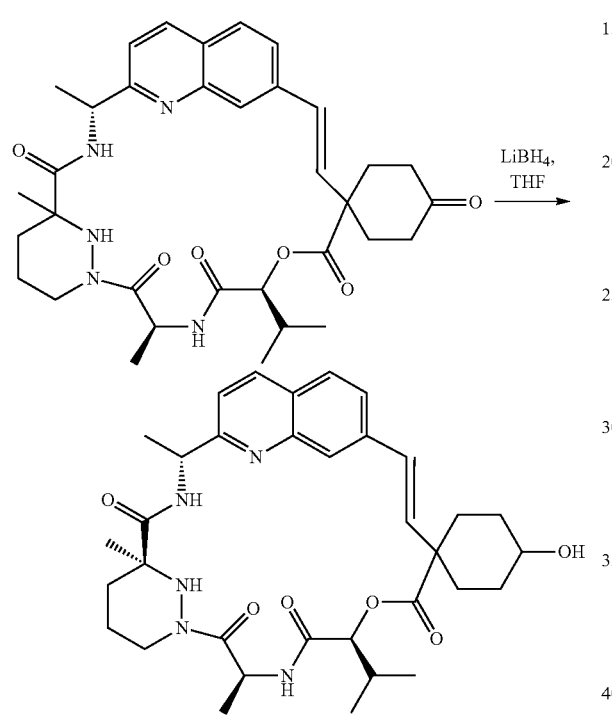

A solution of compound 94e (41 mg, 0.066 mmol) in anhydrous tetrahydrofuran (4 mL) was stirred at −78° C. under nitrogen. Lithium borohydride solution (2 M in tetrahydrofuran, 0.15 mL, 0.23 mmol) was added and the reaction mixture was stirred at −78° C. for 30 min. Hydrochloric acid (2 M) and ethyl acetate were added and the reaction mixture was warmed to room temperature. The organic layer was separated and the aqueous layer was extracted with ethyl acetate. The organic extracts were combined and washed with brine. The organic solution was filtered through a hydrophobic frit and the filtrate was evaporated. The orange residue was purified by reverse phase preparative HPLC eluting with acetonitrile (modified with 0.1% formic acid)/water (modified with 0.1% formic acid) 3:7. Fractions containing the product were combined and evaporated. The residue was dissolved in ethyl acetate and the solution was washed with a small volume of saturated sodium hydrogen carbonate solution and brine. The organic solution was filtered through a hydrophobic frit and the filtrate was evaporated to afford the title compound (12 mg, 29%) as a white solid and as a 9:1 mixture of diastereoisomers. $^1$H NMR (300 MHz, CD$_3$OD) (peaks for major diastereoisomer) δ1.04 (d, J=6.5 Hz, 3H), 1.10 (d, J=6.7 Hz, 3H), 1.20-1.40 (m, 3H), 1.48 (s, 3H), 1.58 (d, J=7.1 Hz, 3H), 1.59 (d, J=7.3 Hz, 3H), 1.65-1.80 (m, 3H), 1.95-2.25 (m, 4H), 2.34-2.38 (m, 1H), 2.56-2.71 (m, 2H), 3.35-3.40 (m, 1H), 3.60-3.67 (m, 1H), 4.42-4.50 (m, 1H), 5.14 (q, J=7.2 Hz, 1H), 5.27 (d, J=7.4 Hz, 1H), 5.74 (q, J=7.1 Hz, 1H), 6.34 (d, J=16.3 Hz, 1H), 6.60 (d, J=16.3 Hz, 1H), 7.46 (d, J=8.5 Hz, 1H), 7.58 (d, J=8.3 Hz, 1H), 7.84 (d, J=8.3 Hz, 1H), 7.93 (br s, 1H), 8.26 (d, J=8.5 Hz, 1H). LCMS (m/z) 620.2 [M+H], Tr=2.17 min.

Example 95

Compound 95

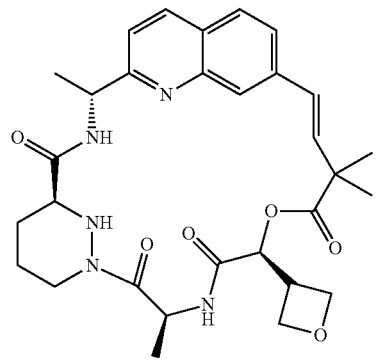 [SMILES: C[C@@H]1NC(=O)[C@H](C2COC2)OC(=O)C(C)(C)/C=C/c2ccc3ccc(nc3c2)[C@@H](C)NC(=O)[C@@H]2CCCN(N2)C1=O]

Compound 95a. Hydroxy-oxetan-3-yl-acetic acid ethyl ester

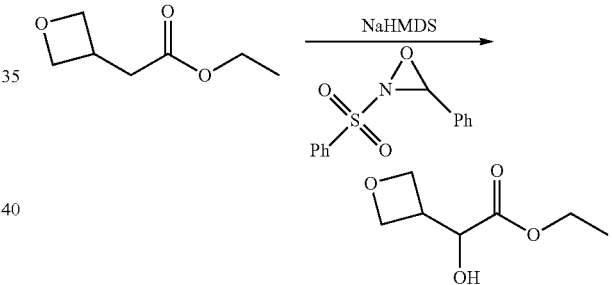

To a stirred solution of oxetan-3-yl-acetic acid ethyl ester (obtained from Activate Scientific GmbH), (1.04 g, 7.21 mmol) in anhydrous tetrahydrofuran (72 mL) at −78° C. under nitrogen was added dropwise sodium hexamethyldisilazide (0.6 M in toluene, 14.4 mL, 8.66 mmol) to give a yellow orange solution. The reaction mixture was stirred at −78° C. for 30 min and then a solution of 2-(phenylsulfonyl)-3-phenyl-oxaziridine (2.83 g, 10.8 mmol) in tetrahydrofuran (7 mL) was added over 2 min. The reaction mixture was stirred at −78° C. for 90 min and then saturated ammonium chloride solution (10 mL) was added via syringe. The reaction mixture was allowed to warm to ambient temperature and after 5 min further saturated ammonium chloride solution (10 mL) was added and then stirred at ambient temperature for 1 h. The reaction mixture was neutralised to pH 7 with hydrochloric acid (2 M) and the mixture diluted with water and extracted with ethyl acetate (4×). The combined organic extracts were washed with brine, dried over anhydrous magnesium sulfate, filtered and partially evaporated to about ~10 mL. The mixture was diluted with dichloromethane and the solids were filtered off, the filtrate was evaporated and the residue was purified by silica gel chromatography using a gradient of iso-hexanes/diethyl ether 1:0 to 1:3 to give the title compound (688 mg, 60%) as a white gum. $^1$H NMR (300 MHz, CDCl$_3$) δ 1.30 (t, J=7.2 Hz, 3H), 2.95 (d, J=5.1 Hz, 1H), 3.26-3.38 (m, 1H), 4.26 (q, J=7.1 Hz, 2H), 4.42 (dd, J=7.4, 5.1 Hz, 1H), 4.67-4.81 (m, 4H). LCMS (m/z) 161.2 [M+H] Tr=0.72 min Compound 95b. 2,2-Dimethyl-but-3-enoic acid ethoxycarbonyl-oxetan-3-yl-methyl ester

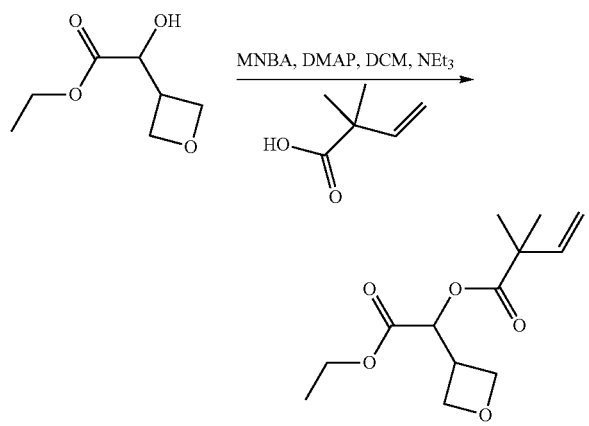

To a stirred solution of hydroxy-oxetan-3-yl-acetic acid ethyl ester (330 mg, 2.06 mmol), 2-methyl-6-nitrobenzoic anhydride (1.42 g, 4.12 mmol) and 4-dimethylamino pyridine (100 mg, 0.82 mmol) in dichloromethane (4 mL) was added a solution of 2,2-dimethyl-but-3-enoic acid (294 mg, 2.58 mmol) in dichloromethane (4 mL). The reaction mixture was stirred for 4 h and then evaporated. The residue was purified by silica gel chromatography using iso-hexanes/diethyl ether 4:1 to give the title compound (383 mg, 73%) as a white solid. $^1$H NMR (300 MHz, CDCl$_3$) δ 1.27 (t, J=7.1 Hz, 3H), 1.39 (s, 3H), 1.41 (s, 3H), 3.48-3.61 (m, 1H), 4.20 (q, J=7.1 Hz, 2H), 4.62-4.68 (m, 2H), 4.72-4.85 (m, 2H), 5.12-5.24 (m, 3H), 6.09 (dd, J=17.5, 10.6 Hz, 1H). LCMS (m/z) 257.1[M+H], Tr=2.31 min Compound 95c. 2,2-Dimethyl-but-3-enoic acid carboxy-oxetan-3-yl-methyl ester

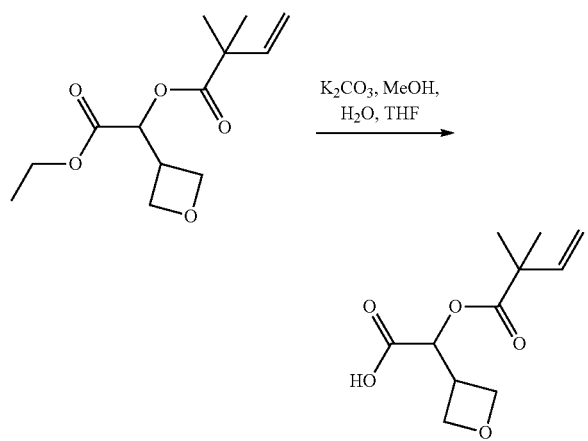

To a stirred solution of 2,2-dimethyl-but-3-enoic acid ethoxycarbonyl-oxetan-3-yl-methyl ester (207 mg, 0.808 mmol) in tetrahydrofuran (81 mL) was added a solution of potassium carbonate (123 mg, 0.888 mmol) in water (20.25 mL) followed by methanol (4.05 mL). The reaction mixture was heated to reflux for 7 h and then allowed to cool. Hydrochloric acid (2 M, 400 µL) was added (pH 7) and the solvents were evaporated. The residue was extracted with dichloromethane (2×) and the washes discarded. The aqueous was acidified with hydrochloric acid (2 M) to pH 5, extracted with dichloromethane (2×) and the combined organic extracts passed through a hydrophobic frit and evaporated. To the aqueous layer was added hydrochloric acid (about 5 drops) and the mixture was extracted with dichloromethane (2×) and the combined organic extracts passed through a hydrophobic frit, evaporated and combined with previous material to give the title compound (123 mg, 67%) as a yellow/green oil. $^1$H NMR (300 MHz, CDCl$_3$) δ 1.39 (s, 3H), 1.40 (s, 3H), 3.54-3.67 (m, 1H), 4.67-4.75 (m, 2H), 4.81-4.92 (m, 2H), 5.14 (d, J=10.9 Hz, 1H), 5.15-5.32 (m, 2H), 6.08 (dd, J=17.5, 10.5 Hz, 1H), 9.30 (br s, 1H). LCMS (m/z) 229.1 [M+H] Tr=1.67 min.

Compound 95d. (S)-1-((S)-2-Amino-propionyl)-hexahydro-pyridazine-3-carboxylic acid

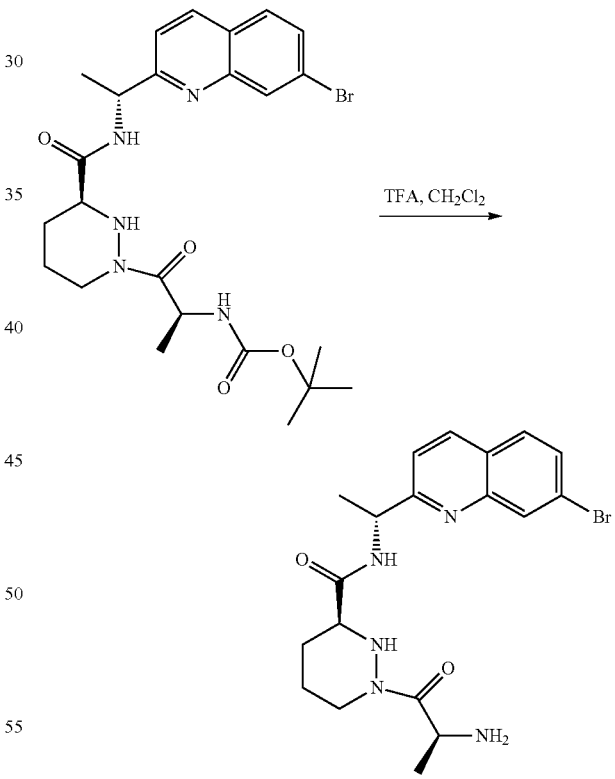

To a stirred solution of (S)-1-((S)-2-amino-propionyl)-hexahydro-pyridazine-3-carboxylic acid [(R)-1-(7-bromo-quinolin-2-yl)-ethyl]-amide (330 mg, 0.618 mmol) in dichloromethane (10 mL) at 0° C. was added trifluoroacetic acid (3.3 mL) and the reaction mixture stirred for 1 hour and then evaporated. The residue was dissolved in dichloromethane and washed with saturated bicarbonate solution (2×), the aqueous extracts washed with dichloromethane and the combined organic extracts passed through a hydrophobic frit and evaporated to give a yellow foam (232 mg) that was carried through to the next step directly.

Compound 95e. 2,2-Dimethyl-but-3-enoic acid ((S)-2-{(S)-3-[(R)-1-(7-bromo-quinolin-2-yl)-ethylcarbamoyl]-tetrahydro-pyridazin-1-yl}-1-methyl-2-oxo-ethylcarbamoyl)-oxetan-3-yl-methyl ester

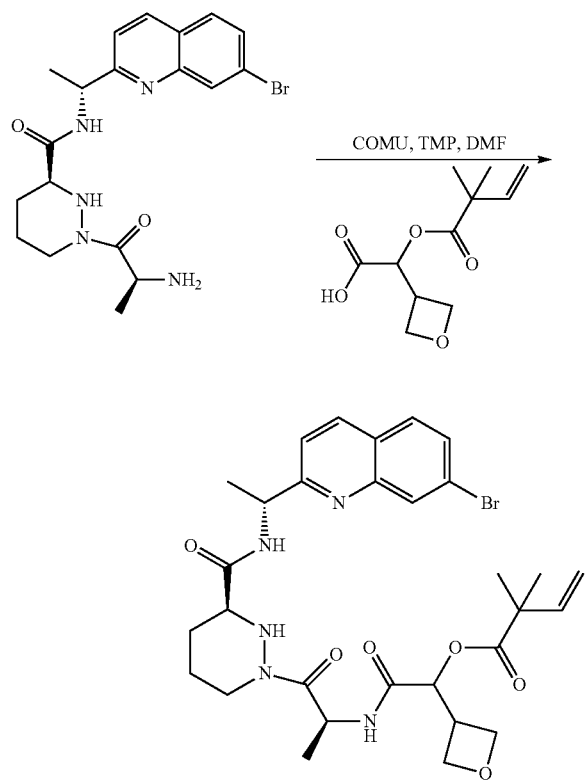

A stirred solution of (S)-1-((S)-2-amino-propionyl)-hexahydro-pyridazine-3-carboxylic acid [(R)-1-(7-bromo-quinolin-2-yl)-ethyl]-amide (141 mg, 0.618 mmol) and 2,2-dimethyl-but-3-enoic acid carboxy-oxetan-3-yl-methyl ester (315 mg, 0.725 mmol) in anhydrous N,N-dimethylformamide (10 mL) was cooled to 0° C. under nitrogen. 2,2,6,6-Tetramethylpiperidine (261 mg, 313 µL, 1.85 mmol) was added, rapidly followed by (1-cyano-2-ethoxy-2-oxoethylidenaminooxy)dimethylamino-morpholino-carbenium hexafluorophosphate (371 mg, 0.865 mmol). The reaction mixture was allowed to warm to room temperature and stirred for 15 h. The reaction mixture was diluted with dichloromethane and washed with saturated ammonium chloride solution (2×), saturated sodium bicarbonate solution (2×), the organic layer was filtered through a phase-separator and evaporated. The residue was purified by silica gel chromatography using a gradient of iso-hexanes/ethyl acetate 1:0 to 0:1 to give the title compound (167 mg, 42%) as a yellow/brown foam and as an approximate 1:1 mixture of diastereoisomers. LCMS (m/z) 644.2, 646.1[M+H], Tr=2.63 min.

Compound 95

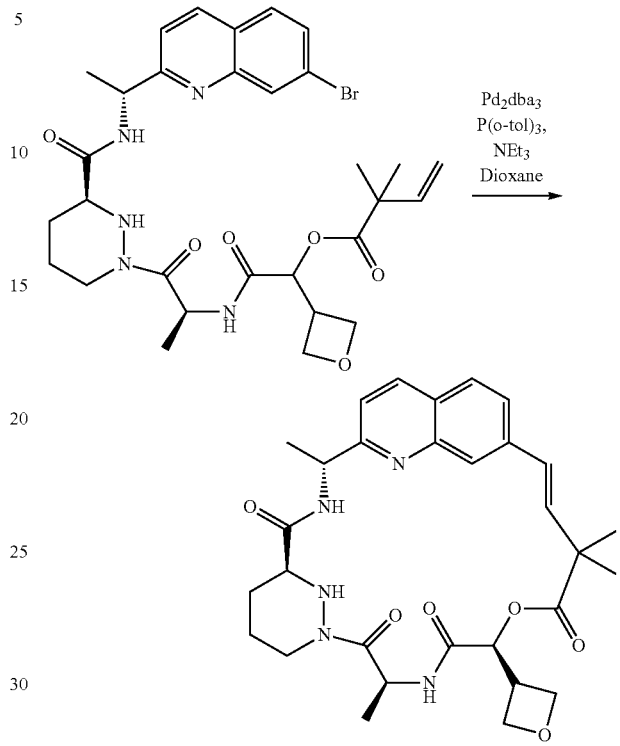

A solution of 2,2-dimethyl-but-3-enoic acid ((S)-2-{(S)-3-[(R)-1-(7-bromo-quinolin-2-yl)-ethylcarbamoyl]-tetrahydro-pyridazin-1-yl}-1-methyl-2-oxo-ethylcarbamoyl)-oxetan-3-yl-methyl ester (167 mg, 0.259 mmol), triethylamine (79 mg, 108 µL, 0.777 mmol) and tri(o-tolyl)phosphine (16 mg, 0.052 mmol) in 1,4-dioxane (86 mL) was degassed with nitrogen for 10 min and then warmed to 50° C. under nitrogen with stirring. Tris(dibenzylideneacetone)dipalladium(0) (24 mg, 0.026 mmol) was added and the reaction mixture was heated to 80° C. for 90 min and then more tri(o-tolyl)phosphine (32 mg, 0.104 mmol) and tris(dibenzylideneacetone)dipalladium(0) (48 mg, 0.052 mmol) were added. The reaction mixture was heated to 80° C. for 2 h, and more tri(o-tolyl)phosphine (16 mg, 0.52 mmol) and tris(dibenzylideneacetone)dipalladium(0) (24 mg, 0.026 mmol) were added. After heating at 80° C. for 1.5 h, more tri(o-tolyl)phosphine (16 mg, 0.52 mmol) and tris(dibenzylideneacetone)dipalladium(0) (24 mg, 0.026 mmol) were added. After heating at 80° C. for 30 min, the mixture was cooled and filtered over Celite and the filtrate was evaporated. The residue was purified by reverse phase preparative HPLC using a gradient of acetonitrile/water 1:9 to 7:3 to give the title compound (15.6 mg, 11%) as a yellow solid. $^1$H NMR (300 MHz, CD$_3$OD) δ 1.46 (s, 3H), 1.50-1.73 (m, 1H), 1.56 (s, 3H), 1.59 (d, J=6.7 Hz, 3H), 1.64 (d, J=7.2 Hz, 3H), 1.90-2.01 (m, 1H), 2.23-2.32 (m, 1H), 2.63-2.74 (m, 1H), 3.47-3.62 (m, 2H), 4.37-4.45 (m, 1H), 4.64 (t, J=6.5 Hz, 1H), 4.72-4.82 (m, 4H), 5.09 (q, J=6.7 Hz, 1H), 5.75 (q, J=7.4 Hz, 1H), 5.82 (d, J=6.9 Hz, 1H), 6.38 (d, J=16.3 Hz, 1H), 6.60 (d, J=16.3 Hz, 1H), 7.45 (d, J=8.5 Hz, 1H), 7.61 (dd, J=8.5, 1.6 Hz, 1H), 7.81 (br s, 1H), 7.85 (d, J=8.5 Hz, 1H), 8.26 (d, J=8.5 Hz, 1H). LCMS (m/z) 564.2 [M+H], Tr=2.16 min.

Example 96

Compound 96

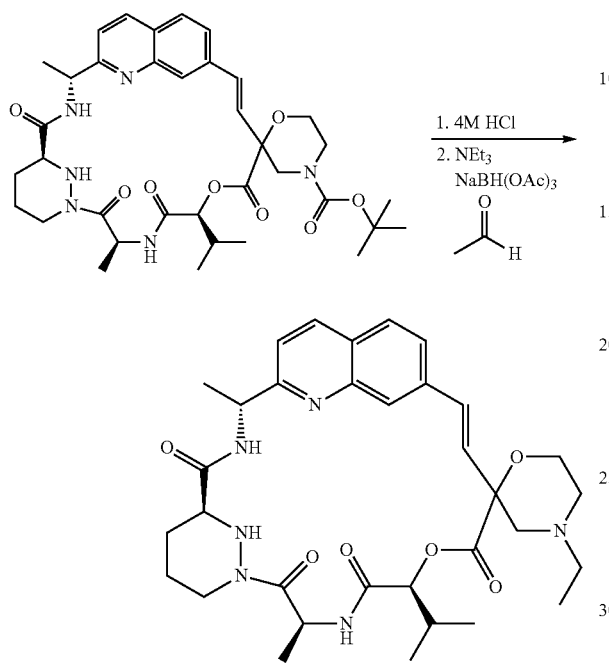

A cooled (0° C.) solution of compound 45 (63.0 mg, 0.091 mmol) in dichloromethane (10 mL) was treated with a solution of hydrogen chloride (4 M) in 1,4-dioxane (0.12 mL, 0.455 mmol). After stirring at room temperature for 6 days, dichloromethane (10 mL) and hydrogen chloride (4 M) in 1,4-dioxane (0.12 mL, 0.455 mmol) were added. After stirring for 4 h at room temperature, the volatiles were removed in vacuo and the residual water was azeotroped off with toluene to provide a white solid which was suspended in dichloromethane (5 mL) and the mixture was subsequently treated with triethylamine (0.02 mL, 0.136 mmol) and acetaldehyde (0.01 mL, 0.182 mmol). After stirring at room temperature for 30 min, the reaction mixture was treated with sodium triacetoxyborohydride (38.6 mg, 0.182 mmol). After stirring for 1 h at room temperature the reaction mixture was quenched with a few drops of saturated sodium bicarbonate and filtered through a phase separator. The volatiles were removed in vacuo and the residue was purified by reverse phase preparative HPLC using a gradient of acetonitrile/water 5:95 to 3:7 modified with 0.1% formic acid. After evaporation of the volatiles, the white solid was partitioned between ethyl acetate and a saturated solution of sodium bicarbonate. The organics were filtered through a phase separator and the volatiles were removed in vacuo to provide the title compound (8.3 mg, 15% over 2 steps) as a white solid. $^1$H NMR (300 MHz, CD$_3$OD): δ 1.02-1.18 (m, 9H), 1.22-1.33 (m, 1H), 1.51-1.73 (m, 7H), 1.89-2.00 (m, 1H), 2.11 (d, J=11.6 Hz, 1H), 2.16-2.36 (m, 3H), 2.39-2.57 (m, 2H), 2.61-2.73 (m, 1H), 2.74-2.82 (m, 1H), 3.54-3.67 (m, 2H), 3.87-4.02 (m, 2H), 4.38-4.47 (m, 1H), 4.99 (d, J=12.0 Hz, 1H), 5.05-5.14 (m, 2H), 5.79 (q, J=7.4 Hz, 1H), 6.13 (d, J=16.3 Hz, 1H), 6.92 (d, J=16.3 Hz, 1H), 7.46 (d, J=8.5 Hz, 1H), 7.60 (dd, J=8.5, 1.6 Hz, 1H), 7.86 (d, J=8.5 Hz, 1H), 7.91 (s, 1H), 8.26 (d, J=8.5 Hz, 1H). LCMS (m/z) 621.3 [M+H], Tr=1.20 min.

Example 97

Compound 97

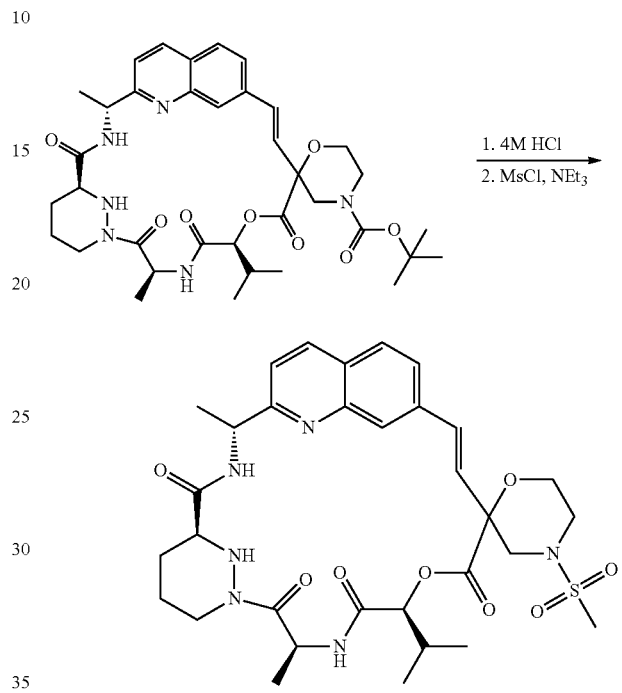

A cooled (0° C.) solution of compound 45 (85.3 mg, 0.123 mmol) in dichloromethane (10 mL) was treated with a solution of hydrogen chloride (4 M) in 1,4-dioxane (0.31 mL, 1.231 mmol). After stirring at room temperature for 2 days, more hydrogen chloride (4 M) in 1,4-dioxane (0.3 mL, 1.2 mmol) was added. After stirring for 1.5 h at room temperature, the volatiles were removed in vacuo and the residual water was azeotroped off with toluene to provide a white solid which was suspended in dichloromethane (5 mL) and the mixture was subsequently treated with triethylamine (0.04 mL, 0.246 mmol) and methanesulfonyl chloride (0.01 mL, 0.148 mmol). After stirring at room temperature for 30 min, the reaction mixture was treated with sodium triacetoxyborohydride (38.6 mg, 0.182 mmol). After stirring for 1 h at room temperature the reaction mixture was quenched with a saturated sodium bicarbonate solution. The aqueous layer was extracted with dichloromethane. The organics were combined and filtered through a phase separator. The volatiles were removed in vacuo and the residue was purified by reverse phase preparative HPLC using a gradient of acetonitrile/water 5:95 to 1:0 to provide the title compound (14.7 mg, 18% over 2 steps) as a white solid. $^1$H NMR (300 MHz, CD$_3$OD) δ 1.05-1.12 (m, 6H), 1.52-1.73 (m, 8H), 1.91-2.00 (m, 1H), 2.17-2.30 (m, 2H), 2.62-2.74 (m, 1H), 2.93 (s, 3H), 3.01 (d, J=11.8 Hz, 1H), 3.05-3.13 (m, 1H), 3.51-3.68 (m, 2H), 3.83-3.94 (m, 1H), 4.07-4.15 (m, 1H), 4.24-4.31 (m, 1H), 4.39-4.47 (m, 1H), 5.02 (d, J=11.8 Hz, 1H), 5.10 (q, J=6.7 Hz, 1H), 5.19 (d, J=8.7 Hz, 1H), 5.81 (q, J=7.3 Hz, 1H), 6.19 (d, J=16.3 Hz, 1H), 6.99 (d, J=16.3 Hz, 1H), 7.48 (d, J=8.5 Hz, 1H), 7.62 (dd, J=8.5, 1.6 Hz, 1H), 7.87 (d, J=8.5 Hz, 1H), 7.93 (s, 1H), 8.27 (d, J=8.2 Hz, 1H). LCMS (m/z) 671.3 [M+H], Tr=2.07 min.

Example 98

Compound 98

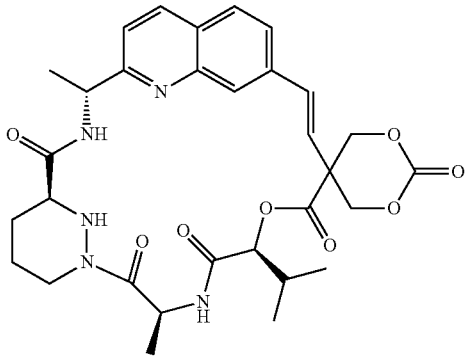 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)COC(=O)OC2]

Compound 98a.
2,2-Bis-hydroxymethyl-3-oxo-butyric acid tert-butyl ester

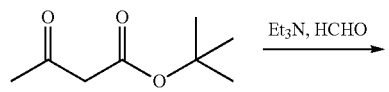

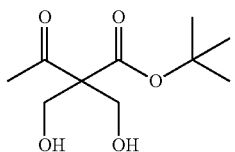

A solution of 3-oxo-butyric acid tert-butyl ester (15.8 g, 100 mmol) and aqueous formaldehyde (37% solution in water, 18 mL, 230 mmol) in 1,4-dioxane (50 mL) was stirred at 0° C. under nitrogen. A solution of triethylamine (505 mg, 0.7 mL, 5 mmol) in tetrahydrofuran (5 mL) was added dropwise and the reaction mixture was stirred at 40° C. for 1 h and then at room temperature for 20 h. The majority of the solvent was evaporated, water was added and the mixture was extracted with ethyl acetate. The organic extracts were combined and washed with brine. The organic solution was filtered through a hydrophobic frit and the filtrate was evaporated. The residue was purified by silica gel chromatography using a gradient of iso-hexanes/ethyl acetate 7:3 to 1:1 to afford 2,2-bis-hydroxymethyl-3-oxo-butyric acid tert-butyl ester (8.67 g, 40%) as a clear oil. $^1$H NMR (300 MHz, d$_6$-DMSO) δ1.38 (s, 9H), 2.07 (s, 3H), 3.81-3.86 (m, 4H), 4.77 (t, J=5.1 Hz, 2H). LCMS (m/z) 217.0 [M−H], Tr=1.45 min.

Compound 98b.
5-Acetyl-2,2-dimethyl-[1,3]dioxane-5-carboxylic acid tert-butyl ester

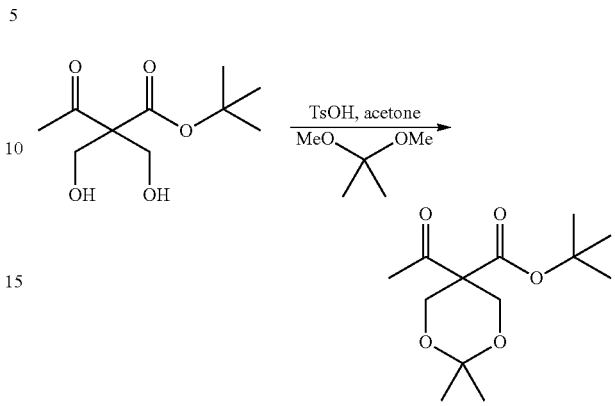

A mixture of 2,2-bis-hydroxymethyl-3-oxo-butyric acid tert-butyl ester (8.67 g, 40 mmol), acetone (30 mL, 400 mmol), 2,2-dimethoxypropane (41.6 g, 50 mL, 400 mmol) and 4-toluenesulfonic acid hydrate (152 mg, 0.8 mmol) was stirred at room temperature for 18 h. The solvent was partially evaporated to a volume of ~20 mL. Saturated sodium hydrogen carbonate solution was added and the mixture was extracted with ethyl acetate. The organic extracts were combined, washed with water and brine. The organic layer was filtered through a hydrophobic frit and the filtrate was evaporated. The residue was purified by silica gel chromatography using a gradient of iso-hexanes/ethyl acetate 9:1 to 4:1 to afford the title compound (7.82 g, 75%) as a clear oil. $^1$H NMR (300 MHz, CDCl$_3$) δ 1.39 (s, 3H), 1.44 (s, 3H), 1.48 (s, 9H), 2.32 (s, 3H), 6.36 (ABq, Δδ$_{AB}$=0.05, J$_{AB}$=11.8 Hz, 4H). LCMS (m/z) 281.2 [M+Na], Tr=2.44 min.

Compound 98c.
2,2-Dimethyl-5-vinyl-[1,3]dioxane-5-carboxylic acid tert-butyl ester

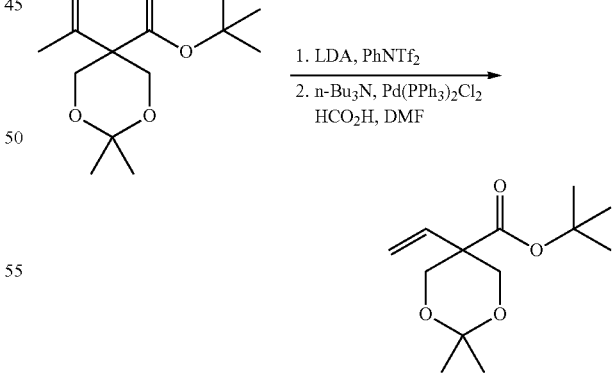

A solution of N,N-diisopropylamine (1.51 g, 2.1 mL, 15 mmol) in anhydrous tetrahydrofuran (30 mL) was stirred at −78° C. under nitrogen. n-Butyl lithium (2.5 M in hexanes, 5.6 mL, 14 mmol) was added dropwise and the reaction mixture was stirred at −78° C. for 30 min. A solution of 5-acetyl-2,2-dimethyl-[1,3]dioxane-5-carboxylic acid tert-butyl ester (2.58 g, 10 mmol) in tetrahydrofuran (5 mL) was added and the reaction mixture was stirred at −78° C. for 15 min. A solution of N-phenyl-(bis-trifluoromethanesulfonamide) (3.93 g, 11 mmol) in tetrahydrofuran (30 mL) was added and the reaction mixture was stirred at −78° C. for 15 min. The cooling bath was removed and the reaction mixture was stirred at room temperature for 30 min. The solvent was evaporated and diethyl ether (50 mL) was added. The solution was cooled to 5° C. and was washed with cold sodium hydroxide solution (1 M, 3×30 mL) and brine. The organic solution was separated, dried over anhydrous magnesium sulfate, filtered and the solvent evaporated to afford 2,2-dimethyl-5-(1-trifluoromethanesulfonyloxy-vinyl)-[1,3]dioxane-5-carboxylic acid tert-butyl ester (3.84 g, 10 mmol) as a yellow oil. A solution of 2,2-dimethyl-5-(1-trifluoromethanesulfonyloxy-vinyl)-[1,3]dioxane-5-carboxylic acid tert-butyl ester (3.84 g, 10 mmol) and tri-n-butylamine (5.55 g, 7 mL, 30 mmol) in N,N-dimethylformamide (20 mL) was stirred at room temperature under nitrogen. Bis(triphenylphosphine)palladium(II) dichloride (350 mg, 0.5 mmol) and formic acid (920 mg, 0.77 mL, 20 mmol) were added and the reaction mixture was heated at 60° C. for 90 min. The reaction mixture was cooled to room temperature and ethyl acetate and water were added. The organic extracts were washed with water (5×) and brine. The organic solution was filtered through a hydrophobic frit and the filtrate was evaporated. The residue was purified by silica gel chromatography using iso-hexanes/ethyl acetate 9:1 followed by silica gel chromatography using a gradient of iso-hexanes/ethyl acetate 19:1 to 9:1 to afford the title compound (1.09 g, 45%) as a clear oil. $^1$H NMR (300 MHz, CDCl$_3$) δ 1.41 (s, 3H), 1.45 (s, 3H), 1.50 (s, 9H), 3.82 (d, J=11.8 Hz, 2H), 4.25 (d, J=11.8 Hz, 2H), 5.25 (d, J=17.2 Hz, 1H), 5.26 (d, J=10.7 Hz, 1H), 5.73 (dd, J=17.2, 11.7 Hz, 1H).

Compound 98d. 2,2-Bis-hydroxymethyl-but-3-enoic acid tert-butyl ester

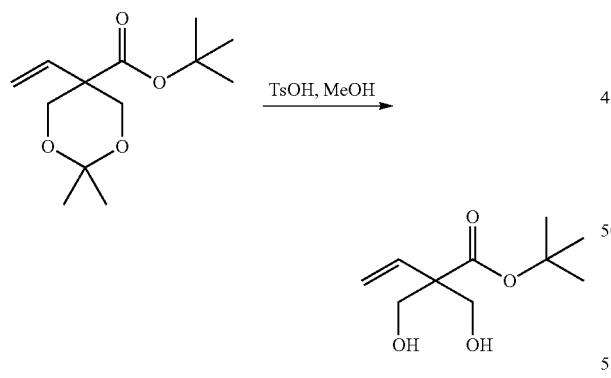

A solution of 2,2-dimethyl-5-vinyl-[1,3]dioxane-5-carboxylic acid tert-butyl ester (969 mg, 4 mmol) and 4-toluenesulfonic acid hydrate (76 mg, 0.4 mmol) in methanol (10 mL) was stirred at room temperature for 30 min. The solvent was evaporated and the residue was purified by silica gel chromatography using a gradient of iso-hexanes/ethyl acetate 4:1 to 1:1 to afford the title compound (660 mg, 82%) as a white solid. $^1$H NMR (300 MHz, d$_6$-DMSO): δ 1.38 (s, 9H), 3.54-3.68 (m, 4H), 4.56 (t, J=5.4 Hz, 2H), 5.12 (d, J=10.5 Hz, 1H), 5.14 (d, J=18.3 Hz, 1H), 5.80 (dd, J=18.3, 10.5 Hz, 1H). LCMS (m/z) 225.2 [M+Na], Tr=1.47 min.

Compound 98e.
2-Oxo-5-vinyl-[1,3]dioxane-5-carboxylic acid tert-butyl ester

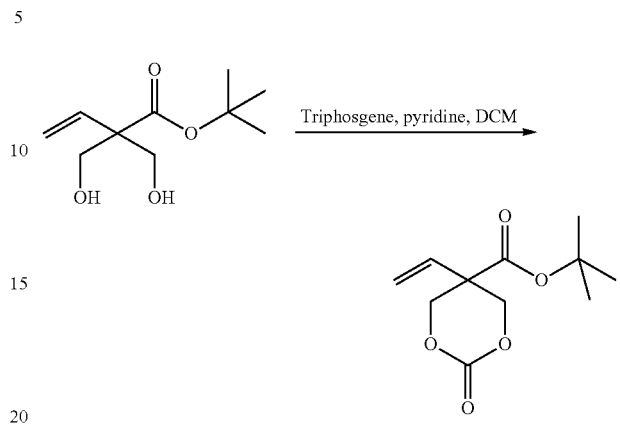

A solution of 2,2-bis-hydroxymethyl-but-3-enoic acid tert-butyl ester (202 mg, 1 mmol) and pyridine (0.5 mL, 6 mmol) in dichloromethane (5 mL) was stirred at −78° C. under nitrogen. A solution of triphosgene (150 mg, 0.5 mmol) in dichloromethane (2.5 mL) was added dropwise and the reaction mixture was stirred at −78° C. for 1 h. The reaction mixture was warmed to room temperature and stirred at room temperature for 15 min and saturated ammonium chloride solution was added. The organic layer was separated, washed with hydrochloric acid (1 M), saturated sodium hydrogen carbonate solution and brine. The organic solution was filtered through a hydrophobic frit and the filtrate was evaporated. The residue was purified by silica gel chromatography using a gradient of iso-hexanes/ethyl acetate 4:1 to 3:2 to afford the title compound (204 mg, 89%) as a clear gum. $^1$H NMR (300 MHz, CDCl$_3$): δ 1.48 (s, 9H), 4.38 (d, J=10.7 Hz, 2H), 4.71 (d, J=10.7 Hz, 2H), 5.39 (d, J=17.4 Hz, 1H), 5.47 (d, J=10.7 Hz, 1H), 5.77 (dd, J=17.4, 10.7 Hz, 1H). LCMS (m/z) 229.1 [M+H], Tr=2.04 min.

Compound 98f.
2-Oxo-5-vinyl-[1,3]dioxane-5-carboxylic acid

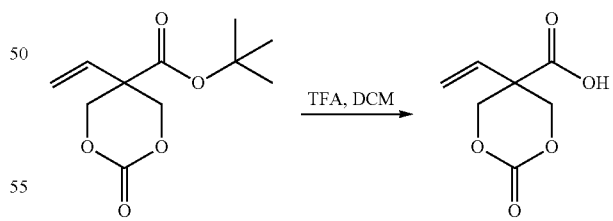

A solution of 2-oxo-5-vinyl-[1,3]dioxane-5-carboxylic acid tert-butyl ester (200 mg, 0.88 mmol) in dichloromethane (4 mL) was stirred at 0° C. Trifluoroacetic acid (2 mL) was added and the reaction mixture was stirred at 0° C. for 30 min and then at room temperature for 3 h. The solvent was evaporated and the residue was triturated with diethyl ether/iso-hexanes (1:1) to afford the title compound (135 mg, 90%) as a white solid. $^1$H NMR (300 MHz, d$_6$-DMSO) δ4.51 (d, J=10.5 Hz, 2H), 4.67 (d, J=10.5 Hz, 2H), 5.38 (d, J=17.6 Hz, 1H), 5.43 (d, J=10.7 Hz, 1H), 5.83 (dd, J=17.6, 10.7 Hz, 1H), 13.5-14.0 (br s, 1H). LCMS (m/z) 173.2 [M+H], Tr=0.62 min.

Compound 98

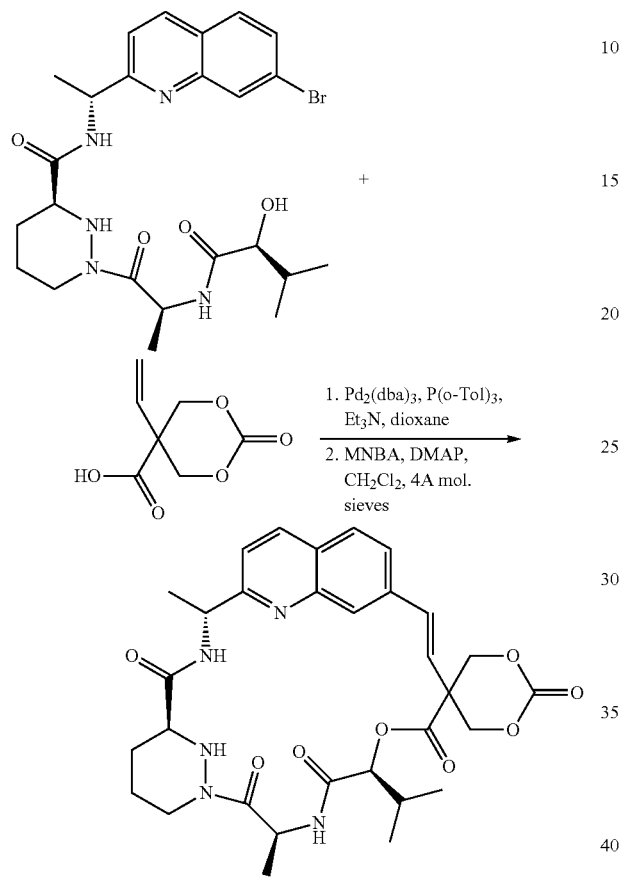

A stirred solution of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (164 mg, 0.3 mmol), 2-oxo-5-vinyl-[1,3]dioxane-5-carboxylic acid (57 mg, 0.33 mmol), tri(o-tolyl)phosphine (18 mg, 0.06 mmol) and triethylamine (91 mg, 0.13 mL, 0.9 mmol) in 1,4-dioxane (10 mL) was degassed with nitrogen for 15 min. The solution was heated to 50° C. and tris(dibenzylideneacetone)dipalladium(0) (28 mg, 0.03 mmol) was added. The reaction mixture was heated at 80° C. for 45 min. The reaction mixture was cooled to room temperature and the mixture was filtered through a hydrophobic frit and the filtrate was evaporated to afford crude 5-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-2-oxo-[1,3]dioxane-5-carboxylic acid (0.3 mmol) as a yellow gum. LCMS (m/z) 626.2 [M+H], Tr=1.67 min. A solution of 2-methyl-6-nitrobenzoic anhydride (206 mg, 0.6 mmol) and 4-(dimethylamino)-pyridine (146 mg, 1.2 mmol) in dichloromethane (200 mL) containing 4 Å molecular sieves (200 mg) was stirred at room temperature under nitrogen. A solution of crude 5-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-2-oxo-[1,3]dioxane-5-carboxylic acid (0.3 mmol) in dichloromethane (5 mL) was added dropwise over 4 h and the reaction mixture was stirred at room temperature for 16 h. The reaction mixture was filtered through Celite and the solution was partially evaporated to a volume of ~50 mL. The solution was washed with ice-cold saturated ammonium chloride solution, ice-cold saturated sodium bicarbonate solution and brine. The organic solution was filtered through a hydrophobic frit and the filtrate was evaporated. The residue was purified by silica gel chromatography eluting with a gradient of ethyl acetate/methanol 1:0 to 5:1 then by reverse phase preparative HPLC eluting with acetonitrile/water 7:13. Fractions containing the product were combined and the majority of the organic solvent was evaporated. The resulting aqueous solution was extracted with dichloromethane. The organic extracts were combined, filtered through a hydrophobic frit and the filtrate was evaporated to afford the title compound (3.1 mg, 2%) as a white solid. $^1$H NMR (300 MHz, CD$_3$CN): δ 0.96 (d, J=6.7 Hz, 3H), 1.04 (d, J 15=6.7 Hz, 3H), 1.41-1.49 (m, 2H), 1.54 (d, J=6.7 Hz, 3H), 1.55 (d, J=7.1 Hz, 3H), 1.59-1.64 (m, 1H), 1.88-1.93 (m, 1H), 2.19-2.24 (m, 1H), 2.56-2.64 (m, 1H), 3.48-3.57 (m, 1H), 4.19 (d, J=12.0 Hz, 1H), 4.38-4.43 (m, 1H), 4.59 (d, J=10.9 Hz, 1H), 4.71 (d, J=10.9 Hz, 1H), 4.85-4.91 (m, 2H), 5.06-5.10 (m, 1H), 5.23 (d, J=7.8 Hz, 1H), 5.73-5.79 (m, 1H), 6.26 (d, J=16.5 Hz, 1H), 6.83 (d, J=16.5 Hz, 1H), 7.18 (d, J=8.0 Hz, 1H), 7.48 (d, J=8.5 Hz, 1H), 7.64 (dd, J=8.5, 1.6 Hz, 1H), 7.90 (d, J=8.5 Hz, 1H), 7.99 (br s, 1H), 8.28 (d, J=8.5 Hz, 1H), 8.85 (br d, J=5.0 Hz, 1H). LCMS (m/z) 608.2 [M+H], Tr=2.01 min.

Example 99

Compound 99

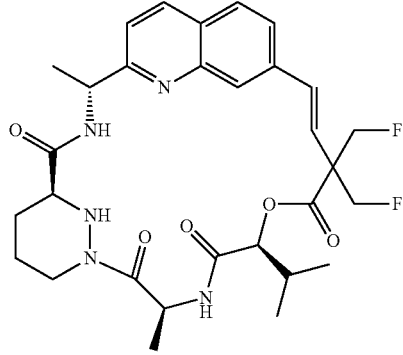 [SMILES: CC(C)[C@@H]1OC(=O)C(CF)(CF)/C=C/c2ccc3ccc(nc3c2)[C@@H](C)NC(=O)[C@@H]2CCCN(N2)C(=O)[C@H](C)NC1=O]

Compound 99a.
5-Acetyl-2,2-dimethyl-[1,3]dioxane-5-carboxylic acid ethyl ester

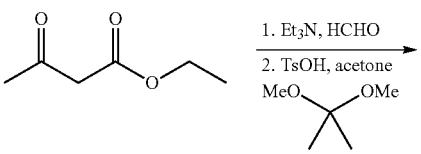

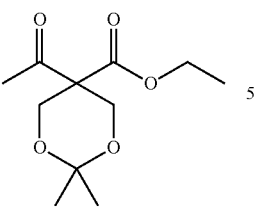

Compound 99a was prepared in the same manner as 5-acetyl-2,2-dimethyl-[1,3]dioxane-5-carboxylic acid tert-butyl ester using ethyl acetoacetate instead of 3-oxo-butyric acid tert-butyl ester in 31% yield over 2 steps. $^1$H NMR (300 MHz, CDCl$_3$) δ 1.29 (t, J=7.1 Hz, 3H), 1.40 (s, 3H), 1.44 (s, 3H), 2.33 (s, 3H), 4.23 (q, J=7.1 Hz, 2H), 4.30 (ABq, Δδ$_{AB}$=0.04, J$_{AB}$=11.9 Hz, 4H).

Compound 99b.
2,2-Dimethyl-5-vinyl-[1,3]dioxane-5-carboxylic acid ethyl ester

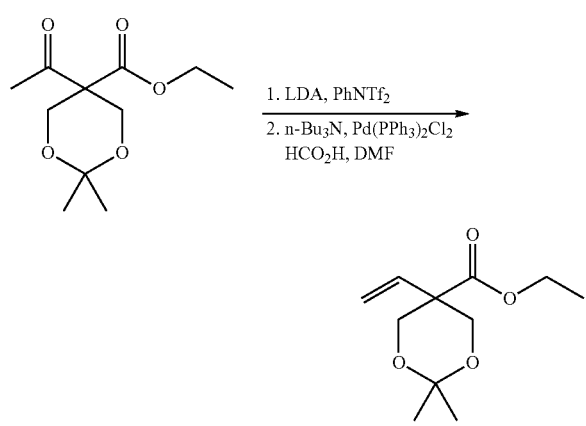

Compound 99b was prepared in the same manner as 2,2-dimethyl-5-vinyl-[1,3]dioxane-5-carboxylic acid tert-butyl ester using 5-acetyl-2,2-dimethyl-[1,3]dioxane-5-carboxylic acid ethyl ester instead of 5-acetyl-2,2-dimethyl-[1,3]dioxane-5-carboxylic acid tert-butyl ester in 50% yield over 2 steps. $^1$H NMR (300 MHz, CDCl$_3$) δ 1.31 (t, J=7.1 Hz, 3H), 1.41 (s, 3H), 1.46 (s, 3H), 4.10 (ABq, Δδ$_{AB}$=0.44, J$_{AB}$=11.9 Hz, 4H), 4.26 (q, J=7.1 Hz, 2H), 5.24 (d, J=17.4 Hz, 1H), 5.28 (d, J=10.9 Hz, 1H), 5.24 (dd, J=17.4, 10.9 Hz, 1H). LCMS (m/z) 237.0 [M+Na], Tr=2.14 min.

Compound 99c. 2,2-Bis-hydroxymethyl-but-3-enoic acid ethyl ester

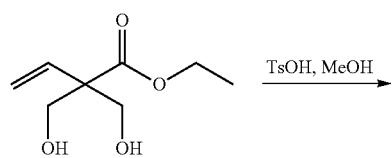

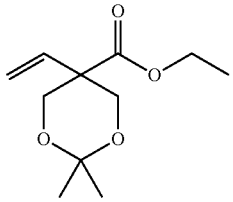

Compound 99c was prepared in the same manner as 2,2-bis-hydroxymethyl-but-3-enoic acid tert-butyl ester using 2,2-dimethyl-5-vinyl-[1,3]dioxane-5-carboxylic acid ethyl ester instead of 2,2-dimethyl-5-vinyl-[1,3]dioxane-5-carboxylic acid tert-butyl ester in 78% yield. $^1$H NMR (300 MHz, d$_6$-DMSO) 61.17 (t, J=7.0 Hz, 3H), 3.59-3.71 (m, 4H), 4.06 (q, J=7.0 Hz, 2H), 4.65 (t, J=5.6 Hz, 2H), 5.13 (d, J=18.5 Hz, 1H), 5.15 (d, J=10.5 Hz, 1H), 5.80 (dd, J=18.5, 10.5 Hz, 1H). LCMS (m/z) 197.1 [M+Na], Tr=0.96 min.

Compound 99d. 2,2-Bis-fluoromethyl-but-3-enoic acid

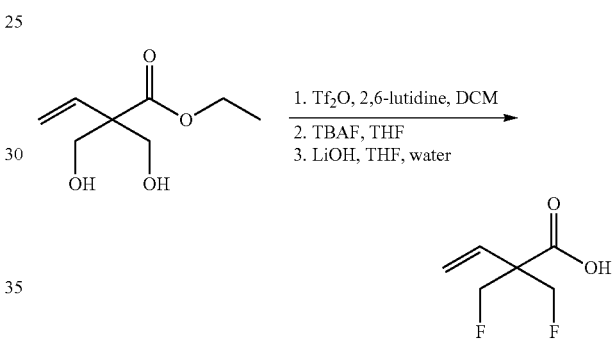

To a solution of 2,2-bis-hydroxymethyl-but-3-enoic acid ethyl ester (338 mg, 1.9 mmol) and 2,6-lutidine (813 mg, 0.88 mL, 7.6 mmol) in dichloromethane (10 mL) at −78° C. under nitrogen was added dropwise trifluoromethanesulfonic anhydride (1.07 g, 0.66 mL, 3.8 mmol) and the reaction mixture was warmed to room temperature and stirred at room temperature for 30 min. The solution was washed with ice-cold hydrochloric acid (1 M) and brine. The organic solution was filtered through a hydrophobic frit and the filtrate was evaporated to afford crude 2,2-bis-trifluoromethanesulfonyloxymethyl-but-3-enoic acid ethyl ester (1.9 mmol) as an orange oil which was used immediately in the next step. A solution of 2,2-bis-trifluoromethanesulfonyloxymethyl-but-3-enoic acid ethyl ester (1.9 mmol) in tetrahydrofuran (5 mL) was stirred at 0° C. under nitrogen. Tetra-n-butylammonium fluoride (1 M in tetrahydrofuran, 4.75 mL, 4.75 mmol) was added and the reaction mixture was stirred at 0° C. for 30 min and then at room temperature for 2 h. The solvent was evaporated. The residue was dissolved in dichloromethane and the solution was washed with saturated sodium hydrogen carbonate solution, water and brine. The organic solution was filtered through a hydrophobic frit and the filtrate was evaporated. The residue was purified by silica gel chromatography using a gradient of pentane/diethyl ether 19:1 to 4:1 to afford 2,2-bis-fluoromethyl-but-3-enoic acid ethyl ester (1.9 mmol) contaminated with solvent as a clear oil. A solution of crude 2,2-bis-fluoromethyl-but-3-enoic acid ethyl ester (1.9 mmol) in tetrahydrofuran (10 mL) was stirred at 0° C. under nitrogen. A solution of lithium hydroxide monohydrate (240 mg, 5.7 mmol) in water (2.5 mL) was added and the reaction mixture was stirred at 0° C. for 1 h and then at room temperature for 24 h. The reaction mixture was acidified to pH 2 with hydrochloric acid (2 M). Water was added and the mixture was extracted with diethyl ether. The organic extracts were combined, washed with brine. The organic solution was filtered through a hydrophobic frit and the filtrate was evaporated to afford the title compound (400 mg) as a clear oil. $^1$H NMR (300 MHz, d$_6$-DMSO) δ 4.54-4.83 (m, 4H), 5.33 (d, J=17.8 Hz, 1H), 5.36 (d, J=10.7 Hz, 1H), 5.81 (dd, J=17.8, 10.7 Hz, 1H), 13.0-13.5 (br s, 1H). LCMS (m/z) 149.2 [M−H], Tr=1.45 min.

Compound 99e. (S)-1-[(S)-2-((S)-2-{(E)-4-[2-((R)-1-tert-Butoxycarbonylamino-ethyl)-quinolin-7-yl]-2,2-bis-fluoromethyl-but-3-enoyloxy}-3-methyl-butyrylamino)-propionyl]-hexahydro-pyridazine-3-carboxylic acid 2,2,2-trichloro-ethyl ester

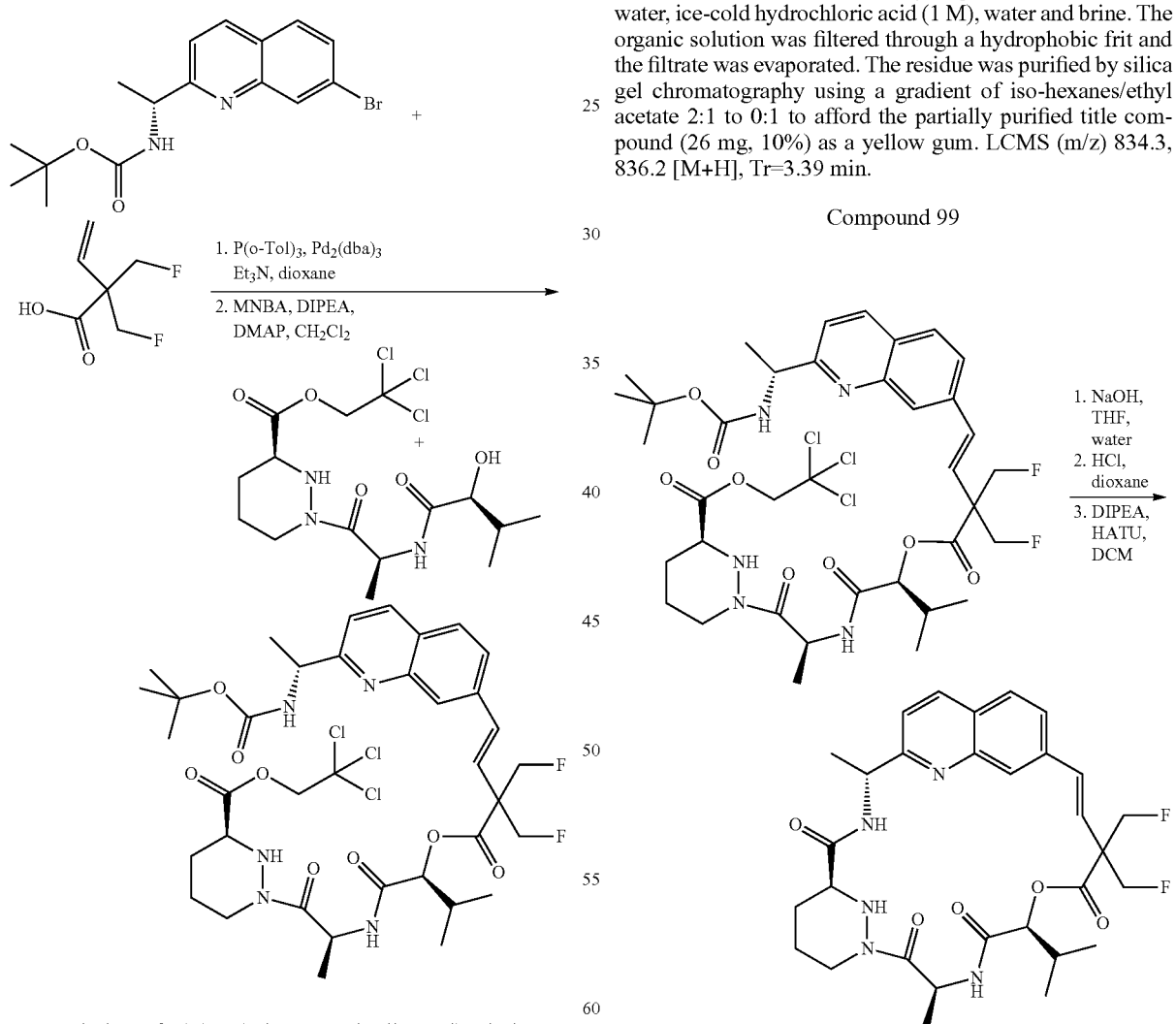

A solution of [(R)-1-(7-bromo-quinolin-2-yl)-ethyl]-carbamic acid tert-butyl ester (105 mg, 0.3 mmol), 2,2-bis-fluoromethyl-but-3-enoic acid (50 mg, 0.33 mmol), tri(o-tolyl)phosphine (18 mg, 0.06 mmol) and triethylamine (91 mg, 0.13 mL, 0.9 mmol) in 1,4-dioxane (3 mL) was degassed with nitrogen for 15 min. Tris(dibenzylideneacetone)dipalladium (0) (28 mg, 0.03 mmol) was added and the reaction mixture was heated to 60° C. for 1 h. The reaction mixture was cooled to room temperature and the mixture was filtered through a hydrophobic frit and the filtrate was evaporated to afford crude (E)-4-[2-((R)-1-tert-butoxycarbonylamino-ethyl)-quinolin-7-yl]-2,2-bis-fluoromethyl-but-3-enoic acid (0.3 mmol) as a yellow gum. LCMS (m/z) 421.1 [M+H], Tr=2.27 min. A solution of crude (E)-4-[2-((R)-1-tert-butoxycarbonylamino-ethyl)-quinolin-7-yl]-2,2-bis-fluoromethyl-but-3-enoic acid (0.3 mmol), N,N-diisopropylethylamine (96 mg, 0.13 mL, 0.75 mmol), 4-(dimethylamino)-pyridine (73 mg, 0.6 mmol) and 2-methyl-6-nitrobenzoic anhydride (193 mg, 0.56 mmol) in anhydrous dichloromethane (5 mL) was stirred at 0° C. under nitrogen. A solution of (S)-1-[(S)-2-((S)-2-hydroxy-3-methyl-butyrylamino)-propionyl]-hexahydro-pyridazine-3-carboxylic acid 2,2,2-trichloro-ethyl ester (142 mg, 0.33 mmol) in dichloromethane (2 mL) was added and the reaction mixture was stirred at 0° C. for 30 min and then at room temperature for 18 h. The reaction mixture was diluted with dichloromethane and the solution was washed with ice-cold saturated sodium hydrogen carbonate solution, water, ice-cold hydrochloric acid (1 M), water and brine. The organic solution was filtered through a hydrophobic frit and the filtrate was evaporated. The residue was purified by silica gel chromatography using a gradient of iso-hexanes/ethyl acetate 2:1 to 0:1 to afford the partially purified title compound (26 mg, 10%) as a yellow gum. LCMS (m/z) 834.3, 836.2 [M+H], Tr=3.39 min.

Compound 99

A solution of (S)-1-[(S)-2-((S)-2-{(E)-4-[2-((R)-1-tert-butoxycarbonylamino-ethyl)-quinolin-7-yl]-2,2-bis-fluoromethyl-but-3-enoyloxy}-3-methyl-butyrylamino)-propionyl]-hexahydro-pyridazine-3-carboxylic acid 2,2,2-trichloro-ethyl ester (100 mg, 0.11 mmol) in tetrahydrofuran (3 mL)

was stirred at 0° C. under nitrogen. An ice-cold aqueous solution of sodium hydroxide (0.1 M, 1.1 mL, 0.11 mmol) was added and the reaction mixture was stirred at 0° C. for 20 min. Cold hydrochloric acid (1 M) was added to acidify the mixture to pH 2 and the solvent was evaporated. The residue was co-evaporated with tetrahydrofuran/toluene (1:1, 3×) and the residue was triturated with diethyl ether (2×) and the resulting solid was dried to afford (S)-1-[(S)-2-((S)-2-{(E)-4-[2-((R)-1-tert-butoxycarbonylamino-ethyl)-quinolin-7-yl]-2,2-bis-fluoromethyl-but-3-enoyloxy}-3-methyl-butyrylamino)-propionyl]-hexahydro-pyridazine-3-carboxylic acid (0.1 mmol) as a yellow solid which was used crude in the next reaction. LCMS (m/z) 704.3 [M+H], Tr=2.61 min. A mixture of crude (S)-1-[(S)-2-((S)-2-{(E)-4-[2-((R)-1-tert-butoxycarbonylamino-ethyl)-quinolin-7-yl]-2,2-bis-fluoromethyl-but-3-enoyloxy}-3-methyl-butyrylamino)-propionyl]-hexahydro-pyridazine-3-carboxylic acid (0.1 mmol) in hydrochloric acid (4 M in 1,4-dioxane, 2 mL) was stirred at room temperature for 30 min. The solvent was evaporated and the residue was co-evaporated with diethyl ether (2×) and the resulting solid was dried to afford (S)-1-[(S)-2-((S)-2-{(E)-4-[2-((R)-1-amino-ethyl)-quinolin-7-yl]-2,2-bis-fluoromethyl-but-3-enoyloxy}-3-methyl-butyrylamino)-propionyl]-hexahydro-pyridazine-3-carboxylic acid hydrochloride (0.1 mmol) as an off-white solid which was used crude in the next reaction. LCMS (m/z) 604.3 [M+H], Tr=1.53 min. A suspension of crude (S)-1-[(S)-2-((S)-2-{(E)-4-[2-((R)-1-amino-ethyl)-quinolin-7-yl]-2,2-bis-fluoromethyl-but-3-enoyloxy}-3-methyl-butyrylamino)-propionyl]-hexahydro-pyridazine-3-carboxylic acid hydrochloride (0.1 mmol) in dichloromethane (100 mL) was stirred at 0° C. under nitrogen. A solution of N,N-diisopropylethylamine (52 mg, 0.07 mL, 0.4 mmol) in dichloromethane (5 mL) was added and the resulting solution was stirred at 0° C. 2-(1H-7-Azabenzotriazol-1-yl)-1,1,3,3-tetramethyl uronium hexafluorophosphate methanaminium (76 mg, 0.2 mmol) was added and the reaction mixture was stirred at 0° C. for 30 min and then at room temperature for 18 h. The solvent was partially evaporated to a volume of ~30 mL. The solution was washed with ice-cold saturated sodium hydrogen carbonate solution, ice-cold hydrochloric acid (1 M) and brine. The organic solution was filtered through a hydrophobic frit and the filtrate was evaporated. The residue was purified by silica gel chromatography eluting with a gradient of iso-hexanes/ethyl acetate 1:1 to 0:1 followed silica gel chromatography eluting with iso-hexanes/acetone 3:2. The residue was triturated with diethyl ether and the resulting solid was dried to afford the title compound (4 mg, 7% over 3 steps) as a white solid. $^1$H NMR (300 MHz, CD$_3$OD) δ 1.01 (d, J=6.5 Hz, 3H), 1.09 (d, J=6.9 Hz, 3H), 1.49-1.55 (m, 2H), 1.61 (d, J=6.9 Hz, 3H), 1.64 (d, J=7.1 Hz, 3H), 1.93-1.98 (m, 1H), 2.15-2.28 (m, 2H), 2.68-2.76 (m, 1H), 3.59-3.63 (m, 1H), 4.41-4.46 (m, 1H), 4.70-5.13 (m, 5H), 5.35 (d, J=8.9 Hz, 1H), 5.84 (q, J=7.1 Hz, 1H), 6.27 (d, J=16.5 Hz, 1H), 6.81 (d, J=16.5 Hz, 1H), 7.49 (d, J=7.9 Hz, 1H), 7.70 (dd, J=8.5, 1.6 Hz, 1H), 7.82 (br s, 1H), 7.88 (d, J=8.5 Hz, 1H), 8.28 (d, J=8.5 Hz, 1H). LCMS (m/z) 586.2 [M+H], Tr=2.48 min.

Examples 100 and 101. Compounds 100 and 101

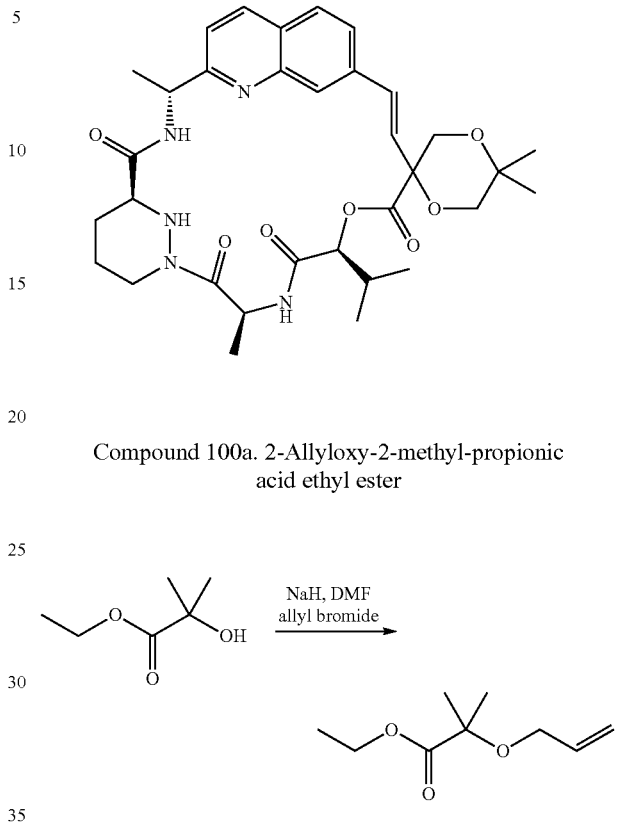

Compound 100a. 2-Allyloxy-2-methyl-propionic acid ethyl ester

A solution of 2-hydroxy-2-methyl-propionic acid ethyl ester (2.64 g, 2.7 mL, 20 mmol) in N,N-dimethylformamide (20 mL) was stirred at 0° C. under nitrogen. Sodium hydride (60% dispersion in oil, 880 mg, 22 mmol) was added and the reaction mixture was stirred at 0° C. for 5 min. Allyl bromide (2.18 g, 1.6 mL, 18 mmol) was added and the reaction mixture was stirred at 0° C. for 30 min and then at room temperature for 18 h. The reaction mixture was cooled to 0° C. and saturated ammonium chloride solution was cautiously added to quench the reaction. Diethyl ether was added and the organic layer was separated, washed with water (3×) and brine. The organic solution was filtered through a hydrophobic frit and the filtrate was evaporated. The residue was purified by silica gel chromatography using a gradient of pentane/diethyl ether 12:1 to 4:1 to afford the title compound (2.33 g, 67%) as an clear oil. $^1$H NMR (300 MHz, CDCl$_3$) δ 1.31 (t, J=7.1 Hz, 3H), 1.47 (s, 6H), 3.95-3.98 (m, 2H), 4.21 (q, J=7.1 Hz, 2H), 5.15-5.20 (m, 1H), 5.27-5.39 (m, 1H), 5.90-6.03 (m, 1H). LCMS (m/z) 195.2 [M+Na], Tr=2.24 min.

Compound 100b.
(5,5-Dimethyl-[1,4]dioxan-2-yl)-methanol

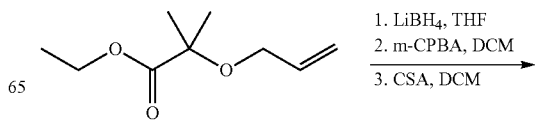

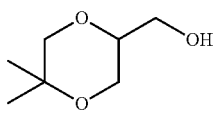

A solution of 2-allyloxy-2-methyl-propionic acid ethyl ester (1.72 g, 10 mmol) in anhydrous tetrahydrofuran (40 mL) was stirred at room temperature under nitrogen. Lithium borohydride (44 mg, 20 mmol) was added portion-wise and the reaction mixture was stirred at room temperature for 20 h. The reaction mixture was cooled to 0° C. and saturated ammonium chloride solution was cautiously added followed by hydrochloric acid (2 M) to acidify the reaction mixture to pH 2. The mixture was extracted with diethyl ether and the organic extracts were combined and washed with brine. The organic solution was filtered through a hydrophobic frit and the filtrate was evaporated to afford 2-allyloxy-2-methyl-propan-1-ol (10 mmol) which was used crude in the next step. LCMS (m/z) 153.2 [M+Na], Tr=1.16 min. A suspension of 2-allyloxy-2-methyl-propan-1-ol (10 mmol) in dichloromethane (40 mL) was stirred at 0° C. Meta-chloroperbenzoic acid (70% pure containing 20% water and 10% meta-chlorobenzoic acid, 2.9 g, 12 mmol) was added and the reaction mixture was stirred at 0° C. for 30 min and then at room temperature for 24 h. The reaction mixture was cooled to 0° C. and saturated sodium hydrogen carbonate solution and sodium thiosulfate solution were added and the mixture was stirred at 0° C. for 15 min. The organic layer was separated and the aqueous layer was extracted with dichloromethane (4×). The organic extracts were combined and washed with brine. The organic solution was filtered through a hydrophobic frit and the filtrate was evaporated to afford 2-methyl-2-oxiranylmethoxy-propan-1-ol (10 mmol) which was used crude in the next step. LCMS (m/z) 169.2 [M+Na], Tr=0.72 min. A solution of 2-methyl-2-oxiranylmethoxy-propan-1-ol (10 mmol) in dichloromethane (50 mL) and racemic camphor-10-sulfonic acid (765 mg, 3.3 mmol) was stirred at room temperature for 18 h. Saturated sodium hydrogen carbonate solution was added and the organic layer separated. The aqueous layer was extracted with dichloromethane and the organic extracts were combined, filtered through a hydrophobic frit and the filtrate was evaporated. The residue was purified by silica gel chromatography using a gradient of pentane/diethyl ether 2:3 to 1:4 to afford the title compound (826 mg, 57% over 3 steps) as a yellow oil. $^{1}$H NMR (300 MHz, $d_6$-DMSO): δ 1.02 (s, 3H), 1.20 (s, 3H), 3.23 (d, J=11.1 Hz, 1H), 3.30-3.50 (m, 6H), 4.68 (t, J=5.4 Hz, 1H). LCMS (m/z) 169.2 [M+Na], Tr=0.72 min.

Compound 100c.
5,5-Dimethyl-[1,4]dioxane-2-carboxylic acid benzyl ester

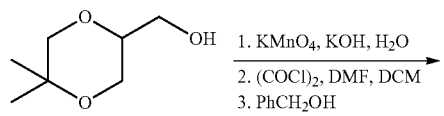

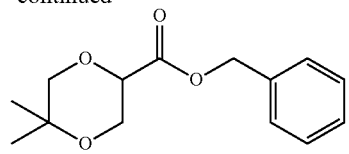

A solution of (5,5-dimethyl-[1,4]dioxan-2-yl)-methanol (657 mg, 4.5 mmol) in 1 M potassium hydroxide solution (6.7 mL, 6.7 mmol) was stirred at 5° C. A solution of potassium permanganate (1.42 g, 9 mmol) in water (10 mL) was added dropwise maintaining the internal temperature below 10° C. The reaction mixture was stirred at 5° C. for 1 h and then at room temperature for 18 h. The reaction mixture was filtered through Celite and the filter pad was washed with water and methanol and the filtrate was evaporated. The residue was acidified to pH 2 with hydrochloric acid (2 M) and the mixture was extracted with ethyl acetate and chloroform. The organic extracts were combined and washed with a small volume of brine. The organic solution was filtered through a hydrophobic frit and the filtrate was evaporated to afford crude 5,5-dimethyl-[1,4]dioxane-2-carboxylic acid (694 mg, 4.5 mmol) as a waxy solid. LCMS (m/z) 159.1 [M−H], Tr=0.88 min. A solution of 5,5-dimethyl-[1,4]dioxane-2-carboxylic acid (750 mg, 4.7 mmol), oxalyl chloride (600 mg, 0.4 mL, 4.7 mmol) and N,N-dimethylformamide (2 drops) in dichloromethane (15 mL) was stirred at room temperature under nitrogen for 2 h. A solution of benzyl alcohol (508 mg, 0.5 mL, 4.7 mmol) in dichloromethane (2 mL) was added and the reaction mixture was stirred at room temperature for 20 h. Additional benzyl alcohol (0.5 mL, 4.7 mmol) was added and the reaction mixture was stirred at room temperature for 18 h. The solvent was evaporated and the residue was purified by silica gel chromatography using a gradient of iso-hexanes/ethyl acetate 9:1 to 1:1 to afford the title compound (870 mg, 74%) as an oil. $^{1}$H NMR (300 MHz, CDCl$_3$) δ 1.19 (s, 3H), 1.32 (s, 3H), 3.43 (d, J=11.4 Hz, 1H), 3.72 (d, J=11.4 Hz, 1H), 3.88-3.92 (m, 2H), 4.21 (dd, J=8.2, 4.7 Hz, 1H), 5.24 (s, 2H), 7.34-7.39 (m, 5H). LCMS (m/z) 273.1 [M+Na], Tr=2.41 min.

Compound 100d. 2-(1-Hydroxy-ethyl)-5,5-dimethyl-[1,4]dioxane-2-carboxylic acid benzyl ester

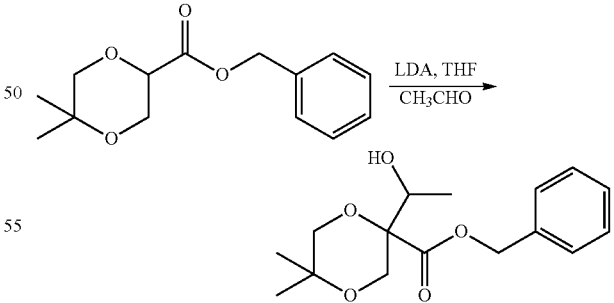

A solution of N,N-diisopropylamine (530 mg, 0.73 mL, 5.25 mmol) in anhydrous tetrahydrofuran (4 mL) was stirred at −78° C. under nitrogen. n-Butyl lithium (2.1 mL, 5.25 mmol, 2.5 M solution in hexane) was added dropwise and the reaction mixture was stirred at −78° C. for 30 min. A solution of 5,5-dimethyl-[1,4]dioxane-2-carboxylic acid benzyl ester (870 mg, 3.5 mmol) in tetrahydrofuran (8 mL) was added and the reaction mixture was stirred at −78° C. for 20 min. Acetaldehyde (462 mg, 0.6 mL, 10.5 mmol) was added in one portion. The cooling bath was removed and the reaction mixture was stirred at room temperature for 1 h. The reaction mixture was cooled to 0° C. and ice-cold hydrochloric acid (2 M) was added to acidify the reaction mixture to pH 2. Sodium chloride was added to saturate the aqueous phase and the mixture was extracted with diethyl ether. The organic extracts were combined and washed with brine. The organic solution was filtered through a hydrophobic frit and the filtrate was evaporated. The residue was purified by silica gel chromatography using a gradient of iso-hexanes/ethyl acetate 6:1 to 0:1 followed by silica gel chromatography using iso-hexanes/ethyl acetate 3:1 to 0:1 to the title compound (400 mg, 40%) as an oil and as a 2:1 mixture of diastereoisomers. LCMS (m/z) 295.1 [M+H], Tr=2.11 min.

Compound 100e.
5,5-Dimethyl-2-vinyl-[1,4]dioxane-2-carboxylic acid benzyl ester

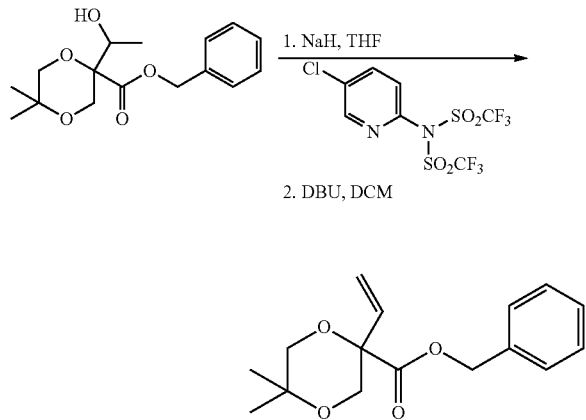

A suspension of sodium hydride (80 mg, 2 mmol, 60% dispersion in mineral oil) in anhydrous tetrahydrofuran (3 mL) was stirred at −78° C. under nitrogen. A solution of 2-(1-hydroxy-ethyl)-5,5-dimethyl-[1,4]dioxane-2-carboxylic acid benzyl ester (400 mg, 1.36 mmol) in tetrahydrofuran (3 mL) was added and the reaction mixture was stirred at −78° C. for 15 min. A solution of N-(5-chloro-2-pyridyl)bis(trifluoromethanesulfonimide) (1.06 g, 2.7 mmol) in tetrahydrofuran (5 mL) was added and the reaction mixture was stirred at −78° C. for 30 min. The reaction mixture was warmed to room temperature and then stirred at room temperature for 5 h. The reaction mixture was cooled to 5° C., saturated ammonium chloride solution was cautiously added and the mixture was extracted with ethyl acetate. The organic extracts were combined and washed with brine. The organic solution was filtered through a hydrophobic frit and the filtrate was evaporated. The residue was purified by silica gel chromatography using a gradient of iso-hexanes/ethyl acetate 9:1 to 4:1 to afford crude 5,5-dimethyl-2-(1-trifluoromethanesulfonyloxy-ethyl)-[1,4]dioxane-2-carboxylic acid benzyl ester (833 mg, 1.3 mmol) as a yellow oil which darkened upon standing and as a 2:1 mixture of diastereoisomers which was used immediately in the next step. LCMS (m/z) 449.0 [M+H], Tr=3.29 min. A solution of 5,5-dimethyl-2-(1-trifluoromethanesulfonyloxy-ethyl)-[1,4]dioxane-2-carboxylic acid benzyl ester (833 mg, 1.3 mmol) in dichloromethane (5 mL) was stirred at room temperature under nitrogen. 1,8-Diazabicycloundec-7-ene (790 mg, 0.8 mL, 5.2 mmol) was added and the reaction mixture was stirred at room temperature for 72 h. The reaction mixture was cooled to 0° C. and acidified to pH 2 with ice cold hydrochloric acid (2 M). The mixture was extracted with dichloromethane. The organic extracts were combined and washed with brine. The organic solution was filtered through a hydrophobic frit and the filtrate was evaporated. The residue was purified by silica gel chromatography using a gradient of iso-hexanes/diethyl ether 9:1 to 3:1 to afford the title compound (189 mg, 52% over two steps) as a colorless oil. $^1$H NMR (300 MHz, CDCl$_3$): δ 1.13 (s, 3H), 1.32 (s, 3H), 3.53 (d, J=11.8 Hz, 1H), 3.66 (d, J=11.8 Hz, 1H), 3.72 (d, J=12.1 Hz, 1H), 4.24 (d, J=12.1 Hz, 1H), 5.19-5.35 (m, 3H), 5.51 (dd, J=17.4, 0.9 Hz, 1H), 5.80 (dd, J=17.4, 10.7 Hz, 1H), 7.35-7.40 (m, 5H). LCMS (m/z) 277.1 [M+H], Tr=2.81 min.

Compound 100f.
5,5-Dimethyl-2-vinyl-[1,4]dioxane-2-carboxylic acid

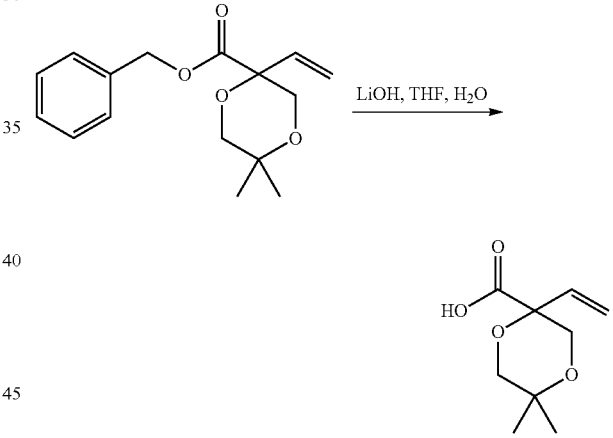

To a stirred solution of 5,5-dimethyl-2-vinyl-[1,4]dioxane-2-carboxylic acid benzyl ester (189 mg, 0.684 mmol) in tetrahydrofuran (7 mL) at 0° C. was added a solution of lithium hydroxide hydrate (34 mg, 0.821 mmol) in water (1.6 mL). The reaction mixture was stirred at 0° C. for 30 min and allowed to warm to ambient temperature and stirred for 19 h. The mixture was diluted with water and washed with ethyl acetate (2×). The aqueous layer was acidified to pH 5 with hydrochloric acid (2 M) and extracted with ethyl acetate (2×). The organic extracts were dried over anhydrous magnesium sulfate, filtered and evaporated to give the title compound (69 mg, 54%) as a colorless oil. $^1$H NMR (300 MHz, CDCl$_3$): δ 1.19 (s, 3H), 1.32 (s, 3H), 3.58 (d, J=11.8 Hz, 1H), 3.72 (d, J=11.8 Hz, 1H), 3.75 (d, J=12.3 Hz, 1H), 4.21 (d, J=12.3 Hz, 1H), 5.39 (dd, J=10.7, 0.9 Hz, 1H), 5.60 (dd, J=17.4, 0.9 Hz, 1H), 5.84 (dd, J=17.4, 10.7 Hz, 1H). LCMS (m/z) 185.2 [M−H], Tr=1.32 min.

Compound 100 g. 2-((E)-2-{2-[(R)-1-({(S)-1-[(S)-2-((S)-2-Hydroxy-3-methyl-butyrylamino)-propionyl]-hexahydro-pyridazine-3-carbonyl}-amino)-ethyl]-quinolin-7-yl}-vinyl)-5,5-dimethyl[1,4]dioxane-2-carboxylic acid

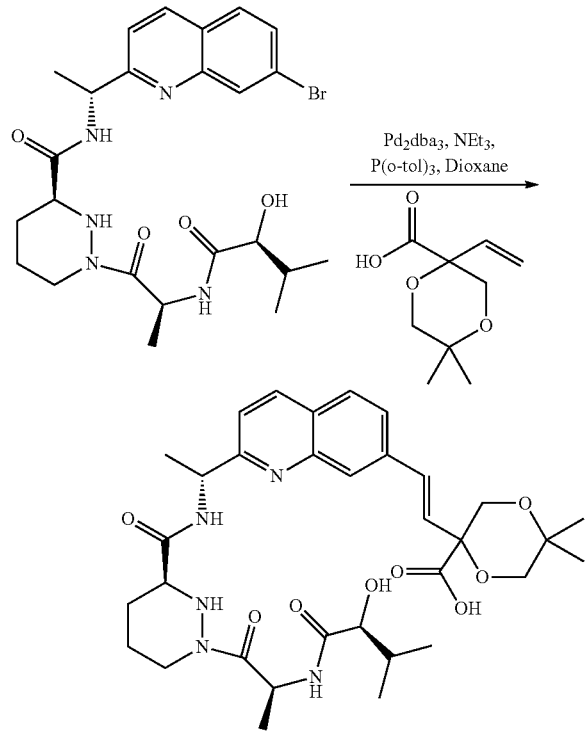

A mixture of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (198 mg, 0.371 mmol), 5,5-dimethyl-2-vinyl-[1,4]dioxane-2-carboxylic acid (69 mg, 0.371 mmol), triethylamine (112 mg, 155 μL, 1.11 mmol) and tri(o-tolyl)phosphine (23 mg, 0.074 mmol) in 1,4-dioxane (7.5 mL) was degassed with nitrogen for 5 min and then warmed to 50° C. under nitrogen with stirring. Tris(dibenzylideneacetone)dipalladium(0) (34 mg, 0.037 mmol) was added and the mixture was heated to 80° C. for 40 min and then allowed to cool to room temperature. The suspension was filtered and evaporated to give crude title compound (0.371 mmol) which was used directly in the next stage. LCMS (m/z) 640.3 [M+H], Tr=1.94 min.

Compounds 100 and 101

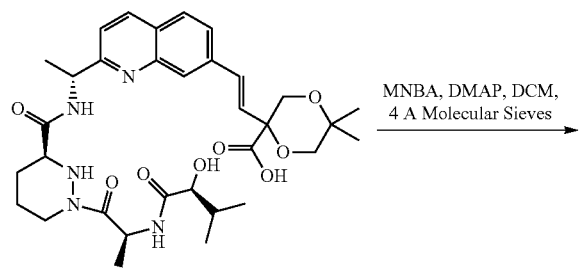

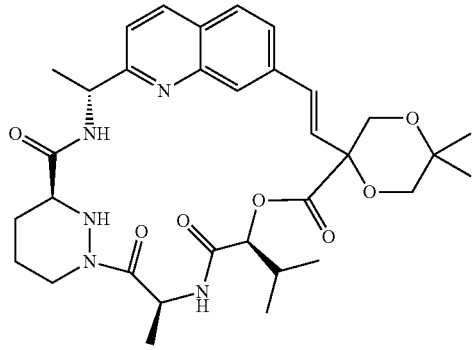

To a stirred mixture of powdered 4 Å molecular sieves (~1 g), 2-methyl-6-nitrobenzoic anhydride (255 mg, 0.742 mmol) and 4-(dimethylamino)-pyridine (181 mg, 1.48 mmol) in dichloromethane (111 mL), under nitrogen, was added a solution of the 2-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-5,5-dimethyl[1,4]dioxane-2-carboxylic acid (0.371 mmol) in dichloromethane (5 mL) over 2.5 h via syringe pump. The flask originally containing the crude acid was washed with dichloromethane (1 mL) and this solution was added to the reaction mixture over 30 min. After the end of addition, the reaction mixture was stirred for 30 min, filtered through Celite and washed successively with ice cold saturated ammonium chloride solution (2×) and ice cold saturated sodium bicarbonate solution (2×), passed through a hydrophobic frit and evaporated. The residue was purified by silica gel chromatography using a gradient of iso-hexanes/acetone 1:0 to 1:1 followed by reverse phase preparative HPLC on an Agilent Eclipse XDB/C18 7 micron, 250×21.2 mm column (flow rate 20 mL/min) using acetonitrile/water 9:11 to give the first eluting more polar diastereoisomer (2.9 mg, 1% over 2 steps) as a white solid and the second eluting less polar diastereoisomer (6.6 mg, 3% over 2 steps) as a white solid.

First eluting diastereoisomer. Compound 100 $^1$H NMR (300 MHz, CD$_3$OD): δ 1.07 (d, J=6.7 Hz, 3H), 1.12 (s, 3H), 1.13 (d, J=6.9 Hz, 3H), 1.43 (s, 3H), 1.52-1.78 (m, 2H), 1.57 (d, J=7.5 Hz, 3H), 1.59 (d, J=6.7 Hz, 3H), 1.93-2.02 (m, 1H), 2.18-2.39 (m, 2H), 2.68-2.80 (m, 1H), 3.55-3.64 (m, 2H), 3.73 (d, J=11.8 Hz, 1H), 3.92 (d, J=12.3 Hz, 1H), 4.39 (d, J=12.3 Hz, 1H), 4.41-4.50 (m, 1H), 5.11 (q, J=6.7 Hz, 1H), 5.39 (d, J=8.5 Hz, 1H), 5.83 (q, J=6.9 Hz, 1H), 6.31 (d, J=16.5 Hz, 1H), 6.98 (d, J=16.5 Hz, 1H), 7.49 (d, J=8.7 Hz, 1H), 7.65 (dd, J=8.5, 1.4 Hz, 1H), 7.85 (s, 1H), 7.89 (d, J=8.5 Hz, 1H), 8.28 (d, J=8.5 Hz, 1H). LCMS (m/z) 622.2 [M+H], Tr=2.48 min.

Second eluting diastereoisomer. Compound 101 $^1$H NMR (300 MHz, CD$_3$OD): δ 1.08 (d, J=6.7 Hz, 3H), 1.09 (d, J=6.5 Hz, 3H), 1.13 (s, 3H), 1.43 (s, 3H), 1.52-1.76 (m, 2H), 1.59 (d, J=6.7 Hz, 3H), 1.64 (d, J=7.4 Hz, 3H), 1.89-1.99 (m, 1H), 2.19-2.28 (m, 2H), 2.62-2.73 (m, 1H), 3.55-3.71 (m, 3H), 3.87 (d, J=12.0 Hz, 1H), 4.30 (d, J=11.8 Hz, 1H), 4.37-4.47 (m, 1H), 5.09 (q, J=6.7 Hz, 1H), 5.21 (d, J=8.9 Hz, 1H), 5.79 (q, J=7.2 Hz, 1H), 6.14 (d, J=16.3 Hz, 1H), 6.89 (d, J=16.3 Hz, 1H), 7.47 (d, J=8.5 Hz, 1H), 7.65 (dd, J=8.5, 1.6 Hz, 1H), 7.86 (d, J=8.2 Hz, 1H), 7.88 (s, 1H), 8.26 (d, J=8.5 Hz, 1H). LCMS (m/z) 622.3 [M+H], Tr=2.47 min.

Examples 102, 103, 104 and 105

Compounds 102, 103, 104 and 105

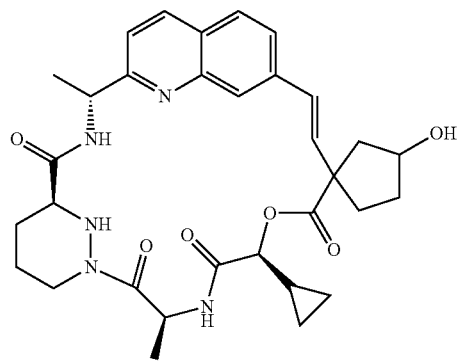 [SMILES: C[C@@H]1NC(=O)[C@H](C2CC2)OC(=O)C2(/C=C/c3ccc4ccc(nc4c3)[C@@H](C)NC(=O)[C@@H]3CCCN(N3)C1=O)CCC(O)C2]

Compound 102a.
3-Triisopropylsilanyloxy-cyclopentanecarboxylic acid ethyl ester

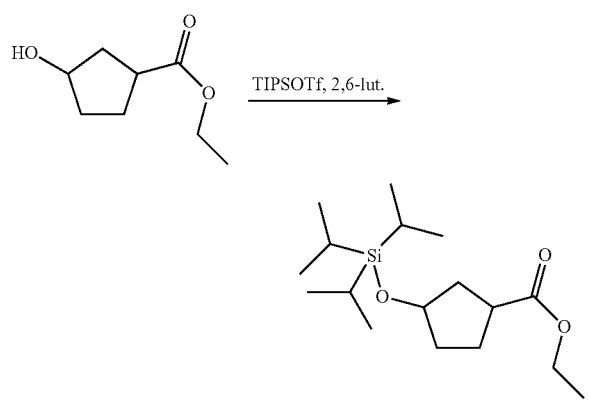

A solution of 3-hydroxy-cyclopentanecarboxylic acid ethyl ester (prepared as described in PCT Int. Appl. 2008131946, 3.180 g, 20.1 mmol) in dichloromethane (100 mL) was subsequently treated with 2,6-lutidine (4.7 mL, 40.2 mmol) and triisopropylsilyl trifluoromethanesulfonate (8.1 mL, 30.15 mmol). After stirring for 3.5 h, the reaction was quenched with pH 4 buffer. The aqueous layer was extracted with dichloromethane. The organics were combined, filtered through a phase separator and the volatiles were removed in vacuo. The residue was purified by silica gel chromatography using a 100 g Isolute cartridge eluted with a continuous gradient of iso-hexanes/diethyl ether 1:0 to 9:1 to afford the title compound (6.15 g, 97%) as a light yellow oil and as a 3.5:1 mixture of diastereoisomers. $^1$H NMR (300 MHz, CDCl$_3$): δ 1.04-1.08 (m, 27H), 1.27 (t, J=7.1 Hz, 4H), 1.70-2.00 (m, 5.2H), 2.04-2.21 (m, 2.6H), 2.66-2.79 (m, 1H), 2.97-3.10 (m, 0.3H), 4.14 (q, J=7.1 Hz, 2.6H), 4.29-4.39 (m, 1H), 4.43-4.50 (m, 0.3H).

Compound 102b. 1-(1-Hydroxy-ethyl)-3-triisopropylsilanyloxy-cyclopentanecarboxylic acid ethyl ester

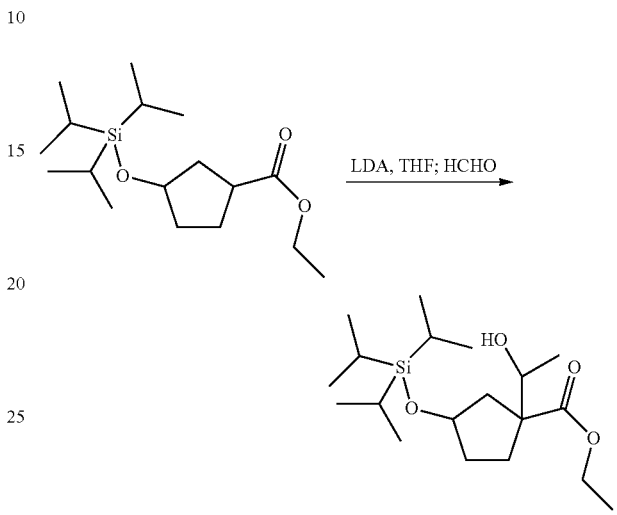

A cooled (−78° C.) solution of N,N-diisopropylamine (4.4 mL, 31.285 mmol) in anhydrous tetrahydrofuran (60 mL) was treated with n-butyllithium (2.5 M in hexanes, 11.7 mL, 29.329 mmol). After stirring at −78° C. for 30 min, the reaction mixture was treated with a solution of 3-triisopropylsilanyloxy-cyclopentanecarboxylic acid ethyl ester (6.15 g, 19.553 mmol) in anhydrous tetrahydrofuran (20 mL). After stirring at −78° C. for 40 min, the reaction mixture was treated with neat acetaldehyde (3.3 mL, 58.659 mmol). The cooling bath was removed and the reaction was stirred at room temperature for 50 min then quenched at 0° C. with a saturated solution of ammonium chloride (100 mL). The aqueous layer was extracted with dichloromethane (2×). The organics were combined, filtered through a phase separator and the volatiles were removed in vacuo. The residue was purified by silica gel chromatography using a 100 g Isolute cartridge eluted with a continuous gradient of iso-hexanes/ethyl acetate 1:0 to 4:1 to afford the title compound (6.61 g, 94%) as a light yellow oil and as a complex mixture of diastereoisomers.

Compound 102c. 3-Triisopropylsilanyloxy-1-vinyl-cyclopentanecarboxylic acid

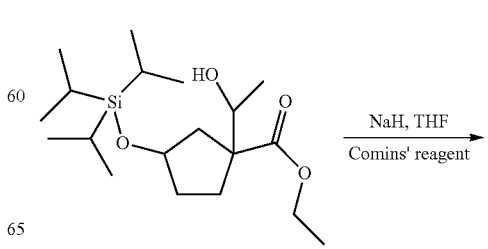

445 -continued

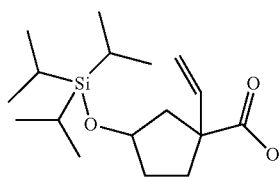

A cooled (−78° C.) suspension of sodium hydride (1.474 g, 36.868 mmol, 60% dispersed in mineral oil) in anhydrous tetrahydrofuran (60 mL) was treated with a solution of 1-(1-hydroxy-ethyl)-3-triisopropylsilanyloxy-cyclopentanecarboxylic acid ethyl ester (6.61 g, 18.434 mmol). After stirring at −78° C. for 10 min, the reaction mixture was treated with a solution of N-(5-chloro-2-pyridyl)bis(trifluoromethanesulfonimide) (13.2 g, 33.615 mmol) in anhydrous tetrahydrofuran (20 mL). The cooling bath was removed and the reaction was allowed to stir at room temperature for 24 h. More sodium hydride (1.474 g, 36.868 mmol, 60% dispersed in mineral oil) was added. After stirring at room temperature for 5 h, more sodium hydride (1.474 g, 36.868 mmol, 60% dispersed in mineral oil) was added. After stirring at room temperature for 17.5 h, the reaction was quenched at 0° C. with a saturated solution of ammonium chloride (100 mL). The aqueous layer was extracted with dichloromethane (2×). The aqueous layer was acidified to pH 2 with hydrochloric acid (2 M) and extracted with dichloromethane. The organics were combined, filtered through a phase separator and the volatiles were removed in vacuo. The residue was purified by silica gel chromatography using a 100 g Isolute cartridge eluted with a continuous gradient of iso-hexanes/ethyl acetate 1:0 to 4:1 followed by silica gel chromatography using a 100 g Isolute cartridge eluted with a continuous gradient of iso-hexanes/diethyl ether 1:0 to 4:1 to afford the title compound (876.9 mg, 15%) as a light yellow oil and as a 3:1 mixture of diastereoisomers. LCMS (m/z) 311.2 [M−H], Tr=4.05 min.

446

Compound 102d. 1-((E)-2-{2-[(R)-1-({(S)-1-[(S)-2-((S)-2-Cyclopropyl-2-hydroxy-acetylamino)-propionyl]-hexahydro-pyridazine-3-carbonyl}-amino)-ethyl]-quinolin-7-yl}-vinyl)-3-triisopropylsilanyloxy-cyclopentanecarboxylic acid

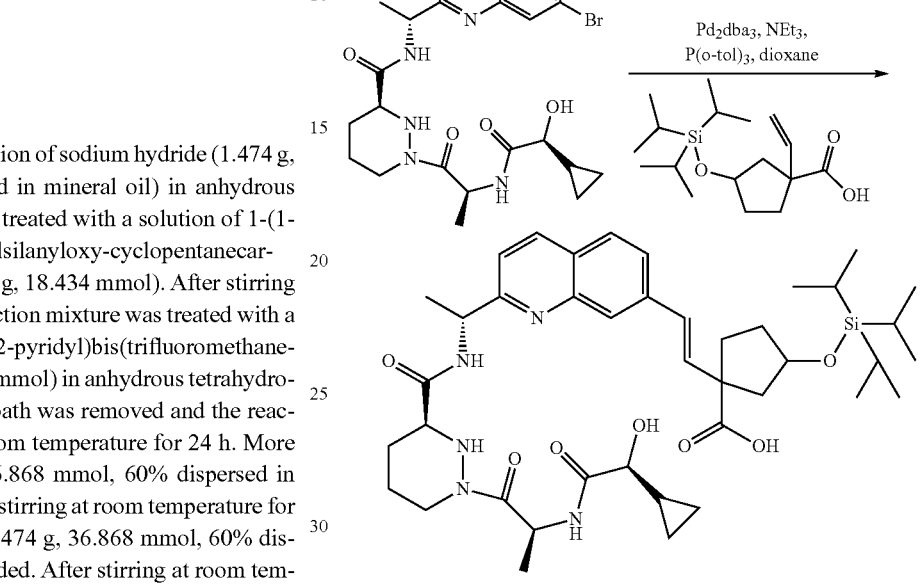

A solution of (S)-1-[(S)-2-((S)-2-cyclopropyl-2-hydroxy-acetylamino)-propionyl]-hexahydro-pyridazine-3-carboxylic acid [(R)-1-(7-bromo-quinolin-2-yl)-ethyl]-amide (795.0 mg, 1.493 mmol), 3-triisopropylsilanyloxy-1-vinyl-cyclopentanecarboxylic acid (466.6 mg, 1.493 mmol), tri(o-tolyl)phosphine (91.0 mg, 0.299 mmol) and triethylamine (0.63 mL, 4.479 mmol) in 1,4-dioxane (20 mL) was deoxygenated by bubbling through nitrogen for 5 min. The reaction mixture was then treated with tris(dibenzylideneacetone)dipalladium (0) (136.7 mg, 0.149 mmol). After stirring at 100° C. for 40 min, the reaction was cooled to room temperature and filtered through Celite. The solid was rinsed with ethyl acetate and the volatiles were removed in vacuo to provide the crude title compound (1.493 mmol) as an orange foam. LCMS (m/z) 764.4 [M−H], Tr=3.53 min.

Compound 102e

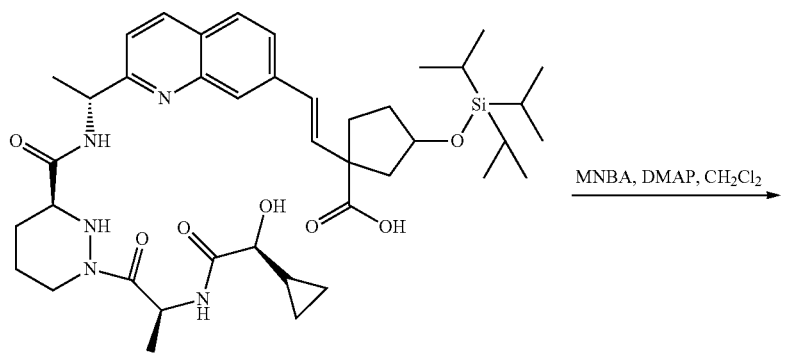

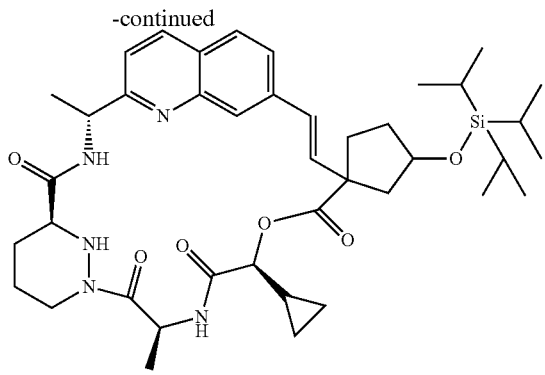

A solution of crude 1-((E)-2-{2-[(R)-1-({(S)-1-[(S)-2-((S)-2-cyclopropyl-2-hydroxy-acetylamino)-propionyl]-hexahydro-pyridazine-3-carbonyl}-amino)-ethyl]-quinolin-7-yl}-vinyl)-3-triisopropylsilanyloxy-cyclopentanecarboxylic acid (1.493 mmol) in dry dichloromethane (20 mL) was added via syringe pump to a solution of 2-methyl-6-nitrobenzoic anhydride (771.0 mg, 2.239 mmol), 4-dimethylaminopyridine (547.1 mg, 4.479 mmol) in dry dichloromethane (500 mL) containing 4 Å molecular sieves over 4.5 h. After the end of the addition, the reaction was stirred at room temperature for 2 h then filtered and the volatiles were partially removed in vacuo. The organics were washed with hydrochloric acid (0.5 M, 40 mL). The acidic aqueous layer was extracted with dichloromethane. The combined organics were washed with a saturated solution of sodium bicarbonate. The basic aqueous layer was extracted with dichloromethane. The combined organics were filtered on a phase separator. The volatiles were removed in vacuo and the residue was purified by silica gel chromatography using a 50 g Isolute cartridge eluted with a continuous gradient of iso-hexanes/acetone 1:0 to 3:2 to afford the title compound (459.6 mg, 41%) as a white solid and as a complex mixture of diastereoisomers. LCMS (m/z) 746.5 [M+H], Tr=4.35 min.

Compounds 102, 103, 104 and 105

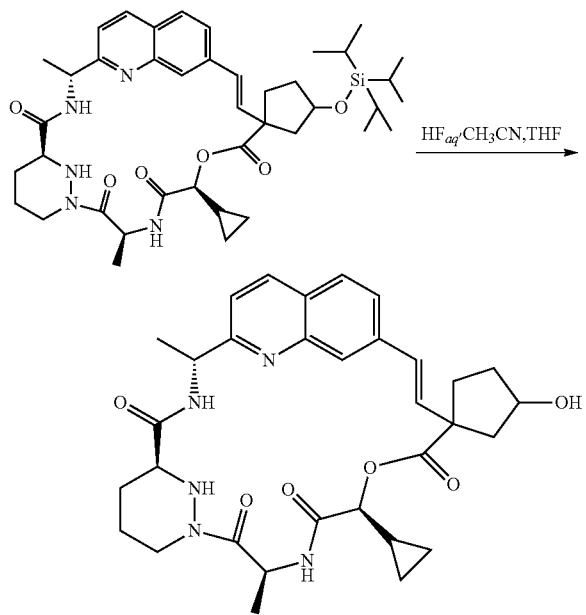

A solution of compound 102e (459.6 mg, 0.616 mmol) in acetonitrile/tetrahydrofuran (20 mL, 9:1) in a 250 mL round-bottom Teflon flask was treated with hydrofluoric acid (48 wt % in water, 1.3 mL, 30.8 mmol). After stirring at room temperature for 17 h, more hydrofluoric acid (48 wt % in water, 1.3 mL, 30.8 mmol) was added. After stirring at room temperature for 7 h, the reaction mixture was slowly poured over a saturated solution of sodium bicarbonate (100 mL). After the bubbling has stopped, the aqueous layer was extracted with dichloromethane (2×). The organics were combined, filtered through a phase separator and the volatiles were removed in vacuo. The residue was purified by silica gel chromatography using a 50 g Isolute cartridge eluted with a continuous gradient of iso-hexanes/acetone 1:0 to 2:3. The mixture was further purified by reverse phase preparative HPLC eluting with a continuous gradient of water (modified with 0.1% trifluoroacetic acid)/acetonitrile (modified with 0.1% trifluoroacetic acid) 9:1 to 3:2 collecting 2 mL fractions to afford, after evaporation of volatiles four different isomers as trifluoroacetate salts.

Compound 102 (41.2 mg, 9.5%) as a light yellow solid. $^1$H NMR (300 MHz, CD$_3$OD): δ 0.46-0.56 (m, 1H), 0.58-0.72 (m, 3H), 1.23-1.36 (m, 1H), 1.56-1.67 (m, 7H), 1.69-1.85 (m, 3H), 1.90-2.00 (m, 1H), 2.01-2.12 (m, 1H), 2.13-2.24 (m, 2H), 2.46-2.54 (m, 1H), 2.62-2.79 (m, 2H), 3.58-3.66 (m, 1H), 4.37-4.47 (m, 2H), 4.94 (d, J=8.7 Hz, 1H), 5.12 (q, J=6.7 Hz, 1H), 5.78-5.91 (m, 1H), 6.50 (app d, J=3.1 Hz, 2H), 7.57 (d, J=8.5 Hz, 1H), 7.73 (d, J=8.5 Hz, 1H), 7.89 (s, 1H), 7.93 (d, J=8.5 Hz, 1H), 8.43 (d, J=8.5 Hz, 1H), 8.66 (d, J=7.1 Hz, 1H). LCMS (m/z) 590.2 [M+H], Tr=1.97 min.

Compound 103 (31.2 mg, 7.2%) as a light yellow gum. $^1$H NMR (300 MHz, CD$_3$OD): δ 0.47-0.57 (m, 1H), 0.60-0.74 (m, 3H), 1.25-1.38 (m, 1H), 1.54-1.79 (m, 9H), 1.91-2.25 (m, 5H), 2.48-2.90 (m, 3H), 3.58-3.66 (m, 1H), 4.37-4.47 (m, 2H), 5.13 (q, J=6.7 Hz, 1H), 5.78-5.91 (m, 1H), 6.48, 6.55 (ABq, J$_{AB}$=16.3 Hz, 2H), 7.57 (d, J=8.5 Hz, 1H), 7.73 (d, J=8.5 Hz, 1H), 7.83-7.96 (m, 2H), 8.43 (d, J=8.5 Hz, 1H), 8.66 (d, J=7.8 Hz, 1H). LCMS (m/z) 590.2 [M+H], Tr=1.88 min.

Compound 104 (13.5 mg, 3.1%) as a light yellow solid. $^1$H NMR (300 MHz, CD$_3$OD): δ 0.44-0.57 (m, 1H), 0.61-0.71 (m, 3H), 1.28-1.40 (m, 1H), 1.54-1.81 (m, 9H), 1.91-2.13 (m, 4H), 2.17-2.29 (m, 1H), 2.43-2.59 (m, 1H), 2.66-2.78 (m, 2H), 3.58-3.66 (m, 1H), 4.30-4.38 (m, 1H), 4.40-4.48 (m, 1H), 5.05-5.15 (m, 1H), 5.78-5.91 (m, 1H), 6.47, 6.54 (ABq, J$_{AB}$=15.8 Hz, 2H), 7.50 (d, J=8.5 Hz, 1H), 7.63-7.74 (m, 1H), 7.80 (s, 1H), 7.88 (d, J=8.5 Hz, 1H), 8.32 (d, J=8.5 Hz, 1H), 8.69-8.76 (m, 1H). LCMS (m/z) 590.2 [M+H], Tr=1.93 min.

Compound 105 (6.0 mg, 1.4%) as a light yellow gum. $^1$H NMR (300 MHz, CD$_3$OD): δ 0.45-0.55 (m, 1H), 0.59-0.72 (m, 3H), 1.27-1.44 (m, 1H), 1.54-1.84 (m, 9H), 1.90-2.00 (m, 2H), 2.01-2.27 (m, 4H), 2.45-2.54 (m, 1H), 2.62-2.81 (m, 2H), 3.57-3.66 (m, 1H), 4.37-4.47 (m, 2H), 4.96 (d, J=8.9 Hz, 1H), 5.11 (q, J=6.9 Hz, 1H), 5.78-5.90 (m, 1H), 6.39-6.62 (m, 2H), 7.52 (d, J=8.5 Hz, 1H), 7.70 (d, J=8.5 Hz, 1H), 7.80-7.92 (m, 2H), 8.35 (d, J=8.5 Hz, 1H), 8.66-8.74 (m, 1H). LCMS (m/z) 590.2 [M+H], Tr=1.97 min.

Example 106

Compound 106

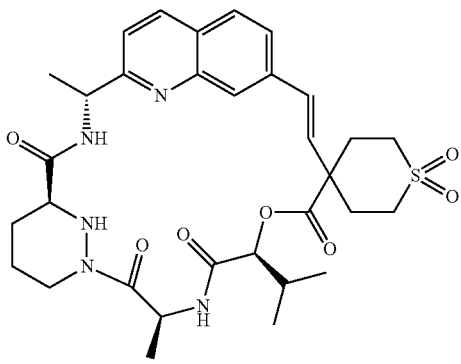 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)CCS(=O)(=O)CC2]

Compound 106a. 4-(1-Hydroxy-ethyl)-tetrahydro-thiopyran-4-carboxylic acid methyl ester

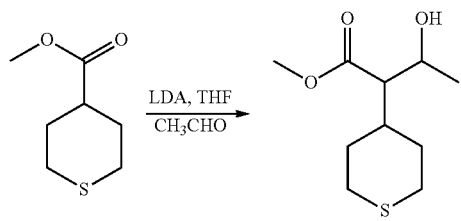

A solution of N,N-diisopropylamine (1.51 g, 2.1 mL, 15 mmol) in anhydrous tetrahydrofuran (10 mL) was stirred at −78° C. under nitrogen. n-Butyl lithium (6 mL, 15 mmol, 2.5 M solution in hexane) was added dropwise and the reaction mixture was stirred at −78° C. for 30 min. A solution of tetrahydro-thiopyran-4-carboxylic acid methyl ester (1.60 g, 10 mmol) in tetrahydrofuran (4 mL) was added and the reaction mixture was stirred at −78° C. for 20 min. Acetaldehyde (1.32 g, 1.7 mL, 30 mmol) was then added in one portion. The cooling bath was removed and the reaction mixture was stirred at room temperature for 1 h. The reaction mixture was cooled to 0° C. and ice-cold hydrochloric acid (2 M) was added to acidify the reaction mixture to pH 2. Sodium chloride was added to saturate the aqueous phase and the mixture was extracted with diethyl ether. The organic extracts were combined and washed with brine. The organic solution was filtered through a hydrophobic frit and the filtrate was evaporated. The residue was purified by silica gel chromatography using a gradient of pentane/diethyl ether 3:1 to 1:3 to afford the title compound (1.77 g, 87%) as a yellow oil. ¹H NMR (300 MHz, d₆-DMSO): δ 0.96 (d, J=6.5 Hz, 3H), 1.46-1.73 (m, 2H), 2.12-2.28 (m, 2H), 2.43-2.57 (m, 4H), 3.50-3.58 (m, 1H), 3.63 (s, 3H), 4.85 (d, J=5.8 Hz, 1H). LCMS (m/z) 227.1 [M+Na], Tr=1.53 min.

Compound 106b. 4-(1-Hydroxy-ethyl)-1,1-dioxo-hexahydro-thiopyran-4-carboxylic acid methyl ester

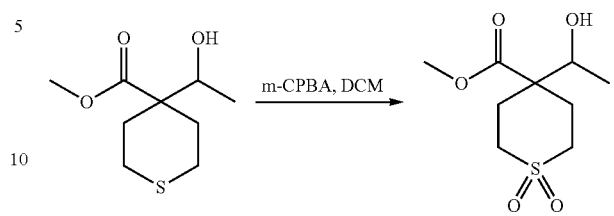

A solution of 4-(1-hydroxy-ethyl)-tetrahydro-thiopyran-4-carboxylic acid methyl ester (408 mg, 2 mmol) in dichloromethane (10 mL) was stirred at 0° C. Meta-chloroperbenzoic acid (70% pure containing 20% water and 10% meta-chlorobenzoic acid, 830 mg, 4.8 mmol) was added and the reaction mixture was stirred at 0° C. for 3 h. Additional meta-chloroperbenzoic acid (70% pure containing 20% water and 10% meta-chlorobenzoic acid, 830 mg, 4.8 mmol) was added and the reaction mixture was stirred at 0° C. for 3 h. Sodium thiosulfate solution and saturated sodium hydrogen carbonate solution were added and the mixture was extracted with dichloromethane. The organic extracts were combined and washed with brine. The organic solution was filtered through a hydrophobic frit and the filtrate was evaporated. The residue was purified by silica gel chromatography using a gradient of iso-hexanes/ethyl acetate 1:1 to 0:1 to afford the title compound (281 mg, 60%) as a white solid. ¹H NMR (300 MHz, d₆-DMSO) δ0.99 (d, J=6.5 Hz, 3H), 1.90-2.30 (m, 4H), 2.92-3.11 (m, 4H), 3.64-3.71 (m, 4H), 5.12 (d, J=5.8 Hz, 1H). LCMS (m/z) 237.1 [M+H], Tr=0.76 min.

Compound 106c. 1,1-Dioxo-4-vinyl-hexahydro-thiopyran-4-carboxylic acid methyl ester

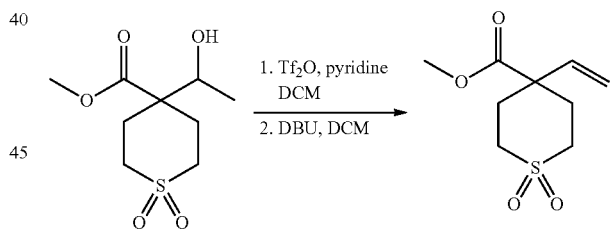

A solution of 4-(1-hydroxy-ethyl)-1,1-dioxo-hexahydro-thiopyran-4-carboxylic acid methyl ester (281 mg, 1.2 mmol) in dichloromethane (10 mL) was stirred at 0° C. under nitrogen. Pyridine (284 mg, 0.3 mL, 3.6 mmol) was added and then trifluoromethanesulfonic anhydride (677 mg, 0.4 mL, 2.4 mmol) was added drop wise and the reaction mixture was stirred at 0° C. for 30 min. Saturated sodium hydrogen carbonate solution was added and the organic layer was separated and washed with brine and filtered through a hydrophobic frit. The filtrate was evaporated to a volume of ~5 mL and the solution of crude 1,1-dioxo-4-(1-trifluoromethanesulfonyloxy-ethyl)-hexahydro-thiopyran-4-carboxylic acid methyl ester (1.2 mmol) was used immediately in the next step. LCMS (m/z) 368.9 [M+H], Tr=2.27 min. A solution of crude 1,1-dioxo-4-(1-trifluoromethanesulfonyloxy-ethyl)-hexahydro-thiopyran-4-carboxylic acid methyl ester (1.2 mmol) in dichloromethane (5 mL) was stirred at room temperature under nitrogen. 1,8-Diazabicycloundec-7-ene (0.6 mL, 3.6 mmol) was added and the reaction mixture was stirred at room temperature for 45 min. The reaction mixture was cooled to 0° C. and acidified to pH 2 with ice-cold hydrochloric acid (2 M). The mixture was extracted with dichloromethane. The organic extracts were combined, washed with water and brine. The organic solution was filtered through a hydrophobic frit and the filtrate was evaporated. The residue was purified by silica gel chromatography using a gradient of iso-hexanes/ethyl acetate 4:1 to 1:1 to afford the title compound (182 mg, 70% over two steps) as a white solid. $^1$H NMR (300 MHz, CDCl$_3$) δ 2.25-2.34 (m, 2H), 2.59-2.66 (m, 2H), 3.05-3.13 (m, 4H), 3.79 (s, 3H), 5.23 (d, J=17.6 Hz, 1H), 5.31 (d, J=10.7 Hz, 1H), 5.82 (dd, J=17.6, 10.7 Hz, 1H). LCMS (m/z) 219.1 [M+H], Tr=1.33 min.

Compound 106d.
1,1-Dioxo-4-vinyl-hexahydro-thiopyran-4-carboxylic acid

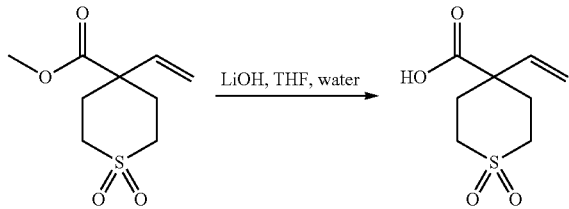

A solution of 1,1-dioxo-4-vinyl-hexahydro-thiopyran-4-carboxylic acid methyl ester (174 mg, 0.8 mmol) in tetrahydrofuran (4 mL) and methanol (0.5 mL) was stirred at room temperature under nitrogen. A solution of lithium hydroxide monohydrate (134 mg, 3.2 mmol) in water (1 mL) was added and the reaction mixture was stirred at room temperature for 1 h. The reaction mixture was cooled to 0° C. and acidified to pH 2 with hydrochloric acid (2 M). Sodium chloride was added and the mixture was extracted with ethyl acetate. The organic extracts were combined and washed with brine. The organic solution was filtered through a hydrophobic frit and the filtrate was evaporated to afford the title compound (163 mg, 100%) as a white solid. $^1$H NMR (300 MHz, d$_6$-DMSO) 2.03-2.12 (m, 2H), 2.33-2.42 (m, 2H), 2.96-3.13 (m, 4H), 5.23 (d, J=17.6 Hz, 1H), 5.25 (d, J=10.7 Hz, 1H), 5.87 (dd, J=17.6, 10.7 Hz, 1H), 12.9-13.1 (br s, 1H). LCMS (m/z) 227.1 [M+Na], Tr=0.96 min.

Compound 106

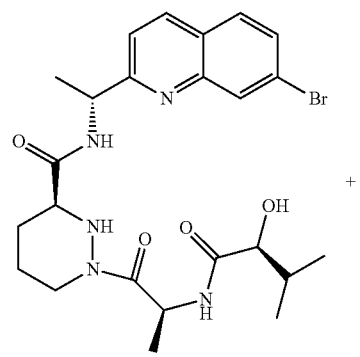

+

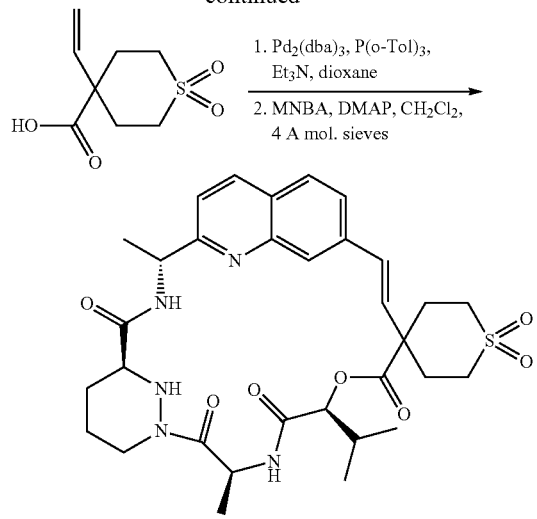

A stirred solution of 1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (187 mg, 0.35 mmol), 1,1-dioxo-4-vinyl-hexahydro-thiopyran-4-carboxylic acid (79 mg, 0.38 mmol), tri(o-tolyl)phosphine (21 mg, 0.07 mmol) and triethylamine (106 mg, 0.15 mL, 1.05 mmol) in 1,4-dioxane (10 mL) was degassed with nitrogen for 15 min. The solution was heated to 50° C. and tris(dibenzylideneacetone)dipalladium(0) (32 mg, 0.035 mmol) was added. The reaction mixture was heated at 80° C. for 30 min. The reaction mixture was cooled to room temperature and the mixture was filtered through a hydrophobic frit and the filtrate was evaporated to afford crude 4-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-1,1-dioxo-hexahydro-thiopyran-4-carboxylic acid (0.35 mmol) as an orange oil. LCMS (m/z) 658.2 [M+H], Tr=1.57 min. A solution of 2-methyl-6-nitrobenzoic anhydride (241 mg, 0.7 mmol) and 4-(dimethylamino)-pyridine (170 mg, 1.4 mmol) in dichloromethane (200 mL) containing 4 Å molecular sieves (200 mg) was stirred at room temperature under nitrogen. A solution of crude 4-((E)-2-{2-[(R)-1-({(S)-1-[(S)-2-((S)-2-hydroxy-3-methyl-butyrylamino)-propionyl]-hexahydro-pyridazine-3-carbonyl}-amino)-ethyl]-quinolin-7-yl}-vinyl)-1,1-dioxo-hexahydro-thiopyran-4-carboxylic acid (0.35 mmol) in dichloromethane (5 mL) was added dropwise over 4 h and the reaction mixture was stirred at room temperature for 4 h. The reaction mixture was filtered through Celite and the solution was evaporated to give a volume of ~30 mL. The solution was washed with ice-cold saturated ammonium chloride solution, ice-cold saturated sodium bicarbonate solution and brine. The organic solution was filtered through a hydrophobic frit and the filtrate was evaporated. The residue was purified by silica gel chromatography eluting with a gradient of iso-hexanes/ethyl acetate/methanol 1:1:0 to 0:1:0 to 0:9:1 followed by reverse phase preparative HPLC eluting with a gradient of acetonitrile (containing 0.1% trifluoroacetic acid)/water (containing 0.1% trifluoroacetic acid) 9:1 to 1:1. Fractions containing the product were combined and evaporated. The residue was partitioned between dichloromethane and saturated sodium hydrogen carbonate solution. The organic layer was separated and washed with brine. The organic solution was filtered through a hydrophobic frit and the filtrate was evaporated to afford the title compound (14 mg, 7% over two steps) as a white solid. $^1$H NMR (300 MHz, CD$_3$OD): δ 1.05 (d, J=6.7 Hz, 3H), 1.09 (d, J=6.7 Hz, 3H), 1.59 (d, J=6.7 Hz, 3H), 1.62 (d, J=7.1 Hz, 3H), 1.63-1.71

(m, 2H), 1.92-1.97 (m, 1H), 2.17-3.25 (m, 11H), 3.55-3.65 (m, 1H), 4.40-4.46 (m, 1H), 5.09 (q, J=6.7 Hz, 1H), 5.33 (d, J=8.3 Hz, 1H), 5.85 (q, J=7.1 Hz, 1H), 6.36 (d, J=16.3 Hz, 1H), 6.73 (d, J=16.3 Hz, 1H), 7.47 (d, J=8.5 Hz, 1H), 7.68 (dd, J=8.5, 1.6 Hz, 1H), 7.85 (br s, 1H), 7.87 (d, J=8.5 Hz, 1H), 8.28 (d, J=8.5 Hz, 1H). LCMS (m/z) 640.2 [M+H], Tr=2.09 min.

Example 107

Compound 107

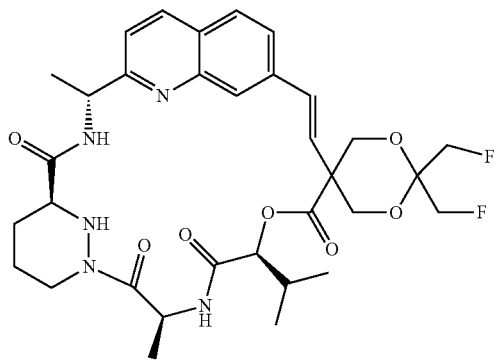 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)COC(CF)(CF)OC2]

Compound 107a. 2,2-Bis-fluoromethyl-5-vinyl-[1,3]dioxane-5-carboxylic acid ethyl ester

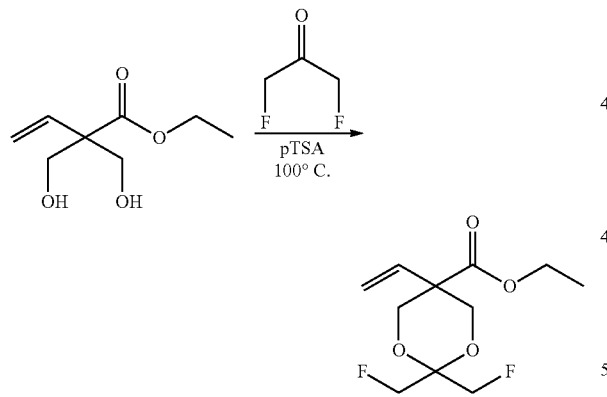

A vial was loaded with 2,2-bis-hydroxymethyl-but-3-enoic acid ethyl ester (0.88 g, 5.05 mmol), 1,3-difluoroacetone (0.95 g, 10.1 mmol) and para-toluene-4-sulfonic acid monohydrate (0.96 g, 5.05 mmol). The vial was sealed and heated in a microwave reactor at 100° C. for 15 min. The resultant brown oil was partitioned between dichloromethane and aqueous sodium bicarbonate solution. The organic layer was filtered through a hydrophobic frit and evaporated to give a brown oil (0.98 g). The oil was purified by silica gel chromatography using iso-hexanes/ethyl acetate 3:1 to yield the title compound (0.619 g, 74%) as a colorless oil. $^1$H NMR (300 MHz, CDCl$_3$): δ 1.31 (t, J=7.1 Hz, 3H), 3.96 (d, J=12.0 Hz, 2H), 4.27 (q, J=7.1 Hz, 2H), 4.34-4.69 (m, 6H), 5.22-5.35 (m, 2H), 5.67-5.79 (m, 1H).

Compound 107b. 2,2-Bis-fluoromethyl-5-vinyl-[1,3]dioxane-5-carboxylic acid

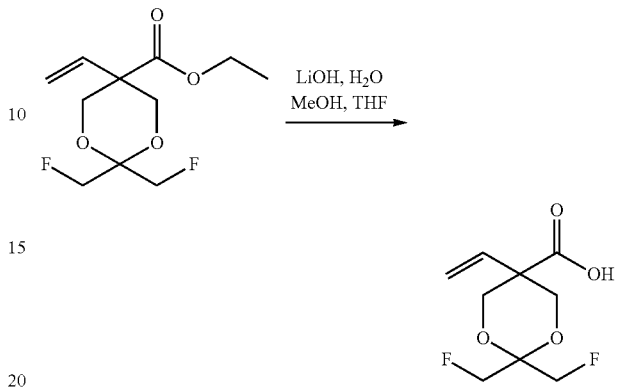

A solution of lithium hydroxide monohydrate (311 mg, 7.42 mmol) in water (8 mL) was added to a stirred solution of 2,2-bis-fluoromethyl-5-vinyl-[1,3]dioxane-5-carboxylic acid ethyl ester (619 mg, 2.47 mmol) in tetrahydrofuran/methanol (12 mL, 4:1). The reaction mixture was stirred at room temperature for 1 h and then cooled to 0° C. before acidifying to pH 4 with hydrochloric acid (1 M). The mixture was saturated with sodium chloride and then extracted with dichloromethane (3×10 mL). The extract was filtered through a hydrophobic frit and evaporated to give the title product (390 mg, 71%) as a colorless gum. $^1$H NMR (300 MHz, CDCl$_3$) δ 4.00 (d, J=12.0 Hz, 2H), 4.35-4.73 (m, 6H), 5.30-5.43 (m, 2H), 5.68-5.81 (m, 1H).

Example 107

Compound 107

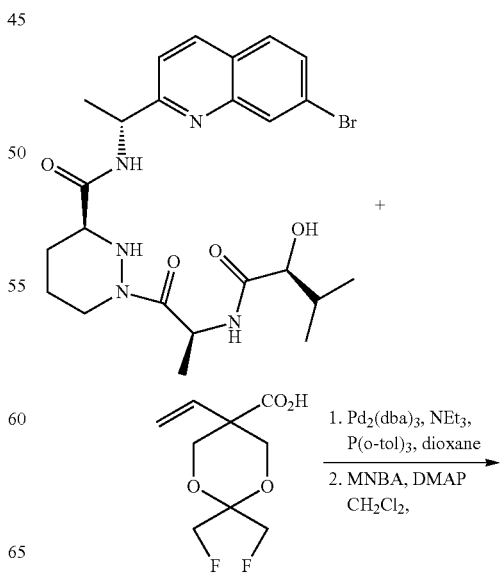

455
-continued

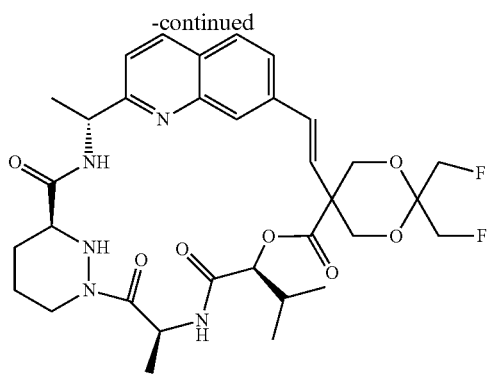

A solution of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (300 mg, 0.56 mmol), 2,2-bis-fluoromethyl-5-vinyl-[1,3]dioxane-5-carboxylic acid (125 mg, 0.56 mmol), triethylamine (234 µL, 1.68 mmol) and tri(o-tolyl)phosphine (34 mg, 0.112 mmol) in 1,4-dioxane (12 mL) was purged with nitrogen for 10 min before adding tris(dibenzylideneacetone) dipalladium(0) (51 mg, 0.056 mmol). The stirred reaction mixture was heated at 60° C. for 1 h. The mixture was cooled to room temperature, filtered through Celite then evaporated to yield an orange foam. The foam was dissolved in dichloromethane (10 mL) and the resulting solution was added over 5 h via syringe pump to a solution of 2-methyl-6-nitro-benzoic anhydride (482 mg, 1.4 mmol) and 4-(dimethylamino)pyridine (350 mg, 2.8 mmol) in dichloromethane (205 mL) containing powdered 3 Å sieves. After the end of addition, the solution was stirred for 20 min, filtered, washed with aqueous sodium bicarbonate solution (150 mL), then filtered through a hydrophobic frit and evaporated to give a brown gum which was purified by reverse phase preparative HPLC using a gradient of water/acetonitrile 4:1 to 0:1 followed by reverse phase preparative HPLC using water (modified with 0.1% ammonium formate)/acetonitrile 3:2 to afford the title compound (39 mg, 10%) as a white solid. $^1$H NMR (300 MHz, CD$_3$OD): δ 1.06 (d, J=6.7 Hz, 3H), 1.12 (d, J=6.7 Hz, 3H), 1.49-1.78 (m, 2H), 1.61 (d, J=6.7 Hz, 3H), 1.66 (d, J=7.1 Hz, 3H), 1.92-2.02 (m, 1H), 2.13-2.30 (m, 2H), 2.64-2.78 (m, 1H), 3.58-3.66 (m, 1H), 4.12-4.25 (m, 3H), 4.35-4.92 (m, 6H), 5.07 (q, J=6.7 Hz, 1H), 5.38 (d, J=9.1 Hz, 1H), 5.82 (q, J=7.1 Hz, 1H), 6.17 (d, J=16.5 Hz, 1H), 6.65 (d, J=16.5 Hz, 1H), 7.48 (d, J=8.5 Hz, 1H), 7.67-7.76 (m, 2H), 7.87 (d, J=8.5 Hz, 1H), 8.27 (d, J=8.5 Hz, 1H). LCMS (m/z) 658.2 [M+H], Tr=2.46 min.

Example 108

Compound 108

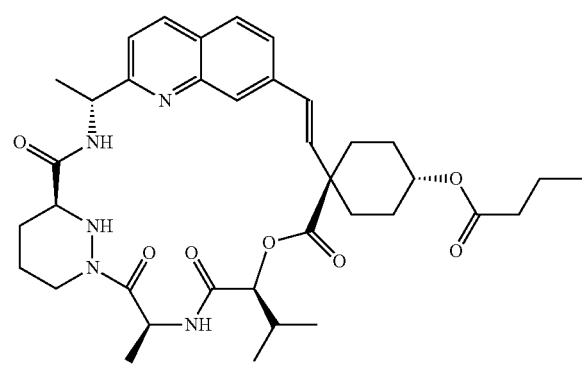 [SMILES: CCCC(=O)O[C@H]1CC[C@@]2(/C=C/c3ccc4ccc(nc4c3)[C@@H](C)NC(=O)[C@@H]3CCCN(N3)C(=O)[C@H](C)NC(=O)[C@H](C(C)C)OC2=O)CC1]

456
Compound 108

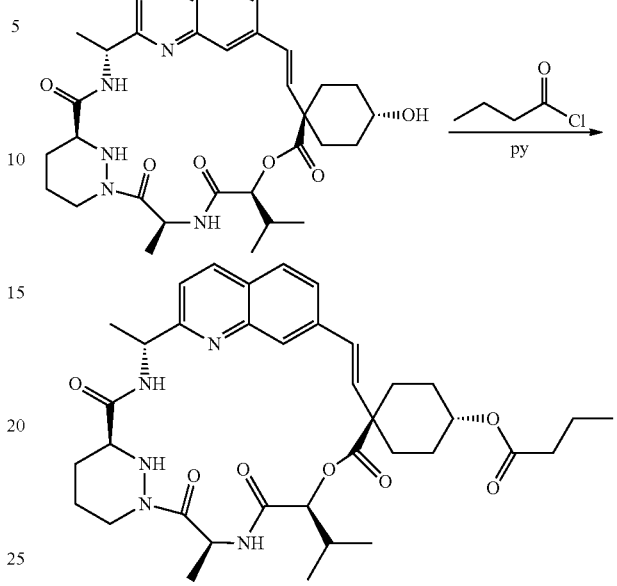

To a solution of the reactant 74 (7.5 mg, 0.012 mmol) in pyridine (3 drops) was added n-butyryl chloride (1 drop) at rt. After 1 h at rt, the mixture was diluted with ethyl acetate, washed with 10% citric acid solution (×1) and saturated NaHCO$_3$ solution (×1). After the aqueous fractions were extracted with ethyl acetate (×1), two organic fractions were combined, dried (MgSO$_4$), and concentrated. The residue was purified by CombiFlash using hexanes-ethyl acetate as eluents to obtain 4.6 mg (55%) of the product Compound 108. $^1$H NMR (400 MHz, Methanol-d$_4$): δ 8.23 (d, J=8.5 Hz, 1H), 7.83 (d, J=8.4 Hz, 1H), 7.78 (s, 1H), 7.63 (dd, J=8.7, 1.6 Hz, 1H), 7.43 (d, J=8.5 Hz, 1H), 6.60 (d, J=16.3 Hz, 1H), 6.29 (d, J=16.4 Hz, 1H), 5.80 (q, J=7.2 Hz, 1H), 5.25 (d, J=8.5 Hz, 1H), 5.07 (q, J=6.6 Hz, 1H), 4.99 (s, 1H), 4.41 (d, J=13.2 Hz, 1H), 3.57 (m, 1H), 2.75-2.59 (m, 1H), 2.34 (t, J=7.3 Hz, 2H), 2.31-2.06 (m, 3H), 2.05-1.75 (m, 6H), 1.75-1.62 (m, 3H), 1.60 (d, J=7.0 Hz, 3H), 1.57 (d, J=7.0 Hz, 3H), 1.28 (s, 3H), 1.06 (d, J=6.8 Hz, 3H), 1.01 (d, J=6.8 Hz, 3H), 0.98 (t, J=6.8 Hz, 3H).

LCMS (m/z) 676.4 [M+H], Tr 1.77 min (3 min run).

Example 109

Compound 109

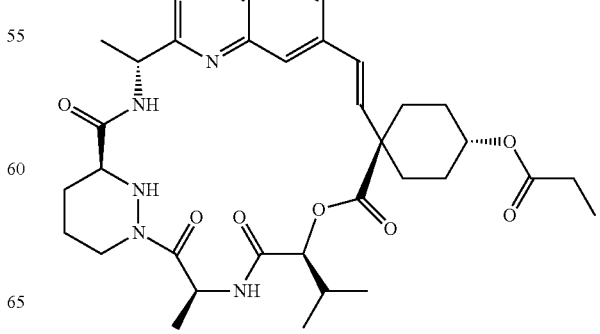

Compound 109

Example 110

Compound 110

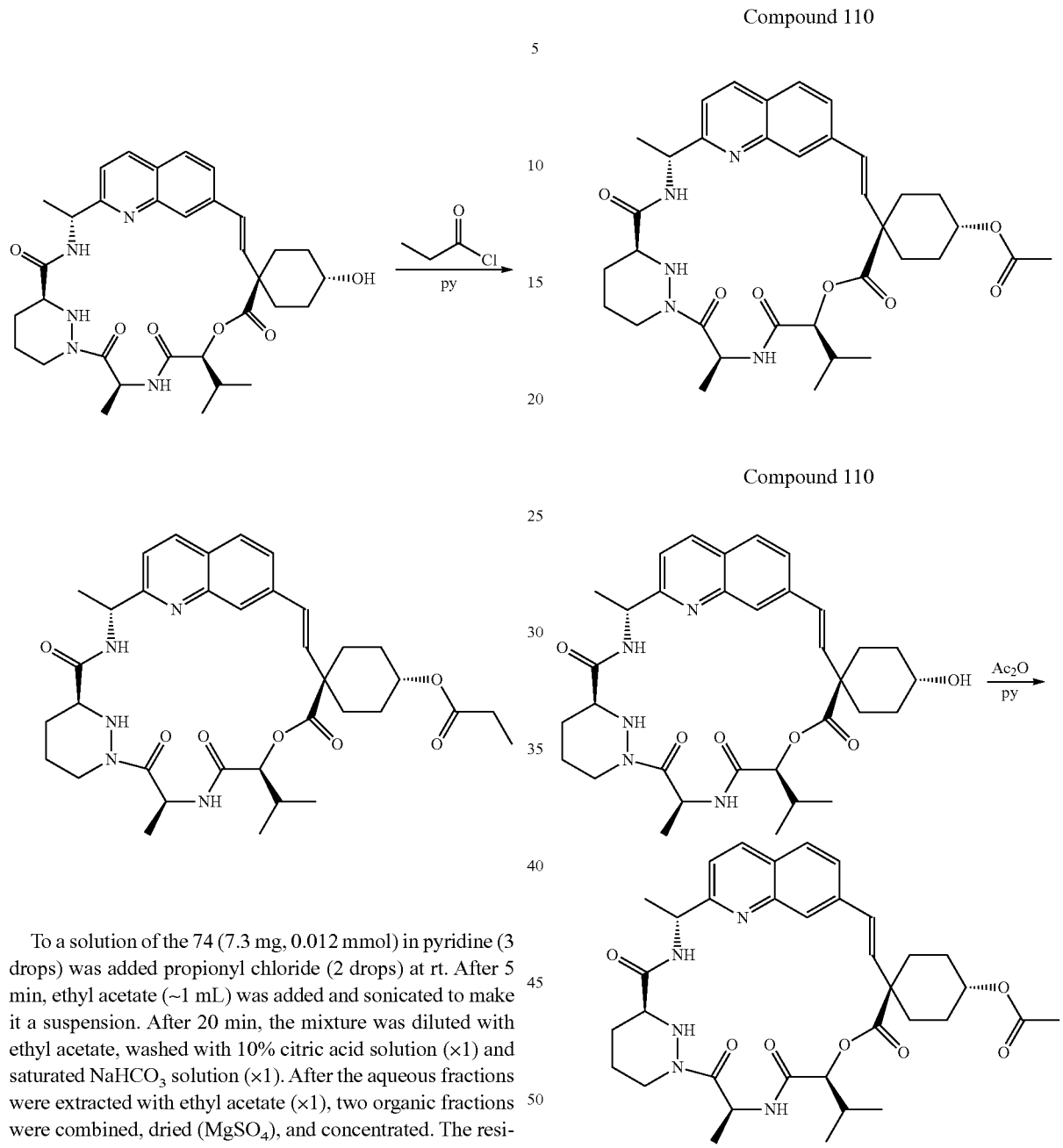

Compound 110

To a solution of the 74 (7.3 mg, 0.012 mmol) in pyridine (3 drops) was added propionyl chloride (2 drops) at rt. After 5 min, ethyl acetate (~1 mL) was added and sonicated to make it a suspension. After 20 min, the mixture was diluted with ethyl acetate, washed with 10% citric acid solution (×1) and saturated NaHCO$_3$ solution (×1). After the aqueous fractions were extracted with ethyl acetate (×1), two organic fractions were combined, dried (MgSO$_4$), and concentrated. The residue was purified by CombiFlash using hexanes-ethyl acetate as eluents to obtain 6.0 mg (75%) of the product Compound 109. $^1$H NMR (400 MHz, Methanol-d$_4$): δ 8.46 (d, J=5.6 Hz, 1H), 8.23 (d, J=8.5 Hz, 1H), 7.83 (d, J=8.5 Hz, 1H), 7.78 (s, 1H), 7.63 (dd, J=8.5, 1.7 Hz, 1H), 7.43 (d, J=8.4 Hz, 1H), 6.60 (d, J=16.3 Hz, 1H), 6.29 (d, J=16.3 Hz, 1H), 5.80 (q, J=7.2 Hz, 1H), 5.25 (d, J=8.5 Hz, 1H), 5.07 (q, J=6.5 Hz, 1H), 4.98 (s, 1H), 4.47-4.34 (m, 1H), 3.57 (dd, J=11.8, 3.0 Hz, 1H), 2.68 (td, J=13.0, 3.1 Hz, 1H), 2.38 (q, J=7.6 Hz, 2H), 2.28 (dd, J=24.6, 13.3 Hz, 1H), 2.20-2.07 (m, 1H), 2.05-1.74 (m, 5H), 1.74-1.63 (m, 1H), 1.60 (d, J=7.3 Hz, 3H), 1.57 (d, J=6.7 Hz, 3H), 1.37-1.19 (m, 3H), 1.15 (t, J=7.6 Hz, 3H), 1.06 (d, J=6.8 Hz, 3H), 1.01 (d, J=6.6 Hz, 3H), 0.94-0.67 (m, 2H).

LCMS (m/z) 662.4 [M+H], Tr 1.65 min (3 min run).

To a solution of the reactant 74 (7.1 mg, 0.012 mmol) in pyridine (3 drops) was added acetic anhydride (2 drops) at rt. After 21 h, the mixture was diluted with ethyl acetate, washed with 10% citric acid solution (×1) and saturated NaHCO$_3$ solution (×1). After the aqueous fractions were extracted with ethyl acetate (×1), two organic fractions were combined, dried (MgSO$_4$), and concentrated. The residue was purified by CombiFlash using hexanes-ethyl acetate as eluents to obtain 6.6 mg (87%) of the product Compound 110. $^1$H NMR (400 MHz, Methanol-d$_4$): δ 8.23 (d, J=8.5 Hz, 1H), 7.83 (d, J=8.4 Hz, 1H), 7.78 (s, 1H), 7.62 (dd, J=8.4, 1.7 Hz, 1H), 7.43 (d, J=8.5 Hz, 1H), 6.61 (d, J=16.3 Hz, 1H), 6.29 (d, J=16.3 Hz, 1H), 5.80 (q, J=7.2 Hz, 1H), 5.25 (d, J=8.5 Hz, 1H), 5.07

(q, J=6.6 Hz, 1H), 4.96 (s, 1H), 4.41 (dd, J=13.5, 4.3 Hz, 1H), 3.57 (dd, J=11.8, 2.9 Hz, 1H), 2.68 (td, J=13.0, 3.2 Hz, 1H), 2.39-2.20 (m, 2H), 2.20-2.09 (m, 1H), 2.07 (s, 3H), 2.05-1.75 (m, 6H), 1.75-1.62 (m, 2H), 1.60 (d, J=7.3 Hz, 3H), 1.57 (d, J=6.7 Hz, 3H), 1.06 (d, J=6.8 Hz, 3H), 1.01 (d, J=6.6 Hz, 3H), 0.98-0.69 (m, 2H).

LCMS (m/z) 648.5 [M+H], Tr 1.54 min (3 min run).

Example 111

Compound 111

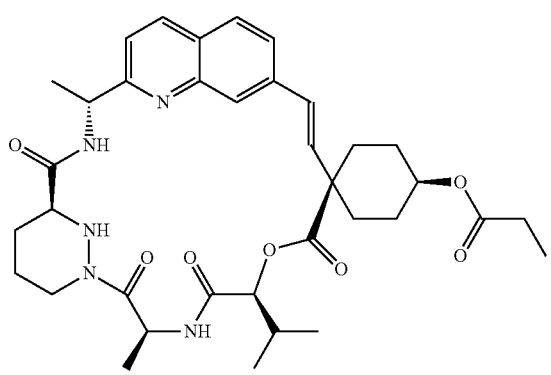 [SMILES: CCC(=O)O[C@H]1CC[C@]2(/C=C/c3ccc4ccc(nc4c3)[C@@H](C)NC(=O)[C@@H]3CCCN(N3)C(=O)[C@H](C)NC(=O)[C@H](C(C)C)OC2=O)CC1]

Compound 111

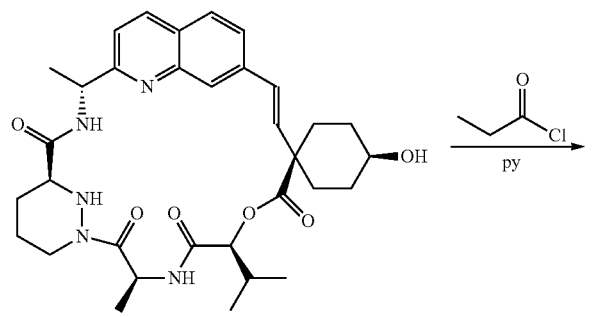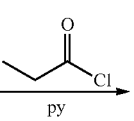

To a solution of the reactant 75 (7.1 mg, 0.012 mmol) in pyridine (3 drops) was added propionyl chloride (2 drops) at rt. After 5 min, ethyl acetate (~1 mL) was added and sonicated to make it a suspension. After 20 min, the mixture was diluted with ethyl acetate, washed with 10% citric acid solution (×1) and saturated NaHCO₃ solution (×1). After the aqueous fractions were extracted with ethyl acetate (×1), two organic fractions were combined, dried (MgSO₄), and concentrated. The residue was purified by CombiFlash using hexanes-ethyl acetate as eluents to obtain 7.3 mg (94%) of the product Compound 111. ¹H NMR (400 MHz, Methanol-d₄): δ 8.23 (d, J=8.5 Hz, 1H), 7.82 (d, J=8.4 Hz, 1H), 7.77 (d, J=1.7 Hz, 1H), 7.61 (dd, J=8.5, 1.7 Hz, 1H), 7.43 (d, J=8.5 Hz, 1H), 6.55 (d, J=16.4 Hz, 1H), 6.26 (d, J=16.4 Hz, 1H), 5.80 (q, J=7.2 Hz, 1H), 5.28 (d, J=8.6 Hz, 1H), 5.06 (q, J=6.4 Hz, 1H), 4.78 (dt, J=10.8, 6.2 Hz, 1H), 4.41 (d, J=13.3 Hz, 1H), 3.58 (dd, J=11.7, 3.1 Hz, 1H), 2.68 (td, J=12.9, 3.2 Hz, 1H), 2.58 (d, J=14.1 Hz, 1H), 2.42-2.11 (m, 4H), 2.10-1.87 (m, 3H), 1.80-1.63 (m, 3H), 1.61 (d, J=7.2 Hz, 3H), 1.57 (d, J=6.8 Hz, 3H), 1.53-1.37 (m, 2H), 1.17-1.06 (m, 6H), 1.03 (d, J=6.6 Hz, 3H), 0.96-0.69 (m, 2H).

LCMS (m/z) 662.5 [M+H], Tr 1.66 min (3 min run).

Example 112

Compound 112

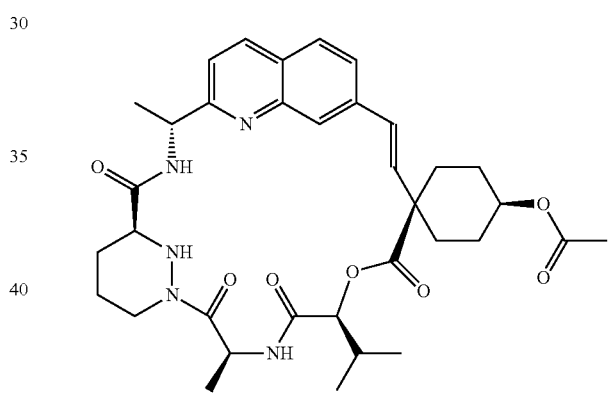

Compound 112

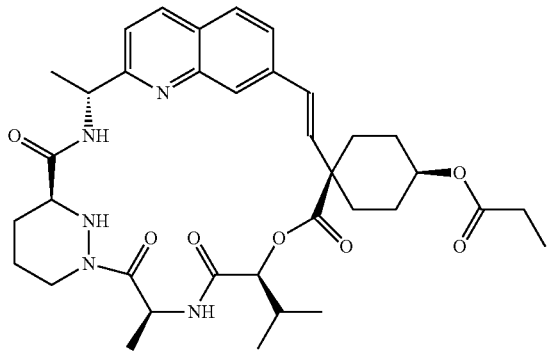

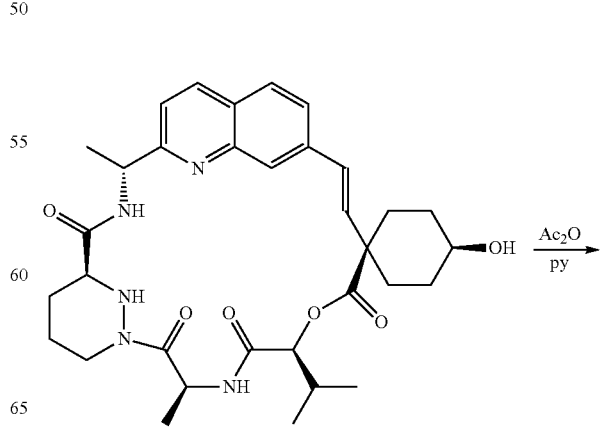

461
-continued

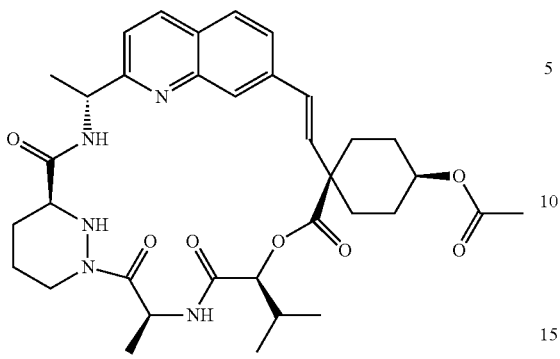

To a solution of 75 (7.3 mg, 0.012 mmol) in pyridine (3 drops) was added acetic anhydride (2 drops) at rt. After 18 h, the mixture was diluted with ethyl acetate, washed with 10% citric acid solution (×1) and saturated NaHCO$_3$ solution (×1). After the aqueous fractions were extracted with ethyl acetate (×1), two organic fractions were combined, dried (MgSO$_4$), and concentrated. The residue was purified by CombiFlash using hexanes-ethyl acetate as eluents to obtain 5.76 mg (73%) of the product Compound 112. $^1$H NMR (400 MHz, Methanol-d$_4$): δ 8.23 (d, J=7.6 Hz, 1H), 7.82 (d, J=8.5 Hz, 1H), 7.76 (s, 1H), 7.61 (dd, J=8.5, 1.7 Hz, 1H), 7.43 (d, J=8.5 Hz, 1H), 6.55 (d, J=16.3 Hz, 1H), 6.26 (d, J=16.3 Hz, 1H), 5.80 (q, J=7.2 Hz, 1H), 5.28 (d, J=8.6 Hz, 1H), 5.06 (m, 1H), 4.77 (dt, J=10.6, 6.1 Hz, 1H), 4.48-4.34 (m, 1H), 3.64-3.51 (m, 1H), 2.68 (td, J=13.0, 3.3 Hz, 1H), 2.58 (d, J=14.6 Hz, 1H), 2.35 (d, J=12.8 Hz, 1H), 2.29-2.21 (m, 1H), 2.17 (ddd, J=13.0, 7.9, 6.4 Hz, 1H), 2.02 (s, 3H), 2.10-1.90 (m, 2H), 1.80-1.63 (m, 3H), 1.61 (d, J=7.2 Hz, 3H), 1.57 (d, J=6.7 Hz, 3H), 1.54-1.39 (m, 2H), 1.07 (d, J=6.8 Hz, 3H), 1.03 (d, J=6.6 Hz, 3H), 0.89 (m, 2H).

LCMS (m/z) 648.4 [M+H], Tr 1.53 min (3 min run).

Example 113

Compound 113

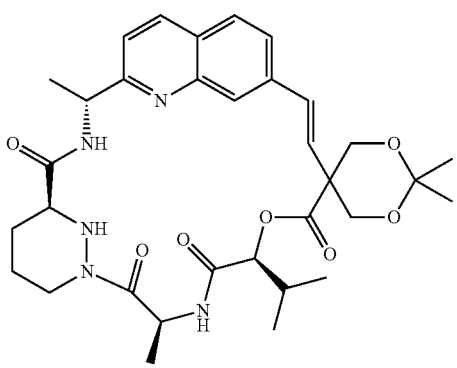 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)COC(C)(C)OC2]

462

Compound 113a.
2,2-Dimethyl-5-vinyl-[1,3]dioxane-5-carboxylic acid

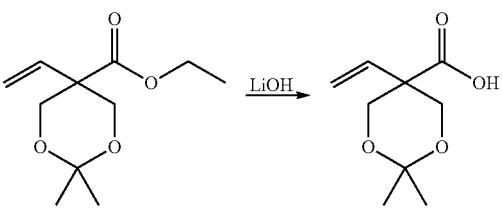

A solution of 2,2-dimethyl-5-vinyl-[1,3]dioxane-5-carboxylic acid ethyl ester (150 mg, 0.7 mmol) in tetrahydrofuran (3 mL) was stirred at 5° C. under nitrogen. A solution of lithium hydroxide monohydrate (59 mg, 1.4 mmol) in water (1 mL) was added and the reaction mixture was stirred at 5° C. for 30 minutes and then at room temperature for 5 hours. Methanol (0.5 mL) was added to give a clear solution and the reaction mixture was stirred at room temperature for 22 hours. The solvent was evaporated. Water (2 mL) was added to the residue and the solution was acidified to pH 2 with 2 M hydrochloric acid. Brine was added and the mixture was extracted with ethyl acetate. The organic extracts were combined, washed with brine. The organic extract was separated, washed with water (×5), and brine. The organic solution was filtered through a hydrophobic frit and the filtrate was evaporated to afford the title compound (117 mg, 90%) as a colorless oil. $^1$H NMR (300 MHz, CDCl$_3$) δ 1.44 (s, 3H), 1.49 (s, 3H), 3.91 (d, J=12.0 Hz, 2H), 4.32 (d, J=12.0 Hz, 2H), 5.30 (d, J=17.8 Hz, 1H), 5.35 (d, J=10.7 Hz, 1H), 5.76 (dd, J=17.8, 10.7 Hz, 1H). LCMS (m/z) 185.1 [M–H], Tr=1.26 min.

Compound 113

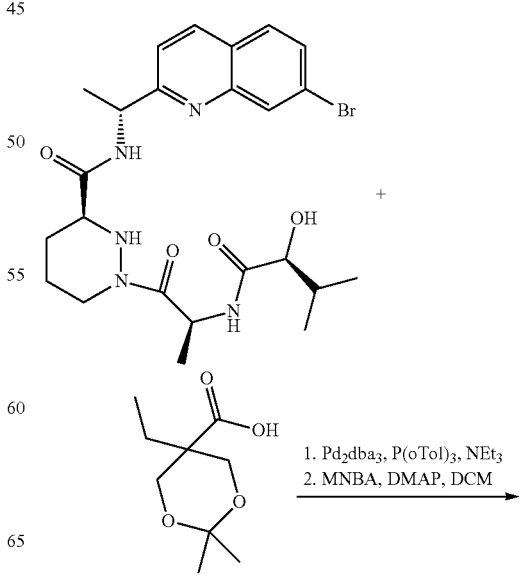

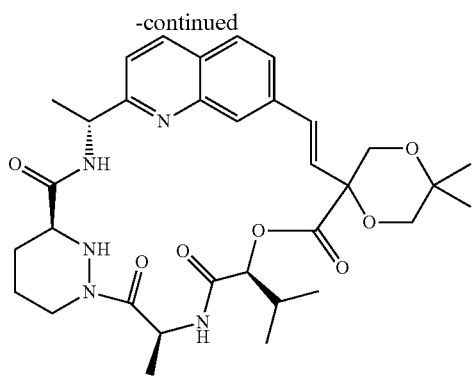

A solution of (S)-1-[(S)-2-((S)-2-hydroxy-3-methyl-butyrylamino)-propionyl]-hexahydro-pyridazine-3-carboxylic acid [(R)-1-(7-bromo-quinolin-2-yl)-ethyl]-amide (228 mg, 0.426 mmol), 2,2-dimethyl-5-vinyl-[1,3]dioxane-5-carboxylic acid (79 mg, 0.426 mmol), triethylamine (178 μL, 1.28 mmol) and tri(o-tolyl)phosphine (26 mg, 0.085 mmol) in 1,4-dioxane (9 mL) was purged with nitrogen for 10 minutes before adding tris(dibenzylideneacetone)dipalladium(0) (39 mg, 0.042 mmol). The stirred reaction mixture was heated at 60° C. for 1 h. The mixture was filtered and evaporated to yield an orange solid. The solid was dissolved in dichloromethane (8 mL) and the resulting solution was added over 4.25 h, using a syringe pump, to a solution of 2-methyl-6-nitro-benzoic anhydride (366 mg, 1.07 mmol) and 4-(dimethylamino)pyridine (266 mg, 2.13 mmol) in dichloromethane (156 mL) containing powdered 4 Å sieves. After the end of addition, the mixture was stirred for 30 minutes, filtered then washed with aqueous sodium bicarbonate solution (75 mL), filtered through a hydrophobic frit and evaporated to give a yellow gum. The gum was purified by reverse phase preparative HPLC eluting with water/acetonitrile 3:2 to afford 113 (53 mg, 20%) as a white solid. $^1$H NMR (300 MHz, CD$_3$OD) δ 1.06 (d, J=6.7 Hz, 3H), 1.11 (d, J=6.7 Hz, 3H), 1.35 (s, 3H), 1.55 (s, 3H), 1.58-1.77 (m, 2H), 1.60 (d, J=6.7 Hz, 3H), 1.64 (d, J=7.4 Hz, 3H), 1.90-2.00 (m, 1H), 2.14-2.29 (m, 2H), 2.65-2.80 (m, 1H), 3.56-3.64 (m, 1H), 4.03-4.16 (m, 2H), 4.29-4.37 (m, 1H), 4.39-4.51 (m, 2H), 5.01-5.12 (m, 1H), 5.38 (d, J=9.1 Hz, 1H), 5.75-5.87 (m, 1H), 6.17 (d, J=16.7 Hz, 1H), 6.64 (d, J=16.7 Hz, 1H), 7.46 (d, J=8.7 Hz, 1H), 7.66-7.74 (m, 2H), 7.84 (d, J=8.5 Hz, 1H), 8.24 (d, J=8.5 Hz, 1H). LCMS (m/z) 622.3 [M+H], Tr=2.38 min.

Example 114

Compound 114

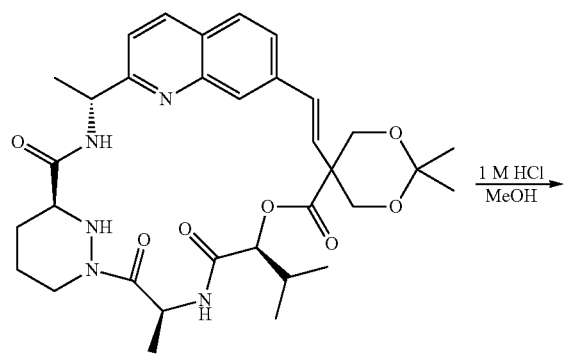

A solution of compound 113 (20 mg, 0.032 mmol) in methanol (1 mL) was prepared and hydrochloric acid (1 M, 3 mL) was added. The reaction mixture was stirred for 1 h at room temperature and then was neutralised by addition of saturated sodium bicarbonate solution. Sodium chloride was added to saturate the solution. The aqueous layer was extracted with dichloromethane, filtered through a hydrophobic frit and evaporated to yield 114 (14 mg, 75%) as a white solid. $^1$H NMR (300 MHz, CD$_3$OD) δ 1.01 (d, J=6.7 Hz, 3H), 1.04 (d, J=6.7 Hz, 3H), 1.49-1.77 (m, 2H), 1.60 (d, J=6.9 Hz, 3H), 1.65 (d, J=7.4 Hz, 3H), 1.84-1.96 (m, 1H), 2.08-2.28 (m, 2H), 2.64-2.77 (m, 1H), 3.56-3.64 (m, 1H), 3.93-4.16 (m, 4H), 4.37-4.46 (m, 1H), 5.06 (q, J=6.7 Hz, 1H), 5.32 (d, J=9.1 Hz, 1H), 5.81 (q, J=7.3 Hz, 1H), 6.31 (d, J=16.7 Hz, 1H), 6.63 (d, J=16.7 Hz, 1H), 7.45 (d, J=8.5 Hz, 1H), 7.65-7.74 (m, 2H), 7.84 (d, J=8.5 Hz, 1H), 8.24 (d, J=8.5 Hz, 1H). LCMS (m/z) 582.5 [M+H], Tr=1.60 min.

Biological Examples

Inhibition of Peptidyl-Prolyl Isomerase (PPIase) Activity

The PPIase assay was based on the procedure reported by Janowski et al. (*Anal. Biochem.* 1997, 252, 299). Assay buffer (1980 L of a solution containing 35 mM HEPES pH 7.8, 50M DTT, and 0.01% NP40) was pre-equilibrated to 10° C. in a quartz cuvette equipped with an overhead stirrer. To this solution was added 10 L of compound in DMSO (final concentration: 0.5% DMSO), followed by 5 L of a 2 M stock solution of cyclophilin A (final concentration: 5 nM). The reaction was initiated with the addition of 5 L of 40 mM of the tetrapeptide Succ-AAPF-pNA (100 M final concentration) dissolved in a solution of 0.5 M LiCl in trifluoroethanol. Upon the initiation of the reaction, the absorbance of the peptide substrate was monitored at 330 nm for five minutes using a Beckman Coulter DU800 spectrophotometer. Progress curves were fit with a single-exponential decay model to calculate rates. The IC$_{50}$ values were calculated with a four-parameter logistic fit using GraphPad Prism software.

Cyclophilin A TR-FRET Competitive Binding Assay

Inhibitor potency was measured using a competitive binding assay with a time-resolved fluorescence resonance energy transfer (TR-FRET) readout. To a reaction buffer consisting of 35 mM HEPES pH 7.8, 100 mM NaCl, 0.01% NP-40 (Pierce), 1 mM DTT, and 1% DMSO were added the following: 5 nM of cyclophilin A modified at the N-terminus with an 8× histidine affinity tag (CypA); 150 nM of cyclosporin A modified with a linker attached to a Cy5 fluorophore (CsA-Cy5); 1 nM Eu-labeled anti-(6×His) antibody (Perkin-Elmer); and test compound at one of various concentrations.

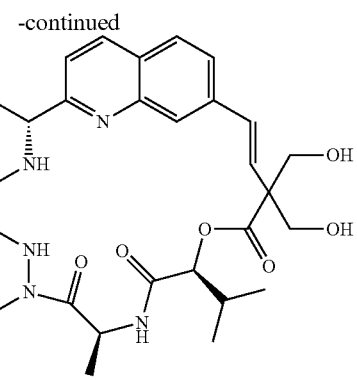

The total volume of the assay solution was 100 L. After a two-hour incubation, the TR-FRET was measured using a Perkin Elmer Envision plate reader (excitation at 340 nm, emission measured at 590 nm and 665 nm). The signal was calculated as the ratio of the emission at 665 nm to that at 590 nm. An $IC_{50}$ value was calculated using a four-parameter logistic fit.

When tested, certain compounds of this invention were found to inhibit cyclophilin binding as listed in Table 1. The $IC_{50}$'s (TR-FRET) are presented as ranges wherein A is ≤100 nM, B is 101 to 1000 nM and C is 1001 to 10,000 nM.

Antiviral Activity

The antiviral activity of a compound can be measured using standard screening protocols: for example, cell-based Flavivirus immunodetection assay and cell-based Flavivirus cytopathic effect assay as described in U.S. Patent Publication Number US 20130022573, which is hereby incorporated by reference in its entirety.

One aspect of the invention relates to methods of inhibiting viral infections, comprising the step of treating a sample or subject suspected of needing such inhibition with a composition of the invention. The antiviral activity of a compound of the invention can be measured using standard screening protocols that are known.

The anti-HCV activity of the compounds of this invention was tested in a human hepatoma Huh-7 cell line harboring a HCV replicon. The assay comprised the following steps:

Step 1 (Compound Preparation and Serial Dilution):

Serial dilution was performed in 100% DMSO in a 384-well plate. A solution containing a compound at 225-fold concentration of the starting final serial dilution concentration was prepared in 100% DMSO and 15 µL added to the pre-specified wells in column 3 or 13 of a polypropylene 384-well plate. The rest of the 384-well plate was filled with 10 µL 100% DMSO except for columns 23 and 24, where 10 µL of 500 µM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2 (Cell Culture Plate Preparation and Compound Addition):

To each well of a black polypropylene 384-well plate, 90 µL of cell media containing 1600 suspended Huh-7 HCV replicon cells was added with a Biotek uFlow Workstation. A volume of 0.4 µL of the compound solution was transferred from the serial dilution plate to the cell culture plate on a Biomek FX Workstation. The DMSO concentration in the final assay condition was 0.44%. The plates were incubated for 3 days at 37° C. with 5% $CO_2$ and 85% humidity.

Step 3 (Detection of Cytotoxicity and Inhibition of Viral Replication):

a) Assessment of cytotoxicity: The media in the 384-well cell culture plate was aspirated with a Biotek EL405 plate-washer. A volume of 50 µL of a solution containing 400 nM Calcein AM in 100% PBS was added to each well of the plate with a Biotek uFlow Workstation. The plate was incubated for 30 minutes at room temperature before the fluorescence signal (emission 490 nm, exitation 520 nm) was measured with a Perkin Elmer Envision Plate Reader.

b) Assessment of Inhibition of Viral Replication:

The calcein-PBS solution in the 384-well cell culture plate was aspirated with a Biotek EL405 plate-washer. A volume of 20 µL of Dual-Glo luciferase buffer (Promega, Dual-Glo Luciferase Assay Reagent, cat. #E298B) was added to each well of the plate with a Biotek uFlow Workstation. The plate was incubated for 10 minutes at room temperature. A volume of 20 µL of a solution containing 1:100 mixture of Dual-Glo Stop & Glo substrate (Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at room temperature for 10 minutes before the luminescence signal was measured with a Perkin Elmer Envision Plate Reader.

Step 4 (Calculation):

The percent cytotoxicity was determined by calcein AM conversion to fluorescent product. The average fluorescent signal from the DMSO control wells were defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO controls wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition} = 100\%/[(EC_{50}/[I])^b + 1]$$

where b is Hill's coefficient. See, for reference, Hill, A. V., *The Possible Effects of the Aggregation of the Molecules of Haemoglobin on its Dissociation Curves*, J. Physiol. 40: iv-vii. (1910). % inhibition values at a specific concentration, for example 2 µM, can also be derived from the formula above.

When tested, certain compounds of this invention were found to inhibit viral replication as listed in Table 1. A is ≤1 µM, B is 1.1 to 10 µM and C is 10.1 to 100 µM.

When tested, certain compounds of this invention were found to inhibit viral replication as listed in Table 1. The $EC_{50}$'s are presented as a % inhibition against the 1b replicon.

TABLE 1

| Example | TR-FRET $IC_{50}$ | $EC_{50}$ | Replicon 1b % inhibition at 1 µM |
|---|---|---|---|
| 1 | A | A | 97 |
| 2 | A | A | 98 |
| 3 | A | A | 89 |
| 4 | A | A | 100 |
| 5 | A | A | 93 |
| 6 | A | A | 94 |
| 7 | A | A | 94 |
| 8 | A | A | 95 |
| 9 | A | A | 100 |
| 10 | A | A | 92 |
| 11 | A | A | 96 |
| 12 | A | A | 100 |
| 13 | A | A | 100 |
| 14 | A | A | 100 |
| 15 | A | A | 98 |
| 16 | A | B | 20 |
| 17 | B | B | 39 |
| 18 | A | A | 100 |
| 19 | A | A | 100 |
| 20 | B | A | 88 |
| 21 | B | A | 71 |
| 22 | A | A | 91 |
| 23 | A | A | 97 |
| 24 | A | A | 83 |
| 25 | A | A | 98 |
| 26 | B | A | 68 |
| 27 | A | A | 92 |
| 28 | A | A | 99 |

TABLE 1-continued

| Example | TR-FRET IC$_{50}$ | EC$_{50}$ | Replicon 1b % inhibition at 1 µM |
|---|---|---|---|
| 29 | A | A | 99 |
| 30 | A | A | 84 |
| 31 | A | A | 88 |
| 32 | B | B | 56 |
| 33 | A | A | 97 |
| 34 | A | A | 91 |
| 35 | A | A | 88 |
| 36 | A | A | 99 |
| 37 | A | A | 98 |
| 38 | A | A | 99 |
| 39 | B | B | 16 |
| 40 | A | A | 99 |
| 41 | A | A | 98 |
| 42 | A | A | 96 |
| 43 | A | A | 99 |
| 44 | B | A | 86 |
| 45 | A | — | — |
| 46 | — | — | — |
| 47 | A | A | 100 |
| 48 | A | A | 100 |
| 49 | A | A | 100 |
| 50 | A | A | 100 |
| 51 | A | A | 100 |
| 52 | A | A | 100 |
| 53 | A | A | 99 |
| 54 | B | A | 77 |
| 55 | A | A | 100 |
| 56 | A | A | 99 |
| 57 | A | A | 100 |
| 58 | A | — | — |
| 59 | A | A | 99 |
| 60 | A | A | 96 |
| 61 | B | B | 46 |
| 62 | A | A | 84 |
| 63 | A | A | 100 |
| 64 | A | A | 100 |
| 65 | A | A | 99 |
| 66 | A | A | 97 |
| 67 | B | A | 67 |
| 68 | A | A | 93 |
| 69 | A | A | 100 |
| 70 | C | A | 57 |
| 71 | A | A | 96 |
| 72 | C | B | −6 |
| 73 | A | A | 97 |
| 74 | A | A | 100 |
| 75 | A | A | 100 |
| 76 | A | A | 69 |
| 77 | B | A | 56 |
| 78 | A | A | 99 |
| 79 | C | B | 3 |
| 80 | A | A | 99 |
| 81 | A | A | 100 |
| 82 | A | A | 99 |
| 83 | A | A | 100 |
| 84 | C | B | 10 |
| 85 | A | A | 98 |
| 86 | B | A | 93 |
| 87 | A | A | 61 |
| 88 | A | A | 100 |
| 89 | A | A | 82 |
| 90 | A | A | 99 |
| 91 | A | A | 100 |
| 92 | A | A | 100 |
| 93 | A | A | 98 |
| 94 | A | A | 94 |
| 95 | A | A | 88 |
| 96 | A | A | 91 |
| 97 | A | A | 96 |
| 98 | A | A | 90 |
| 99 | A | A | 100 |
| 100 | A | A | 100 |
| 101 | A | A | 98 |
| 102 | A | B | 13 |
| 103 | A | A | 90 |
| 104 | A | A | 56 |
| 105 | B | B | 2 |
| 106 | A | A | 95 |
| 107 | A | A | 100 |
| 108 | A | A | 99 |
| 109 | A | A | 99 |
| 110 | A | A | 100 |
| 111 | A | A | 99 |
| 112 | A | A | 100 |

The specific pharmacological and biochemical responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention.

What is claimed is:

1. A compound of Formula I:

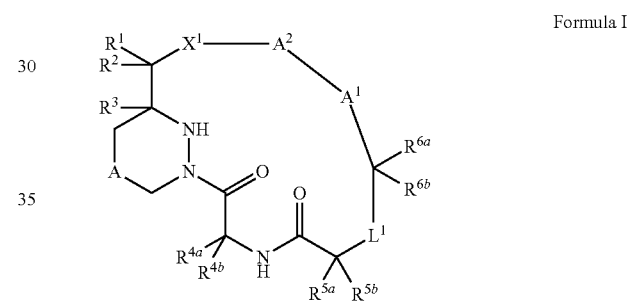

Formula I or a pharmaceutically acceptable salt, isotope, stereoisomer, mixture of stereoisomers, tautomer, ester or prodrug thereof, wherein:

A is a bond, —O—, —S(O)$_n$—, —NH—, —N((C$_1$-C$_4$)alkyl)- or (C$_1$-C$_2$)alkylene;

A$^1$ is (C$_1$-C$_5$)alkylene, (C$_2$-C$_5$)alkenylene, (C$_2$-C$_5$)alkynylene, arylene, heteroarylene, cycloalkylene, heterocycloalkylene, aryl(C$_1$-C$_2$)alkylene, heteroaryl(C$_1$-C$_2$)alkylene, cycloalkyl(C$_1$-C$_2$)alkylene or heterocycloalkyl(C$_1$-C$_2$)alkylene, wherein a sp$^3$ carbon atom of A$^1$ is optionally replaced by —O—, —S(O)$_n$—, —NH— or —N((C$_1$-C$_4$)alkyl)-, and wherein a sp$^3$ or sp$^2$ carbon atom of A$^1$ is optionally substituted with one or more groups selected from the group consisting of halo, (C$_1$-C$_8$)alkyl, (C$_2$-C$_8$)alkenyl, (C$_2$-C$_8$)alkynyl, aryl, heterocycloalkyl, cycloalkyl, aryl(C$_1$-C$_4$)alkyl, cycloalkyl(C$_1$-C$_4$)alkyl, heterocycloalkyl(C$_1$-C$_4$)alkyl, arylheterocycloalkyl(C$_1$-C$_4$)alkyl, —OR$^9$, —SR$^9$, —S(O)R$^9$, —S(O)$_2$R$^9$ and —N(R$^9$)$_2$;

A$^2$ is —CH(R$^8$)-arylene, —CH(R$^8$)-heteroarylene, —CH(R$^8$)-heterocycloalkylene, —CH(R$^8$)-cycloalkylene, arylene, cycloalkylene, (C$_1$-C$_3$)alkylene, (C$_2$-C$_3$)alkenylene or (C$_2$-C$_3$)alkynylene, wherein A$^2$ is optionally substituted with one or more substituents selected from the group consisting of —OR$^9$, —SR$^9$, —S(O)R$^9$, —S(O)$_2$R$^9$, —N(R$^9$)$_2$, halo, halo(C$_1$-C$_4$)alkyl, halo(C$_1$-C$_4$)alkoxy, cyano and (C$_1$-C$_8$)alkyl;

$L^1$ is —O—C(O)—, —O—CH$_2$—, —NR$^{11}$—CH$_2$—, —NH—C(R$^{10}$)$_2$— or —NH—S(O)$_2$—, wherein each R$^{10}$ is independently H, (C$_1$-C$_4$)alkyl, halo(C$_1$-C$_4$)alkyl, (C$_1$-C$_4$)alkenyl or cycloalkyl; and R$^{11}$ is (C$_1$-C$_4$)alkyl, halo(C$_1$-C$_4$)alkyl, (C$_1$-C$_4$)alkenyl or cycloalkyl;

X$^1$ is a bond, —O—, —NH—, —N((C$_1$-C$_4$)alkyl)- or heterocycloalkylene;

R$^1$ and R$^2$ are independently H, (C$_1$-C$_4$)alkyl, (C$_2$-C$_4$)alkenyl, (C$_2$-C$_4$)alkynyl, halo, cyano or —C(O)—(C$_1$-C$_4$)alkyl; or R$^1$ and R$^2$, when taken together with the carbon to which they are both attached, form —C(═O)—, —C(═S)— or —C(═N(C$_1$-C$_4$)alkyl)-;

R$^3$ is H or (C$_1$-C$_4$)alkyl which is optionally substituted with halo, cyano, hydroxyl or (C$_1$-C$_4$)alkoxy;

R$^{4a}$ and R$^{4b}$ are independently H, (C$_1$-C$_8$)alkyl, aryl, aryl(C$_1$-C$_4$)alkyl, heterocycloalkyl, heterocycloalkyl(C$_1$-C$_4$)alkyl, cycloalkyl or cycloalkyl(C$_1$-C$_4$)alkyl, wherein each R$^{4a}$ and R$^{4b}$ is optionally substituted with one or more substituents selected from the group consisting of cyano, —COOH, halo, hydroxyl, amino, (C$_1$-C$_8$)alkoxy, mono(C$_1$-C$_8$)alkylamino, di(C$_1$-C$_8$)alkylamino, aryl and heteroaryl;

R$^{5a}$ and R$^{5b}$ are independently H, (C$_1$-C$_8$)alkyl, (C$_2$-C$_8$)alkenyl, (C$_2$-C$_8$)alkynyl, (C$_1$-C$_8$)alkoxy, aryl, heterocycloalkyl, cycloalkyl, aryl(C$_1$-C$_4$)alkyl, cycloalkyl(C$_1$-C$_4$)alkyl or heterocycloalkyl(C$_1$-C$_4$)alkyl, wherein each R$^{5a}$ and R$^{5b}$ is optionally substituted with one or more substituents selected from the group consisting of —N$_3$, cyano, —COOH, halo, hydroxyl, amino, mono(C$_1$-C$_8$)alkylamino, di(C$_1$-C$_8$)alkylamino, (C$_1$-C$_8$)alkoxy, aryl and heteroaryl, or R$^{5a}$ and R$^{5b}$ together form a spirocycle having Formula (a):

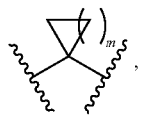
(a)

wherein one or more carbon ring atoms of Formula (a) is optionally replaced by a nitrogen, oxygen or sulfur atom, and wherein a ring atom of Formula (a) optionally has one or more substituents selected from the group consisting of oxo, ═N(C$_1$-C$_4$)alkoxy, halo, hydroxyl, —NH$_2$, (C$_1$-C$_4$)alkyl, halo(C$_1$-C$_4$)alkyl, (C$_1$-C$_4$)alkoxy, —OC(O)R$^9$, —C(O)$_2$R$^9$, and —S(O)$_2$R$^9$;

R$^{6a}$ and R$^{6b}$ are independently H, hydroxyl, (C$_1$-C$_8$)alkyl, (C$_2$-C$_8$)alkenyl, (C$_2$-C$_8$)alkynyl, (C$_1$-C$_8$)alkoxy, —CH$_2$CH$_2$CR$^9$(═N(C$_1$-C$_4$)alkoxy), aryl, heterocycloalkyl, cycloalkyl, —SR$^9$, —S(O)R$^9$, —S(O)$_2$R$^9$ and —N(R$^9$)$_2$, wherein each of R$^{6a}$ and R$^{6b}$ is optionally substituted with one or more substituents selected from the group consisting of halo, hydroxyl, cyano, (C$_1$-C$_4$)alkyl, (C$_1$-C$_4$)alkoxy, halo(C$_1$-C$_4$)alkoxy, aryl, cycloalkyl, heterocycloalkyl, mono(C$_1$-C$_8$)alkylamino, di(C$_1$-C$_8$)alkylamino, —NHS(O)R$^9$, —NHC(O)R$^9$ and (C$_1$-C$_8$)alkanoyl; or R$^{6a}$ and R$^{6b}$ together form a spirocycle having Formula (a);

each R$^8$ is independently H, (C$_1$-C$_4$)alkyl, halo(C$_1$-C$_4$)alkyl, (C$_2$-C$_4$)alkenyl, (C$_2$-C$_4$)alkynyl, aryl, heteroaryl, heterocycloalkyl or cycloalkyl, wherein R$^8$ is optionally substituted with —OR, —N(R$^9$)$_2$, —CON(R$^9$)$_2$, or cyano;

each R$^9$ is independently H, (C$_1$-C$_4$)alkyl, halo(C$_1$-C$_4$)alkyl, (C$_2$-C$_4$)alkenyl or (C$_2$-C$_4$)alkynyl;

each n is independently 0, 1 or 2; and m is 1, 2, 3, 4 or 5.

2. The compound of claim 1, wherein A$^1$ is ethenylene, propenylene, butenylene, ethylene, propylene, butylene, oxypropylene, oxypropylene, pyrazolylene, phenylene or pyrimidinylene.

3. The compound of claim 1, wherein A$^2$ is —CH(R$^8$)-quinolinylene, —CH(R$^8$)-isoquinolinylene, —CH(R$^8$)-naphthyridinylene, —CH(R$^8$)-cinnolinylene, —CH(R$^8$)-quinoxalinylene, —CH(R$^8$)-phenylene or —CH(R$^8$)-halophenylene.

4. The compound of claim 1, wherein R$^8$ is methyl.

5. The compound of claim 1, wherein X$^1$ is —O—, —NH— or —N(CH$_3$)—; R$^1$ and R$^2$, when taken together with the carbon to which they are both attached, form —C(═O)—; and R$^3$ is H.

6. The compound of claim 1, wherein X$^1$ is —O—, —NH— or —N(CH$_3$)—; R$^1$ and R$^2$, when taken together with the carbon to which they are both attached, form —C(═O)—; R$^3$ is H; one of R$^{4a}$ and R$^{4b}$ is H and the other is methyl; and one of R$^{5a}$ and R$^{5b}$ is H and the other is isopropyl.

7. The compound of claim 1, wherein X$^1$ is —O—, —NH— or —N(CH$_3$)—; R$^1$ and R$^2$, when taken together with the carbon to which they are both attached, form —C(═O)—; R$^3$ is H; one of R$^{4a}$ and R$^{4b}$ is H and the other is methyl; one of R$^{5a}$ and R$^{5b}$ is H and the other is isopropyl; A$^2$ is —CH(R$^8$)-heteroarylene; and R$^8$ is methyl.

8. The compound of claim 1, wherein one of R$^{6a}$ and R$^{6b}$ is H; and the other H, hydroxyl, –CH$_2$CH$_2$CR$^9$(═N(C$_1$-C$_4$)alkoxy), (C$_1$-C$_8$)alkyl or (C$_1$-C$_8$)alkoxy, wherein R$^{6a}$ or R$^{6b}$ is optionally substituted with one or more substituents selected from the group consisting of halo, hydroxyl, (C$_1$-C$_4$)alkoxy, halo(C$_1$-C$_4$)alkoxy, heterocycloalkyl, (C$_1$-C$_4$)alkanoyl and di(C$_1$-C$_4$)alkylamino.

9. The compound of claim 1, wherein R$^{6a}$ and R$^{6b}$ together form a spirocycle having Formula (a):

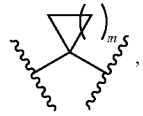
(a)

wherein one or more carbon ring atoms of Formula (a) is optionally replaced by a nitrogen, oxygen or sulfur atom, and wherein a ring atom of Formula (a) optionally has one or more substituents selected from the group consisting of oxo, ═N(C$_1$-C$_4$)alkoxy, halo, hydroxyl, —NH$_2$, (C$_1$-C$_4$)alkyl, halo(C$_1$-C$_4$)alkyl, (C$_1$-C$_4$)alkoxy, —OC(O)R$^9$, —C(O)$_2$R$^9$, and —S(O)$_2$R$^9$.

10. The compound of claim 1, which is a compound of Formula

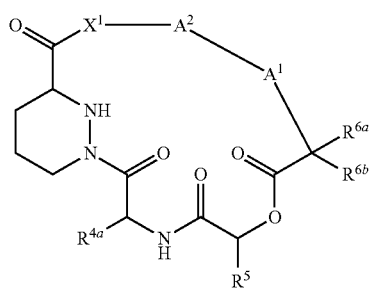
Formula II or a pharmaceutically acceptable salt, isotope, stereoisomer, mixture of stereoisomers, tautomer, ester or prodrug thereof, wherein:

$A^1$ is

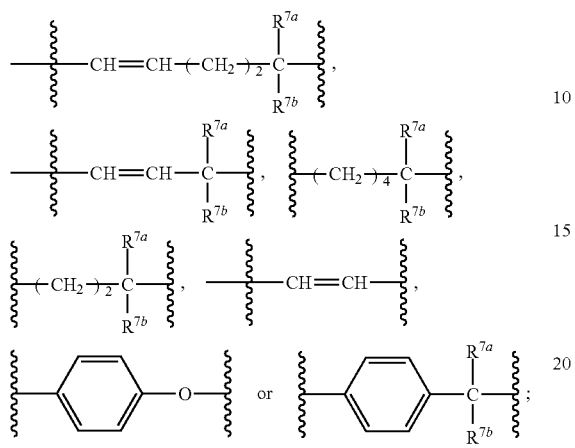

$A^2$ is —CH($R^8$)-arylene, —CH($R^8$)-heteroarylene, —CH($R^8$)-heterocycloalkylene, —CH($R^8$)-cycloalkylene, arylene or cycloalkylene;

$X^1$ is a bond, —CH$_2$—, —O—, —NH—, —N(CH$_3$)—,

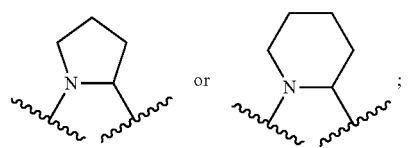 [SMILES: *C1CCCN1* ; *C1CCCCN1*]

$R^{4a}$ is H, (C$_1$-C$_4$)alkoxy, halo(C$_1$-C$_4$)alkoxy, hydroxyl(C$_1$-C$_8$)alkyl, (C$_1$-C$_4$)alkoxy(C$_1$-C$_8$)alkyl or (C$_1$-C$_8$)alkyl;

$R^5$ is H, (C$_1$-C$_4$)alkyl, halo(C$_1$-C$_8$)alkyl, hydroxy(C$_1$-C$_4$)alkyl, (C$_1$-C$_4$)alkoxy(C$_1$-C$_8$)alkyl, cycloalkyl or heterocycloalkyl;

$R^{6a}$ and $R^{6b}$ are independently H, hydroxyl, (C$_1$-C$_8$)alkyl, (C$_2$-C$_8$)alkenyl, (C$_2$-C$_8$)alkynyl, (C$_1$-C$_8$)alkoxy, —CH$_2$CH$_2$CR$^9$(=N(C$_1$-C$_4$)alkoxy), aryl, heterocycloalkyl, cycloalkyl, —SR$^9$, —S(O)R$^9$, —S(O)$_2$R$^9$ or —N(R$^9$)$_2$, wherein each of $R^{6a}$ and $R^{6b}$ is optionally substituted with one or more substituents selected from the group consisting of halo, hydroxyl, cyano, (C$_1$-C$_4$)alkyl, (C$_1$-C$_4$)alkoxy, halo(C$_1$-C$_4$)alkoxy, aryl, cycloalkyl, heterocycloalkyl, mono(C$_1$-C$_8$)alkylamino, di(C$_1$-C$_8$)alkylamino, —NHS(O)R$^9$, —NHC(O)R$^9$ and (C$_1$-C$_8$)alkanoyl where such an optional substitution is chemically feasible; or $R^{6a}$ and $R^{6b}$ together form a spirocycle having Formula (a); or $R^{6a}$ and $R^{6b}$ together form a spirocycle having Formula (a):

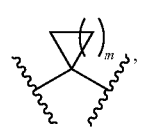

(a)

wherein one or more carbon ring atoms of Formula (a) is optionally replaced by a nitrogen, oxygen or sulfur atom, and wherein a ring atom of Formula (a) optionally has one or more substituents selected from the group consisting of oxo, =N(C$_1$-C$_4$)alkoxy, halo, hydroxyl, —NH$_2$, (C$_1$-C$_4$)alkyl, halo(C$_1$-C$_4$)alkyl, (C$_1$-C$_4$)alkoxy, —OC(O)R$^9$, —C(O)$_2$R$^9$, and —S(O)$_2$R$^9$;

$R^{7a}$ and $R^{7b}$ are independently H, —OH, (C$_1$-C$_4$)alkoxy, halo(C$_1$-C$_4$)alkoxy or (C$_1$-C$_8$)alkyl;

$R^8$ is H or (C$_1$-C$_4$)alkyl; and each $R^9$ is independently H, (C$_1$-C$_4$)alkyl, halo(C$_1$-C$_4$)alkyl, (C$_2$-C$_4$)alkenyl or (C$_2$-C$_4$)alkynyl.

11. The compound of claim 1, wherein $R^{4a}$ is methyl; $R^5$ is isopropyl; $R^8$ is methyl; and $A^2$ is

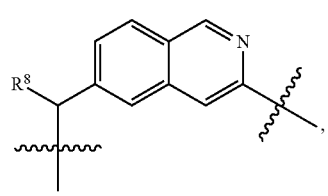

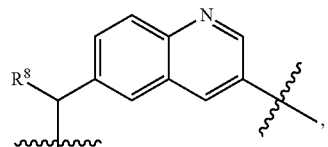

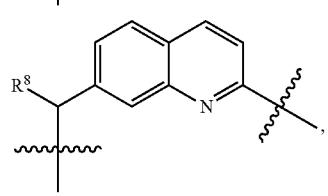

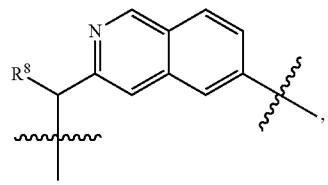

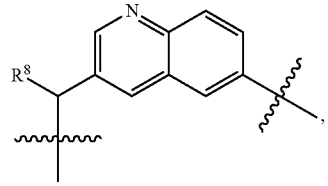

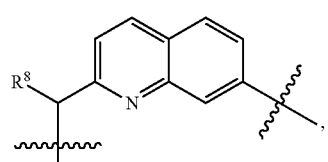

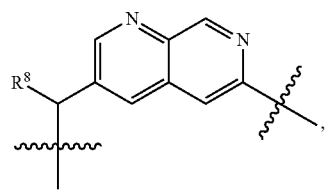

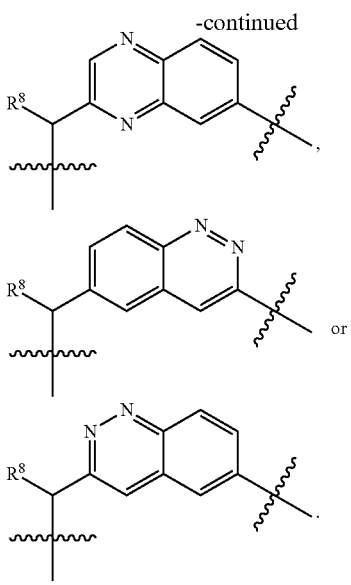

12. The compound of claim 10, wherein $R^{4a}$ is methyl; $R^5$ is isopropyl; $R^8$ is methyl; and $A^2$ is

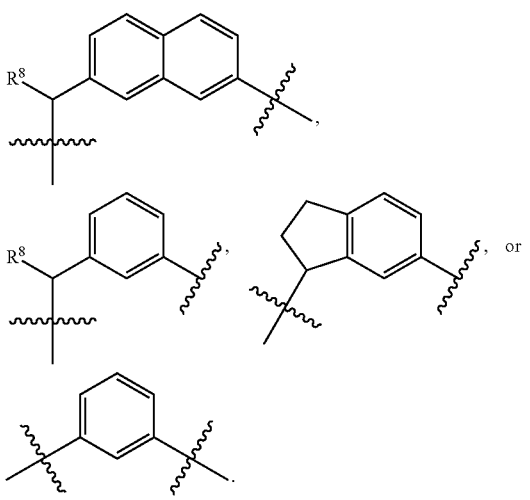

13. The compound of claim 1, which is a compound of Formula II-c:

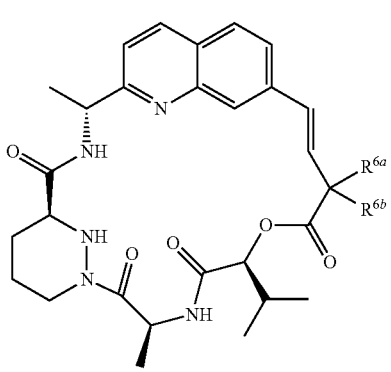

Formula II-c or a pharmaceutically acceptable salt, isotope, stereoisomer, mixture of stereoisomers, tautomer, ester or prodrug thereof, wherein:

$R^{6a}$ and $R^{6b}$ are independently H, hydroxyl, $(C_1$-$C_8)$alkyl, $(C_2$-$C_8)$alkenyl, $(C_2$-$C_8)$alkynyl, $(C_1$-$C_8)$alkoxy, —$CH_2CH_2CR^9$(=N($C_1$-$C_4$)alkoxy), aryl, heterocycloalkyl, cycloalkyl, —$SR^9$, —$S(O)R^9$, —$S(O)_2R^9$ or —$N(R^9)_2$, wherein each of $R^{6a}$ and $R^{6b}$ is optionally substituted with one or more substituents selected from the group consisting of halo, hydroxyl, cyano, $(C_1$-$C_4)$ alkyl, $(C_1$-$C_4)$alkoxy, halo$(C_1$-$C_4)$alkoxy, aryl, cycloalkyl, heterocycloalkyl, mono$(C_1$-$C_8)$alkylamino, di$(C_1$-$C_8)$alkylamino, —$NHS(O)R^9$, —$NHC(O)R^9$ and $(C_1$-$C_8)$alkanoyl where such an optional substitution is chemically feasible; or $R^{6a}$ and $R^{6b}$ together form a spirocycle having Formula (a); or $R^{6a}$ and $R^{6b}$ together form a spirocycle having Formula (a):

(a)

wherein one or more carbon ring atoms of Formula (a) is optionally replaced by a nitrogen, oxygen or sulfur atom, and wherein a ring atom of Formula (a) optionally has one or more substituents selected from the group consisting of oxo, =N($C_1$-$C_4$)alkoxy, halo, hydroxyl, —$NH_2$, $(C_1$-$C_4)$alkyl, halo$(C_1$-$C_4)$alkyl, $(C_1$-$C_4)$alkoxy, —$OC(O)R^9$, —$C(O)_2R^9$, and —$S(O)_2R^9$; and each $R^9$ is independently H, $(C_1$-$C_4)$alkyl, halo$(C_1$-$C_4)$ alkyl, $(C_2$-$C_4)$alkenyl or $(C_2$-$C_4)$alkynyl.

14. The compound of claim 13, wherein $R^{6a}$ and $R^{6b}$ are independently H, —OH, $(C_1$-$C_4)$alkoxy, halo$(C_1$-$C_4)$alkoxy, $(C_1$-$C_8)$alkyl, hydroxy$(C_1$-$C_8)$alkyl, halo$(C_1$-$C_8)$alkyl, $(C_1$-$C_4)$alkoxy$(C_1$-$C_8)$alkyl, halo$(C_1$-$C_4)$alkoxy$(C_1$-$C_8)$alkyl,

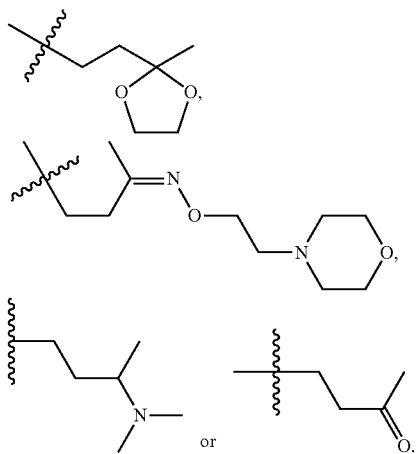

15. The compound of claim 13, wherein $R^{6a}$ and $R^{6b}$ together form

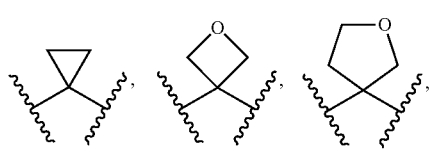

-continued
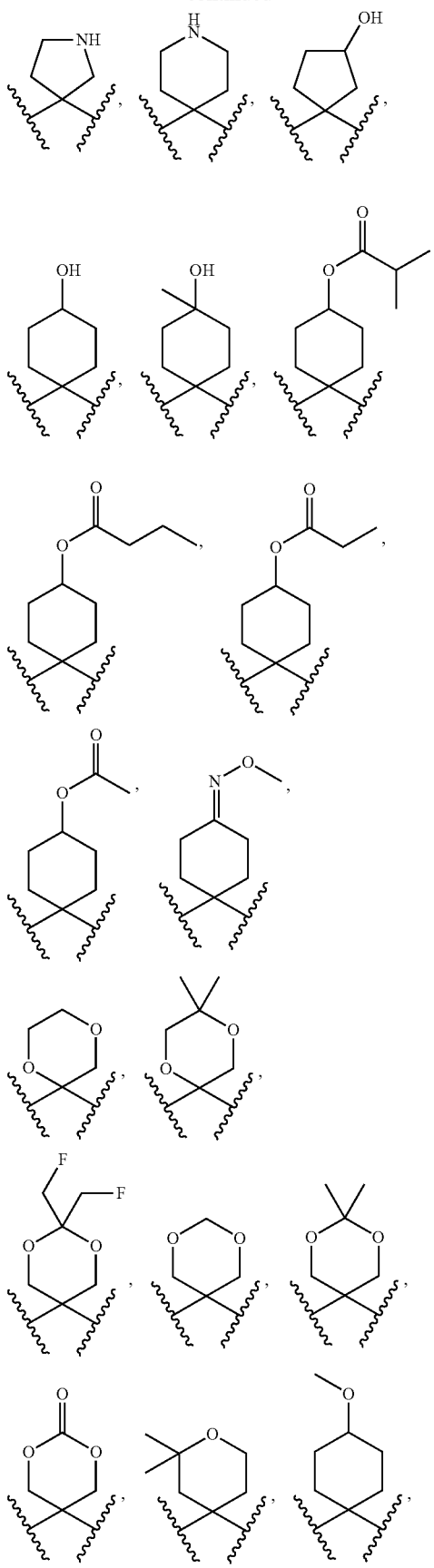
-continued
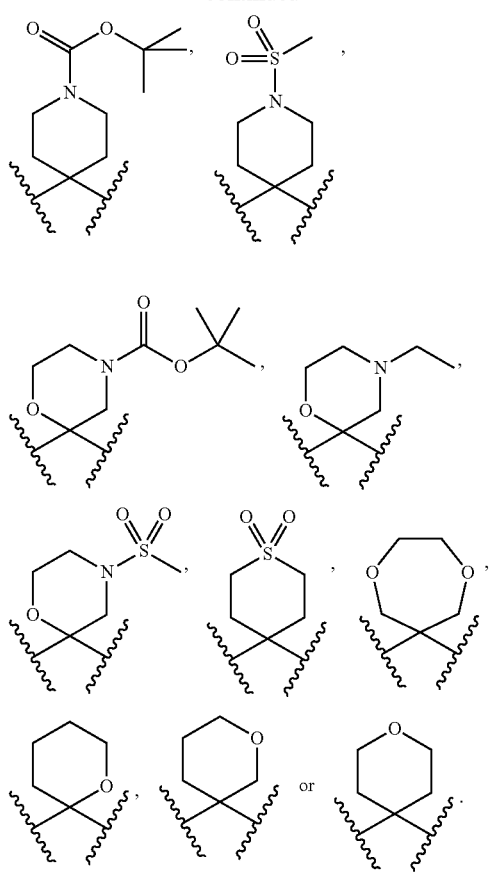
16. The compound of claim 13, wherein $R^{6a}$ and $R^{6b}$ together form
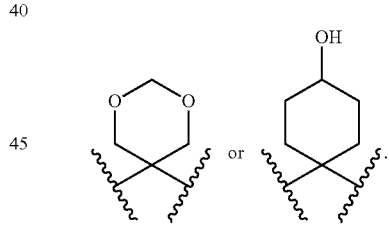
17. The compound of claim 1, which is
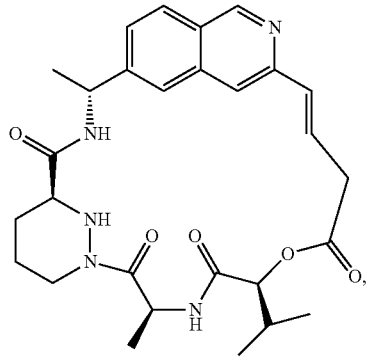

477
-continued
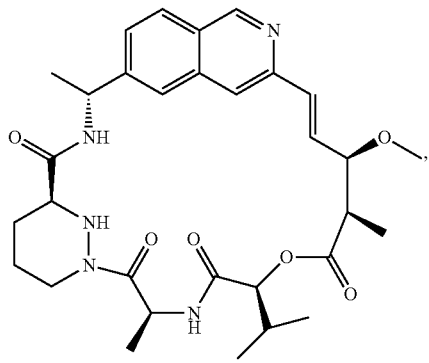
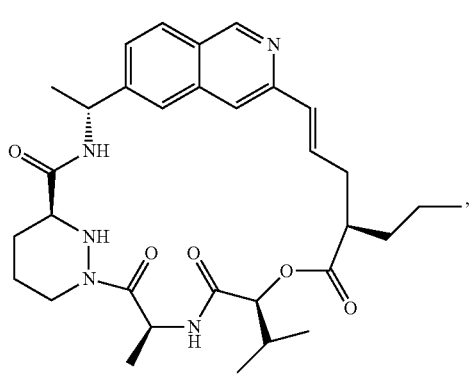
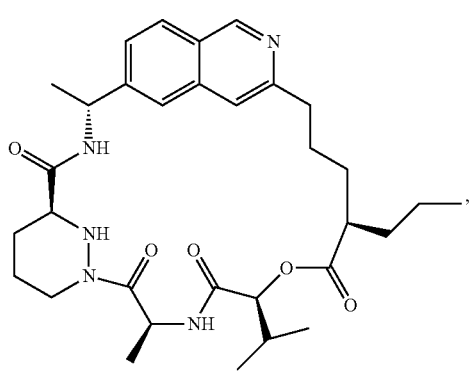
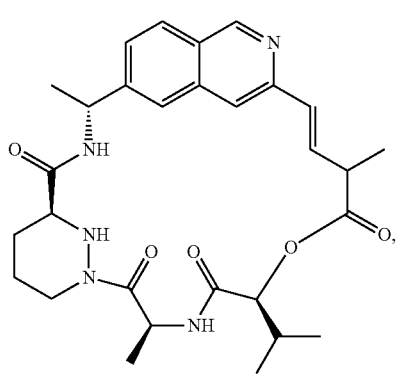
478
-continued
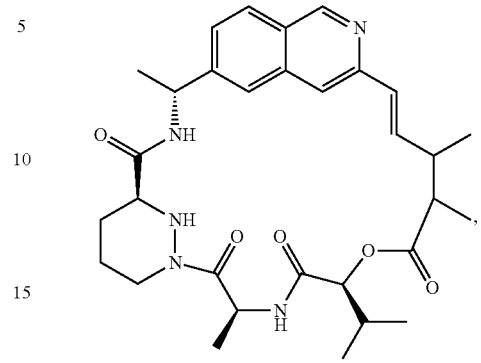
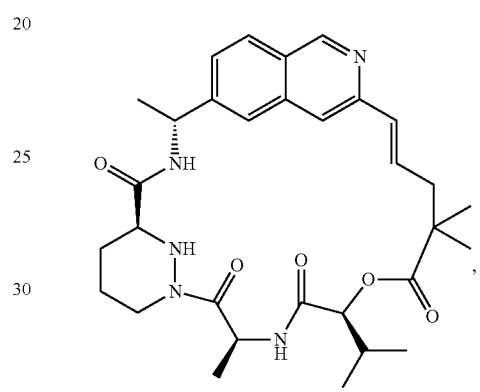
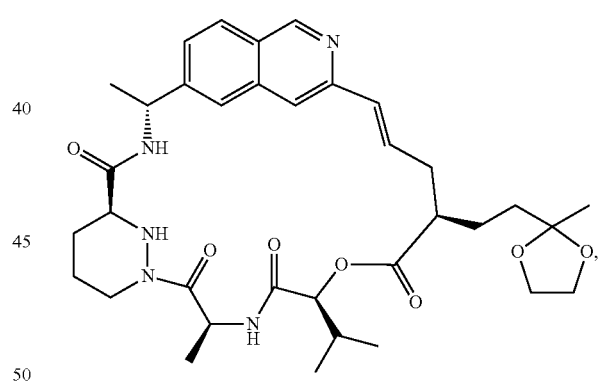
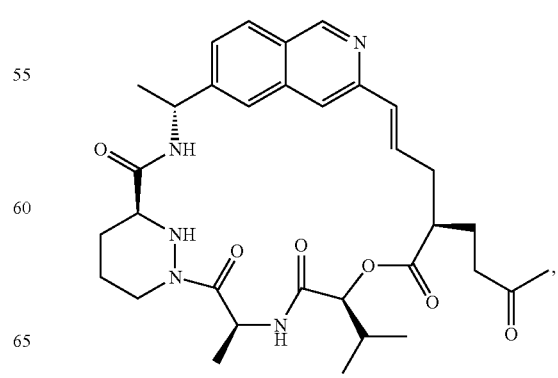

479 480
-continued -continued

481
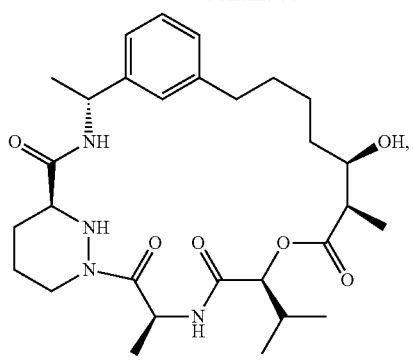
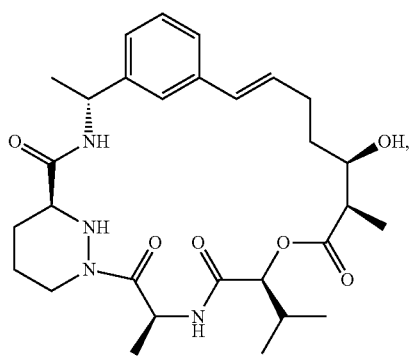
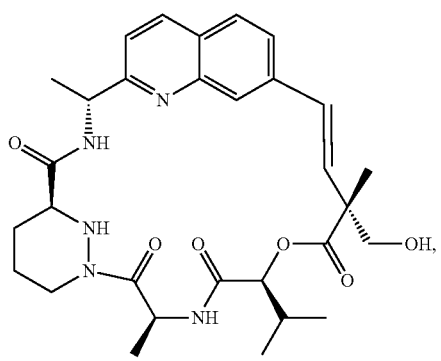
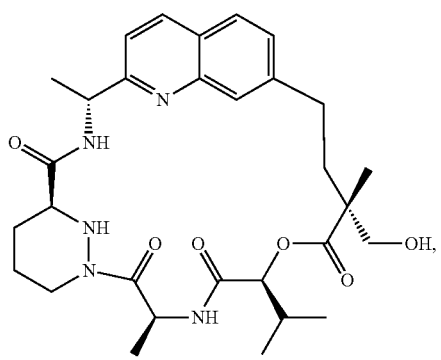
482
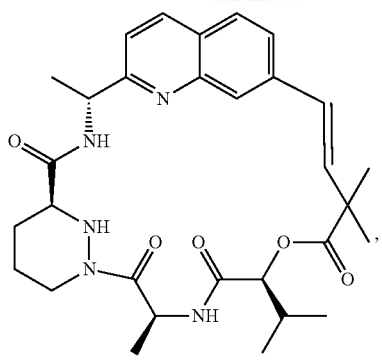
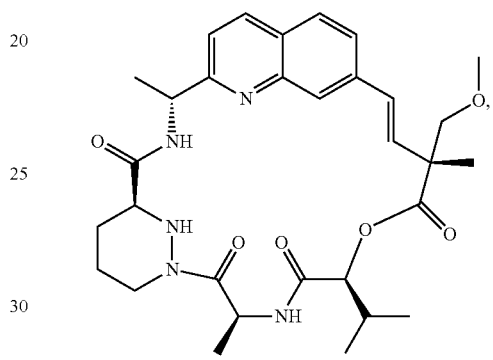
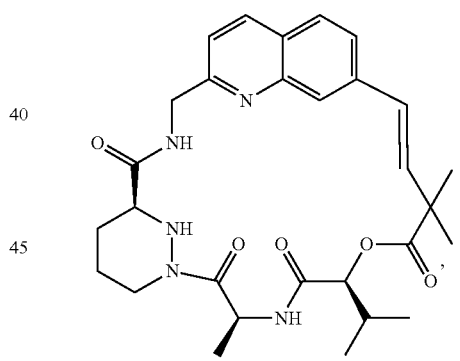
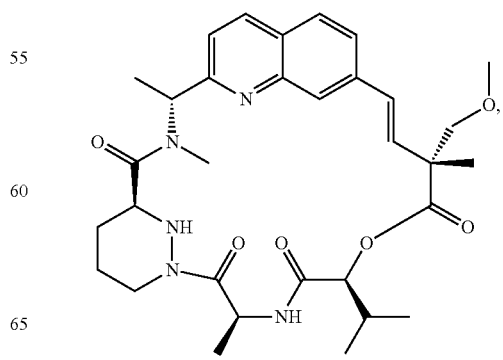

483
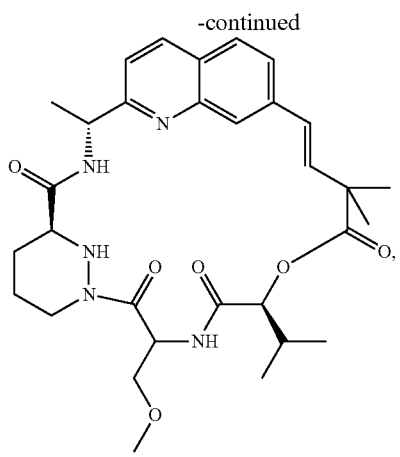
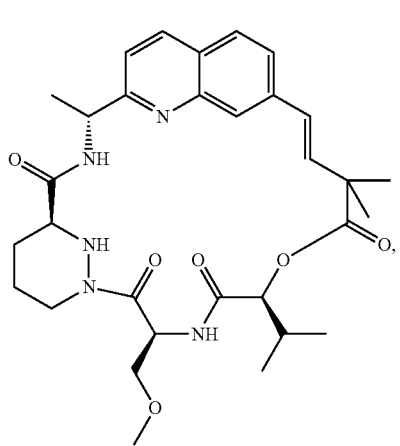
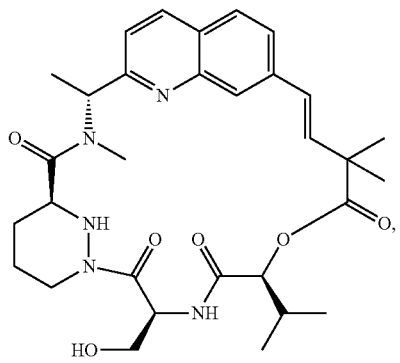
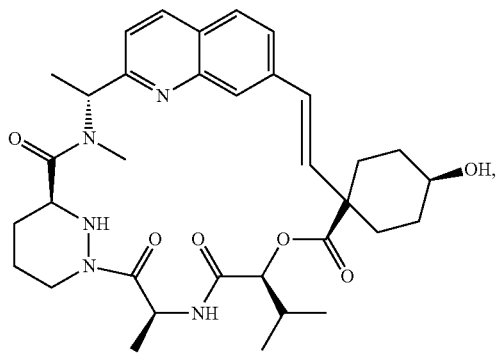
484
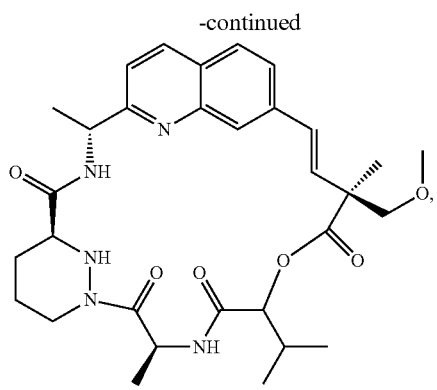
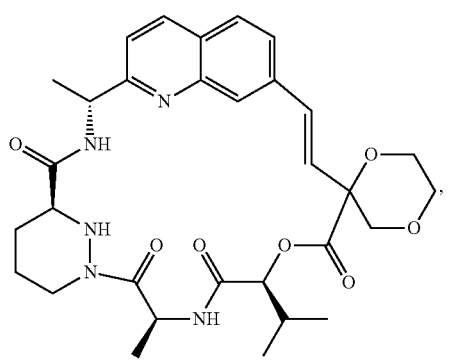
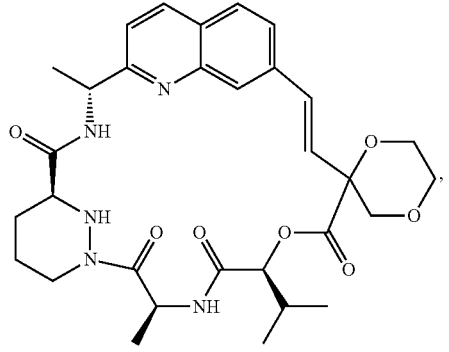
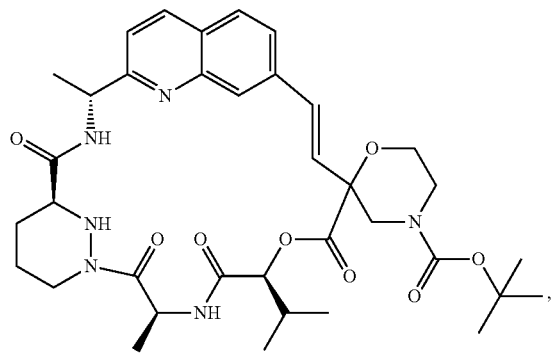

485
-continued
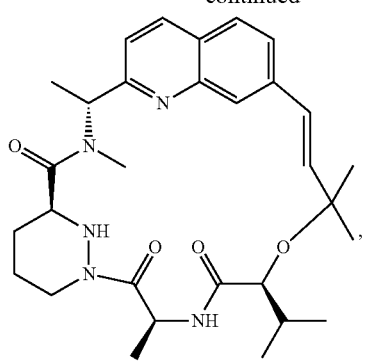
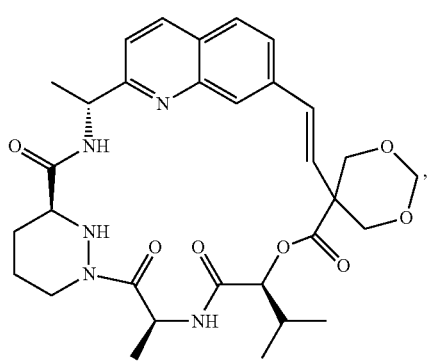
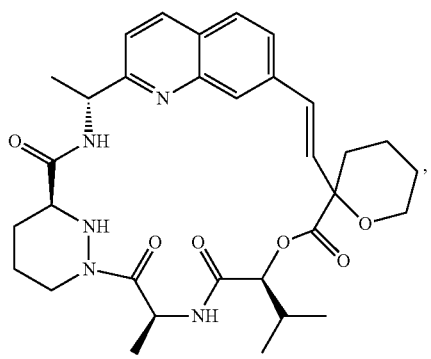
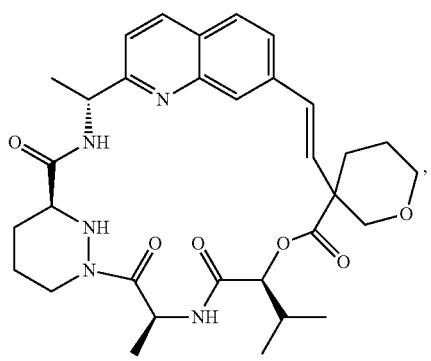
486
-continued
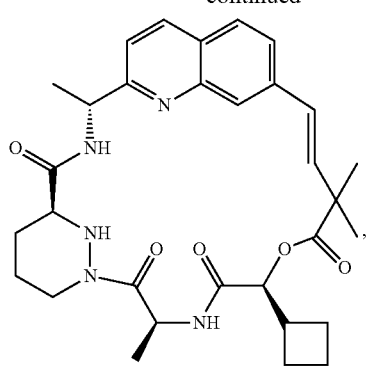
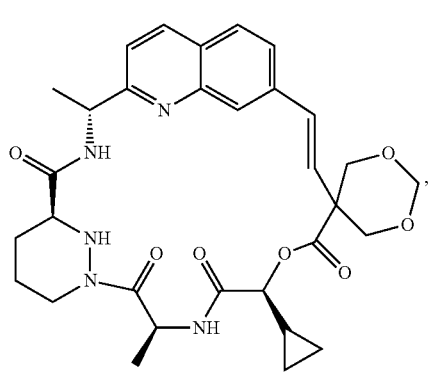
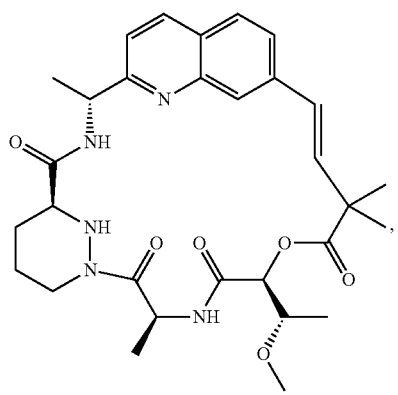
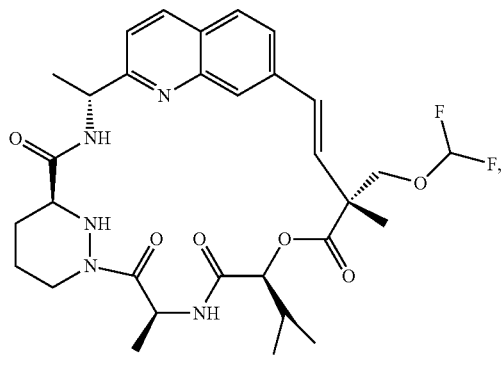

487
-continued
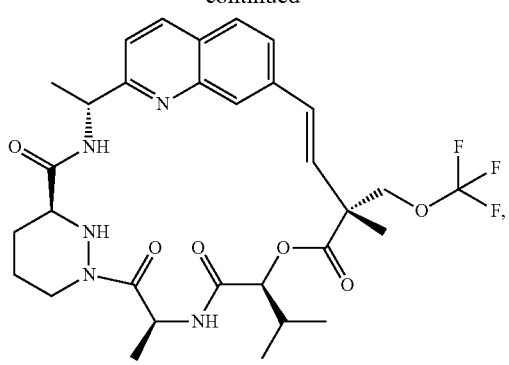
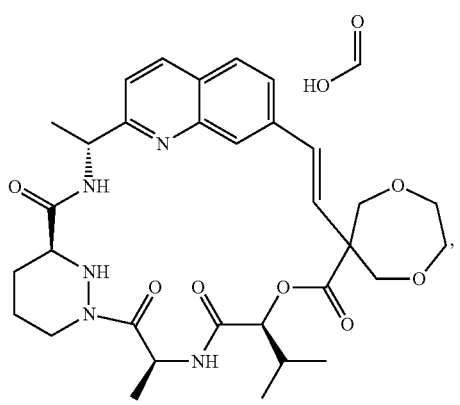
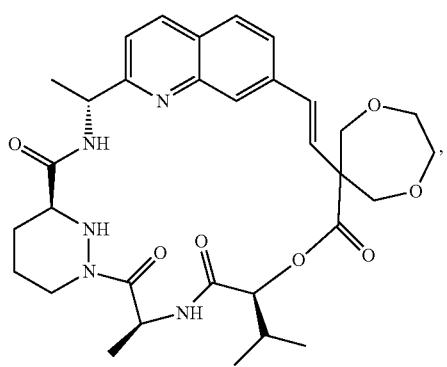
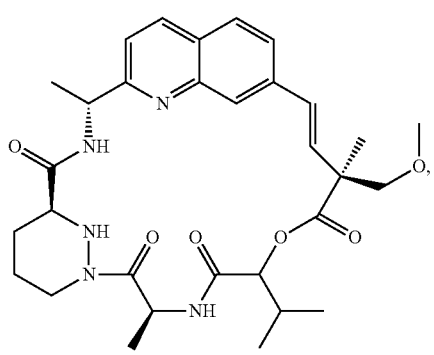
488
-continued
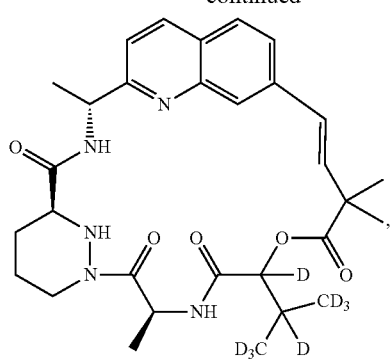
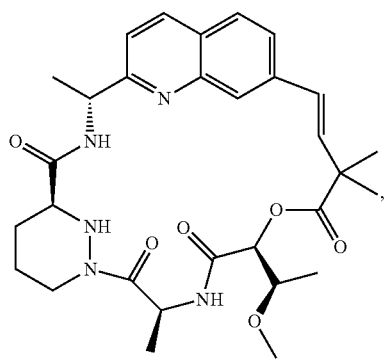
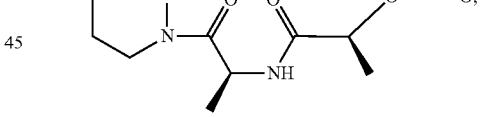
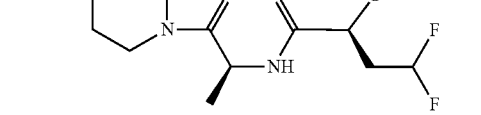

489
-continued
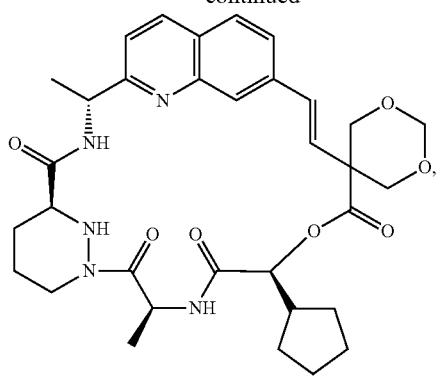
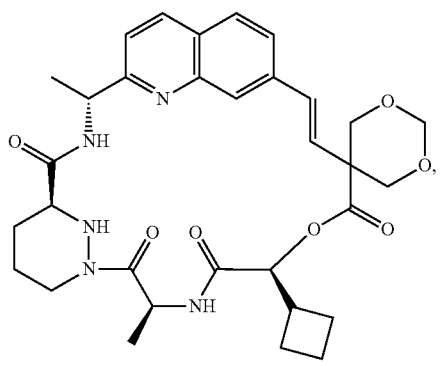
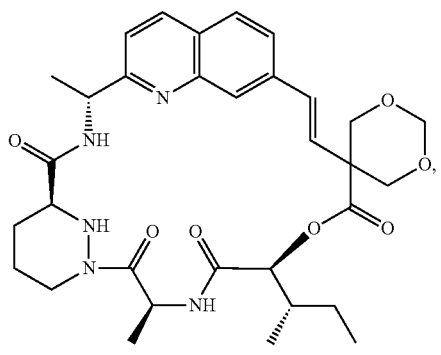
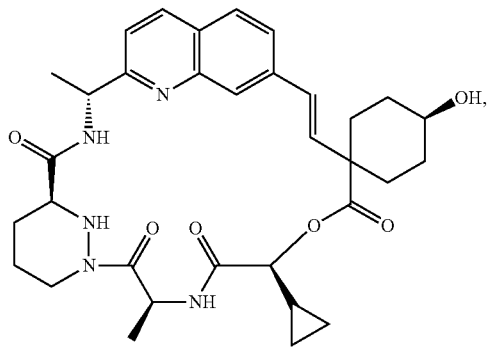
490
-continued
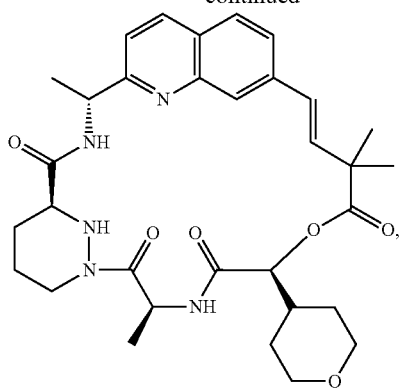
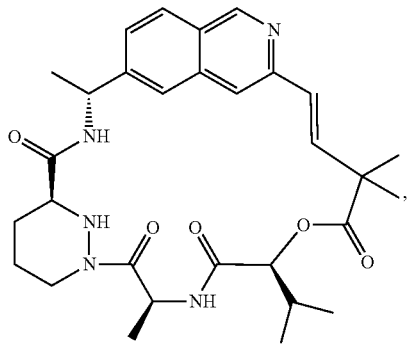
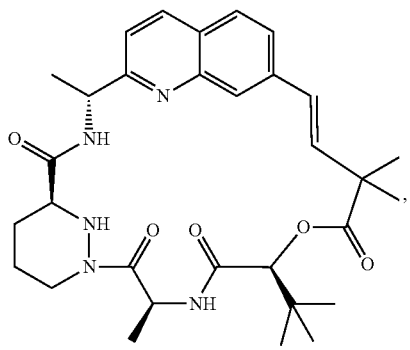

491
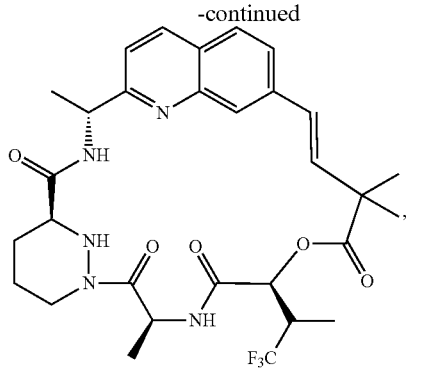
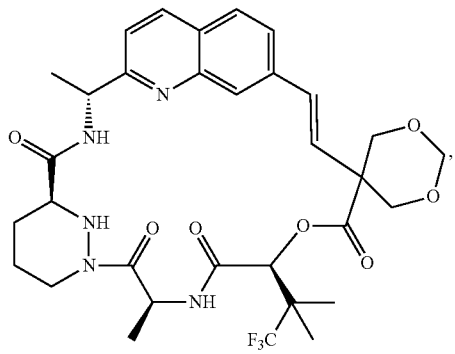
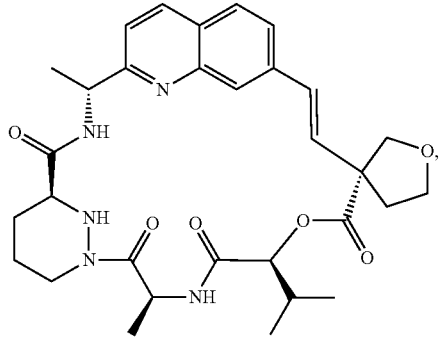
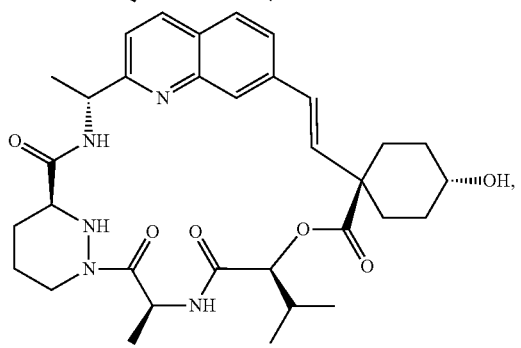
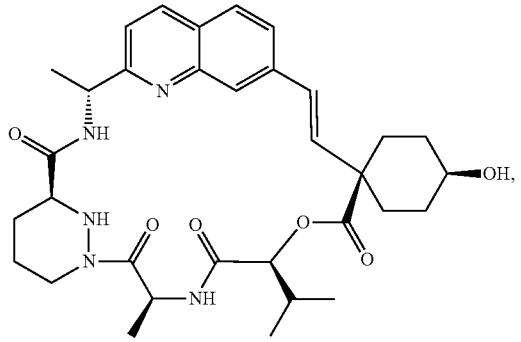
492
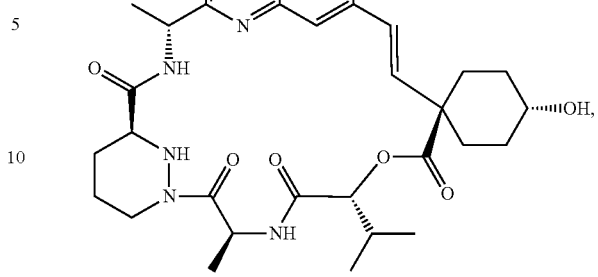
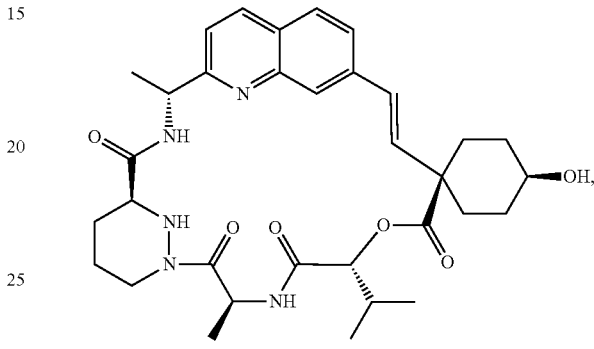
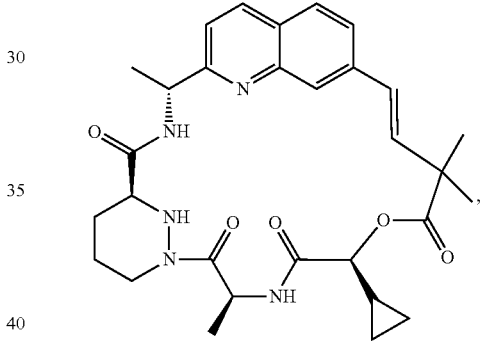
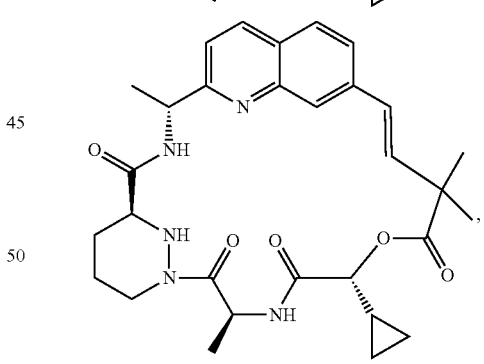
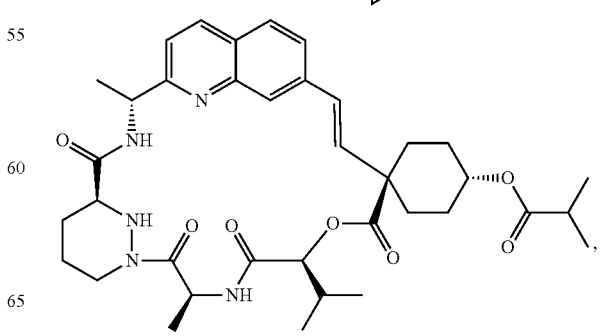

493
-continued
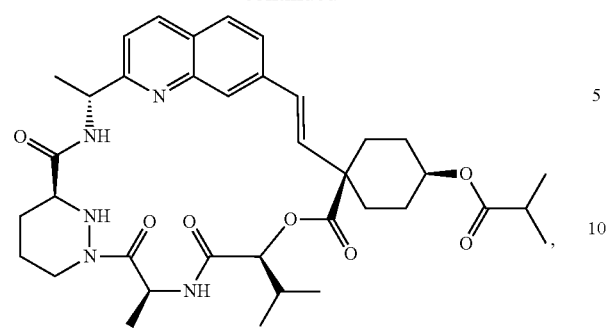
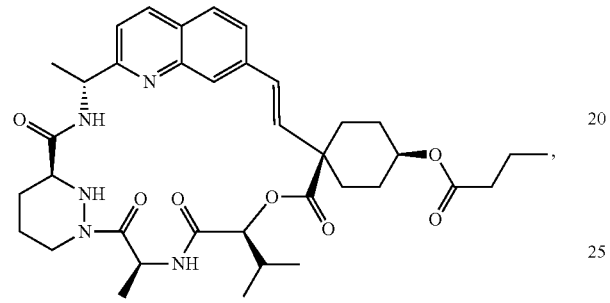
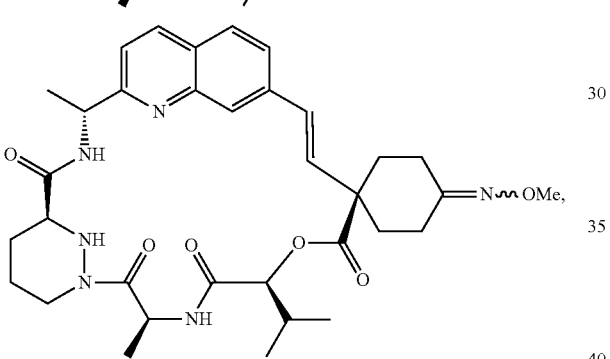
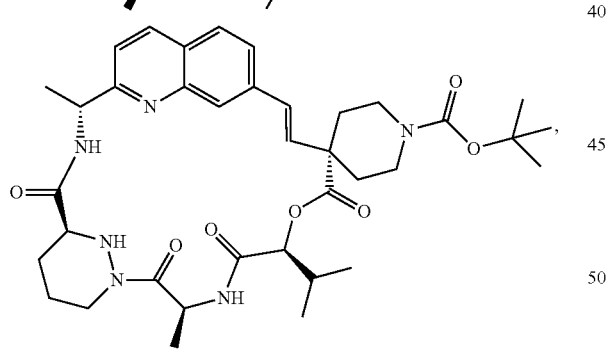
494
-continued
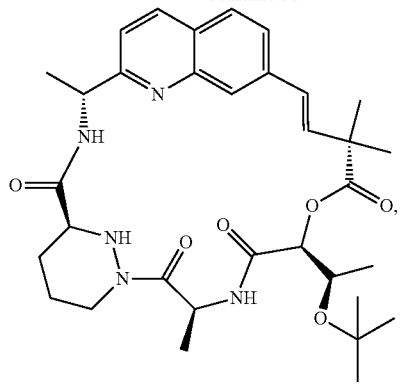
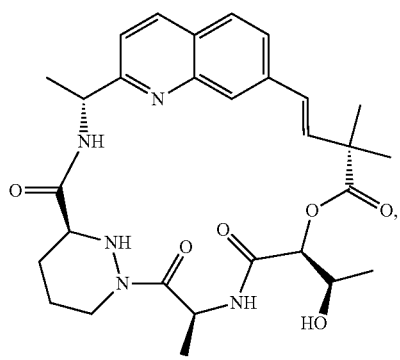
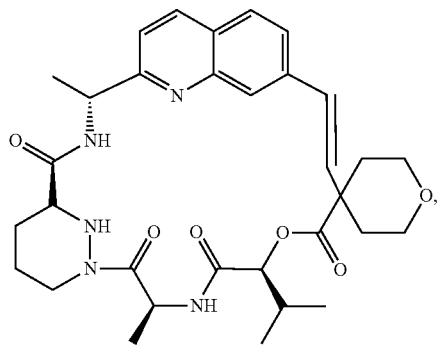
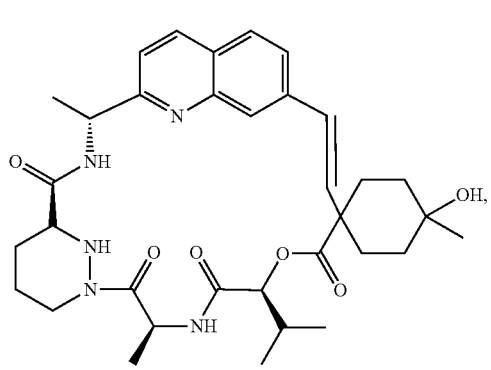

495                                           496
-continued                                    -continued
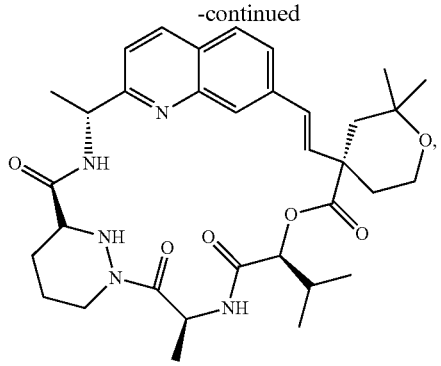
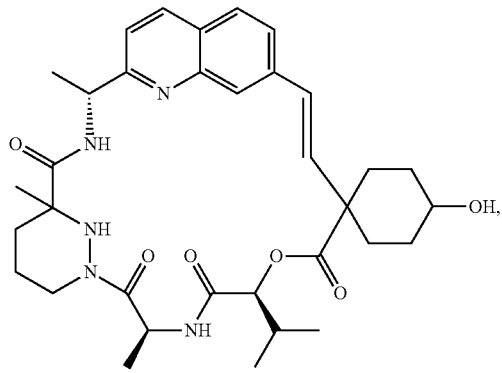
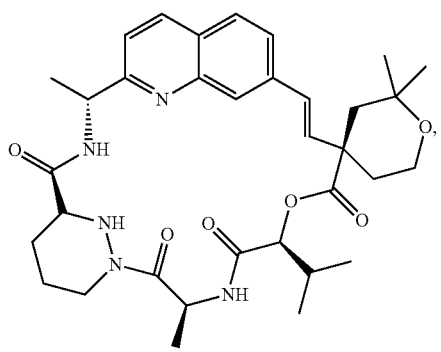
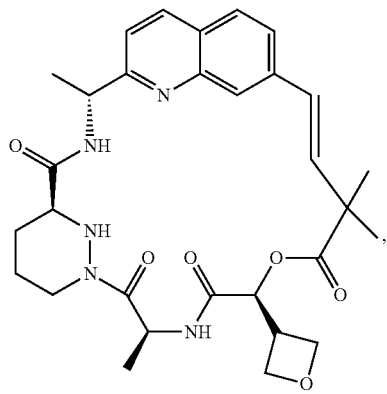
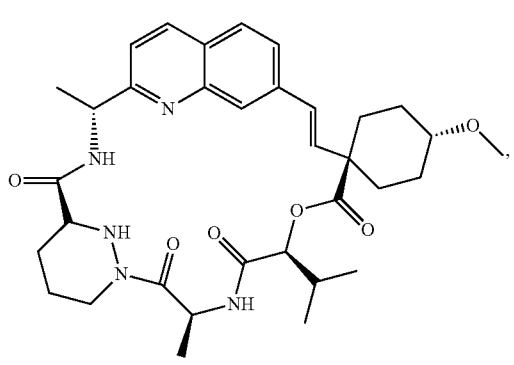
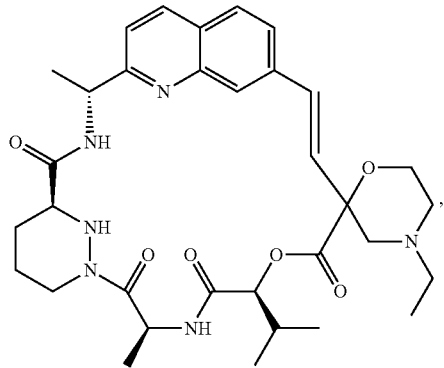
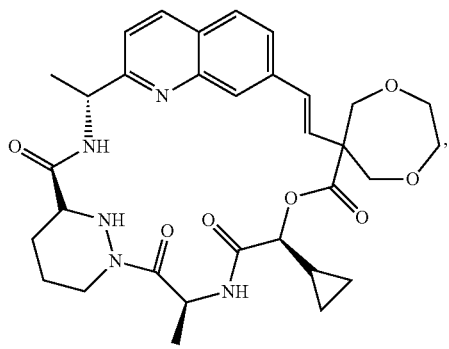
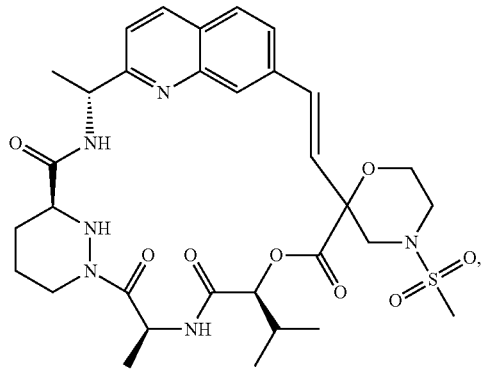

497
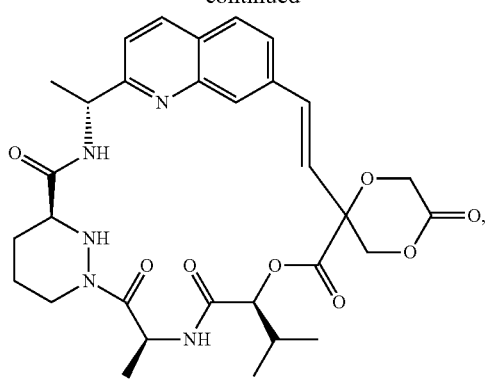
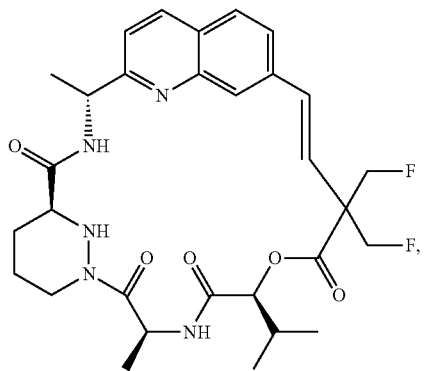
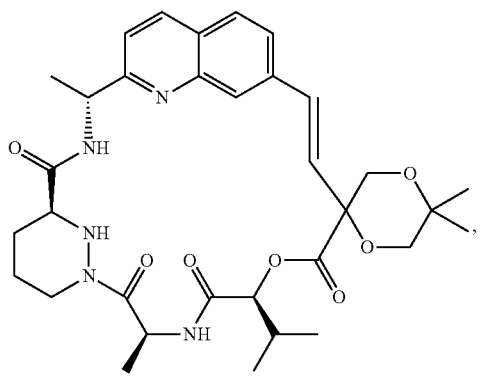
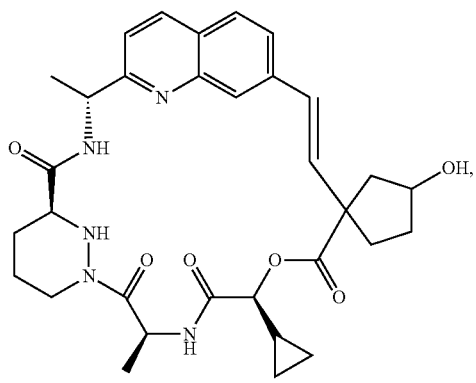
498
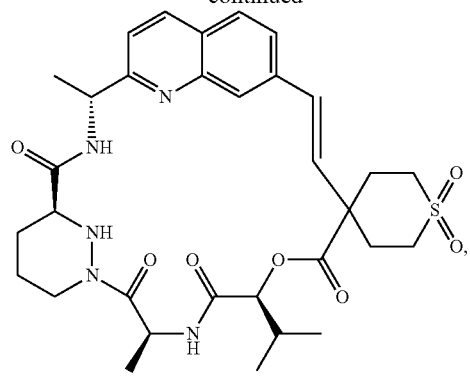
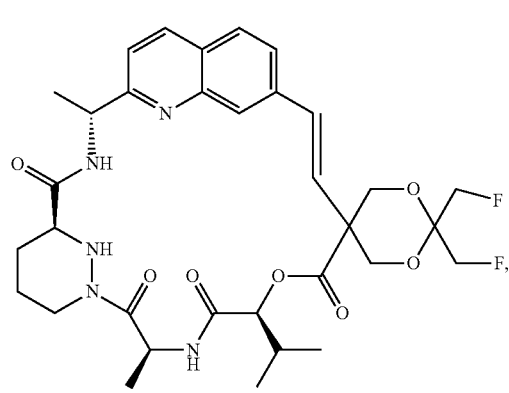
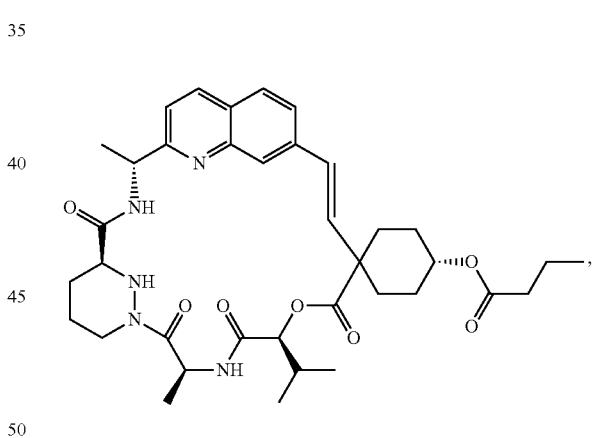
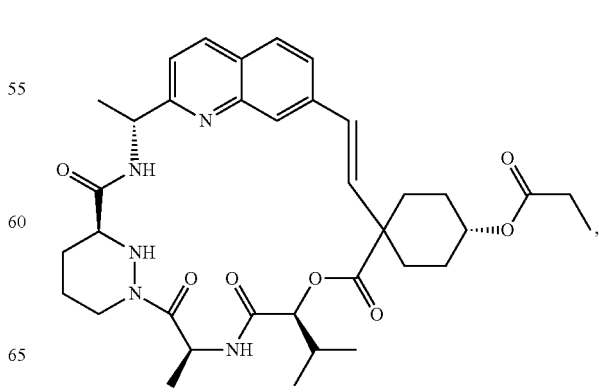

499

-continued

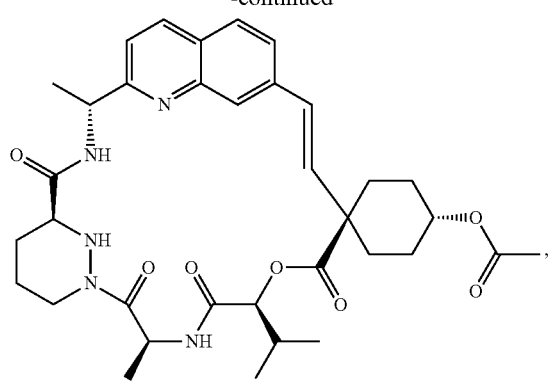

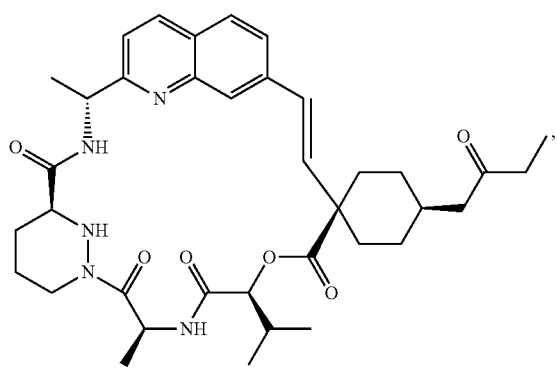

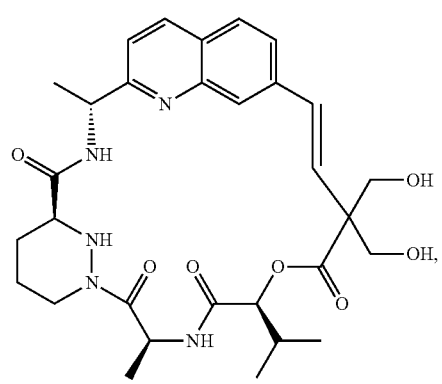

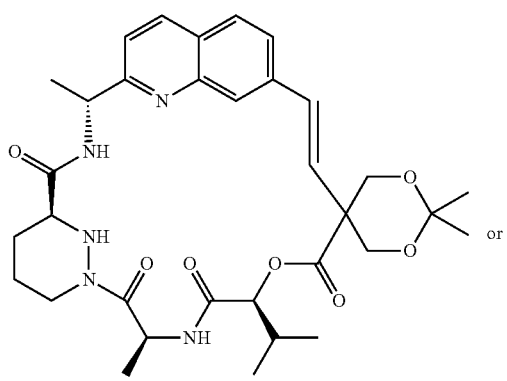 or

500

-continued

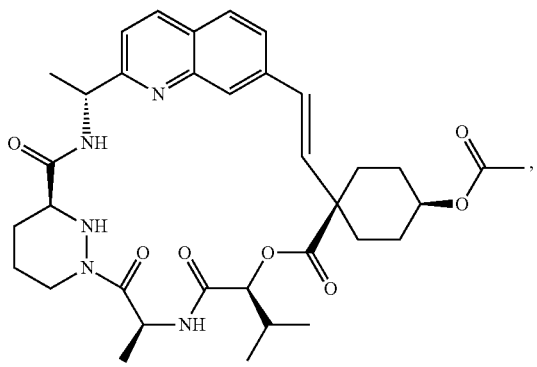

or a pharmaceutically acceptable salt, isotope, stereoisomer, mixture of stereoisomers, tautomer, ester or prodrug thereof.

18. A compound which is:

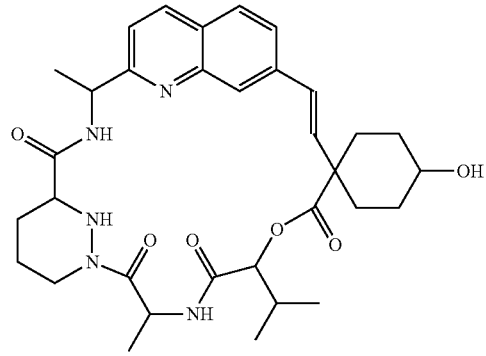 [SMILES: CC1NC(=O)C(C(C)C)OC(=O)C2(/C=C/c3ccc4ccc(nc4c3)C(C)NC(=O)C3CCCN(N3)C1=O)CCC(O)CC2]

or a pharmaceutically acceptable salt, isotope, stereoisomer, mixture of stereoisomers, tautomer, ester or prodrug thereof.

19. A compound which is:

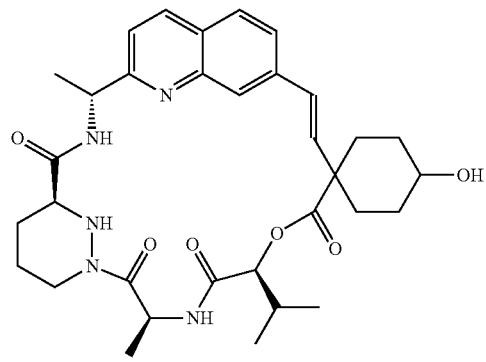 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)CCC(O)CC2]

or a pharmaceutically acceptable salt, isotope, stereoisomer, mixture of stereoisomers, tautomer, ester or prodrug thereof.

20. A compound which is:

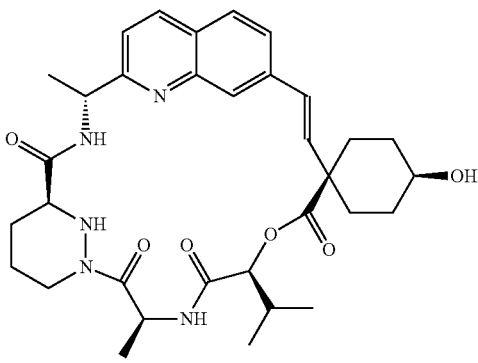 [SMILES: CC(C)[C@@H]1OC(=O)[C@]2(/C=C/c3ccc4ccc(nc4c3)[C@@H](C)NC(=O)[C@@H]3CCCN(N3)C(=O)[C@H](C)NC1=O)CC[C@H](O)CC2]

or a pharmaceutically acceptable salt, isotope, stereoisomer, mixture of stereoisomers, tautomer, ester or prodrug thereof.

21. A compound which is:

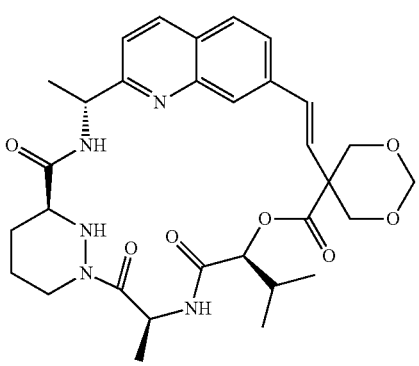 [SMILES: CC(C)[C@@H]1OC(=O)C2(/C=C/c3ccc4ccc(nc4c3)[C@@H](C)NC(=O)[C@@H]3CCCN(N3)C(=O)[C@H](C)NC1=O)COCOC2]

or a pharmaceutically acceptable salt, isotope, stereoisomer, mixture of stereoisomers, tautomer, ester or prodrug thereof.

22. The compound of claim 1, which is a compound of Formula III:

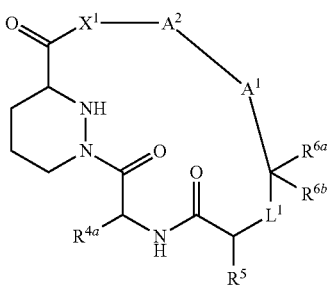

Formula III or a pharmaceutically acceptable salt, isotope, stereoisomer, mixture of stereoisomers, tautomer, ester or prodrug thereof, wherein $L^1$ is —O—$CH_2$, NH—$CH_2$—, —N($CH_3$)—$CH_2$—, —NH—CH($CF_3$)— or —NH—$S(O)_2$—;

$A^1$ is

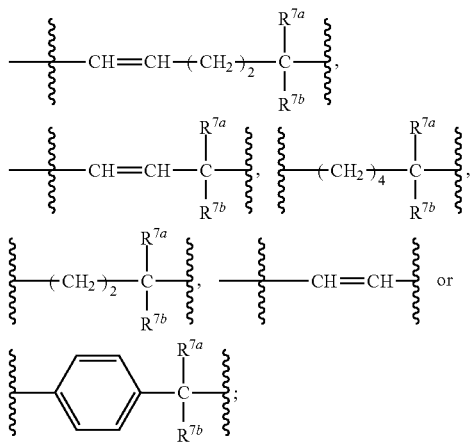

$A^2$ is —CH($R^8$)-arylene, —CH($R^8$)-heteroarylene, —CH($R^8$)-heterocycloalkylene, —CH($R^8$)-cycloalkylene, arylene or cycloalkylene;

$X^1$ is —O—, —N($CH_3$)— or —NH—;

$R^{4a}$ is H, ($C_1$-$C_4$)alkoxy, halo($C_1$-$C_4$)alkoxy or ($C_1$-$C_8$) alkyl;

$R^5$ is H or ($C_1$-$C_4$)alkyl;

$R^{6a}$ and $R^{6b}$ are independently H, hydroxyl, —$CH_2CH_2CR^9$(=N($C_1$-$C_4$)alkoxy), ($C_1$-$C_8$)alkyl or ($C_1$-$C_8$)alkoxy, optionally substituted with one or more substituents selected from the group consisting of halo, hydroxyl, ($C_1$-$C_4$)alkoxy, halo($C_1$-$C_4$)alkoxy, heterocycloalkyl, ($C_1$-$C_4$)alkanoyl or di($C_1$-$C_4$)alkylamino; or $R^{6a}$ and $R^{6b}$ together form a spirocycle having Formula (a):

(a)

wherein one or more carbon ring atoms of Formula (a) is optionally replaced by a nitrogen, oxygen or sulfur atom, and wherein a ring atom of Formula (a) optionally has one or more substituents selected from the group consisting of oxo, halo, hydroxyl, —$NH_2$, ($C_1$-$C_4$)alkyl, ($C_1$-$C_4$)alkoxy, —OC(O)$R^9$, —C(O)$_2R^9$, and —S(O)$_2$ $R^9$;

$R^{7a}$ and $R^{7b}$ are independently H, —OH, ($C_1$-$C_4$)alkoxy, halo($C_1$-$C_4$)alkoxy or ($C_1$-$C_8$)alkyl; and $R^8$ is H or ($C_1$-$C_4$)alkyl.

23. The compound of claim 22, wherein $L^1$ is —NH—$CH_2$—; $R^{4a}$ is methyl; $R^5$ is isopropyl; $R^8$ is methyl; and $A^2$ is

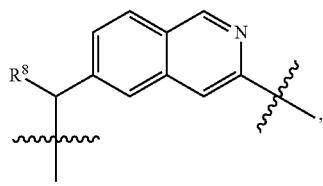

503
-continued
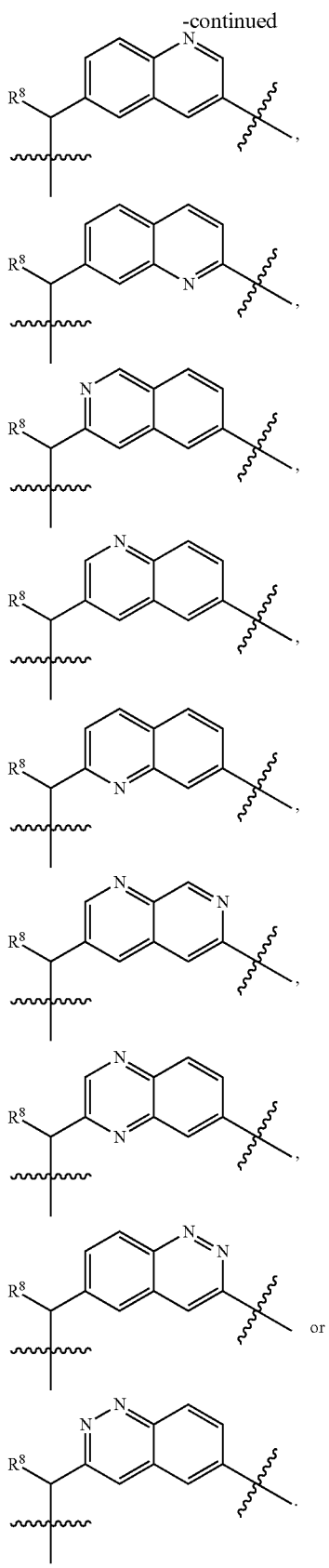
504
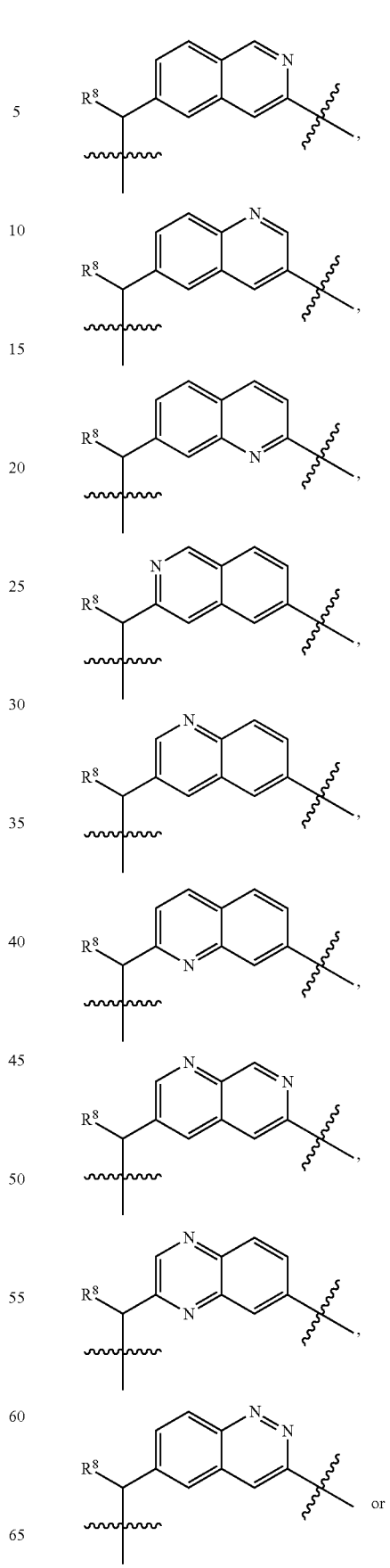
24. The compound of claim 23, wherein L¹ is —NH—S(O)₂—; R⁴ᵃ is methyl; R⁵ is isopropyl; R⁸ is methyl; and A² is -continued
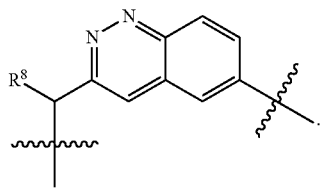
25. The compound of claim 23, wherein L¹ is —O—CH₂—; R⁴ᵃ is methyl; R⁵ is isopropyl; R⁸ is methyl; and A² is
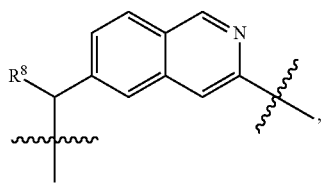
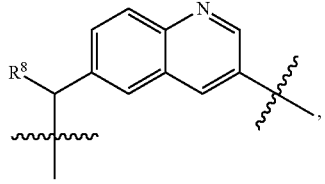
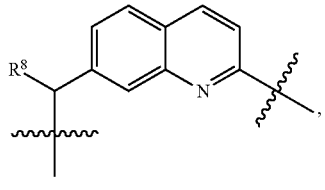
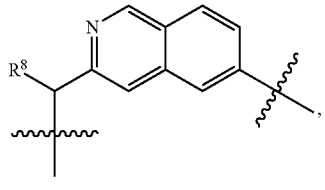
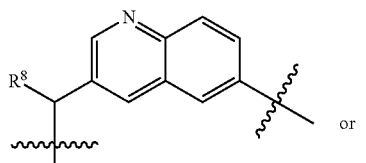 or
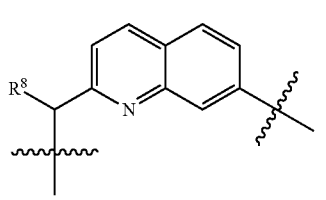
26. The compound of claim 23, which is
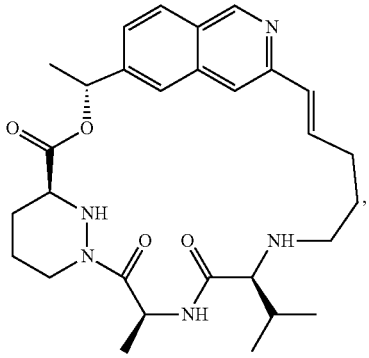
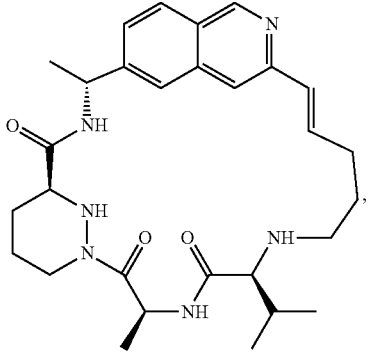 [SMILES: CC(C)[C@@H]1NCCC/C=C/c2cc3cc(ccc3cn2)[C@@H](C)OC(=O)[C@@H]2CCCN(N2)C(=O)[C@H](C)NC1=O]
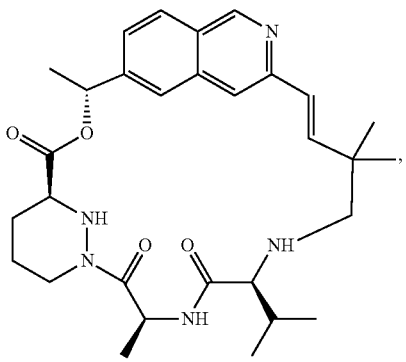
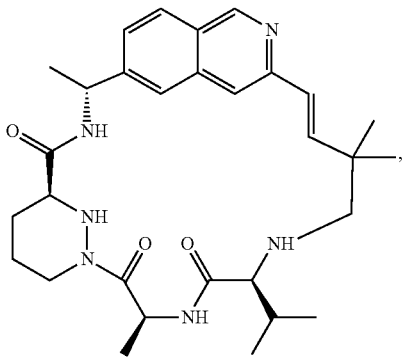

507
-continued
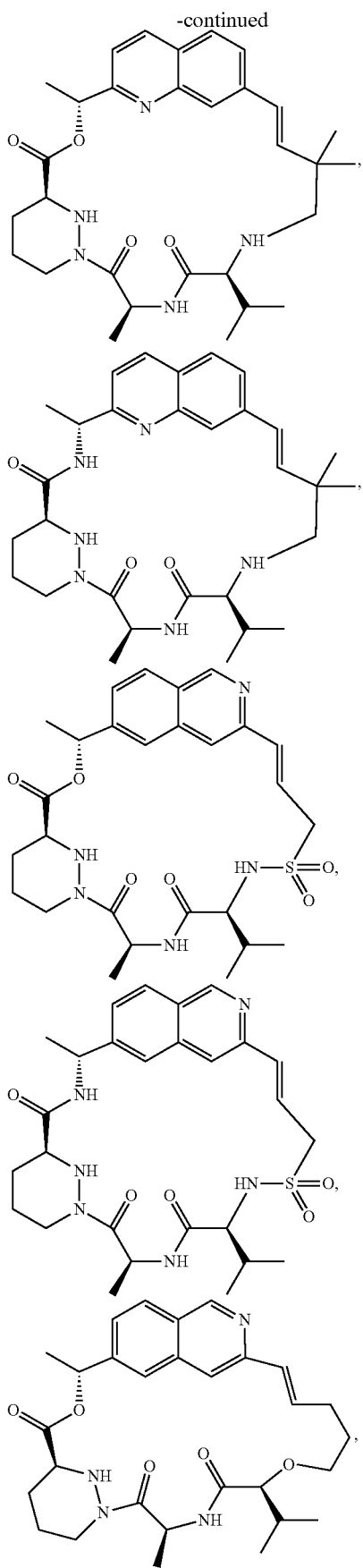
508
-continued
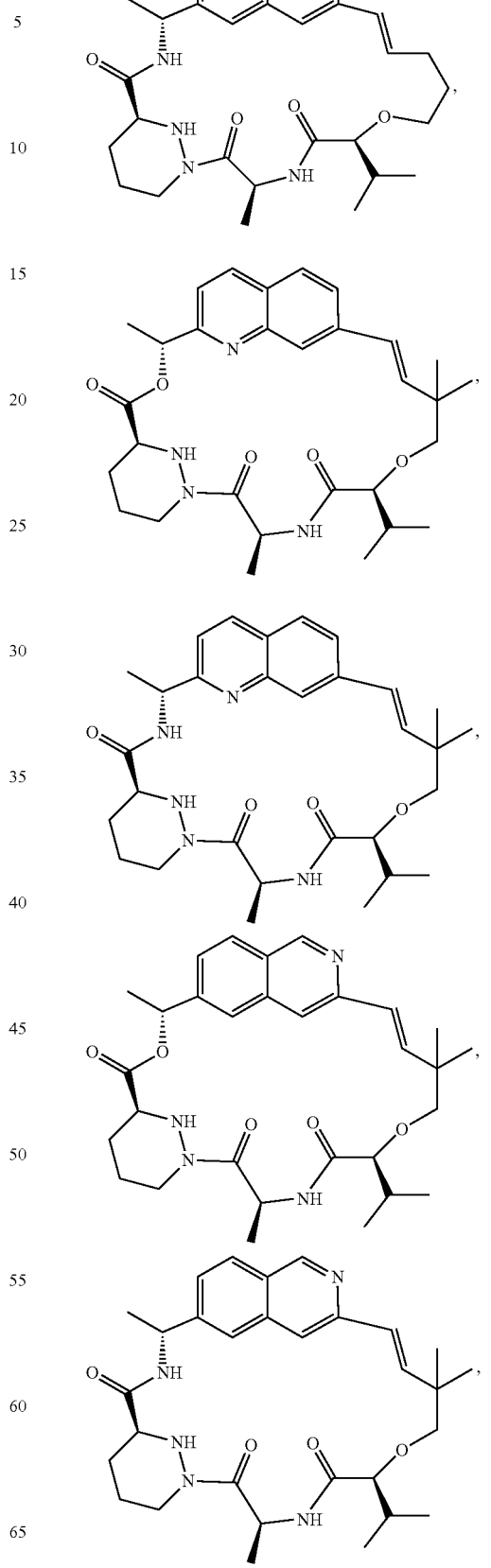

509

-continued

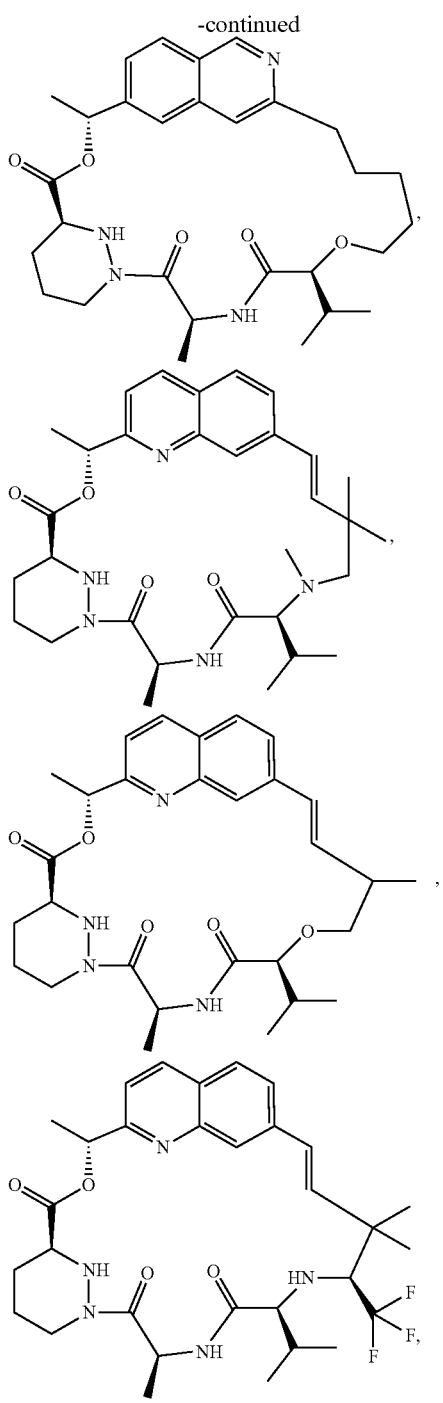

510

-continued

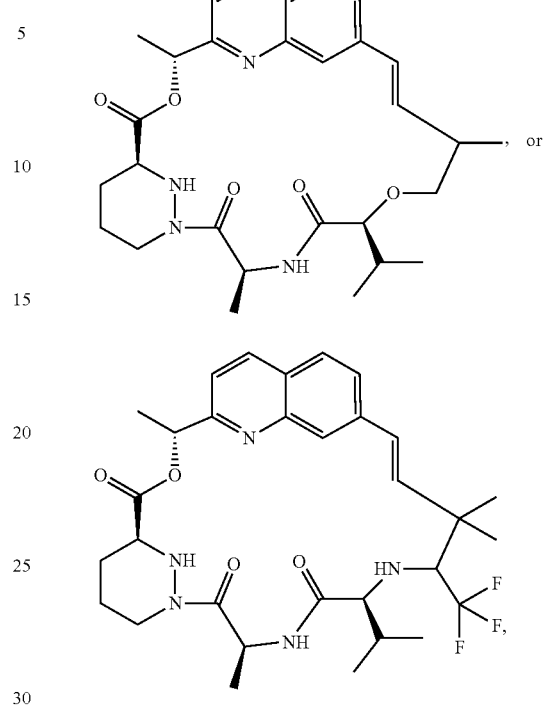

or a pharmaceutically acceptable salt, isotope, stereoisomer, mixture of stereoisomers, tautomer, ester or prodrug thereof.

27. A pharmaceutical composition comprising a therapeutically effective amount of a compound of claim 1 or a pharmaceutically acceptable salt, isotope, stereoisomer, mixture of stereoisomers, tautomer, ester or prodrug thereof and a pharmaceutically acceptable excipient.

28. The pharmaceutical composition of claim 27, further comprising at least one additional therapeutic agent selected from the group consisting of interferons, ribavirin, HCV NS3 protease inhibitors, HCV NS5a inhibitors, nucleoside or nucleotide inhibitors of HCV NS5B polymerase, non-nucleoside inhibitors of HCV NS5B polymerase, and TLR-7 agonists; or a mixture thereof.

29. The pharmaceutical composition of claim 28, wherein the at least one addition therapeutic agent is ribavirin, telaprevir, boceprevir or sofosbuvir.

* * * * *